(12) United States Patent
Malchano et al.

(10) Patent No.: US 10,307,611 B2
(45) Date of Patent: Jun. 4, 2019

(54) METHODS AND SYSTEMS FOR NEURAL STIMULATION VIA VISUAL, AUDITORY AND PERIPHERAL NERVE STIMULATIONS

(71) Applicant: Cognito Therapeutics, Inc., Newton, MA (US)

(72) Inventors: Zachary John Hambrecht Malchano, Boston, MA (US); Martin Warren Williams, San Francisco, CA (US)

(73) Assignee: COGNITO THERAPEUTICS, INC., Newton, MA (US)

( * ) Notice: Subject to any disclaimer, the term of this patent is extended or adjusted under 35 U.S.C. 154(b) by 0 days.

(21) Appl. No.: 15/816,238

(22) Filed: Nov. 17, 2017

(65) Prior Publication Data
US 2018/0133507 A1    May 17, 2018

Related U.S. Application Data

(60) Provisional application No. 62/423,532, filed on Nov. 17, 2016, provisional application No. 62/423,517, (Continued)

(51) Int. Cl.
*A61N 5/06*    (2006.01)
*A61B 5/0484*    (2006.01)
(Continued)

(52) U.S. Cl.
CPC ........ *A61N 5/0622* (2013.01); *A61B 5/04842* (2013.01); *A61B 5/04845* (2013.01);
(Continued)

(58) Field of Classification Search
CPC . A61B 5/7264; A61B 5/04845; A61B 5/4088; A61B 5/4836; A61B 5/486;
(Continued)

(56) References Cited

U.S. PATENT DOCUMENTS

| 5,534,953 A | 7/1996 | Schmielau |
| 5,923,398 A | 7/1999 | Goldman |

(Continued)

FOREIGN PATENT DOCUMENTS

| KR | 1020160129752 A | 11/2016 |
| WO | WO-2014/162271 A2 | 10/2014 |

OTHER PUBLICATIONS

International Search Report and Written Opinion for International Application No. PCT/US2017/062333, dated Jun. 20, 2018.
(Continued)

*Primary Examiner* — Deborah L Malamud
(74) *Attorney, Agent, or Firm* — Foley & Lardner LLP; James F. Ewing; Shabbi S. Khan

(57) ABSTRACT

Systems and methods of the present disclosure are directed to systems and methods for treating cognitive dysfunction in a subject in need thereof. The system can include a light source and a speaker. A visual neural stimulation system provides, via the light source, visual stimulation having a first value of a first parameter. An auditory neural stimulation system provides, via the speaker, audio stimulation having a second value of the second parameter. A stimuli orchestration component selects, for a first time interval, one of the visual stimulation or the audio stimulation to vary based on a policy, selects, for the first time interval, the other of the visual stimulation or the audio stimulation to keep constant based on the policy, and provides causes the one of the visual neural stimulation system or the auditory neural stimulation system to vary the one of the visual stimulation or the audio stimulation.

26 Claims, 82 Drawing Sheets

Related U.S. Application Data filed on Nov. 17, 2016, provisional application No. 62/423,569, filed on Nov. 17, 2016, provisional application No. 62/423,598, filed on Nov. 17, 2016, provisional application No. 62/423,536, filed on Nov. 17, 2016, provisional application No. 62/423,557, filed on Nov. 17, 2016, provisional application No. 62/423,452, filed on Nov. 17, 2016, provisional application No. 62/431,702, filed on Dec. 8, 2016, provisional application No. 62/431,698, filed on Dec. 8, 2016, provisional application No. 62/431,720, filed on Dec. 8, 2016, provisional application No. 62/431,725, filed on Dec. 8, 2016.

(51) Int. Cl.
  *A61N 1/36* (2006.01)
  *A61B 5/00* (2006.01)
  *A61N 1/05* (2006.01)

(52) U.S. Cl.
  CPC ..... *A61N 1/36036* (2017.08); *A61N 1/36082* (2013.01); *A61B 5/4088* (2013.01); *A61N 1/0551* (2013.01)

(58) Field of Classification Search
  CPC . A61B 5/0004; A61B 5/04001; A61B 5/4041; A61B 5/4064; H04R 1/1008; H04R 1/1016; H04R 29/00; G06F 3/015; A61N 1/0456; A61N 1/0472; A61N 1/36132; A61N 1/36139; A61N 1/36146; A61N 5/0622; A61N 1/0408; A61N 1/36025; A61N 1/3606; A61N 1/36125; A61N 1/36135; A61N 2005/063; A61N 2005/0648; A61N 2005/0662; A63B 2220/805; A63B 2220/808; A63B 2230/045; A63B 2230/08; A63B 71/0622; A61H 2201/10
  See application file for complete search history.

(56) References Cited

U.S. PATENT DOCUMENTS

| | | | |
|---|---|---|---|
| 6,066,163 | A | 5/2000 | John |
| 6,071,229 | A | 6/2000 | Rubins |
| 6,167,298 | A | 12/2000 | Levin |
| 8,070,669 | B2 | 12/2011 | Brunelle et al. |
| 8,239,030 | B1 | 8/2012 | Hagedorn et al. |
| 8,328,420 | B2 * | 12/2012 | Abreu ............ A61B 5/0008 374/163 |
| 2004/0158119 | A1 | 8/2004 | Osorio et al. |
| 2007/0179557 | A1 | 8/2007 | Maschino et al. |
| 2007/0191727 | A1 * | 8/2007 | Fadem ............ A61B 5/0002 600/544 |
| 2007/0253561 | A1 | 11/2007 | Williams et al. |
| 2008/0255949 | A1 | 10/2008 | Genco et al. |
| 2009/0005837 | A1 | 1/2009 | Olmstead |
| 2009/0270776 | A1 | 10/2009 | Chang |
| 2010/0241021 | A1 | 9/2010 | Morikawa et al. |
| 2010/0331912 | A1 | 12/2010 | Tass et al. |
| 2011/0066586 | A1 | 3/2011 | Sabel et al. |
| 2012/0016174 | A1 | 1/2012 | De Taboada et al. |
| 2012/0150545 | A1 | 6/2012 | Simon |
| 2013/0066395 | A1 | 3/2013 | Simon et al. |
| 2013/0083173 | A1 | 4/2013 | Geisner et al. |
| 2013/0216055 | A1 | 8/2013 | Wanca |
| 2014/0107525 | A1 | 4/2014 | Tass |
| 2014/0200432 | A1 | 7/2014 | Banerji et al. |
| 2014/0303424 | A1 | 10/2014 | Glass |
| 2015/0305667 | A1 | 10/2015 | Durand |
| 2016/0067087 | A1 | 3/2016 | Tedford et al. |
| 2017/0072162 | A1 | 3/2017 | Kim et al. |

OTHER PUBLICATIONS

U.S. Non-Final Office Action for U.S. Appl. No. 15/816,222, dated Jun. 15, 2018.
U.S. Non-Final Office Action for U.S. Appl. No. 15/816,233, dated Sep. 21, 2018.
International Search Report and Written Opinion for International Appl. No. PCT/US2017/062328, dated May 3, 2018.
International Search Report and Written Opinion for International Appl. No. PCT/US2017/062335, dated Apr. 12, 2018.

* cited by examiner

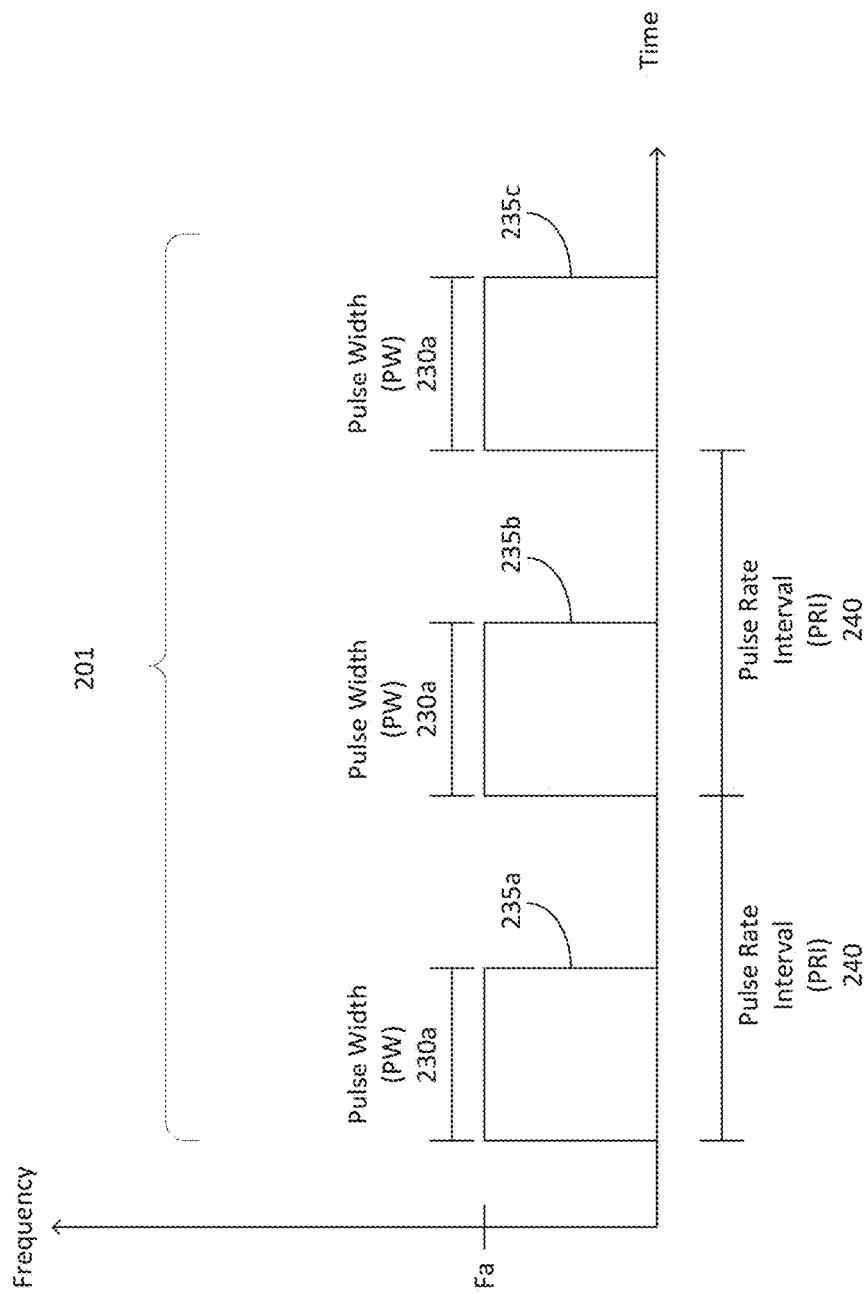

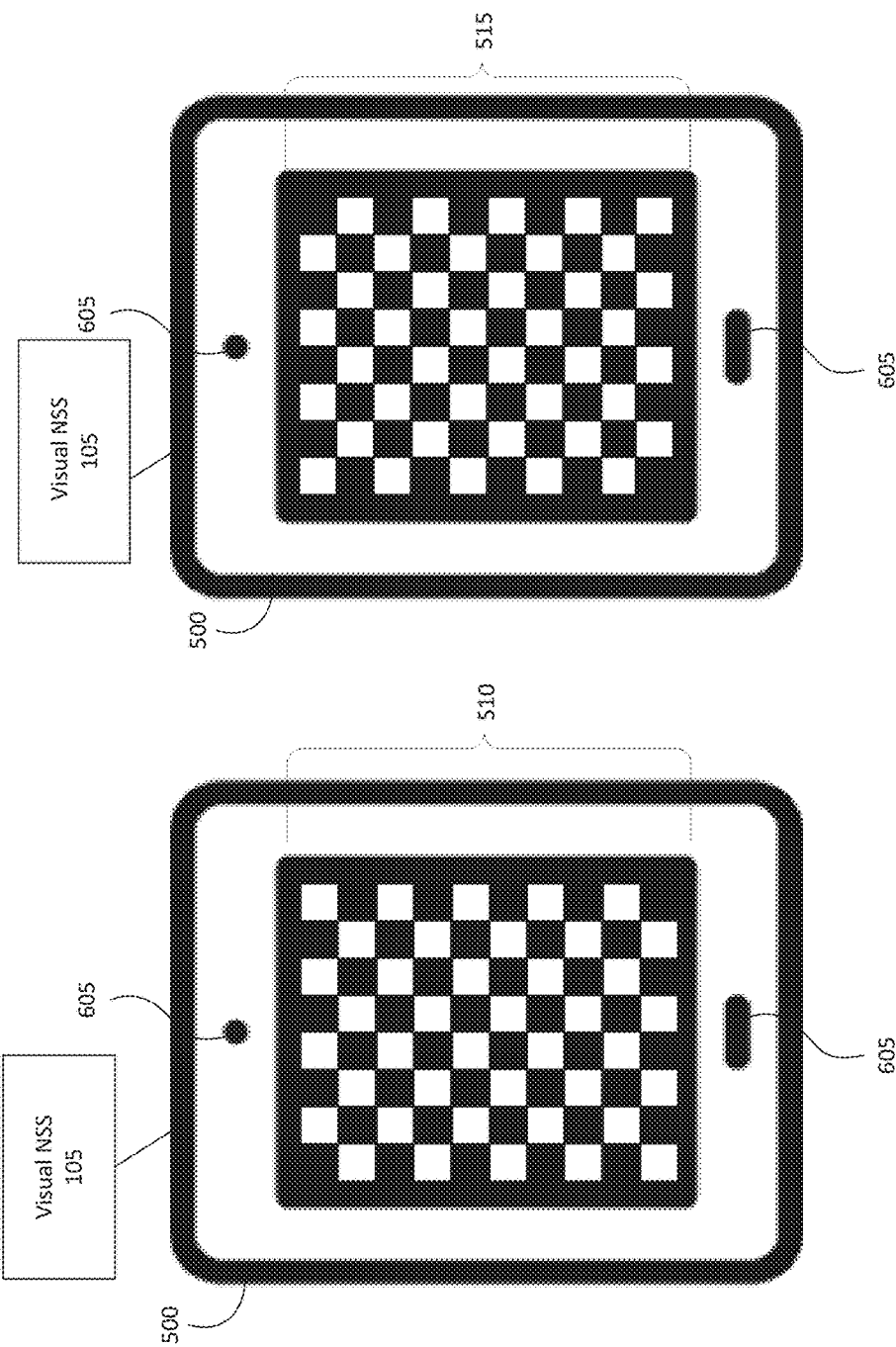

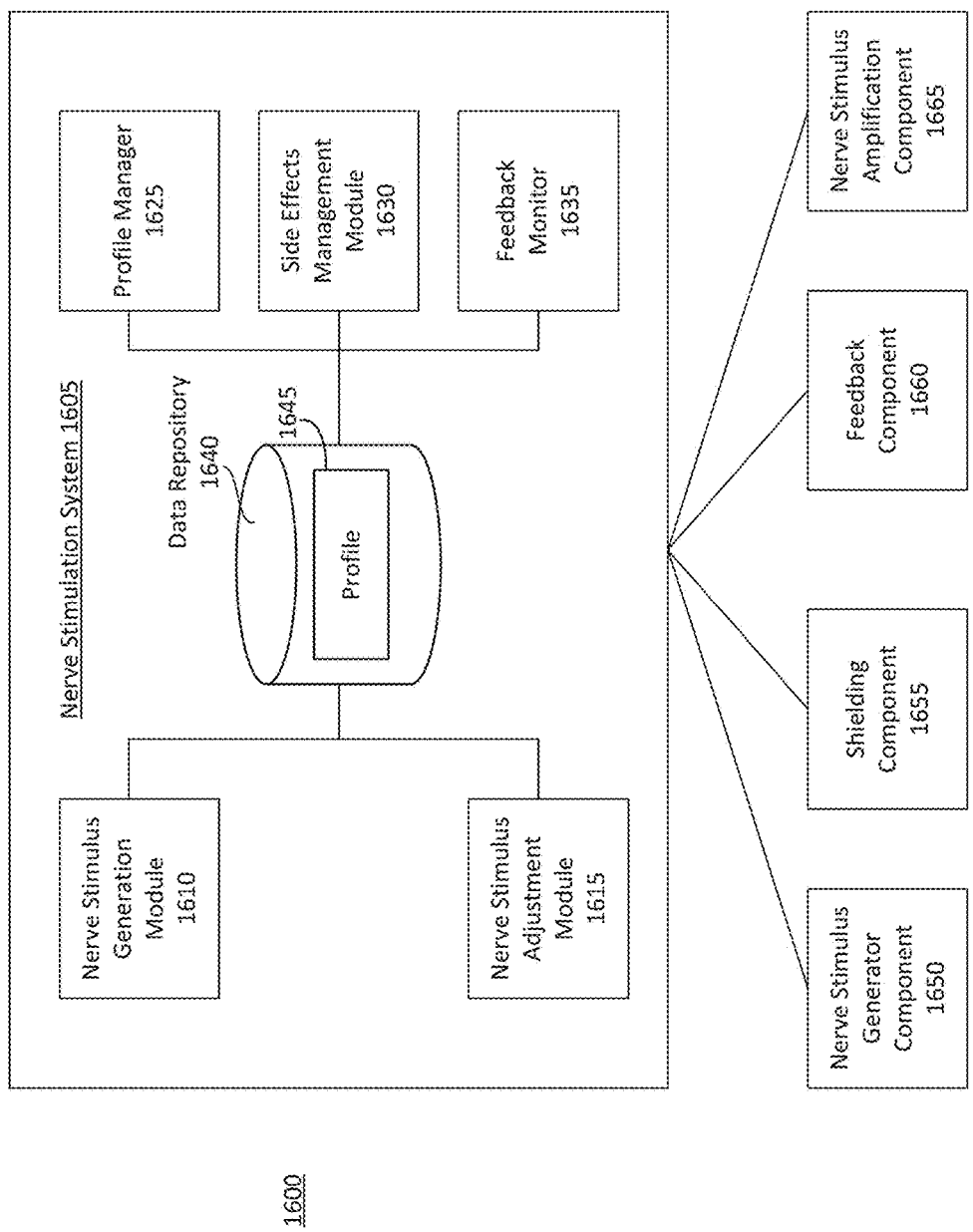

METHODS AND SYSTEMS FOR NEURAL STIMULATION VIA VISUAL, AUDITORY AND PERIPHERAL NERVE STIMULATIONS

CROSS-REFERENCE TO RELATED APPLICATIONS

The present disclosure claims the benefit of and priority to U.S. Provisional Application No. 62/423,452, titled "METHODS AND SYSTEMS FOR NEURAL STIMULATION VIA VISUAL STIMULATION," filed Nov. 17, 2016, U.S. Provisional Application No. 62/431,698, titled "METHODS AND SYSTEMS FOR NEURAL STIMULATION VIA VISUAL STIMULATION," filed Dec. 8, 2016, U.S. Provisional Application No. 62/423,569, titled "METHODS AND SYSTEMS FOR NEURAL STIMULATION VIA AUDITORY STIMULATION," filed Nov. 17, 2016, U.S. Provisional Application No. 62/431,702, titled "METHODS AND SYSTEMS FOR NEURAL STIMULATION VIA AUDITORY STIMULATION," filed Dec. 8, 2016, U.S. Provisional Application No. 62/423,517, titled "METHODS AND SYSTEMS FOR NEURAL STIMULATION VIA PERIPHERAL NERVE STIMULATION," filed Nov. 17, 2016. U.S. Provisional Application No. 62/431,720, titled "METHODS AND SYSTEMS FOR NEURAL STIMULATION VIA PERIPHERAL NERVE STIMULATION," filed Dec. 8, 2016, U.S. Provisional Application No. 62/423,598, titled "METHODS AND SYSTEMS FOR NEURAL STIMULATION VIA VISUAL AND AUDITORY STIMULATIONS," filed Nov. 17, 2016, U.S. Provisional Application No. 62/431,725, titled "METHODS AND SYSTEMS FOR NEURAL STIMULATION VIA VISUAL AND AUDITORY STIMULATIONS." filed Dec. 8, 2016. U.S. Provisional Application No. 62/423,557, titled "METHODS AND SYSTEMS OF SENSING FOR NEURAL STIMULATION." filed Nov. 17, 2016, U.S. Provisional Application No. 62/423,536, titled "SYSTEMS AND METHODS FOR PROVIDING ASSESSMENTS FOR NEURAL STIMULATION," filed Nov. 17, 2016, and U.S. Provisional Application No. 62/423,532, titled "METHODS AND SYSTEMS OF DOSING FOR NEURAL STIMULATION," filed Nov. 17, 2016, the entire disclosures of which are incorporated herein in their entireties for any and all purposes.

FIELD OF THE DISCLOSURE

This disclosure relates generally to methods and systems for neural stimulation. In particular, the methods and system of the present disclosure can provide stimulation signals, including visual, auditory and peripheral nerve stimulation signals, to induce synchronized neural oscillations in the brain of a subject.

BACKGROUND

Neural oscillation occurs in humans or animals and includes rhythmic or repetitive neural activity in the central nervous system. Neural tissue can generate oscillatory activity by mechanisms within individual neurons or by interactions between neurons. Oscillations can appear as either oscillations in membrane potential or as rhythmic patterns of action potentials, which can produce oscillatory activation of post-synaptic neurons. Synchronized activity of a group of neurons can give rise to macroscopic oscillations, which can be observed by electroencephalography ("EEG"). Neural oscillations can be characterized by their frequency, amplitude and phase. Neural oscillations can give rise to electrical impulses that form a brainwave. These signal properties can be observed from neural recordings using time-frequency analysis.

BRIEF SUMMARY OF THE DISCLOSURE

Systems and methods of the present disclosure are directed to neural stimulation via visual stimulation. Visual stimulation, including visual signals, can affect frequencies of neural oscillations. The visual stimulation can elicit brainwave effects or stimulation via modulated visual input. The visual stimulation can adjust, control or otherwise manage the frequency of the neural oscillations to provide beneficial effects to one or more cognitive states or cognitive functions of the brain or the immune system, while mitigating or preventing adverse consequences on a cognitive state or cognitive function. For example, systems and methods of the present technology can treat, prevent, protect against or otherwise affect Alzheimer's Disease.

External signals, such as light pulses, can be observed or perceived by the brain. The brain can observe or perceive the light pulses via the process of transduction in which specialized light sensing cells receive the light pulse and conduct electrons or information to the brain via optical nerves. The brain, in response to observing or perceiving the light pulses, can adjust, manage, or control the frequency of neural oscillations. This stimulation can result in repeated activation of portions of the brain which are known to process input, such as the visual cortex. For example, light pulses generated at predetermined frequency and perceived by ocular means via a direct visual field or a peripheral visual field can trigger neural activity in the brain to cause a predetermined or resulting frequency of neural oscillations. The frequency of neural oscillations can be affected by or correspond to the frequency of light pulses. Thus, systems and methods of the present disclosure can provide brainwave entrainment (or neural entrainment) using external visual stimulus such as light pulses emitted at a predetermined frequency to synchronize electrical activity among groups of neurons based on the frequency of light pulses. Brain entrainment (or neural entrainment) can be observed based on the aggregate frequency of oscillations produced by the synchronous electrical activity in ensembles of cortical neurons.

At least one aspect is directed to a system for neural stimulation via visual stimulation. The system can include or refer to a neural stimulation system or a visual neural stimulation system. The neural stimulation system can include, interface with, or otherwise communicate with a light generation module, light adjustment module, unwanted frequency filtering module, profile manager, side effects management module, or feedback monitor. The neural stimulation system can include, interface with, or otherwise communicate with a visual signaling component, filtering component, or feedback component.

At least one aspect is directed to a method of neural stimulation via visual stimulation. The method can include a neural stimulation system identifying a visual signal to provide. The neural stimulation system can generate and transmit the identified visual signal. The neural stimulation system can receive or determine feedback associated with neural activity, physiological activity, environmental parameters, or device parameters. The neural stimulation system can manage, control, or adjust the visual signal based on the feedback.

Systems and methods of the present disclosure are directed to neural stimulation via auditory stimulation. For example, systems and methods of the present disclosure can affect frequencies of neural oscillations using auditory stimulation. The auditory stimulation can elicit brainwave effects or stimulation via modulated auditory input. The auditory stimulation can adjust, control or otherwise manage the frequency of the neural oscillations to provide beneficial effects to one or more cognitive states or cognitive functions of the brain or the immune system, while mitigating or preventing adverse consequences on a cognitive state or cognitive function. For example, systems and methods of the present technology can treat, prevent, protect against or otherwise affect Alzheimer's Disease.

External signals, such as audio signals, can be observed or perceived by the brain. The brain can observe or perceive the audio signals via the process of transduction in which specialized acoustic sensing cells receive the audio signals and conduct electrons or information to the brain via cochlear cells or nerves. The brain, in response to perceiving the audio signals, can adjust, manage, or control the frequency of neural oscillations. This stimulation can result in repeated activation of portions of the brain which are known to process input, such as the auditory cortex. For example, audio signals having a predetermined modulation frequency and perceived by the auditory cortex via cochlear means can trigger neural activity in the brain to cause a predetermined or resulting frequency of neural oscillations. The frequency of neural oscillations can be affected by or correspond to the modulation frequency of the audio signals. Thus, systems and methods of the present disclosure can perform neural stimulation via auditory stimulation. Systems and methods of the present disclosure can provide brainwave entrainment (also referred to as neural entrainment or brain entrainment) using external auditory stimulus such as audio signals forming acoustic pulses emitted at a predetermined modulation frequency to synchronize electrical activity among groups of neurons based on the modulation frequency of the audio signals. Brainwave entrainment can be observed based on the aggregate frequency of oscillations produced by the synchronous electrical activity in ensembles of cortical neurons which the acoustic pulses can adjust to synchronize with frequency of the acoustic pulses.

At least one aspect is directed to a system for neural stimulation via auditory stimulation. The system can include or refer to an neural stimulation system. The neural stimulation system can include, interface with, or otherwise communicate with an audio generation module, audio adjustment module, unwanted frequency filtering module, profile manager, side effects management module, or feedback monitor. The neural stimulation system can include, interface with, or otherwise communicate with an audio signaling component, filtering component, or feedback component.

At least one aspect is directed to a method of performing neural stimulation via auditory stimulation. The method can include a neural stimulation system identifying an audio signal to provide. The neural stimulation system can generate and transmit the identified audio signal. The neural stimulation system can receive or determine feedback associated with neural activity, physiological activity, environmental parameters, or device parameters. The neural stimulation system can manage, control, or adjust the audio signal based on the feedback.

Systems and methods of the present disclosure are directed to neural stimulation via peripheral nerve stimulation. Peripheral nerve stimulation can include stimulation of nerves of the peripheral nerve system. Peripheral nerve stimulation can include stimulation of nerves that are peripheral to or remote from the brain. Peripheral nerve stimulation can include stimulation of nerves which may be part of, associated with, or connected to the spinal cord. The peripheral nerve stimulation can adjust, control or otherwise manage the frequency of the neural oscillations to provide beneficial effects to one or more cognitive states or cognitive functions of the brain, while mitigating or preventing adverse consequences on a cognitive state or cognitive function. For example, systems and methods of the present technology can treat, prevent, protect against or otherwise affect Alzheimer's disease.

Peripheral nerve stimulation can include controlled delivery of an electric current (e.g., a discharge of an electric current) to peripheral portions of the body through the skin (e.g., transcutaneous electrical nerve stimulation, "TENS"), which can cause or induce electrical activity in targeted nerves of the peripheral nervous system, such as sensory nerves. In response, the sensory nerves and the peripheral nervous system transmit signals to the central nervous system and the brain. The brain, in response to the peripheral nerve stimulation, can adjust, manage, or control the frequency of neural oscillations. For example, peripheral nerve stimulations having a predetermined frequency (e.g., a frequency of the underlying electric current, or a modulation frequency at which an amplitude of the current is modulated) can trigger neural activity in the brain to cause a predetermined or desired frequency of neural oscillations. The frequency of neural oscillations can be based on or correspond to the frequency of the peripheral nerve stimulations. Thus, systems and methods of the present disclosure can cause or induce neural oscillations, which may be associated with brainwave entrainment (also referred to as neural entrainment or brain entrainment), using peripheral nerve stimulation, such as electrical currents applied to or across the peripheral nervous system, at a predetermined frequency, or based on feedback, to synchronize electrical activity among groups of neurons based on the frequency of the stimulation. Brainwave entrainment can be observed based on the aggregate frequency of oscillations produced by the synchronous electrical activity in ensembles of cortical neurons, and the peripheral nerve stimulation pulses can be adjusted in frequency to synchronize with the oscillations.

At least one aspect is directed to a system for inducing neural oscillations via peripheral nerve stimulation. The system can include or refer to a peripheral nerve stimulation system (e.g., peripheral nerve stimulation neural stimulation system). The peripheral nerve stimulation system can include, interface with, or otherwise communicate with a nerve stimulus generation module, nerve stimulus adjustment module, side effects management module, or feedback monitor. The peripheral nerve stimulation system can include, interface with, or otherwise communicate with a nerve stimulus generator component, shielding component, feedback component, or nerve stimulus amplification component.

At least one aspect is directed to a method of inducing neural oscillations via peripheral nerve stimulation. The method can include a peripheral nerve stimulation system generating a control signal indicating instructions to generate a nerve stimulus. The nerve stimulation system can generate and output the nerve stimulus based on the control signal. The nerve stimulation system can receive or determine feedback associated with neural activity, physiological activity, environmental parameters, or device parameters.

The nerve stimulation system can manage, control, or modify stimulus parameters based on the feedback. The nerve stimulation system can modify the control signal based on the stimulus parameters in order to modify the nerve stimulus based on the feedback.

Systems and methods of the present disclosure are directed to neural stimulation via multiple modalities of stimulation, including, e.g., visual signals or visual stimulation and audio signals or auditory stimulation and peripheral nerve signals or peripheral nerve stimulation. The multi-modal stimuli can elicit brainwave effects or stimulation. The multi-modal stimuli can adjust, control or otherwise affect the frequency of the neural oscillations to provide beneficial effects to one or more cognitive states, cognitive functions, the immune system or inflammation, while mitigating or preventing adverse consequences on a cognitive state or cognitive function. For example, systems and methods of the present technology can treat, prevent, protect against or otherwise affect Alzheimer's Disease.

Multi-modal stimuli, such as light pulses and audio pulses, can be observed or perceived by the brain. The brain can observe or perceive the light pulses via the process of transduction in which specialized light sensing cells receive the light pulse and conduct electrons or information to the brain via optical nerves. The brain, in response to observing or perceiving the light pulses, can adjust, manage, or control the frequency of neural oscillations. This stimulation can result in repeated activation of portions of the brain which are known to process input, such as the visual cortex. For example, light pulses generated at predetermined frequency and perceived by ocular means via a direct visual field or a peripheral visual field can trigger neural activity in the brain to cause a predetermined or resulting frequency of neural oscillations.

The brain can observe or perceive the audio signals via the process of transduction in which specialized acoustic sensing cells receive the audio signals and conduct electrons or information to the brain via cochlear cells or nerves. The brain, in response to perceiving the audio signals, can adjust, manage, or control the frequency of neural oscillations. This stimulation can result in repeated activation of portions of the brain which are known to process input, such as the auditory cortex. For example, audio signals having a predetermined modulation frequency and perceived by the auditory cortex via cochlear means can trigger neural activity in the brain to cause a predetermined or resulting frequency of neural oscillations.

The frequency of neural oscillations can be affected by or correspond to the frequency of light pulses or audio pulses. Thus, systems and methods of the present disclosure can provide brainwave entrainment (or neural entrainment) using multi-modal stimuli such as light pulses and audio pulses emitted at a predetermined frequency to synchronize electrical activity among groups of neurons based on the frequency or frequencies of the multi-modal stimuli. Brain entrainment (or neural entrainment) can be observed based on the aggregate frequency of oscillations produced by the synchronous electrical activity in ensembles of cortical neurons.

At least one aspect is directed to a system for neural stimulation via at least a combination of visual stimulation and auditory stimulation and peripheral nerve stimulation. The system can include or refer to a neural stimulation system. The neural stimulation system can include, interface with, or otherwise communicate with a stimuli generation module, stimuli adjustment module, unwanted frequency filtering module, profile manager, side effects management module, or feedback monitor. The neural stimulation system can include, interface with, or otherwise communicate with a signaling component, filtering component, or feedback component.

At least one aspect is directed to a method for neural stimulation via visual stimulation and auditory stimulation. The method can include a neural stimulation system identifying a signal to provide. The neural stimulation system can generate and transmit the identified signal. The neural stimulation system can receive or determine feedback associated with neural activity, physiological activity, environmental parameters, or device parameters. The neural stimulation system can manage, control, or adjust the signal based on the feedback.

Systems and methods of the present disclosure are directed to selecting dosing parameters of stimulation signals to induce synchronized neural oscillations in the brain of a subject. Multi-modal stimuli (e.g., visual, auditory, among others) can elicit brainwave effects or stimulation. The multi-modal stimuli can adjust, control or otherwise manage the frequency of the neural oscillations to provide beneficial effects to one or more cognitive states or cognitive functions of the brain or the immune system, while mitigating or preventing adverse consequences on a cognitive state or cognitive function.

Multi-modal stimuli, such as light pulses, audio pulses, and other stimulation signals, can be observed or perceived by the brain. The brain can observe or perceive light pulses via the process of transduction in which specialized light sensing cells receive the light pulse and conduct electrons or information to the brain via optical nerves. The brain, in response to observing or perceiving the stimulation signals, can adjust, manage, or control the frequency of neural oscillations. This stimulation can result in repeated activation of portions of the brain which are known to process input, such as the visual cortex. For example, light pulses generated at predetermined frequency and perceived by ocular means via a direct visual field or a peripheral visual field can trigger neural activity in the brain to cause a predetermined or resulting frequency of neural oscillations.

The brain can observe or perceive auditory (or audio) signals via the process of transduction in which specialized acoustic sensing cells receive the audio signals and conduct electrons or information to the brain via cochlear cells or nerves. The brain, in response to perceiving the audio signals, can adjust, manage, or control the frequency of neural oscillations. This stimulation can result in repeated activation of portions of the brain which are known to process input, such as the auditory cortex. For example, audio signals having a predetermined modulation frequency and perceived by the auditory cortex via cochlear means can trigger neural activity in the brain to cause a predetermined or resulting frequency of neural oscillations. The brain also can observe or perceive various other forms of stimulation (e.g., deep-brain, olfactory, touch, etc.) via other mechanisms, which can cause neural oscillations in the brain to occur at a particular frequency, based on the stimulation signals.

The frequency of neural oscillations can be affected by or can correspond to the frequency of stimulation signals, such as light pulses or audio pulses. Thus, systems and methods of the present disclosure can provide brainwave entrainment (or neural entrainment) using multi-modal stimuli such as light pulses and audio pulses emitted at a predetermined frequency to synchronize electrical activity among groups of neurons based on the frequency or frequencies of the multi-modal stimuli. Brain entrainment (or neural entrainment)

can be observed based on the aggregate frequency of oscillations produced by the synchronous electrical activity in ensembles of cortical neurons.

The frequency of neural oscillations, as well as other factors that may be relevant to the efficacy of treatment, also can be affected by various factors that may be specific to the subject. Subjects having certain characteristics (e.g., age, gender, dominant hand, cognitive function, mental illness, etc.) may respond differently to stimulation signals based on these or other characteristics, traits or habits. In addition, other non-inherent factors, such as the stimulus method, the subject's attention level, the time of day at which the therapy is administered, and various factors related to the subject's diet (e.g., blood sugar, caffeine intake, nicotine intake, etc.), state of mind, physical and/or mental condition also may impact the efficacy of treatment. These and other factors also may impact the quality of therapy indirectly by affecting the subject's adherence to a therapy regimen and by increasing or decreasing unpleasant or undesirable side effects or otherwise rendering the therapy intolerable for the subject.

In addition to the subject-specific factors described above, other factors also may impact the efficacy of treatment for certain subjects. Parameters related to stimulus signals may increase or decrease the efficacy of therapy for certain subjects. Such parameters may generally be referred to as dosing parameters. For example, subjects may respond to therapies differently based on dosing parameters such as the modality (or the ordered combination of modalities) of deliverance for the stimulation signal, the duration of a stimulus signal, the intensity of the stimulus signal, and the brain region targeted by the stimulus signal. Monitoring conditions associated with the subject in real time (e.g., during the course of the stimulation therapy), as well as over a longer period of time (e.g., days, weeks, months, or years) can provide information that may be used to adjust a therapy regimen to make the therapy more effective and/or more tolerable for an individual subject. In some instances, the therapy also may be adjusted based in part of the subject-specific factors described above.

At least one aspect of the disclosure is directed to a system for selecting dosing parameters of stimulation signals to induce synchronized neural oscillations in the brain of the subject. The system can include or refer to a neural stimulation system. The neural stimulation system can include, interface with, or otherwise communicate with a dosing management module, unwanted frequency filtering module, profile manager, side effects management module, or feedback monitor. The neural stimulation system can include, interface with, or otherwise communicate with a signaling component, filtering component, or feedback component.

At least one aspect is directed to a method of selecting dosing parameters of stimulation signals to induce synchronized neural oscillations in the brain of the subject. The method can be implemented by a neural stimulation system that can determine personalization parameters and can identify a signal to provide. The neural stimulation system can generate and transmit the identified signal. The neural stimulation system can receive or determine feedback associated with neural activity, physiological activity, environmental parameters, or device parameters. The neural stimulation system can manage, control, or adjust the signal based on the feedback.

Systems and methods of the present disclosure are directed to providing assessments for neural stimulation on subjects in response to external stimuli. The external stimuli may adjust, control, or otherwise manage the frequency of the neural oscillations of the brain. When the neural oscillations of the brain are entrained to a particular frequency, there may be beneficial effects to the cognitive states or functions of the brain, while mitigating or preventing adverse consequence to the cognitive state or functions. To determine whether the application of the external stimuli entrains the brain of a subject to the particular frequency and affects the cognitive states or functions of the brain, cognitive assessments may be performed on the subject.

To determine select which type of external stimuli is to be applied to the nervous system of a subject, a cognitive and physiological assessment may be performed on the subject. Certain types of external stimuli may not be effective in entraining the neural oscillations of the brain to the particular frequency. For example, applying an auditory stimulus to a subject with severe hearing loss may not result in the neural oscillations of the brain to be entrained to the particular frequency, as the auditory system of the brain may not pick up the external stimuli due to hearing loss. Based on the results of the cognitive and physiological assessments, the type of external stimuli to apply to the nervous system of the subject may be identified.

By applying the external stimuli to the nervous system of the subject, neural oscillations may be induced in the brain of the subject. The external stimuli may be delivered to the nervous system of the subject via the visual system of the subject using visual stimuli, auditory system of the subject using auditory stimuli, or peripheral nerve stimuli. The neural oscillations of the brain of the subject may be monitored using brain wave sensors, electroencephalography (EEG) devices, electrooculography (EOG) devices, and magnetoencephalography (MEG) devices. Various other signs and indications (e.g., attentiveness, physiology, etc.) from the subject may also be monitored. After having applied the external stimuli to the nervous system of the subject, additional cognitive and physiological assessments may be repeatedly performed over time to determine whether the external stimuli were effective in entraining the brain of the subject to the particular frequency and in improving the cognitive states or functions of the brain.

At least one aspect is directed to a system for providing assessments for neural stimulation on a subject in response to external stimulation. The system may include an assessment administration module, a subject assessment monitor, a subject physiological monitor, a stimulus generator module, a neural oscillation module, an assessment application device, a stimulus output device, and a measurement device. The assessment administration module can send a control signal to the assessment application device. The control signal can specify a type of assessment, a time duration of assessment, and/or one or more characteristics or parameters (for example, intensity, color, pulse frequency, signal frequency, etc.) of stimulus of the assessment. Using the control signal, the assessment application device can administer the assessment to a subject. The subject assessment monitor can, via one or more of the measurement device, measure a task response of the subject to the administered assessment. The subject physiological monitor can, via one or more of the measurement device, measure a physiological response of the subject, while the assessment is administered. The stimulus generation device can send a control signal to the stimulus output device to apply the stimulus to the subject. The neural oscillation monitor can, via the one or more of measurement device, measure a neural response of the subject to the stimulus. Using feedback data from the subject assessment monitor, the subject physiological monitor, and/or the neural oscillation monitor, the assessment administration module can modify the control signal sent to the assessment application device and modify the assessment administered to the subject. Using feedback data from the subject assessment monitor, the subject physiological monitor, and/or the neural oscillation monitor, the stimulus generator module can modify the control signal sent to the stimulus output device and can modify the stimulus applied to the subject.

At least one aspect is directed to a method of providing assessments for neural stimulation on a subject in response to stimulation. A cognitive assessment system can send a control signal to the assessment application device. The control signal can specify a type of assessment, a time duration of assessment, and/or an intensity of stimulus of the assessment. Using the control signal, the cognitive assessment system can administer the assessment to a subject. The cognitive assessment system can, via the measurement device, measure a task response of the subject to the administered assessment. The cognitive assessment system can, via the measurement device, measure a physiological response of the subject, while the assessment is administered. The cognitive assessment system can send a control signal to the stimulus output device to apply the stimulus to the subject. The cognitive assessment system can, via the measurement device, measure a neural response of the subject to the stimulus. Using feedback data, the cognitive assessment system can modify the control signal sent to the assessment application device and modify the assessment administered to the subject. Using feedback data, the cognitive assessment system can modify the control signal sent to the stimulus output device and can modify the stimulus applied to the subject.

Systems and methods of the present disclosure are directed to stimulation sensing. An external stimulus may adjust, control, or otherwise manage the frequency of the neural oscillations of the brain. When the neural oscillations of the brain are entrained to a particular frequency, there may be beneficial effects to the cognitive states or functions of the brain, while mitigating or preventing adverse consequence to the cognitive state or functions. To ensure that the neural oscillations of the brain are entrained to the specific frequency, the external stimuli may be adjusted, modified, or changed based on measurements of the neural oscillations of the brain as well as other physiological traits of the subject.

To induce neural oscillations in a brain of a subject, external stimuli may be applied to the nervous system of a subject. The external stimuli may be delivered to the nervous system of the subject via the visual system of the subject using visual stimuli, auditory system of the subject using auditory stimuli, or peripheral nerve stimuli. The neural oscillations of the brain of the subject may be monitored using electroencephalography) (EEG) and magnetoencephalography (MEG) readings. Various other signs and indications (e.g., attentiveness, physiology, etc.) from the subject may also be monitored, while applying the external stimuli. These measurements may then be used to adjust, modify, or change the external stimuli to ensure that the neural oscillations are entrained to the specified frequency. The measurements may also be used to determine whether the subject is receiving the external stimuli.

At least one aspect is directed to a system for stimulation sensing. The system may include a neural oscillation monitor, a subject attentiveness monitor, a subject physiological monitor, a stimulus generator module, a stimulus control module, a simulated response module, a stimulus generation policy, a sensor log, a multi-stimuli synchronization module, one or more stimulus output devices, and one or more measurement devices. The stimulus generator module can generate a stimulus control signal for the one or more stimulus output devices to convert to an external stimulus to apply to a subject. The stimulus control module can adjust the stimulus control signal based on the stimulus generation policy. The simulated response module can determine a simulated response to the external stimulus. The neural oscillation monitor can use the one or more measurement devices to monitor neural oscillations of the subject. The subject attentiveness monitor can use the one or more measurement devices to monitor whether the subject is attentive while the external stimulus is applied. The subject physiological monitor can use the one or more measurement devices to monitor physiological status of the subject while the external stimulus is applied. The sensor log can store the neural oscillations, attentiveness, and physiological status of the subject.

At least one aspect is directed to a method of stimulation sensing. The neural stimulation sensing system can generate a stimulus control signal for a stimulus output device to convert to an external stimulus to apply to a subject. The neural stimulation sensing system can adjust the stimulus control signal based on a stimulus generation policy. The neural stimulation sensing system can determine a simulated response to the external stimulus. The neural stimulation sensing system can use the one or more measurement devices to monitor neural oscillations of the subject, to monitor whether the subject is attentive while the external stimulus is applied, and to monitor physiological status of the subject while the external stimulus is applied. The neural stimulation sensing system can store the neural oscillations, attentiveness, and physiological status of the subject.

At least one aspect is directed to a system for sensing neural oscillations induced by external stimulus. The neural stimulation sensing system can include a stimulus generator module, a stimulus output device, a first measurement device, a second measurement device, a simulated response module, a neural oscillation monitor, and a stimulus control module. The stimulus generator module can generate a stimulus control signal. The stimulus output device can convert the stimulus control signal to an external stimulus and apply the external stimulus to a subject. The first measurement device can measure the outputted external stimulus from the stimulus output device and ambient noise, and relay the measurement to the simulated response module. The simulated response module can generate a simulated neural oscillation of the subject based on the outputted external stimulus and the ambient noise, and can relay the simulated neural oscillation to the neural oscillation monitor. The second measurement device can measure neural oscillations of the subject and relay the measurement to the neural oscillation monitor. The neural oscillation monitor can receive the measurements from the second measurement device and the simulated neural oscillations from the simulated response module. The neural oscillation monitor can identify an artefact from the received measurements and the simulated neural oscillations, and relay to the stimulus control module. The stimulus control module can determine an adjustment to the external stimulus based on the artefact identified by the neural oscillation monitor and the stimulus generation policy. The stimulus generator module can adjust the stimulus control signal based on the adjustment determined by the stimulus control module.

At least one aspect is directed to a method of sensing neural oscillations induced by external stimulus. A neural stimulation sensing system can generate a stimulus control signal. The neural stimulation sensing system can convert the stimulus control signal to an external stimulus and apply the external stimulus to a subject. The neural stimulation sensing system can measure the outputted external stimulus and ambient noise. The neural stimulation sensing system can generate a simulated neural oscillation of the subject based on the outputted external stimulus and the ambient noise. The neural stimulation sensing system can measure neural oscillations of the subject. The neural stimulation sensing system can identify an artefact from the received measurements and the simulated neural oscillations. The neural stimulation sensing system can determine an adjustment to the external stimulus based on the artefact and a stimulus generation policy. The neural stimulation sensing system can adjust the stimulus control signal based on the determined adjustment.

At least one aspect is directed to a system for monitoring subject attentiveness during application of an external stimulus to induce neural oscillation. The neural stimulation sensing system can include a stimulus generator module, a stimulus output device, a first measurement device, a second measurement device, a subject attentiveness monitor, a stimulus control module. The stimulus generator module can generate a stimulus control signal. The stimulus output device can convert the stimulus control signal to an external stimulus and apply the external stimulus to a subject. The first measurement device can measure the outputted external stimulus from the stimulus output device and ambient noise, and relay the measurement to the subject attentiveness monitor. The second measurement device can monitor the subject and relay the measurement to the subject attentiveness monitor. The subject attentiveness monitor can determine whether the subject is attentive based on the monitoring of the subject and relay the determination to the stimulus control module. The stimulus control module can determine an adjustment to the external stimulus based on the determination of the subject attentiveness monitor and the stimulus generation policy. The stimulus generator module can adjust the stimulus control signal based on the adjustment determined by the stimulus control module.

At least one aspect is directed to a method of monitoring subject attentiveness during application of an external stimulus to induce neural oscillation. A neural stimulation sensing system can generate a stimulus control signal. The neural stimulation sensing system can convert the stimulus control signal to an external stimulus and apply the external stimulus to a subject. The neural stimulation sensing system can measure the outputted external stimulus from the stimulus output device and ambient noise. The neural stimulation sensing system can monitor the subject. The neural stimulation system can determine whether the subject is attentive based on the monitoring of the subject. The neural stimulation system can determine an adjustment to the external stimulus based on the determination and a stimulus generation policy. The neural stimulation system can adjust the stimulus control signal based on the determined adjustment.

At least one aspect is directed to a system for monitoring subject physiological status during application of an external stimulus to induce neural oscillation. The neural stimulation sensing system can include a stimulus generator module, a stimulus output device, a first measurement device, a second measurement device, a subject physiological monitor, a stimulus control module. The stimulus generator module can generate a stimulus control signal. The stimulus output device can convert the stimulus control signal to an external stimulus and apply the external stimulus to a subject. The first measurement device can measure the outputted external stimulus from the stimulus output device and ambient noise, and relay the measurement to the subject attentiveness monitor. The second measurement device can monitor the subject and relay the measurement to the subject attentiveness monitor. The subject physiological monitor can identify a physiological status of the subject based on the monitoring of the subject and relay the determination to the stimulus control module. The stimulus control module can determine an adjustment to the external stimulus based on the physiological status identified by the subject physiological monitor and the stimulus generation policy. The stimulus generator module can adjust the stimulus control signal based on the adjustment determined by the stimulus control module.

At least one aspect is directed to a method of monitoring subject physiological status during application of an external stimulus to induce neural oscillation. Neural stimulation sensing system can generate a stimulus control signal. The neural stimulation sensing system can convert the stimulus control signal to an external stimulus and apply the external stimulus to a subject. The neural stimulation sensing system can measure the outputted external stimulus from the stimulus output device and ambient noise. The neural stimulation sensing system can monitor the subject. The neural stimulation system can identify a physiological status of the subject based on the monitoring of the subject. The neural stimulation system can determine an adjustment to the external stimulus based on the identified physiological status and a stimulus generation policy. The neural stimulation system can adjust the stimulus control signal based on the determined adjustment.

At least one aspect is directed to a system for synchronizing multiple stimuli to induce neural oscillation. The neural stimulation sensing system can include a stimulus generator module, a stimulus output device, a first measurement device, a second measurement device, a simulated response module, a neural oscillation monitor, a stimulus control module, and a multi-stimuli synchronization module. The stimulus generator module can generate a plurality of stimuli waveforms. The stimulus output device can convert the plurality of stimuli waveforms to a plurality of external stimuli and apply the plurality of external stimuli to a subject. The first measurement device can measure the outputted plurality of external stimuli from the stimulus output device and ambient noise, and relay the measurement to the simulated response module. The simulated response module can generate a simulated neural oscillation of the subject based on the outputted plurality of external stimuli and the ambient noise, and can relay the simulated neural oscillation to the neural oscillation monitor. The second measurement device can measure neural oscillations of the subject and relay the measurement to the neural oscillation monitor. The neural oscillation monitor can receive the measurements from the second measurement device and the simulated neural oscillations from the simulated response module. The neural oscillation monitor can identify an artefact from the received measurements and the simulated neural oscillations, and relay to the multi-stimuli synchronization module. The multi-stimuli synchronization module can identify phase differences between the neural oscillation measurements. The stimulus control module can determine an adjustment to the external stimuli based on the artefact identified by the neural oscillation monitor, the phase differences between the neural oscillation measurements, and the stimulus generation policy. The stimulus generator module can adjust the stimuli waveform based on the adjustment determined by the stimulus control module.

At least one aspect is directed to a method of synchronizing multiple stimuli to induce neural oscillation. A neural stimulation sensing system can generate a plurality of stimulus control signals. The neural stimulation sensing system can convert the plurality of stimulus control signals to a plurality of external stimuli and apply the plurality of external stimuli to a subject. The neural stimulation sensing system can measure the outputted external stimulus and ambient noise. The neural stimulation sensing system can generate a simulated neural oscillation of the subject based on the outputted plurality of external stimuli and the ambient noise. The neural stimulation sensing system can measure neural oscillations of the subject. The neural stimulation sensing system can identify an artefact from the received measurements and the simulated neural oscillations. The neural stimulation sensing system can identify phase differences between the neural oscillation measurements. The neural stimulation sensing system can determine an adjustment to the external stimulus based on the artefact, the identified phase differences, and a stimulus generation policy. The neural stimulation sensing system can adjust the stimulus control signal based on the determined adjustment.

At least one aspect of the disclosure is directed to a system for treating cognitive dysfunction in a subject in need thereof. The system may include eyeglasses. The eyeglasses may be formed from a wireframe. The system may include a photodiode. The photodiode may be coupled to the wireframe and positioned to detect an ambient light level between the wireframe and a fovea of a subject. The system may include a plurality of light sources. The plurality of light sources may be coupled to the wireframe and positioned to direct light towards the fovea of the subject. The system may include a profile manager executed by a neural stimulation system comprising a processor. The profile manager may retrieve, based on a lookup, a profile corresponding to the identifier of the subject. The profile manager may select, based on the profile, a light pattern having a fixed parameter and a variable parameter. The system may include a light adjustment module, executed by the neural stimulation system. The light adjustment module may set a value of the variable parameter based on applying a policy associated with the profile using the ambient light level. The system may include a light generation module, executed by the neural stimulation system. The light generation module may construct an output signal based on the light pattern, the fixed parameter and the variable parameter that is set by the ambient level. The light generation module, executed by the neural stimulation system, may provide the output signal to the plurality of light sources to direct light towards the fovea of the subject in accordance with the constructed output signal.

In some embodiments, the system can administer a pharmacological agent to the subject prior to, simultaneous to, or subsequent to administration of the stimulus. The pharmacological agent can be a monoclonal antibody. The monoclonal antibody can be aducanumab.

In some embodiments, the method includes administering a pharmacological agent to the subject prior to, simultaneous to, or subsequent to administration of the stimulus. The pharmacological agent can be a monoclonal antibody. The monoclonal antibody can be aducanumab.

In some embodiments, the fixed parameter may correspond to a stimulation frequency, and the variable parameter may correspond to an intensity level. In some embodiments, at least one of the plurality of light sources may be positioned to direct the light towards within 15 degrees of the fovea of the subject. In some embodiments, a feedback monitor may track, via a feedback sensor, movement of the fovea of the subject. In some embodiments, the light adjustment module may adjust, responsive to the movement of the fovea of the subject, at least one of the plurality of light sources to direct the light towards within 15 degrees of the fovea of the subject.

In some embodiments, a feedback monitor may measure physiological conditions using a feedback sensor. In some embodiments, a side effects management module may receive the measured physiological conditions from the feedback monitor. The side effects management module may generate an instruction to adjust the variable parameter to a second value. The side effects management module may transmit the instruction to the light adjustment module. In some embodiments, the light adjustment module may receive the instruction from the side effects management module. The light adjustment module may determine a second value for the variable parameter of the light pattern.

In some embodiments, a feedback monitor may measure a heart rate of the subject using a pulse rate monitor. In some embodiments, a side effects management module may receive the heart rate measured by the feedback monitor. The side effects management module may compare the heart rate with a threshold. The side effects management module may determine, based on the comparison, that the heart rate exceeds the threshold. The side effects management module may adjust, responsive to the determination that the heart rate exceeds the threshold, the variable parameter to a second value to lower an intensity of the light. In some embodiments, the light adjustment module may receive the second value of the variable parameter. In some embodiments, the light adjustment module may provide a second output signal to cause the plurality of light sources to direct light at a lower intensity corresponding to the second value.

In some embodiments, a feedback monitor may measure a heart rate of the subject using a pulse rate monitor. The feedback monitor may measure brain wave activity using a brain wave sensor. In some embodiments, a side effects management module may receive the heart rate measured by the feedback monitor. The side effects management module may receive the brain wave activity measured by the brain wave sensor. The side effects management module may determine that the heart rate is less than a first threshold. The side effects management module may determine that the brain wave activity is less than a second threshold. The side effects management module may adjust, responsive to the determination that the heart rate is less the first threshold and the brain wave activity is less than the second threshold, the variable parameter to a second value to increase an intensity of the light. In some embodiments, the light adjustment module may receive the second value of the variable parameter. The light adjustment module may provide a second output signal to cause the plurality of light sources to direct light at an increased intensity corresponding to the second value. In some embodiments, the cognitive dysfunction may include Alzheimer's disease.

At least one aspect of the disclosure is directed to a system for treating cognitive dysfunction in a subject in need thereof. The system may include eyeglasses. The system may include a sensor. The sensor may be coupled to a portion of the eyeglasses and positioned to detect an ambient light level between the portion of the eyeglasses and a fovea of a subject. The system may include a plurality of light sources. The plurality of light sources may be coupled to the eyeglasses and positioned to direct light towards the fovea of the subject. The system may include a neural stimulation system comprising a processor. The neural stimulation system may retrieve, based on a lookup, a profile corresponding to the identifier of the subject. The neural stimulation system may select, based on the profile, a light pattern having a fixed parameter and a variable parameter. The neural stimulation system may set a value of the variable parameter based on applying a policy associated with the profile using the ambient light level. The neural stimulation system may construct an output signal based on the light pattern, the fixed parameter and the variable parameter that is set by the ambient level. The neural stimulation system may provide the output signal to the plurality of light sources to direct light towards the fovea of the subject in accordance with the constructed output signal.

In some embodiments, the system can administer a pharmacological agent to the subject prior to, simultaneous to, or subsequent to administration of the stimulus. The pharmacological agent can be a monoclonal antibody. The monoclonal antibody can be aducanumab.

In some embodiments, the fixed parameter may correspond to a stimulation frequency, and the variable parameter may correspond to an intensity level. In some embodiments, at least one of the plurality of light sources may be positioned to direct the light towards within 15 degrees of the fovea of the subject. In some embodiments, the neural stimulation system may track, via a feedback sensor, movement of the fovea of the subject. In some embodiments, the neural stimulation system may adjust, responsive to the movement of the fovea of the subject, at least one of the plurality of light sources to direct the light towards within 15 degrees of the fovea of the subject.

In some embodiments, the neural stimulation system may measure physiological conditions using a feedback sensor. In some embodiments, the neural stimulation system may receive the measured physiological conditions from the feedback monitor. In some embodiments, the neural stimulation system may generate an instruction to adjust the variable parameter to a second value. In some embodiments, the neural stimulation system may transmit the instruction to a light adjustment module. In some embodiments, the neural stimulation system may determine a second value for the variable parameter of the light pattern.

In some embodiments, the neural stimulation system may measure a heart rate of the subject using a pulse rate monitor. In some embodiments, the neural stimulation system may compare the heart rate with a threshold. In some embodiments, the neural stimulation system may determine, based on the comparison, that the heart rate exceeds the threshold. In some embodiments, the neural stimulation system may adjust, responsive to the determination that the heart rate exceeds the threshold, the variable parameter to a second value to lower an intensity of the light. In some embodiments, the neural stimulation system may provide a second output signal to cause the plurality of light sources to direct light at a lower intensity corresponding to the second value.

In some embodiments, the neural stimulation system may measure a heart rate of the subject using a pulse rate monitor. In some embodiments, the neural stimulation system may measure brain wave activity using a brain wave sensor. In some embodiments, the neural stimulation system may determine that the heart rate is less than a first threshold. In some embodiments, the neural stimulation system may determine that the brain wave activity is less than a second threshold. In some embodiments, the neural stimulation system may adjust, responsive to the determination that the heart rate is less the first threshold and the brain wave activity is less than the second threshold, the variable parameter to a second value to increase an intensity of the light. In some embodiments, the neural stimulation system may provide a second output signal to cause the plurality of light sources to direct light at an increased intensity corresponding to the second value. In some embodiments, the cognitive dysfunction may include Alzheimer's disease.

At least one aspect of the disclosure is directed to a system for treating cognitive dysfunction in a subject in need thereof. The system may include eyeglasses. The system may a sensor. The sensor may be coupled to a portion of the eyeglasses and positioned to detect an ambient light level between the portion of the eyeglasses and a fovea of a subject. The system may include a plurality of light sources. A plurality of light sources may be coupled to the eyeglasses and positioned to direct light towards the fovea of the subject. The system may include one or more processors. The one or more processors may execute one or more programs to treat a subject in need of a treatment of a brain disease. The one or more programs may include instructions for conducting a therapy session. The therapy session may include identifying a profile corresponding to the identifier of the subject. The therapy session may include selecting, based on the profile, a light pattern having a fixed parameter and a variable parameter. The therapy session may include setting a value of the variable parameter based on applying a policy associated with the profile using the ambient light level. The therapy session may include constructing an output signal based on the light pattern, the fixed parameter and the variable parameter that is set by the ambient level. The therapy session may include providing the output signal to the plurality of light sources to direct light towards the fovea of the subject in accordance with the constructed output signal.

In some embodiments, the therapy session includes administering a pharmacological agent to the subject prior to, simultaneous to, or subsequent to administration of the stimulus. The pharmacological agent can be a monoclonal antibody. The monoclonal antibody can be aducanumab.

In some embodiments, the fixed parameter may correspond to a stimulation frequency, and the variable parameter may correspond to an intensity level. In some embodiments, at least one of the plurality of light sources may be positioned to direct the light towards within 15 degrees of the fovea of the subject. In some embodiments, the therapy session may include tracking, via a feedback sensor, movement of the fovea of the subject. In some embodiments, the therapy session may include adjusting, responsive to the movement of the fovea of the subject, at least one of the plurality of light sources to direct the light towards within 15 degrees of the fovea of the subject.

In some embodiments, the therapy session may include measuring physiological conditions using a feedback sensor. In some embodiments, the therapy session may include comparing the heart rate with a threshold. In some embodiments, the therapy session may include determining, based on the comparison, that the heart rate exceeds the threshold. In some embodiments, the therapy session may include adjusting, responsive to the determination that the heart rate exceeds the threshold, the variable parameter to a second value to lower an intensity of the light. In some embodiments, the therapy session may include providing a second output signal to cause the plurality of light sources to direct light at a lower intensity corresponding to the second value.

At least one aspect of the disclosure is directed to a method of treating cognitive dysfunction in a subject in need thereof. The method may include administering a stimulus to the subject using a system. The system may include eyeglasses. The eye glasses may be formed from a wireframe. The system may include a photodiode. The photodiode may be coupled to the wireframe and positioned to detect an ambient light level between the wireframe and a fovea of a subject. The system may include a plurality of light sources. The plurality of light sources may be coupled to the wireframe and positioned to direct light towards the fovea of the subject. The system may include an input device. The input device may receive an identifier of the subject. The system may include a profile manager executed by a neural stimulation system comprising a processor. The profile manager may retrieve, based on a lookup, a profile corresponding to the identifier of the subject. The profile manager may select, based on the profile, a light pattern having a fixed parameter and a variable parameter. The system may include a light adjustment module executed by the neural stimulation system. The light adjustment module may set a value of the variable parameter based on applying a policy associated with the profile using the ambient light level. The system may include a light generation module executed by the neural stimulation system. The light generation module may construct an output signal based on the light pattern, the fixed parameter and the variable parameter that is set by the ambient level. The light generation module may provide the output signal to the plurality of light sources to direct light towards the fovea of the subject in accordance with the constructed output signal. In some embodiments, the cognitive dysfunction may include Alzheimer's disease.

In some embodiments, the method includes administering a pharmacological agent to the subject prior to, simultaneous to, or subsequent to administration of the stimulus. The pharmacological agent can be a monoclonal antibody. The monoclonal antibody can be aducanumab.

At least one aspect of the disclosure is directed to a system for treating cognitive dysfunction in a subject in need thereof. The system may include a feedback monitor executed by at least one processor of a neural stimulation system. The feedback monitor may receive an indication of an ambient audio signal detected by a microphone. The system may include a profile manager executed by the neural stimulation system. The profile manager may receive an identifier of the subject and select, from a profile corresponding to the identifier, an audio signal comprising a fixed parameter and a variable parameter. The system may include an audio generation module executed by the neural stimulation system. The audio generation module may set the variable parameter to a first value based on the variable parameter. The system may include an audio generation module executed by the neural stimulation system. The audio generation module may generate an output signal based on the fixed parameter and the first value of the variable parameter, and provide the output signal to the speaker to cause the speaker to provide the sound to the subject. The feedback monitor may measure, via a feedback sensor, a physiological condition of the subject during a first time interval. The system may include an audio adjustment module executed by the neural stimulation system. The audio adjustment module may adjust the variable parameter to a second value. The audio generation module may generate a second output signal based on the fixed parameter and the second value of the variable parameter, and provide the output signal to the speaker to cause the speaker to provide modified sound to the subject.

In some embodiments, the system can administer a pharmacological agent to the subject prior to, simultaneous to, or subsequent to administration of the stimulus. The pharmacological agent can be a monoclonal antibody. The monoclonal antibody can be aducanumab.

In some embodiments, the neural stimulation system may determine, based on the physiological condition measured by the feedback monitor during a second time interval subsequent to the first time interval, a level of attention. In some embodiments, the neural stimulation system may compare the level of attention with a threshold. In some embodiments, the neural stimulation system may determine, based on the comparison, that the level of attention does not satisfy the threshold. In some embodiments, the neural stimulation system may adjust, responsive to the level attention not satisfying the threshold, the variable parameter to a third value greater than the second value.

In some embodiments, the neural stimulation system may determine a second physiological condition measured by the feedback monitor during a second time interval. In some embodiments, the neural stimulation system may adjust the variable parameter to a third value less than the second value. In some embodiments, the neural stimulation system may determine a second physiological condition measured by the feedback monitor during a second time interval. In some embodiments, the neural stimulation system may overlay an audio signal on the output signal based on the second physiological condition.

In some embodiments, the neural stimulation system may detect a second physiological condition measured by the feedback monitor during a second time interval. In some embodiments, the neural stimulation system may overlay, responsive to the detection, an audio signal on the output signal based on the second physiological condition. The audio signal may indicate a duration remaining in a therapy session for treating the cognitive dysfunction.

In some embodiments, the neural stimulation system may detect a second physiological condition measured by the feedback monitor during a second time interval. In some embodiments, the neural stimulation system may select, using a policy, a prerecorded audio signal based on the second physiological condition. In some embodiments, the neural stimulation system may overlay, responsive to the detection, the prerecorded audio signal on the output signal based on the second physiological condition. The audio signal may indicate a duration remaining in a therapy session for treating the cognitive dysfunction. In some embodiments, the cognitive dysfunction may include Alzheimer's disease.

At least one aspect of the disclosure is directed to a system for treating cognitive dysfunction in a subject in need thereof. The system may include a microphone, a speaker, a feedback sensor, and a neural stimulation system. The neural stimulation system may include at least one processors and may be coupled to the microphone and the speaker. The neural stimulation system may receive an indication of an ambient audio signal detected by a microphone. The neural stimulation system may receive an identifier of the subject. The neural stimulation system may select, from a profile corresponding to the identifier, an audio signal comprising a fixed parameter and a variable parameter. The neural stimulation system may the variable parameter to a first value based on the variable parameter. The neural stimulation system may generate an output signal based on the fixed parameter and the first value of the variable parameter. The neural stimulation system may provide the output signal to the speaker to cause the speaker to provide the sound to the subject. The neural stimulation system may measure, via the feedback sensor, a physiological condition of the subject during a first time interval. The neural stimulation system may adjust the variable parameter to a second value. The neural stimulation system may generate a second output signal based on the fixed parameter and the second value of the variable parameter, and may provide the output signal to the speaker to cause the speaker to provide modified sound to the subject.

In some embodiments, the system can administer a pharmacological agent to the subject prior to, simultaneous to, or subsequent to administration of the stimulus. The pharmacological agent can be a monoclonal antibody. The monoclonal antibody can be aducanumab.

In some embodiments, the neural stimulation system may determine, based on the physiological condition measured by the feedback monitor during a second time interval subsequent to the first time interval, a level of attention. In some embodiments, the neural stimulation system may compare the level of attention with a threshold. In some embodiments, the neural stimulation system may determine, based on the comparison, that the level of attention does not satisfy the threshold. In some embodiments, the neural stimulation system may adjust, responsive to the level attention not satisfying the threshold, the variable parameter to a third value greater than the second value.

In some embodiments, the neural stimulation system may determine a second physiological condition measured by the feedback monitor during a second time interval. In some embodiments, the neural stimulation system may adjust the variable parameter to a third value less than the second value. In some embodiments, the neural stimulation system may determine a second physiological condition measured by the feedback monitor during a second time interval. In some embodiments, the neural stimulation system may overlay an audio signal on the output signal based on the second physiological condition.

In some embodiments, the neural stimulation system may detect a second physiological condition measured by the feedback monitor during a second time interval. In some embodiments, the neural stimulation system may overlay, responsive to the detection, an audio signal on the output signal based on the second physiological condition. The audio signal may indicate a duration remaining in a therapy session for treating the cognitive dysfunction.

In some embodiments, the neural stimulation system may detect a second physiological condition measured by the feedback monitor during a second time interval. In some embodiments, the neural stimulation system may select, using a policy, a prerecorded audio signal based on the second physiological condition. In some embodiments, the neural stimulation system may overlay, responsive to the detection, the prerecorded audio signal on the output signal based on the second physiological condition. The audio signal may indicate a duration remaining in a therapy session for treating the cognitive dysfunction. In some embodiments, the cognitive dysfunction may include Alzheimer's disease.

At least one aspect of the disclosure is directed to a system for treating cognitive dysfunction in a subject in need thereof. The system may include a microphone, a speaker, a feedback sensor, and one or more processors. The one or more processors may execute one or more programs to treat a subject in need of a treatment of a brain disease. The one or more programs may include instructions for conducting a therapy session. The therapy session may include receiving an indication of an ambient audio signal detected by a microphone. The therapy session may include receiving an identifier of the subject. The therapy session may include selecting, from a profile corresponding to the identifier, an audio signal comprising a fixed parameter and a variable parameter. The therapy session may include providing the output signal to the speaker to cause the speaker to provide the sound to the subject. The therapy session may include measuring, via the feedback sensor, a physiological condition of the subject during a first time interval. The therapy session may include adjusting the variable parameter to a second value. The therapy session may include generating a second output signal based on the fixed parameter and the second value of the variable parameter, and providing the output signal to the speaker to cause the speaker to provide modified sound to the subject.

In some embodiments, the therapy session includes administering a pharmacological agent to the subject prior to, simultaneous to, or subsequent to administration of the stimulus. The pharmacological agent can be a monoclonal antibody. The monoclonal antibody can be aducanumab.

In some embodiments, the therapy session may include determining, based on the physiological condition measured during a second time interval subsequent to the first time interval, a level of attention. In some embodiments, the therapy session may include comparing the level of attention with a threshold. In some embodiments, the therapy session may include determining, based on the comparison, that the level of attention does not satisfy the threshold. In some embodiments, the therapy session may include adjusting, responsive to the level attention not satisfying the threshold, the variable parameter to a third value greater than the second value.

In some embodiments, the therapy session may include determining a second physiological condition measured during a second time interval. In some embodiments, the therapy session may include adjusting the variable parameter to a third value less than the second value. In some embodiments, the therapy session may include determining a second physiological condition measured during a second time interval. In some embodiments, the therapy session may include overlaying an audio signal on the output signal based on the second physiological condition.

In some embodiments, the therapy session may include detecting a second physiological condition measured during a second time interval. In some embodiments, the therapy session may include overlaying, responsive to the detection, an audio signal on the output signal based on the second physiological condition. In some embodiments, the therapy session may include detecting a second physiological condition measured during a second time interval. In some embodiments, the therapy session may include overlaying, responsive to the detection, an audio signal on the output signal based on the second physiological condition. The audio signal may indicate a duration remaining in a therapy session for treating the cognitive dysfunction. In some embodiments, the cognitive dysfunction may include Alzheimer's disease.

At least one aspect of the disclosure is directed to a method of treating cognitive dysfunction in a subject in need thereof. The method may include administering a stimulus to the subject using a system. The system may include a microphone, a speaker, a feedback sensor, and a neural stimulation system. The neural stimulation system may include at least one processors and may be coupled to the microphone and the speaker. The neural stimulation system may receive an indication of an ambient audio signal detected by a microphone. The neural stimulation system may receive an identifier of the subject. The neural stimulation system may select, from a profile corresponding to the identifier, an audio signal comprising a fixed parameter and a variable parameter. The neural stimulation system may the variable parameter to a first value based on the variable parameter. The neural stimulation system may generate an output signal based on the fixed parameter and the first value of the variable parameter. The neural stimulation system may provide the output signal to the speaker to cause the speaker to provide the sound to the subject. The neural stimulation system may measure, via the feedback sensor, a physiological condition of the subject during a first time interval. The neural stimulation system may adjust the variable parameter to a second value. The neural stimulation system may generate a second output signal based on the fixed parameter and the second value of the variable parameter, and may provide the output signal to the speaker to cause the speaker to provide modified sound to the subject. In some embodiments, the cognitive dysfunction may include Alzheimer's disease.

In some embodiments, the method includes administering a pharmacological agent to the subject prior to, simultaneous to, or subsequent to administration of the stimulus. The pharmacological agent can be a monoclonal antibody. The monoclonal antibody can be aducanumab.

At least one aspect is directed to a system for treating cognitive dysfunction in a subject in need thereof. The system may include a light source and a speaker. The system may include a visual signaling component executed by a visual neural stimulation system. The visual signaling component may provide, via the light source, visual stimulation having a first value of a first parameter. The system may include an audio signaling component executed by an auditory neural stimulation system. The audio signaling component may provide, via the speaker, audio stimulation having a second value of the second parameter. The system may include a stimuli orchestration component executed by a neural stimulation orchestration system. The stimuli orchestration component may select, for a first time interval, one of the visual stimulation or the audio stimulation to vary based on a policy. The stimuli orchestration component may select, for the first time interval, the other of the visual stimulation or the audio stimulation to keep constant based on the policy. The stimuli orchestration component may provide instructions to the visual neural stimulation system or the auditory neural stimulation system corresponding to the selected one of the visual stimulation or the audio stimulation to vary to cause the one of the visual neural stimulation system or the auditory neural stimulation system to vary the one of the visual stimulation or the audio stimulation.

In some embodiments, the system can administer a pharmacological agent to the subject prior to, simultaneous to, or subsequent to administration of the stimulus. The pharmacological agent can be a monoclonal antibody. The monoclonal antibody can be aducanumab.

In some embodiments, the neural stimulation orchestration system may select, for a second time interval subsequent to the first time interval, the other of the visual stimulation or the audio stimulation to vary based on the policy. In some embodiments, the neural stimulation orchestration system may select, for the second time interval, the other of the visual stimulation or the audio stimulation to keep constant based on the policy. In some embodiments, the neural stimulation orchestration system may provide instructions to the visual neural stimulation system or the auditory neural stimulation system corresponding to the selected one of the visual stimulation or the audio stimulation to vary during the second time interval to cause the one of the visual neural stimulation system or the auditory neural stimulation system to vary the one of the visual stimulation or the audio stimulation during the second time interval.

In some embodiments, the system may include a feedback monitor. The feedback monitor may detect a physiological condition of the subject during the first time interval. In some embodiments, the neural stimulation orchestration system may select, using the policy and based on the detected physiological condition, one of the visual stimulation or the audio stimulation to vary during the first time interval.

In some embodiments, the system may include a feedback monitor. The feedback monitor may detect a physiological condition of the subject during the first time interval. In some embodiments, the neural stimulation orchestration system may select, responsive to detecting the physiological condition, the other of the visual stimulation or the audio stimulation to vary during a second time interval subsequent to the first time interval. In some embodiments, the neural stimulation orchestration system may select, for the second time interval, the other of the visual stimulation or the audio stimulation to keep constant. In some embodiments, the neural stimulation orchestration system may provide instructions to the visual neural stimulation system or the auditory neural stimulation system corresponding to the selected one of the visual stimulation or the audio stimulation to vary during the second time interval to cause the one of the visual neural stimulation system or the auditory neural stimulation system to vary the one of the visual stimulation or the audio stimulation during the second time interval.

In some embodiments, the system may include a microphone. The microphone may detect an ambient sound level. In some embodiments, the system may include a photodiode. The photodiode may detect an ambient light level. In some embodiments, the neural stimulation orchestration system may select, based on the ambient sound level and the ambient light level, one of the visual stimulation or the audio stimulation to vary during the first time interval.

In some embodiments, the system may include an electrode. The electrode may provide peripheral nerve stimulation to the subject. In some embodiments, the neural stimulation orchestration system may select, based on the policy, one of the visual stimulation, the audio stimulation, or the peripheral nerve stimulation to vary during a second time interval.

In some embodiments, the visual stimulation may be is selected for varying during the first time interval. In some embodiments, the system may include an electrode. The electrode may provide peripheral nerve stimulation to the subject during the first time interval. In some embodiments, the system may include a feedback monitor. The feedback monitor may detect a physiological condition of the subject during the first time interval. In some embodiments, the neural stimulation orchestration system may select, responsive to detecting the physiological condition, one of the audio stimulation or the peripheral nerve stimulation to vary during a second time interval subsequent to the first time interval. In some embodiments, the neural stimulation orchestration system may select, for the second time interval, the visual stimulation to keep constant. In some embodiments, the neural stimulation orchestration system may provide instructions to the visual neural stimulation system to keep constant during the second time interval. In some embodiments, the neural stimulation orchestration system may provide instructions to the auditory neural stimulation system to vary during the second time interval. In some embodiments, the neural stimulation orchestration system may provide instructions to the electrode to keep constant during the second time interval. In some embodiments, the cognitive dysfunction may include Alzheimer's disease.

At least one aspect of the disclosure is directed to a system for treating cognitive dysfunction in a subject in need thereof. The system may include a visual neural stimulation system. The visual neural stimulation system may provide, via a light output source, visual stimulation having a first value of a first parameter. The system may include an auditory neural stimulation system. The auditory neural stimulation system may provide, via an audio output source, audio stimulation having a second value of the second parameter. The system may include a neural stimulation orchestration system. The neural stimulation orchestration system may select, for a first time interval, one of the visual stimulation or the audio stimulation to vary based on a policy. The neural stimulation orchestration system may select, for the first time interval, the other of the visual stimulation or the audio stimulation to keep constant based on the policy. The neural stimulation orchestration system may provide instructions to the visual neural stimulation system or the auditory neural stimulation system corresponding to the selected one of the visual stimulation or the audio stimulation to vary to cause the one of the visual neural stimulation system or the auditory neural stimulation system to vary the one of the visual stimulation or the audio stimulation.

In some embodiments, the neural stimulation orchestration system may select, for a second time interval subsequent to the first time interval, the other of the visual stimulation or the audio stimulation to vary based on the policy. In some embodiments, the neural stimulation orchestration system may select, for the second time interval, the other of the visual stimulation or the audio stimulation to keep constant based on the policy. In some embodiments, the neural stimulation orchestration system may provide instructions to the visual neural stimulation system or the auditory neural stimulation system corresponding to the selected one of the visual stimulation or the audio stimulation to vary during the second time interval to cause the one of the visual neural stimulation system or the auditory neural stimulation system to vary the one of the visual stimulation or the audio stimulation during the second time interval.

In some embodiments, the system may include a feedback monitor. The feedback monitor may detect a physiological condition of the subject during the first time interval. In some embodiments, the neural stimulation orchestration system may select, using the policy and based on the detected physiological condition, one of the visual stimulation or the audio stimulation to vary during the first time interval.

In some embodiments, the system may include a feedback monitor. The feedback monitor may detect a physiological condition of the subject during the first time interval. In some embodiments, the neural stimulation orchestration system may select, responsive to detecting the physiological condition, the other of the visual stimulation or the audio stimulation to vary during a second time interval subsequent to the first time interval. In some embodiments, the neural stimulation orchestration system may select, for the second time interval, the other of the visual stimulation or the audio stimulation to keep constant. In some embodiments, the neural stimulation orchestration system may provide instructions to the visual neural stimulation system or the auditory neural stimulation system corresponding to the selected one of the visual stimulation or the audio stimulation to vary during the second time interval to cause the one of the visual neural stimulation system or the auditory neural stimulation system to vary the one of the visual stimulation or the audio stimulation during the second time interval.

In some embodiments, the system may include a microphone. The microphone may detect an ambient sound level. In some embodiments, the system may include a photodiode. The photodiode may detect an ambient light level. In some embodiments, the neural stimulation orchestration system may select, based on the ambient sound level and the ambient light level, one of the visual stimulation or the audio stimulation to vary during the first time interval.

In some embodiments, the system may include an electrode. The electrode may provide peripheral nerve stimulation to the subject. In some embodiments, the neural stimulation orchestration system may select, based on the policy, one of the visual stimulation, the audio stimulation, or the peripheral nerve stimulation to vary during a second time interval.

In some embodiments, the visual stimulation may be is selected for varying during the first time interval. In some embodiments, the system may include an electrode. The electrode may provide peripheral nerve stimulation to the subject during the first time interval. In some embodiments, the system may include a feedback monitor. The feedback monitor may detect a physiological condition of the subject during the first time interval. In some embodiments, the neural stimulation orchestration system may select, responsive to detecting the physiological condition, one of the audio stimulation or the peripheral nerve stimulation to vary during a second time interval subsequent to the first time interval. In some embodiments, the neural stimulation orchestration system may select, for the second time interval, the visual stimulation to keep constant. In some embodiments, the neural stimulation orchestration system may provide instructions to the visual neural stimulation system to keep constant during the second time interval. In some embodiments, the neural stimulation orchestration system may provide instructions to the auditory neural stimulation system to vary during the second time interval. In some embodiments, the neural stimulation orchestration system may provide instructions to the electrode to keep constant during the second time interval. In some embodiments, the cognitive dysfunction may include Alzheimer's disease.

At least one aspect of the disclosure is directed to a system for treating cognitive dysfunction in a subject in need thereof. The system may include a visual neural stimulation system, an auditory neural stimulation system, a neural stimulation orchestration system, a light output source, an audio output source, and one or more processors. The one or more processors may execute one or more programs to treat a subject in need of a treatment of a brain disease. The one or more programs may include instructions for conducting a therapy session. The therapy session may include providing, via the light output source, visual stimulation having a first value of a first parameter. The therapy session may include providing, via the audio output source, audio stimulation having a second value of the second parameter. The therapy session may include selecting, for a first time interval, one of the visual stimulation or the audio stimulation to vary based on a policy. The therapy session may include selecting, for the first time interval, the other of the visual stimulation or the audio stimulation to keep constant based on the policy. The therapy session may include providing instructions to the visual neural stimulation system or the auditory neural stimulation system corresponding to the selected one of the visual stimulation or the audio stimulation to vary to cause the one of the visual neural stimulation system or the auditory neural stimulation system to vary the one of the visual stimulation or the audio stimulation.

In some embodiments, the therapy session may include selecting, for a second time interval subsequent to the first time interval, the other of the visual stimulation or the audio stimulation to vary based on the policy. In some embodiments, the therapy session may include selecting, for the second time interval, the other of the visual stimulation or the audio stimulation to keep constant based on the policy. In some embodiments, the therapy session may include providing instructions to the visual neural stimulation system or the auditory neural stimulation system corresponding to the selected one of the visual stimulation or the audio stimulation to vary during the second time interval to cause the one of the visual neural stimulation system or the auditory neural stimulation system to vary the one of the visual stimulation or the audio stimulation during the second time interval.

In some embodiments, the therapy session may include detecting a physiological condition of the subject during the first time interval. In some embodiments, the therapy session may include selecting, using the policy and based on the detected physiological condition, one of the visual stimulation or the audio stimulation to vary during the first time interval.

In some embodiments, the therapy session may include detecting a physiological condition of the subject during the first time interval. In some embodiments, the therapy session may include selecting, responsive to detecting the physiological condition, the other of the visual stimulation or the audio stimulation to vary during a second time interval subsequent to the first time interval. In some embodiments, the therapy session may include selecting, for the second time interval, the other of the visual stimulation or the audio stimulation to keep constant. In some embodiments, the therapy session may include providing instructions to the visual neural stimulation system or the auditory neural stimulation system corresponding to the selected one of the visual stimulation or the audio stimulation to vary during the second time interval to cause the one of the visual neural stimulation system or the auditory neural stimulation system to vary the one of the visual stimulation or the audio stimulation during the second time interval.

In some embodiments, the therapy session may include detecting an ambient sound level. In some embodiments, the therapy session may include detecting an ambient light level. In some embodiments, the therapy session may include selecting, based on the ambient sound level and the ambient light level, one of the visual stimulation or the audio stimulation to vary during the first time interval. In some embodiments, the therapy session may include providing, via an electrode, peripheral nerve stimulation to the subject. In some embodiments, the therapy session may include selecting, based on the policy, one of the visual stimulation, the audio stimulation, or the peripheral nerve stimulation to vary during a second time interval.

In some embodiments, the visual stimulation may be selected for varying during the first time interval. In some embodiments, the therapy session may include providing, via an electrode, peripheral nerve stimulation to the subject during the first time interval. In some embodiments, the therapy session may include detecting a physiological condition of the subject during the first time interval. In some embodiments, the therapy session may include selecting, responsive to detecting the physiological condition, one of the audio stimulation or the peripheral nerve stimulation to vary during a second time interval subsequent to the first time interval. In some embodiments, the therapy session may include selecting, for the second time interval, the visual stimulation to keep constant. In some embodiments, the therapy session may include providing instructions to the visual neural stimulation system to keep constant during the second time interval. In some embodiments, the therapy session may include providing instructions to the auditory neural stimulation system to vary during the second time interval. In some embodiments, the therapy session may include providing instructions to the electrode to keep constant during the second time interval. In some embodiments, the cognitive dysfunction may include Alzheimer's disease.

At least one aspect of the disclosure is directed to a method for treating cognitive dysfunction in a subject in need thereof. The method may include administering a stimulus to the subject using a system. The system may include a light source and a speaker. The system may include a visual signaling component executed by a visual neural stimulation system. The visual signaling component may provide, via the light source, visual stimulation having a first value of a first parameter. The system may include an audio signaling component executed by an auditory neural stimulation system. The audio signaling component may provide, via the speaker, audio stimulation having a second value of the second parameter. The system may include a stimuli orchestration component executed by a neural stimulation orchestration system. The stimuli orchestration component may select, for a first time interval, one of the visual stimulation or the audio stimulation to vary based on a policy. The stimuli orchestration component may select, for the first time interval, the other of the visual stimulation or the audio stimulation to keep constant based on the policy. The stimuli orchestration component may provide instructions to the visual neural stimulation system or the auditory neural stimulation system corresponding to the selected one of the visual stimulation or the audio stimulation to vary to cause the one of the visual neural stimulation system or the auditory neural stimulation system to vary the one of the visual stimulation or the audio stimulation.

In some embodiments, the cognitive dysfunction may include Alzheimer's Disease.

In some embodiments, the method includes administering a pharmacological agent to the subject prior to, simultaneous to, or subsequent to administration of the stimulus. The pharmacological agent can be a monoclonal antibody. The monoclonal antibody can be aducanumab.

At least one aspect of the disclosure is directed to a method of evaluating neural responses to different stimulation modalities for subjects. The method may include sequentially applying a plurality of first neural stimuli to a subject. Each first neural stimulus may be defined by a predetermined amplitude. Each first neural stimulus associated with a different modality of neural stimulus may include an auditory stimulation modality, a visual stimulation modality, and a peripheral nerve stimulation modality. The method may include sensing, while applying each first neural stimulus to the subject, a first electroencephalogram (EEG) response to the corresponding first neural stimulus. The method may include generating, based on each first neural stimulus, a corresponding first simulated EEG response to the first neural stimulus. The method may include comparing each first EEG response to each corresponding first simulated response to determine whether the first EEG response indicates a particular neural activity response of the subject. The method may include selecting, based on the comparison, a candidate first neural stimuli associated with an EEG response associated with the particular neural activity response of the subject. The method may include applying, for the candidate first neural stimulus, a plurality of second neural stimuli to the subject, the second neural stimuli having varying values of amplitude. The method may include sensing, while applying each second neural stimulus to the subject, a second EEG response of the subject. The method may include generating, based on each second neural stimulus, a corresponding second simulated EEG response to the second neural stimulus. The method may include comparing each second EEG response to each corresponding second simulated EEG response to determine whether the second EEG response indicates the particular neural activity response of the subject. The method may include selecting, based on the comparison, a therapy amplitude for a therapy neural stimulus corresponding to the second neural stimulus associated with the particular neural response. The method may include applying the therapy neural stimulus to the subject using the therapy amplitude.

In some embodiments, the method may include sensing an attentiveness response of the subject by executing at least one of eye tracking of eyes of the subject, monitoring heart rate of the subject, or monitoring an orientation of at least one of a head or a body of the subject, and using the attentiveness response to determine whether the particular neural activity response is indicated. In some embodiments, generating each simulated response may include maintaining a model for the subject based on historical response data for one or more subjects. The historical response data may be associated prior physiological responses with corresponding neural stimuli. The model may be based on at least one of an age parameter, a height parameter, a weight parameter, or a heart rate parameter of the subject.

In some embodiments, applying at least one of the plurality of first neural stimuli may include applying multiple modalities simultaneously. In some embodiments, applying at least one of the plurality of first neural stimuli may include applying multiple modalities simultaneously. In some embodiments, the method may include applying a plurality of the therapy neural stimuli by varying a therapy parameter of each therapy neural stimulus In some embodiments, the therapy parameter may be a duty cycle. In some embodiments, the duty cycle of each of the plurality of therapy neural stimuli may be less than or equal to fifty percent. In some embodiments, the modality of the therapy neural stimuli may be the auditory stimulation modality, and the therapy parameter may be a pitch. In some embodiments, the modality of therapy neural stimuli may be the visual stimulation modality, and the therapy parameter may include at least one of a color or an image selection. In some embodiments, the modality of the therapy neural stimuli may be the peripheral neural stimulation modality, and the therapy parameter may be a location.

At least one aspect of the disclosure is directed to a system for evaluating neural responses to different stimulation modalities for subject. The system may include one or more processors coupled to a memory device. The memory device may store instructions. The instructions, which when executed by the one or more processors, may cause the one or more processors to sequentially apply a plurality of first neural stimuli to a subject. Each first neural stimulus may be defined by a predetermined amplitude. A different modality of neural stimulus may include an auditory stimulation modality, a visual stimulation modality, and a peripheral nerve stimulation modality. The instructions may cause the one or more processors to sense, while applying each first neural stimulus to the subject, a first electroencephalogram (EEG) response to the corresponding first neural stimulus. The instructions may cause the one or more processors to generate, based on each first neural stimulus, a corresponding first simulated EEG response to the first neural stimulus. The instructions may cause the one or more processors to compare each first EEG response to each corresponding first simulated response to determine whether the first EEG response indicates a particular neural activity response of the subject. The instructions may cause the one or more processors to select, based on the comparison, a candidate first neural stimuli associated with an EEG response associated with the particular neural activity response of the subject. The instructions may cause the one or more processors to apply, for the candidate first neural stimulus, a plurality of second neural stimuli to the subject, the second neural stimuli having varying values of amplitude. The instructions may cause the one or more processors to sense, while applying each second neural stimulus to the subject, a second EEG response of the subject. The instructions may cause the one or more processors to generate, based on each second neural stimulus, a corresponding second simulated EEG response to the second neural stimulus. The instructions may cause the one or more processors to compare each second EEG response to each corresponding second simulated EEG response to determine whether the second EEG response indicates the particular neural activity response of the subject. The instructions may cause the one or more processors to select, based on the comparison, a therapy amplitude for a therapy neural stimulus corresponding to the second neural stimulus associated with the particular neural response. The instructions may cause the one or more processors to apply the therapy neural stimulus to the subject using the therapy amplitude.

In some embodiments, the one or more processors may sense an attentiveness response of the subject by executing at least one of eye tracking of eyes of the subject, monitoring heart rate of the subject, or monitoring an orientation of at least one of a head or a body of the subject, and using the attentiveness response to determine whether the particular neural activity response is indicated. In some embodiments, the one or more processors may generate each simulated response by maintaining a model for the subject based on historical response data for one or more subjects, the historical response data associated prior physiological responses with corresponding neural stimuli, the model based on at least one of an age parameter, a height parameter, a weight parameter, or a heart rate parameter of the subject. In some embodiments, the one or more processors may apply at least one of the plurality of first neural stimuli by applying multiple modalities simultaneously.

In some embodiments, the one or more processors may apply a plurality of the therapy neural stimuli by varying a therapy parameter of each therapy neural stimulus. In some embodiments, the therapy parameter may be a duty cycle. In some embodiments, the duty cycle of each of the plurality of therapy neural stimuli may be less than or equal to fifty percent. In some embodiments, the modality of the therapy neural stimuli may be the auditory stimulation modality, and the therapy parameter may be a pitch. In some embodiments, the modality of therapy neural stimuli may be the visual stimulation modality, and the therapy parameter may include at least one of a color or an image selection. In some embodiments, the modality of the therapy neural stimuli may be the peripheral neural stimulation modality, and the therapy parameter may be a location.

At least one aspect of the disclosure is directed to a-transient computer readable medium for evaluating neural responses to different stimulation modalities for subjects. The non-transient computer readable medium may store instructions. The instructions, which when executed by one or more processors, may cause the one or more processors to sequentially apply a plurality of first neural stimuli to a subject. Each first neural stimulus may be defined by a predetermined amplitude. Each first neural stimulus associated with a different modality of neural stimulus may include an auditory stimulation modality, a visual stimulation modality, and a peripheral nerve stimulation modality. The instructions may cause the one or more processors to sense, while applying each first neural stimulus to the subject, a first electroencephalogram (EEG) response to the corresponding first neural stimulus. The instructions may cause the one or more processors to generate, based on each first neural stimulus, a corresponding first simulated EEG response to the first neural stimulus. The instructions may cause the one or more processors to compare each first EEG response to each corresponding first simulated response to determine whether the first EEG response indicates a particular neural activity response of the subject. The instructions may cause the one or more processors to select, based on the comparison, a candidate first neural stimuli associated with an EEG response associated with the particular neural activity response of the subject. The instructions may cause the one or more processors to apply, for the candidate first neural stimulus, a plurality of second neural stimuli to the subject, the second neural stimuli having varying values of amplitude. The instructions may cause the one or more processors to sense, while applying each second neural stimulus to the subject, a second EEG response of the subject. The instructions may cause the one or more processors to generate, based on each second neural stimulus, a corresponding second simulated EEG response to the second neural stimulus. The instructions may cause the one or more processors to compare each second EEG response to each corresponding second simulated EEG response to determine whether the second EEG response indicates the particular neural activity response of the subject. The instructions may cause the one or more processors to select, based on the comparison, a therapy amplitude for a therapy neural stimulus corresponding to the second neural stimulus associated with the particular neural response. The instructions may cause the one or more processors to apply the therapy neural stimulus to the subject using the therapy amplitude.

In some embodiments, the instructions may cause the one or more processors to sense an attentiveness response of the subject by executing at least one of eye tracking of eyes of the subject, monitoring heart rate of the subject, or monitoring an orientation of at least one of a head or a body of the subject, and using the attentiveness response to determine whether the particular neural activity response is indicated, In some embodiments, the instructions may cause the one or more processors to generate each simulated response by maintaining a model for the subject based on historical response data for one or more subjects. The historical response data may be associated prior physiological responses with corresponding neural stimuli. The model may be based on at least one of an age parameter, a height parameter, a weight parameter, or a heart rate parameter of the subject.

In some embodiments, the instructions may cause the one or more processors to apply a plurality of the therapy neural stimuli by varying a therapy parameter of each therapy neural stimulus. In some embodiments, the therapy parameter may be a duty cycle. In some embodiments, the duty cycle of each of the plurality of therapy neural stimuli may be less than or equal to fifty percent. In some embodiments, the modality of the therapy neural stimuli may be the auditory stimulation modality, and the therapy parameter may be a pitch. In some embodiments, the modality of therapy neural stimuli may be the visual stimulation modality, and the therapy parameter may include at least one of a color or an image selection. In some embodiments, the modality of the therapy neural stimuli may be the peripheral neural stimulation modality, and the therapy parameter may be a location.

At least one aspect of the disclosure is directed to a method of generating therapy regimens based on comparison of assessments for different stimulation modalities. For each of an auditory stimulation modality, a visual stimulation modality, and a peripheral nerve stimulation modality, the method may include performing steps. The steps may include providing a first assessment to the subject. The steps may include determining, based on the first assessment, a first task response of the subject. The steps may include applying a first neural stimulus to the subject. The steps may include, subsequent to applying the first neural stimulus, providing a second assessment to the subject. The steps may include determining, based on the second assessment, a second task response of the subject. The steps may include comparing the second task response to the first task response to determine whether the second task response indicates a particular neural activity response of the subject. The steps may include selecting a candidate stimulation modality from the auditory stimulation modality, the visual stimulation modality, and the peripheral nerve stimulation modality based on the comparisons of the first and second task responses. The steps may include generating a therapy regimen for the subject using the candidate stimulation modality.

In some embodiments, the first and second assessments each may include at least one of an N-back task, a serial reaction time test, a visual coordination test, a voluntary movement test, or a force production test. In some embodiments, selecting the candidate stimulation modality may include selecting the modality associated with at least one of a highest increase in score of the second assessment or a highest score of the second assessment. In some embodiments, selecting the candidate stimulation modality may include selecting at least one modality associated with at least one of an increase in score of the second assessment being greater than an increase threshold or a score of the second assessment being greater than a score threshold. In some embodiments, the first neural stimuli for each modality may be provided at a same predetermined frequency.

At least one aspect of the disclosure is directed to a system for generating therapy regimens based on comparison of assessments for different stimulation modalities. The system may include one or more processors coupled to a memory device. The memory device may store instructions. The instructions, which when executed by the one or more processors, may cause the one or more processors to, for each of an auditory stimulation modality, a visual stimulation modality, and a peripheral nerve stimulation modality, perform steps. The steps may include providing a first assessment to the subject. The steps may include determining, based on the first assessment, a first task response of the subject. The steps may include applying a first neural stimulus to the subject. The steps may include, subsequent to applying the first neural stimulus, providing a second assessment to the subject. The steps may include determining, based on the second assessment, a second task response of the subject. The steps may include comparing the second task response to the first task response to determine whether the second task response indicates a particular neural activity response of the subject. The steps may include selecting a candidate stimulation modality from the auditory stimulation modality, the visual stimulation modality, and the peripheral nerve stimulation modality based on the comparisons of the first and second task responses. The steps may include generating a therapy regimen for the subject using the candidate stimulation modality.

In some embodiments, the first and second assessments each may include at least one of an N-back task, a serial reaction time test, a visual coordination test, a voluntary movement test, or a force production test. In some embodiments, selecting the candidate stimulation modality may include selecting the modality associated with at least one of a highest increase in score of the second assessment or a highest score of the second assessment. In some embodiments, selecting the candidate stimulation modality may include selecting at least one modality associated with at least one of an increase in score of the second assessment being greater than an increase threshold or a score of the second assessment being greater than a score threshold. In some embodiments, the first neural stimuli for each modality may be provided at a same predetermined frequency.

At least one aspect of the disclosure is directed to a non-transient computer readable medium for generating therapy regimens based on comparison of assessments for different stimulation modalities. The non-transient computer readable medium may store instructions. The instructions, which when executed by one or more processors, may cause the one or more processors to for each of an auditory stimulation modality, a visual stimulation modality, and a peripheral nerve stimulation modality, perform the steps. The steps may include providing a first assessment to the subject. The steps may include determining, based on the first assessment, a first task response of the subject. The steps may include applying a first neural stimulus to the subject. The steps may include, subsequent to applying the first neural stimulus, providing a second assessment to the subject. The steps may include determining, based on the second assessment, a second task response of the subject. The steps may include comparing the second task response to the first task response to determine whether the second task response indicates a particular neural activity response of the subject. The steps may include selecting a candidate stimulation modality from the auditory stimulation modality, the visual stimulation modality, and the peripheral nerve stimulation modality based on the comparisons of the first and second task responses. The steps may include generating a therapy regimen for the subject using the candidate stimulation modality.

In some embodiments, the first and second assessments each may include at least one of an N-back task, a serial reaction time test, a visual coordination test, a voluntary movement test, or a force production test. In some embodiments, selecting the candidate stimulation modality may include selecting the modality associated with at least one of a highest increase in score of the second assessment or a highest score of the second assessment. In some embodiments, selecting the candidate stimulation modality may include selecting at least one modality associated with at least one of an increase in score of the second assessment being greater than an increase threshold or a score of the second assessment being greater than a score threshold. In some embodiments, the first neural stimuli for each modality may be provided at a same predetermined frequency.

At least one aspect of the disclosure is directed to a method of conducting a therapy session. The method may include selecting a frequency at which to provide a first neural stimulation having a first stimulation modality, a second neural stimulation having a second stimulation modality, and a third neural stimulation having the second stimulation modality. The method may include providing, to a subject for a duration, the first neural stimulation as a plurality of first pulses at the frequency. The method may include providing, to the subject during a first portion of the duration, the second neural stimulation as a plurality of second pulses at the frequency. The plurality of second pulses may be offset from the plurality of first pulses by a first offset. The method may include terminating the second neural stimulation. The method may include, subsequent to terminating the second neural stimulation, providing to the subject during a second portion of the duration, a third neural stimulation as a plurality of third pulses at the frequency. The plurality of third pulses may be offset from the plurality of first pulses by a second offset different from the first offset. The third neural stimulation and the second neural stimulation may have a same stimulation modality.

In some embodiments, the first offset and second offset may be each selected as a random value greater than zero and less than a time constant equal to an inverse of the frequency. In some embodiments, the first stimulation modality may be one of an auditory stimulation modality, a visual stimulation modality, or a peripheral nerve stimulation modality. The second stimulation modality may be another of the auditory stimulation modality, the visual stimulation modality, or the peripheral nerve stimulation modality. In some embodiments, a pulse width of the plurality of first pulses may be different from a pulse width of at least one of the plurality of second pulses or the plurality of third pulses.

At least one aspect of the disclosure is directed to a system. The system may include one or more processors coupled to a memory device. The memory device may store instructions. The instructions, which when executed by the one or more processors, may cause the one or more processors to select a frequency at which to provide a first neural stimulation having a first stimulation modality, a second neural stimulation having a second stimulation modality, and a third neural stimulation having the second stimulation modality. The instructions may cause the one or more processors to provide, to a subject for a duration, the first neural stimulation as a plurality of first pulses at the frequency. The instructions may cause the one or more processors to provide, to the subject during a first portion of the duration, the second neural stimulation as a plurality of second pulses at the frequency. The plurality of second pulses may be offset from the plurality of first pulses by a first offset. The instructions may cause the one or more processors to terminate the second neural stimulation. The instructions may cause the one or more processors to, subsequent to terminating the second neural stimulation, provide to the subject during a second portion of the duration, a third neural stimulation as a plurality of third pulses at the frequency. The plurality of third pulses may be offset from the plurality of first pulses by a second offset different from the first offset. The third neural stimulation and the second neural stimulation may have a same stimulation modality.

In some embodiments, the first offset and second offset may be each selected as a random value greater than zero and less than a time constant equal to an inverse of the frequency. In some embodiments, the first stimulation modality may be one of an auditory stimulation modality, a visual stimulation modality, or a peripheral nerve stimulation modality. The second stimulation modality may be another of the auditory stimulation modality, the visual stimulation modality, or the peripheral nerve stimulation modality. In some embodiments, a pulse width of the plurality of first pulses may be different from a pulse width of at least one of the plurality of second pulses or the plurality of third pulses.

At least one aspect of the disclosure is directed to a non-transient computer readable medium for conducting a therapy session. The non-transient computer readable medium may store instructions. The instructions, which when executed by one or more processors, may cause the one or more processors to select a frequency at which to provide a first neural stimulation having a first stimulation modality, a second neural stimulation having a second stimulation modality, and a third neural stimulation having the second stimulation modality. The instructions may cause the one or more processors to provide, to a subject for a duration, the first neural stimulation as a plurality of first pulses at the frequency. The instructions may cause the one or more processors to provide, to the subject during a first portion of the duration, the second neural stimulation as a plurality of second pulses at the frequency. The plurality of second pulses may be offset from the plurality of first pulses by a first offset. The instructions may cause the one or more processors to terminate the second neural stimulation. The instructions may cause the one or more processors to, subsequent to terminating the second neural stimulation, provide to the subject during a second portion of the duration, a third neural stimulation as a plurality of third pulses at the frequency. The plurality of third pulses may be offset from the plurality of first pulses by a second offset different from the first offset. The third neural stimulation and the second neural stimulation may have a same stimulation modality In some embodiments, the first offset and second offset may be each selected as a random value greater than zero and less than a time constant equal to an inverse of the frequency. In some embodiments, the first stimulation modality may be one of an auditory stimulation modality, a visual stimulation modality, or a peripheral nerve stimulation modality. The second stimulation modality may be another of the auditory stimulation modality, the visual stimulation modality, or the peripheral nerve stimulation modality. In some embodiments, a pulse width of the plurality of first pulses may be different from a pulse width of at least one of the plurality of second pulses or the plurality of third pulses.

At least one aspect of the disclosure is directed to a method of counteracting distraction while applying a neural stimulus. The method may include applying a first neural stimulus to a subject. The method may include applying, at a plurality of first time points during the first neural stimulus, a plurality of first counter-distraction measures. The plurality of first counter-distraction measures may include at least one of an audible alert or a visible alert. The method may include measuring, during the first neural stimulus, an attentiveness parameter including at least one of an eye direction, a head position, a heart rate, or a respiration rate of the subject. The method may include comparing the attentiveness parameter to a corresponding first threshold to identify a distraction and a corresponding time of distraction. The method may include determining whether each first counter-distraction measure is effective by comparing a change in the attentiveness parameter before and after each counter-distraction measure to a corresponding second threshold. The method may include, responsive to determining that a first counter-distraction measure is effective, including the counter-distraction measure in a plurality of second counter-distraction measures. The method may include selecting a plurality of second time points closer to each time of distraction than the plurality of first time points. The method may include applying a second neural stimulus to the subject while applying, at the plurality of second time points, the plurality of second counter-distraction measures.

In some embodiments, the method may include incrementing a count of distractions in response to identifying each distraction. In some embodiments, the method may include resetting the count of distractions subsequent to each effective first counter-distraction measure. In some embodiments, the method may include ranking the plurality of first counter-distraction measures based on a magnitude of the corresponding count of distractions. In some embodiments, the first neural stimulus may include at least one of an auditory stimulus, a visual stimulus, or a peripheral nerve stimulus.

At least one aspect of the disclosure is directed to a system for counteracting distraction while applying a neural stimulus. The system may include one or more processors coupled to a memory device. The memory device may instructions. The instructions, which when executed by the one or more processors, may cause the one or more processors to apply a first neural stimulus to a subject. The instructions may cause the one or more processors to apply, at a plurality of first time points during the first neural stimulus, a plurality of first counter-distraction measures. The plurality of first counter-distraction measures may include at least one of an audible alert or a visible alert. The instructions may cause the one or more processors to measure, during the first neural stimulus, an attentiveness parameter including at least one of an eye direction, a head position, a heart rate, or a respiration rate of the subject. The instructions may cause the one or more processors to compare the attentiveness parameter to a corresponding first threshold to identify a distraction and a corresponding time of distraction. The instructions may cause the one or more processors to determine whether each first counter-distraction measure is effective by comparing a change in the attentiveness parameter before and after each counter-distraction measure to a second threshold. The instructions may cause the one or more processors to, responsive to determining that a first counter-distraction measure is effective, include the counter-distraction measure in a plurality of second counter-distraction measures. The instructions may cause the one or more processors to select a plurality of second time points closer to each time of distraction than the plurality of first time points. The instructions may cause the one or more processors to apply a second neural stimulus to the subject while applying, at the plurality of second time points, the plurality of second counter-distraction measures.

In some embodiments, the instructions may cause the one or more processors to increment a count of distractions in response to identifying each distraction. In some embodiments, the instructions may cause the one or more processors to reset the count of distractions subsequent to each effective first counter-distraction measure. In some embodiments, the instructions may cause the one or more processors to rank the plurality of first counter-distraction measures based on a magnitude of the corresponding count of distractions. In some embodiments, the first neural stimulus may include at least one of an auditory stimulus, a visual stimulus, or a peripheral nerve stimulus.

At least one aspect of the disclosure is directed to a-transient computer readable medium for counteracting distractions while applying a neural stimulus. The non-transient computer readable medium may store instructions. The instructions, which when executed by the one or more processors, may cause the one or more processors to apply a first neural stimulus to a subject. The instructions may cause the one or more processors to apply, at a plurality of first time points during the first neural stimulus, a plurality of first counter-distraction measures. The plurality of first counter-distraction measures may include at least one of an audible alert or a visible alert. The instructions may cause the one or more processors to measure, during the first neural stimulus, an attentiveness parameter including at least one of an eye direction, a head position, a heart rate, or a respiration rate of the subject. The instructions may cause the one or more processors to compare the attentiveness parameter to a corresponding first threshold to identify a distraction and a corresponding time of distraction. The instructions may cause the one or more processors to determine whether each first counter-distraction measure is effective by comparing a change in the attentiveness parameter before and after each counter-distraction measure to a second threshold. The instructions may cause the one or more processors to, responsive to determining that a first counter-distraction measure is effective, include the counter-distraction measure in a plurality of second counter-distraction measures. The instructions may cause the one or more processors to select a plurality of second time points closer to each time of distraction than the plurality of first time points. The instructions may cause the one or more processors to apply a second neural stimulus to the subject while applying, at the plurality of second time points, the plurality of second counter-distraction measures.

In some embodiments, the instructions may cause the one or more processors to increment a count of distractions in response to identifying each distraction. In some embodiments, the instructions may cause the one or more processors to reset the count of distractions subsequent to each effective first counter-distraction measure. In some embodiments, the instructions may cause the one or more processors to rank the plurality of first counter-distraction measures based on a magnitude of the corresponding count of distractions. In some embodiments, the first neural stimulus may include at least one of an auditory stimulus, a visual stimulus, or a peripheral nerve stimulus.

BRIEF DESCRIPTION OF THE FIGURES

The details of one or more embodiments of the subject matter described in this specification are set forth in the accompanying drawings and the description below. Other features, aspects, and advantages of the subject matter will become apparent from the description, the drawings, and the claims.

FIGS. 2A-2F illustrate visual signals for visual brain entrainment in accordance with some embodiments.

FIGS. 5A-5D illustrate devices configured to transmit visual signals for visual brain entrainment in accordance with some embodiments.

FIG. 16 is a block diagram depicting a system to induce neural oscillations via peripheral nerve stimulation in accordance with an embodiment.

Figure 1:
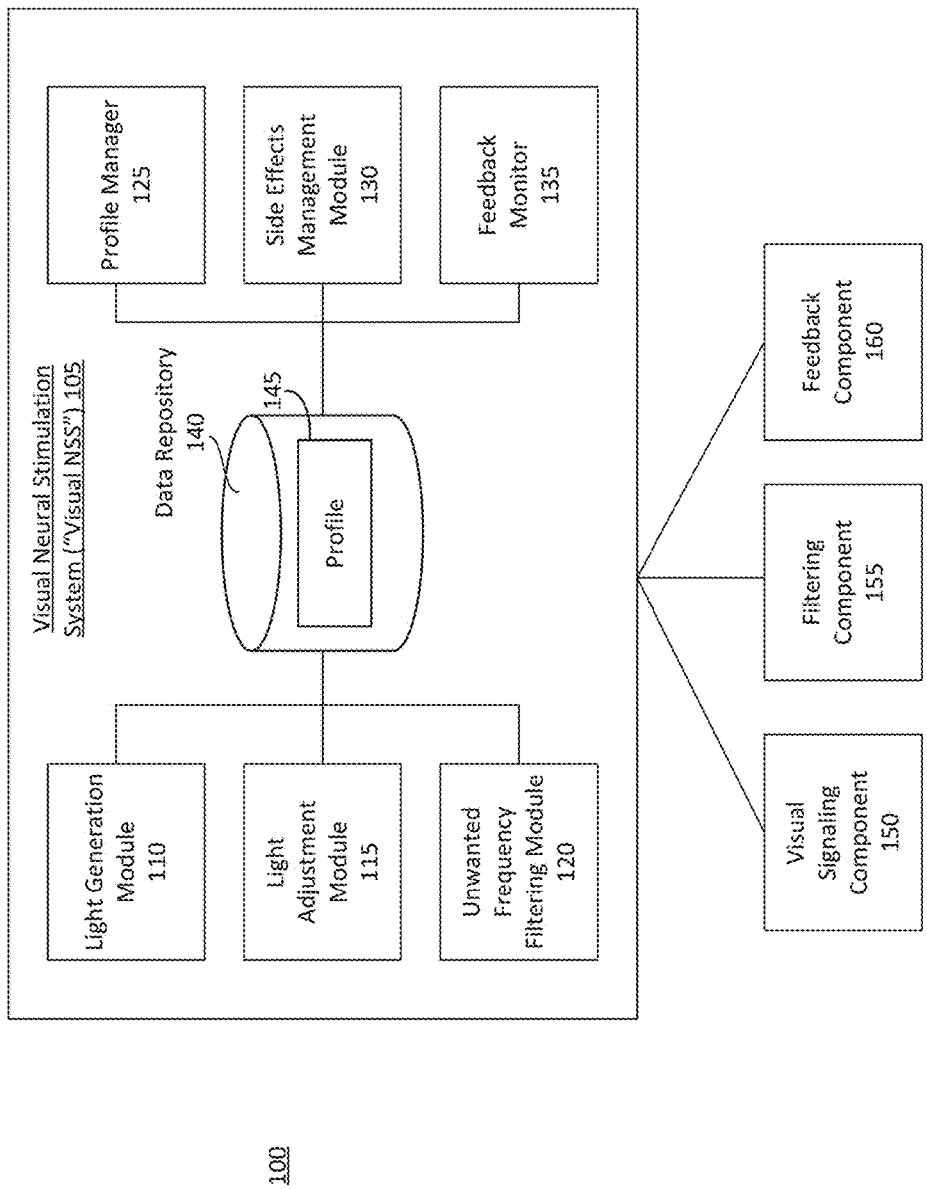
FIG. 1 is a bock diagram depicting a system to perform visual brain entrainment in accordance with an embodiment.

The features and advantages of the present solution will become more apparent from the detailed description set forth below when taken in conjunction with the drawings, in which like reference characters identify corresponding elements throughout. In the drawings, like reference numbers generally indicate like elements.

DETAILED DESCRIPTION

For purposes of reading the description of the various embodiments below, the following descriptions of the sections of the specification and their respective contents may be helpful:

Section A describes neural stimulation via visual stimulation, in accordance with some embodiments;

Section B describes systems and devices configured to perform neural stimulation via visual stimulation, in accordance with some embodiments;

Section C describes a computing environment which may be useful for practicing embodiments described herein;

Section D describes a method for performing neural stimulation via visual stimulation, in accordance with an embodiment:

Section E describes an NSS operating with a frame, in accordance with an embodiment;

Section F describes an NSS operating with a virtual reality headset, in accordance with an embodiment;

Section G describes an NSS operating with a tablet, in accordance with an embodiment;

Section H describes neural stimulation via auditory stimulation, in accordance with some embodiments;

Section I describes systems and devices for neural stimulation via auditory stimulation, in accordance with some embodiments;

Section J describes a method for neural stimulation via auditory stimulation, in accordance with an embodiment;

Section K describes how the neural stimulation system can operate with headphones, in accordance with some embodiments;

Section L describes inducing neural oscillations via peripheral nerve stimulation, in accordance with some embodiments;

Section M describes systems and devices configured to induce neural oscillations via peripheral nerve stimulation, in accordance with some embodiments;

Section N describes a method for inducing neural oscillations via peripheral nerve stimulation, in accordance with an embodiment.

Section O describes neural stimulation via multiple modes of stimulation, in accordance with an embodiment;

Section P describes neural stimulation via a combination of audio stimulation and visual stimulation, in accordance with an embodiment;

Section Q describes a method for neural stimulation via a combination of audio stimulation and visual stimulation, in accordance with an embodiment;

Section R describes selecting dosing parameters of stimulation signals to induce synchronized neural oscillations in the brain of the subject, in accordance with an embodiment;

Section S describes a system for selecting dosing parameters of stimulation signals to induce synchronized neural oscillations in the brain of the subject, in accordance with an embodiment;

Section T describes a subject profile that can be used to store subject-specific data, in accordance with an embodiment;

Section U describes generation of a personalized therapy regimen for a subject, in accordance with an embodiment;

Section V describes techniques for generating and utilizing a predictive model to generate a therapy regimen of a subject, in accordance with an embodiment;

Section W describes techniques for promoting subject adherence to a therapy regimen, in accordance with an embodiment;

Section X describes open loop therapy techniques, in accordance with an embodiment;

Section Y describes closed loop therapy techniques, in accordance with an embodiment;

Section Z describes a method for selecting dosing parameters of stimulation signals to induce synchronized neural oscillations in the brain of the subject, in accordance with an embodiment;

Section AA describes environments for modifying an external stimulus based on feedback from a subject performing an assessment task, in accordance to an embodiment;

Section BB describes an overview of systems for performing assessments to measure effects of stimulation, in accordance to an embodiment;

Section CC describes the modules for administering assessments or applying the stimulus on the subject in the systems for performing assessments to measure effects of stimulation, in accordance to an embodiment;

Section DD describes the modules for measuring the data from the subject during the administration of the assessments in the system for performing assessments to measure effects of stimulation, in accordance to an embodiment;

Section EE describes the modules for modifying the assessment or the stimulus in response to feedback data in the systems for performing assessments to measure effects of stimulation, in accordance to an embodiment;

Section FF describes methods of performing assessments to measure effects of stimulation, in accordance to an embodiment;

Section GG describes systems for adjusting an external stimulus to induce neural oscillations based on measurement on a subject, in accordance to an embodiment;

Section HH describes systems for neural stimulation sensing, in accordance to an embodiment;

Section II describes adjusting the stimulus to further entrain neural oscillations to a target frequency, in accordance to an embodiment;

Section JJ describes measurement devices for measuring neural oscillations, in accordance to an embodiment;

Section KK describes systems for monitoring subject attentiveness during application of an external stimulus to induce neural oscillations, in accordance to an embodiment;

Section LL describes systems for monitoring subject physiology during application of an external stimulus to induce neural oscillations, in accordance to an embodiment;

Section MM describes systems for synchronizing multiple stimuli during application of an external stimulus to induce neural oscillations, in accordance to an embodiment; and Section NN describes a method of adjusting an external stimulus to induce neural oscillations based on measurement on a subject.

A. Neural Stimulation Via Visual Stimulation

Systems and methods of the present disclosure are directed to controlling frequencies of neural oscillations using visual signals. The visual stimulation can adjust, control or otherwise affect the frequency of the neural oscillations to provide beneficial effects to one or more cognitive states or cognitive functions of the brain, or the immune system, while mitigating or preventing adverse consequences on a cognitive state or cognitive function. The visual stimulation can result in brainwave entrainment that can provide beneficial effects to one or more cognitive states of the brain, cognitive functions of the brain, the immune system, or inflammation. In some cases, the visual stimulation can result in local effect, such as in the visual cortex and associate regions. The brainwave entrainment can treat disorders, maladies, diseases, inefficiencies, injuries or other issues related to a cognitive function of the brain, cognitive state of the brain, the immune system, or inflammation.

Neural oscillation occurs in humans or animals and includes rhythmic or repetitive neural activity in the central nervous system. Neural tissue can generate oscillatory activity by mechanisms within individual neurons or by interactions between neurons. Oscillations can appear as either oscillations in membrane potential or as rhythmic patterns of action potentials, which can produce oscillatory activation of post-synaptic neurons. Synchronized activity of a group of neurons can give rise to macroscopic oscillations, which, for example, can be observed by electroencephalography ("EEG"), magnetoencephalography ("MEG"), functional magnetic resonance imaging ("fMRI"), or electrocorticography ("ECoG"). Neural oscillations can be characterized by their frequency, amplitude and phase. These signal properties can be observed from neural recordings using time-frequency analysis.

For example, an EEG can measure oscillatory activity among a group of neurons, and the measured oscillatory activity can be categorized into frequency bands as follows: delta activity corresponds to a frequency band from 1-4 Hz; theta activity corresponds to a frequency band from 4-8 Hz; alpha activity corresponds to a frequency band from 8-12 Hz; beta activity corresponds to a frequency band from 13-30 Hz; and gamma activity corresponds to a frequency band from 30-70 Hz.

The frequency and presence or activity of neural oscillations can be associated with cognitive states or cognitive functions such as information transfer, perception, motor control and memory. Based on the cognitive state or cognitive function, the frequency of neural oscillations can vary. Further, certain frequencies of neural oscillations can have beneficial effects or adverse consequences on one or more cognitive states or function. However, it may be challenging to synchronize neural oscillations using external stimulus to provide such beneficial effects or reduce or prevent such adverse consequences.

Brainwave entrainment (e.g., neural entrainment or brain entrainment) occurs when an external stimulation of a particular frequency is perceived by the brain and triggers neural activity in the brain that results in neurons oscillating at a frequency corresponding to the particular frequency of the external stimulation. Thus, brain entrainment can refer to synchronizing neural oscillations in the brain using external stimulation such that the neural oscillations occur at a frequency that corresponds to the particular frequency of the external stimulation.

Systems and methods of the present disclosure can provide external visual stimulation to achieve brain entrainment. For example, external signals, such as light pulses or high-contrast visual patterns, can be perceived by the brain. The brain, responsive to observing or perceiving the light pulses, can adjust, manage, or control the frequency of neural oscillations. The light pulses generated at a predetermined frequency and perceived by ocular means via a direct visual field or a peripheral visual field can trigger neural activity in the brain to induce brainwave entrainment. The frequency of neural oscillations can be affected at least in part by the frequency of light pulses. While high-level cognitive function may gate or interfere with some regions being entrained, the brain can react to the visual stimulation at the sensory cortices. Thus, systems and methods of the present disclosure can provide brainwave entrainment using external visual stimulus such as light pulses emitted at a predetermined frequency to synchronize electrical activity among groups of neurons based on the frequency of light pulses. The entrainment of one or more portion or regions of the brain can be observed based on the aggregate frequency of oscillations produced by the synchronous electrical activity in ensembles of cortical neurons. The frequency of the light pulses can cause or adjust this synchronous electrical activity in the ensembles of cortical neurons to oscillate at a frequency corresponding to the frequency of the light pulses.

FIG. 1 is a block diagram depicting a system to perform visual brain entrainment in accordance with an embodiment. The system 100 can include a neural stimulation system ("NSS") 105. The NSS 105 can be referred to as visual NSS 105 or NSS 105. In brief overview, the NSS 105 can include, access, interface with, or otherwise communicate with one or more of a light generation module 110, light adjustment module 115, unwanted frequency filtering module 120, profile manager 125, side effects management module 130, feedback monitor 135, data repository 140, visual signaling component 150, filtering component 155, or feedback component 160. The light generation module 110, light adjustment module 115, unwanted frequency filtering module 120, profile manager 125, side effects management module 130, feedback monitor 135, visual signaling component 150, filtering component 155, or feedback component 160 can each include at least one processing unit or other logic device such as programmable logic array engine, or module configured to communicate with the database repository 140. The light generation module 110, light adjustment module 115, unwanted frequency filtering module 120, profile manager 125, side effects management module 130, feedback monitor 135, visual signaling component 150, filtering component 155, or feedback component 160 can be separate components, a single component, or part of the NSS 105. The system 100 and its components, such as the NSS 105, may include hardware elements, such as one or more processors, logic devices, or circuits. The system 100 and its components, such as the NSS 105, can include one or more hardware or interface component depicted in system 700 in FIGS. 7A and 7B. For example, a component of system 100 can include or execute on one or more processors 721, access storage 728 or memory 722, and communicate via network interface 718.

Still referring to FIG. 1, and in further detail, the NSS 105 can include at least one light generation module 110. The light generation module 110 can be designed and constructed to interface with a visual signaling component 150 to provide instructions or otherwise cause or facilitate the generation of a visual signal, such as a light pulse or flash of light, having one or more predetermined parameter. The light generation module 110 can include hardware or software to receive and process instructions or data packets from one or more module or component of the NSS 105. The light generation module 110 can generate instructions to cause the visual signaling component 150 to generate a visual signal. The light generation module 110 can control or enable the visual signaling component 150 to generate the visual signal having one or more predetermined parameters.

The light generation module 110 can be communicatively coupled to the visual signaling component 150. The light generation module 110 can communicate with the visual signaling component 150 via a circuit, electrical wire, data port, network port, power wire, ground, electrical contacts or pins. The light generation module 110 can wirelessly communicate with the visual signaling component 150 using one or more wireless protocols such as BlueTooth, BlueTooth Low Energy, Zigbee, Z-Wave, IEEE 802.11, WIFI, 3G, 4G. LTE, near field communications ("NFC"), or other short, medium or long range communication protocols, etc. The light generation module 110 can include or access network interface 718 to communicate wirelessly or over a wire with the visual signaling component 150.

The light generation module 110 can interface, control, or otherwise manage various types of visual signaling components 150 in order to cause the visual signaling component 150 to generate, block, control, or otherwise provide the visual signal having one or more predetermined parameters. The light generation module 110 can include a driver configured to drive a light source of the visual signaling component 150. For example, the light source can include a light emitting diode ("LED"), and the light generation module 110 can include an LED driver, chip, microcontroller, operational amplifiers, transistors, resistors, or diodes configured to drive the LED light source by providing electricity or power having certain voltage and current characteristics.

Figure 2A:
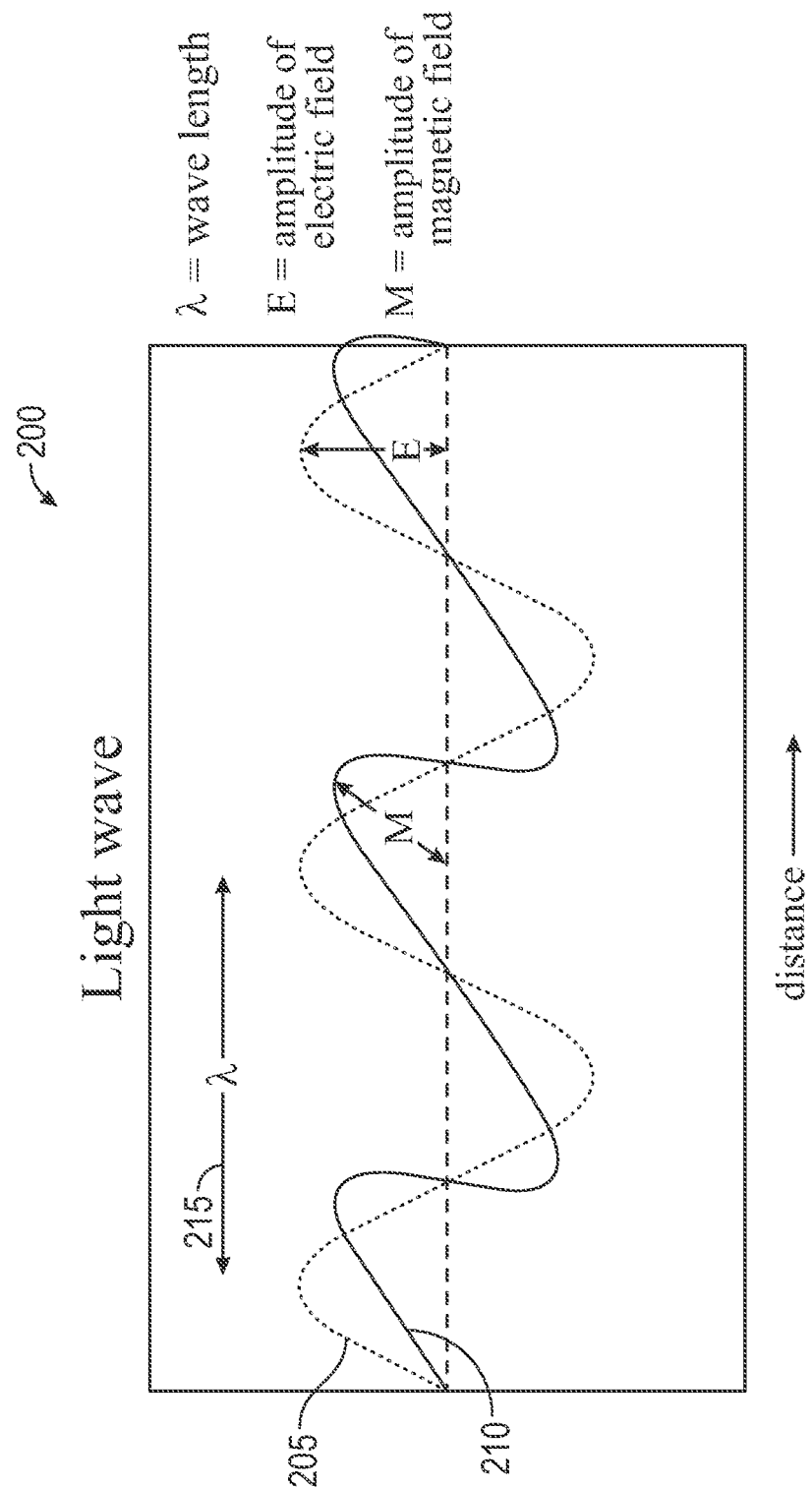

In some embodiments, the light generation module 110 can instruct the visual signaling component 150 to provide a visual signal that include a light wave 200 as depicted in FIG. 2A. The light wave 200 can include or be formed of electromagnetic waves. The electromagnetic waves of the light wave can have respective amplitudes and travel orthogonal to one another as depicted by the amplitude of the electric field 205 versus time and the amplitude of the magnetic field 210 versus time. The light wave 200 can have a wavelength 215. The light wave can also have a frequency. The product of the wavelength 215 and the frequency can be the speed of the light wave. For example, the speed of the light wave can be approximately 299,792,458 meters per second in a vacuum.

The light generation module 110 can instruct the visual signaling component 150 to generate light waves having one or more predetermined wavelength or intensity. The wavelength of the light wave can correspond to the visible spectrum, ultraviolet spectrum, infrared spectrum, or some other wavelength of light. For example, the wavelength of the light wave within the visible spectrum range can range from 390 to 700 nanometers ("nm"). Within the visible spectrum, the light generation module 110 can further specify one or more wavelengths corresponding to one or more colors. For example, the light generation module 110 can instruct the visual signaling component 150 to generate visual signals comprising one or more light waves having one or more wavelength corresponding to one or more of ultraviolet (e.g., 10-380 nm); violet (e.g., 380-450 nm), blue (e.g., 450-495 nm), green (e.g., 495-570 nm), yellow (e.g., 570-590 nm), orange (e.g., 590-620 nm), red (e.g., 620-750 nm); or infrared (e.g., 750-1000000 nm). The wavelength can range from 10 nm to 100 micrometers. In some embodiments, the wavelength can be in the range of 380 to 750 nm.

Figure 2B:
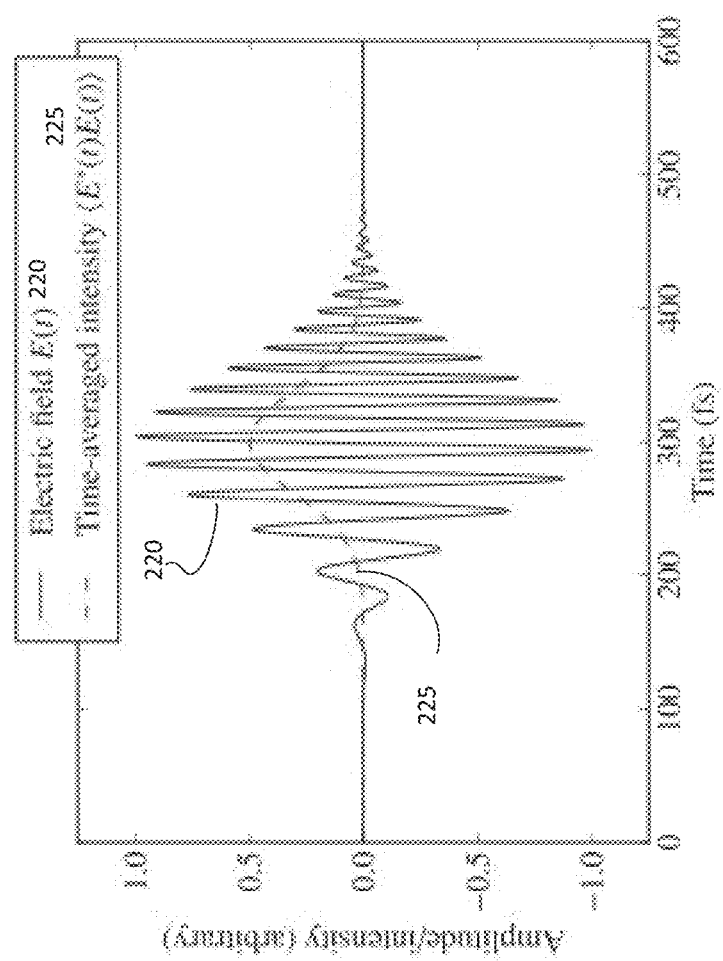

The light generation module 110 can determine to provide visual signals that include light pulses. The light generation module 110 can instruct or otherwise cause the visual signaling component 150 to generate light pulses. A light pulse can refer to a burst of light waves. For example, FIG. 2B illustrates a burst of a light wave. The burst of light wave can refer to a burst of an electric field 250 generated by the light wave. The burst of the electric field 250 of the light wave can be referred to as a light pulse or a flash of light. For example, a light source that is intermittently turned on and off can create bursts, flashes or pulses of light.

FIG. 2C illustrates pulses of light 235a-c in accordance with an embodiment. The light pulses 235a-c can be illustrated via a graph in the frequency spectrum where the y-axis represent frequency of the light wave (e.g., the speed of the light wave divided by the wavelength) and the x-axis represents time. The visual signal can include modulations of light wave between a frequency of $F_a$ and frequency different from $F_a$. For example, the NSS 105 can modulate a light wave between a frequency in the visible spectrum, such as $F_a$, and a frequency outside the visible spectrum. The NSS 105 can modulate the light wave between two or more frequencies, between an on state and an off state, or between a high power state and a low power state.

In some cases, the frequency of the light wave used to generate the light pulse can be constant at $F_a$, thereby generating a square wave in the frequency spectrum. In some embodiments, each of the three pulses 235a-c can include light waves having a same frequency $F_a$.

Figure 2D:
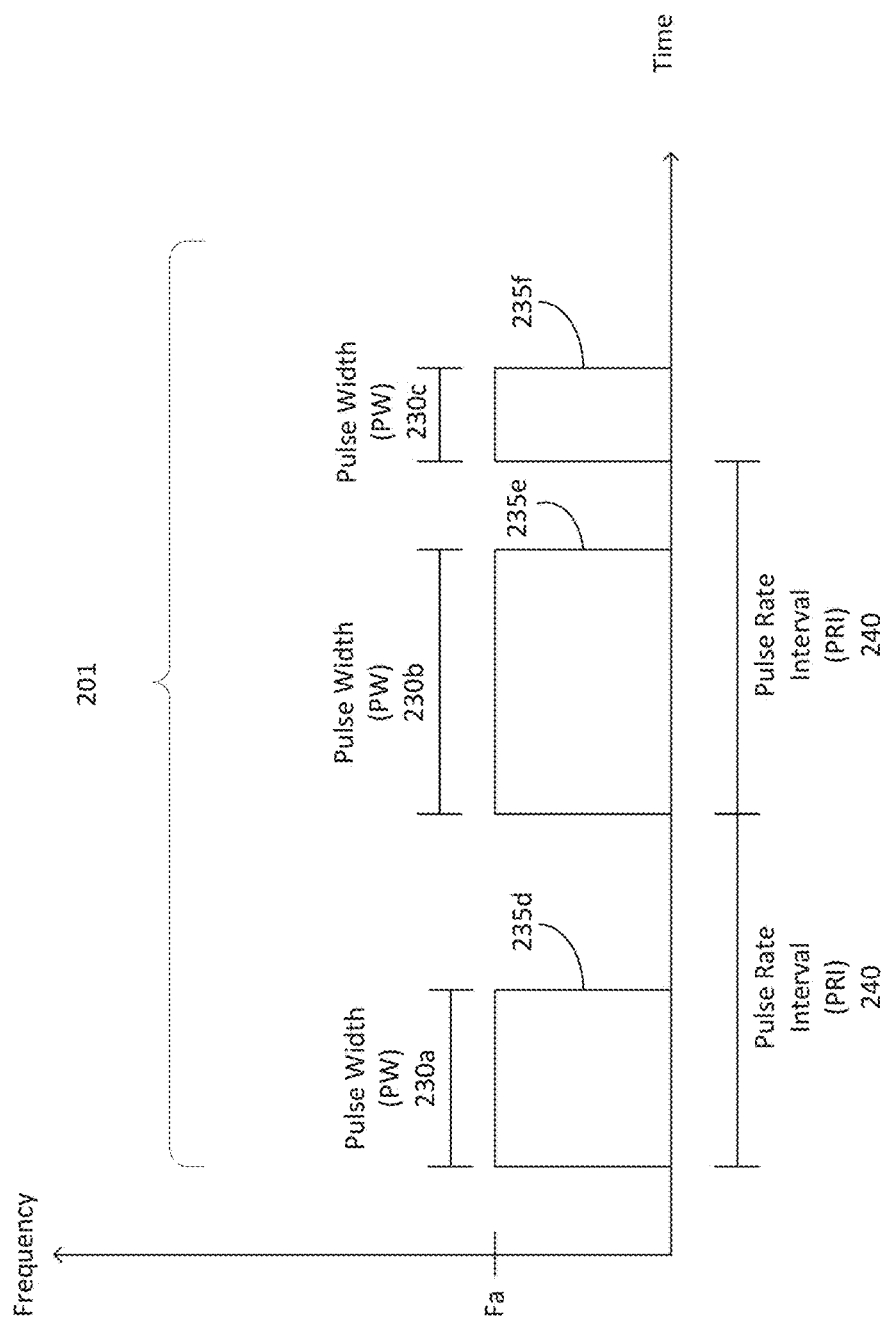

The width of each of the light pulses (e.g., the duration of the burst of the light wave) can correspond to a pulse width 230a. The pulse width 230a can refer to the length or duration of the burst. The pulse width 230a can be measured in units of time or distance. In some embodiments, the pulses 235a-c can include lights waves having different frequencies from one another. In some embodiments, the pulses 235a-c can have different pulse widths 230a from one another, as illustrated in FIG. 2D. For example, a first pulse 235d of FIG. 2D can have a pulse width 230a, while a second pulse 235e has a second pulse width 230b that is greater than the first pulse width 230a. A third pulse 235f can have a third pulse width 230c that is less than the second pulse width 230b. The third pulse width 230c can also be less than the first pulse width 230a. While the pulse widths 230a-c of the pulses 235d-f of the pulse train may vary, the light generation module 110 can maintain a constant pulse rate interval 240 for the pulse train.

The pulses 235a-c can form a pulse train having a pulse rate interval 240. The pulse rate interval 240 can be quantified using units of time. The pulse rate interval 240 can be based on a frequency of the pulses of the pulse train 201. The frequency of the pulses of the pulse train 201 can be referred to as a modulation frequency. For example, the light generation module 110 can provide a pulse train 201 with a predetermined frequency corresponding to gamma activity, such as 40 Hz. To do so, the light generation module 110 can determine the pulse rate interval 240 by taking the multiplicative inverse (or reciprocal) of the frequency (e.g., 1 divided by the predetermined frequency for the pulse train). For example, the light generation module 110 can take the multiplicative inverse of 40 Hz by dividing 1 by 40 Hz to determine the pulse rate interval 240 as 0.025 seconds. The pulse rate interval 240 can remain constant throughout the pulse train. In some embodiments, the pulse rate interval 240 can vary throughout the pulse train or from one pulse train to a subsequent pulse train. In some embodiments, the number of pulses transmitted during a second can be fixed, while the pulse rate interval 240 varies.

Figure 2E:
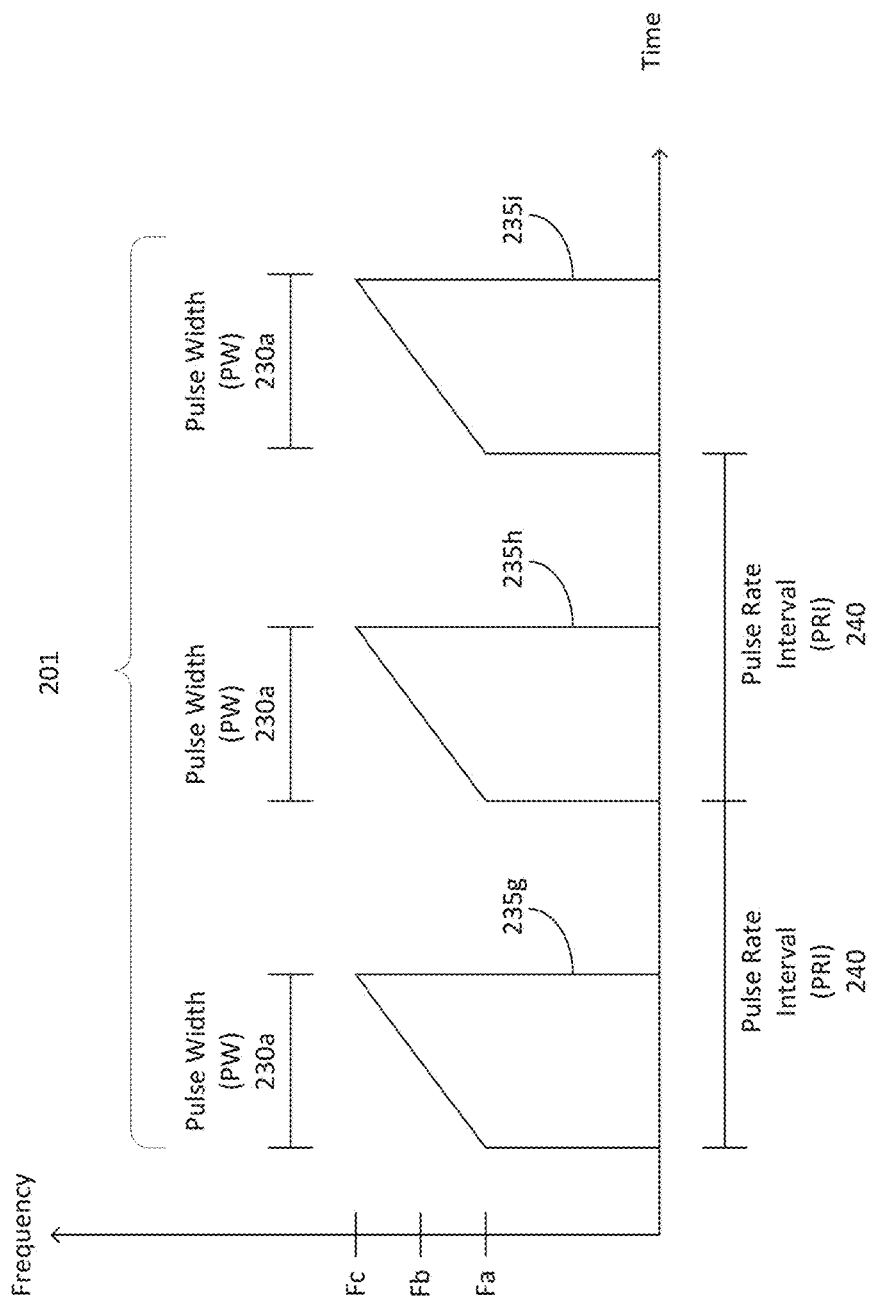

In some embodiments, the light generation module 110 can generate a light pulse having a light wave that varies in frequency. For example, the light generation module 110 can generate up-chirp pulses where the frequency of the light wave of the light pulse increases from the beginning of the pulse to the end of the pulse as illustrated in FIG. 2E. For example, the frequency of a light wave at the beginning of pulse 235g can be $F_a$. The frequency of the light wave of the pulse 235g can increase from $F_a$ to $F_b$ in the middle of the pulse 235g, and then to a maximum of Fc at the end of the pulse 235g. Thus, the frequency of the light wave used to generate the pulse 235g can range from $F_a$ to $F_c$. The frequency can increase linearly, exponentially, or based on some other rate or curve.

Figure 2F:
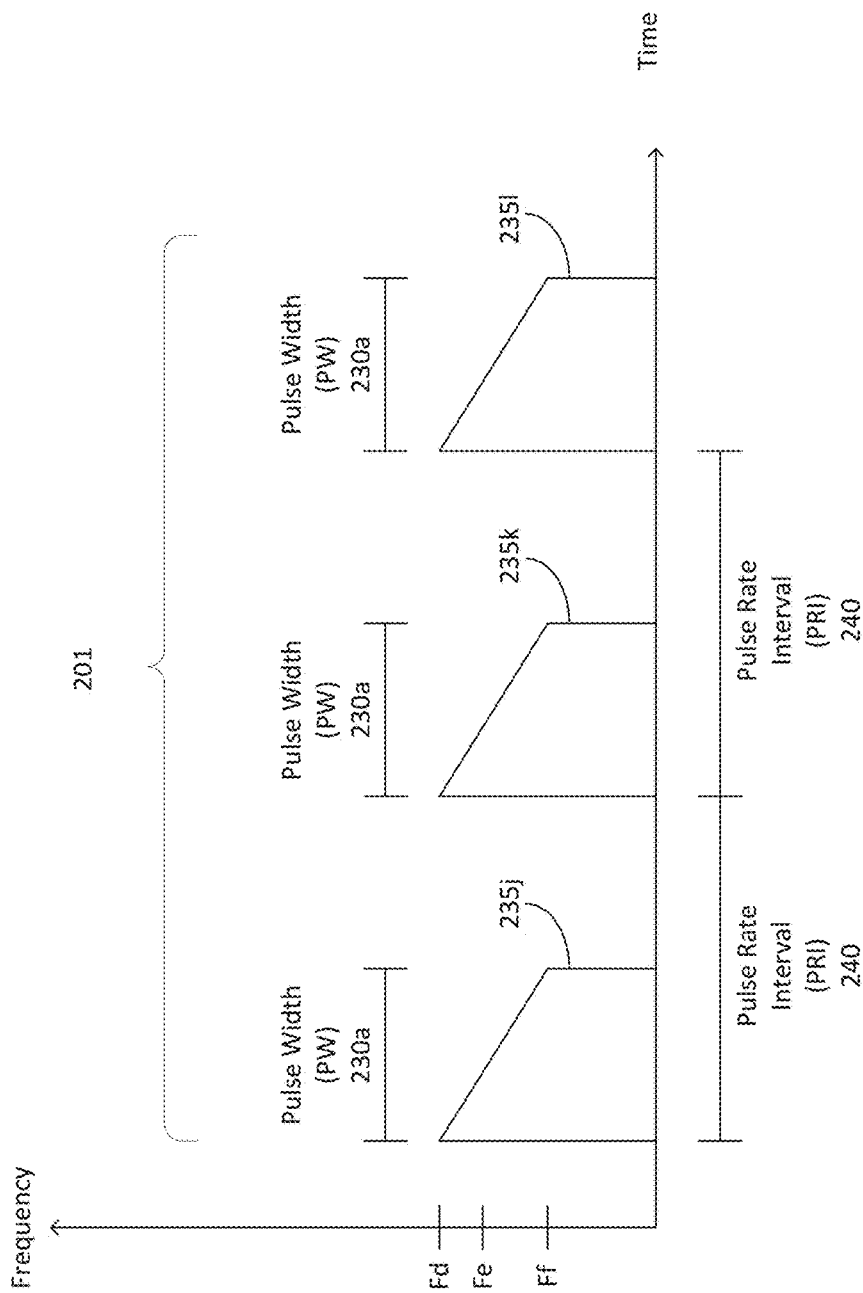

The light generation module 110 can generate down-chirp pulses, as illustrated in FIG. 2F, where the frequency of the light wave of the light pulse decreases from the beginning of the pulse to the end of the pulse. For example, the frequency of a light wave at the beginning of pulse 235j can be $F_d$. The frequency of the light wave of the pulse 235j can decrease from Fd to Fe in the middle of the pulse 235j, and then to a minimum of Ff at the end of the pulse 235j. Thus, the frequency of the light wave used to generate the pulse 235j can range from $F_d$ to $F_f$. The frequency can decrease linearly, exponentially, or based on some other rate or curve.

Visual signaling component 150 can be designed and constructed to generate the light pulses responsive to instructions from the light generation module 110. The instructions can include, for example, parameters of the light pulse such as a frequency or wavelength of the light wave, intensity, duration of the pulse, frequency of the pulse train, pulse rate interval, or duration of the pulse train (e.g., a number of pulses in the pulse train or the length of time to transmit a pulse train having a predetermined frequency). The light pulse can be perceived, observed, or otherwise identified by the brain via ocular means such as eyes. The light pulses can be transmitted to the eye via direct visual field or peripheral visual field.

Figure 3A:
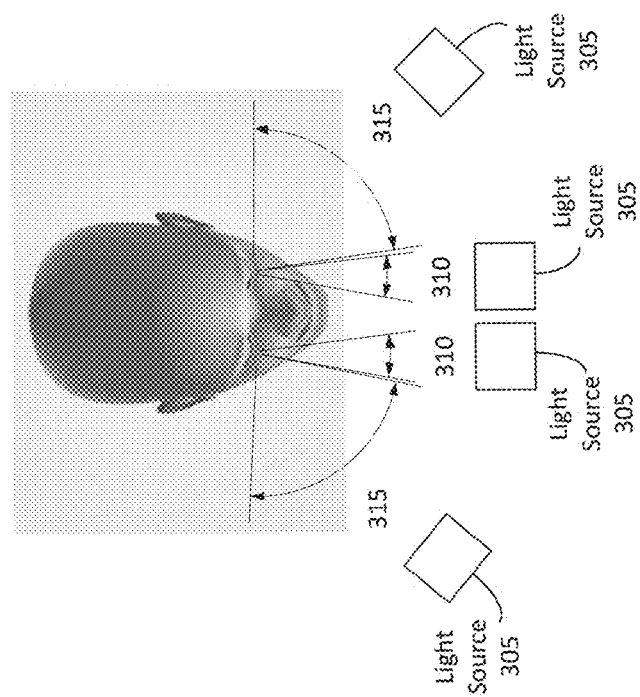
FIGS. 3A-3C illustrate fields of vision in which visual signals can be transmitted for visual brain entrainment in accordance with some embodiments.
Figure 3B:
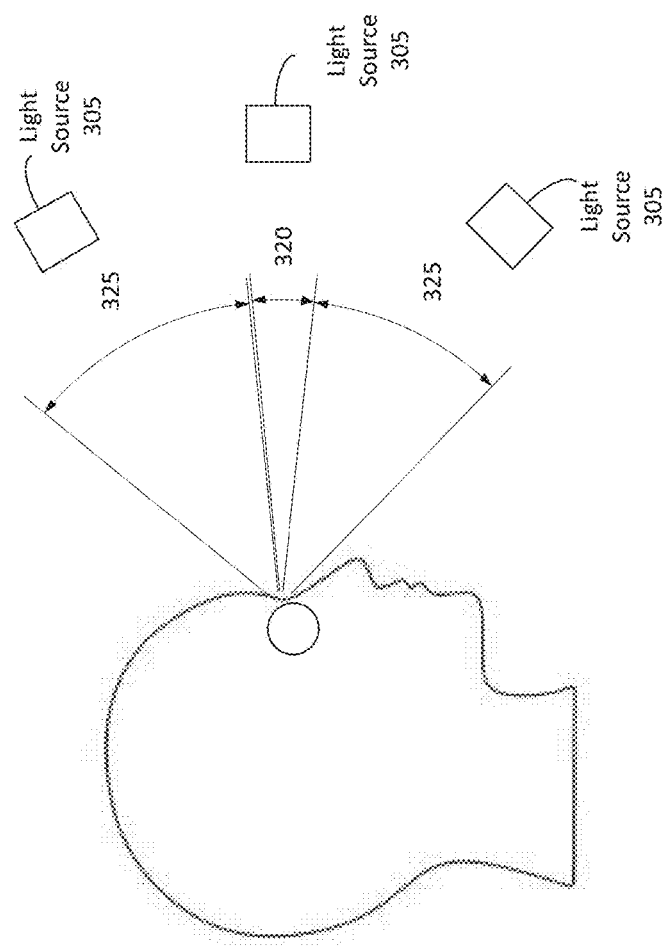
Figure 3C:
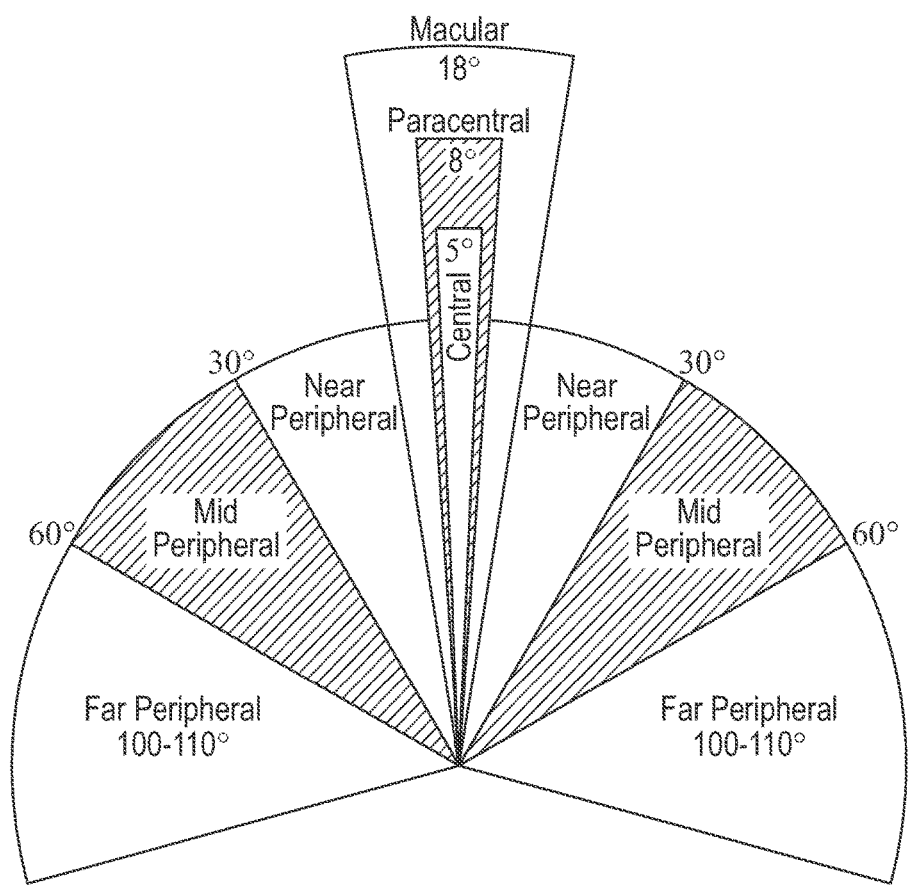

FIG. 3A illustrates a horizontal direct visual field 310 and a horizontal peripheral visual field. FIG. 3B illustrates a vertical direct visual field 320 and a vertical peripheral visual field 325. FIG. 3C illustrates degrees of direct visual fields and peripheral visual fields, including relative distances at which visual signals might be perceived in the different visual fields. The visual signaling component 150 can include a light source 305. The light source 305 can be positioned to transmit light pulses into the direct visual field 310 or 320 of a person's eyes. The NSS 105 can be configured to transmit light pulses into the direct visual field 310 or 320 because this may facilitate brain entrainment as the person may pay more attention to the light pulses. The level of attention can be quantitatively measured directly in the brain, indirectly through the person's eye behavior, or by active feedback (e.g., mouse tracking).

The light source 305 can be positioned to transmit light pulses into a peripheral visual field 315 or 325 of a person's eyes. For example, the NSS 105 can transmit light pulses into the peripheral visual field 315 or 325 as these light pulses may be less distracting to the person who might be performing other tasks, such as reading, walking, driving, etc. Thus, the NSS 105 can provide subtle, on-going visual stimulation by transmitting light pulses via the peripheral visual field.

In some embodiments, the light source 305 can be head-worn, while in other embodiments the light source 305 can be held by a subject's hands, placed on a stand, hung from a ceiling, or connected to a chair or otherwise positioned to direct light towards the direct or peripheral visual fields. For example, a chair or externally supported system can include or position the light source 305 to provide the visual input while maintaining a fixed/pre-specified relationship between the subject's visual field and the visual stimulus. The system can provide an immersive experience. For example, the system can include an opaque or partially opaque dome that includes the light source. The dome can positioned over the subject's head while the subject sits or reclines in chair. The dome can cover portions of the subject's visual field, thereby reducing external distractions and facilitating entrainment of regions of the brain.

The light source 305 can include any type of light source or light emitting device. The light source can include a coherent light source, such as a laser. The light source 305 can include an LED, Organic LED, fluorescent light source, incandescent light, or any other light emitting device. The light source can include a lamp, light bulb, or one or more light emitting diodes of various colors (e.g., white, red, green, blue). In some embodiments, the light source includes a semiconductor light emitting device, such as a light emitting diode of any spectral or wavelength range. In some embodiments, the light source 305 includes a broadband lamp or a broadband light source. In some embodiments, the light source includes a black light. In some embodiments, light source 305 includes a hollow cathode lamp, a fluorescent tube light source, a neon lamp, an argon lamp, a plasma lamp, a xenon flash lamp, a mercury lamp, a metal halide lamp, or a sulfur lamp. In some embodiments, the light source 305 includes a laser, or a laser diode. In some embodiments, light source 305 includes an OLED, PHOLED, QDLED, or any other variation of a light source utilizing an organic material. In some embodiments, light source 305 includes a monochromatic light source. In some embodiments, light source 305 includes a polychromatic light source. In some embodiments, the light source 305 includes a light source emitting light partially in the spectral range of ultraviolet light. In some embodiments, light source 305 includes a device, product or a material emitting light partially in the spectral range of visible light. In some embodiments, light source 305 is a device, product or a material partially emanating or emitting light in the spectral range of the infrared light. In some embodiments, light source 305 includes a device, product or a material emanating or emitting light in the visible spectral range. In some embodiments, light source 305 includes a light guide, an optical fiber or a waveguide through which light is emitted from the light source.

In some embodiments, light source 305 includes one or more mirrors for reflecting or redirecting of light. For example, the mirrors can reflect or redirect light towards the direct visual field 310 or 320, or the peripheral visual field 315 or 325. The light source 305 can include interact with microelectromechanical devices ("MEMS"). The light source 305 can include or interact with a digital light projector ("DLP"). In some embodiments, the light source 305 can include ambient light or sunlight. The ambient light or sunlight can be focused by one or more optical lenses and directed towards the direct visual field or peripheral field. The ambient light or sunlight can be directed by one or more mirrors towards the directed visual field or peripheral visual field.

Figure 4A:
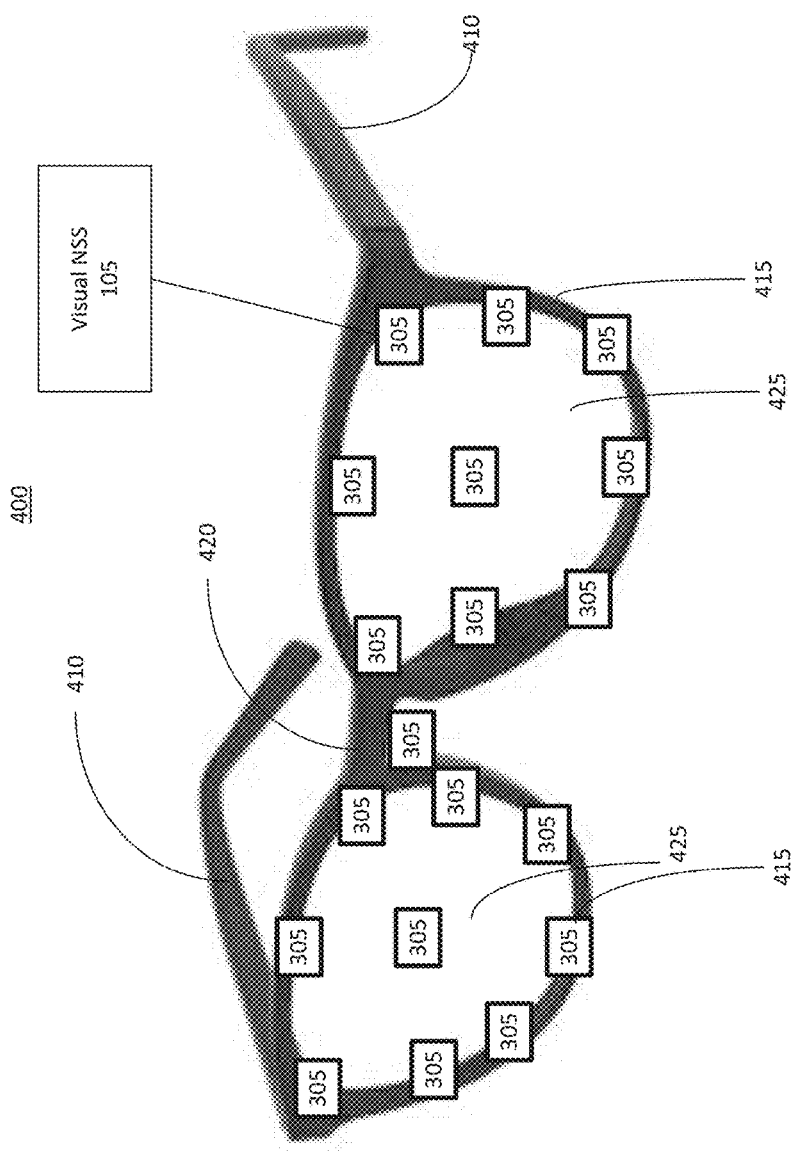
FIGS. 4A-4C illustrate devices configured to transmit visual signals for visual brain entrainment in accordance with some embodiments.

In cases where the light source is ambient light, the ambient light is not positioned but the ambient light can enter the eye via a direct visual field or peripheral visual field. In some embodiments, the light source 305 can be positioned to direct light pulses towards the direct visual field or peripheral field. For example, one or more light sources 305 can be attached, affixed, coupled, mechanically coupled, or otherwise provided with a frame 400 as illustrated in FIG. 4A. In some embodiments, the visual signaling component 150 can include the frame 400. Additional details of the operation of the NSS 105 in conjunction with the frame 400 including one or more light sources 305 are provided below in Section E.

Thus, the light source can include any type of light source such as an optical light source, mechanical light source, or chemical light source. The light source can include any material or object that is reflective or opaque that can generate, emit, or reflect oscillating patterns of light, such as a fan rotating in front of a light, or bubbles. In some embodiments, the light source can include optical illusions that are invisible, physiological phenomena that are within the eye (e.g., pressing the eyeball), or chemicals applied to the eye.

B. Systems and Devices Configured for Neural Stimulation Via Visual Stimulation

Referring now to FIG. 4A, the frame 400 can be designed and constructed to be placed or positioned on a person's head. The frame 400 can be configured to be worn by the person. The frame 400 can be designed and constructed to stay in place. The frame 400 can be configured to be worn and stay in place as a person sits, stands, walks, runs, or lays down flat. The light source 305 can be configured on the frame 400 to project light pulses towards the person's eyes during these various positions. In some embodiments, the light source 305 can be configured to project light pulses towards the person's eyes if their eyelids are closed such that the light pulse penetrates the eyelid to be perceived by the retina. The frame 400 can include a bridge 420. The frame 400 can include one or more eye wires 415 coupled to the bridge 420. The bridge 420 can be positioned in between the eye wires 415. The frame 400 can include one or more temples extending from the one or more eye wires 415. In some embodiments, the eye wires 415 can include or hold a lens 425. In some embodiments, the eye wires 415 can include or hold a solid material 425 or cover 425. The lens, solid material, or cover 425 can be transparent, semi-transparent, opaque, or completely block out external light.

The frame 400 can be referred to as glasses or eyeglasses. The frame 400 can be formed of various materials, including, for example, metal, alloy, aluminum, plastic, rubber, steel, or any other material that provides sufficient structural support for the light sources 305 and can be placed on a subject or user. Eyeglasses or frame 400 can refer to any structure configured to house or hold one or more light sources 305 and be positioned or placed on a subject such that the light sources 305 can directed light towards the fovea or eye of the subject.

One or more light sources 305 can be positioned on or adjacent to the eye wire 415, lens or other solid material 425, or bridge 420. For example, a light source 305 can be positioned in the middle of the eye wire 415 on a solid material 425 in order to transmit light pulses into the direct visual field. In some embodiments, a light source 305 can be positioned at a corner of the eye wire 415, such as a corner of the eye wire 415 coupled to the temple 410, in order to transmit light pulses towards a peripheral field. The lens or solid material 425 can provide visibility through the frame 400. The lens or solid material 425 can provide full visibility, or limited visibility. The lens or solid material 425 can be tinted, opaque, or switchable. For example, a user or subject can change or replace the lens or solid 425 material (e.g., different prescription lens, or different color or level of tint). The NSS 105 can switch or change the lens or solid material 425 (e.g., electrochromic or a liquid crystal display). The NSS 105 can switch or change the lens or solid material 425 to increase or decrease a contrast ratio between the visual stimulation signal provided by the light sources 305 and the ambient light. The NSS 105 can switch or change the lens or solid material 425 to improve adherence, such as by increasing visibility so the subject is more aware of the surrounding environment.

In some cases, a diffuser element can be added between the light source 305 and the eyes or fovea of the subject in order to create a more uniform light distribution. The diffuser can facilitate spreading the light from the light sources 305, thereby making the visual stimulation signal less harsh on the subject.

The NSS 105 can perform visual brain entrainment via a single eye or both eyes. For example, the NSS 105 can direct light pulses to a single eye or both eyes. The NSS 105 can interface with a visual signaling component 150 that includes a frame 400 and two eye wires 415. However, the visual signaling component 150 may include a single light source 305 configured and positioned to direct light pulses to a first eye. The visual signaling component 150 can further include a light blocking component that keeps out or blocks the light pulses generated from the light source 305 from entering a second eye. The visual signaling component 150 can block or prevent light from entering the second eye during the brain entrainment process.

In some embodiments, the visual signaling component 150 can alternatively transmit or direct light pulses to the first eye and the second eye. For example, the visual signaling component 150 can direct light pulses to the first eye for a first time interval. The visual signaling component 150 can direct light pulses to the second eye for a second time interval. The first time interval and the second time interval can be a same time interval, overlapping time intervals, mutually exclusive time intervals, or subsequent time intervals.

Figure 4B:
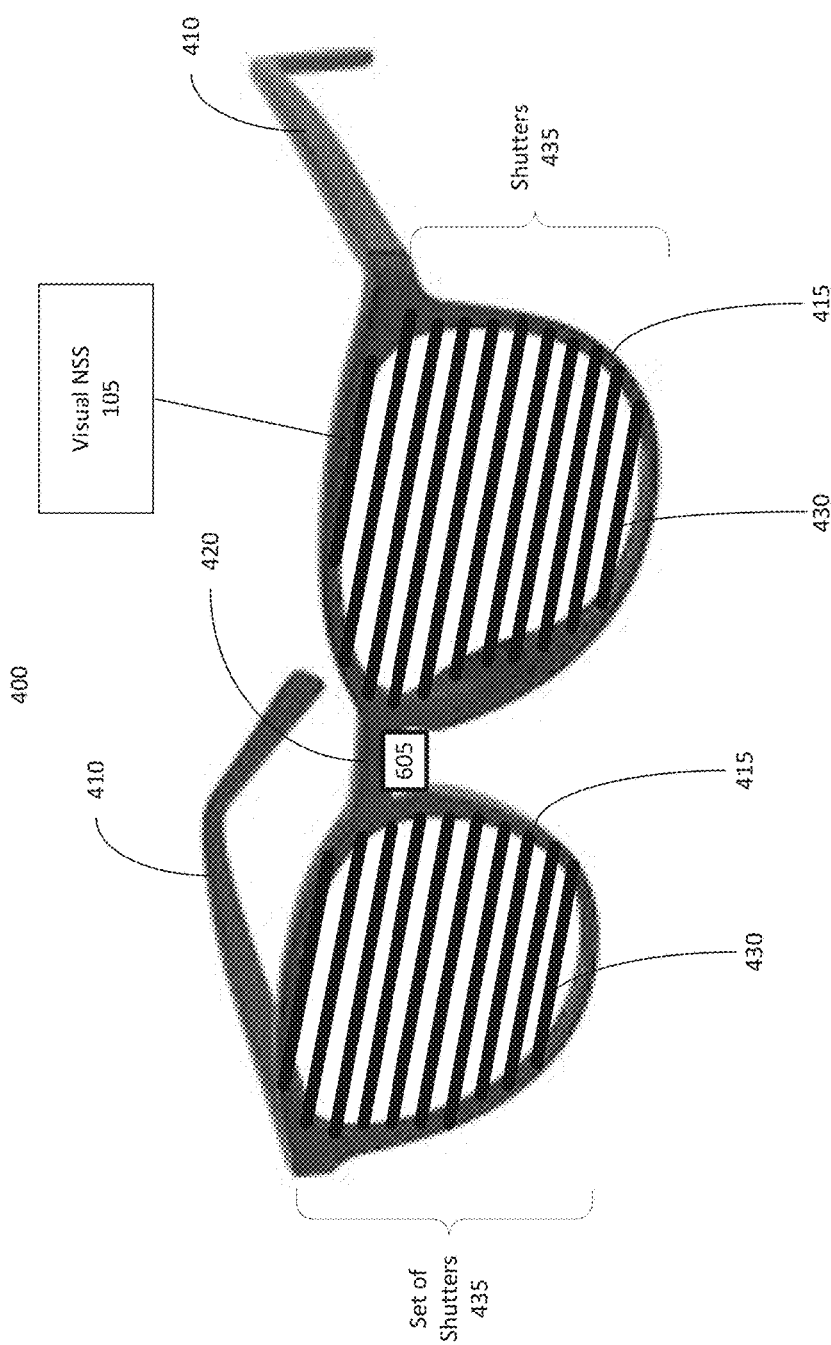

FIG. 4B illustrates a frame 400 comprising a set of shutters 435 that can block at least a portion of light that enters through the eye wire 415. The set of shutters 435 can intermittently block ambient light or sunlight that enters through the eye wire 415. The set of shutters 435 can open to allow light to enter through the eye wire 415, and close to at least partially block light that enters through the eye wire 415. Additional details of the operation of the NSS 105 in conjunction with the frame 400 including one or more shutters 430 are provided below in Section E.

The set of shutters 435 can include one or more shutter 430 that is opened and closed by one or more actuator. The shutter 430 can be formed from one or more materials. The shutter 430 can include one or more materials. The shutter 430 can include or be formed from materials that are capable of at least partially blocking or attenuating light.

The frame 400 can include one or more actuators configured to at least partially open or close the set of shutters 435 or an individual shutter 430. The frame 400 can include one or more types of actuators to open and close the shutters 435. For example, the actuator can include a mechanically driven actuator. The actuator can include a magnetically driven actuator. The actuator can include a pneumonic actuator. The actuator can include a hydraulic actuator. The actuator can include a piezoelectric actuator. The actuator can include a micro-electromechanical systems ("MEMS").

The set of shutters 435 can include one or more shutter 430 that is opened and closed via electrical or chemical techniques. For example, the shutter 430 or set of shutters 435 can be formed from one or more chemicals. The shutter 430 or set of shutters can include one or more chemicals. The shutter 430 or set of shutters 435 can include or be formed from chemicals that are capable of at least partially blocking or attenuating light.

For example, the shutter 430 or set of shutters 435 can include can include photochromic lenses configured to filter, attenuate or block light. The photochromic lenses can automatically darken when exposed to sunlight. The photochromic lens can include molecules that are configured to darken the lens. The molecules can be activated by light waves, such as ultraviolet radiation or other light wavelengths. Thus, the photochromic molecules can be configured to darken the lens in response to a predetermined wavelength of light.

The shutter 430 or set of shutters 435 can include electrochromic glass or plastic. Electrochromic glass or plastic can change from light to dark (e.g., clear to opaque) in response to an electrical voltage or current. Electrochromic glass or plastic can include metal-oxide coatings that are deposited on the glass or plastic, multiple layers, and lithium ions that travel between two electrodes between a layer to lighten or darken the glass.

The shutter 430 or set of shutters 435 can include micro shutters. Micro shutters can include tiny windows that measure 100 by 200 microns. The micro shutters can be arrayed in the eye frame 415 in a waffle-like grid. The individual micro shutters can be opened or closed by an actuator. The actuator can include a magnetic arm that sweeps past the micro shutter to open or close the micro shutter. An open micro shutter can allow light to enter through the eye frame 415, while a closed micro shutter can block, attenuate, or filter the light.

The NSS 105 can drive the actuator to open and close one or more shutters 430 or the set of shutters 435 at a predetermined frequency such as 40 Hz. By opening and closing the shutter 430 at the predetermined frequency, the shutter 430 can allow flashes of light to pass through the eye wire 415 at the predetermined frequency. Thus, the frame 400 including a set of shutters 435 may not include or use separate light source coupled to the frame 400, such as a light source 305 coupled to frame 400 depicted in FIG. 4A.

Figure 4C:
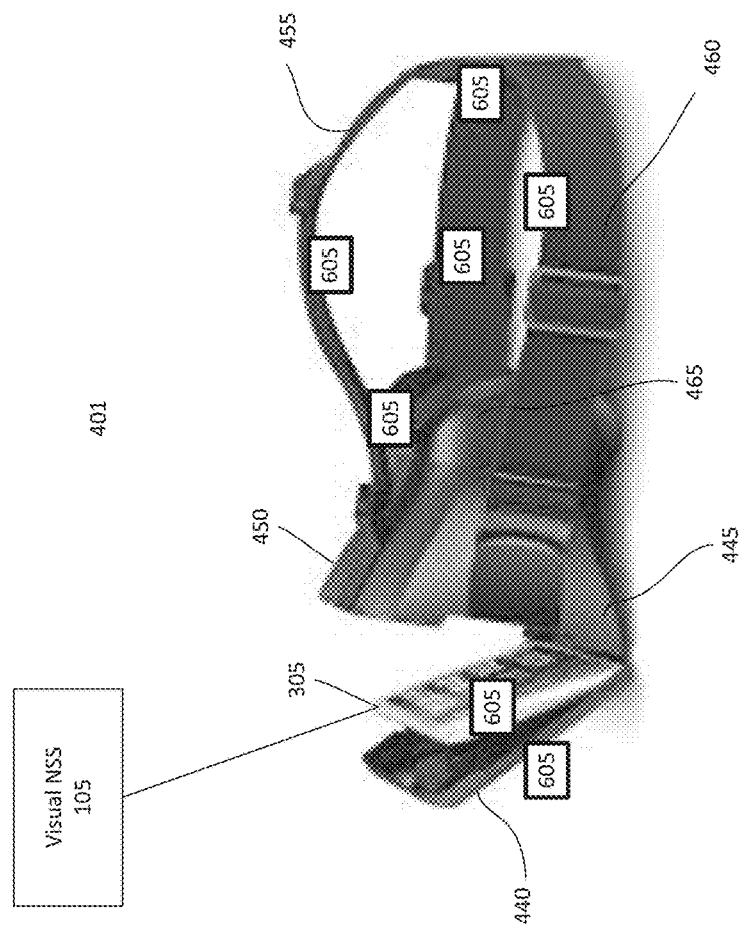

In some embodiments, the visual signaling component 150 or light source 305 can refer to or be included in a virtual reality headset 401, as depicted in FIG. 4C. For example, the virtual reality headset 401 can be designed and constructed to receive a light source 305. The light source 305 can include a computing device having a display device, such as a smartphone or mobile telecommunications device. The virtual reality headset 401 can include a cover 440 that opens to receive the light source 305. The cover 440 can close to lock or hold the light source 305 in place. When closed, the cover 440 and case 450 and 445 can form an enclosure for the light source 305. This enclosure can provide an immersive experience that minimize or eliminates unwanted visual distractions. The virtual reality headset can provide an environment to maximize brainwave entrainment. The virtual reality headset can provide an augmented reality experience. In some embodiments, the light source 305 can form an image on another surface such that the image is reflected off the surface and towards a subject's eye (e.g., a heads up display that overlays on the screen a flickering object or an augmented portion of reality). Additional details of the operation of the NSS 105 in conjunction with the virtual reality headset 401 are provided below in Section B.

The virtual reality headset 401 includes straps 455 and 460 configured to secure the virtual reality headset 401 to a person's head. The virtual reality headset 401 can be secured via straps 455 and 460 such to minimize movement of the headset 401 worn during physical activity, such as walking or running. The virtual reality headset 401 can include a skull cap formed from 460 or 455.

The feedback sensor 605 can include an electrode, dry electrode, gel electrode, saline soaked electrode, or adhesive-based electrodes.

FIGS. 5A-5D illustrate embodiments of the visual signaling component 150 that can include a tablet computing device 500 or other computing device 500 having a display screen 305 as the light source 305. The visual signaling component 150 can transmit light pulses, light flashes, or patterns of light via the display screen 305 or light source 305.

Figure 5B:
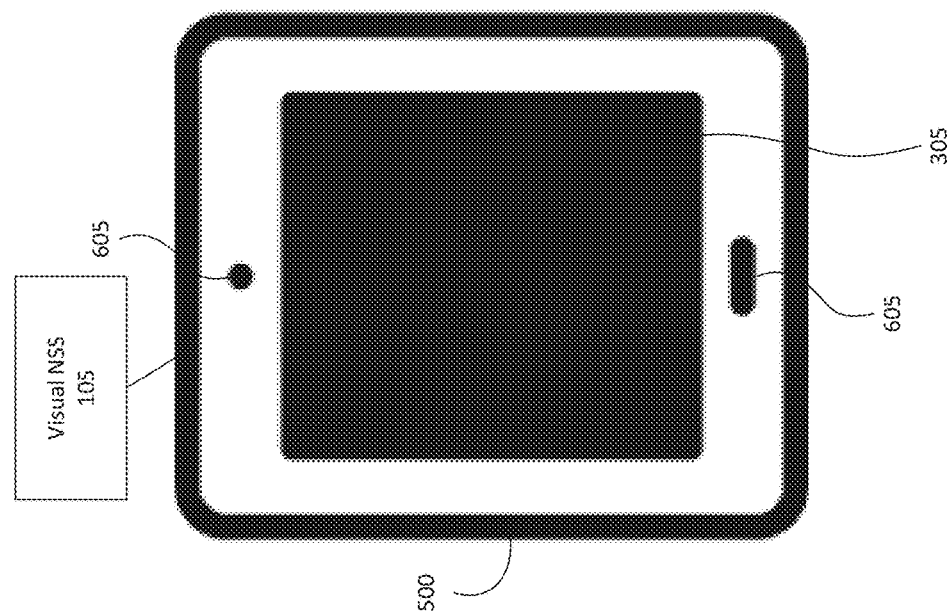
Figure 5A:
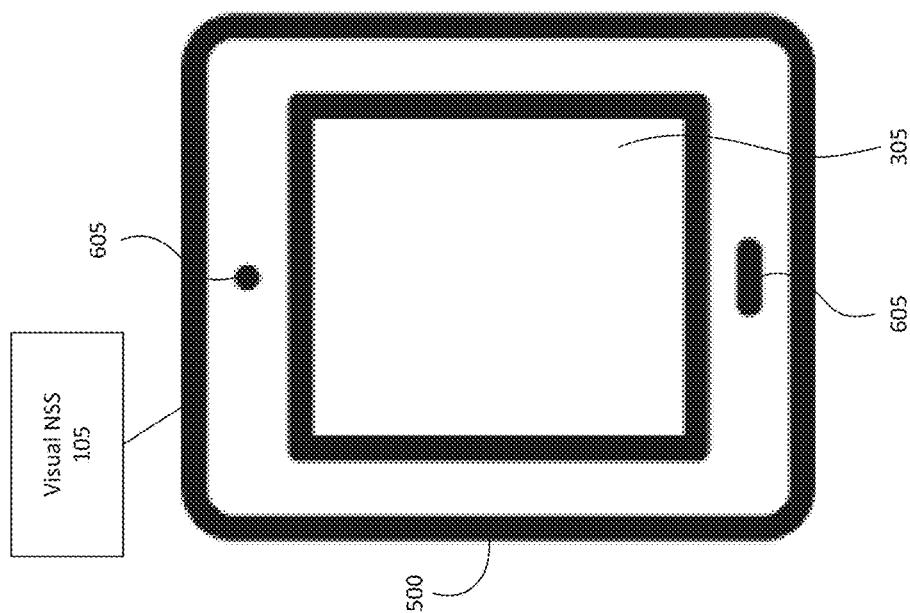

FIG. 5A illustrates a display screen 305 or light source 305 that transmits light. The light source 305 can transmit light comprising a wavelength in the visible spectrum. The NSS 105 can instruct the visual signaling component 150 to transmit light via the light source 305. The NSS 105 can instruct the visual signaling component 150 to transmit flashes of light or light pulses having a predetermined pulse rate interval. For example, FIG. 5B illustrates the light source 305 turned off or disabled such that the light source does not emit light, or emits a minimal or reduced amount of light. The visual signaling component 150 can cause the tablet computing device 500 to enable (e.g., FIG. 5A) and disable (e.g., FIG. 5B) the light source 305 such that flashes of light have a predetermined frequency, such as 40 Hz. The visual signaling component 150 can toggle or switch the light source 305 between two or more states to generate flashes of light or light pulses with the predetermined frequency.

In some embodiments, the light generation module 110 can instruct or cause the visual signaling component 150 to display a pattern of light via display device 305 or light source 305, as depicted in FIGS. 5C and 5D. The light generation module 110 can cause the visual signaling component 150 can flicker, toggle or switch between two or more patterns to generate flashes of light or light pulses. Patterns can include, for example, alternating checkerboard patterns 510 and 515. The pattern can include symbols, characters, or images that can be toggled or adjusted from one state to another state. For example, the color of a character or text relative to a background color can be inverted to cause a switch between a first state 510 and a second state 515. Inverting a foreground color and background color at a predetermined frequency can generate light pulses by way of indicating visual changes that can facilitate adjusting or managing a frequency of neural oscillations. Additional details of the operation of the NSS 105 in conjunction with the tablet 500 are provided below in Section G.

In some embodiments, the light generation module 110 can instruct or cause the visual signaling component 150 to flicker, toggle, or switch between images configured to stimulate specific or predetermined portions of the brain or a specific cortex. The presentation, form, color, motion and other aspects of the light or an image based stimuli can dictate which cortex or cortices are recruited to process the stimuli. The visual signaling component 150 can stimulate discrete portions of the cortex by modulating the presentation of the stimuli to target specific or general regions of interest. The relative position in the field of view, the color of the input, or the motion and speed of the light stimuli can dictate which region of the cortex is stimulated.

For example, the brain can include at least two portions that process predetermined types of visual stimuli: the primary visual cortex on the left side of the brain, and the calcarine fissure on the right side of the brain. Each of these two portions can have one or more multiple sub-portions that process predetermined types of visual stimuli. For example, the calcarine fissure can include a sub-portion referred to as area V5 that can include neurons that respond strongly to motion but may not register stationary objects. Subjects with damage to area V5 may have motion blindness, but otherwise normal vision. In another example, the primary visual cortex can include a sub-portion referred to as area V4 that can include neurons that are specialized for color perception. Subjects with damage to area V4 may have color blindness and only perceive objects in shades of gray. In another example, the primary visual cortex can include a sub-portion referred to as area V1 that includes neurons that respond strongly to contrast edges and helps segment the image into separate objects.

Thus, the light generation module 110 can instruct or cause the visual signaling component 150 to form a type of still image or video, or generate a flicker, or toggle between images that configured to stimulate specific or predetermined portions of the brain or a specific cortex. For example, the light generation module 110 can instruct or cause the visual signaling component 150 to generate images of human faces to stimulate a fusiform face area, which can facilitate brain entrainment for subjects having prosopagnosia or face blindness. The light generation module 110 can instruct or cause the visual signaling component 150 to generate images of faces flickering to target this area of the subject's brain. In another example, the light generation module 110 can instruct the visual signaling component 150 to generate images that include edges or line drawings to stimulate neurons of the primary visual cortex that respond strongly to contrast edges. In some embodiments, The NSS 105 can include, access, interface with, or otherwise communicate with at least one light adjustment module 115. The light adjustment module 115 can be designed and constructed to measure or verify an environmental variable (e.g., light intensity, timing, incident light, ambient light, eye lid status, etc.) to adjust a parameter associated with the visual signal, such as a frequency, amplitude, wavelength, intensity pattern or other parameter of the visual signal. The light adjustment module 115 can automatically vary a parameter of the visual signal based on profile information or feedback. The light adjustment module 115 can receive the feedback information from the feedback monitor 135. The light adjustment module 115 can receive instructions or information from a side effects management module 130. The light adjustment module 115 can receive profile information from profile manager 125.

The NSS 105 can include, access, interface with, or otherwise communicate with at least one unwanted frequency filtering module 120. The unwanted frequency filtering module 120 can be designed and constructed to block mitigate, reduce, or otherwise filter out frequencies of visual signals that are undesired to prevent or reduce an amount of such visual signals from being perceived by the brain. The unwanted frequency filtering module 120 can interface, instruct, control, or otherwise communicate with a filtering component 155 to cause the filtering component 155 to block, attenuate, or otherwise reduce the effect of the unwanted frequency on the neural oscillations.

The NSS 105 can include, access, interface with, or otherwise communicate with at least one profile manager 125. The profile manager 125 can be designed or constructed to store, update, retrieve or otherwise manage information associated with one or more subjects associated with the visual brain entrainment. Profile information can include, for example, historical treatment information, historical brain entrainment information, dosing information, parameters of light waves, feedback, physiological information, environmental information, or other data associated with the systems and methods of brain entrainment.

The NSS 105 can include, access, interface with, or otherwise communicate with at least one side effects management module 130. The side effects management module 130 can be designed and constructed to provide information to the light adjustment module 115 or the light generation module 110 to change one or more parameter of the visual signal in order to reduce a side effect. Side effects can include, for example, nausea, migraines, fatigue, seizures, eye strain, or loss of sight.

The side effects management module 130 can automatically instruct a component of the NSS 105 to alter or change a parameter of the visual signal. The side effects management module 130 can be configured with predetermined thresholds to reduce side effects. For example, the side effects management module 130 can be configured with a maximum duration of a pulse train, maximum intensity of light waves, maximum amplitude, maximum duty cycle of a pulse train (e.g., the pulse width multiplied by the frequency of the pulse train), maximum number of treatments for brainwave entrainment in a time period (e.g., 1 hour, 2 hours, 12 hours, or 24 hours).

The side effects management module 130 can cause a change in the parameter of the visual signal in response to feedback information. The side effect management module 130 can receive feedback from the feedback monitor 135. The side effects management module 130 can determine to adjust a parameter of the visual signal based on the feedback. The side effects management module 130 can compare the feedback with a threshold to determine to adjust the parameter of the visual signal.

The side effects management module 130 can be configured with or include a policy engine that applies a policy or a rule to the current visual signal and feedback to determine an adjustment to the visual signal. For example, if feedback indicates that a patient receiving visual signals has a heart rate or pulse rate above a threshold, the side effects management module 130 can turn off the pulse train until the pulse rate stabilizes to a value below the threshold, or below a second threshold that is lower than the threshold.

The NSS 105 can include, access, interface with, or otherwise communicate with at least one feedback monitor 135. The feedback monitor can be designed and constructed to receive feedback information from a feedback component 160. Feedback component 160 can include, for example, a feedback sensor 605 such as a temperature sensor, heart or pulse rate monitor, physiological sensor, ambient light sensor, ambient temperature sensor, sleep status via actigraphy, blood pressure monitor, respiratory rate monitor, brain wave sensor, EEG probe, electrooculography ('EOG') probes configured to measure the corneo-retinal standing potential that exists between the front and the back of the human eye, accelerometer, gyroscope, motion detector, proximity sensor, camera, microphone, or photo detector.

In some embodiments, a computing device 500 can include the feedback component 160 or feedback sensor 605, as depicted in FIGS. 5C and 5D. For example, the feedback sensor on tablet 500 can include a front-facing camera that can capture images of a person viewing the light source 305.

Figure 6A:
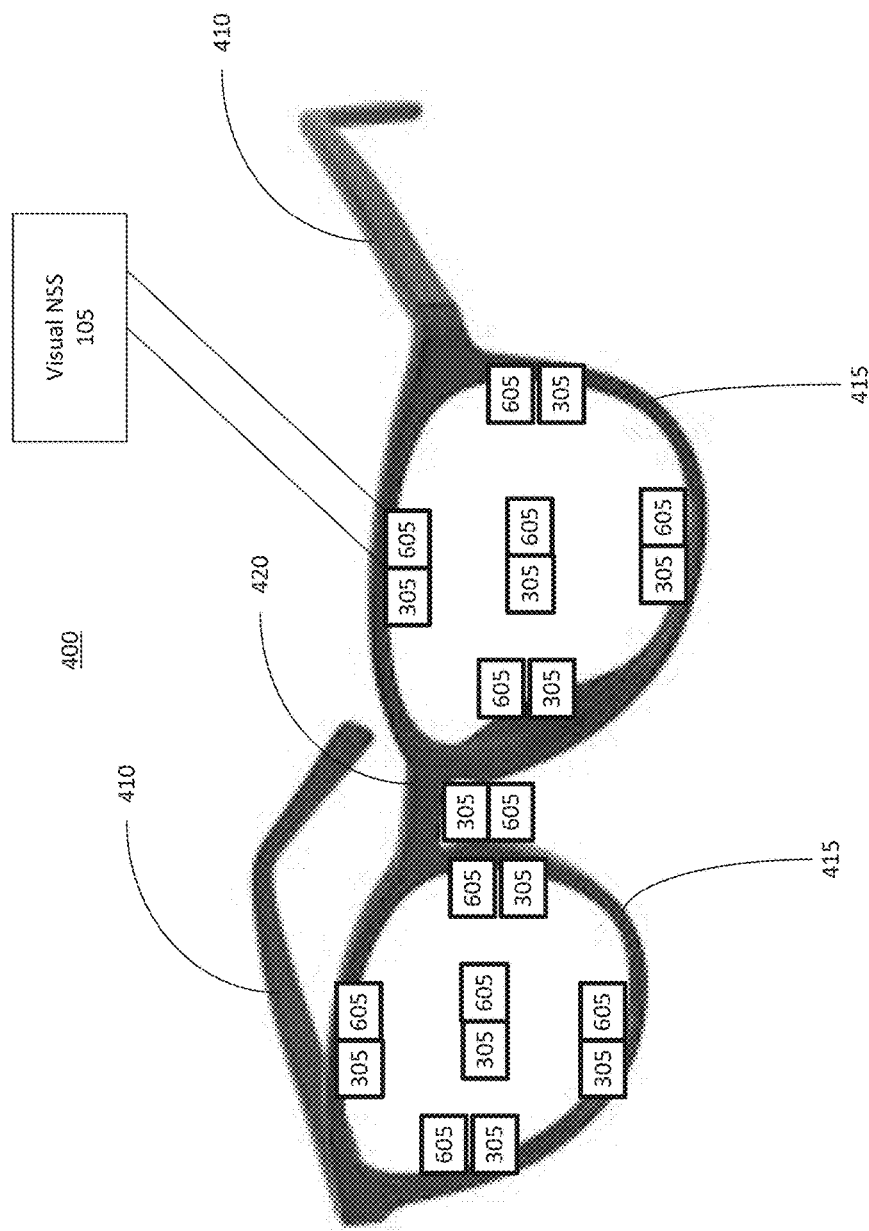
FIGS. 6A and 6B illustrate devices configured to receive feedback to facilitate visual brain entrainment in accordance with some embodiments.

FIG. 6A depicts one or more feedback sensors 605 provided on a frame 400. In some embodiments, a frame 400 can include one or feedback sensors 605 provided on a portion of the frame, such as the bridge 420 or portion of the eye wire 415. The feedback sensor 605 can be provided with or coupled to the light source 305. The feedback sensor 605 can be separate from the light source 305.

The feedback sensor 605 can interact with or communicate with NSS 105. For example, the feedback sensor 605 can provide detected feedback information or data to the NSS 105 (e.g., feedback monitor 135). The feedback sensor 605 can provide data to the NSS 105 in real-time, for example as the feedback sensor 605 detects or senses or information. The feedback sensor 605 can provide the feedback information to the NSS 105 based on a time interval, such as 1 minute, 2 minutes, 5 minutes, 10 minutes, hourly, 2 hours, 4 hours, 12 hours, or 24 hours. The feedback sensor 605 can provide the feedback information to the NSS 105 responsive to a condition or event, such as a feedback measurement exceeding a threshold or falling below a threshold. The feedback sensor 605 can provide feedback information responsive to a change in a feedback parameter. In some embodiments, the NSS 105 can ping, query, or send a request to the feedback sensor 605 for information, and the feedback sensor 605 can provide the feedback information in response to the ping, request, or query.

Figure 6B:
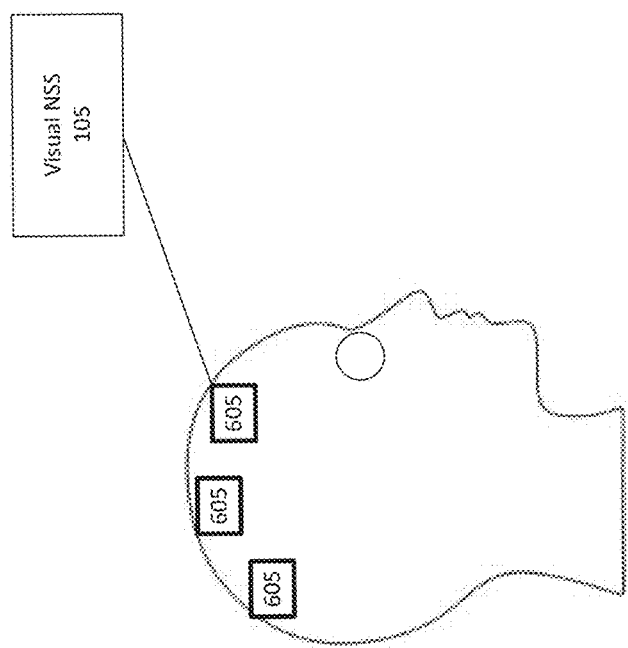

FIG. 6B illustrates feedback sensors 605 placed or positioned at, on, or near a person's head. Feedback sensors 605 can include, for example, EEG probes that detect brain wave activity.

The feedback monitor 135 can detect, receive, obtain, or otherwise identify feedback information from the one or more feedback sensors 605. The feedback monitor 135 can provide the feedback information to one or more component of the NSS 105 for further processing or storage. For example, the profile manager 125 can update profile data structure 145 stored in data repository 140 with the feedback information. Profile manager 125 can associate the feedback information with an identifier of the patient or person undergoing the visual stimulation, as well as a time stamp and date stamp corresponding to receipt or detection of the feedback information.

The feedback monitor 135 can determine a level of attention. The level of attention can refer to the focus provided to the light pulses used for stimulation. The feedback monitor 135 can determine the level of attention using various hardware and software techniques. The feedback monitor 135 can assign a score to the level of attention (e.g., 1 to 10 with 1 being low attention and 10 being high attention, or vice versa, 1 to 100 with 1 being low attention and 100 being high attention, or vice versa, 0 to 1 with 0 being low attention and 1 being high attention, or vice versa), categorize the level of attention (e.g., low, medium, high), grade the attention (e.g., A, B, C, D, or F), or otherwise provide an indication of a level of attention.

In some cases, the feedback monitor 135 can track a person's eye movement to identify a level of attention. The feedback monitor 135 can interface with a feedback component 160 that includes an eye-tracker. The feedback monitor 135 (e.g., via feedback component 160) can detect and record eye movement of the person and analyze the recorded eye movement to determine an attention span or level of attention. The feedback monitor 135 can measure eye gaze which can indicate or provide information related to covert attention. For example, the feedback monitor 135 (e.g., via feedback component 160) can be configured with electro-oculography ("EOG") to measure the skin electric potential around the eye, which can indicate a direction the eye faces relative to the head. In some embodiments, the EOG can include a system or device to stabilize the head so it cannot move in order to determine the direction of the eye relative to the head. In some embodiments, the EOG can include or interface with a head tracker system to determine the position of the heads, and then determine the direction of the eye relative to the head.

In some embodiments, the feedback monitor 135 and feedback component 160 can determine or track the direction of the eye or eye movement using video detection of the pupil or corneal reflection. For example, the feedback component 160 can include one or more camera or video camera. The feedback component 160 can include an infra-red source that sends light pulses towards the eyes. The light can be reflected by the eye. The feedback component 160 can detect the position of the reflection. The feedback component 160 can capture or record the position of the reflection. The feedback component 160 can perform image processing on the reflection to determine or compute the direction of the eye or gaze direction of the eye.

The feedback monitor 135 can compare the eye direction or movement to historical eye direction or movement of the same person, nominal eye movement, or other historical eye movement information to determine a level of attention. For example, if the eye is focused on the light pulses during the pulse train, then the feedback monitor 135 can determine that the level of attention is high. If the feedback monitor 135 determines that the eye moved away from the pulse train for 25% of the pulse train, then the feedback monitor 135 can determine that the level of attention is medium. If the feedback monitor 135 determines that the eye movement occurred for more than 50% of the pulse train or the eye was not focused on the pulse train for greater than 50%, then the feedback monitor 135 can determine that the level of attention is low.

In some embodiments, the system 100 can include a filter (e.g., filtering component 155) to control the spectral range of the light emitted from the light source. In some embodiments, light source includes a light reactive material affecting the light emitted, such as a polarizer, filter, prism or a photochromic material, or electrochromic glass or plastic. The filtering component 155 can receive instructions from the unwanted frequency filtering module 120 to block or attenuate one or more frequencies of light.

The filtering component 155 can include an optical filter that can selectively transmit light in a particular range of wavelengths or colors, while blocking one or more other ranges of wavelengths or colors. The optical filter can modify the magnitude or phase of the incoming light wave for a range of wavelengths. The optical filter can include an absorptive filter, or an interference or dichroic filter. An absorptive filter can take energy of a photon to transform the electromagnetic energy of a light wave into internal energy of the absorber (e.g., thermal energy). The reduction in intensity of a light wave propagating through a medium by absorption of a part of its photons can be referred to as attenuation.

An interference filter or dichroic filter can include an optical filter that reflects one or more spectral bands of light, while transmitting other spectral bands of light. An interference filter or dichroic filter may have a nearly zero coefficient of absorption for one or more wavelengths. Interference filters can be high-pass, low-pass, bandpass, or band-rejection. An interference filter can include one or more thin layers of a dielectric material or metallic material having different refractive indices.

In an illustrative implementation, the NSS 105 can interface with a visual signaling component 150, a filtering component 155, and a feedback component 160. The visual signaling component 150 can include hardware or devices, such as glass frames 400 and one or more light sources 305. The filtering component 155 can include hardware or devices, such as a feedback sensor 605. The filtering component 155 can include hardware, materials or chemicals, such as a polarizing lens, shutters, electrochromic materials or photochromic materials.

C. Computing Environment

Figure 7A:
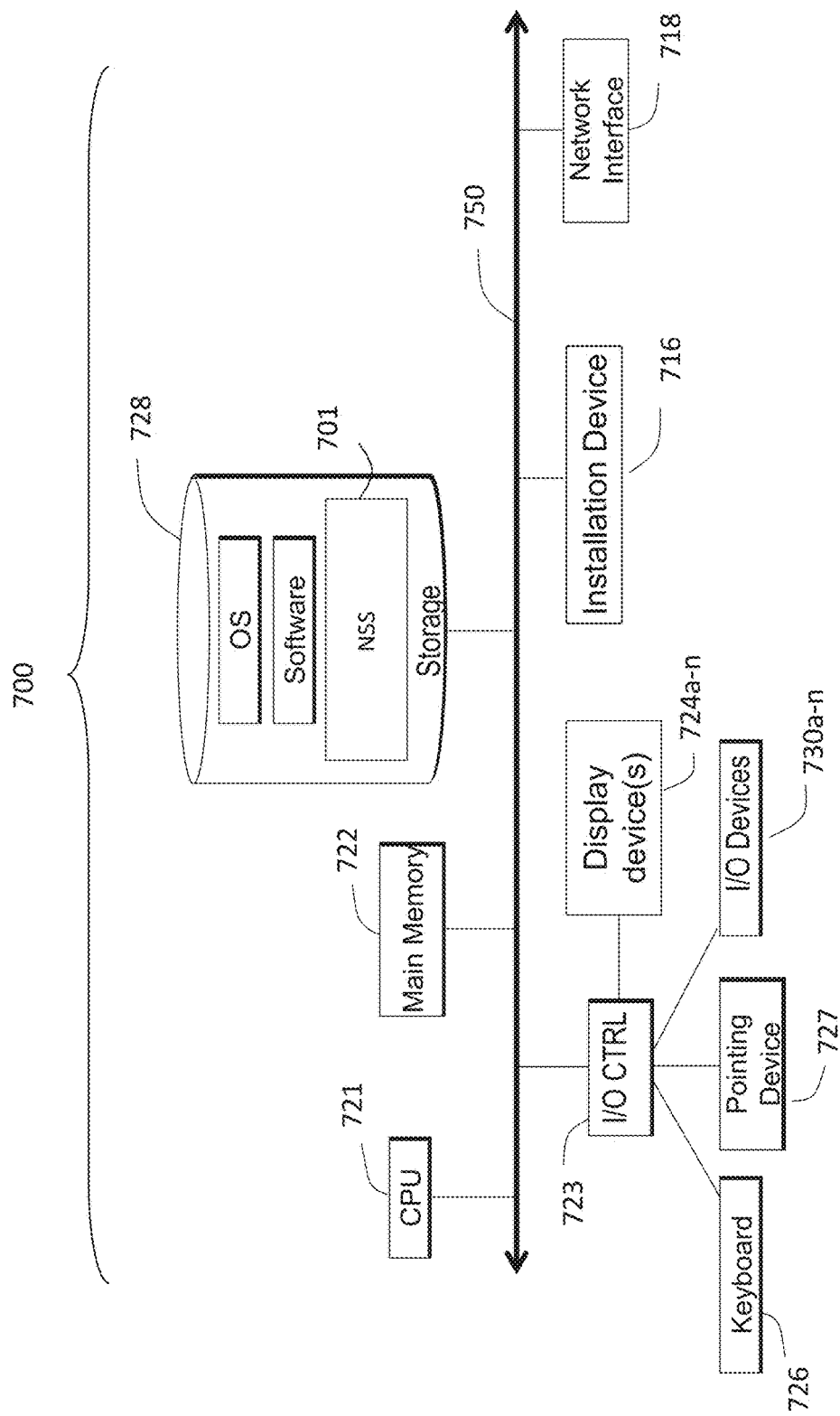
FIGS. 7A and 7B are block diagrams depicting embodiments of computing devices useful in connection with the systems and methods described herein.
Figure 7B:
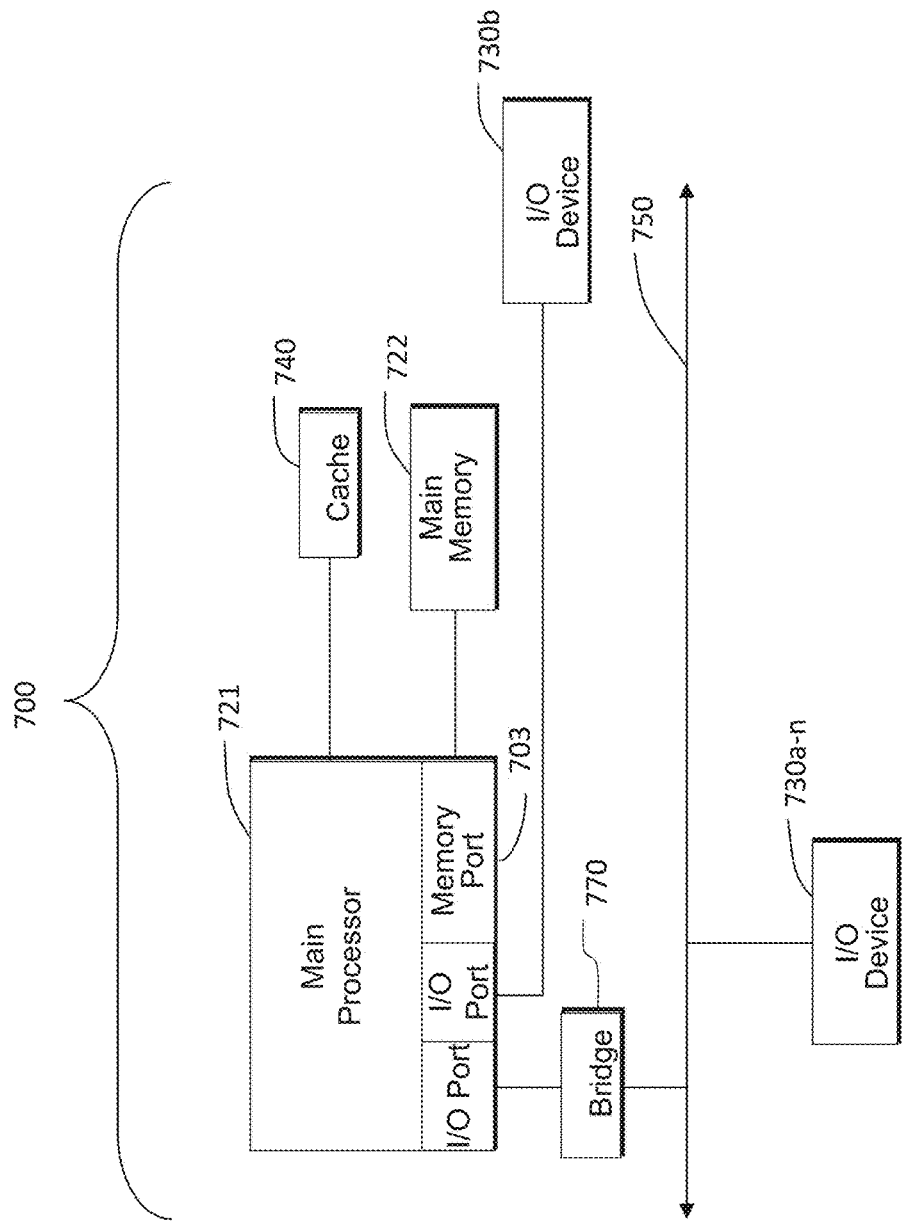

FIGS. 7A and 7B depict block diagrams of a computing device 700. As shown in FIGS. 7A and 7B, each computing device 700 includes a central processing unit 721, and a main memory unit 722. As shown in FIG. 7A, a computing device 700 can include a storage device 728, an installation device 716, a network interface 718, an I/O controller 723, display devices 724a-724n, a keyboard 726 and a pointing device 727, e.g. a mouse. The storage device 728 can include, without limitation, an operating system, software, and software of a neural stimulation system ("NSS") 701. The NSS 701 can include or refer to one or more of Visual NSS 105, NSS 905, NSOS 2305, NSS 2605, Cognitive Assessment System 3105, NSSS 3705. As shown in FIG. 7B, each computing device 700 can also include additional optional elements, e.g. a memory port 703, a bridge 770, one or more input/output devices 730a-730n (generally referred to using reference numeral 730), and a cache memory 740 in communication with the central processing unit 721.

The central processing unit 721 is any logic circuitry that responds to and processes instructions fetched from the main memory unit 722. In many embodiments, the central processing unit 721 is provided by a microprocessor unit, e.g.: those manufactured by Intel Corporation of Mountain View, Calif. those manufactured by Motorola Corporation of Schaumburg, Ill.; the ARM processor (from, e.g., ARM Holdings and manufactured by ST, TI, ATMEL, etc.) and TEGRA system on a chip (SoC) manufactured by Nvidia of Santa Clara, Calif.; the POWER7 processor, those manufactured by International Business Machines of White Plains, N.Y.; or those manufactured by Advanced Micro Devices of Sunnyvale, Calif.; or field programmable gate arrays ("FPGAs") from Altera in San Jose, Calif., Intel Corporation, Xlinix in San Jose, Calif., or MicroSemi in Aliso Viejo, Calif., etc. The computing device 700 can be based on any of these processors, or any other processor capable of operating as described herein. The central processing unit 721 can utilize instruction level parallelism, thread level parallelism, different levels of cache, and multi-core processors. A multi-core processor can include two or more processing units on a single computing component. Examples of multi-core processors include the AMD PHENOM IIX2, INTEL CORE i5 and INTEL CORE i7.

Main memory unit 722 can include one or more memory chips capable of storing data and allowing any storage location to be directly accessed by the microprocessor 721. Main memory unit 722 can be volatile and faster than storage 728 memory. Main memory units 722 can be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 722 or the storage 728 can be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 722 can be based on any of the above described memory chips, or any other available memory chips capable of operating as described herein. In the embodiment shown in FIG. 7A, the processor 721 communicates with main memory 722 via a system bus 750 (described in more detail below). FIG. 7B depicts an embodiment of a computing device 700 in which the processor communicates directly with main memory 722 via a memory port 703. For example, in FIG. 7B the main memory 722 can be DRDRAM.

FIG. 7B depicts an embodiment in which the main processor 721 communicates directly with cache memory 740 via a secondary bus, sometimes referred to as a backside bus. In other embodiments, the main processor 721 communicates with cache memory 740 using the system bus 750. Cache memory 740 typically has a faster response time than main memory 722 and is typically provided by SRAM, BSRAM, or EDRAM. In the embodiment shown in FIG. 7B, the processor 721 communicates with various I/O devices 730 via a local system bus 750. Various buses can be used to connect the central processing unit 721 to any of the I/O devices 730, including a PCI bus, a PCI-X bus, or a PCI-Express bus, or a NuBus. For embodiments in which the I/O device is a video display 724, the processor 721 can use an Advanced Graphics Port (AGP) to communicate with the display 724 or the I/O controller 723 for the display 724. FIG. 7B depicts an embodiment of a computer 700 in which the main processor 721 communicates directly with I/O device 730b or other processors 721' via HYPERTRANSPORT, RAPIDIO, or INFINIBAND communications technology. FIG. 7B also depicts an embodiment in which local busses and direct communication are mixed: the processor 721 communicates with I/O device 730a using a local interconnect bus while communicating with I/O device 730b directly.

A wide variety of I/O devices 730a-730n can be present in the computing device 700. Input devices can include keyboards, mice, trackpads, trackballs, touchpads, touch mice, multi-touch touchpads and touch mice, microphones (analog or MEMS), multi-array microphones, drawing tablets, cameras, single-lens reflex camera (SLR), digital SLR (DSLR), CMOS sensors, CCDs, accelerometers, inertial measurement units, infrared optical sensors, pressure sensors, magnetometer sensors, angular rate sensors, depth sensors, proximity sensors, ambient light sensors, gyroscopic sensors, or other sensors. Output devices can include video displays, graphical displays, speakers, headphones, inkjet printers, laser printers, and 3D printers.

Devices 730a-730n can include a combination of multiple input or output devices, including, e.g., Microsoft KINECT, Nintendo Wiimote for the WII, Nintendo WII U GAMEPAD, or Apple IPHONE. Some devices 730a-730n allow gesture recognition inputs through combining some of the inputs and outputs. Some devices 730a-730n provides for facial recognition which can be utilized as an input for different purposes including authentication and other commands. Some devices 730a-730n provides for voice recognition and inputs, including, e.g., Microsoft KINECT, SIRI for IPHONE by Apple, Google Now or Google Voice Search.

Additional devices 730a-730n have both input and output capabilities, including, e.g., haptic feedback devices, touchscreen displays, or multi-touch displays. Touchscreen, multi-touch displays, touchpads, touch mice, or other touch sensing devices can use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices can allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, can have larger surfaces, such as on a table-top or on a wall, and can also interact with other electronic devices. Some I/O devices 730a-730n, display devices 724a-724n or group of devices can be augmented reality devices. The I/O devices can be controlled by an I/O controller 721 as shown in FIG. 7A. The I/O controller 721 can control one or more I/O devices, such as, e.g., a keyboard 126 and a pointing device 727, e.g., a mouse or optical pen. Furthermore, an I/O device can also provide storage and/or an installation medium 116 for the computing device 700. In still other embodiments, the computing device 700 can provide USB connections (not shown) to receive handheld USB storage devices. In further embodiments, an I/O device 730 can be a bridge between the system bus 750 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 724a-724n can be connected to I/O controller 721. Display devices can include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays can use, e.g. stereoscopy, polarization filters, active shutters, or autostereoscopy. Display devices 724a-724n can also be a head-mounted display (HMD). In some embodiments, display devices 724a-724n or the corresponding I/O controllers 723 can be controlled through or have hardware support for OPENGL or DIRECTX API or other graphics libraries.

In some embodiments, the computing device 700 can include or connect to multiple display devices 724a-724n, which each can be of the same or different type and/or form. As such, any of the I/O devices 730a-730n and/or the I/O controller 723 can include any type and/or form of suitable hardware, software, or combination of hardware and software to support, enable or provide for the connection and use of multiple display devices 724a-724n by the computing device 700. For example, the computing device 700 can include any type and/or form of video adapter, video card, driver, and/or library to interface, communicate, connect or otherwise use the display devices 724a-724n. In one embodiment, a video adapter can include multiple connectors to interface to multiple display devices 724a-724n. In other embodiments, the computing device 700 can include multiple video adapters, with each video adapter connected to one or more of the display devices 724a-724n. In some embodiments, any portion of the operating system of the computing device 700 can be configured for using multiple displays 724a-724n. In other embodiments, one or more of the display devices 724a-724n can be provided by one or more other computing devices 700a or 700b connected to the computing device 700, via the network 740. In some embodiments software can be designed and constructed to use another computer's display device as a second display device 724a for the computing device 700. For example, in one embodiment, an Apple iPad can connect to a computing device 700 and use the display of the device 700 as an additional display screen that can be used as an extended desktop. One ordinarily skilled in the art will recognize and appreciate the various ways and embodiments that a computing device 700 can be configured to have multiple display devices 724a-724n.

Referring again to FIG. 7A, the computing device 700 can comprise a storage device 728 (e.g. one or more hard disk drives or redundant arrays of independent disks) for storing an operating system or other related software, and for storing application software programs such as any program related to the software for the NSS. Examples of storage device 728 include, e.g., hard disk drive (HDD); optical drive including CD drive, DVD drive, or BLU-RAY drive; solid-state drive (SSD); USB flash drive; or any other device suitable for storing data. Some storage devices can include multiple volatile and non-volatile memories, including, e.g., solid state hybrid drives that combine hard disks with solid state cache. Some storage device 728 can be non-volatile, mutable, or read-only. Some storage device 728 can be internal and connect to the computing device 700 via a bus 750. Some storage device 728 can be external and connect to the computing device 700 via a I/O device 730 that provides an external bus. Some storage device 728 can connect to the computing device 700 via the network interface 718 over a network, including, e.g., the Remote Disk for MACBOOK AIR by Apple. Some client devices 700 can not require a non-volatile storage device 728 and can be thin clients or zero clients 202. Some storage device 728 can also be used as an installation device 716, and can be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Computing device 700 can also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc.

Furthermore, the computing device 700 can include a network interface 718 to interface to the network 740 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 700 communicates with other computing devices 700' via any type and/or form of gateway or tunneling protocol e.g. Secure Socket Layer (SSL) or Transport Layer Security (TLS), or the Citrix Gateway Protocol manufactured by Citrix Systems. Inc. of Ft. Lauderdale, Fla. The network interface 118 can comprise a built-in network adapter, network interface card, PCMCIA network card. EXPRESSCARD network card, card bus network adapter, wireless network adapter, USB network adapter, modem or any other device suitable for interfacing the computing device 700 to any type of network capable of communication and performing the operations described herein.

A computing device 700 of the sort depicted in FIG. 7A can operate under the control of an operating system, which controls scheduling of tasks and access to system resources. The computing device 700 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 7000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Wash.; MAC OS and iOS, manufactured by Apple, Inc. of Cupertino, Calif.; and Linux, a freely-available operating system. e.g. Linux Mint distribution ("distro") or Ubuntu, distributed by Canonical Ltd. of London, United Kingdom; or Unix or other Unix-like derivative operating systems; and Android, designed by Google, of Mountain View, Calif. among others. Some operating systems, including, e.g., the CHROME OS by Google, can be used on zero clients or thin clients, including, e.g., CHROMEBOOKS.

The computer system 700 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 700) has sufficient processor power and memory capacity to perform the operations described herein. In some embodiments, the computing device 700 can have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 700 is a gaming system. For example, the computer system 700 can comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, or an XBOX 360 device manufactured by the Microsoft Corporation of Redmond, Wash., or an OCULUS RIFT or OCULUS VR device manufactured BY OCULUS VR, LLC of Menlo Park, Calif.

In some embodiments, the computing device 700 is a digital audio player such as the Apple IPOD, IPOD Touch, and IPOD NANO lines of devices, manufactured by Apple Computer of Cupertino, Calif. Some digital audio players can have other functionality, including, e.g., a gaming system or any functionality made available by an application from a digital application distribution platform. For example, the IPOD Touch can access the Apple App Store. In some embodiments, the computing device 700 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 700 is a tablet e.g. the IPAD line of devices by Apple; GALAXY TAB family of devices by Samsung; or KINDLE FIRE, by Amazon.com, Inc. of Seattle, Wash. In other embodiments, the computing device 700 is an eBook reader, e.g. the KINDLE family of devices by Amazon.com, or NOOK family of devices by Barnes & Noble, Inc. of New York City, N.Y.

In some embodiments, the communications device 700 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc.; or a Motorola DROID family of smartphones. In yet another embodiment, the communications device 700 is a laptop or desktop computer equipped with a web browser and a microphone and speaker system, e.g. a telephony headset. In these embodiments, the communications devices 700 are web-enabled and can receive and initiate phone calls. In some embodiments, a laptop or desktop computer is also equipped with a webcam or other video capture device that enables video chat and video call.

In some embodiments, the status of one or more machines 700 in the network are monitored, generally as part of network management. In one of these embodiments, the status of a machine can include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information can be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

D. A Method for Neural Stimulation

Figure 8:
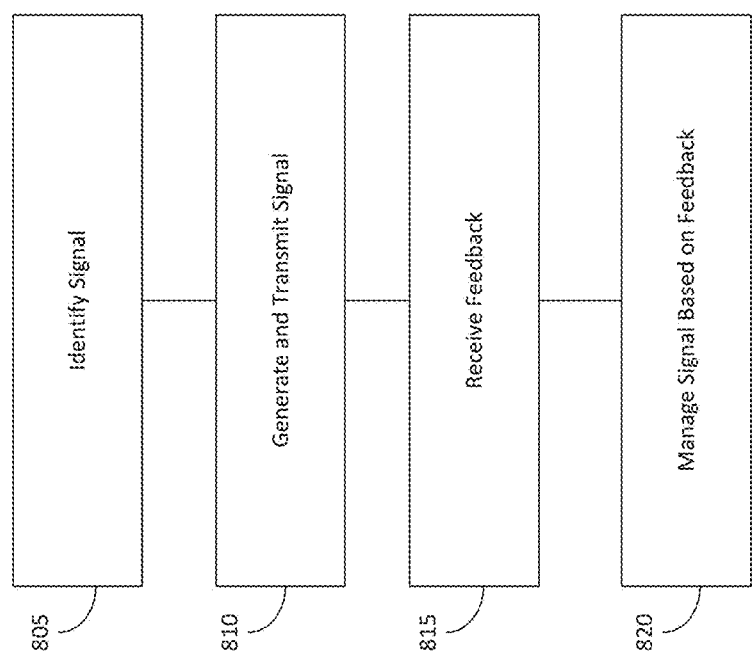
FIG. 8 is a flow diagram of a method of performing visual brain entrainment in accordance with an embodiment.

FIG. 8 is a flow diagram of a method of performing visual brain entrainment in accordance with an embodiment. The method 800 can be performed by one or more system, component, module or element depicted in FIGS. 1-7B, including, for example, a neural stimulation system (NSS). In brief overview, the NSS can identify a visual signal to provide at block 805. At block 810, the NSS can generate and transmit the identified visual signal. At 815 the NSS can receive or determine feedback associated with neural activity, physiological activity, environmental parameters, or device parameters. At 820 the NSS can manage, control, or adjust the visual signal based on the feedback.

E. NSS Operating with a Frame

The NSS 105 can operate in conjunction with the frame 400 including a light source 305 as depicted in FIG. 4A. The NSS 105 can operate in conjunction with the frame 400 including a light source 30 and a feedback sensor 605 as depicted in FIG. 6A. The NSS 105 can operate in conjunction with the frame 400 including at least one shutter 430 as depicted in FIG. 4B. The NSS 105 can operate in conjunction with the frame 400 including at least one shutter 430 and a feedback sensor 605.

In operation, a user of the frame 400 can wear the frame 400 on their head such that eye wires 415 encircle or substantially encircle their eyes. In some cases, the user can provide an indication to the NSS 105 that the glass frames 400 have been worn and that the user is ready to undergo brainwave entrainment. The indication can include an instruction, command, selection, input, or other indication via an input/output interface, such as a keyboard 726, pointing device 727, or other I/O devices 730a-n. The indication can be a motion-based indication, visual indication, or voice-based indication. For example, the user can provide a voice command that indicates that the user is ready to undergo brainwave entrainment.

In some cases, the feedback sensor 605 can determine that the user is ready to undergo brainwave entrainment. The feedback sensor 605 can detect that the glass frames 400 have been placed on a user's head. The NSS 105 can receive motion data, acceleration data, gyroscope data, temperature data, or capacitive touch data to determine that the frames 400 have been placed on the user's head. The received data, such as motion data, can indicate that the frames 400 were picked up and placed on the user's head. The temperature data can measure the temperature of or proximate to the frames 400, which can indicate that the frames are on the user's head. In some cases, the feedback sensor 605 can perform eye tracking to determine a level of attention a user is paying to the light source 305 or feedback sensor 605. The NSS 105 can detect that the user is ready responsive to determining that the user is paying a high level of attention to the light source 305 or feedback sensor 605. For example, staring at, gazing or looking in the direction of the light source 305 or feedback sensor 605 can provide an indication that the user is ready to undergo brainwave entrainment.

Thus, the NSS 105 can detect or determine that the frames 400 have been worn and that the user is in a ready state, or the NSS 105 can receive an indication or confirmation from the user that the user has worn the frames 400 and the user is ready to undergo brainwave entrainment. Upon determining that the user is ready, the NSS 105 can initialize the brainwave entrainment process. In some embodiments, the NSS 105 can access a profile data structure 145. For example, a profile manager 125 can query the profile data structure 145 to determine one or more parameter for the external visual stimulation used for the brain entrainment process. Parameters can include, for example, a type of visual stimulation, an intensity of the visual stimulation, frequency of the visual stimulation, duration of the visual stimulation, or wavelength of the visual stimulation. The profile manager 125 can query the profile data structure 145 to obtain historical brain entrainment information, such as prior visual stimulation sessions. The profile manager 125 can perform a lookup in the profile data structure 145. The profile manager 125 can perform a look-up with a username, user identifier, location information, fingerprint, biometric identifier, retina scan, voice recognition and authentication, or other identifying technique.

The NSS 105 can determine a type of external visual stimulation based on the hardware 400. The NSS 105 can determine the type of external visual stimulation based on the type of light source 305 available. For example, if the light source 305 includes a monochromatic LED that generates light waves in the red spectrum, the NSS 105 can determine that the type of visual stimulation includes pulses of light transmitted by the light source. However, if the frames 400 do not include an active light source 305, but, instead, include one or more shutters 430, the NSS 105 can determine that the light source is sunlight or ambient light that is to be modulated as it enters the user's eye via a plane formed by the eye wire 415.

In some embodiments, the NSS 105 can determine the type of external visual stimulation based on historical brainwave entrainment sessions. For example, the profile data structure 145 can be pre-configured with information about the type of visual signaling component 150.

The NSS 105 can determine, via the profile manager 125, a modulation frequency for the pulse train or the ambient light. For example, NSS 105 can determine, from the profile data structure 145, that the modulation frequency for the external visual stimulation should be set to 40 Hz. Depending on the type of visual stimulation, the profile data structure 145 can further indicate a pulse length, intensity, wavelength of the light wave forming the light pulse, or duration of the pulse train.

In some cases, the NSS 105 can determine or adjust one or more parameter of the external visual stimulation. For example, the NSS 105 (e.g., via feedback component 160 or feedback sensor 605) can determine a level or amount of ambient light. The NSS 105 (e.g., via light adjustment module 115 or side effects management module 130) can establish, initialize, set, or adjust the intensity or wavelength of the light pulse. For example, the NSS 105 can determine that there is a low level of ambient light. Due to the low level of ambient light, the user's pupils may be dilated. The NSS 105 can determine, based on detecting a low level of ambient light, that the user's pupils are likely dilated. In response to determining that the user's pupils are likely dilated, the NSS 105 can set a low level of intensity for the pulse train. The NSS 105 can further use a light wave having a longer wavelength (e.g., red), which may reduce strain on the eyes.

The light adjustment module 115 can increase or decrease a contrast ratio between the light stimulation signal and an ambient light level. For example, the light adjustment module 115 can determine or detect the ambient light level at or proximate to a fovea of the subject. The light adjustment module 115 can increase or decrease the intensity of the light source or visual stimulation signal relative to the ambient light level. The light adjustment module 115 can increase or decrease this contrast ratio to facilitate adherence to the treatment or therapy session or reduce side effects. The light adjustment module 115 can, for example, increase the contrast ratio upon detecting a low level of attention, or lack of satisfactory neural stimulation.

In some embodiments, the NSS 105 can monitor (e.g., via feedback monitor 135 and feedback component 160) the level of ambient light throughout the brainwave entrainment process to automatically and periodically adjust the intensity or color of light pulses. For example, if the user began the brainwave entrainment process when there was a high level of ambient light, the NSS 105 can initially set a higher intensity level for the light pulses and use a color that includes light waves having lower wavelengths (e.g., blue). However, in some embodiments in which the ambient light level decreases throughout the brainwave entrainment process, the NSS 105 can automatically detect the decrease in ambient light and, in response to the detection, adjust or lower the intensity while increasing the wavelength of the light wave. The NSS 105 can adjust the light pulses to provide a high contrast ratio to facilitate brainwave entrainment.

In some embodiments, the NSS 105 (e.g., via feedback monitor 135 and feedback component 160) can monitor or measure physiological conditions to set or adjust a parameter of the light wave. For example, the NSS 105 can monitor or measure a level of pupil dilation to adjust or set a parameter of the light wave. In some embodiments, the NSS 105 can monitor or measure heart rate, pulse rate, blood pressure, body temperature, perspiration, or brain activity to set or adjust a parameter of the light wave.

In some embodiments, the NSS 105 can be preconfigured to initially transmit light pulses having a lowest setting for light wave intensity (e.g., low amplitude of the light wave or high wavelength of the light wave) and gradually increase the intensity (e.g., increase the amplitude of the light wave or decrease the wavelength of the light wave) while monitoring feedback until an optimal light intensity is reached. An optimal light intensity can refer to a highest intensity without adverse physiological side effects, such as blindness, seizures, heart attack, migraines, or other discomfort. The NSS 105 (e.g., via side effects management module 130) can monitor the physiological symptoms to identify the adverse side effects of the external visual stimulation, and adjust (e.g., via light adjustment module 115) the external visual stimulation accordingly to reduce or eliminate the adverse side effects.

In some embodiments, the NSS 105 (e.g., via light adjustment module 115) can adjust a parameter of the light wave or light pulse based on a level of attention. For example, during the brainwave entrainment process, the user may get bored, lose focus, fall asleep, or otherwise not pay attention to the light pulses. Not paying attention to the light pulses may reduce the efficacy of the brainwave entrainment process, resulting in neurons oscillating at a frequency different from the desired modulation frequency of the light pulses.

NSS 105 can detect the level of attention the user is paying to the light pulses using the feedback monitor 135 and one or more feedback component 160. The NSS 105 can perform eye tracking to determine the level of attention the user is providing to the light pulses based on the gaze direction of the retina or pupil. The NSS 105 can measure eye movement to determine the level of attention the user is paying to the light pulses. The NSS 105 can provide a survey or prompt asking for user feedback that indicates the level of attention the user is paying to the light pulses. Responsive to determining that the user is not paying a satisfactory amount of attention to the light pulses (e.g., a level of eye movement that is greater than a threshold or a gaze direction that is outside the direct visual field of the light source 305), the light adjustment module 115 can change a parameter of the light source to gain the user's attention. For example, the light adjustment module 115 can increase the intensity of the light pulse, adjust the color of the light pulse, or change the duration of the light pulse. The light adjustment module 115 can randomly vary one or more parameters of the light pulse. The light adjustment module 115 can initiate an attention seeking light sequence configured to regain the user's attention. For example, the light sequence can include a change in color or intensity of the light pulses in a predetermined, random, or pseudo-random pattern. The attention seeking light sequence can enable or disable different light sources if the visual signaling component 150 includes multiple light sources. Thus, the light adjustment module 115 can interact with the feedback monitor 135 to determine a level of attention the user is providing to the light pulses, and adjust the light pulses to regain the user's attention if the level of attention falls below a threshold.

In some embodiments, the light adjustment module 115 can change or adjust one or more parameter of the light pulse or light wave at predetermined time intervals (e.g., every 5 minutes, 10 minutes, 15 minutes, or 20 minutes) to regain or maintain the user's attention level.

In some embodiments, the NSS 105 (e.g., via unwanted frequency filtering module 120) can filter, block, attenuate, or remove unwanted visual external stimulation. Unwanted visual external stimulation can include, for example, unwanted modulation frequencies, unwanted intensities, or unwanted wavelengths of light waves. The NSS 105 can deem a modulation frequency to be unwanted if the modulation frequency of a pulse train is different or substantially different (e.g., 1%, 2%, 5%, 10%, 15%, 20%, 25%, or more than 25%) from a desired frequency.

For example, the desired modulation frequency for brainwave entrainment can be 40 Hz. However, a modulation frequency of 20 Hz or 80 Hz can hinder brainwave entrainment. Thus, the NSS 105 can filter out the light pulses or light waves corresponding to the 20 Hz or 80 Hz modulation frequency.

In some embodiments, the NSS 105 can detect, via feedback component 160, that there are light pulses from an ambient light source that corresponds to an unwanted modulation frequency of 20 Hz. The NSS 105 can further determine the wavelength of the light waves of the light pulses corresponding to the unwanted modulation frequency. The NSS 105 can instruct the filtering component 155 to filter out the wavelength corresponding to the unwanted modulation frequency. For example, the wavelength corresponding to the unwanted modulation frequency can correspond to the color blue. The filtering component 155 can include an optical filter that can selectively transmit light in a particular range of wavelengths or colors, while blocking one or more other ranges of wavelengths or colors. The optical filter can modify the magnitude or phase of the incoming light wave for a range of wavelengths. For example, the optical filter can be configured to block, reflect or attenuate the blue light wave corresponding to the unwanted modulation frequency. The light adjustment module 115 can change the wavelength of the light wave generated by the light generation module 110 and light source 305 such that the desired modulation frequency is not blocked or attenuated by the unwanted frequency filtering module 120.

F. NSS Operating with a Virtual Reality Headset

The NSS 105 can operate in conjunction with the virtual reality headset 401 including a light source 305 as depicted in FIG. 4C. The NSS 105 can operate in conjunction with the virtual reality headset 401 including a light source 305 and a feedback sensor 605 as depicted in FIG. 4C. In some embodiments, the NSS 105 can determine that the visual signaling component 150 hardware includes a virtual reality headset 401. Responsive to determining that the visual signaling component 150 includes a virtual reality headset 401, the NSS 105 can determine that the light source 305 includes a display screen of a smartphone or other mobile computing device.

The virtual reality headset 401 can provide an immersive, non-disruptive visual stimulation experience. The virtual reality headset 401 can provide an augmented reality experience. The feedback sensors 605 can capture pictures or video of the physical, real world to provide the augmented reality experience. The unwanted frequency filtering module 120 can filter out unwanted modulation frequencies prior to projecting, displaying or providing the augmented reality images via the display screen 305.

In operation, a user of the frame 401 can wear the frame 401 on their head such that the virtual reality headset eye sockets 465 cover the user's eyes. The virtual reality headset eye sockets 465 can encircle or substantially encircle their eyes. The user can secure the virtual reality headset 401 to the user's headset using one or more straps 455 or 460, a skull cap, or other fastening mechanism. In some cases, the user can provide an indication to the NSS 105 that the virtual reality headset 401 has been placed and secured to the user's head and that the user is ready to undergo brainwave entrainment. The indication can include an instruction, command, selection, input, or other indication via an input/output interface, such as a keyboard 726, pointing device 727, or other I/O devices 730*a-n*. The indication can be a motion-based indication, visual indication, or voice-based indication. For example, the user can provide a voice command that indicates that the user is ready to undergo brainwave entrainment.

In some cases, the feedback sensor 605 can determine that the user is ready to undergo brainwave entrainment. The feedback sensor 605 can detect that the virtual reality headset 401 has been placed on a user's head. The NSS 105 can receive motion data, acceleration data, gyroscope data, temperature data, or capacitive touch data to determine that the virtual reality headset 401 has been placed on the user's head. The received data, such as motion data, can indicate that the virtual reality headset 401 was picked up and placed on the user's head. The temperature data can measure the temperature of or proximate to the virtual reality headset 401, which can indicate that the virtual reality headset 401 is on the user's head. In some cases, the feedback sensor 605 can perform eye tracking to determine a level of attention a user is paying to the light source 305 or feedback sensor 605. The NSS 105 can detect that the user is ready responsive to determining that the user is paying a high level of attention to the light source 305 or feedback sensor 605. For example, staring at, gazing or looking in the direction of the light source 305 or feedback sensor 605 can provide an indication that the user is ready to undergo brainwave entrainment.

In some embodiments, a sensor 605 on the straps 455, straps 460 or eye socket 605 can detect that the virtual reality headset 401 is secured, placed, or positioned on the user's head. The sensor 605 can be a touch sensor that senses or detects the touch of the user's head.

Thus, the NSS 105 can detect or determine that the virtual reality headset 401 has been worn and that the user is in a ready state, or the NSS 105 can receive an indication or confirmation from the user that the user has worn the virtual reality headset 401 and the user is ready to undergo brainwave entrainment. Upon determining that the user is ready, the NSS 105 can initialize the brainwave entrainment process. In some embodiments, the NSS 105 can access a profile data structure 145. For example, a profile manager 125 can query the profile data structure 145 to determine one or more parameter for the external visual stimulation used for the brain entrainment process. Parameters can include, for example, a type of visual stimulation, an intensity of the visual stimulation, frequency of the visual stimulation, duration of the visual stimulation, or wavelength of the visual stimulation. The profile manager 125 can query the profile data structure 145 to obtain historical brain entrainment information, such as prior visual stimulation sessions. The profile manager 125 can perform a lookup in the profile data structure 145. The profile manager 125 can perform a look-up with a username, user identifier, location information, fingerprint, biometric identifier, retina scan, voice recognition and authentication, or other identifying technique.

The NSS 105 can determine a type of external visual stimulation based on the hardware 401. The NSS 105 can determine the type of external visual stimulation based on the type of light source 305 available. For example, if the light source 305 includes a smartphone or display device, the visual stimulation can include turning on and off the display screen of the display device. The visual stimulation can include displaying a pattern on the display device 305, such as a checkered pattern, that can alternate in accordance with the desired frequency modulation. The visual stimulation can include light pulses generated by a light source 305 such as an LED that is placed within the virtual reality headset 401 enclosure.

In cases where the virtual reality headset 401 provides an augmented reality experience, the visual stimulation can include overlaying content on the display device and modulating the overlaid content at the desired modulation frequency. For example, the virtual reality headset 401 can include a camera 605 that captures the real, physical world. While displaying the captured image of the real, physical world, the NSS 105 can also display content that is modulated at the desired modulation frequency. The NSS 105 can overlay the content modulated at the desired modulation frequency. The NSS 105 can otherwise modify, manipulate, modulation, or adjust a portion of the display screen or a portion of the augmented reality to generate or provide the desired modulation frequency.

For example, the NSS 105 can modulate one or more pixels based on the desired modulation frequency. The NSS 105 can turn pixels on and off based on the modulation frequency. The NSS 105 can turn of pixels on any portion of the display device. The NSS 105 can turn on and off pixels in a pattern. The NSS 105 can turn on and off pixels in the direct visual field or peripheral visual field. The NSS 105 can track or detect a gaze direction of the eye and turn on and off pixels in the gaze direction so the light pulses (or modulation) are in the direct vision field. Thus, modulating the overlaid content or otherwise manipulated the augmented reality display or other image provided via a display device in the virtual reality headset 401 can generate light pulses or light flashes having a modulation frequency configured to facilitate brainwave entrainment.

The NSS 105 can determine, via the profile manager 125, a modulation frequency for the pulse train or the ambient light. For example, NSS 105 can determine, from the profile data structure 145, that the modulation frequency for the external visual stimulation should be set to 40 Hz. Depending on the type of visual stimulation, the profile data structure 145 can further indicate a number of pixels to modulate, intensity of pixels to modulate, pulse length, intensity, wavelength of the light wave forming the light pulse, or duration of the pulse train.

In some cases, the NSS 105 can determine or adjust one or more parameter of the external visual stimulation. For example, the NSS 105 (e.g., via feedback component 160 or feedback sensor 605) can determine a level or amount of light in captured image used to provide the augmented reality experience. The NSS 105 (e.g., via light adjustment module 115 or side effects management module 130) can establish, initialize, set, or adjust the intensity or wavelength of the light pulse based on the light level in the image data corresponding to the augmented reality experience. For example, the NSS 105 can determine that there is a low level of light in the augmented reality display because it may be dark outside. Due to the low level of light in the augmented reality display, the user's pupils may be dilated. The NSS 105 can determine, based on detecting a low level of light, that the user's pupils are likely dilated. In response to determining that the user's pupils are likely dilated, the NSS 105 can set a low level of intensity for the light pulses or light source providing the modulation frequency. The NSS 105 can further use a light wave having a longer wavelength (e.g., red), which may reduce strain on the eyes.

In some embodiments, the NSS 105 can monitor (e.g., via feedback monitor 135 and feedback component 160) the level of light throughout the brainwave entrainment process to automatically and periodically adjust the intensity or color of light pulses. For example, if the user began the brainwave entrainment process when there was a high level of ambient light, the NSS 105 can initially set a higher intensity level for the light pulses and use a color that includes light waves having lower wavelengths (e.g., blue). However, as the light level decreases throughout the brainwave entrainment process, the NSS 105 can automatically detect the decrease in light and, in response to the detection, adjust or lower the intensity while increasing the wavelength of the light wave. The NSS 105 can adjust the light pulses to provide a high contrast ratio to facilitate brainwave entrainment.

In some embodiments, the NSS 105 (e.g., via feedback monitor 135 and feedback component 160) can monitor or measure physiological conditions to set or adjust a parameter of the light pulses while the user is wearing the virtual reality headset 401. For example, the NSS 105 can monitor or measure a level of pupil dilation to adjust or set a parameter of the light wave. In some embodiments, the NSS 105 can monitor or measure, via one or more feedback sensor of the virtual reality headset 401 or other feedback sensor, a heart rate, pulse rate, blood pressure, body temperature, perspiration, or brain activity to set or adjust a parameter of the light wave.

In some embodiments, the NSS 105 can be preconfigured to initially transmit, via display device 305, light pulses having a lowest setting for light wave intensity (e.g., low amplitude of the light wave or high wavelength of the light wave) and gradually increase the intensity (e.g., increase the amplitude of the light wave or decrease the wavelength of the light wave) while monitoring feedback until an optimal light intensity is reached. An optimal light intensity can refer to a highest intensity without adverse physiological side effects, such as blindness, seizures, heart attack, migraines, or other discomfort. The NSS 105 (e.g., via side effects management module 130) can monitor the physiological symptoms to identify the adverse side effects of the external visual stimulation, and adjust (e.g., via light adjustment module 115) the external visual stimulation accordingly to reduce or eliminate the adverse side effects.

In some embodiments, the NSS 105 (e.g., via light adjustment module 115) can adjust a parameter of the light wave or light pulse based on a level of attention. For example, during the brainwave entrainment process, the user may get bored, lose focus, fall asleep, or otherwise not pay attention to the light pulses generated via the display screen 305 of the virtual reality headset 401. Not paying attention to the light pulses may reduce the efficacy of the brainwave entrainment process, resulting in neurons oscillating at a frequency different from the desired modulation frequency of the light pulses.

NSS 105 can detect the level of attention the user is paying or providing to the light pulses using the feedback monitor 135 and one or more feedback component 160 (e.g., including feedback sensors 605). The NSS 105 can perform eye tracking to determine the level of attention the user is providing to the light pulses based on the gaze direction of the retina or pupil. The NSS 105 can measure eye movement to determine the level of attention the user is paying to the light pulses. The NSS 105 can provide a survey or prompt asking for user feedback that indicates the level of attention the user is paying to the light pulses. Responsive to determining that the user is not paying a satisfactory amount of attention to the light pulses (e.g., a level of eye movement that is greater than a threshold or a gaze direction that is outside the direct visual field of the light source 305), the light adjustment module 115 can change a parameter of the light source 305 or display device 305 to gain the user's attention. For example, the light adjustment module 115 can increase the intensity of the light pulse, adjust the color of the light pulse, or change the duration of the light pulse. The light adjustment module 115 can randomly vary one or more parameters of the light pulse. The light adjustment module 115 can initiate an attention seeking light sequence configured to regain the user's attention. For example, the light sequence can include a change in color or intensity of the light pulses in a predetermined, random, or pseudo-random pattern. The attention seeking light sequence can enable or disable different light sources if the visual signaling component 150 includes multiple light sources. Thus, the light adjustment module 115 can interact with the feedback monitor 135 to determine a level of attention the user is providing to the light pulses, and adjust the light pulses to regain the user's attention if the level of attention falls below a threshold.

In some embodiments, the light adjustment module 115 can change or adjust one or more parameter of the light pulse or light wave at predetermined time intervals (e.g., every 5 minutes, 10 minutes, 15 minutes, or 20 minutes) to regain or maintain the user's attention level.

In some embodiments, the NSS 105 (e.g., via unwanted frequency filtering module 120) can filter, block, attenuate, or remove unwanted visual external stimulation. Unwanted visual external stimulation can include, for example, unwanted modulation frequencies, unwanted intensities, or unwanted wavelengths of light waves. The NSS 105 can deem a modulation frequency to be unwanted if the modulation frequency of a pulse train is different or substantially different (e.g., 1%, 2%, 5%, 10%, 15%, 20%, 25%, or more than 25%) from a desired frequency.

For example, the desired modulation frequency for brainwave entrainment can be 40 Hz. However, a modulation frequency of 20 Hz or 80 Hz can hinder brainwave entrainment. Thus, the NSS 105 can filter out the light pulses or light waves corresponding to the 20 Hz or 80 Hz modulation frequency. For example, the virtual reality headset 401 can detect unwanted modulation frequencies in the physical, real world and eliminate, attenuate, filter out or otherwise remove the unwanted frequencies providing to generating the or providing the augmented reality experience. The NSS 105 can include an optical filter configured to perform digital signal processing or digital image processing to detect the unwanted modulation frequency in the real world captured by the feedback sensor 605. The NSS 105 can detect other content, image or motion having an unwanted parameter (e.g., color, brightness, contrast ratio, modulation frequency), and eliminate same from the augmented reality experience projected to the user via the display screen 305. The NSS 105 can apply a color filter to adjust the color or remove a color of the augmented reality display. The NSS 105 can adjust, modify, or manipulate the brightness, contrast ratio, sharpness, tint, hue, or other parameter of the image or video displayed via the display device 305.

In some embodiments, the NSS 105 can detect, via feedback component 160, that there is captured image or video content from the real, physical world that corresponds to an unwanted modulation frequency of 20 Hz. The NSS 105 can further determine the wavelength of the light waves of the light pulses corresponding to the unwanted modulation frequency. The NSS 105 can instruct the filtering component 155 to filter out the wavelength corresponding to the unwanted modulation frequency. For example, the wavelength corresponding to the unwanted modulation frequency can correspond to the color blue. The filtering component 155 can include a digital optical filter that can digital remove content or light in a particular range of wavelengths or colors, while allowing one or more other ranges of wavelengths or colors. The digital optical filter can modify the magnitude or phase of the image for a range of wavelengths. For example, the digital optical filter can be configured to attenuate, erase, replace or otherwise alter the blue light wave corresponding to the unwanted modulation frequency. The light adjustment module 115 can change the wavelength of the light wave generated by the light generation module 110 and display device 305 such that the desired modulation frequency is not blocked or attenuated by the unwanted frequency filtering module 120.

G. NSS Operating with a Tablet

The NSS 105 can operate in conjunction with the tablet 500 as depicted in FIGS. 5A-5D. In some embodiments, the NSS 105 can determine that the visual signaling component 150 hardware includes a tablet device 500 or other display screen that is not affixed or secured to a user's head. The tablet 500 can include a display screen that has one or more component or function of the display screen 305 or light source 305 depicted in conjunction with FIGS. 4A and 4C. The light source 305 in a tablet can be the display screen. The tablet 500 can include one or more feedback sensor that includes one or more component or function of the feedback sensor depicted in conjunction with FIGS. 4B, 4C and 6A.

The tablet 500 can communicate with the NSS 105 via a network, such as a wireless network or a cellular network. The NSS 105 can, in some embodiments, execute the NSS 105 or a component thereof. For example, the tablet 500 can launch, open or switch to an application or resource configured to provide at least one functionality of the NSS 105. The tablet 500 can execute the application as a background process or a foreground process. For example, the graphical user interface for the application can be in the background while the application causes the display screen 305 of the tablet to overlay content or light that changes or modulates at a desired frequency for brain entrainment (e.g., 40 Hz).

The tablet 500 can include one or more feedback sensors 605. In some embodiments, the tablet can use the one or more feedback sensors 605 to detect that a user is holding the tablet 500. The tablet can use the one or more feedback sensors 605 to determine a distance between the light source 305 and the user. The tablet can use the one or more feedback sensors 605 to determine a distance between the light source 305 and the user's head. The tablet can use the one or more feedback sensors 605 to determine a distance between the light source 305 and the user's eyes.

In some embodiments, the tablet 500 can use a feedback sensor 605 that includes a receiver to determine the distance. The tablet can transmit a signal and measure the amount of time it takes for the transmitted signal to leave the tablet 500, bounce on the object (e.g., user's head) and be received by the feedback sensor 605. The tablet 500 or NSS 105 can determine the distance based on the measured amount of time and the speed of the transmitted signal (e.g., speed of light).

In some embodiments, the tablet 500 can include two feedback sensors 605 to determine a distance. The two feedback sensors 605 can include a first feedback sensor 605 that is the transmitter and a second feedback sensor that is the receiver.

In some embodiments, the tablet 500 can include two or more feedback sensors 605 that include two or more cameras. The two or more cameras can measure the angles and the position of the object (e.g., the user's head) on each camera, and use the measured angles and position to determine or compute the distance between the tablet 500 and the object.

In some embodiments, the tablet 500 (or application thereof) can determine the distance between the tablet and the user's head by receiving user input. For example, user input can include an approximate size of the user's head. The tablet 500 can then determine the distance from the user's head based on the inputted approximate size.

The tablet 500, application, or NSS 105 can use the measured or determined distance to adjust the light pulses or flashes of light emitted by the light source 305 of the tablet 500. The tablet 500, application, or NSS 105 can use the distance to adjust one or more parameter of the light pulses, flashes of light or other content emitted via the light source 305 of the tablet 500. For example, the tablet 500 can adjust the intensity of the light pulses emitted by light source 305 based on the distance. The tablet 500 can adjust the intensity based on the distance in order to maintain a consistent or similar intensity at the eye irrespective of the distance between the light source 305 and the eye. The tablet can increase the intensity proportional to the square of the distance.

The tablet 500 can manipulate one or more pixels on the display screen 305 to generate the light pulses or modulation frequency for brainwave entrainment. The tablet 500 can overlay light sources, light pulses or other patterns to generate the modulation frequency for brainwave entrainment. Similar to the virtual reality headset 401, the tablet can filter out or modify unwanted frequencies, wavelengths or intensity.

Similar to the frames 400, the tablet 500 can adjust a parameter of the light pulses or flashes of light generated by the light source 305 based on ambient light, environmental parameters, or feedback.

In some embodiments, the tablet 500 can execute an application that is configured to generate the light pulses or modulation frequency for brainwave entrainment. The application can execute in the background of the tablet such that all content displayed on a display screen of the tablet are displayed as light pulses at the desired frequency. The tablet can be configured to detect a gaze direction of the user. In some embodiments, the tablet may detect the gaze direction by capturing an image of the user's eye via the camera of the tablet. The tablet 500 can be configured to generate light pulses at particular locations of the display screen based on the gaze direction of the user. In embodiments where direct vision field is to be employed, the light pulses can be displayed at locations of the display screen that correspond to the user's gaze. In embodiments where peripheral vision field is to be employed, the light pulses can be displayed at locations of the displays screen that are outside the portion of the display screen corresponding to the user's gaze.

H. Neural Stimulation Via Auditory, Stimulation

Figure 9:
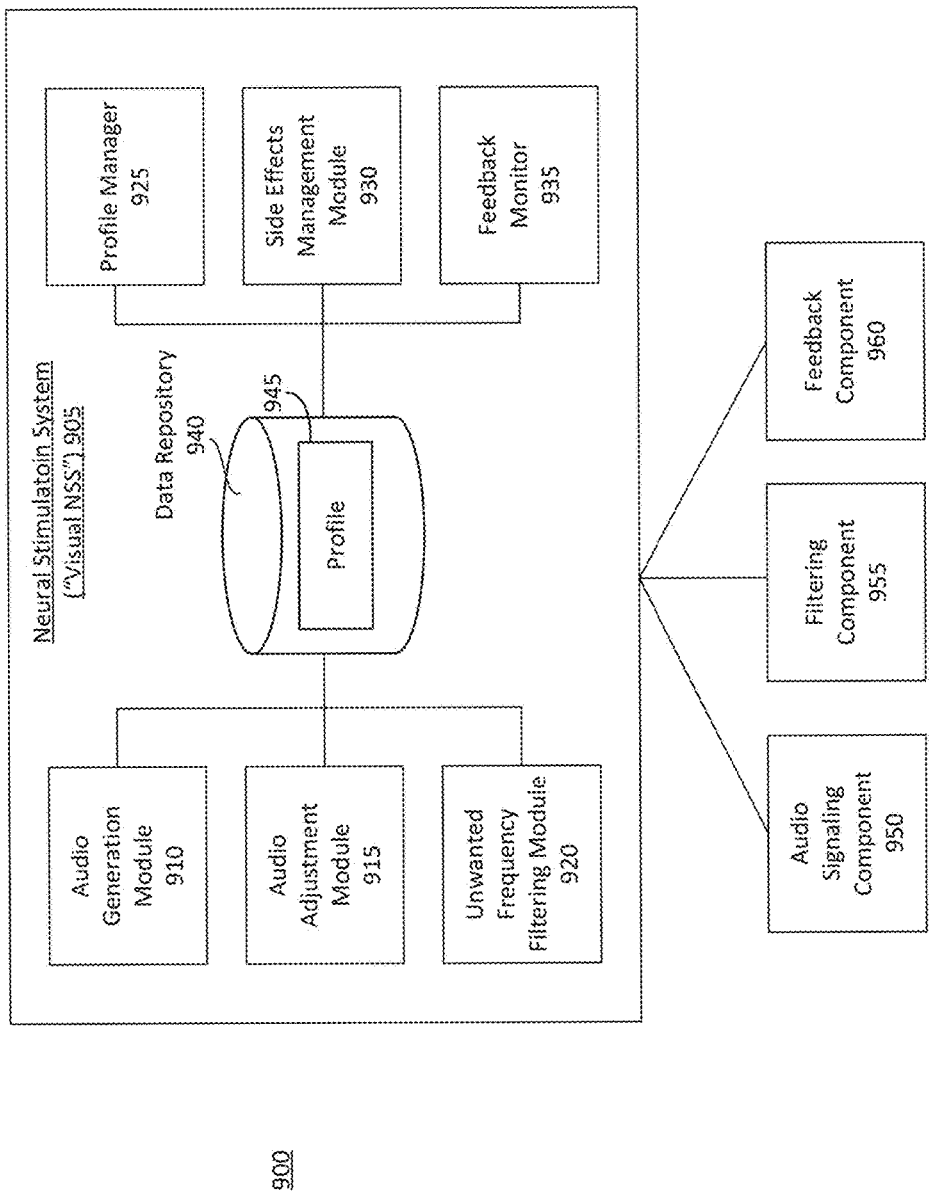
FIG. 9 is a block diagram depicting a system to induce neural oscillations via auditory stimulation in accordance with an embodiment.

FIG. 9 is a block diagram depicting a system for neural stimulation via auditory stimulation in accordance with an embodiment. The system 900 can include a neural stimulation system ("NSS") 905. The NSS 905 can be referred to as an auditory NSS 905 or NSS 905. In brief overview, the auditory neural stimulation system ("NSS") 905 can include, access, interface with, or otherwise communicate with one or more of an audio generation module 910, audio adjustment module 915, unwanted frequency filtering module 920, profile manager 925, side effects management module 930, feedback monitor 935, data repository 940, audio signaling component 950, filtering component 955, or feedback component 960. The audio generation module 910, audio adjustment module 915, unwanted frequency filtering module 920, profile manager 925, side effects management module 930, feedback monitor 935, audio signaling component 950, filtering component 955, or feedback component 960 can each include at least one processing unit or other logic device such as programmable logic array engine, or module configured to communicate with the database repository 940. The audio generation module 910, audio adjustment module 915, unwanted frequency filtering module 920, profile manager 925, side effects management module 930, feedback monitor 935, audio signaling component 950, filtering component 955, or feedback component 960 can be separate components, a single component, or part of the NSS 905. The system 100 and its components, such as the NSS 905, may include hardware elements, such as one or more processors, logic devices, or circuits. The system 100 and its components, such as the NSS 905, can include one or more hardware or interface component depicted in system 700 in FIGS. 7A and 7B. For example, a component of system 100 can include or execute on one or more processors 721, access storage 728 or memory 722, and communicate via network interface 718.

Still referring to FIG. 9, and in further detail, the NSS 905 can include at least one audio generation module 910. The audio generation module 910 can be designed and constructed to interface with an audio signaling component 950 to provide instructions or otherwise cause or facilitate the generation of an audio signal, such as an audio burst, audio pulse, audio chirp, audio sweep, or other acoustic wave having one or more predetermined parameters. The audio generation module 910 can include hardware or software to receive and process instructions or data packets from one or more module or component of the NSS 905. The audio generation module 910 can generate instructions to cause the audio signaling component 950 to generate an audio signal. The audio generation module 910 can control or enable the audio signaling component 950 to generate the audio signal having one or more predetermined parameters.

The audio generation module 910 can be communicatively coupled to the audio signaling component 950. The audio generation module 910 can communicate with the audio signaling component 950 via a circuit, electrical wire, data port, network port, power wire, ground, electrical contacts or pins. The audio generation module 910 can wirelessly communicate with the audio signaling component 950 using one or more wireless protocols such as BlueTooth, BlueTooth Low Energy, Zigbee, Z-Wave, IEEE 802.11. WIFI, 3G, 4G. LTE, near field communications ("NFC"), or other short, medium or long range communication protocols, etc. The audio generation module 910 can include or access a network interface 718 to communicate wirelessly or over a wire with the audio signaling component 950.

The audio generation module 910 can interface, control, or otherwise manage various types of audio signaling components 950 in order to cause the audio signaling component 950 to generate, block, control, or otherwise provide the audio signal having one or more predetermined parameters. The audio generation module 910 can include a driver configured to drive an audio source of the audio signaling component 950. For example, the audio source can include a speaker, and the audio generation module 910 (or the audio signaling component) can include a transducer that converts electrical energy to sound waves or acoustic waves. The audio generation module 910 can include a computing chip, microchip, circuit, microcontroller, operational amplifiers, transistors, resistors, or diodes configured to provide electricity or power having certain voltage and current characteristics to drive the speaker to generate an audio signal with desired acoustic characteristics.

Figure 10A:
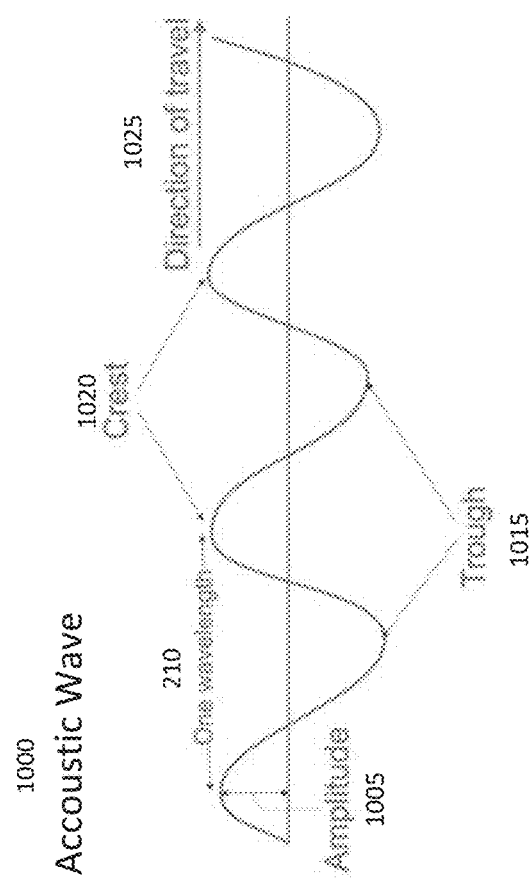
FIGS. 10A-10I illustrate audio signals and types of modulations to audio signals used to induce neural oscillations via auditory stimulation in accordance with some embodiments.

In some embodiments, the audio generation module 910 can instruct the audio signaling component 950 to provide an audio signal. For example, the audio signal can include an acoustic wave 1000 as depicted in FIG. 10A. The audio signal can include multiple acoustic waves. The audio signal can generate one or more acoustic waves. The acoustic wave 1000 can include or be formed of a mechanical wave of pressure and displacement that travels through media such as gases, liquids, and solids. The acoustic wave can travel through a medium to cause vibration, sound, ultrasound or infrasound. The acoustic wave can propagate through air, water or solids as longitudinal waves. The acoustic wave can propagate through solids as a transverse wave.

The acoustic wave can generate sound due to the oscillation in pressure, stress, particle displacement, or particle velocity propagated in a medium with internal forces (e.g., elastic or viscous), or the superposition of such propagated oscillation. Sound can refer to the auditory sensation evoked by this oscillation. For example, sound can refer to the reception of acoustic waves and their perception by the brain.

The audio signaling component 950 or audio source thereof can generate the acoustic waves by vibrating a diaphragm of the audio source. For example, the audio source can include a diaphragm such as a transducer configured to inter-convert mechanical vibrations to sounds. The diaphragm can include a thin membrane or sheet of various materials, suspended at its edges. The varying pressure of sound waves imparts mechanical vibrations to the diaphragm which can then create acoustic waves or sound.

The acoustic wave 1000 illustrated in FIG. 10A includes a wavelength 1010. The wavelength 1010 can refer to a distance between successive crests 1020 of the wave. The wavelength 1010 can be related to the frequency of the acoustic wave and the speed of the acoustic wave. For example, the wavelength can be determined as the quotient of the speed of the acoustic wave divided by the frequency of the acoustic wave. The speed of the acoustic wave can the product of the frequency and the wavelength. The frequency of the acoustic wave can be the quotient of the speed of the acoustic wave divided by the wavelength of the acoustic wave. Thus, the frequency and the wavelength of the acoustic wave can be inversely proportional. The speed of sound can vary based on the medium through which the acoustic wave propagates. For example, the speed of sound in air can be 343 meters per second.

A crest 1020 can refer to the top of the wave or point on the wave with the maximum value. The displacement of the medium is at a maximum at the crest 1020 of the wave. The trough 1015 is the opposite of the crest 1020. The trough 1015 is the minimum or lowest point on the wave corresponding to the minimum amount of displacement.

The acoustic wave 1000 can include an amplitude 1005. The amplitude 1005 can refer to a maximum extent of a vibration or oscillation of the acoustic wave 1000 measured from a position of equilibrium. The acoustic wave 1000 can be a longitudinal wave if it oscillates or vibrates in the same direction of travel 1025. In some cases, the acoustic wave 1000 can be a transverse wave that vibrates at right angles to the direction of its propagation.

The audio generation module 910 can instruct the audio signaling component 950 to generate acoustic waves or sound waves having one or more predetermined amplitude or wavelength. Wavelengths of the acoustic wave that are audible to the human ear range from approximately 17 meters to 17 millimeters (or 20 Hz to 20 kHz). The audio generation module 910 can further specify one or more properties of an acoustic wave within or outside the audible spectrum. For example, the frequency of the acoustic wave can range from 0 to 50 kHz. In some embodiments, the frequency of the acoustic wave can range from 8 to 12 kHz. In some embodiments, the frequency of the acoustic wave can be 10 kHz.

Figure 10B:
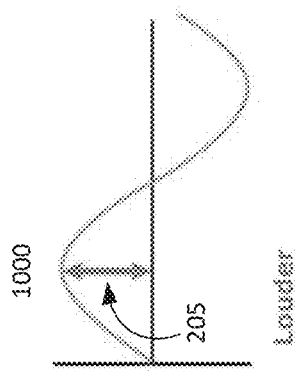
Figure 10C:
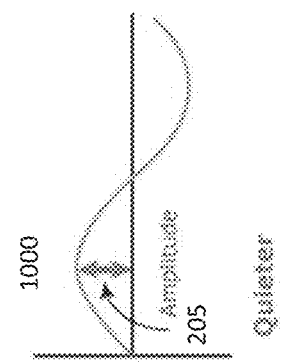

The NSS 905 can modulate, modify, change or otherwise alter properties of the acoustic wave 1000. For example, the NSS 905 can modulate the amplitude or wavelength of the acoustic wave. As depicted in FIG. 10B and FIG. 10C, the NSS 905 can adjust, manipulate, or otherwise modify the amplitude 1005 of the acoustic wave 1000. For example, the NSS 905 can lower the amplitude 1005 to cause the sound to be quieter, as depicted in FIG. 10B, or increase the amplitude 1005 to cause the sound to be louder, as depicted in FIG. 10C.

Figure 10D:
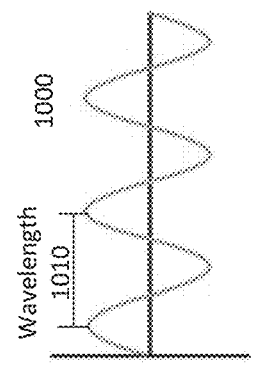
Figure 10E:
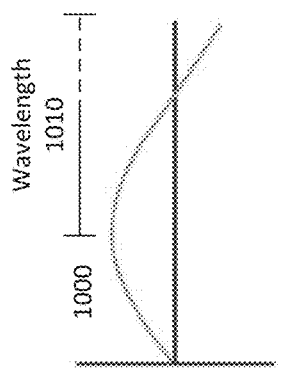

In some cases, the NSS 905 can adjust, manipulate or otherwise modify the wavelength 1010 of the acoustic wave. As depicted in FIG. 10D and FIG. 10E, the NSS 905 can adjust, manipulate, or otherwise modify the wavelength 1010 of the acoustic wave 1000. For example, the NSS 905 can increase the wavelength 1010 to cause the sound to have a lower pitch, as depicted in FIG. 10D, or reduce the wavelength 1010 to cause the sound to have a higher pitch, as depicted in FIG. 10E.

The NSS 905 can modulate the acoustic wave. Modulating the acoustic wave can include modulating one or more properties of the acoustic wave. Modulating the acoustic wave can include filtering the acoustic wave, such as filtering out unwanted frequencies or attenuating the acoustic wave to lower the amplitude. Modulating the acoustic wave can include adding one or more additional acoustic waves to the original acoustic wave. Modulating the acoustic wave can include combining the acoustic wave such that there is constructive or destructive interference where the resultant, combined acoustic wave corresponds to the modulated acoustic wave.

The NSS 905 can modulate or change one or more properties of the acoustic wave based on a time interval. The NSS 905 can change the one or more properties of the acoustic at the end of the time interval. For example, the NSS 905 can change a property of the acoustic wave every 30 seconds, 1 minute, 2 minutes, 3 minutes, 5 minutes, 7 minutes, 10 minutes, or 15 minutes. The NSS 905 can change a modulation frequency of the acoustic wave, where the modulation frequency refers to the repeated modulations or inverse of the pulse rate interval of the acoustic pulses. The modulation frequency can be a predetermined or desired frequency. The modulation frequency can correspond to a desired stimulation frequency of neural oscillations. The modulation frequency can be set to facilitate or cause brainwave entrainment. The NSS 905 can set the modulation frequency to a frequency in the range of 0.1 Hz to 10,000 Hz. For example, the NSS 905 can set the modulation frequency to 0.1 Hz 1 Hz, 5 Hz, 10 Hz, 20 Hz, 25 Hz, 30 Hz, 31 Hz, 32 Hz, 33 Hz, 34 Hz, 35 Hz, 36 Hz, 37 Hz, 38 Hz, 39 Hz, 40 Hz, 41 Hz, 42 Hz, 43 Hz, 44 Hz, 45 Hz, 46 Hz, 47 Hz, 48 Hz, 49 Hz, 50 Hz, 60 Hz, 70 Hz, 80 Hz, 90 Hz, 100 Hz, 150 Hz, 200 Hz, 250 Hz, 300 Hz, 400 Hz, 500 Hz, 1000 Hz, 2000 Hz, 3000 Hz, 4,000 Hz, 5000 Hz, 6,000 Hz, 7,000 Hz, 8,000 Hz, 9,000 Hz, or 10,000 Hz.

The audio generation module 910 can determine to provide audio signals that include bursts of acoustic waves, audio pulses, or modulations to acoustic waves. The audio generation module 910 can instruct or otherwise cause the audio signaling component 950 to generate acoustic bursts or pulses. An acoustic pulse can refer to a burst of acoustic waves or a modulation to a property of an acoustic wave that is perceived by the brain as a change in sound. For example, an audio source that is intermittently turned on and off can create audio bursts or changes in sound. The audio source can be turned on and off based on a predetermined or fixed pulse rate interval, such as every 0.025 seconds, to provide a pulse repetition frequency of 40 Hz. The audio source can be turned on and off to provide a pulse repetition frequency in the range of 0.1 Hz to 10 kHz or more.

For example, FIGS. 10F-10I illustrates bursts of acoustic waves or bursts of modulations that can be applied to acoustic waves. The bursts of acoustic waves can include, for example, audio tones, beeps, or clicks. The modulations can refer to changes in the amplitude of the acoustic wave, changes in frequency or wavelength of the acoustic wave, overlaying another acoustic wave over the original acoustic wave, or otherwise modifying or changing the acoustic wave.

Figure 10F:
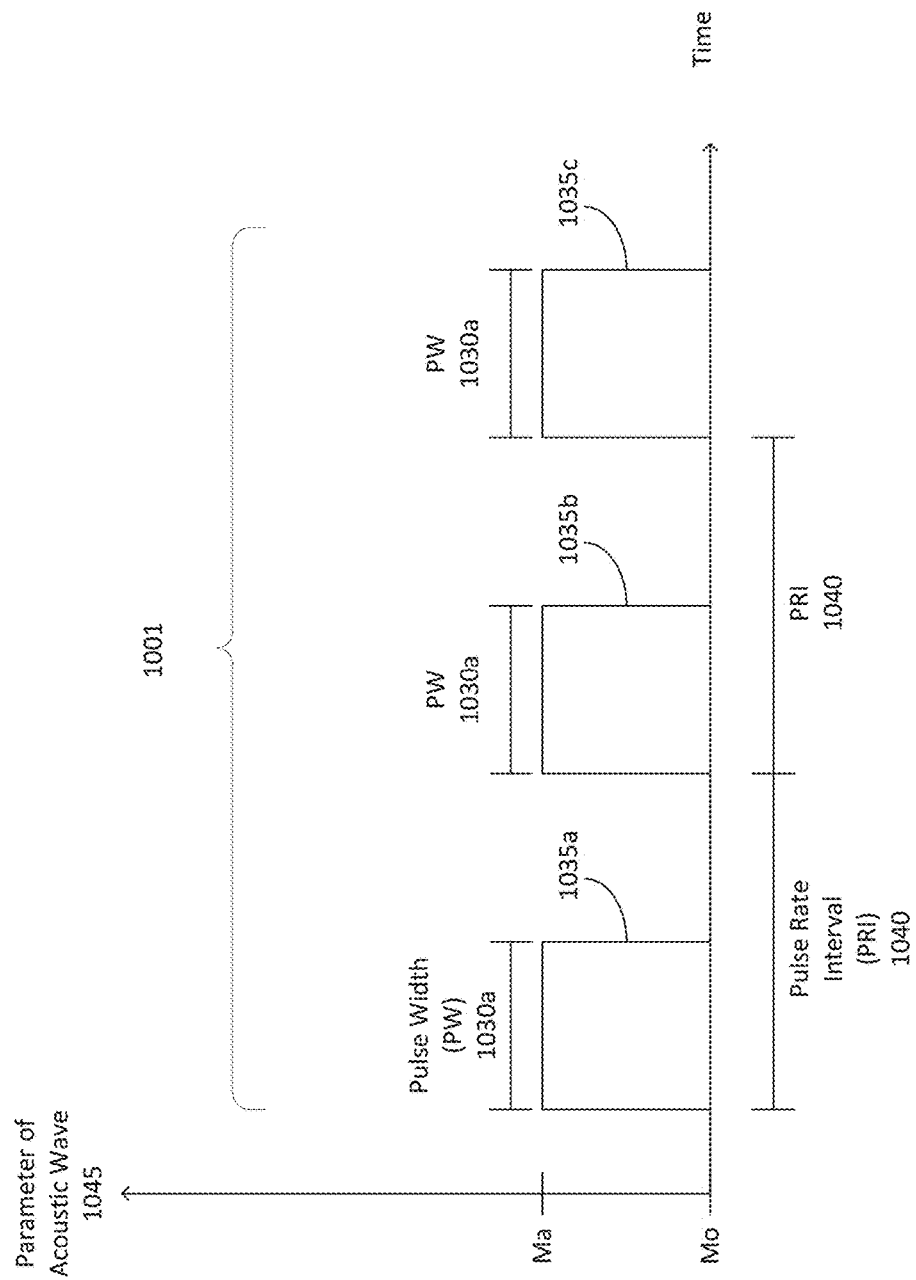

For example, FIG. 10F illustrates acoustic bursts 1035a-c (or modulation pulses 1035a-c) in accordance with an embodiment. The acoustic bursts 1035a-c can be illustrated via a graph where the y-axis represents a parameter of the acoustic wave (e.g., frequency, wavelength, or amplitude) of the acoustic wave. The x-axis can represent time (e.g., seconds, milliseconds, or microseconds).

The audio signal can include a modulated acoustic wave that is modulated between different frequencies, wavelengths, or amplitudes. For example, the NSS 905 can modulate an acoustic wave between a frequency in the audio spectrum, such as $M_a$, and a frequency outside the audio spectrum, such as $M_o$. The NSS 905 can modulate the acoustic wave between two or more frequencies, between an on state and an off state, or between a high power state and a low power state.

The acoustic bursts 1035a-c can have an acoustic wave parameter with value $M_a$ that is different from the value $M_o$ of the acoustic wave parameter. The modulation $M_a$ can refer to a frequency or wavelength, or amplitude. The pulses 1035a-c can be generated with a pulse rate interval (PRI) 1040.

For example, the acoustic wave parameter can be the frequency of the acoustic wave. The first value $M_o$ can be a low frequency or carrier frequency of the acoustic wave, such as 10 kHz. The second value, $M_a$, can be different from the first frequency $M_o$. The second frequency $M_a$ can be lower or higher than the first frequency $M_o$. For example, the second frequency $M_a$ can be 11 kHz. The difference between the first frequency and the second frequency can be determined or set based on a level of sensitivity of the human ear. The difference between the first frequency and the second frequency can be determined or set based on profile information 945 for the subject. The difference between the first frequency $M_e$ and the second frequency $M_a$ can be determined such that the modulation or change in the acoustic wave facilitate brainwave entrainment.

In some cases, the parameter of the acoustic wave used to generate the acoustic burst 1035a can be constant at $M_a$, thereby generating a square wave as illustrated in FIG. 10F. In some embodiments, each of the three pulses 1035a-c can include acoustic waves having a same frequency $M_a$.

Figure 10G:
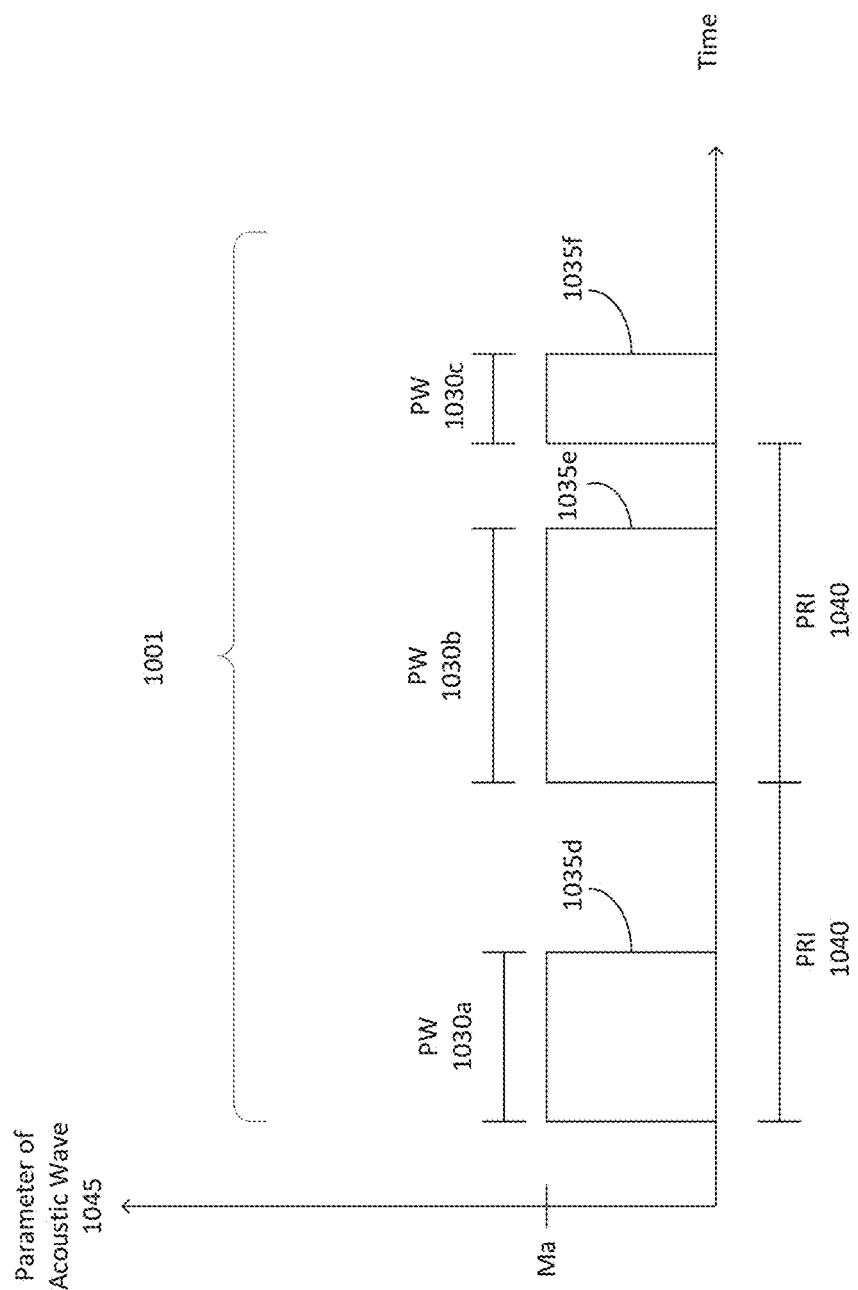

The width of each of the acoustic bursts or pulses (e.g., the duration of the burst of the acoustic wave with the parameter $M_a$) can correspond to a pulse width 1030a. The pulse width 1030a can refer to the length or duration of the burst. The pulse width 1030a can be measured in units of time or distance. In some embodiments, the pulses 1035a-c can include acoustic waves having different frequencies from one another. In some embodiments, the pulses 1035a-c can have different pulse widths 1030a from one another, as illustrated in FIG. 10G. For example, a first pulse 1035d of FIG. 10G can have a pulse width 1030a, while a second pulse 1035e has a second pulse width 1030b that is greater than the first pulse width 1030a. A third pulse 1035f can have a third pulse width 1030c that is less than the second pulse width 1030b. The third pulse width 1030c can also be less than the first pulse width 1030a. While the pulse widths 1030a-c of the pulses 1035d-f of the pulse train may vary, the audio generation module 910 can maintain a constant pulse rate interval 1040 for the pulse train.

The pulses 1035a-c can form a pulse train having a pulse rate interval 1040. The pulse rate interval 1040 can be quantified using units of time. The pulse rate interval 1040 can be based on a frequency of the pulses of the pulse train 201. The frequency of the pulses of the pulse train 201 can be referred to as a modulation frequency. For example, the audio generation module 910 can provide a pulse train 201 with a predetermined frequency, such as 40 Hz. To do so, the audio generation module 910 can determine the pulse rate interval 1040 by taking the multiplicative inverse (or reciprocal) of the frequency (e.g., 1 divided by the predetermined frequency for the pulse train). For example, the audio generation module 910 can take the multiplicative inverse of 40 Hz by dividing 1 by 40 Hz to determine the pulse rate interval 1040 as 0.025 seconds. The pulse rate interval 1040 can remain constant throughout the pulse train. In some embodiments, the pulse rate interval 1040 can vary throughout the pulse train or from one pulse train to a subsequent pulse train. In some embodiments, the number of pulses transmitted during a second can be fixed, while the pulse rate interval 1040 varies.

Figure 10H:
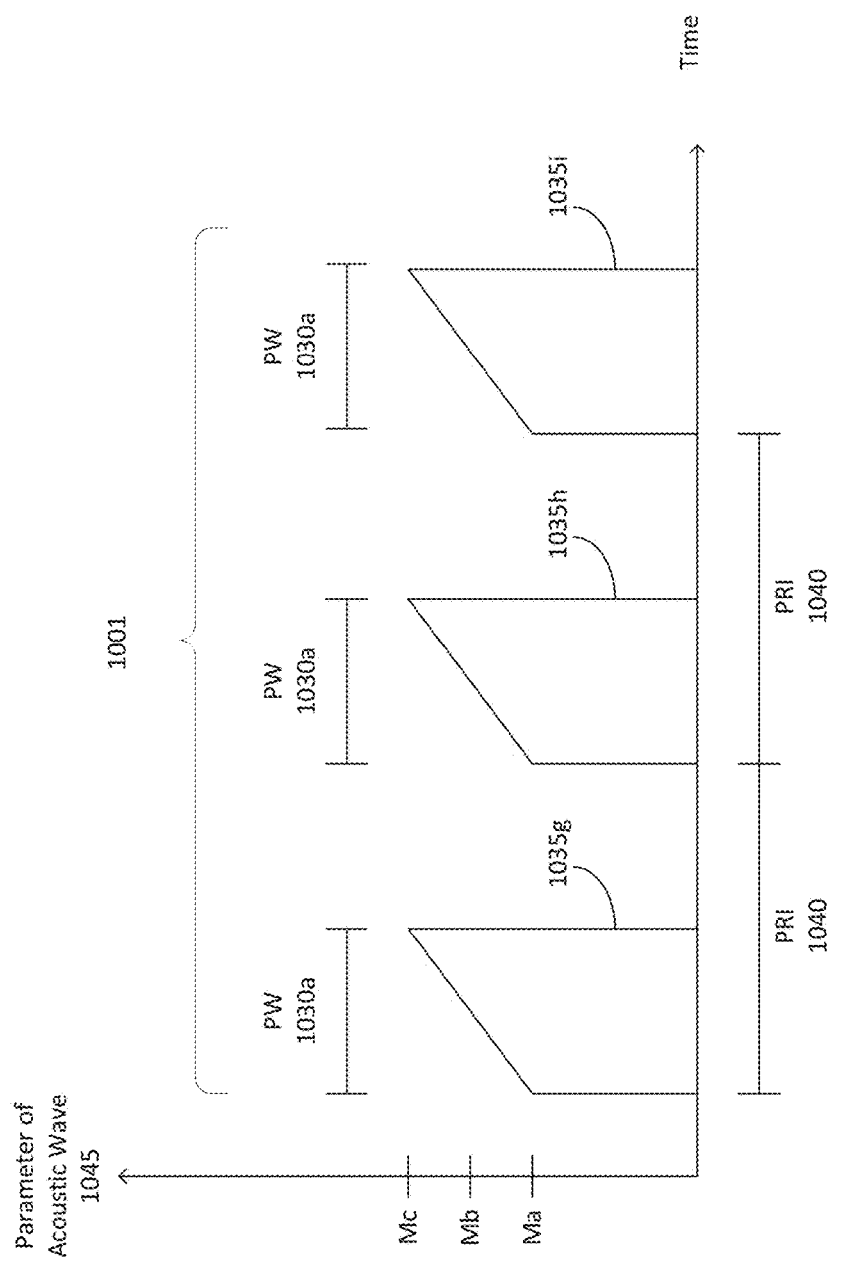

In some embodiments, the audio generation module 910 can generate an audio burst or audio pulse having an acoustic wave that varies in frequency, amplitude, or wavelength. For example, the audio generation module 910 can generate up-chirp pulses where the frequency, amplitude or wavelength of the acoustic wave of the audio pulse increases from the beginning of the pulse to the end of the pulse as illustrated in FIG. 10H. For example, the frequency, amplitude or wavelength of the acoustic wave at the beginning of pulse 1035g can be $M_a$. The frequency, amplitude or wavelength of the acoustic wave of the pulse 1035g can increase from $M_a$ to $M_b$ in the middle of the pulse 1035g, and then to a maximum of $M_c$ at the end of the pulse 1035g. Thus, the frequency, amplitude or wavelength of the acoustic wave used to generate the pulse 1035g can range from $M_a$ to $M_c$. The frequency, amplitude or wavelength can increase linearly, exponentially, or based on some other rate or curve. One or more of the frequency, amplitude or wavelength of the acoustic wave can change from the beginning of the pulse to the end of the pulse.

Figure 10I:
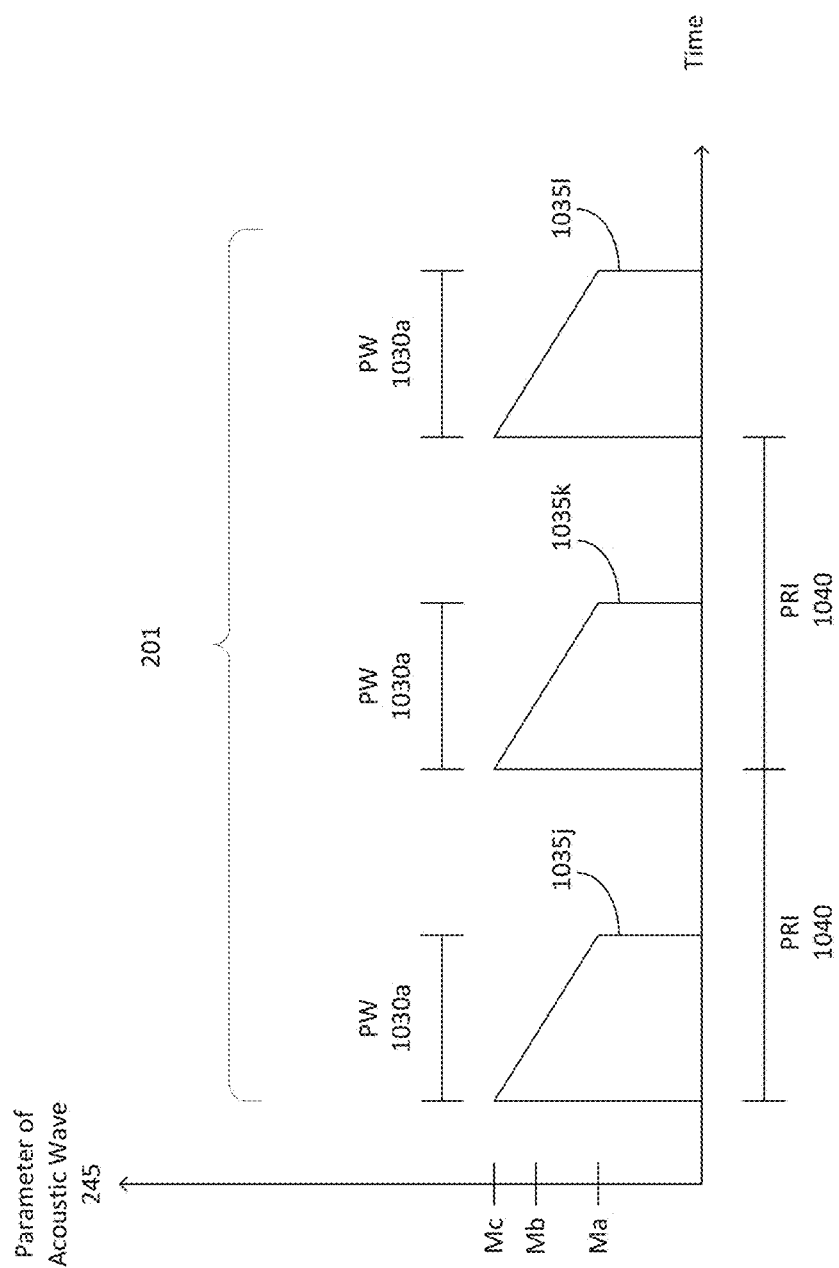

The audio generation module 910 can generate downchirp pulses, as illustrated in FIG. 10I, where the frequency, amplitude or wavelength of the acoustic wave of the acoustic pulse decreases from the beginning of the pulse to the end of the pulse. For example, the frequency, amplitude or wavelength of an acoustic wave at the beginning of pulse 1035j can be $M_c$. The frequency, amplitude or wavelength of the acoustic wave of the pulse 1035j can decrease from $M_c$ to $M_b$ in the middle of the pulse 1035j, and then to a minimum of $M_a$ at the end of the pulse 1035j. Thus, the frequency, amplitude or wavelength of the acoustic wave used to generate the pulse 1035j can range from Mc to $M_a$. The frequency, amplitude or wavelength can decrease linearly, exponentially, or based on some other rate or curve. One or more of the frequency, amplitude or wavelength of the acoustic wave can change from the beginning of the pulse to the end of the pulse.

In some embodiments, the audio generation module 910 can instruct or cause the audio signaling component 950 to generate audio pulses to stimulate specific or predetermined portions of the brain or a specific cortex. The frequency, wavelength, modulation frequency, amplitude and other aspects of the audio pulse, tone or music based stimuli can dictate which cortex or cortices are recruited to process the stimuli. The audio signaling component 950 can stimulate discrete portions of the cortex by modulating the presentation of the stimuli to target specific or general regions of interest. The modulation parameters or amplitude of the audio stimuli can dictate which region of the cortex is stimulated. For example, different regions of the cortex are recruited to process different frequencies of sound, called their characteristic frequencies. Further, ear laterality of stimulation can have an effect on cortex response since some subjects can be treated by stimulating one ear as opposed to both ears.

Audio signaling component 950 can be designed and constructed to generate the audio pulses responsive to instructions from the audio generation module 910. The instructions can include, for example, parameters of the audio pulse such as a frequency, wavelength or of the acoustic wave, duration of the pulse, frequency of the pulse train, pulse rate interval, or duration of the pulse train (e.g., a number of pulses in the pulse train or the length of time to transmit a pulse train having a predetermined frequency). The audio pulse can be perceived, observed, or otherwise identified by the brain via cochlear means such as ears. The audio pulses can be transmitted to the ear via an audio source speaker in close proximity to the ear, such as headphones, earbuds, bone conduction transducers, or cochlear implants. The audio pulses can be transmitted to the ear via an audio source or speaker not in close proximity to the ear, such as a surround sound speaker system, bookshelf speakers, or other speaker not directly or indirectly in contact with the ear.

Figure 11A:
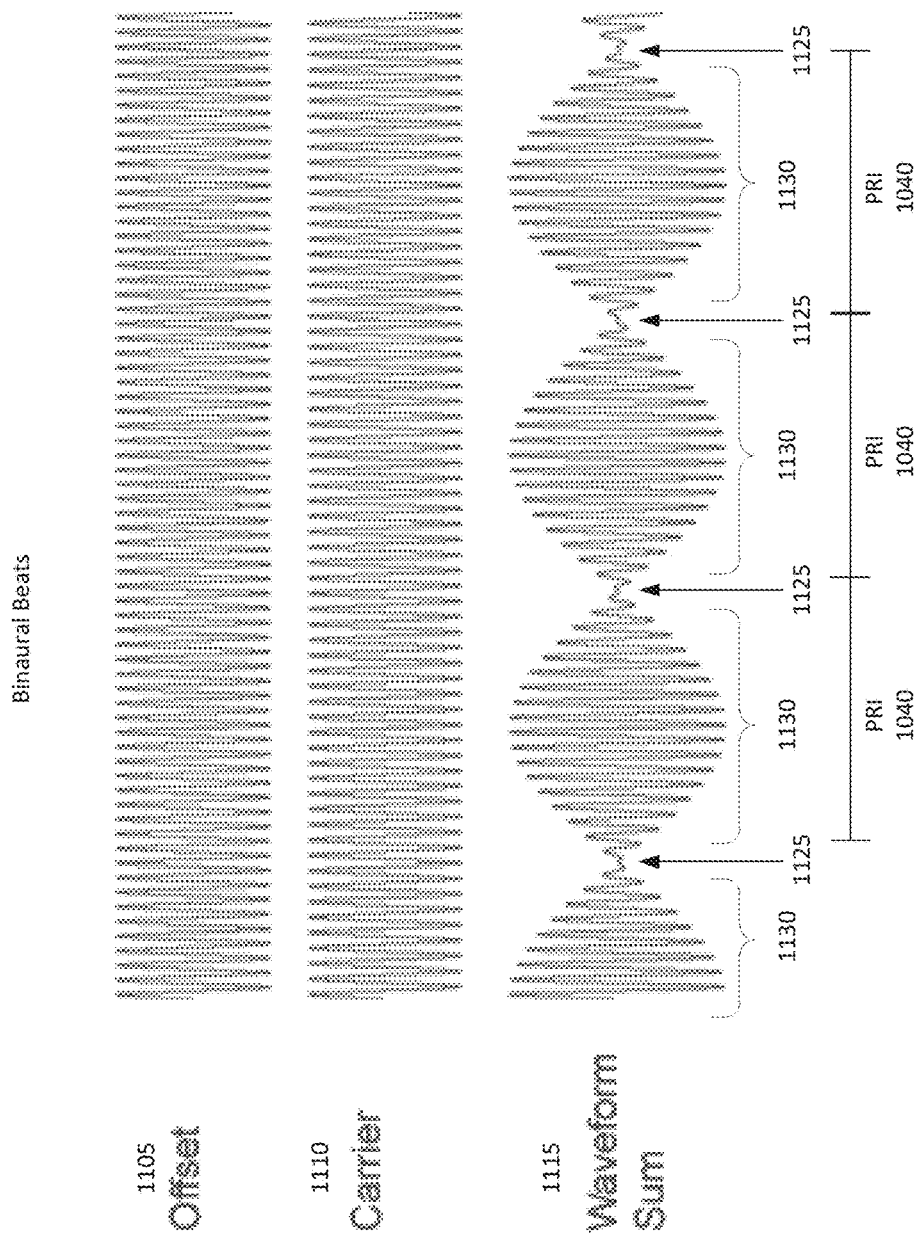
FIG. 11A illustrates audio signals generated using binaural beats, in accordance with an embodiment.

FIG. 11A illustrates audio signals using binaural beats or binaural pulses, in accordance with an embodiment. In brief summary, binaural beats refers to providing a different tone to each ear of the subject. When the brain perceives the two different tones, the brain mixes the two tones together to create a pulse. The two different tones can be selected such that the sum of the tones creates a pulse train having a desired pulse rate interval 1040.

The audio signaling component 950 can include a first audio source that provides an audio signal to the first ear of a subject, and a second audio source that provides a second audio signal to the second ear of a subject. The first audio source and the second audio source can be different. The first ear may only perceive the first audio signal from the first audio source, and the second ear may only receive the second audio signal from the second audio source. Audio sources can include, for example, headphones, earbuds, or bone conduction transducers. The audio sources can include stereo audio sources.

The audio generation component 910 can select a first tone for the first ear and a different second tone for the second ear. A tone can be characterized by its duration, pitch, intensity (or loudness), or timbre (or quality). In some cases, the first tone and the second tone can be different if they have different frequencies. In some cases, the first tone and the second tone can be different if they have different phase offsets. The first tone and the second tone can each be pure tones. A pure tone can be a tone having a sinusoidal waveform with a single frequency.

As illustrated in FIG. 11A, the first tone or offset wave 1105 is slightly different from the second tone 1110 or carrier wave 1110. The first tone 1105 has a higher frequency than the second tone 1110. The first tone 1105 can be generated by a first earbud that is inserted into one of the subject's ears, and the second tone 1110 can be generated by a second earbud that is inserted into the other of the subject's ears. When the auditory cortex of the brain perceives the first tone 1105 and the second tone 1110, the brain can sum the two tones. The brain can sum the acoustic waveforms corresponding to the two tones. The brain can sum the two waveforms as illustrated by waveform sum 1115. Due to the first and second tones having a different parameter (such as a different frequency or phase offset), portions of the waves can add and subtract from another to result in waveform 1115 having one or more pulses 1130 (or beats 1130). The pulses 1130 can be separated by portions 1125 that are at equilibrium. The pulses 1130 perceived by the brain by mixing these two different waveforms together can induce brainwave entrainment.

In some embodiments, the NSS 905 can generate binaural beats using a pitch panning technique. For example, the audio generation module 910 or audio adjustment module 915 can include or use a filter to modulate the pitch of a sound file or single tone up and down, and at the same time pan the modulation between stereo sides, such that one side will have a slightly higher pitch while the other side has a pitch that is slightly lower. The stereo sides can refer to the first audio source that generates and provides the audio signal to the first ear of the subject, and the second audio source that generates and provides the audio signal to the second ear of the subject. A sound file can refer to a file format configured to store a representation of, or information about, an acoustic wave. Example sound file formats can include .mp3, .wav, .aac, .m4a, .smf, etc.

The NSS 905 can use this pitch panning technique to generate a type of spatial positioning that, when listened to through stereo headphones, is perceived by the brain in a manner similar to binaural beats. The NSS 905 can, therefore, use this pitch panning technique to generate pulses or beats using a single tone or a single sound file.

In some cases, the NSS 905 can generate monaural beats or monaural pulses. Monaural beats or pulses are similar to binaural beats in that they are also generated by combining two tones to form a beat. The NSS 905 or component of system 100 can form monaural beats by combining the two tones using a digital or analog technique before the sound reaches the ears, as opposed to the brain combining the waveforms as in binaural beats. For example, the NSS 905 (or audio generation component 910) can identify and select two different waveforms that, when combined, produce beats or pulses having a desired pulse rate interval. The NSS 905 can identify a first digital representation of a first acoustic waveform, and identify a second digital representation of a second acoustic waveform have a different parameter than the first acoustic waveform. The NSS 905 can combine the first and second digital waveforms to generate a third digital waveform different from the first digital waveform and the second digital waveform. The NSS 905 can then transmit the third digital waveform in a digital form to the audio signaling component 950. The NSS 905 can translate the digital waveform to an analog format and transmit the analog format to the audio signaling component 950. The audio signaling component 950 can then, via an audio source, generate the sound to be perceived by one or both ears. The same sound can be perceived by both ears. The sound can include the pulses or beats spaced at the desired pulse rate interval 1040.

Figure 11B:
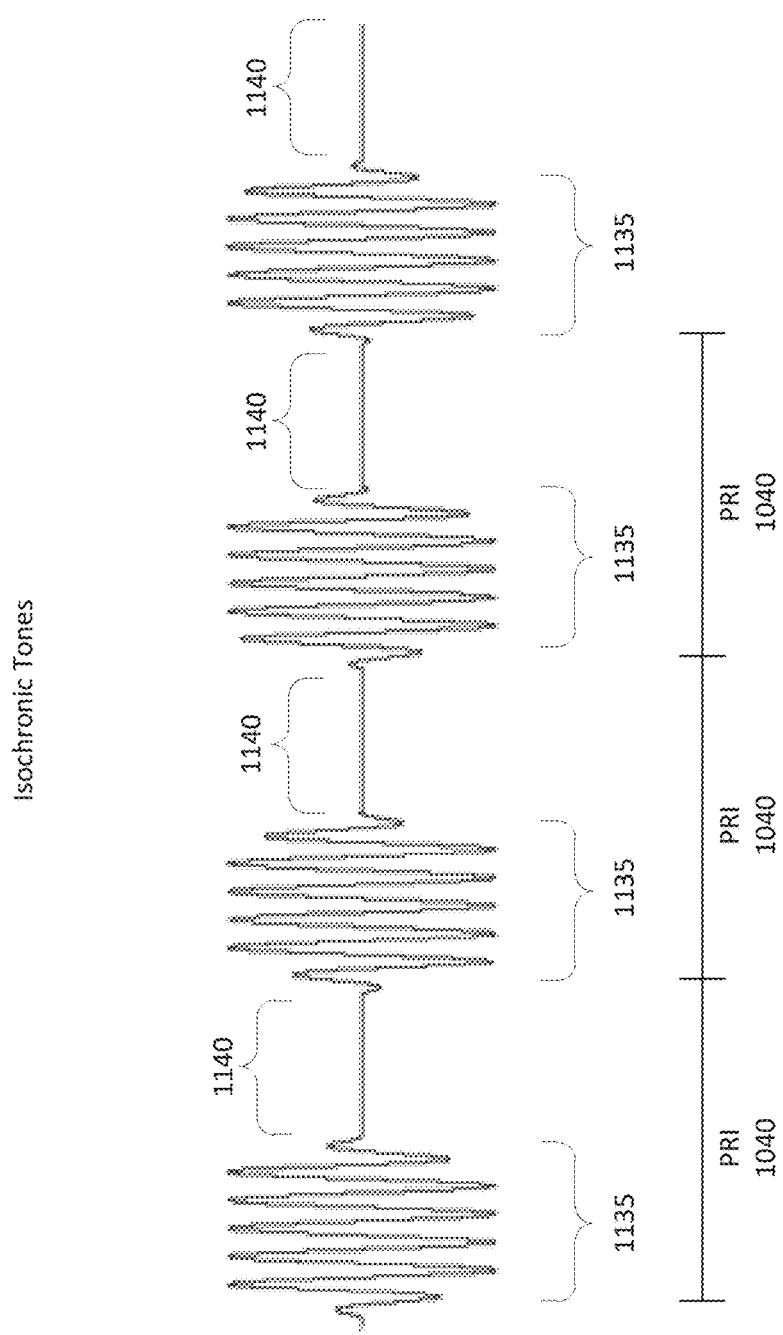
FIG. 11B illustrates acoustic pulses having isochronic tones, in accordance with an embodiment.

FIG. 11B illustrates acoustic pulses having isochronic tones, in accordance with an embodiment. Isochronic tones are evenly spaced tone pulses. Isochronic tones can be created without having to combine two different tones. The NSS 905 or other component of system 100 can create the isochronic tone by turning a tone on and off. The NSS 905 can generate the isochronic tones or pulses by instructing the audio signaling component to turn on and off. The NSS 905 can modify a digital representation of an acoustic wave to remove or set digital values of the acoustic wave such that sound is generated during the pulses 1135 and no sound is generated during the null portions 1140.

By turning on and off the acoustic wave, the NSS 905 can establish acoustic pulses 1135 that are spaced apart by a pulse rate interval 1040 that corresponds to a desired stimulation frequency, such as 40 Hz. The isochronic pulses spaced part at the desired PRI 1040 can induce brainwave entrainment.

Figure 11C:
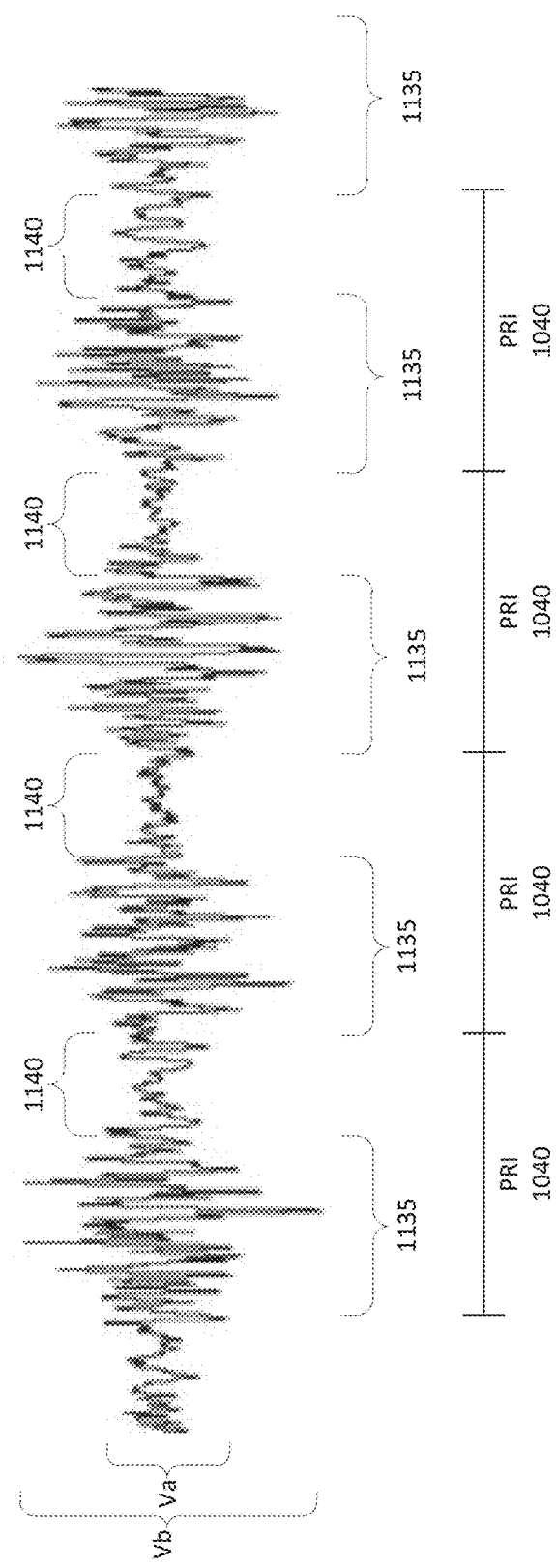
FIG. 11C illustrates audio signals having a modulation technique including audio filters, in accordance with an embodiment.

FIG. 11C illustrates audio pulses generated by the NSS 905 using a sound track, in accordance with an embodiment. A sound track can include or refer to a complex acoustical wave that includes multiple different frequencies, amplitudes, or tones. For example, a sound track can include a voice track, a musical instrument track, a musical track having both voice and musical instruments, nature sounds, or white noise.

The NSS 905 can modulate the sound track to induce brainwave entrainment by rhythmically adjusting a component in the sound. For example, the NSS 905 can modulate the volume by increasing and decreasing the amplitude of the acoustic wave or sound track to create the rhythmic stimulus corresponding to the stimulation frequency for inducing brainwave entrainment. Thus, the NSS 905 can embed, into a sound track acoustic pulses having a pulse rate interval corresponding to the desired stimulation frequency to induce brainwave entrainment. The NSS 905 can manipulate the sound track to generate a new, modified sound track having acoustic pulses with a pulse rate interval corresponding to the desired stimulation frequency to induce brainwave entrainment.

As illustrated in FIG. 11C, pulses 1135 are generated by modulating the volume from a first level $V_a$ to a second level $V_b$. During portions 1140 of the acoustic wave 345, the NSS 905 can set or keep the volume at $V_a$. The volume $V_a$ can refer to an amplitude of the wave, or a maximum amplitude or crest of the wave 345 during the portion 1140. The NSS 905 can then adjust, change, or increase the volume to $V_b$ during portion 1135. The NSS 905 can increase the volume by a predetermined amount, such as a percentage, a number of decibels, a subject-specified amount, or other amount. The NSS 905 can set or maintain the volume at $V_b$ for a duration corresponding to a desired pulse length for the pulse 1135.

In some embodiments, the NSS 905 can include an attenuator to attenuate the volume from level $V_b$ to level $V_a$. In some embodiments, the NSS 905 can instruct an attenuator (e.g., an attenuator of audio signaling component 950) to attenuate the volume from level $V_b$ to level $V_a$. In some embodiments, the NSS 905 can include an amplifier to amplify or increase the volume from $V_a$ to $V_b$. In some embodiments, the NSS 905 can instruct an amplifier (e.g., an amplifier of the audio signaling component 950) to amplify or increase the volume from $V_a$ to $V_b$.

Referring back to FIG. 9, the NSS 905 can include, access, interface with, or otherwise communicate with at least one audio adjustment module 915. The audio adjustment module 915 can be designed and constructed to adjust a parameter associated with the audio signal, such as a frequency, amplitude, wavelength, pattern or other parameter of the audio signal. The audio adjustment module 915 can automatically vary a parameter of the audio signal based on profile information or feedback. The audio adjustment module 915 can receive the feedback information from the feedback monitor 935. The audio adjustment module 915 can receive instructions or information from a side effects management module 930. The audio adjustment module 915 can receive profile information from profile manager 925.

The audio adjustment module 915 can increase or decrease a contrast ratio between the auditory stimulation signal and an ambient sound level. For example, the audio adjustment module 915 can determine or detect the ambient sound level at or proximate to an ear of the subject. The audio adjustment module 915 can increase or decrease the volume or tone of the audio source or auditory stimulation signal relative to the ambient sound level. The audio adjustment module 915 can increase or decrease this contrast ratio to facilitate adherence to the treatment or therapy session or reduce side effects. The audio adjustment module 915 can, for example, increase the contrast ratio upon detecting a low level of attention, or lack of satisfactory neural stimulation.

The NSS 905 can include, access, interface with, or otherwise communicate with at least one unwanted frequency filtering module 920. The unwanted frequency filtering module 920 can be designed and constructed to block, mitigate, reduce, or otherwise filter out frequencies of audio signals that are undesired to prevent or reduce an amount of such audio signals from being perceived by the brain. The unwanted frequency filtering module 920 can interface, instruct, control, or otherwise communicate with a filtering component 955 to cause the filtering component 955 to block, attenuate, or otherwise reduce the effect of the unwanted frequency on the neural oscillations.

Figure 12A:
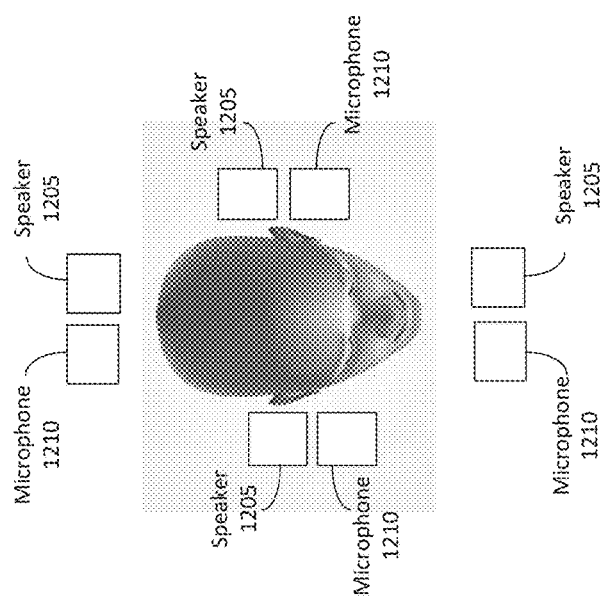
FIGS. 12A-12C illustrate system configurations for auditory brain entrainment in accordance with some embodiments.
Figure 12B:
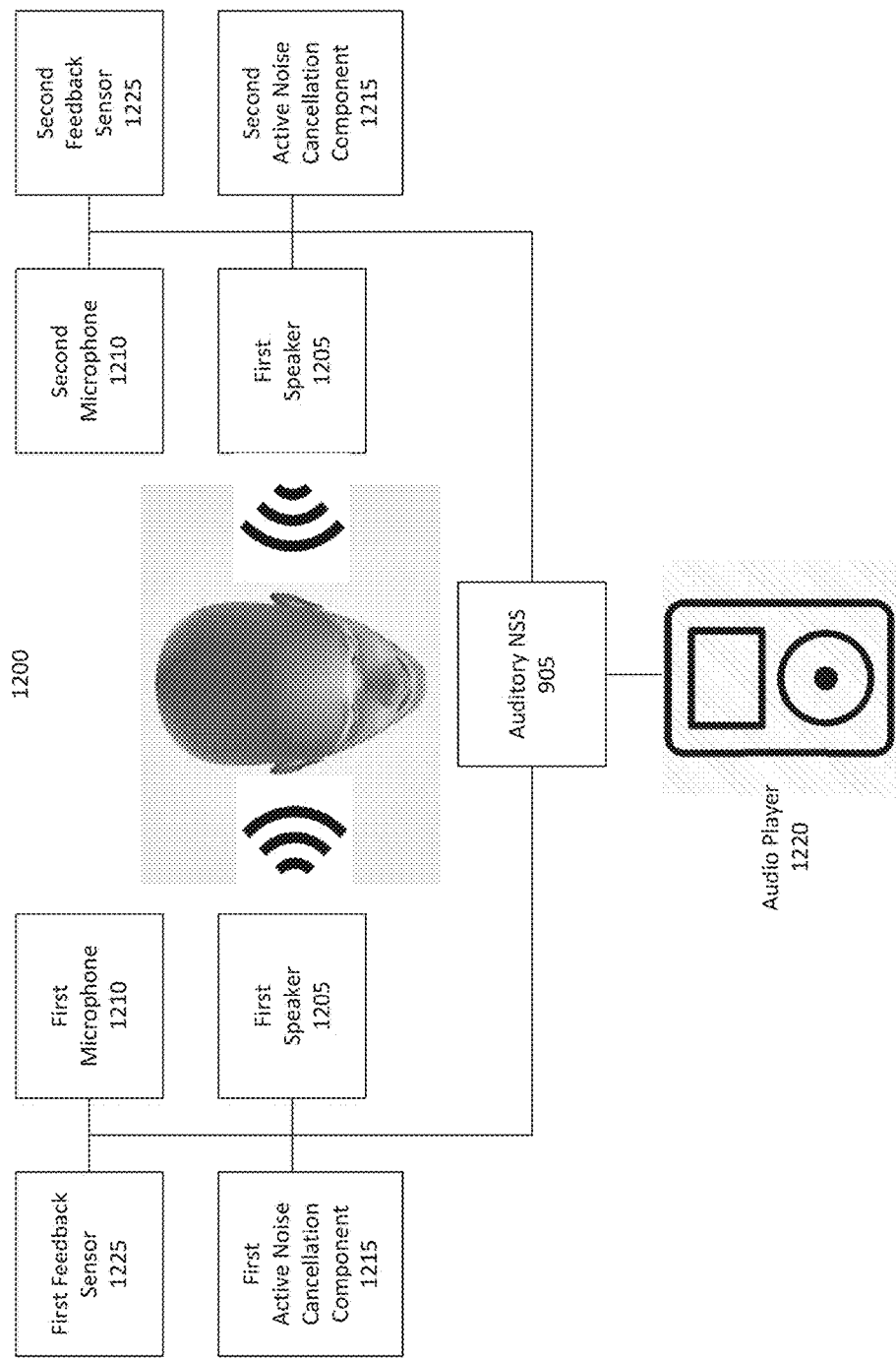
Figure 12C:
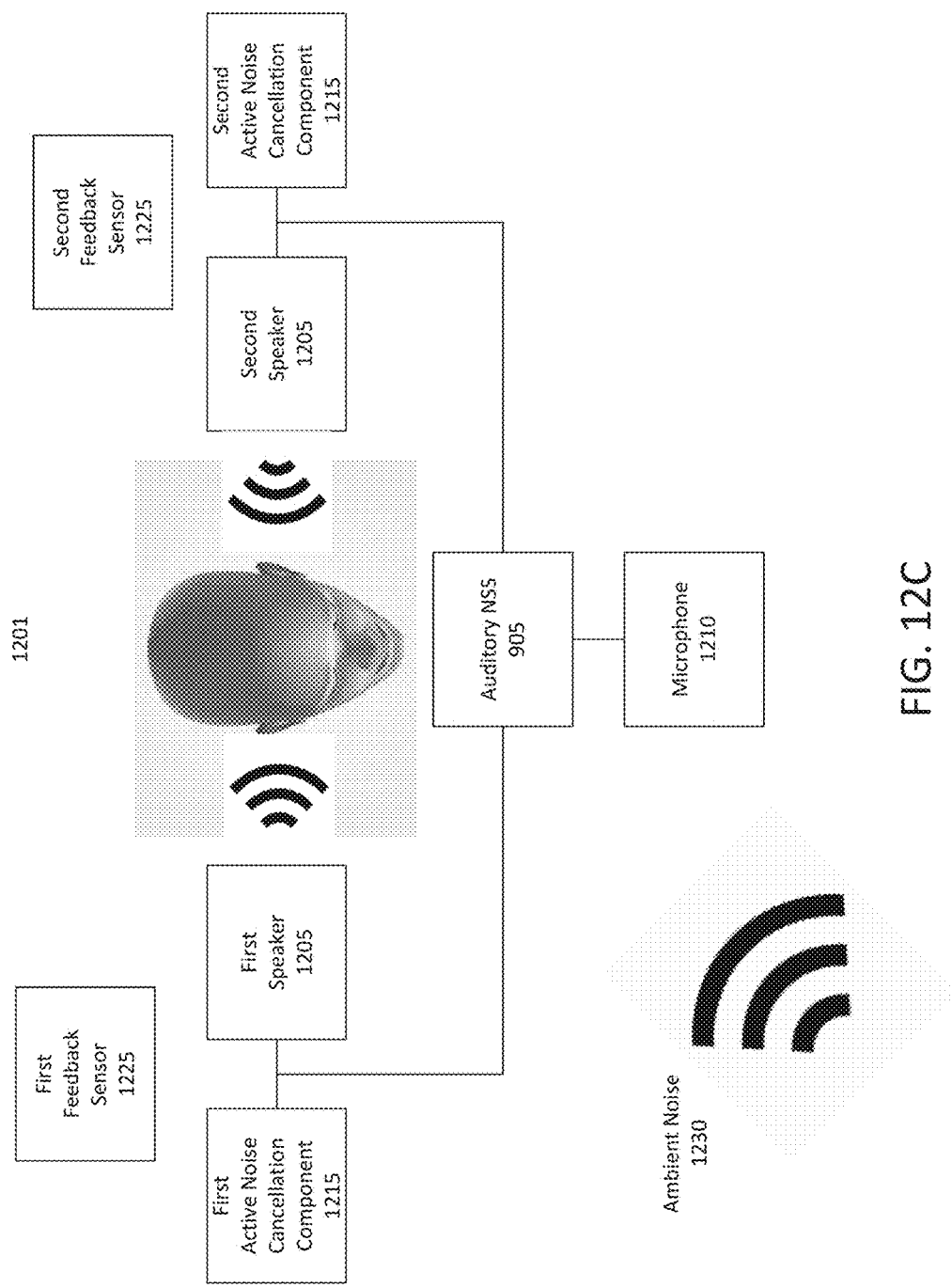

The unwanted frequency filtering module 920 can include an active noise control component (e.g., active noise cancellation component 1215 depicted in FIG. 12B). Active noise control can be referred to or include active noise cancellation or active noise reduction. Active noise control can reduce an unwanted sound by adding a second sound having a parameter specifically selected to cancel or attenuate the first sound. In some cases, the active noise control component can emit a sound wave with the same amplitude but with an inverted phase (or antiphase) to the original unwanted sound. The two waves can combine to form a new wave, and effectively cancel each other out by destructive interference.

The active noise control component can include analog circuits or digital signal processing. The active noise control component can include adaptive techniques to analyze waveforms of the background aural or monaural noise. Responsive to the background noise, the active noise control component can generate an audio signal that can either phase shift or invert the polarity of the original signal. This inverted signal can be amplified by a transducer or speaker to create a sound wave directly proportional to the amplitude of the original waveform, creating destructive interference. This can reduce the volume of the perceivable noise.

In some embodiments, a noise-cancellation speaker can be co-located with a sound source speaker. In some embodiments, a noise cancellation speaker can be co-located with a sound source that is to be attenuated.

The unwanted frequency filtering module 920 can filter out unwanted frequencies that can adversely impact auditory brainwave entrainment. For example, an active noise control component can identify that audio signals include acoustic bursts having the desired pulse rate interval, as well as acoustic bursts having an unwanted pulse rate interval. The active noise control component can identify the waveforms corresponding to the acoustic bursts having the unwanted pulse rate interval, and generate an inverted phase waveform to cancel out or attenuate the unwanted acoustic bursts.

The NSS 905 can include, access, interface with, or otherwise communicate with at least one profile manager 925. The profile manager 925 can be designed or constructed to store, update, retrieve or otherwise manage information associated with one or more subjects associated with the auditory brain entrainment. Profile information can include, for example, historical treatment information, historical brain entrainment information, dosing information, parameters of acoustic waves, feedback, physiological information, environmental information, or other data associated with the systems and methods of brain entrainment.

The NSS 905 can include, access, interface with, or otherwise communicate with at least one side effects management module 930. The side effects management module 930 can be designed and constructed to provide information to the audio adjustment module 915 or the audio generation module 910 to change one or more parameter of the audio signal in order to reduce a side effect. Side effects can include, for example, nausea, migraines, fatigue, seizures, ear strain, deafness, ringing, or tinnitus.

The side effects management module 930 can automatically instruct a component of the NSS 905 to alter or change a parameter of the audio signal. The side effects management module 930 can be configured with predetermined thresholds to reduce side effects. For example, the side effects management module 930 can be configured with a maximum duration of a pulse train, maximum amplitude of acoustic waves, maximum volume, maximum duty cycle of a pulse train (e.g., the pulse width multiplied by the frequency of the pulse train), maximum number of treatments for brainwave entrainment in a time period (e.g., 1 hour, 2 hours, 12 hours, or 24 hours).

The side effects management module 930 can cause a change in the parameter of the audio signal in response to feedback information. The side effect management module 930 can receive feedback from the feedback monitor 935. The side effects management module 930 can determine to adjust a parameter of the audio signal based on the feedback. The side effects management module 930 can compare the feedback with a threshold to determine to adjust the parameter of the audio signal.

The side effects management module 930 can be configured with or include a policy engine that applies a policy or a rule to the current audio signal and feedback to determine an adjustment to the audio signal. For example, if feedback indicates that a patient receiving audio signals has a heart rate or pulse rate above a threshold, the side effects management module 930 can turn off the pulse train until the pulse rate stabilizes to a value below the threshold, or below a second threshold that is lower than the threshold.

The NSS 905 can include, access, interface with, or otherwise communicate with at least one feedback monitor 935. The feedback monitor can be designed and constructed to receive feedback information from a feedback component 960. Feedback component 960 can include, for example, a feedback sensor 1405 such as a temperature sensor, heart or pulse rate monitor, physiological sensor, ambient noise sensor, microphone, ambient temperature sensor, blood pressure monitor, brain wave sensor, EEG probe, electrooculography ("EOG") probes configured measure the corneoretinal standing potential that exists between the front and the back of the human eye, accelerometer, gyroscope, motion detector, proximity sensor, camera, microphone, or photo detector.

The NSS 905 can, responsive to feedback, adjust the audio stimulation signal. The NSS 905 can increase or decrease a parameter of the audio stimulation signal responsive to physiological conditions, such as heart rate, blood pressure, level of attention, agitation, temperature, etc. The NSS 905 can overlay an auditory signal over the audio stimulation signal. The NSS 905 can overlay an audio prompt or message over the auditory stimulation signal. The audio prompt can indicate a duration remaining in the therapy session. The audio prompt can include a prerecorded message, such as a message from a person known to the subject or user receiving the auditory stimulation. The audio prompt can include words of guidance, training, encouragement, reminders, motivational messages, or other messages that can facilitate adherence, improve attentiveness, or reduce agitation in the subject.

I. Systems and Devices Configured for Neural Stimulation Via Auditory Stimulation FIG. 12A illustrates a system for auditory brain entrainment in accordance with an embodiment. The system 1200 can include one or more speakers 1205. The system 1200 can include one or more microphones. In some embodiments, the system can include both speakers 1205 and microphones 1210. In some embodiments, the system 1200 includes speakers 1205 and may not include microphones 1210. In some embodiments, the system 1200 includes microphones 1210 and may not include speakers 1210.

The speakers 1205 can be integrated with the audio signaling component 950. The audio signaling component 950 can include speakers 1205. The speakers 1205 can interact or communicate with audio signaling component 950. For example, the audio signaling component 950 can instruct the speaker 1205 to generate sound.

The microphones 1210 can be integrated with the feedback component 960. The feedback component 960 can include microphones 1210. The microphones 1210 can interact or communicate with feedback component 960. For example, the feedback component 960 can receive information, data or signals from microphone 1210.

In some embodiments, the speaker 1205 and the microphone 1210 can be integrated together or a same device. For example, the speaker 1205 can be configured to function as the microphone 1210. The NSS 905 can toggle the speaker 1205 from a speaker mode to a microphone mode.

In some embodiments, the system 1200 can include a single speaker 1205 positioned at one of the ears of the subject. In some embodiments, the system 1200 can include two speakers. A first speaker of the two speakers can be positioned at a first ear, and the second speaker of the two speakers can be positioned at the second ear. In some embodiments, additional speakers can be positioned in front of the subject's head, or behind the subject's head. In some embodiments, one or more microphones 1210 can be positioned at one or both ears, in front of the subject's head, or behind the subject's head.

The speaker 1205 can include a dynamic cone speaker configured to produce sound from an electrical signal. The speaker 1205 can include a full-range driver to produce acoustic waves with frequencies over some or all of the audible range (e.g., 60 Hz to 20,000 Hz). The speaker 1205 can include a driver to produce acoustic waves with frequencies outside the audible range, such as 0 to 60 Hz, or in the ultrasonic range such as 20 kHz to 4 GHz. The speaker 1205 can include one or more transducers or drivers to produce sounds at varying portions of the audible frequency range. For example, the speaker 1205 can include tweeters for high range frequencies (e.g., 2,000 Hz to 20,000 Hz), mid-range drivers for middle frequencies (e.g., 250 Hz to 2000 Hz), or woofers for low frequencies (e.g., 60 Hz to 250 Hz).

The speaker 1205 can include one or more types of speaker hardware, components or technology to produce sound. For example, the speaker 1205 can include a diaphragm to produce sound. The speaker 1205 can include a moving-iron loudspeaker that uses a stationary coil to vibrate a magnetized piece of metal. The speaker 1205 can include a piezoelectric speaker. A piezoelectric speaker can use the piezoelectric effect to generate sound by applying a voltage to a piezoelectric material to generate motion, which is converted into audible sound using diaphragms and resonators.

The speaker 1205 can include various other types of hardware or technology, such as magnetostatic loudspeakers, magnetostrictive speakers, electrostatic loudspeakers, a ribbon speaker, planar magnetic loudspeakers, bending wave loudspeakers, coaxial drivers, horn loudspeakers, Heil air motion transducers, or transparent ionic conductions speaker.

In some cases, the speaker 1205 may not include a diaphragm. For example, the speaker 1205 can be a plasma arc speaker that uses electrical plasma as a radiating element. The speaker 1205 can be a thermoacoustic speakers that uses carbon nanotube thin film. The speaker 1205 can be a rotary woofer that includes a fan with blades that constantly change their pitch.

In some embodiments, the speaker 1205 can include a headphone or a pair of headphones, earspeakers, earphones, or earbuds. Headphones can be relatively small speakers as compared to loudspeakers, headphones can be designed and constructed to be placed in the ear, around the ear, or otherwise at or near the ear. Headphones can include electroacoustic transducers that convert an electrical signal to a corresponding sound in the subject's ear. In some embodiments, the headphones 1205 can include or interface with a headphone amplifier, such as an integrated amplifier or a standalone unit.

In some embodiments, the speaker 1205 can include headphones that can include an air jet that pushes air into the auditory canal, pushing the tympanum in a manner similar to that of a sound wave. The compression and rarefaction of the tympanic membrane through bursts of air (with or without any discernible sound) can control frequencies of neural oscillations similar to auditory signals. For example, the speaker 1205 can include air jets or a device that resembles in-ear headphones that either push, pull or both push and pull air into and out of the ear canal in order to compress or pull the tympanic membrane to affect the frequencies of neural oscillations. The NSS 905 can instruct, configure or cause the air jets to generate bursts of air at a predetermined frequency.

In some embodiments, the headphones can connect to the audio signaling component 950 via a wired or wireless connection. In some embodiments, the audio signaling component 950 can include the headphones. In some embodiments, the headphones 1205 can interface with one or more components of the NSS 905 via a wired or wireless connection. In some embodiments, the headphones 1205 can include one or more components of the NSS 905 or system 100, such as the audio generation module 910, audio adjustment module 915, unwanted frequency filtering module 920, profile manager 925, side effects management module 930, feedback monitor 935, audio signaling component 950, filtering component 955, or feedback component 960.

The speaker 1205 can include or be integrated into various types of headphones. For example, the headphones can include, for example, circumaural headphones (e.g., full size headphones) that include circular or ellipsoid earpads that are designed and constructed to seal against the head to attenuate external noise. Circumaural headphones can facilitate providing an immersive auditory brainwave wave stimulation experience, while reducing external distractions. In some embodiments, headphones can include supra-aural headphones, which include pads that press against the ears rather than around them. Supra-aural headphones may provide less attenuation of external noise.

Both circumaural headphones and supra-aural headphones can have an open back, closed back, or semi open back. An open back leaks more sound and allows more ambient sounds to enter, but provides a more natural or speaker-like sound. Closed back headphones block more of the ambient noise as compared to open back headphones, thus providing a more immersive auditory brainwave stimulation experience while reducing external distractions.

In some embodiments, headphones can include ear-fitting headphones, such as earphones or in-ear headphones. Earphones (or earbuds) can refer to small headphones that are fitted directly in the outer ear, facing but not inserted in the ear canal. Earphones, however, provide minimal acoustic isolation and allow ambient noise to enter. In-ear headphones (or in-ear monitors or canalphones) can refer to small headphones that can be designed and constructed for insertion into the ear canal. In-ear headphones engage the ear canal and can block out more ambient noise as compared to earphones, thus providing a more immersive auditory brainwave stimulation experience. In-ear headphones can include ear canal plugs made or formed from one or more material, such as silicone rubber, elastomer, or foam. In some embodiments, in-ear headphones can include custom-made castings of the ear canal to create custom-molded plugs that provide added comfort and noise isolation to the subject, thereby further improving the immersiveness of the auditory brainwave stimulation experience.

In some embodiments, one or more microphones 1210 can be used to detect sound. A microphone 1210 can be integrated with a speaker 1205. The microphone 1210 can provide feedback information to the NSS 905 or other component of system 100. The microphone 1210 can provide feedback to a component of the speaker 1205 to cause the speaker 1205 to adjust a parameter of audio signal.

The microphone 1210 can include a transducer that converts sound into an electrical signal. The Microphone 1210 can use electromagnetic induction, capacitance change, or piezoelectricity to produce the electrical signal from air pressure variations. In some cases, the microphone 1210 can include or be connected to a pre-amplifier to amplify the signal before it is recorded or processed. The microphone 1210 can include one or more type of microphone, including, for example, a condenser microphone, RF condenser microphone, electret condenser, dynamic microphone, moving-coil microphone, ribbon microphone, carbon microphone, piezoelectric microphone, crystal microphone, fiber optic microphone, laser microphone, liquid or water microphone, microelectromechanical systems ("MEMS") microphone, or speakers as microphones.

The feedback component 960 can include or interface with the microphone 1210 to obtain, identify, or receive sound. The feedback component 960 can obtain ambient noise. The feedback component 960 can obtain sound from the speakers 1205 to facilitate the NSS 905 adjusting a characteristic of the audio signal generated by the speaker 1205. The microphone 1210 can receive voice input from the subject, such as audio commands, instructions, requests, feedback information, or responses to survey questions.

In some embodiments, one or more speakers 1205 can be integrated with one or more microphones 1210. For example, the speaker 1205 and microphone 1210 can form a headset, be placed in a single enclosure, or may even be the same device since the speaker 1205 and the microphone 1210 may be structurally designed to toggle between a sound generation mode and a sound reception mode.

FIG. 12B illustrates a system configuration for auditory brain entrainment in accordance with an embodiment. The system 1200 can include at least one speaker 1205. The system 1200 can include at least one microphone 1210. The system 1200 can include at least one active noise cancellation component 1215. The system 1200 can include at least one feedback sensor 1225. The system 1200 can include or interface with the NSS 905. The system 1200 can include or interface with an audio player 1220.

The system 1200 can include a first speaker 1205 positioned at a first ear. The system 1200 can include a second speaker 1205 positioned at a second year. The system 1200 can include a first active noise cancellation component 1215 communicatively coupled with the first microphone 1210. The system 1200 can include a second active noise cancellation component 1215 communicatively coupled with the second microphone 1210. In some cases, the active noise cancellation component 1215 can communicate with both the first speaker 1205 and the second speaker 1205, or both the first microphone 1210 and the second microphone 1210. The system 1200 can include a first microphone 1210 communicatively coupled with the active noise cancellation component 1215. The system 1200 can include a second microphone 1210 communicatively coupled with the active noise cancelation component 1215. In some embodiments, each of the microphone 1210, speaker 1205 and active noise cancellation component can communicate or interface with the NSS 905. In some embodiments, the system 1200 can include a feedback sensor 1225 and a second feedback sensor 1225 communicatively coupled to the NSS 905, the speaker 1205, microphone 1210, or active noise cancellation component 1215.

In operation, and in some embodiments, the audio player 1220 can play a musical track. The audio player 1220 can provide the audio signal corresponding to the musical track via a wired or wireless connection to the first and second speakers 1205. In some embodiments, the NSS 905 can intercept the audio signal from the audio player. For example, the NSS 905 can receive the digital or analog audio signal from the audio player 1220. The NSS 905 can be intermediary to the audio player 1220 and a speaker 1205. The NSS 905 can analyze the audio signal corresponding to the music in order to embed an auditory brainwave stimulation signal. For example, the NSS 905 can adjust the volume of the auditory signal from the audio player 1220 to generate acoustic pulses having a pulse rate interval as depicted in FIG. 11C. In some embodiments, the NSS 905 can use a binaural beats technique to provide different auditory signals to the first and second speakers that, when perceived by the brain, is combined to have the desired stimulation frequency.

In some embodiments, the NSS 905 can adjust for any latency between first and second speakers 1205 such that the brain perceives the audio signals at the same or substantially same time (e.g., within 1 milliseconds, 2 milliseconds, 5 milliseconds, or 10 milliseconds). The NSS 905 can buffer the audio signals to account for latency such that audio signals are transmitted from the speakers at the same time.

In some embodiments, the NSS 905 may not be intermediary to the audio player 1220 and the speaker. For example, the NSS 905 can receive the musical track from a digital music repository. The NSS 905 can manipulate or modify the musical track to embed acoustic pulses in accordance with the desired PRI. The NSS 905 can then provide the modified musical track to the audio player 1220 to provide the modified audio signal to the speaker 1205.

In some embodiments, an active noise cancellation component 1215 can receive ambient noise information from the microphone 1210, identify unwanted frequencies or noise, and generate an inverted phase waveform to cancel out or attenuate the unwanted waveforms. In some embodiments, the system 1200 can include an additional speaker that generates the noise canceling waveform provided by the noise cancellation component 1215. The noise cancellation component 1215 can include the additional speaker.

The feedback sensor 1225 of the system 1200 can detect feedback information, such as environmental parameters or physiological conditions. The feedback sensor 1225 can provide the feedback information to NSS 905. The NSS 905 can adjust or change the audio signal based on the feedback information. For example, the NSS 905 can determine that a pulse rate of the subject exceeds a predetermined threshold, and then lower the volume of the audio signal. The NSS 905 can detect that the volume of the auditory signal exceeds a threshold, and decrease the amplitude. The NSS 905 can determine that the pulse rate interval is below a threshold, which can indicate that a subject is losing focus or not paying a satisfactory level of attention to the audio signal, and the NSS 905 can increase the amplitude of the audio signal or change the tone or music track. In some embodiments, the NSS 905 can vary the tone or the music track based on a time interval. Varying the tone or the music track can cause the subject to pay a greater level of attention to the auditory stimulation, which can facilitate brainwave entrainment.

In some embodiments, the NSS 905 can receive neural oscillation information from EEG probes 1225, and adjust the auditory stimulation based on the EEG information. For example, the NSS 905 can determine, from the probe information, that neurons are oscillating at an undesired frequency. The NSS 905 can then identify the corresponding undesired frequency in ambient noise using the microphone 1210. The NSS 905 can then instruct the active noise cancellation component 1215 to cancel out the waveforms corresponding to the ambient noise having the undesired frequency.

In some embodiments, the NSS 905 can enable a passive noise filter. A pass noise filter can include a circuit having one or more or a resistor, capacitor or an inductor that filters out undesired frequencies of noise. In some cases, a passive filter can include a sound insulating material, sound proofing material, or sound absorbing material.

FIG. 4C illustrates a system configuration for auditory brain entrainment in accordance with an embodiment. The system 401 can provide auditory brainwave stimulation using ambient noise source 1230. For example, system 401 can include the microphone 1210 that detects the ambient noise 1230. The microphone 1210 can provide the detected ambient noise to NSS 905. The NSS 905 can modify the ambient noise 1230 before providing it to the first speaker 1205 or the second speaker 1205. In some embodiments, the system 401 can be integrated or interface with a hearing aid device. A hearing aid can be a device designed to improve hearing.

The NSS 905 can increase or decrease the amplitude of the ambient noise 1230 to generate acoustic bursts having the desired pulse rate interval. The NSS 905 can provide the modified audio signals to the first and second speakers 1205 to facilitate auditory brainwave entrainment.

In some embodiments, the NSS 905 can overlay a click train, tones, or other acoustic pulses over the ambient noise 1230. For example, the NSS 905 can receive the ambient noise information from the microphone 1210, apply an auditory stimulation signal to the ambient noise information, and then present the combined ambient noise information and auditory stimulation signal to the first and second speakers 1205. In some cases, the NSS 905 can filter out unwanted frequencies in the ambient noise 1230 prior to providing the auditory stimulation signal to the speakers 1205.

Thus, using the ambient noise 1230 as part of the auditory stimulation, a subject can observe the surroundings or carry on with their daily activities while receiving auditory stimulation to facilitate brainwave entrainment.

Figure 13:
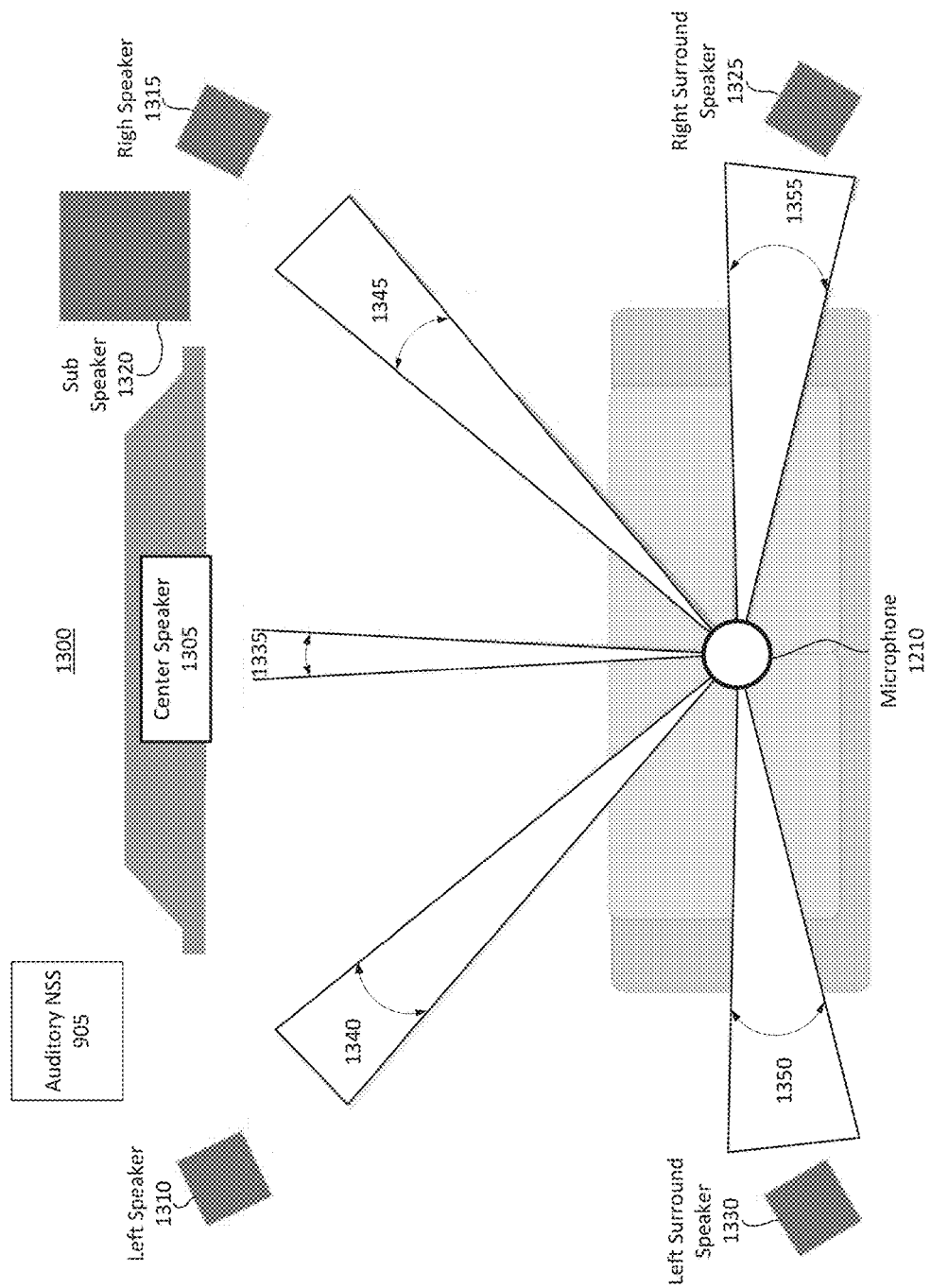
FIG. 13 illustrates a system configuration for room-based auditory brain entrainment in accordance with an embodiment.

FIG. 13 illustrates a system configuration for auditory brain entrainment in accordance with an embodiment. The system 1300 can provide auditory stimulation for brainwave entrainment using a room environment. The system 1300 can include one or more speakers. The system 1300 can include a surround sound system. For example, the system 1300 includes a left speaker 1310, right speaker 1315, center speaker 1305, right surround speaker 1325, and left surround speaker 1330. System 1300 an include a sub-woofer 1320. The system 1300 can include the microphone 1210. The system 1300 can include or refer to a 5.1 surround system. In some embodiments, the system 1300 can have 1, 2, 3, 4, 5, 6, 7 or more speakers.

When providing auditory stimulation using a surround system, the NSS 905 can provide the same or different audio signals to each of the speakers in the system 1300. The NSS 905 can modify or adjust audio signals provided to one or more of the speakers in system 1300 in order to facilitate brainwave entrainment. For example, the NSS 905 can receive feedback from microphone 1210 and modify, manipulate or otherwise adjust the audio signal to optimize the auditory stimulation provided to a subject located at a position in the room that corresponds to the location of the microphone 1210. The NSS 905 can optimize or improve the auditory stimulation perceived at the location corresponding to microphone 1210 by analyzing the acoustic beams or waves generated by the speakers that propagate towards the microphone 1210.

The NSS 905 can be configured with information about the design and construction of each speaker. For example, speaker 1305 can generate sound in a direction that has an angle of 1335; speaker 1310 can generate sound that travels in a direction having an angle of 1340; speaker 1315 can generate sound that travels in a direction having an angle of 1345; speaker 1325 can generate sound that travels in a direction having an angle of 1355; and speaker 1330 can generate sound that travels in a direction having an angle of 1350. These angles can be the optimal or predetermined angles for each of the speakers. These angles can refer to the optimal angle of each speaker such that a person positioned at location corresponding to microphone 1210 can receive the optimum auditory stimulation. Thus, the speakers in system 1300 can be oriented to transmit auditory stimulation towards the subject.

In some embodiments, the NSS 905 can enable or disable one or more speakers. In some embodiments, the NSS 905 can increase or decrease the volume of the speakers to facilitate brainwave entrainment. The NSS 905 can intercept musical tracks, television audio, movie audio, internet audio, audio output from a set top box, or other audio source. The NSS 905 can adjust or manipulate the received audio, and transmit the adjusted audio signals to the speakers in system 1300 to induce brainwave entrainment.

Figure 14:
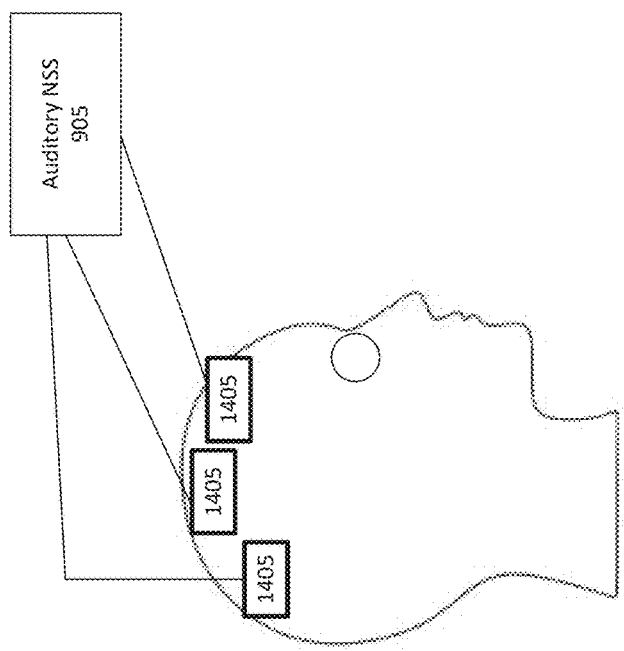
FIG. 14 illustrate devices configured to receive feedback to facilitate auditory brain entrainment in accordance with some embodiments.

FIG. 14 illustrates feedback sensors 1405 placed or positioned at, on, or near a person's head. Feedback sensors 1405 can include, for example, EEG probes that detect brain wave activity.

The feedback monitor 935 can detect, receive, obtain, or otherwise identify feedback information from the one or more feedback sensors 1405. The feedback monitor 935 can provide the feedback information to one or more component of the NSS 905 for further processing or storage. For example, the profile manager 925 can update profile data structure 945 stored in data repository 940 with the feedback information. Profile manager 925 can associate the feedback information with an identifier of the patient or person undergoing the auditory stimulation, as well as a time stamp and date stamp corresponding to receipt or detection of the feedback information.

The feedback monitor 935 can determine a level of attention. The level of attention can refer to the focus provided to the acoustic pulses used for stimulation. The feedback monitor 935 can determine the level of attention using various hardware and software techniques. The feedback monitor 935 can assign a score to the level of attention (e.g., 1 to 10 with 1 being low attention and 10 being high attention, or vice versa, 1 to 100 with 1 being low attention and 100 being high attention, or vice versa, 0 to 1 with 0 being low attention and 1 being high attention, or vice versa), categorize the level of attention (e.g., low, medium, high), grade the attention (e.g., A, B, C, D, or F), or otherwise provide an indication of a level of attention.

In some cases, the feedback monitor 935 can track a person's eye movement to identify a level of attention. The feedback monitor 935 can interface with a feedback component 960 that includes an eye-tracker. The feedback monitor 935 (e.g., via feedback component 960) can detect and record eye movement of the person and analyze the recorded eye movement to determine an attention span or level of attention. The feedback monitor 935 can measure eye gaze which can indicate or provide information related to covert attention. For example, the feedback monitor 935 (e.g., via feedback component 960) can be configured with electro-oculography ("EOG") to measure the skin electric potential around the eye, which can indicate a direction the eye faces relative to the head. In some embodiments, the EOG can include a system or device to stabilize the head so it cannot move in order to determine the direction of the eye relative to the head. In some embodiments, the EOG can include or interface with a head tracker system to determine the position of the heads, and then determine the direction of the eye relative to the head.

In some embodiments, the feedback monitor 935 and feedback component 960 can determine a level of attention the subject is paying to the auditory stimulation based on eye movement. For example, increased eye movement may indicate that the subject is focusing on visual stimuli, as opposed to the auditory stimulation. To determine the level of attention the subject is paying to visual stimuli as opposed to the auditory stimulation, the feedback monitor 935 and feedback component 960 can determine or track the direction of the eye or eye movement using video detection of the pupil or corneal reflection. For example, the feedback component 960 can include one or more camera or video camera. The feedback component 960 can include an infra-red source that sends light pulses towards the eyes. The light can be reflected by the eye. The feedback component 960 can detect the position of the reflection. The feedback component 960 can capture or record the position of the reflection. The feedback component 960 can perform image processing on the reflection to determine or compute the direction of the eye or gaze direction of the eye.

The feedback monitor 935 can compare the eye direction or movement to historical eye direction or movement of the same person, nominal eye movement, or other historical eye movement information to determine a level of attention. For example, the feedback monitor 935 can determine a historical amount of eye movement during historical auditory stimulation sessions. The feedback monitor 935 can compare the current eye movement with the historical eye movement to identify a deviation. The NSS 905 can determine, based on the comparison, an increase in eye movement and further determine that the subject is paying less attention to the current auditory stimulation based on the increase in eye movement. In response to detecting the decrease in attention, the feedback monitor 935 can instruct the audio adjustment module 915 to change a parameter of the audio signal to capture the subject's attention. The audio adjustment module 915 can change the volume, tone, pitch, or music track to capture the subject's attention or increase the level of attention the subject is paying to the auditory stimulation. Upon changing the audio signal, the NSS 905 can continue to monitor the level of attention. For example, upon changing the audio signal, the NSS 905 can detect a decrease in eye movement which can indicate an increase in a level of attention provided to the audio signal.

The feedback sensor 1405 can interact with or communicate with NSS 905. For example, the feedback sensor 1405 can provide detected feedback information or data to the NSS 905 (e.g., feedback monitor 935). The feedback sensor 1405 can provide data to the NSS 905 in real-time, for example as the feedback sensor 1405 detects or senses or information. The feedback sensor 1405 can provide the feedback information to the NSS 905 based on a time interval, such as 1 minute, 2 minutes, 5 minutes, 10 minutes, hourly, 2 hours, 4 hours, 12 hours, or 24 hours. The feedback sensor 1405 can provide the feedback information to the NSS 905 responsive to a condition or event, such as a feedback measurement exceeding a threshold or falling below a threshold. The feedback sensor 1405 can provide feedback information responsive to a change in a feedback parameter. In some embodiments, the NSS 905 can ping, query, or send a request to the feedback sensor 1405 for information, and the feedback sensor 1405 can provide the feedback information in response to the ping, request, or query.

J. Method for Neural Stimulation Via Auditory Stimulation

Figure 15:
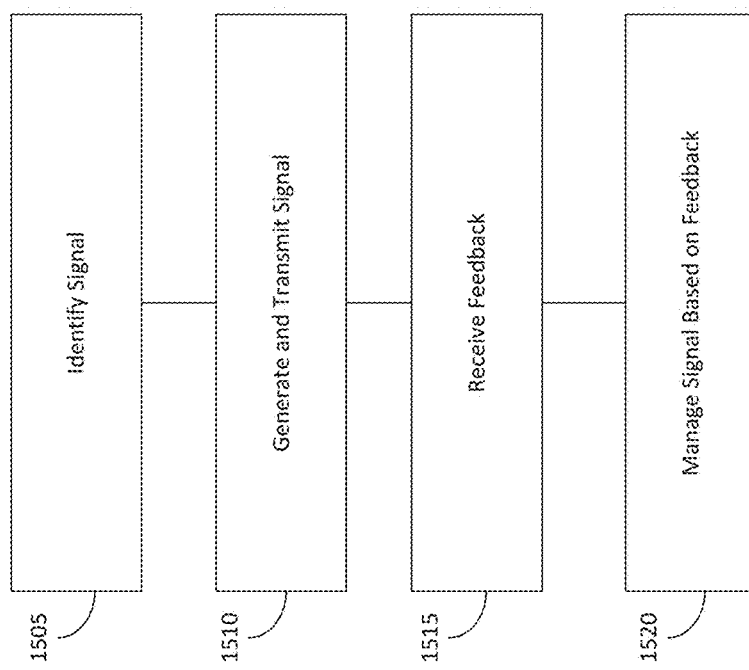
FIG. 15 is a flow diagram of a method of performing auditory brain entrainment in accordance with an embodiment.

FIG. 15 is a flow diagram of a method of performing auditory brain entrainment in accordance with an embodiment. The method 800 can be performed by one or more system, component, module or element depicted in FIGS. 7A, 7B, and 9-14, including, for example, a neural stimulation system (NSS). In brief overview, the NSS can identify an audio signal to provide at block 1505. At block 1510, the NSS can generate and transmit the identified audio signal. At 1515 the NSS can receive or determine feedback associated with neural activity, physiological activity, environmental parameters, or device parameters. At 1520 the NSS can manage, control, or adjust the audio signal based on the feedback.

K. NSS Operating with Headphones

The NSS 905 can operate in conjunction with the speakers 1205 as depicted in FIG. 12A. The NSS 905 can operate in conjunction with earphones or in-ear phones including the speaker 1205 and a feedback sensor 1405.

In operation, a subject using the headphones can wear the headphones on their head such that speakers or placed at or in the ear canals. In some cases, the subject can provide an indication to the NSS 905 that the headphones have been worn and that the subject is ready to undergo brainwave entrainment. The indication can include an instruction, command, selection, input, or other indication via an input/output interface, such as a keyboard 726, pointing device 727, or other I/O devices 730*a-n*. The indication can be a motion-based indication, visual indication, or voice-based indication. For example, the subject can provide a voice command that indicates that the subject is ready to undergo brainwave entrainment.

In some cases, the feedback sensor 1405 can determine that the subject is ready to undergo brainwave entrainment. The feedback sensor 1405 can detect that the headphones have been placed on a subject's head. The NSS 905 can receive motion data, acceleration data, gyroscope data, temperature data, or capacitive touch data to determine that the headphones have been placed on the subject's head. The received data, such as motion data, can indicate that the headphones were picked up and placed on the subject's head. The temperature data can measure the temperature of or proximate to the headphones, which can indicate that the headphones are on the subject's head. The NSS 905 can detect that the subject is ready responsive to determining that the subject is paying a high level of attention to the headphones or feedback sensor 1405.

Thus, the NSS 905 can detect or determine that the headphones have been worn and that the subject is in a ready state, or the NSS 905 can receive an indication or confirmation from the subject that the subject has worn the headphones and the subject is ready to undergo brainwave entrainment. Upon determining that the subject is ready, the NSS 905 can initialize the brainwave entrainment process. In some embodiments, the NSS 905 can access a profile data structure 945. For example, a profile manager 925 can query the profile data structure 945 to determine one or more parameter for the external auditory stimulation used for the brain entrainment process. Parameters can include, for example, a type of audio stimulation technique, an intensity or volume of the audio stimulation, frequency of the audio stimulation, duration of the audio stimulation, or wavelength of the audio stimulation. The profile manager 925 can query the profile data structure 945 to obtain historical brain entrainment information, such as prior auditory stimulation sessions. The profile manager 925 can perform a lookup in the profile data structure 945. The profile manager 925 can perform a look-up with a username, user identifier, location information, fingerprint, biometric identifier, retina scan, voice recognition and authentication, or other identifying technique.

The NSS 905 can determine a type of external auditory stimulation based on the components connected to the headphones. The NSS 905 can determine the type of external auditory stimulation based on the type of speakers 1205 available. For example, if the headphones are connected to an audio player, the NSS 905 can determined to embed acoustic pulses. If the headphones are not connected to an audio player, but only the microphone, the NSS 905 can determine to inject a pure tone or modify ambient noise.

In some embodiments, the NSS 905 can determine the type of external auditory stimulation based on historical brainwave entrainment sessions. For example, the profile data structure 945 can be pre-configured with information about the type of audio signaling component 950.

The NSS 905 can determine, via the profile manager 925, a modulation frequency for the pulse train or the audio signal. For example, NSS 905 can determine, from the profile data structure 945, that the modulation frequency for the external auditory stimulation should be set to 40 Hz. Depending on the type of auditor) stimulation, the profile data structure 945 can further indicate a pulse length, intensity, wavelength of the acoustic wave forming the audio signal, or duration of the pulse train.

In some cases, the NSS 905 can determine or adjust one or more parameter of the external auditory stimulation. For example, the NSS 905 (e.g., via feedback component 960 or feedback sensor 1405) can determine an amplitude of the acoustic wave or volume level for the sound. The NSS 905 (e.g., via audio adjustment module 915 or side effects management module 930) can establish, initialize, set, or adjust the amplitude or wavelength of the acoustic waves or acoustic pulses. For example, the NSS 905 can determine that there is a low level of ambient noise. Due to the low level of ambient noise, subject's hearing may not be impaired or distracted. The NSS 905 can determine, based on detecting a low level of ambient noise, that it may not be necessary to increase the volume, or that it may be possible to reduce the volume to maintain the efficacy of brainwave entrainment.

In some embodiments, the NSS 905 can monitor (e.g., via feedback monitor 935 and feedback component 960) the level of ambient noise throughout the brainwave entrainment process to automatically and periodically adjust the amplitude of the acoustic pulses. For example, if the subject began the brainwave entrainment process when there was a high level of ambient noise, the NSS 905 can initially set a higher amplitude for the acoustic pulses and use a tone that includes frequencies that are easier to perceive, such as 10 kHz. However, in some embodiments in which the ambient noise level decreases throughout the brainwave entrainment process, the NSS 905 can automatically detect the decrease in ambient noise and, in response to the detection, adjust or lower the volume while decreasing the frequency of the acoustic wave. The NSS 905 can adjust the acoustic pulses to provide a high contrast ratio with respect to ambient noise to facilitate brainwave entrainment.

In some embodiments, the NSS 905 (e.g., via feedback monitor 935 and feedback component 960) can monitor or measure physiological conditions to set or adjust a parameter of the acoustic wave. In some embodiments, the NSS 905 can monitor or measure heart rate, pulse rate, blood pressure, body temperature, perspiration, or brain activity to set or adjust a parameter of the acoustic wave.

In some embodiments, the NSS 905 can be preconfigured to initially transmit acoustic pulses having a lowest setting for the acoustic wave intensity (e.g., low amplitude or high wavelength) and gradually increase the intensity (e.g., increase the amplitude of the or decrease the wavelength) while monitoring feedback until an optimal audio intensity is reached. An optimal audio intensity can refer to a highest intensity without adverse physiological side effects, such as deafness, seizures, heart attack, migraines, or other discomfort. The NSS 905 (e.g., via side effects management module 930) can monitor the physiological symptoms to identify the adverse side effects of the external auditory stimulation, and adjust (e.g., via audio adjustment module 915) the external auditory stimulation accordingly to reduce or eliminate the adverse side effects.

In some embodiments, the NSS 905 (e.g., via audio adjustment module 915) can adjust a parameter of the audio wave or acoustic pulse based on a level of attention. For example, during the brainwave entrainment process, the subject may get bored, lose focus, fall asleep, or otherwise not pay attention to the acoustic pulses. Not paying attention to the acoustic pulses may reduce the efficacy of the brainwave entrainment process, resulting in neurons oscillating at a frequency different from the desired modulation frequency of the acoustic pulses.

NSS 905 can detect the level of attention the subject is paying to the acoustic pulses using the feedback monitor 935 and one or more feedback component 960. Responsive to determining that the subject is not paying a satisfactory amount of attention to the acoustic pulses, the audio adjustment module 915 can change a parameter of the audio signal to gain the subject's attention. For example, the audio adjustment module 915 can increase the amplitude of the acoustic pulse, adjust the tone of the acoustic pulse, or change the duration of the acoustic pulse. The audio adjustment module 915 can randomly vary one or more parameters of the acoustic pulse. The audio adjustment module 915 can initiate an attention seeking acoustic sequence configured to regain the subject's attention. For example, the audio sequence can include a change in frequency, tone, amplitude, or insert words or music in a predetermined, random, or pseudo-random pattern. The attention seeking audio sequence can enable or disable different acoustic sources if the audio signaling component 950 includes multiple audio sources or speakers. Thus, the audio adjustment module 915 can interact with the feedback monitor 935 to determine a level of attention the subject is providing to the acoustic pulses, and adjust the acoustic pulses to regain the subject's attention if the level of attention falls below a threshold.

In some embodiments, the audio adjustment module 915 can change or adjust one or more parameter of the acoustic pulse or acoustic wave at predetermined time intervals (e.g., every 5 minutes, 10 minutes, 15 minutes, or 20 minutes) to regain or maintain the subject's attention level.

In some embodiments, the NSS 905 (e.g., via unwanted frequency filtering module 920) can filter, block, attenuate, or remove unwanted auditory external stimulation. Unwanted auditory external stimulation can include, for example, unwanted modulation frequencies, unwanted intensities, or unwanted wavelengths of sound waves. The NSS 905 can deem a modulation frequency to be unwanted if the modulation frequency of a pulse train is different or substantially different (e.g., 1%, 2%, 5%, 10%, 15%, 20%, 25%, or more than 25%) from a desired frequency.

For example, the desired modulation frequency for brainwave entrainment can be 40 Hz. However, a modulation frequency of 20 Hz or 80 Hz can reduce the beneficial effects to cognitive functioning of the brain, a cognitive state of the brain, the immune system, or inflammation that can result from brainwave entrainment at other frequencies, such as 40 Hz. Thus, the NSS 905 can filter out the acoustic pulses corresponding to the 20 Hz or 80 Hz modulation frequency.

In some embodiments, the NSS 905 can detect, via feedback component 960, that there are acoustic pulses from an ambient noise source that corresponds to an unwanted modulation frequency of 20 Hz. The NSS 905 can further determine the wavelength of the acoustic waves of the acoustic pulses corresponding to the unwanted modulation frequency. The NSS 905 can instruct the filtering component 955 to filter out the wavelength corresponding to the unwanted modulation frequency.

L. Inducing Neural Oscillations Via Peripheral Nerve Stimulation

Systems and methods of the present disclosure are directed to peripheral nerve stimulation. As described herein, peripheral nerve stimulation can include stimulation of nerves of the peripheral nerve system. Peripheral nerve stimulation can include stimulation of nerves that are peripheral to or remote from the brain. Peripheral nerve stimulation can include stimulation of nerves which may be part of, associated with, or connected to the spinal cord. The peripheral nerve stimulation can adjust, control or otherwise manage the frequency of the neural oscillations to provide beneficial effects to one or more cognitive states or cognitive functions of the brain, while mitigating or preventing adverse consequences on a cognitive state or cognitive function. For example, the stimulation can treat, prevent, protect against or otherwise affect Alzheimer's disease. The peripheral nerve stimulation can result in neural oscillations associated with brainwave entrainment that can provide beneficial effects to one or more cognitive states or cognitive functions of the brain. For example, brainwave entrainment (or the neural oscillations associated thereto) can treat disorders, maladies, diseases, inefficiencies, injuries or other issues related to a cognitive function or cognitive state of the brain.

Neural oscillation occurs in humans or animals and includes rhythmic or repetitive neural activity in the central nervous system. Neural tissue can generate oscillatory activity by mechanisms within individual neurons or by interactions between neurons. Oscillations can appear as either oscillations in membrane potential or as rhythmic patterns of action potentials, which can produce oscillatory activation of post-synaptic neurons. Synchronized activity of a group of neurons can give rise to macroscopic oscillations, which can be observed by electroencephalography ("EEG"). Neural oscillations can be characterized by their frequency, amplitude and phase. These signal properties can be observed from neural recordings using time-frequency analysis.

For example, an EEG can measure oscillatory activity among a group of neurons, and the measured oscillatory activity can be categorized into frequency bands as follows: delta activity corresponds to a frequency band from 1-4 Hz; theta activity corresponds to a frequency band from 4-8 Hz; alpha activity corresponds to a frequency band from 8-12 Hz; beta activity corresponds to a frequency band from 163-30 Hz; and gamma activity corresponds to a frequency band from 30-60 Hz.

The frequency of neural oscillations can be associated with cognitive states or cognitive functions such as information transfer, perception, motor control and memory. Based on the cognitive state or cognitive function, the frequency of neural oscillations can vary. Further, certain frequencies of neural oscillations can have beneficial effects or adverse consequences on one or more cognitive states or function. However, it may be challenging to synchronize neural oscillations using external stimulus to provide such beneficial effects or reduce or prevent such adverse consequences.

Brainwave entrainment (e.g., neural entrainment or brain entrainment) occurs when an external stimulation of a particular frequency is perceived by the brain and triggers neural activity in the brain that results in neurons oscillating at a frequency corresponding to the particular frequency of the external stimulation. Thus, brain entrainment can refer to synchronizing neural oscillations in the brain using external stimulation such that the neural oscillations occur at frequency that corresponds to the particular frequency of the external stimulation.

Systems and methods of the present disclosure can provide peripheral nerve stimulation to cause or induce neural oscillations. For example, electric currents on or through the skin around sensory nerves forming part of or connected to the peripheral nervous system can cause or induce electrical activity in the sensory nerves, causing a transmission to the brain via the central nervous system, which can be perceived by the brain or can cause or induce electrical and neural activity in the brain, including activity resulting in neural oscillations. The brain, responsive to receiving the peripheral nerve stimulations, can adjust, manage, or control the frequency of neural oscillations. The electric currents can result in depolarization of neural cells, such as due to electric current stimuli such as time-varying pulses. The electric current pulse may directly cause depolarization. Secondary effects in other regions of the brain may be gated or controlled by the brain in response to the depolarization. The peripheral nerve stimulations generated at a predetermined frequency can trigger neural activity in the brain to cause or induce neural oscillations. The frequency of neural oscillations can be based on or correspond to the frequency of the peripheral nerve stimulations, or a modulation frequency associated with the peripheral nerve stimulations. Thus, systems and methods of the present disclosure can cause or induce neural oscillations using peripheral nerve stimulations such as electric current pulses modulated at a predetermined frequency to synchronize electrical activity among groups of neurons based on the frequency of the peripheral nerve stimulations. Brain entrainment associated with neural oscillations can be observed based on the aggregate frequency of oscillations produced by the synchronous electrical activity in ensembles of cortical neurons. The frequency of the modulation of the electric currents, or pulses thereof, can cause or adjust this synchronous electrical activity in the ensembles of cortical neurons to oscillate at a frequency corresponding to the frequency of the peripheral nerve stimulation pulses.

FIG. 16 is a block diagram depicting a system to perform peripheral nerve stimulation to cause or induce neural oscillations, such as to cause brain entrainment, in accordance with an embodiment. The system 1600 can include a peripheral nerve stimulation system 1605. In brief overview, the peripheral nerve stimulation system (or peripheral nerve stimulation neural stimulation system) ("NSS") 1605 can include, access, interface with, or otherwise communicate with one or more of a nerve stimulus generation module 1610, nerve stimulus adjustment module 1615, profile manager 1625, side effects management module 1630, feedback monitor 1635, data repository 1640, nerve stimulus generator component 1650, shielding component 1655, feedback component 1660, or nerve stimulus amplification component 1665. The nerve stimulus generation module 1610, nerve stimulus adjustment module 1615, profile manager 1625, side effects management module 1630, feedback monitor 1635, nerve stimulus generator component 1650, shielding component 1655, feedback component 1660, or nerve stimulus amplification component 1665 can each include at least one processing unit or other logic device such as programmable logic array engine, or module configured to communicate with the database repository 1650. The nerve stimulus generation module 1610, nerve stimulus adjustment module 1615, profile manager 1625, side effects management module 1630, feedback monitor 1635, nerve stimulus generator component 1650, shielding component 1655, feedback component 1660, or nerve stimulus amplification component 1665 can be separate components, a single component, or part of the NSS 1605. The system 1600 and its components, such as the NSS 1605, may include hardware elements, such as one or more processors, logic devices, or circuits. The system 1600 and its components, such as the NSS 1605, can include one or more hardware or interface component depicted in system 700 in FIGS. 7A and 7B. For example, a component of system 1600 can include or execute on one or more processors 721, access storage 728 or memory 722, and communicate via network interface 718.

Still referring to FIG. 16, and in further detail, the NSS 1605 can include at least one nerve stimulus generation module 1610. The nerve stimulus generation module 1610 can be designed and constructed to interface with a nerve stimulus generator component 1650 to provide instructions or otherwise cause or facilitate the generation of a nerve stimulus, such as an electric current controlled or modulated as a wave, burst, pulse, chirp, sweep, or other modulated current having one or more predetermined parameters. The nerve stimulus generation module 1610 can include hardware or software to receive and process instructions or data packets from one or more module or component of the NSS 1605. The nerve stimulus generation module 1610 can generate instructions to cause the nerve stimulus generator component 1650 to generate a nerve stimulus. The nerve stimulus may be an electric current controlled according to one or more desired characteristics, such as amplitude, voltage, frequency (e.g., alternating current frequency, or a corresponding wavelength), or modulation frequency (e.g., a frequency at which an amplitude of a direct current stimulus is modulated, or at which a current stimulus is turned on or off). The characteristics may be provided to the nerve stimulus generator component 1650 as predetermined parameters, or the predetermined parameters may include instructions or other control commands causing the nerve stimulus generator component 1650 to generate a nerve stimulus according to the desired characteristics. The nerve stimulus generation module 1610 can control or enable the nerve stimulus generator component 1650 to generate the nerve stimulus having one or more predetermined parameters.

The nerve stimulus generation module 1610 can be communicatively coupled to the nerve stimulus generator component 1650. The nerve stimulus generation module 1610 can communicate with the nerve stimulus generator component 1650 via a circuit, electrical wire, data port, network port, power wire, ground, electrical contacts or pins. The nerve stimulus generation module 1610 can wirelessly communicate with the nerve stimulus generator component 1650 using one or more wireless protocols such as BlueTooth, BlueTooth Low Energy, Zigbee, Z-Wave, IEEE 802, WIFI, 3G, 4G, LTE, near field communications ("NFC"), or other short, medium or long range communication protocols, etc. The nerve stimulus generation module 1610 can include or access network interface 2120 to communicate wirelessly or over a wire with the nerve stimulus generator component 1650.

The nerve stimulus generation module 1610 can interface, control, or otherwise manage various types of nerve stimulus generator components 1650 in order to cause the nerve stimulus generator component 1650 to generate, control, modulate, or otherwise provide the nerve stimulus having one or more predetermined parameters. The nerve stimulus generation module 1610 can include a driver configured to drive the nerve stimulus generator component 1650. For example, the nerve stimulus generator component 1650 can include electrodes and a power supply configured to deliver current to be discharged between the electrodes. The nerve stimulus generation module 1610 can include a computing chip, microchip, circuit, microcontroller, operational amplifiers, transistors, resistors, or diodes configured to drive the power supply to provide electricity or power having certain voltage and current characteristics to drive the electrodes to output or discharge an electric current with desired characteristics. The nerve stimulus generation module 1610 may also directly drive the electrodes.

The nerve stimulus can be an electric current characterized by an amplitude. The amplitude may represent a strength of the electric current, and thus indicate a magnitude of a force that will induce or cause electrical activity in the peripheral nervous system and, in turn, the brain. The nerve stimulus generator component 1650 can be configured to output variable current, such that the amplitude can be controlled.

The nerve stimulus generator component 1650 can be configured to output at least one of direct current or alternating current. Where the nerve stimulus generator component 1650 is configured to output alternating current, the nerve stimulus can be characterized by a frequency (or a corresponding wavelength) of the alternating current.

The nerve stimulus may also be characterized by a modulation frequency of intermittent features of the electric current. For example, the amplitude of the electric current may be modulated by the nerve stimulus generation module 1610 at a predetermined frequency, such as by turning a power supply delivering current through the electrodes on or off, or driving the current as a variable current. The nerve stimulus may also be characterized by a voltage of the electric current. The nerve stimulus generation module 1610 can instruct the nerve stimulus generator component 1650 to generate electric currents having one or more of a predetermined amplitude, voltage, or frequency.

The NSS 1605 can modulate, modify, change or otherwise alter properties of the nerve stimulus. For example, the NSS 1605 can modulate the amplitude, voltage, or frequency of the electric current of the nerve stimulus. Where the nerve stimulus generator component 1650 is configured to be driven with a variable current, the NSS 1605 can lower the amplitude to cause the electric current to have a lesser strength (e.g., to reduce a resulting effect on electrical activity in the peripheral nervous system and the brain), or increase the amplitude to cause the electric current to have a greater strength (e.g., to increase a resulting effect on electrical activity in the peripheral nervous system and the brain).

The NSS 1605 can modulate or change one or more properties of the nerve stimulus based on a time interval. For example, the NSS 1605 can change a property of the nerve stimulus every 10 seconds, 15 seconds, 30 seconds, 1 minute, 2 minutes, 3 minutes, 20 minutes, 7 minutes, 10 minutes, or 15 minutes. The NSS 1605 can change a modulation frequency of the nerve stimulus, where the modulation frequency refers to the repeated modulations or inverse of the pulse rate interval of the nerve stimulus. The modulation frequency can be a predetermined or desired frequency. The modulation frequency can correspond to a desired stimulation frequency of neural oscillations. The modulation frequency can be set to facilitate or cause neural oscillations, which may be associated with brain entrainment. The NSS 1605 can set the frequency or modulation frequency of the electric current to a frequency in the range of 0.1 Hz to 10,000 Hz. For example, the NSS 1605 can set the modulation frequency to 0.1 Hz, 1 Hz, 5 Hz, 10 Hz, 20 Hz, 25 Hz, 30 Hz, 31 Hz, 32 Hz, 33 Hz, 34 Hz, 35 Hz, 36 Hz, 37 Hz 38 Hz, 39 Hz, 40 Hz, 41 Hz, 42 Hz, 43 Hz, 44 Hz, 45 Hz, 46 Hz, 47 Hz, 48 Hz, 49 Hz, 50 Hz, 60 Hz, 70 Hz, 80 Hz, 90 Hz, 100 Hz, 1650 Hz, 200 Hz, 250 Hz, 300 Hz, 400 Hz, 500 Hz, 1000 Hz, 2000 Hz, 3000 Hz, 4,000 Hz, 5000 Hz, 6,000 Hz, 7,000 Hz, 8,000 Hz, 9,000 Hz, or 10,000 Hz.

Referring now to FIGS. 17A-17D, various implementations of pulse schemes for peripheral nerve stimulation, including peripheral nerve stimulation by the NSS 1605, are illustrated according to some embodiments. The nerve stimulus generation module 1610 can determine to provide peripheral nerve stimulations that include bursts of electric currents, electric current pulses, or modulations to electric currents. The nerve stimulus generation module 1610 can instruct or otherwise cause the nerve stimulus generator component 1650 to generate electric current bursts or pulses. An electric current pulse can refer to a burst of electric currents or a modulation to a property of an electric current that causes or induces a change in electrical activity in the brain. An electric current that is intermittently turned on and off can create electric current pulses. For example, a current driven through and output by electrodes of the nerve stimulus generator component 1650 can be turned on and off to create electric current pulses. The electric current can be turned on and off based on a predetermined or fixed pulse rate interval, such as every 0.025 seconds, to provide a pulse repetition frequency of 40 Hz. The electric current can be turned on and off to provide a pulse repetition frequency in the range of 0.1 Hz to 10 kHz.

FIGS. 17A-17D illustrates bursts of electric currents or bursts of modulations that can be applied to cause peripheral nerve stimulation. The modulations can refer to changes in the amplitude or magnitude of the electric current, changes in frequency (or wavelength) of the modulation of alternating currents, changes in voltage of the electric current, or otherwise modifying or changing the electric current. The pulse schemes (e.g., pulse width modulation schemes) shown in FIGS. 17A-17D can be generated as or incorporated as instructions in a control signal transmitted from the nerve stimulus generation module 1610 to the nerve stimulus generator component 1650. For example, the nerve stimulus generation module 1610 can modulate an output of the control signal according to a pulse scheme; the nerve stimulus generation module 1610 can also generate the control signal to include instructions indicating a pulse scheme, such that the nerve stimulus generator component 1650 can extract the pulse scheme from the instructions of the control signal and control modulation of the electric current based on the pulse scheme.

In some embodiments, the control signal indicates at least one of an amplitude, voltage, frequency, or modulation frequency of the electric current. Multiple such characteristics may be indicated, for example where a particular region or cortex of the brain is to be targeted by the electric current peripheral nerve stimulus. For example, the control signal can indicate characteristics for the nerve stimulus such that a particular region of the brain receives an electric current having a magnitude between a lower threshold below which desired neural oscillations do not occur (e.g., below which neural oscillations or a change in neural oscillations does not occur) and an upper threshold above which adverse side effects may occur. The nerve stimulus may be controlled such that only a targeted cortex receives the nerve stimulus within such thresholds (e.g., the electric current generated according to the control signal have a desired magnitude, and are targeted to particular sensory nerves, such that only a targeted cortex receives a portion of the nerve stimulus having a magnitude that is greater than the lower threshold).

Figure 17A:
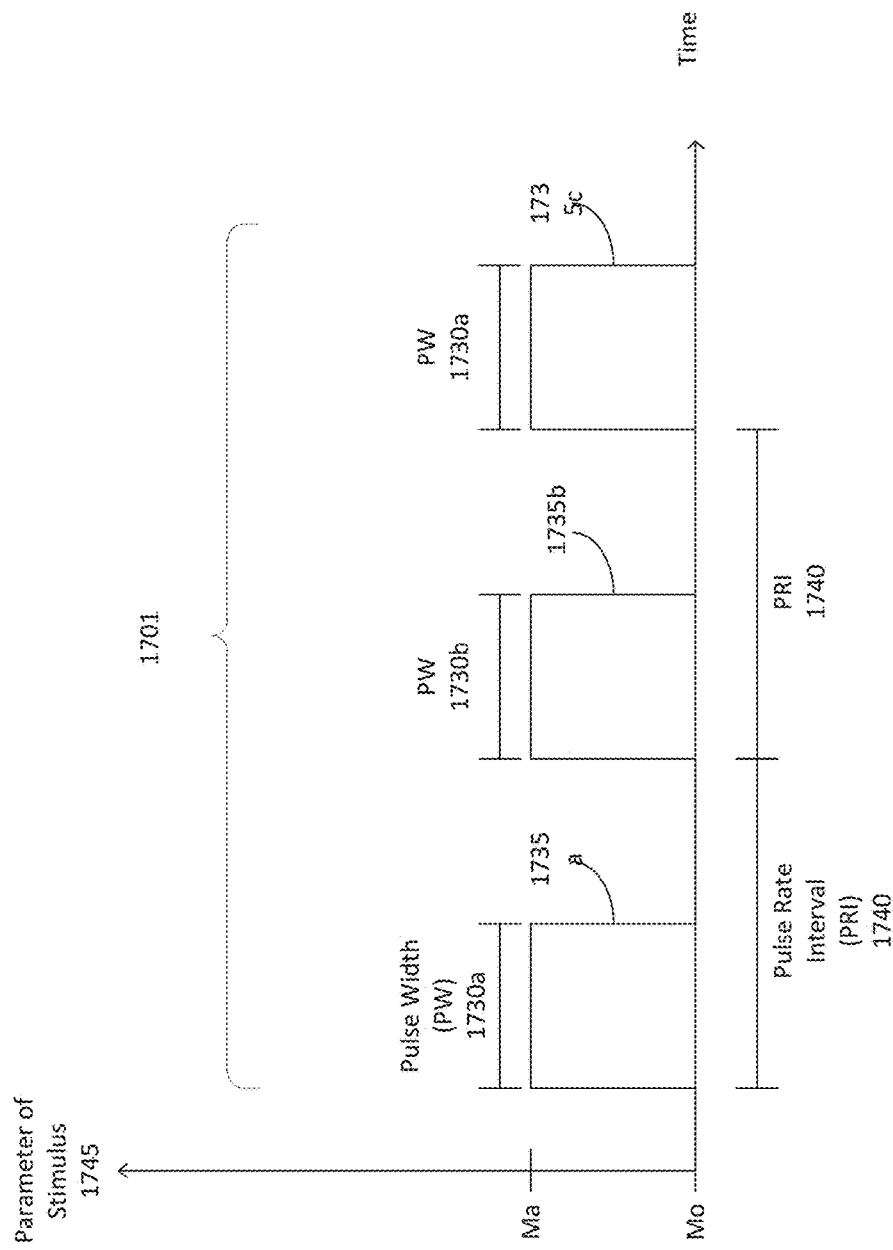
FIGS. 17A-17D illustrate peripheral nerve stimulations and types of modulations to peripheral nerve stimulations used to induce neural oscillations via peripheral nerve stimulation in accordance with some embodiments.

FIG. 17A illustrates electric current bursts 1735a-c (or modulation pulses 1735a-c) in accordance with an embodiment. The electric current bursts 1735a-c can be illustrated via a graph where the y-axis represents a parameter of the electric current (e.g., frequency (or wavelength), amplitude) of the electric current. The x-axis can represent time (e.g., seconds, milliseconds, or microseconds).

The nerve stimulus can include a modulated electric current that is modulated between different frequencies (or wavelengths), amplitudes, or voltages. For example, the NSS 1605 can modulate an electric current between a first frequency, such as $M_a$, and a second frequency, such as $M_o$. The NSS 1605 can modulate the electric current between two or more frequencies.

The NSS 1605 can modulate an amplitude of the electric current. For example, the NSS 1605 can control operation of a power supply delivering current through electrodes between an on state and an off state, or between a high power state and a low power state. The NSS 1605 can modulate the amplitude where the system is configured to output a variable current, such as between a relatively high amplitude current and a relatively low amplitude current.

The pulses 1735*a-c* can be generated with a pulse rate interval (PRI) 1740. The PRI 1740 may indicate points in time at which an electric current is turned on, outputted, or transmitted. Modulation of the PRI 1740 can allow for control of the modulation frequency of the electric current.

The nerve stimulus parameter can be the frequency of the electric current (e.g., an intermittency of when the electric current is turned on). The first value $M_o$ can be a low frequency or baseline frequency of the nerve stimulus, such as zero frequency or a baseline frequency at which the electric current is generated in the absence of a control signal from the nerve stimulus generation module 1610. The second value, $M_a$, can be different from the first frequency $M_o$. The second frequency $M_a$ can be lower or higher than the first frequency $M_o$. For example, the second frequency $M_a$ can be in the range of 1 Hz-60 Hz. The difference between the first frequency and the second frequency can be determined or set based on a level of sensitivity of the brain to electrical activity caused by peripheral nerve stimulation. The difference between the first frequency and the second frequency can be determined or set based on profile information 1645 for the subject. The difference between the first frequency $M_o$ and the second frequency $M_a$ can be determined such that the modulation or change in the nerve stimulus facilitates causing or inducing neural oscillations.

The nerve stimulus parameter can be the amplitude of the electric field, and can be selected, determined, received, transmitted, and/or generated in a manner similar to the frequency. The first value $M_o$ can be a low magnitude or baseline magnitude of the electric current, such as zero magnitude or a minimum magnitude at which the nerve stimulus generator component 1650 is configured to generator or output the electric current. The second value, $M_a$, can be different from the first value $M_o$, such as to be a treatment magnitude selected to facilitate causing or inducing neural oscillations.

In some cases, the parameter of the nerve stimulus used to generate the electric current burst 1735*a* can be constant at $M_a$, thereby generating a square wave as illustrated in FIG. 17A. In some embodiments, each of the three pulses 1735*a-c* can include electric currents having a same parameter of stimulus $M_a$.

Figure 17B:
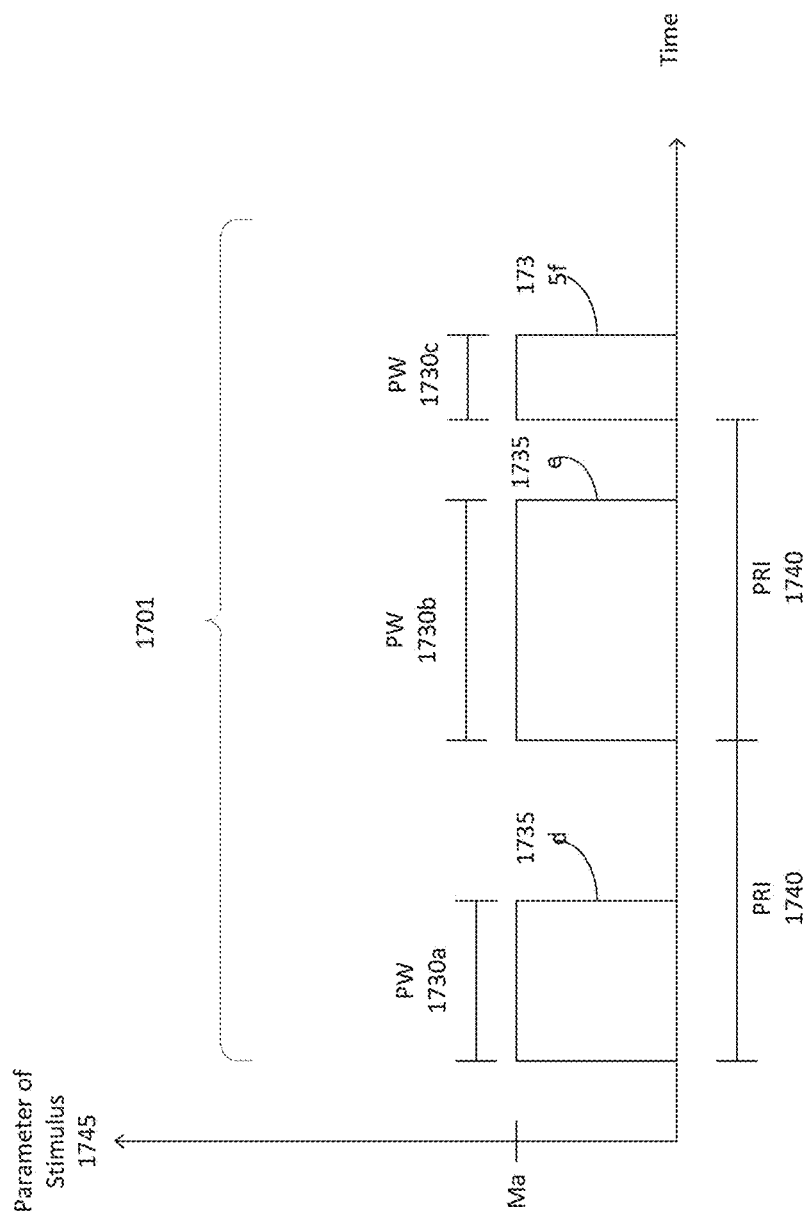

The width of each of the electric current bursts or pulses (e.g., the duration of the burst of the electric current with the parameter $M_a$) can correspond to a pulse width 1730*a*. The pulse width 1730*a* can refer to the length or duration of the burst. The pulse width 1730*a* can be measured in units of time or distance. In some embodiments, the pulses 1735*a-c* can include electric current modulated at different frequencies from one another. In some embodiments, the pulses 1735*a-c* can have different pulse widths 1730*a* from one another, as illustrated in FIG. 17B. For example, a first pulse 1735*d* of FIG. 17B can have a pulse width 1730*a*, while a second pulse 1735*e* has a second pulse width 1730*b* that is greater than the first pulse width 1730*a*. A third pulse 1735*f* can have a third pulse width 1730*c* that is less than the second pulse width 1730*b*. The third pulse width 1730*c* can also be less than the first pulse width 1730*a*. While the pulse widths 1730*a-c* of the pulses 1735*d-f* of the pulse train may vary, the nerve stimulus generation module 1610 can maintain a constant pulse rate interval 1740 for the pulse train. In some embodiments, the pulse rate interval 1740 and/or the pulse widths 1730 of the pulse train may be limited by a minimum on time, minimum off time, minimum ramp up time, or minimum ramp down time for the nerve stimulus generator component 1650.

The pulses 1735*a-c* can form a pulse train 1701 having a pulse rate interval 1740. The pulse rate interval 1740 can be quantified using units of time. The pulse rate interval 1740 can be based on a frequency of the pulses of the pulse train 1701. The frequency of the pulses of the pulse train 1701 can be referred to as a modulation frequency. For example, the nerve stimulus generation module 1610 can provide a pulse train 1701 with a predetermined frequency, such as 40 Hz. To do so, the nerve stimulus generation module 1610 can determine the pulse rate interval 1740 by taking the multiplicative inverse (or reciprocal) of the frequency (e.g., 1 divided by the predetermined frequency for the pulse train). For example, the nerve stimulus generation module 1610 can take the multiplicative inverse of 40 Hz by dividing 1 by 40 Hz to determine the pulse rate interval 1740 as 0.025 seconds. The pulse rate interval 1740 can remain constant throughout the pulse train. In some embodiments, the pulse rate interval 1740 can vary throughout the pulse train or from one pulse train to a subsequent pulse train. In some embodiments, the number of pulses transmitted during a second can be fixed, while the pulse rate interval 1740 varies.

Figure 17C:
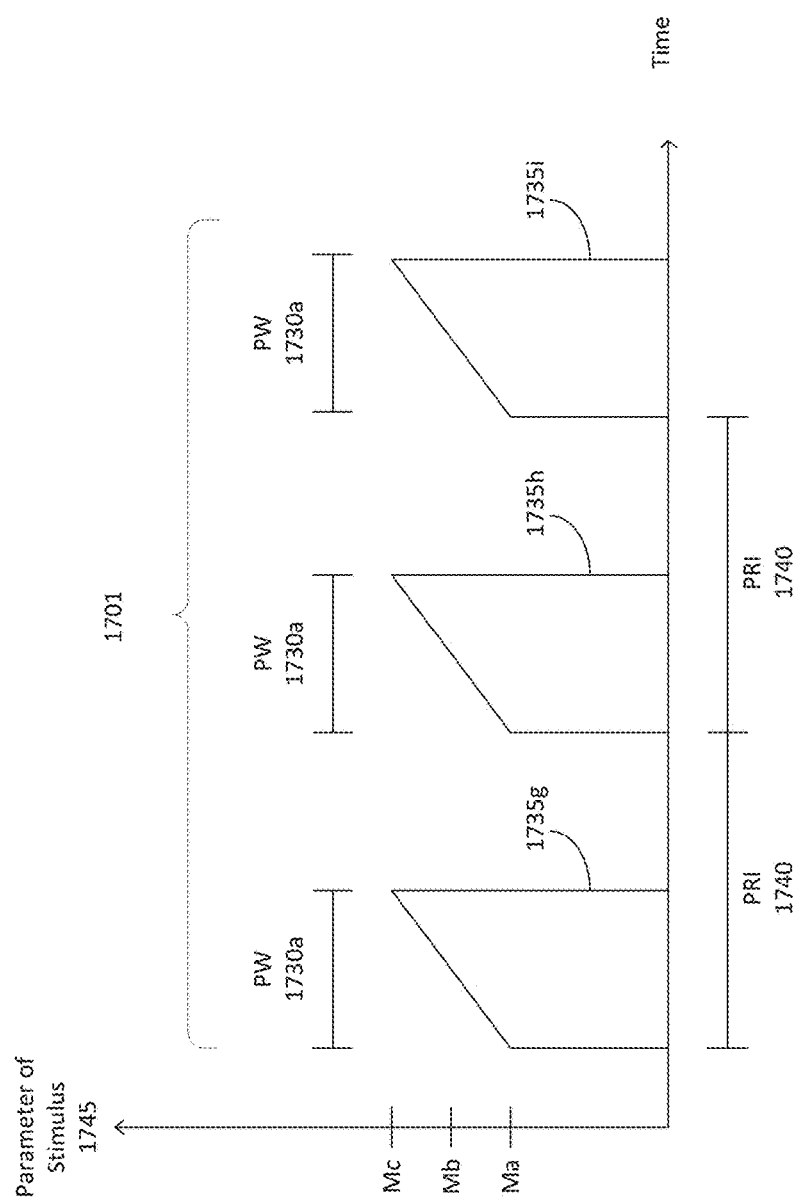

In some embodiments, the nerve stimulus generation module 1610 can generate an electric current as a burst or pulse having that varies in frequency, amplitude, voltage. For example, the nerve stimulus generation module 1610 can generate up-chirp pulses where the frequency, amplitude, or voltage of the electric current pulse increases from the beginning of the pulse to the end of the pulse as illustrated in FIG. 17C. For example, the frequency, amplitude or voltage of the electric current at the beginning of pulse 1735*g* can be $M_a$. The frequency, amplitude, or voltage of the electric current of the pulse 1735*g* can increase (or change, in the case of direction) from $M_a$ to $M_b$ in the middle of the pulse 1735*g*, and then to a maximum of $M_c$ at the end of the pulse 1735*g*. Thus, the frequency, amplitude, or voltage of the electric current used to generate the pulse 1735*g* can range from $M_a$ to $M_c$. The frequency, amplitude, or voltage can increase linearly, exponentially, or based on some other rate or curve. One or more of the frequency, amplitude, or voltage of the electric current can change from the beginning of the pulse to the end of the pulse.

Figure 17D:
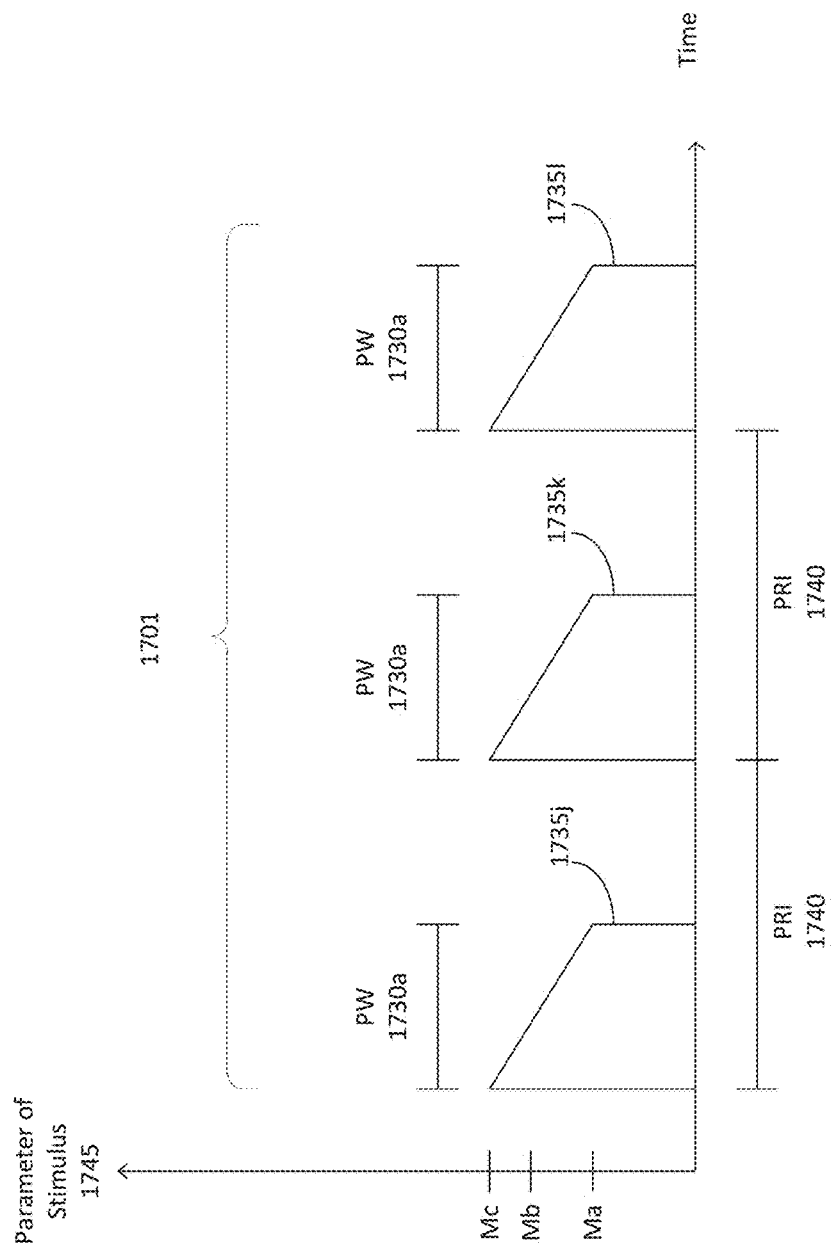

The nerve stimulus generation module 1610 can generate decreasing pulses, as illustrated in FIG. 17D, where the frequency, amplitude, or voltage of the electric current of the pulse decreases from the beginning of the pulse to the end of the pulse. For example, the frequency, amplitude, or voltage of the electric current at the beginning of pulse 1735*j* can be $M_c$. The frequency, amplitude, or voltage of the electric current of the pulse 1735*j* can decrease from $M_c$ to $M_b$ in the middle of the pulse 1735*j*, and then to a minimum of $M_a$ at the end of the pulse 1735*j*. Thus, the frequency, amplitude, or amplitude of the electric current used to generate the pulse 1735*j* can range from $M$ to $M_a$. The frequency, amplitude, or voltage can decrease (or change) linearly, exponentially, or based on some other rate or curve.

One or more of the frequency, amplitude, or voltage of the electric current can change from the beginning of the pulse to the end of the pulse.

In some embodiments, the nerve stimulus generation module 1610 is configured to compensate for a side effect caused by the nerve stimulus. For example, the nerve stimulus generation module 1610 can output the nerve stimulus according to a pulse scheme selected to reduce the likelihood of a side effect such as tetany (e.g., delivering 10 pulses at maximum intensity, such as 8 mA, at 40 Hz, then delivering 10 more pulses at half intensity, at 40 Hz). Such pulse schemes may make the therapy more comfortable.

Nerve stimulus generator component 1650 can be designed and constructed to generate the nerve stimulations responsive to instructions from the nerve stimulus generation module 1610. The instructions can include, for example, parameters of the pulse such as a frequency, amplitude, or voltage, duration of the pulse, frequency of the pulse train, pulse rate interval, or duration of the pulse train (e.g., a number of pulses in the pulse train or the length of time to transmit a pulse train having a predetermined frequency). The nerve stimulus can be generated by a device positioned at a distance from the sensory nerves of the peripheral nervous system of the subject such that the amplitude of the electric current is within guidelines targeted by a therapy (e.g., within thresholds defining targeted neural oscillations or brain entrainment).

Referring back to FIG. 16, the NSS 1605 can include, access, interface with, or otherwise communicate with at least one nerve stimulus adjustment module 1615. The nerve stimulus adjustment module 1615 can be designed and constructed to adjust a parameter associated with the nerve stimulus, such as a frequency (or wavelength), amplitude, voltage, direction, pattern, or other parameter of the nerve stimulus. The nerve stimulus adjustment module 1615 can automatically vary a parameter of the nerve stimulus based on profile information or feedback. The nerve stimulus adjustment module 1615 can receive the feedback information from the feedback monitor 1635. The nerve stimulus adjustment module 1615 can receive instructions or information from a side effects management module 1630. The nerve stimulus adjustment module 1615 can receive profile information from profile manager 1625.

The nerve stimulus generation module 1610 can interface, instruct, control, or otherwise communicate with a shielding component 1655 to cause the shielding component 1655 to shield, block, attenuate, or otherwise reduce the amplitude of the electric currents on the peripheral nervous system, and thus reduce the effect of the nerve stimulus on neural oscillations.

The nerve stimulus generation module 1610 can interface, instruct, control, or otherwise communicate with a nerve stimulus amplification component 165. The nerve stimulus amplification component 165 can be configured to increase (or decrease) a magnitude or amplitude of nerve stimulations caused by the nerve stimulus generator component 1650, such as along a nervous system pathway between a sensory nerve relatively close to where the nerve stimulus generator component 1650 is located and the brain. For example, the nerve stimulus amplification component 165 can be configured to apply a potential difference across a length of a nervous system pathway (e.g., along a spinal cord, along a path between a site at which the nerve stimulus generator component 1650 is located and a position closer to the brain along a nervous system pathway), which can increase a rate of neural transmissions and/or increase a number of neurons that fire or a rate of neuron firing. The nerve stimulus amplification component 165 can be apply a direct current or alternating current stimulus (e.g., to the spinal cord), which can which can increase a rate of neural transmissions and/or increase a number of neurons that fire or a rate of neuron firing. In some embodiments, the nerve stimulus generator component 1650 can be configured to be positioned proximate to (or implanted proximate to) the spinal column of the subject, detect the nerve stimulus (or resulting nervous system activity caused by the nerve stimulus generator component 1650) caused by the nerve stimulus generator 1650 as the nerve stimulus passes to the brain, including a frequency or other parameters or characteristics of the nerve stimulus, and output an electric current controlled to be synchronized with the detected nerve stimulus.

The NSS 1605 can include, access, interface with, or otherwise communicate with at least one profile manager 1625. The profile manager 1625 can be designed or constructed to store, update, retrieve or otherwise manage information associated with one or more subjects associated with the peripheral nerve stimulation. Profile information can include, for example, historical treatment information, historical neural oscillation information, historical brain entrainment information, dosing information, parameters and characteristics of electric currents, feedback, physiological information, environmental information, or other data associated with the systems and methods of peripheral nerve stimulation for causing or inducing neural oscillations.

The peripheral nerve NSS 1605 can include, access, interface with, or otherwise communicate with at least one side effects management module 1630. The side effects management module 1630 can be designed and constructed to provide information to the nerve stimulus adjustment module 1615 or the nerve stimulus generation module 1610 to change one or more parameter of the nerve stimulus in order to reduce a side effect. Side effects can include, for example, nausea, migraines, fatigue, or seizures.

The side effects management module 1630 can automatically instruct a component of the NSS 1605 to alter or change a parameter of the nerve stimulus. The side effects management module 1630 can be configured with predetermined thresholds to reduce side effects. For example, the side effects management module 1630 can be configured with a maximum duration of a pulse train, maximum amplitude of acoustic waves, maximum volume, maximum duty cycle of a pulse train (e.g., the pulse width multiplied by the frequency of the pulse train), maximum number of treatments for causing or inducing neural oscillations in a time period (e.g., 1 hour, 2 hours, 12 hours, or 24 hours).

The side effects management module 1630 can cause a change in the parameter of the nerve stimulus in response to feedback information. The side effect management module 1630 can receive feedback from the feedback monitor 1635. The side effects management module 1630 can determine to adjust a parameter of the nerve stimulus based on the feedback. The side effects management module 1630 can compare the feedback with a threshold to determine to adjust the parameter of the nerve stimulus.

The side effects management module 1630 can be configured with or include a policy engine that applies a policy or a rule to the current nerve stimulus and feedback to determine an adjustment to the nerve stimulus. For example, if feedback indicates that a subject receiving nerve stimulations has a heart rate or pulse rate above a threshold, the side effects management module 1630 can turn off the pulse train until the pulse rate stabilizes to a value below the threshold, or below a second threshold that is lower than the threshold. In some implementations, the side effects management module 1630 may present a user interface to a subject through which the subject can report side effects, such as pain, discomfort, nausea, headaches, among other side effects. Responsive to receiving input from the subject, the side effects management module 1630 can be configured to cause the nerve stimulus to stop or be adjusted to reduce the side effects. Furthermore, the subject profile can be updated to indicate the side effects associated with the stimulus/therapy provided to prevent future occurrences of side effects through the delivery of the same or similar stimulus/therapy.

The peripheral nerve NSS 1605 can include, access, interface with, or otherwise communicate with at least one feedback monitor 1635. The feedback monitor can be designed and constructed to receive feedback information from a feedback component 160. Feedback component 1660 can include, for example, a feedback sensor such as a temperature sensor, heart or pulse rate monitor, physiological sensor, ambient noise sensor, microphone, ambient temperature sensor, blood pressure monitor, brain wave sensor, EEG probe, electrooculography ("EOG") probes configured measure the corneo-retinal standing potential that exists between the front and the back of the human eye, accelerometer, gyroscope, motion detector, proximity sensor, camera, microphone, or photo detector.

Figure 18A:
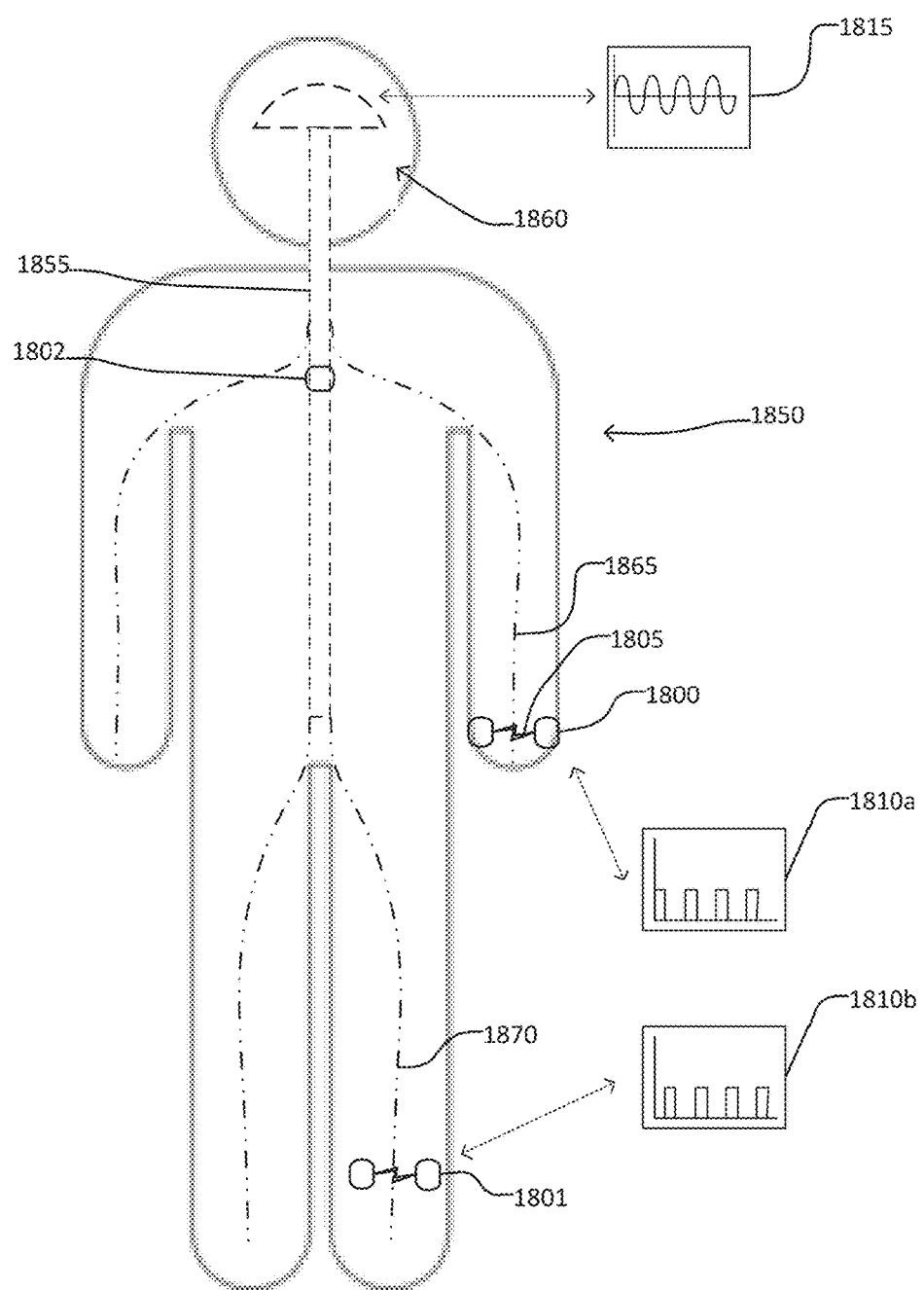
FIGS. 18A-18C illustrate systems for peripheral nerve stimulation in accordance with some embodiments.

M. Systems and Devices Configured to Induce Neural Oscillations Via Peripheral Nerve Stimulation FIG. 18A illustrates devices for peripheral nerve stimulation in accordance with some embodiments. The devices 1800, 1801 can be or include features of the NSS 1605 described with reference to FIG. 1. For example, the devices 1800, 1801 can include the nerve stimulus generator component 1650, and can include, be communicatively coupled to, or be driven by the nerve stimulus generation module 1610. The devices 1800, 1801 can be configured to generate a controllable electric current 1805. For example, the devices 1800, 1801 can include a first electrode (e.g., a stimulation electrode) and a second electrode (e.g., a ground electrode, a reference electrode), and a power source (e.g., power supply, battery, universal power supply, interface to a remote power source) configured to deliver current from the first electrode to the second electrode, such as to discharge an electric current through the body of a subject 1850 in a manner that will cause electrical activity in sensory nerves of the peripheral nervous system of the subject 1850.

In some embodiments, the device 1800 is configured to deliver an electric current as a nerve stimulus 1805 to a hand of the subject 1850. Similarly, the device 1801 can deliver an electric current to a leg or foot. The nerve stimulus 1805 causes or induces electrical activity in the peripheral nerve system (e.g., peripheral nerve 1870 in the hand; peripheral nerve 1865 in the leg), which is transmitted to the brain 1860 via the central nervous system 1855. The nerve stimulus 1805 can be generated by controlling and delivering an electric current in various manners as described herein (e.g., direct current; alternating current; periodically modulating the electric current on/off; periodically modulating the amplitude of the electric current; controlling or modulating an alternating current frequency of the electric current). While FIG. 18A illustrates nerve stimulations being delivered to the hand and foot, in various embodiments, configurations, or treatment protocols, various nerve stimulations may be delivered to various locations on the body of the subject 1850 (including various combinations of stimulations), including the quadriceps just below the knee, the top of the foot, the back of the knee, the legs, the clavicle, the neck, or the lips/teeth/gums. In some embodiments, targeted delivery of nerve stimulations to the body of the subject 1850 may advantageously target cortices or regions of the brain 1860. For example, delivering the nerve stimulus 1805 to one or more of the lips, teeth, or gums may be advantageous because those portions of the body of the subject 1850 are have relatively greater innervation by the peripheral nervous system, and also may more directly cause activity in the hippocampus. For example, the nerve stimulus 1805 may be delivered to locations that have relatively greater or closer access to the trigeminal nerve (e.g., lips, teeth, gums), or to the vagus nerve (e.g., neck).

The device 1800 can be configured to generate the nerve stimulus according to a pulse scheme 1810*a*. The pulse scheme 1810*a* can be analogous to the pulse schemes described with reference to FIGS. 17A-17D above. For example, the pulse scheme 1810*a* can indicate characteristics of the electric current 1805 (e.g., amplitude, frequency, modulation frequency), and/or parameters enabling generation of the electric current (e.g., an amplitude of a current to be delivered to the electrodes to result in a desired amplitude of the nerve stimulus 1805). The device 1800 (or a component thereof) can receive the pulse scheme 1810*a* as a control signal modulated according to the pulse scheme 1810*a*, or as a control signal including instructions indicating the pulse scheme 1810*a*.

The nerve stimulus generated by the device 1800) is configured to induce or cause resulting neural oscillations 1815 in the brain 1860. The characteristics of the electric current 1805*a* can be controlled to cause desired neural oscillations 1815. The electric current 1805 may cause neural oscillations 1815*a* when the electric current 1805 has an amplitude that is greater than a minimum threshold amplitude required to cause or induce neural oscillations; the electric current 1805 may also have an amplitude that is less than a maximum threshold amplitude at which adverse side effects may occur. The electric current 1805 may cause neural oscillations 1815 having a target frequency when the electric current 1805 is modulated or oscillated at the target frequency (e.g., a pulse repetition interval 1740 of the pulse scheme 1810*a* driving the electric current 1805 may correspond to the target frequency).

In some embodiments, the device 1800 is configured to control the electric current 1805 to cause a first state of neural oscillations or neural inducement, and then modify the electric current 1805 to cause a second state of neural oscillations or neural inducement. The first state may be a state at which the brain 1860 is determined to be more receptive to neural oscillations, neural inducement, or brainwave entrainment. For example, the first state may correspond to a frequency or range of frequencies at which the brain 1860 is relatively more receptive to neural oscillations, neural inducement, or brainwave entrainment as compared to other frequencies. The second state may be a desired or targeted state, such as a state at which the neural oscillations 1815 occur at a desired or targeted frequency. In some embodiments, a pulse train of the pulse scheme 1810*a* may include pulses having varying frequencies corresponding to the first and second states. In some embodiments, the pulse train may include pulses having ramp-up or ramp-down configurations (e.g., ramping from a first frequency corresponding to the first state to a second frequency corresponding to the second state).

The device 1800) can be integrated with the feedback component 160. The feedback component 1660 can be an EEG. The device 1800 can interact or communicate with feedback component 160. For example, the feedback component 1660 can transmit or receive information, data or signals to or from the device 1800. As will be described with further reference to FIG. 20, a nerve stimulus system or device in accordance with the embodiments disclosed herein can use feedback received from the feedback component 1660 to modify the nerve stimulus based on the feedback.

The devices 1800, 1801 can be configured to deliver nerve stimulations synchronized to cause neural oscillations 1815. For example, the devices 1800, 1801 can be driven with corresponding pulse schemes 1810a. 1810b, which may be offset in time to result in desired neural oscillations 1815, as will be described further with reference to FIG. 19.

In some embodiments, the devices 1800 can be configured to deliver nerve stimulus to particular locations on the body of the subject 1850 based on an expected response of the subject 1850, such as at least one of a sensation response of the subject 1850, neural oscillations of the subject 1850, or brain entrainment of the subject 1850. For example, delivering the nerve stimulus 1805 to the hand of the subject 1850 with an amplitude of 8 mA may cause the subject 1850 to heavily sense or feel the nerve stimulus 1805, which may be uncomfortable; delivering the nerve stimulus 1805 to the quadriceps with an amplitude of 8 mA may cause or induce a similar (or greater) magnitude of neural oscillations in the brain 1860, without the sensation.

The devices 1800, 1801 can be configured to output nerve stimulations 1805 based on predetermined operating limits, which may be targeted to cause or induce neural oscillations while reducing or minimizing the likelihood of discomfort or other undesired side effects. For example, the devices 1800, 1801 can be configured to output pulses of approximately 1 μs to 300 μs (e.g., 1 μs, 300 μs; greater than or equal to 1 μs and less than or equal to 500 μs), with a voltage range of approximately 0.1 to 200 V (e.g., 0.1 V, 200 V; greater than or equal to 0.1 V and less than or equal to 500 V). For impedances of 2000 to 4000 ohms, the pulses can have a range of corresponding current amplitudes of approximately 0.1 to 50 mA (e.g., 0.1 mA, 50 mA; greater than or equal to 0.1 mA and less than or equal to 100 mA); for impedances of approximately 500 to 2000 ohms, the pulses can have a range of corresponding current amplitudes of approximately 0.1 to 100 mA (e.g., 0.1 mA, 50 mA; greater than or equal to 0.1 mA and less than or equal to 200 mA).

In some embodiments, a nerve stimulus amplification device 1802 is configured to amplify nerve stimulus signals transmitted through the nervous system to the brain 1860 (e.g., through central nervous system 1855). For example, the nerve stimulus amplification device 1802 can be supercutaneous or implantable amplifier configured to apply a potential difference across a nervous system pathway, or to apply a direct current or alternating current stimulus to a location on the nervous system pathway between the site at which stimulus is delivered by the nerve stimulus generator component 1650 and the brain (e.g., at the spinal cord). The nerve stimulus amplification device 1802 can be configured to be always in an ON mode (e.g., always causing amplification), or to be in an ON mode for a duration of time that can be selected based on a control signal from the nerve stimulus generation module 1610 or based on user input. The nerve stimulus amplification device 1802 can be configured to detect nerve activity corresponding to the nerve stimulus 1805 (e.g., using an EEG; using feedback component 160) and output or deliver a synchronized nerve stimulus to the nervous system to increase an effective magnitude of the nerve stimulus 1805.

Figure 18B:
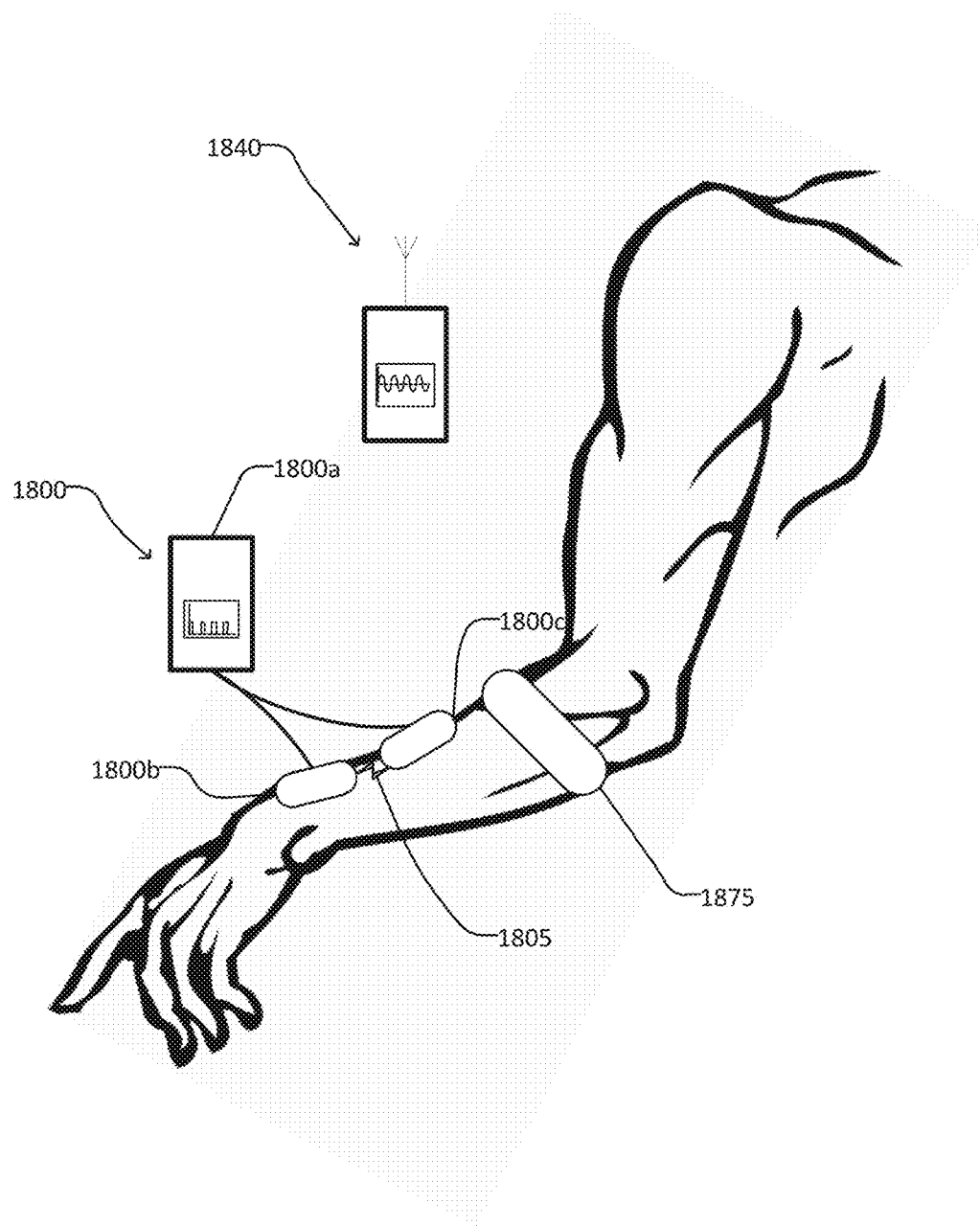

FIG. 18B illustrates the device 1800 configured for peripheral nerve stimulation, such as to cause or induce neural oscillations, in accordance with some embodiments.

The device 1800 can include a control component 200 (e.g., control box). The control component 200 can include a user interface configured to receive user inputs and display information, such as a pulse scheme being operated by the device 1800 or parameters of nerve stimulus outputted by the device 1800.

The device 1800 can be portable. For example, the device 1800 can include an independent power supply (e.g., a battery). The device 1800 can include straps or otherwise be configured to be held or support by the subject. In some embodiments, the device 1800 may have a weight less than a threshold weight supportable by the subject, and further include a power interface configured to receive power from a wall outlet or other remote power supply.

The device 1800 includes a first electrode 1800b (e.g., stimulation electrode) and a second electrode 1800c (e.g., reference electrode, ground electrode). The device 1801 may be configured in a similar manner as the device 1800. The electrodes 1800b, 1800c are configured to deliver, output, transmit, or otherwise provide a nerve stimulus 1805 as an electric current to sensory nerves of the peripheral nerve system. For example, the control component 1800a can be configured to apply a voltage across the electrodes 1800b, 1800c to cause discharge of an electric current according to predetermined parameters from the first electrode 1800b to the second electrode 1800c.

In some embodiments, a feedback device 1850 is configured to detect neural activity caused by the nerve stimulus 1805 outputted by the device 1800. The feedback device 1850 may be similar to the feedback component 1660 described with reference to FIG. 1. The feedback device 1850 may be further configured to detect neural activity along the peripheral nervous system in a vicinity of where the device 1800 delivers the nerve stimulus 1805. For example, the feedback device 1850 can be configured to detect neural activity along the upper arm where the device 1800 delivers the nerve stimulus 1805 to the hand.

In some embodiments, a shielding device 1875 is configured to selectively permit electrical activity caused by the device 1800 to move towards the brain of the subject. The shielding device 1875 can be similar to the shielding component 1655 described with reference to FIG. 1. The shielding device 1875 can be configured to prevent electric currents from travelling along the skin of the subject due to skin conductance. The shielding device 1875 can be or include an electrical insulator configured to increase a resistance to electrical conduction along the skin of the subject. The feedback device 1850 may be used to detect electrical activity on either side of the shielding device 1875 relative to the brain of the subject, to confirm that the shielding device 1875 is increasing the resistance to electrical conduction. The shielding device 1875 may include a cuff, strap, or other component configured to attach the shielding device 1875 to the subject.

In some embodiments, topical ointments, gels, or other materials may be used to augment functionality of the device 1800. For example, electrode gel or other similar materials configured to increase local conductance of the skin can be applied below the electrodes 1800b. 1800c, facilitating transmission of the nerve stimulus 1805 to the targeted sensory nerves. This may advantageously decrease discomfort to the subject from the nerve stimulus 1805, and also decrease the likelihood that the nerve stimulus 1805 travels along the skin to the brain rather than cause activity in the targeted sensory nerve. In some embodiments, pharmacological aids can be used to enhance neural transmissions, increase a speed of neural transmissions, improve sensory nerve sensitivity to external current stimulation, reduce a motor nerve sensitivity to reduce motor response, or decrease a pain nerve sensitivity.

Figure 18C:
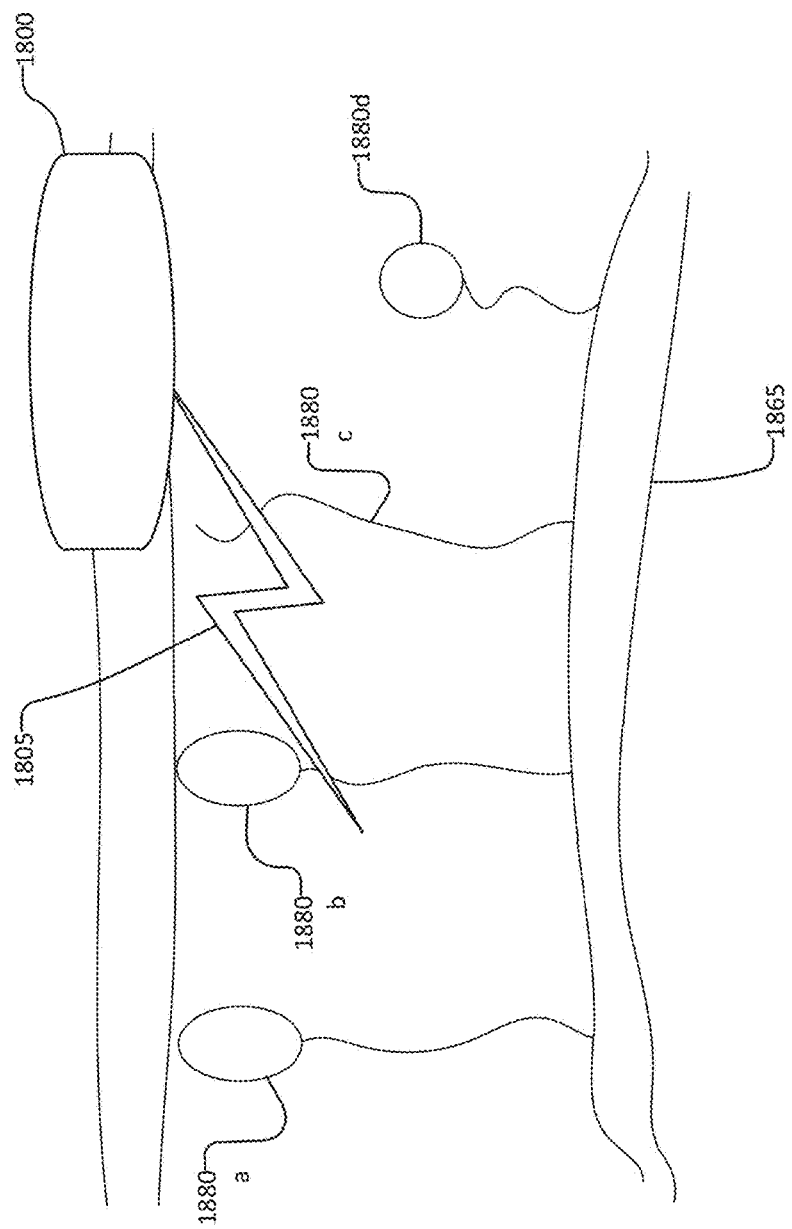

Referring now to FIG. 18C, a schematic diagram illustrating interaction between the device 1800 and the peripheral nerve system is shown according to some embodiments. The device 1800 can be positioned on the skin adjacent to targeted sensory nerves such as a thermos-receptor 1880a, a Meissner's corpuscle 1880b (e.g., a touch receptor), a nociceptor 1880c (e.g., a pain receptor), and Pacinian corpuscle 1880d (e.g., a pressure receptor). The nerve stimulus 1805 delivered by the device 1800 can cause or induce electrical activity in one or more of the receptors 1880a-d, resulting in neural transmissions through the peripheral nervous system 1880 to the brain of the subject, causing neural oscillations corresponding to the nerve stimulus 1805.

In some embodiments, the device 1800 is configured to control delivery or output of the nerve stimulus 1805 based on the receptors 1880a-d. For example, characteristics of the receptors 1880a-d, such as sensitivity to electrical stimulus (e.g., a first threshold at which neural oscillations occur; a second threshold at which discomfort occurs), an amplitude of electrical stimulus associated with resulting neural oscillations, can be used to determine parameters of the nerve stimulus 1805. In some embodiments, the nerve stimulus 1805 (e.g., a characteristic or parameter thereof) is configured to cause electrical activity in the receptors 1880a-d but not in an adjacent motor nerve, which can advantageously make the treatment more comfortable for the subject while reducing the likelihood of distraction due to motor responses.

Figure 19:
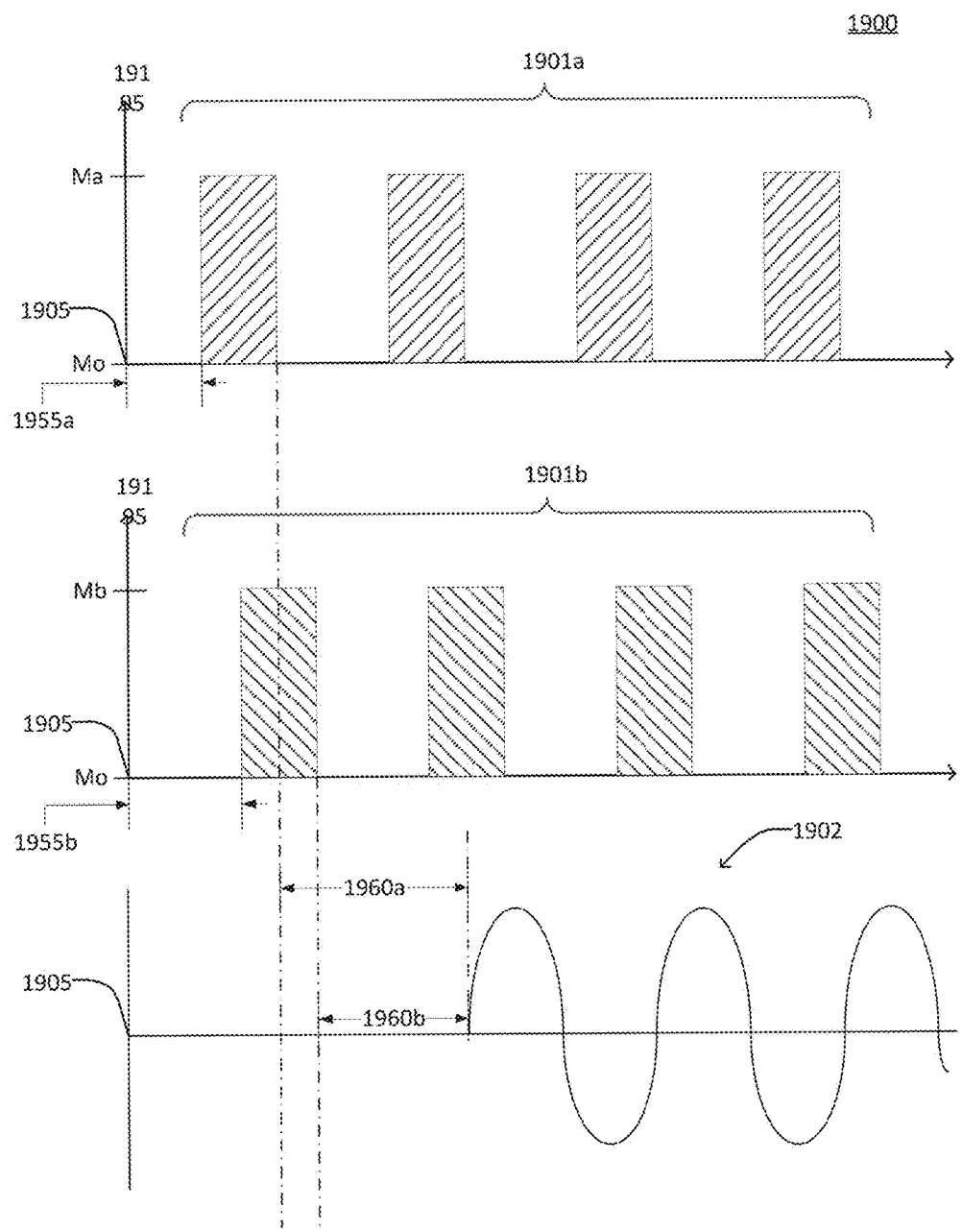
FIG. 19 illustrates a control scheme for synchronized peripheral nerve stimulation by a plurality of devices in accordance with some embodiments.

Referring now to FIG. 19, a control scheme 1900 for controlling operation of a plurality of peripheral nerve stimulation devices (e.g., by NSS 1605; using devices 1800, 1801 described with reference to FIG. 18A; etc.) is shown according to some embodiments. The pulse schemes shown in FIG. 19 can be controlled in a similar manner to those described with reference to FIGS. 2A-2D, with the exception of the further details regarding coordinated control described further herein. The control scheme 1900 can be determined based on characteristics of the peripheral nervous system of the subject, such as a signal delay from a first point in time at which the nerve stimulus 1805 is delivered, and a second point in time at which neural oscillations in the brain of the subject occur (or at which neural oscillations in the brain of the subject are detected, such as by feedback component 160). For example, the profile manager 1625 may store include be configured to access predetermined parameters associated with signal delay from targeted portions of the body of the subject to the brain, and the nerve stimulus generation module 1610 can determine a corresponding offset or time delay between the nerve stimulations (or the corresponding pulse schemes) for electric currents delivered by each device 1800, 1801.

As shown in FIG. 19, a first device (e.g., device 1800) is configured to deliver a first nerve stimulus according to pulse scheme 1901a. After a first delay 1955a from a start time 1905, the pulse scheme 1901a is initiated (it will be appreciated that the start of any of the pulse schemes such as pulse schemes 1901a. 1901b may also serve as a start time). Similarly, after a second delay 1955b from the start time 1905, a second pulse scheme 1901a is initiated. The difference between the delays 1955a, 1955b indicates an offset in time selected (e.g., determined by the nerve stimulus generation module 1610) to cause synchronized neural oscillations in the brain of the subject.

The NSS 1605 can be configured to control operation of stimulation devices according to the pulse schemes 1901a, 1901b to cause neural oscillations 1902 in the brain of the subject. The first delay 1955a may correspond to, be associated with, or be determined based on a first signal delay 1960a between a pulse of the first scheme 1901a (e.g., as shown in FIG. 19, as measured from an end of the pulse) to the start of neural oscillations 1902); similarly, the second delay 1955b may correspond to, be associated with, or be determined based on a second signal delay 1960b between a pulse of the second scheme 1901b and the start of the neural oscillations 1902. For example, the pulse scheme 1901a may be used to deliver the first nerve stimulus by a device located further from the brain (e.g., further along a differential length of the peripheral nervous system) than a device operating according to the second pulse scheme 1901b.

In some embodiments, the NSS 1605 is configured to determine the delays 1955a, 1955b according to feedback information received regarding the neural oscillations 1902. For example, if the feedback component 1660 detects asynchronous neural oscillations 1902, the NSS 1605 can adjust one or both of the delays 1955a, 1955b to decrease a phase delay or other asynchronicity in the neural oscillations 1902 to synchronize the neural oscillations 1902.

Figure 20:
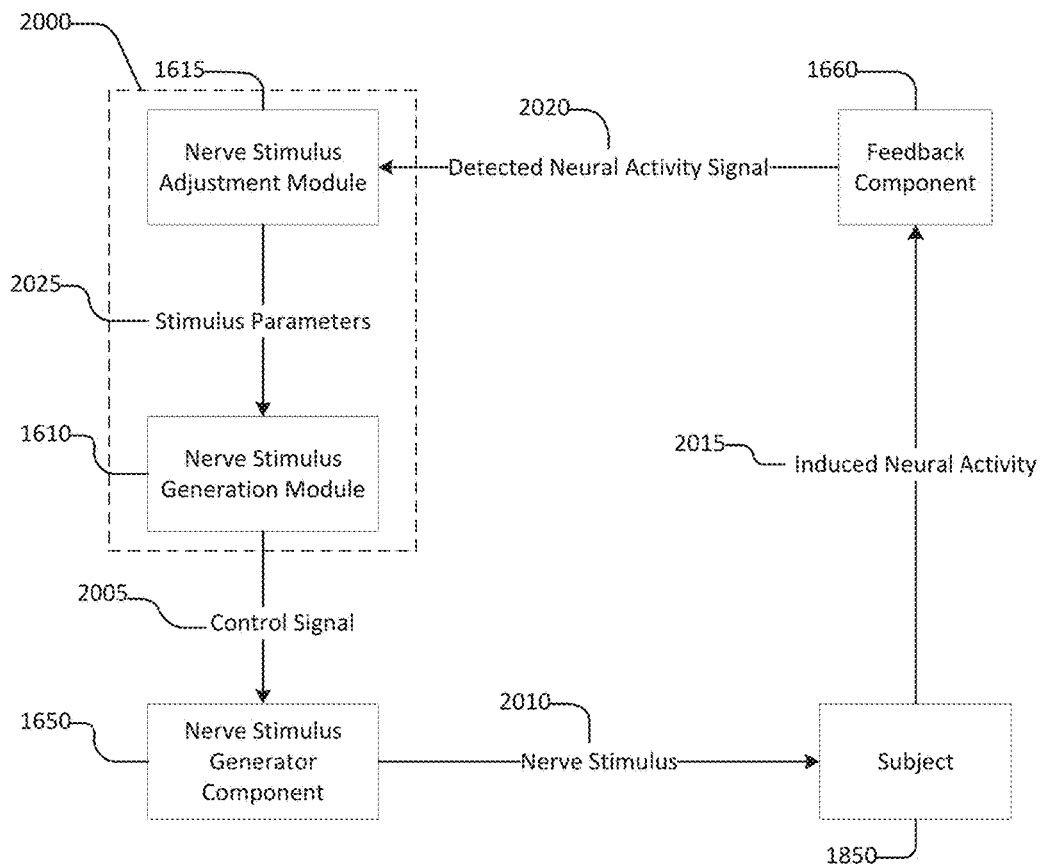
FIG. 20 illustrates a process flow diagram for peripheral nerve stimulation to induce and control neural oscillations in accordance with an embodiment.

FIG. 20 illustrates a process flow for using a peripheral nerve stimulation system 2000 to cause neural oscillations in the subject 1850 according to some embodiments. The peripheral nerve stimulation system 2000) can include the nerve stimulus generation module 1610 and the nerve stimulus adjustment module 1615.

The nerve stimulus generation module 1610 is configured to generate a control signal 2005. The control signal 2005 can indicate desired characteristics or parameters of a nerve stimulus to be applied to the subject 1850 (e.g., to the brain of the subject 1850). For example, the control signal 2005 can indicate values for the characteristics or parameters, or the control signal 2005 can indicate values for operation of the nerve stimulus generator component 1650 (e.g., values for an amplitude of a current delivered to electrodes to generate the desired nerve stimulations) that will result in the desired nerve stimulus. The control signal 2005 can be modulated, generated, transmitted, and/or outputted by the nerve stimulus generation module 1610 to the nerve stimulus generator component 1650. The control signal 2005 can be transmitted and/or output according to a pulse scheme indicating the desired characteristics or parameters, or the control signal 2005 can include instructions indicating the pulse scheme. The control signal 2005 may be determined or generated based on predetermined parameters, such as parameters associated with a predetermined therapy plan (which may be associated with the subject 1850 and stored in or received from the profile 1645).

The nerve stimulus generator component 1650 is configured to generate a nerve stimulus 2010 based on the control signal 2005. For example, the nerve stimulus generator component 1650 can identify the pulse scheme based on how the control signal 2005 is received (e.g., based on a modulation of the control signal 2005) or can extract the pulse scheme from the control signal 2005. Based on the pulse scheme or other instructions extracted from the control signal 2005, the nerve stimulus generator component 1650 can determine characteristics of the nerve stimulus 2010, such as an amplitude, voltage, frequency, and/or modulation frequency of the nerve stimulus 2010. The nerve stimulus generator component 1650 can generate the nerve stimulus 2010 to have the desired amplitude, voltage, frequency, and/or modulation frequency.

The nerve stimulus generator component 1650 generates the nerve stimulus 2010 to have a desired effect on the subject 1850, particularly to cause neural oscillations (e.g., neural oscillations associated with brain entrainment). In some embodiments, the feedback component 1660 is configured to detected induced neural activity 2015 (e.g., neural oscillations, brain entrainment) from the subject 1850. For example, the feedback component 1660 may be an EEG configured to detect electrical activity in the brain of the subject 1850. In some embodiments, such as described with reference to FIG. 18B, the feedback component 1660 can additionally or alternatively be configured to detect neural activity in the peripheral nervous system, such as adjacent to where the nerve stimulus generator component 1650 delivers the nerve stimulus 2010, to detect or confirm the induced neural activity 2015.

The feedback component 1660 is configured to output a detect neural activity signal 2020. The detected neural activity signal 2020 may be an indication of the electrical activity detected in the brain by the EEG (e.g., may be an electroencephalogram). In some embodiments, the system 2000 includes the feedback monitor 1635, which can monitor an output received from the feedback component 160, process the output as described herein, and deliver the processed output to the nerve stimulus adjustment module 1615.

In some embodiments, the nerve stimulus adjustment module 1615 is configured to process the detected neural activity signal 2020 to generate or adjust stimulus parameters 2025. The nerve stimulus adjustment module 1615 may be configured to extract an indication of neural oscillations or brain entrainment from the detected neural activity signal 2020. For example, the nerve stimulus adjustment module 1615 may be configured to identify or extract a frequency of neural oscillations from the detected neural activity signal 2020.

In some embodiments, the feedback component 1660 is configured to process the detected induced neural activity 2015, and output the detected neural activity signal 2020 as an indication of neural oscillations or brain entrainment. For example, the feedback component 1660 can be configured to identify or extract a frequency of neural oscillations from the induced neural activity 2015, and output the extracted frequency in or as the detected neural activity signal 2020. The nerve stimulus adjustment module 1615 may then generate or adjust the stimulus parameters 2025 based on the frequency received from the feedback component 160.

The stimulus parameters 2025 can be generated to cause desired neural oscillations in the subject 1850. For example, the stimulus parameters 2025 may indicate appropriate characteristics or parameters of the nerve stimulus 2010 to cause neural oscillations (e.g., frequency, magnitude, direction, location in the brain of the subject 10). Where the stimulus parameters 2025 are generated based on the detected neural activity signal 2020, the stimulus parameters 2025 may indicate modifications to the nerve stimulus 2010 (e.g., if the frequency of the induced neural activity 2015 is too great, the stimulus parameters 2025 may include instructions to decrease the frequency of the nerve stimulus 2010; if the induced neural activity 2015 indicates that neural oscillations have not occurred, the stimulus parameters 2025 may include instructions to increase the amplitude of the nerve stimulus 2010).

The stimulus parameters 2025 can be determined based on or associated with the nerve stimulus generator component 1650. For example, as will be described further reference to FIGS. 18A-18B, the nerve stimulus generator component 1650 can include two or more electrodes (e.g., four electrodes) or electrical lead wires that can be attached to the skin, and driven to output electric current pulses by a power source or other driver component, such as at a high frequency with an amplitude (e.g., intensity) less than a threshold intensity at which motor response is evoked. A first electrode (e.g., a stimulation electrode) can receive an electrical current from the driver component, where the electrical current is generated and/or controlled based on the control signal 2005 (which can be generated or modulated based on the stimulus parameters 2025). The first electrode can output, pass, transmit, or otherwise deliver the electrical current to the subject 1850 to excite sensory nerves of the peripheral nerve system of the subject 1850 (e.g., to deliver the electrical current to a second electrode, such as a reference electrode).

Referring further to FIG. 16, the feedback component 1660 can detect feedback information, such as environmental parameters or physiological conditions. The feedback component 1660 can provide the feedback information to system 2000 (or NSS 1605). The system 2000 can adjust or change the nerve stimulus based on the feedback information. For example, the system 2000 can determine that a pulse rate of the subject exceeds a predetermined threshold, and then lower the amplitude of the nerve stimulus. The feedback component 1660 can include a detector configured to detect an amplitude of the nerve stimulus 2010, and the system 2000 can determine that the amplitude exceeds a threshold, and decrease the amplitude. The system 2000 can determine that the pulse rate interval is below a threshold, which can indicate that a subject is not being sufficiently affected by the nerve stimulus, and the system 2000 can increase the amplitude of the nerve stimulus. In some embodiments, the system 2000 can vary the nerve stimulus (e.g., vary amplitude, voltage, frequency) based on a time interval. Varying the nerve stimulus can prevent the subject 1850 from adapting to the nerve stimulus (e.g., prevent the brain from determining that the nerve stimulus is a background condition), which can facilitate causing or inducing neural oscillations.

In some embodiments, the feedback component 1660 can include EEG probes, and the nerve stimulus adjustment module 1615 can adjust the nerve stimulation based on the EEG information. For example, the nerve stimulus adjustment module 1615 can determine, from the probe information, that neurons are oscillating at an undesired frequency, and modify the frequency at which the nerve stimulus 2010 is generated accordingly.

The feedback component 1660 can detect, receive, obtain, or otherwise identify feedback information from one or more feedback sensors. The feedback component 1660 can provide the feedback information to one or more component of the system 2000 (or the NSS 1605) for further processing or storage. For example, the profile manager 1625 can update profile data structure 1645 stored in data repository 1640 with the feedback information. Profile manager 1625 can associate the feedback information with an identifier of the subject or person undergoing the peripheral nerve stimulation, as well as a time stamp and date stamp corresponding to receipt or detection of the feedback information.

The feedback component 1660 can determine a level of attention. The level of attention may indicate whether the nerve stimulus is resulting in neural oscillations (e.g., desired neural oscillations; neural oscillations associated with brainwave entrainment). The level of attention can refer to the focus provided to the nerve stimulus. The feedback component 1660 can determine the level of attention using various hardware and software techniques. The feedback component 1660 can assign a score to the level of attention (e.g., 1 to 10 with 1 being low attention and 10 being high attention, or vice versa, 1 to 100 with 1 being low attention and 100 being high attention, or vice versa, 0 to 1 with 0 being low attention and 1 being high attention, or vice versa), categorize the level of attention (e.g., low, medium, high), grade the attention (e.g., A, B, C. D, or F), or otherwise provide an indication of a level of attention.

In some cases, the feedback component 1660 can track a person's eye movement to identify a level of attention. The feedback component 1660 can interface with an eye-tracker. The feedback component 1660 can detect and record eye movement of the person and analyze the recorded eye movement to determine an attention span or level of attention. The feedback component 1660 can measure eye gaze which can indicate or provide information related to covert attention. For example, the feedback component 1660 can be configured with electro-oculography ("EOG") to measure the skin electric potential around the eye, which can indicate a direction the eye faces relative to the head. In some embodiments, the EOG can include a system or device to stabilize the head so it cannot move in order to determine the direction of the eye relative to the head. In some embodiments, the EOG can include or interface with a head tracker system to determine the position of the heads, and then determine the direction of the eye relative to the head.

In some embodiments, the feedback component 1660 can determine a level of attention the subject is paying to the nerve stimulus based on eye movement. For example, increased eye movement may indicate that the subject is focusing on visual stimuli, as opposed to other stimuli. To determine the level of attention the subject is paying to the nerve stimulus, feedback component 1660 can determine or track the direction of the eye or eye movement using video detection of the pupil or corneal reflection. For example, the feedback component 1660 can include one or more camera or video camera. The feedback component 1660 can include an infra-red source that sends light pulses towards the eyes. The light can be reflected by the eye. The feedback component 1660 can detect the position of the reflection. The feedback component 1660 can capture or record the position of the reflection. The feedback component 1660 can perform image processing on the reflection to determine or compute the direction of the eye or gaze direction of the eye.

The feedback component 1660 can compare the eye direction or movement to historical eye direction or movement of the same person, nominal eye movement, or other historical eye movement information to determine a level of attention. For example, the feedback component 1660 can determine a historical amount of eye movement during historical peripheral nerve stimulation sessions. The feedback component 1660 can compare the current eye movement with the historical eye movement to identify a deviation. The system 2000 can determine, based on the comparison, an increase in eye movement and further determine that the subject is paying less attention to the current nerve stimulation based on the increase in eye movement. In response to detecting the decrease in attention, the nerve stimulus adjustment module 1615 can change the stimulus parameters 2025 so that the nerve stimulus 2010 causes or induces neural oscillations.

The feedback component 1660 can interact with or communicate with the system 2000. For example, the feedback component 1660 can provide detected feedback information or data to the system 2000. The feedback component 1660 can provide data to the system 2000 in real-time, for example as the feedback component 1660 detects or senses or information. The feedback component 1660 can provide the feedback information to the system 2000 based on a time interval, such as 1 minute, 2 minutes, 5 minutes, 10 minutes, hourly, 2 hours, 4 hours, 12 hours, or 24 hours. The feedback component 1660 can provide the feedback information to the feedback component 1660 responsive to a condition or event, such as a feedback measurement exceeding a threshold or falling below a threshold. The feedback component 1660 can provide feedback information responsive to a change in a feedback parameter. In some embodiments, the system 2000 can ping, query, or send a request to the feedback component 1660 for information, and the feedback component 1660 can provide the feedback information in response to the ping, request, or query.

Referring now to FIGS. 21A-21D, further embodiments of devices configured to deliver nerve stimulations to cause or induce neural oscillations are shown. The devices shown in FIGS. 21A-21D can be configured in a similar manner as the devices 1800, 1801.

Figure 21A:
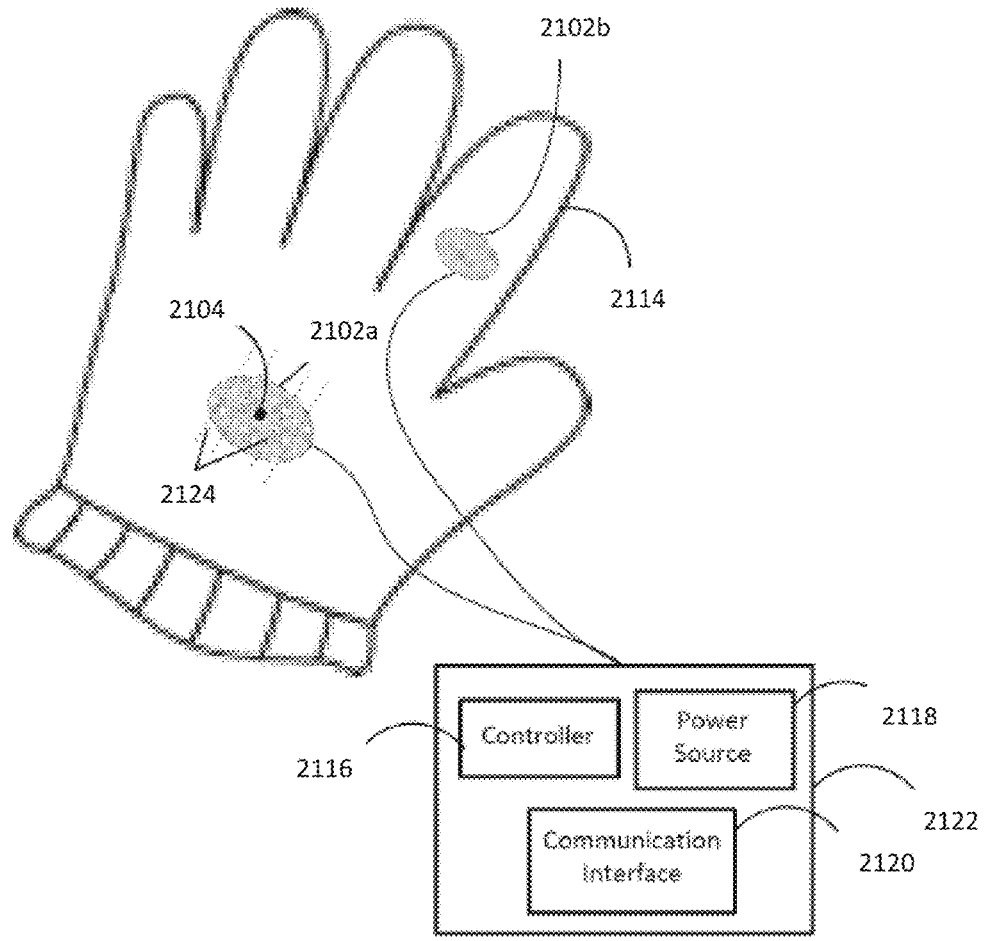
FIGS. 21A-21D illustrate devices configured to deliver peripheral nerve stimulation to targeted parts of the body of a subject in accordance with some embodiments.

As shown in FIG. 21A, a glove 2114 can be configured to deliver peripheral nerve stimulus to cause or induce neural oscillations. The glove 2114 includes a first electrode 2102a, a second electrode 2102b, and a control unit 2104 (the controller may be included in or attached to one or more of the electrodes 2102a, 2102b, or may be in a separate component 2122 that is operatively coupled (e.g., by a wired or wireless connection) to the electrodes 2102a, 2102b. The control unit 2104 is configured to control operation of the electrodes 2102a, 2102b. The control unit 2104 may include a controller 2116, a power source 2118, and a communication interface 2120. The controller 2116 can be configured to control operation of the electrodes 2102a, 2102b. The controller 2116 can include or can be coupled to the nerve stimulus generation module 1610. The controller 2116 can, for example, generate, control, or otherwise process a control signal indicating a pulse scheme for causing a desired nerve stimulus.

The control unit 2104 can include a power source 2118, such as one or more batteries to provide power supply for the control unit 2104 and the electrodes 2102a, 2102b. The communication interface 2120 for communicating with other electronic devices, such as the NSS 1605 or modules thereof. The communication interface 2120 can include a wired communication interface, a wireless communications interface, WiFi communications interface, a BLUETOOTH™ communication interface, a near filed communications (NFC) interface, or the like. The control unit 2104 can transmit data, such as vibration frequency information, motor or touch element setting information, or a combination thereof to the NSS 1605. The NSS 1605 can also transmit signals or data to the control unit 2104.

The glove 2114 can employ active cooling. For example, the glove 2114 can include tubular wires 2124 integrated therein for circulating a relatively cold fluid (e.g., cold water, other cold liquid or cold gas), to cool down the skin or to prevent skin and/or touch element from overheating. The tubular wires 2124 can be positioned in the vicinity of the electrodes 2102a, 2102b (e.g., in close proximity to the stimulation area), or can traverse the glove 2114. The tubular wires 2124 can be coupled to a fluid container and a pump. The pump can cause the cold fluid to circulate through the tubular wires 2124. The pump can be configured to pump fluid when the touch element 2004 is not physically interacting with the stimulation area on the subject's skin. For example, the mechanical stimulus generation module 1615 can instruct the pump to pump the cold fluid during non-stimulation time intervals and stop pumping fluid during the pulse trains 201. In some implementations, the pump can pump the cold fluid continuously throughout the total duration of the stimulation signal 2006.

In some implementations, the glove 2114 can include passive cooling means, such as vents or apertures that allow any heat to dissipate away from the skin of the subject. The glove 2114 can also include heat absorbing material(s) that can absorb heat generated responsive to the physical contact between the electrodes 2102a, 2102b and the skin of the subject. The heat absorbing the material can transfer the absorbed heat into the air. The nerve stimulus generation module 1610 can select durations of pulse schemes during which stimulation is not provided to cool down or prevent overheating. The glove 2114 and/or the NSS 1605 can include a combination of one or more passive cooling mechanisms and/or one or more active cooling mechanisms.

Figure 21B:
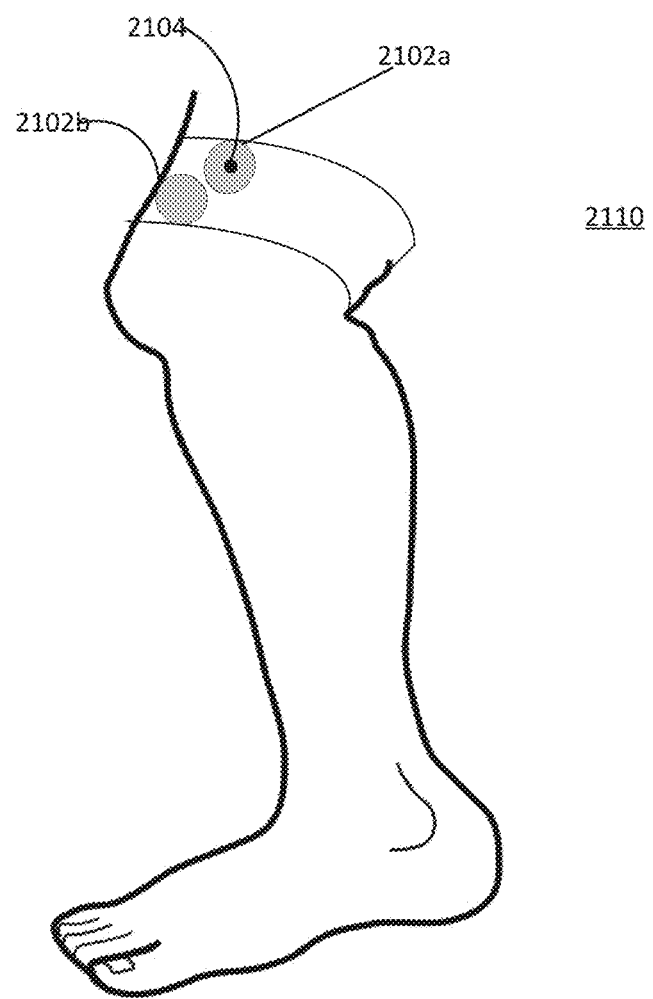

Referring now to FIG. 21B, a stimulation device 2110 is shown according to an embodiment. The stimulation device 2110 can be similar to the glove 2114, except that the stimulation device 2114 is configured as a strap (e.g., cuff, wrap), such as for delivering nerve stimulus to the quadriceps. In some embodiments, the stimulation device 2110 is configured to be adjusted in position. For example, while FIG. 21B shows the stimulation device 2110 with electrodes 2102a, 2102b (and control unit 2104) oriented to deliver nerve stimulus to the quadriceps, the stimulation device 2114 could be rotated or otherwise adjusted in position or orientation such that the electrodes 2102a. 2102b can deliver nerve stimulus to the back of the knee.

Figure 21C:
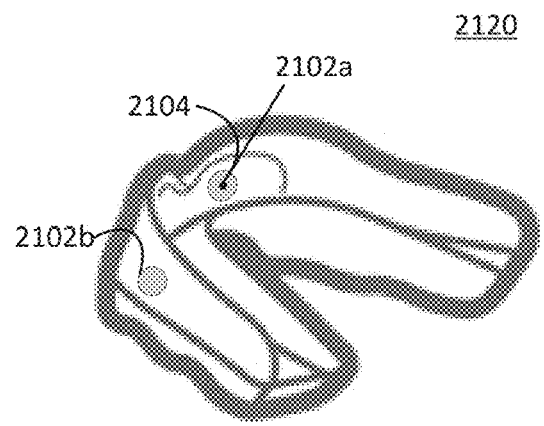

Referring now to FIG. 21C, a stimulation device 2120 (e.g., a mouthpiece) is shown according to an embodiment. The stimulation device 2120 can be similar to the glove 2114 and the stimulation device 2110, except that the stimulation device 2120 is configured as a mouthpiece, such as for delivering nerve stimulus to the lips, teeth, or gums. For example, the locations of electrodes 2102a, 2102b in the stimulation device 2120 can be selected (or modified prior to use, such as through the use of removable electrodes) based on whether the lips, teeth, or gums are targeted by the nerve stimulus. In some embodiments, the electrodes 2102a. 2102b are located in the stimulation device 2120 such that the electrodes 2102a, 2102b will be exposed to relatively low levels of saliva, such as to reduce the likelihood of conduction by the saliva as opposed to the lips, teeth, or gums.

Figure 21D:
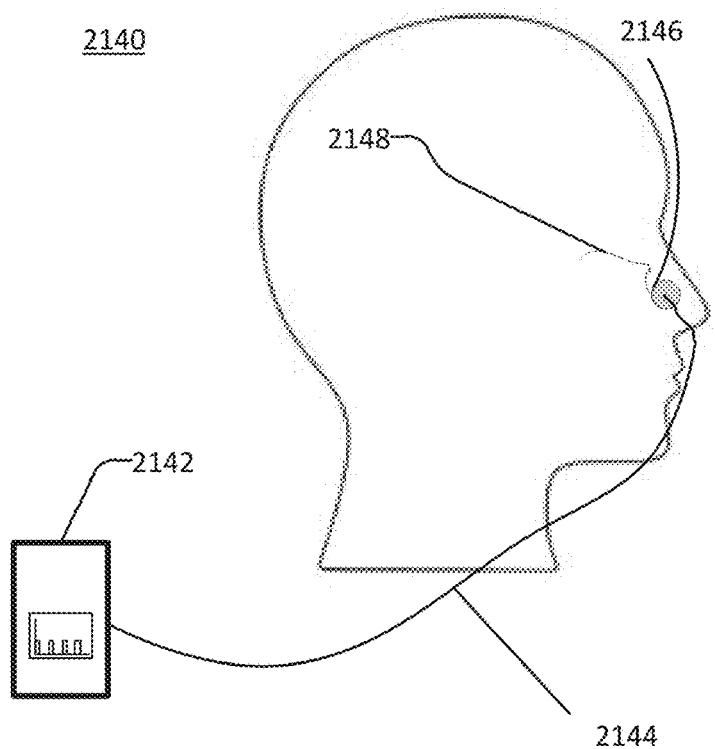

Referring now to FIG. 21D, a stimulation device 2140 (e.g., a nose plug or nose piece) is shown according to an embodiment. The stimulation device 2140 can be similar to the glove 2114, the stimulation device 2110, and the stimulation device 2120, except that the stimulation device 2140 is configured as a nose plug, such as for delivering nerve stimulus to the olfactory nerve 2148. For example, the stimulation device 2140 can include a control component 2142 (e.g., a control component 2142 including a power supply) configured to deliver an electrical current to electrode 2146 (which may be a stimulation electrode paired with a reference electrode) via electrical lead 2144 to deliver nerve stimulus to the olfactory nerve 2148.

N. Method for Inducing Neural Oscillations Via Peripheral Nerve Stimulation

Figure 22:
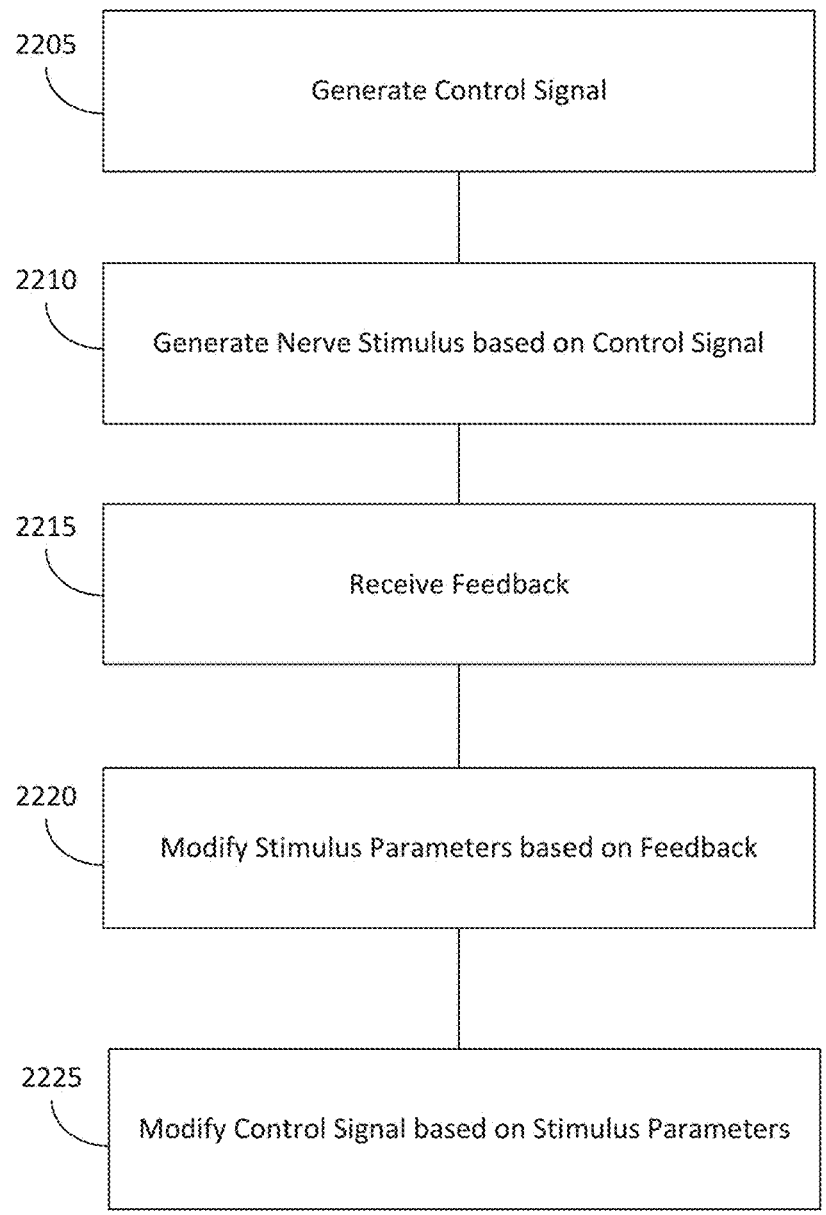
FIG. 22 is a flow diagram of a method of performing peripheral nerve stimulation in accordance with an embodiment.

FIG. 22 is a flow diagram of a method of performing peripheral nerve stimulation, such as to cause or induce neural oscillations, in accordance with an embodiment. The method 2200 can be performed by one or more of the systems, components, modules or elements depicted in FIGS. 16A-16B, including, for example, a peripheral nerve stimulation system (NSS). In brief overview, the NSS can generate a control signal indicating instructions to generate a nerve stimulus having predetermined parameters or characteristics at block 2205. At block 2210, the NSS can generate and output the nerve stimulus based on the control signal. At block 2215, the NSS can receive or determine feedback associated with neural activity, physiological activity, environmental parameters, or device parameters. At block 2220, the NSS can manage, control, or modify stimulus parameters based on the feedback. At block 2225, the NSS can modify the control signal based on the stimulus parameters in order to modify the nerve stimulus based on the feedback.

O. Neural Stimulation Via Multiple Modes of Stimulation

Figure 23A:
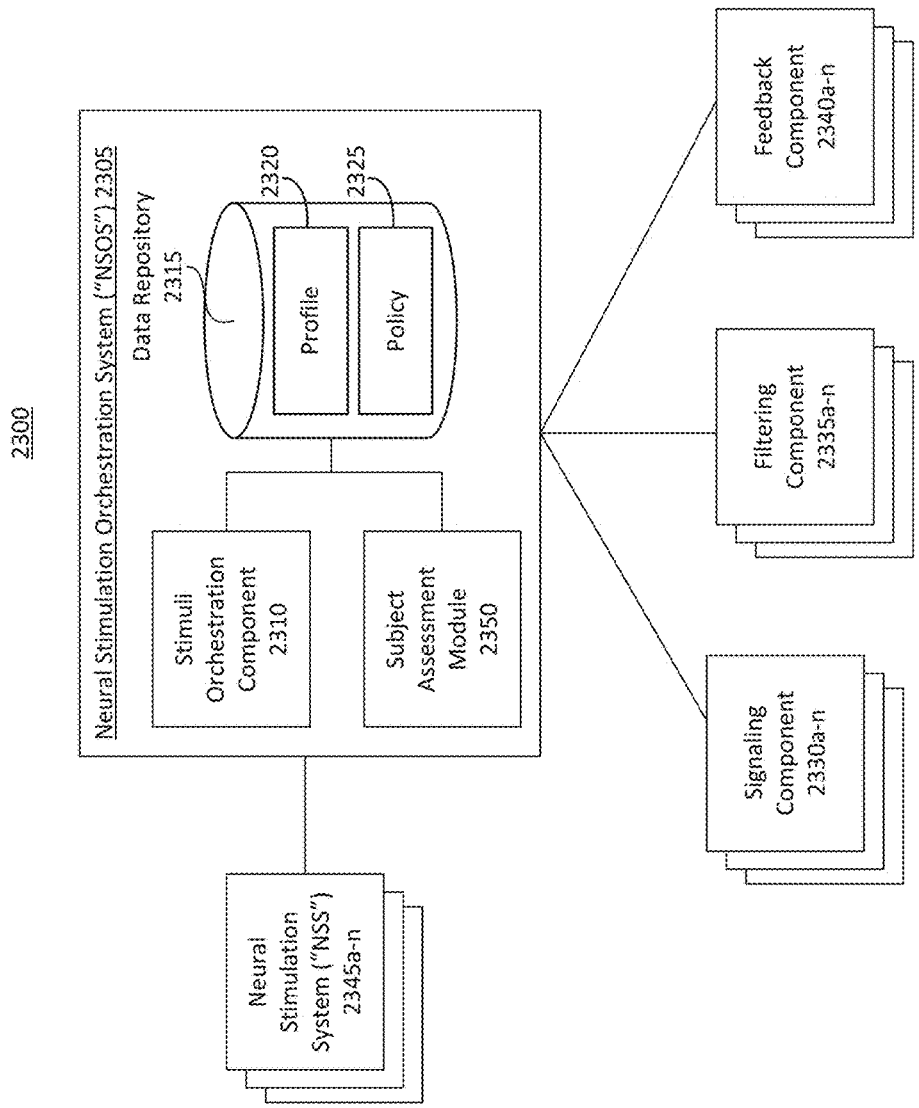
FIG. 23A is a block diagram depicting a system for neural stimulation via multiple stimulation modalities in accordance with an embodiment.

FIG. 23A is a block diagram depicting a system for neural stimulation via multiple stimulation modalities in accordance with an embodiment. The system 2300 can include a neural stimulation orchestration system ("NSOS") 2305. The NSOS 2305 can provide multiple modes of stimulation. For example, the NSOS 2305 can provide a first mode of stimulation that includes visual stimulation, and a second mode of stimulation that includes auditory stimulation. For each mode of stimulation, the NSOS 2305 can provide a type of signal. For example, for the visual mode of stimulation, the NSOS 2305 can provide the following types of signals: light pulses, image patterns, flicker of ambient light, or augmented reality. NSOS 2305 can orchestrate, manage, control, or otherwise facilitate providing multiple modes of stimulation and types of stimulation.

In brief overview, the NSOS 2305 can include, access, interface with, or otherwise communicate with one or more of a stimuli orchestration component 2310, a subject assessment module 2350, a data repository 2315, one or more signaling components 2330a-n, one or more filtering components 2335a-n, one or more feedback components 2340a-n, and one or more neural stimulation systems ("NSS") 2345a-n. The data repository 2315 can include or store a profile data structure 2320 and a policy data structure 2325. The stimuli orchestration component 2310 and subject assessment module 2350 can include at least one processing unit or other logic device such as programmable logic array engine, or module configured to communicate with the database repository 2315. The stimuli orchestration component 2310 and subject assessment module 2350 can be a single component, include separate components, or be part of the NSOS 2305. The system 2300 and its components, such as the NSOS 2305, may include hardware elements, such as one or more processors, logic devices, or circuits. The system 2300 and its components, such as the NSOS 2305, can include one or more hardware or interface component depicted in system 700 in FIGS. 7A and 7B. For example, a component of system 2300 can include or execute on one or more processors 721, access storage 728 or memory 722, and communicate via network interface 718. The system 2300 can include one or more component or functionality depicted in FIGS. 1-15, including, for example, system 100, system 900, visual NSS 105, or auditory NSS 905. For example, at least one of the signaling components 2330a-n can include one or more component or functionality of visual signaling component 150 or audio signaling component 950. At least one of the filtering components 2335a-n can include one or more component or functionality of filtering component 155 or filtering component 955. At least one of the feedback components 2340a-n can include one or more component or functionality of feedback component 230 or feedback component 960. At least one of the NSOS 2345a-n can include one or more component or functionality of visual NSS 105 or auditory NSS 905.

Still referring to FIG. 23A, and in further detail, the NSOS 2305 can include at least stimuli orchestration component 2310. The stimuli orchestration component 2310 can be designed and constructed to perform neural stimulation using multiple modalities of stimulation. The stimuli orchestration component 2310 or NSOS 2305 can interface with at least one of the signaling components 2330a-n, at least one of the filtering components 2335a-n or at least one of the feedback components 2340a-n. One or more of the signaling components 2330a-n can be a same type of signaling component or a different type of signaling component. The type of signaling component can correspond to a mode of stimulation. For example, multiple types of signaling components 2330a-n can correspond to visual signaling components or auditory signaling components. In some cases, at least one of the signaling components 2330a-n includes a visual signaling component 150 such as a light source, LED, laser, tablet computing device, or virtual reality headset. At least one of the signaling components includes an audio signaling component 950, such as headphones, speakers, cochlear implants, or air jets.

One or more of the filtering components 2335a-n can be a same type of filtering component or a different type of filtering component. One or more of the feedback components 2340a-n can be a same type of feedback component or a different type of feedback component. For example, the feedback components 2340a-n can include an electrode, dry electrode, gel electrode, saline soaked electrode, adhesive-based electrodes, a temperature sensor, heart or pulse rate monitor, physiological sensor, ambient light sensor, ambient temperature sensor, sleep status via actigraphy, blood pressure monitor, respiratory rate monitor, brain wave sensor, EEG probe, EOG probes configured measure the corneo-retinal standing potential that exists between the front and the back of the human eye, accelerometer, gyroscope, motion detector, proximity sensor, camera, microphone, or photo detector.

The stimuli orchestration component 2310 can include or be configured with an interface to communicate with different types of signaling components 2330a-n, filtering components 2335a-n or feedback components 2340a-n. The NSOS 2305 or stimuli orchestration component 2310 can interface with system intermediary to one of the signaling components 2330a-n, filtering components 2335a-n, or feedback components 2340a-n. For example, the stimuli orchestration component 2310 can interface with the visual NSS 105 depicted in FIG. 1 or auditory NSS 905 depicted in FIG. 9. Thus, in some embodiments, the stimuli orchestration component 2310 or NSOS 2305 can indirectly interface with at least one of the signaling components 2330a-n, filtering components 2335a-n, or feedback components 2340a-n.

The stimuli orchestration component 2310 (e.g., via the interface) can ping each of the signaling components 2330a-n, filtering components 2335a-n, and feedback components 2340a-n to determine information about the components. The information can include a type of the component (e.g., visual, auditory, attenuator, optical filter, temperature sensor, or light sensor), configuration of the component (e.g., frequency range, amplitude range), or status information (e.g., standby, ready, online, enabled, error, fault, offline, disabled, warning, service needed, availability, or battery level).

The stimuli orchestration component 2310 can instruct or cause at least one of the signaling components 2330a-n to generate, transmit or otherwise provide a signal that can be perceived, received or observed by the brain and affect a frequency of neural oscillations in at least one region or portion of a subject's brain. The signal can be perceived via various means, including, for example, optical nerves or cochlear cells.

The stimuli orchestration component 2310 can access the data repository 2315 to retrieve profile information 2320 and a policy 2325. The profile information 2320 can include profile information 145 or profile information 945. The policy 2325 can include a multi-modal stimulation policy. The policy 2325 can indicate a multi-modal stimulation program. The stimuli orchestration component 2310 can apply the policy 2325 to profile information to determine a type of stimulation (e.g., visual or auditory) and determine a value for a parameter for each type of stimulation (e.g., amplitude, frequency, wavelength, color, etc.). The stimuli orchestration component 2310 can apply the policy 2325 to the profile information 2320 and feedback information received from one or more feedback components 2340a-n to determine or adjust the type of stimulation (e.g., visual or auditory) and determine or adjust the value parameter for each type of stimulation (e.g., amplitude, frequency, wavelength, color, etc.). The stimuli orchestration component 2310 can apply the policy 2325 to profile information to determine a type of filter to be applied by at least one of the filtering components 2335a-n (e.g., audio filter or visual filter) and determine a value for a parameter for the type of filter (e.g., frequency, wavelength, color, sound attenuation, etc.). The stimuli orchestration component 2310 can apply the policy 2325 to profile information and feedback information received from one or more feedback components 2340a-n to determine or adjust the type of filter to be applied by at least one of the filtering components 2335a-n (e.g., audio filter or visual filter) and determine or adjust the value for the parameter for filter (e.g., frequency, wavelength, color, sound attenuation, etc.).

The stimuli orchestration component 2310 can synchronize signals sent via the one or more signaling components 2330a-n. The stimuli orchestration component 2310 can use a policy to synchronize the stimulation signals. For example, the stimuli orchestration component 2310 can identify two signaling components 2330a-n (e.g., visual signaling component and auditory signaling component). The stimuli orchestration component 2310 can determine to keep a phase of the visual stimulation pulse train constant, while varying the phase of the auditory stimulation pulse train. For example, the stimuli orchestration component 2310 can apply a phase offset to one of the stimulation signals so the output stimulation signals appear to be out of synchronization. However, due to the different modalities with which the stimulation signals effect neural stimulation, they neural stimulation in the brain itself may be synchronized, even though the output signals at the respective output sources may be out of synchronization. Thus, the stimuli orchestration component 2310 can facilitate synchronizing neural stimulation, thereby facilitating entrainment, by phase offsetting one or more of the stimulation signals while keeping one or more of the stimulation signals constant. The stimuli orchestration component 2310 can apply further phase offsets to one or more of the stimulation signals during one or more subsequent time periods, thereby incrementally sweeping through the phases until the output stimulation signals appear to be in-phase again. For example, the phase offset can range from 0 to 180 degrees and increment by 1 degree increments, 2 degree increments, 3 degree increments, 5 degree increments, 7 degree increments, 10 degree increments, or any other increment that facilitates performing a sweep and neural stimulation.

The NSOS 2305 can obtain the profile information 2320 via a subject assessment module 2350. The subject assessment module 2350 can be designed and constructed to determine, for one or more subjects, information that can facilitate neural stimulation via one or more modes of stimulation. The subject assessment module 2350 can receive, obtain, detect, determine or otherwise identify the information via feedback components 2340a-n, surveys, queries, questionnaires, prompts, remote profile information accessible via a network, diagnostic tests, or historical treatments.

The subject assessment module 2350 can receive the information prior to initiating neural stimulation, during neural stimulation, or after neural stimulation. For example, the subject assessment module 2350 can provide a prompt with a request for information prior to initiating the neural stimulation session. The subject assessment module 2350 can provide a prompt with a request for information during the neural stimulation session. The subject assessment module 2350 can receive feedback from feedback component 2340a-n (e.g., an EEG probe) during the neural stimulation session. The subject assessment module 2350 can provide a prompt with a request for information subsequent to termination of the neural stimulation session. The subject assessment module 2350 can receive feedback from feedback component 2340a-n subsequent to termination of the neural stimulation session.

The subject assessment module 2350 can use the information to determine an effectiveness of a modality of stimulation (e.g., visual stimulation or auditory stimulation) or a type of signal (e.g., light pulse from a laser or LED source, ambient light flicker, or image pattern displayed by a tablet computing device). For example, the subject assessment module 2350 can determine that the desired neural stimulation resulted from a first mode of stimulation or first type of signal, while the desired neural stimulation did not occur or took longer to occur with the second mode of stimulation or second type of signal. The subject assessment module 2350 can determine that the desired neural stimulation was less pronounced from the second mode of stimulation or second type of signal relative to the first mode of stimulation or first type of signal based on feedback information from a feedback component 2340a-n.

The subject assessment module 2350 can determine the level of effectiveness of each mode or type of stimulation independently, or based on a combination of modes or types of stimulation. A combination of modes of stimulation can refer to transmitting signals from different modes of stimulation at the same or substantially similar time. A combination of modes of stimulation can refer to transmitting signals from different modes of stimulation in an overlapping manner. A combination of modes of stimulation can refer to transmitting signals from different modes of stimulation in a non-overlapping manner, but within a time interval from one another (e.g., transmit a signal pulse train from a second mode of stimulation within 0.5 seconds, 1 second, 1.5 seconds, 2 seconds, 2.5 seconds, 3 seconds, 5 seconds, 7 seconds, 10 seconds, 12 seconds, 15 seconds, 20 seconds, 30 seconds, 45 seconds, 60 seconds, 1 minute, 2 minutes 3 minutes 5 minutes, 10 minutes, or other time interval where the effect on the frequency of neural oscillation by a first mode can overlap with the second mode).

The subject assessment module 2350 can aggregate or compile the information and update the profile data structure 2320 stored in data repository 2315. In some cases, the subject assessment module 2350 can update or generate a policy 2325 based on the received information. The policy 2325 or profile information 2320 can indicate which modes or types of stimulation are more likely to have a desired effect on neural stimulation, while reducing side effects.

The stimuli orchestration component 2310 can instruct or cause multiple signaling components 2330a-n to generate, transmit or otherwise provide different types of stimulation or signals pursuant to the policy 2325, profile information 2320 or feedback information detected by feedback components 2340a-n. The stimuli orchestration component 2310 can cause multiple signaling components 2330a-n to generate, transmit or otherwise provide different types of stimulation or signals simultaneously or at substantially the same time. For example, a first signaling component 2330a can transmit a first type of stimulation at the same time as a second signaling component 2330b transmits a second type of stimulation. The first signaling component 2330a can transmit or provide a first set of signals, pulses or stimulation at the same time the second signaling component 2330b transmits or provides a second set of signals, pulses or stimulation. For example, a first pulse from a first signaling component 2330a can begin at the same time or substantially the same time (e.g., 1%, 2%, 3%, 4%, 5%, 6%, 7%, 10%, 15%, 20%) as a second pulse from a second signaling component 2330b. First and second pulses can end at the same time or substantially same time. In another example, a first pulse train can be transmitted by the first signaling component 2330a at the same or substantially similar time as a second pulse train transmitted by the second signaling component 2330b.

The stimuli orchestration component 2310 can cause multiple signaling components 2330a-n to generate, transmit or otherwise provide different types of stimulation or signals in an overlapping manner. The different pulses or pulse trains may overlap one another, but may not necessary being or end at a same time. For example, at least one pulse in the first set of pulses from the first signaling component 2330a can at least partially overlap, in time, with at least one pulse from the second set of pulses from the second signaling component 2330b. For example, the pulses can straddle one another. In some cases, a first pulse train transmitted or provided by the first signaling component 2330a can at least partially overlap with a second pulse train transmitted or provided by the second signaling component 2330b. The first pulse train can straddle the second pulse train.

The stimuli orchestration component 2310 can cause multiple signaling components 2330a-n to generate, transmit or otherwise provide different types of stimulation or signals such that they are received, perceived or otherwise observed by one or more regions or portions of the brain at the same time, simultaneously or at substantially the same time. The brain can receive different modes of stimulation or types of signals at different times. The duration of time between transmission of the signal by a signaling component 2330a-n and reception or perception of the signal by the brain can vary based on the type of signal (e.g., visual, auditory), parameter of the signal (e.g., velocity or speed of the wave, amplitude, frequency, wavelength), or distance between the signaling component 2330a-n and the nerves or cells of the subject configured to receive the signal (e.g., eyes or ears). The stimuli orchestration component 2310 can offset or delay the transmission of signals such that the brain perceives the different signals at the desired time. The stimuli orchestration component 2310 can offset or delay the transmission of a first signal transmitted by a first signaling component 2330a relative to transmission of a second signal transmitted by a second signaling component 2330b. The stimuli orchestration component 2310 can determine an amount of an offset for each type of signal or each signaling component 2330a-n relative to a reference clock or reference signal. The stimuli orchestration component 2310 can be preconfigured or calibrated with an offset for each signaling component 2330a-n.

The stimuli orchestration component 2310 can determine to enable or disable the offset based on the policy 2325. For example, the policy 2325 may indicate to transmit multiple signals at the same time, in which case the stimuli orchestration component 2310 may disable or not use an offset. In another example, the policy 2325 may indicate to transmit multiple signals such that they are perceived by the brain at the same time, in which case the stimuli orchestration component 2310 may enable or use the offset.

In some embodiments, the stimuli orchestration component 2310 can stagger signals transmitted by different signaling components 2330a-n. For example, the stimuli orchestration component 2310 can stagger the signals such that the pulses from different signaling components 2330a-n are non-overlapping. The stimuli orchestration component 2310 can stagger pulse trains from different signaling components 2330a-n such that they are non-overlapping. The stimuli orchestration component 2310 can set parameters for each mode of stimulation or signaling component 2330a-n such that the signals they are non-overlapping.

Thus, the stimuli orchestration component 2310 can set parameters for signals transmitted by one or more signaling components 2330a-n such that the signals are transmitted in a synchronously or asynchronously, or perceived by the brain synchronously or asynchronously. The stimuli orchestration component 2310 can apply the policy 2325 to available signaling components 2330a-n to determine the parameters to set for each signaling component 2330a-n for the synchronous or asynchronous transmission. The stimuli orchestration component 2310 can adjust parameters such as a time delay, phase offset, frequency, pulse rate interval, or amplitude to synchronize the signals.

Figure 23B:
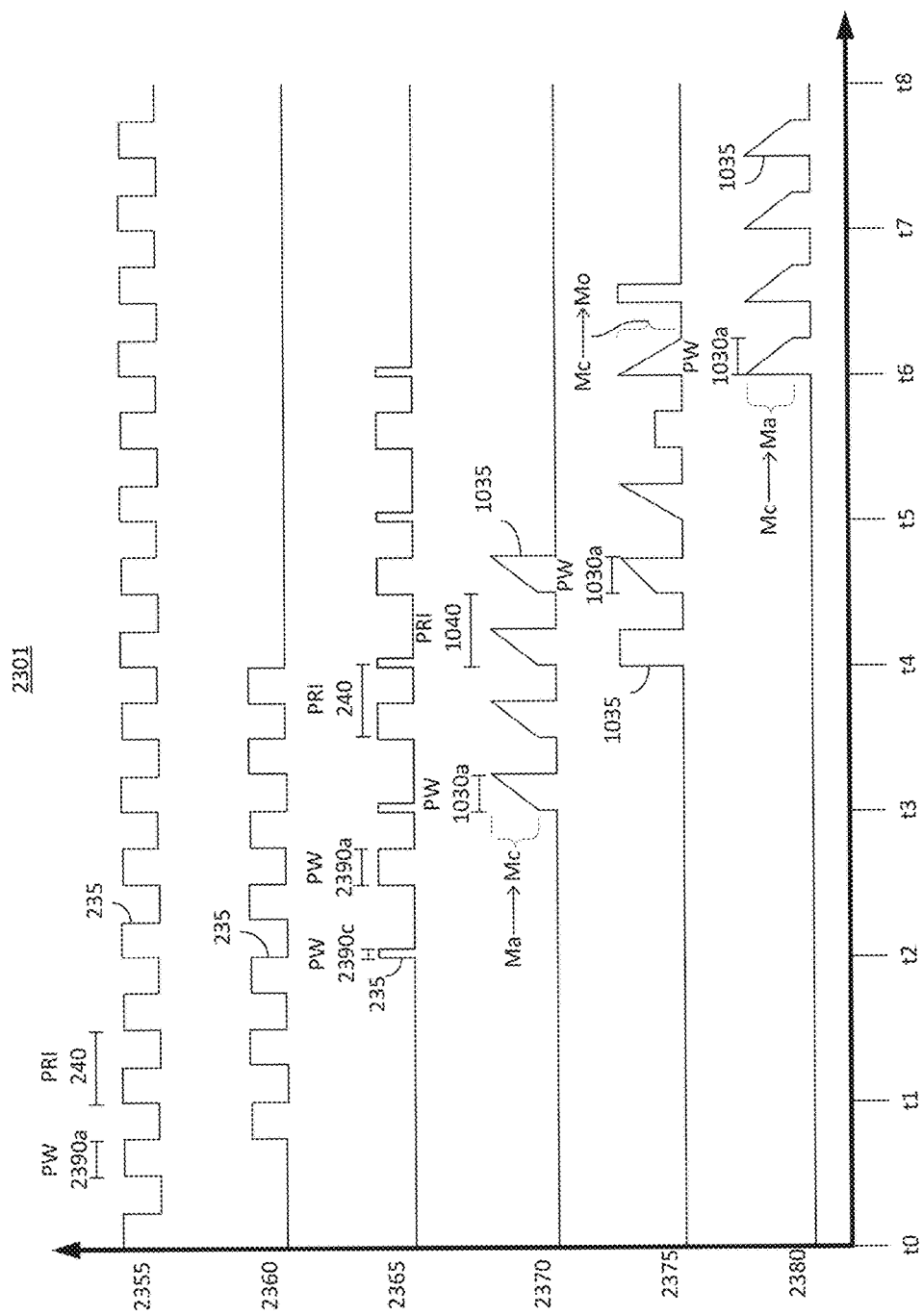
FIG. 23B is a diagram depicting waveforms used for neural stimulation via multiple stimulation modalities in accordance with an embodiment.

FIG. 23B is a diagram depicting waveforms used for neural stimulation via visual stimulation and auditory stimulation in accordance with an embodiment. FIG. 23B illustrates example sequences that the stimuli orchestration component 2310 can generate or cause to be generated by one or more signaling components 2330a-n. The stimuli orchestration component 2310 can retrieve the sequences from a data structure stored in data repository 2315 of NSOS 2305, or a data repository corresponding to an NSS 2345a-n. The sequences can be stored in a table format, such as Table 1 below. In some embodiments, the NSOS 2305 can select predetermined sequences to generate a set of sequences for a treatment session or time period. In some embodiments, the NSOS 2305 can obtain a predetermined or preconfigured set of sequences. In some embodiments, the NSOS 2305 can construct or generate the set of sequences or each sequences based on information obtained from the subject assessment module 2350. In some embodiments, the NSOS 2305 can remove or delete sequences from the set of sequences based on feedback, such as adverse side effects. The NSOS 2305, via subject assessment module 2350, can include sequences that are more likely to stimulate neurons in a predetermined region of the brain to oscillate at a desired frequency.

TABLE 1

Multi-Modal Stimulation Sequences

| Sequence Identifier | Mode | Signal Type | Signal Parameter | Stimulation Frequency | Timing Schedule |
|---|---|---|---|---|---|
| 2355 | Visual | light pulses from a laser light source | color: red; intensity: low; PW: 2390a | 40 Hz | {t0:t8} |
| 2360 | Peripheral nerve | electrical current | location: behind knee; intensity: high; PW: 2390a | 40 Hz | {t1:t4} |
| 2365 | Visual | light pulses from a laser light source | color: red; intensity: low; PW: 2390a | 40 Hz | {t2:t6} |
| 2370 | Audio | acoustic or audio bursts provided by headphones or speakers | PW: 2390a; frequency variation from $M_c$ to $M_o$; | 40 Hz | {t3:t5} |
| 2375 | Audio | acoustic or audio bursts provided by headphones or speakers | PW: 2390a; frequency variation from $M_c$ to $M_o$; | 39.8 Hz | {t4:t7} |
| 2380 | Audio | acoustic or audio bursts provided by headphones or speakers | PW: 2390a; frequency variation from $M_c$ to $M_o$; | 40 Hz | {t6:t8} |

As illustrated in Table 1, each waveform sequence can include one or more characteristics, such as a sequence identifier, a mode, a signal type, one or more signal parameters, a modulation or stimulation frequency, and a timing schedule. As illustrated in FIG. 23B and Table 1, the sequence identifiers are 2355, 2360, 2365, 2365, 2370, 2375, and 2360.

As illustrated in Table 1, each waveform sequence can include one or more characteristics, such as a sequence identifier, a mode, a signal type, one or more signal parameters, a modulation or stimulation frequency, and a timing schedule. As illustrated in FIG. 23B and Table 1, the sequence identifiers are 2355, 2360, 2365, 2365, 2370, 2375, and 2360.

The stimuli orchestration component 2310 can receive the characteristics of each sequence. The stimuli orchestration component 2310 can transmit, configure, load, instruct or otherwise provide the sequence characteristics to a signaling component 2330a-n. In some embodiments, the stimuli orchestration component 2310 can provide the sequence characteristics to an NSS 2345a-n, while in some cases the stimuli orchestration component 2310 can directly provide the sequence characteristics to a signaling component 2330a. In some embodiments, the stimuli orchestration component 2310 can provide the sequence characteristics to the visual NSS 105, the auditory NSS 905, or other NSS designed, constructed and configured for peripheral nerve stimulation, while in some cases the stimuli orchestration component 2310 can directly provide the sequence characteristics to a signaling component, such as the visual signaling component 150, audio signaling component 950, or other signaling component such as a peripheral nerve stimulation signaling component.

The NSOS 2305 can retrieve the data structure storing Table 1 and parse the data structure to determine a mode of stimulation for each sequence. The NSOS 2305 can determine, from the Table 1 data structure, that the mode of stimulation of sequence 2355 is visual stimulation; sequence 2360 is peripheral nerve stimulation; sequence 2365 is visual stimulation; sequence 2370 stimulation is audio stimulation; sequence 2375 stimulation is audio stimulation and 2380 is also audio stimulation. The NSOS 2305, responsive to determining the mode of stimulation, can provide the information or characteristics associated with sequences 2355, 2360 and 2365 to the corresponding NSS configured for providing the mode of stimulation. Each NSS (e.g., NSS 105 via the light generation module 110) can parse the sequence characteristics and then instruct a signaling component (e.g., visual signaling component 150) to generate and transmit the corresponding signals. In some embodiments, the NSOS 2305 can directly instruct the signaling components to generate and transmit signals corresponding to sequences 2355, 2360 and 2365, 2370, 2375, and 2380. Thus, the NSOS 2305 can be configured to interface with various types of NSS's or various types of signaling components to provide neural stimulation via multiple modalities of stimulation.

For example, the first sequence 2355 can include a visual signal. The signal type can include light pulses 2385 generated by a light source 305 that includes a laser. The light pulses can include light waves having a wavelength corresponding to the color red in the visible spectrum. The intensity of the light can be set to low. An intensity level of low can correspond to a low contrast ratio (e.g., relative to the level of ambient light) or a low absolute intensity. The pulse width for the light burst can correspond to pulse width 2390a (e.g., PW 230a depicted in FIG. 2C). The stimulation frequency can be 40 Hz, or correspond to a pulse rate interval ("PRI") of 0.025 seconds. The first sequence 2355 can run from $t_0$ to $t_8$. The first sequence 2355 can run for the duration of the session or treatment. The first sequence 2355 can run while one or more other sequences are other running. The time intervals can refer to absolute times, time periods, number of cycles, or other event. The time interval from $t_0$ to $t_8$ can be, for example, 1 minute, 2 minutes, 3 minutes, 4 minutes, 5 minutes, 7 minutes, 10 minutes, 12 minutes, 15 minutes, 20 minutes or more or less. The time interval can be cut short or terminated by the subject or responsive to feedback information. The time intervals can be adjusted based on profile information or by the subject via an input device.

The second sequence 2360 can include peripheral nerve stimulation that begins at $t_1$ and ends at $t_4$. The second sequence 2360 can include a signal type that includes an electrical current. The signal type, parameters, frequency and other characteristics can correspond to any characteristic depicted in with respect to FIGS. 17A-17D. The signal parameters can include a location of the peripheral nerve, such as behind the knee. The intensity can be set to high. The pulse width can be set to 2390a. The intensity can be high, which can correspond to a high current relative to a baseline current or nominal current. The pulse width for the electrical current can be the same as the pulse width 2390a as in sequence 2355. Sequence 2360 can begin and end at a different time than sequence 2355. For example, sequence 2360 can begin at $t_1$, which can be offset from $t_0$ by 5 seconds, 10 seconds, 15 seconds, 20 seconds, 20 seconds, 30 seconds, 1 minute, 2 minutes, 3 minutes, or more or less. The peripheral nerve signaling component of Appendix A can initiate the second sequence 2360 at $t_1$, and terminate the second sequence at $t_4$. Thus, the second sequence 2360 can overlap with the first sequence 2355.

While pulse trains or sequences 2355 and 2360 can overlap with one another, the pulses 2385 of the second sequence 2360 may not overlap with the pulses 2385 of the first sequence 2355. For example, the pulses 2385 of the second sequence 2360 can be offset from the pulses 2385 of the first sequence 2355 such that they are non-overlapping.

The third sequence 2365c can be similar to the stimulation provided in the first sequence 2365a.

The fourth sequence 2370 and the fifth sequence 2375 can include an audio stimulation mode. The fifth sequence 2375 can include acoustic or audio bursts. The acoustic bursts can be provided by the headphones or speakers 1205 of FIG. 12B. The sequence 2375 can include pulses 2385. The pulses 2385 can vary from one pulse to another pulse in the sequence. The fifth waveform 2375 can be configured to re-focus the subject to increase the subject's attention level to the neural stimulation. The fifth sequence 2375 can increase the subject's attention level by varying parameters of the signal from one pulse to the other pulse. The fifth sequence 2375 can vary the frequency from one pulse to the other pulse. For example, the first pulse 2385 in sequence 2375 can have a higher frequency than the previous sequences. The second pulse can be an upchirp pulse having a frequency that increases from a low frequency to a high frequency. The third pulse can be a sharper upchirp pulse that has frequency that increases from an even lower frequency to the same high frequency. The fifth pulse can have a low stable frequency. The sixth pulse can be a downchirp pulse going from a high frequency to the lowest frequency. The seventh pulse can be a high frequency pulse with a small pulsewidth. The fifth sequence 2375 can begin at $t_4$ and end at $t_7$. The fifth sequence can overlap with sequence 2355; and partially overlap with sequence 2365 and 2370. The fifth sequence may not overlap with sequence 2360. The stimulation frequency can be 39.8 Hz. The sixth sequence 2380 can also include an audio stimulation mode.

The NSOS 2305 can adjust, change, or otherwise modify sequences or pulses based on feedback. In some embodiments, the NSOS 2305 can determine, based on the profile information, policy, and available components, to provide neural stimulation using one or more of the modes depicted in Table 1. The NSOS 2305 can determine to synchronize the transmit times of the pulse trains 2355-2380, or offset the pulse trains 2355-2380.

In some embodiments, the NSOS 2305 can transmit the first sequence 2355 and the second sequence 2460 for a first duration (e.g., 1 minute, 2 minutes, or 3 minutes). At the end of the first duration, the NSOS 2305 can ping feedback sensor such as an EEG probe to determine a frequency of neural oscillation in a region of the brain. If the frequency of oscillation is not at the desired frequency of oscillation, the NSOS 2305 can select an additional sequence out of order or change the timing schedule of a sequence.

For example, the NSOS 2305 can ping a feedback sensor at $t_1$. The NSOS 2305 can determine, at $t_1$, that neurons of the primary visual cortex are oscillating at the desired frequency. Thus, the NSOS 2305 can determine to forego transmitting sequences 2360 and 2365 because there is satisfactory neural oscillation. The NSOS 2305 can determine to disable sequences 2360 and 2365. The NSOS 2305, responsive to the feedback information, can disable the sequences 2360 and 2365. The NSOS 2305, responsive to the feedback information, can modify a flag in the data structure corresponding to Table 1 to indicate that the sequences 2360 and 2365 are disabled.

In some embodiments, the NSOS 2305 can determine, at $t_1$, that while the neurons of the primary visual cortex are oscillating at the desired frequency, the neurons of the sensory cortex are not oscillating at the desired frequency. Responsive to this determination, the NSOS 2305 can enable sequence 2370 for peripheral nerve stimulation and sequence 2480 for audio stimulation. The NSOS 2305 can determine to disable sequences 2360, 2365 and 2375, but enable 2370 and 2380. The NSOS 2305, responsive to the feedback information, can modify a flag in the data structure corresponding to Table 1 to indicate that the sequences 2360, 2365 and 2375 are disabled, and sequences 2370 and 2380 are enabled.

In another example, the NSOS 2305 can receive feedback information at $t_2$. At $t_2$, the NSOS 2305 can determine that the frequency of neural oscillation in the hypothalamus is different from frequency of neural oscillation in the auditory cortex. Responsive to determining the difference, the NSOS 2305 can adjust the stimulation frequency of the electrical signal provided by the peripheral nerve stimulation in sequence 2370 in order to synchronize the frequency of neural oscillation of the hypothalamus with that of the auditory cortex or primary visual cortex or sensory cortex.

Similarly, the NSOS 2305 can enable, disable, or adjust one or more sequences 2355-2380 based on feedback such that the resulting frequency of neural oscillations of one or more portions of the brain satisfy a predetermined value, threshold, or range. In some cases, the NSOS 2305 can determine to disable all modes of stimulation subsequent to sequence 2355 if the visual sequence 2355 is successfully affecting the frequency of neural oscillations in the brain at each time period $t_1$, $t_2$, $t_3$, $t_4$, $t_5$, $t_6$, $t_7$, and $t_8$. In some cases, the NSOS 2305 can determine to disable all modes of stimulation subsequent to sequence 2355 if the visual sequence 2355 causes an adverse side effect, such as a migraine or fatigue.

In some embodiments, the NSOS 2305 can adjust or change the mode of stimulation or a type of signal based on feedback received from a feedback component 2340a-n. The stimuli orchestration component 2310 can adjust the mode of stimulation or type of signal based on feedback on the subject, feedback on the environment, or a combination of feedback on the subject and the environment. Feedback on the subject can include, for example, physiological information, temperature, attention level, level of fatigue, activity (e.g., sitting, laying down, walking, biking, or driving), vision ability, hearing ability, side effects (e.g., pain, migraine, ringing in ear, or blindness), or frequency of neural oscillation at a region or portion of the brain (e.g., EEG probes). Feedback information on the environment can include, for example, ambient temperature, ambient light, ambient sound, battery information, or power source.

The stimuli orchestration component 2310 can determine to maintain or change an aspect of the stimulation treatment based on the feedback. For example, the stimuli orchestration component 2310 can determine that the neurons are not oscillating at the desired frequency in response to the first mode of stimulation. Responsive to determining that the neurons are not oscillating at the desired frequency, the stimuli orchestration component 2310 can disable the first mode of stimulation and enable a second mode of stimulation. The stimuli orchestration component 2310 can again determine (e.g., via feedback component 2340a) that the neurons are not oscillating at the desired frequency in response to the second mode of stimulation. Responsive to determining that the neurons are still not oscillating at the desired frequency, the stimuli orchestration component 2310 can increase an amplitude of the signal corresponding to the second mode of stimulation. The stimuli orchestration component 2310 can determine that the neurons are oscillating at the desired frequency in response to increasing the amplitude of a signal corresponding to the second mode of stimulation.

The stimuli orchestration component 2310 can monitor the frequency of neural oscillations at a region or portion of the brain. The stimuli orchestration component 2310 can determine that neurons in a first region of the brain are oscillating at the desired frequency, whereas neurons in a second region of the brain are not oscillating at the desired frequency. The stimuli orchestration component 2310 can perform a lookup in the profile data structure 2320 to determine a mode of stimulation or type of signal that maps to the second region of the brain. The stimuli orchestration component 2310 can compare the results of the lookup with the currently enabled mode of stimulation to determine that a third mode of stimulation is more likely to cause the neurons in the second region of the brain to oscillate at the desired frequency. Responsive to the determination, the stimuli orchestration component 2310 can identify a signaling component 2330a-n configured to generate and transmit signals corresponding to the selected third mode of stimulation, and instruct or cause the identified signaling component 2330a-n to transmit the signals.

In some embodiments, the stimuli orchestration component 2310 can determine, based on feedback information, that a mode of stimulation is likely to affect the frequency of neural oscillation, or unlikely to affect the frequency of neural oscillation. The stimuli orchestration component 2310 can select a mode of stimulation from a plurality of modes of stimulation that is most likely to affect the frequency of neural stimulation or result in a desired frequency of neural oscillation. If the stimuli orchestration component 2310 determines, based on the feedback information, that a mode of stimulation is unlikely to affect the frequency of neural oscillation, the stimuli orchestration component 2310 can disable the mode of stimulation for a predetermined duration or until the feedback information indicates that the mode of stimulation would be effective.

The stimuli orchestration component 2310 can select one or more modes of stimulation to conserve resources or minimize resource utilization. For example, the stimuli orchestration component 2310 can select one or more modes of stimulation to reduce or minimize power consumption if the power source is a battery or if the battery level is low. In another example, the stimuli orchestration component 2310 can select one or more modes of stimulation to reduce heat generation if the ambient temperature is above a threshold or the temperature of the subject is above a threshold. In another example, the stimuli orchestration component 2310 can select one or more modes of stimulation to increase the level of attention if the stimuli orchestration component 2310 determines that the subject is not focusing on the stimulation (e.g., based on eye tracking or an undesired frequency of neural oscillations).

P. Neural Stimulation Via Visual Stimulation and Auditory Stimulation

Figure 24A:
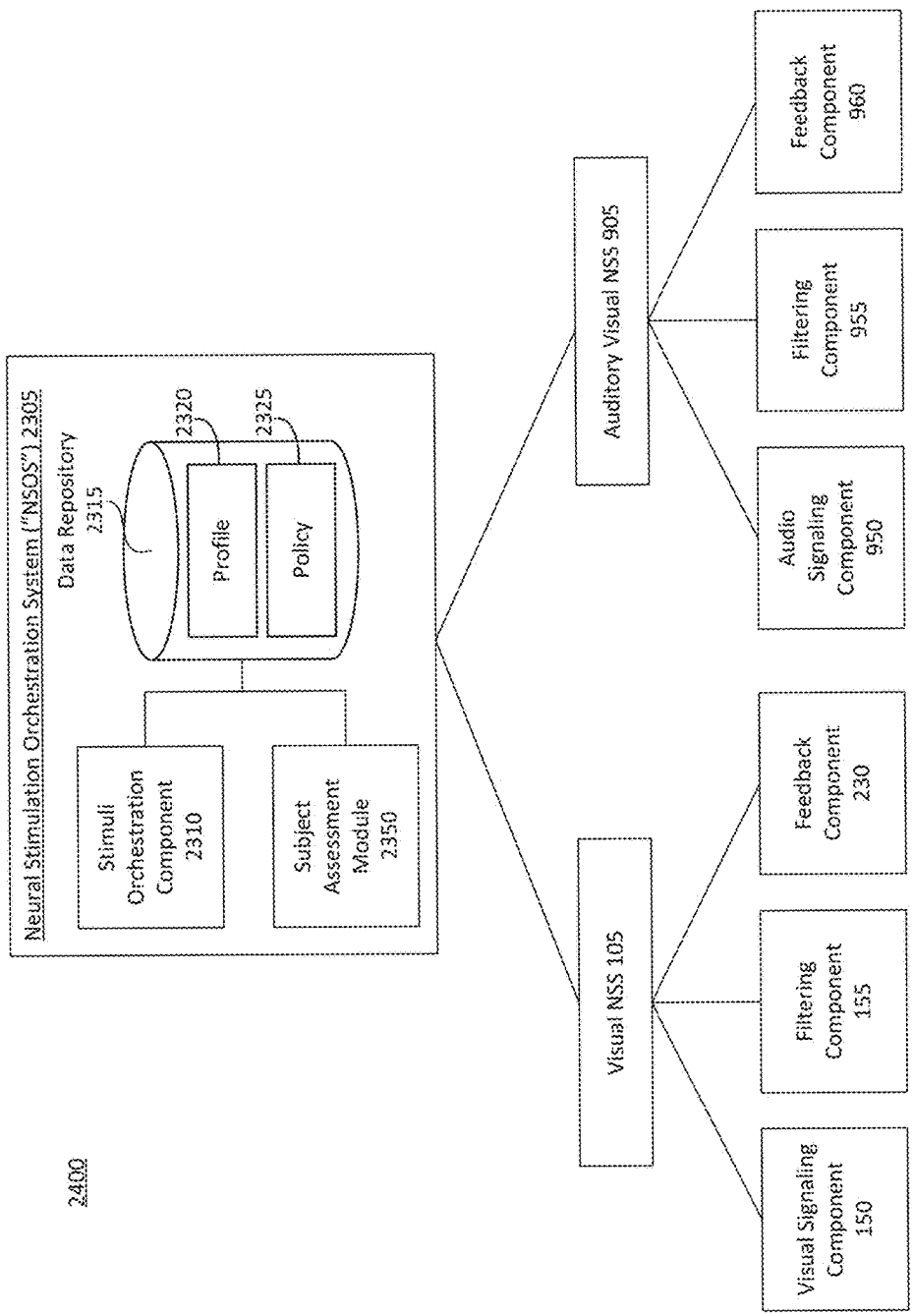
FIG. 24A is a block diagram depicting a system for neural stimulation via visual stimulation and auditory stimulation in accordance with an embodiment.

FIG. 24A is a block diagram depicting an embodiment of a system for neural stimulation via visual stimulation and auditory stimulation. The system 2400 can include the NSOS 2305. The NSOS 2305 can interface with the visual NSS 105 and the auditory NSS 905. The visual NSS 105 can interface or communicate with the visual signaling component 150, filtering component 155, and feedback component 230. The auditory NSS 905 can interface or communicate with the audio signaling component 950, filtering component 955, and feedback component 960.

To provide neural stimulation via visual stimulation and auditory stimulation, the NSOS 2305 can identify the types of available components for the neural stimulation session. The NSOS 2305 can identify the types of visual signals the visual signaling component 150 is configured to generate. The NSOS 2305 can also identify the type of audio signals the audio signaling component 950 is configured to generate. The NSOS 2305 can be configured about the types of visual signals and audio signals the components 150 and 950 are configured to generate. The NSOS 2305 can ping the components 150 and 950 for information about the components 150 and 950. The NSOS 2305 can query the components, send an SNMP request, broadcast a query, or otherwise determine information about the available visual signaling component 150 and audio signaling component 950.

For example, the NSOS 2305 can determine that the following components are available for neural stimulation: the visual signaling component 150 includes the virtual reality headset 401 depicted in FIG. 4C; the audio signaling component 950 includes the speaker 1205 depicted in FIG. 12B; the feedback component 230 includes an ambient light sensor 605, an eye tracker 605 and an EEG probe depicted in FIG. 4C; the feedback component 960 includes a microphone 1210 and feedback sensor 1225 depicted in FIG. 12B; and the filtering component 955 includes a noise cancellation component 1215. The NSOS 2305 can further determine an absence of filtering component 155 communicatively coupled to the visual NSS 105. The NSOS 2305 can determine the presence (available or online) or absence (offline) of components via visual NSS 105 or auditory NSS 905. The NSOS 2305 can further obtain identifiers for each of the available or online components.

The NSOS 2305 can perform a lookup in the profile data structure 2320 using an identifier of the subject to identify one more types of visual signals and audio signals to provide to the subject. The NSOS 2305 can perform a lookup in the profile data structure 2320 using identifiers for the subject and each of the online components to identify one more types of visual signals and audio signals to provide to the subject. The NSOS 2305 can perform a lookup up in the policy data structure 2325 using an identifier of the subject to obtain a policy for the subject. The NSOS 2305 can perform a lookup in the policy data structure 2325 using identifiers for the subject and each of the online components to identify a policy for the types of visual signals and audio signals to provide to the subject.

Figure 24B:
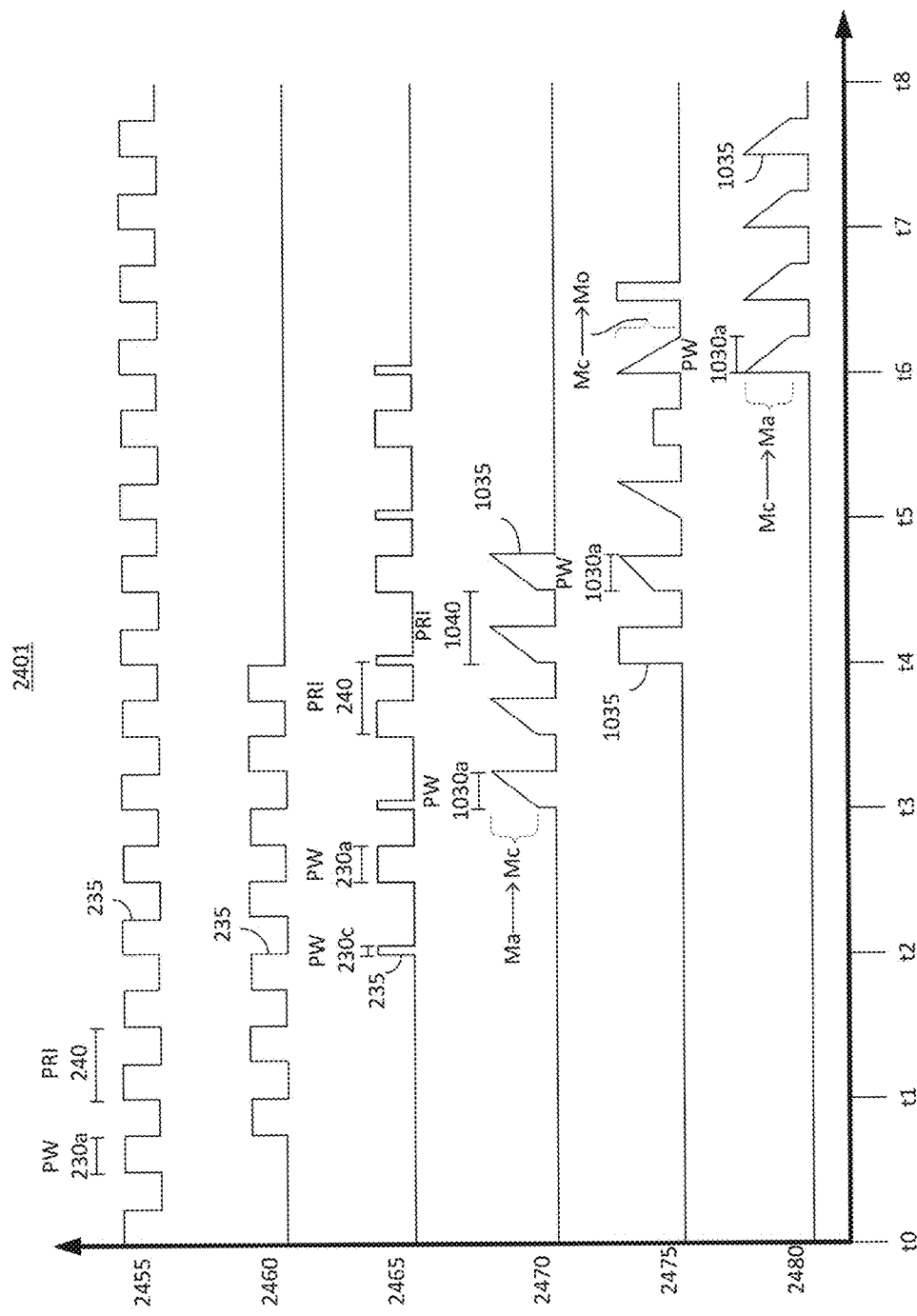
FIG. 24B is a diagram depicting waveforms used for neural stimulation via visual stimulation and auditory stimulation in accordance with an embodiment.

FIG. 24B is a diagram depicting waveforms used for neural stimulation via visual stimulation and auditory stimulation in accordance with an embodiment. FIG. 24B illustrates example sequences or a set of sequences 2401 that the stimuli orchestration component 2310 can generate or cause to be generated by one or more visual signaling components 150 or audio signal components 950. The stimuli orchestration component 2310 can retrieve the sequences from a data structure stored in data repository 2315 of NSOS 2305, or a data repository corresponding to NSS 105 or NSS 905. The sequences can be stored in a table format, such as Table 1 below. In some embodiments, the NSOS 2305 can select predetermined sequences to generate a set of sequences for a treatment session or time period, such as the set of sequences in Table 1. In some embodiments, the NSOS 2305 can obtain a predetermined or preconfigured set of sequences. In some embodiments, the NSOS 2305 can construct or generate the set of sequences or each sequences based on information obtained from the subject assessment module 2350. In some embodiments, the NSOS 2305 can remove or delete sequences from the set of sequences based on feedback, such as adverse side effects. The NSOS 2305, via subject assessment module 2350, can include sequences that are more likely to stimulate neurons in a predetermined region of the brain to oscillate at a desired frequency.

The NSOS 2305 can determine, based on the profile information, policy, and available components, to use the following sequences illustrated in example Table 1 provide neural stimulation using both visual signals and auditory signals.

TABLE 2

Audio and Video Stimulation Sequences

| Sequence Identifier | Mode | Signal Type | Signal Parameter | Stimulation Frequency | Timing Schedule |
|---|---|---|---|---|---|
| 1755 | visual | light pulses from a laser light source | Color: red; Intensity: low; PW: 230a | 40 Hz | {t0:t8} |
| 1760 | visual | checkerboard pattern image from a tablet display screen light source | color: black/white; intensity: high; PW: 230a | 40 Hz | {t1:t4} |
| 1765 | visual | modulated ambient light by a frame with actuated shutters | PW: 230c/230a; | 40 Hz | {t2:t6} |
| 1770 | audio | music from headphones or speakers connected to an audio player | amplitude variation from $M_a$ to $M_c$; PW: 1030a | 40 Hz | {t3:t5} |
| 1775 | audio | acoustic or audio bursts provided by headphones or speakers | PW: 1030a; frequency variation from $M_c$ to $M_a$; | 39.8 Hz | {t4:t7} |
| 1780 | audio | air pressure generated by a cochlear air jet | PW: 1030a; pressure varies from $M_c$ to $M_a$ | 40 Hz | {t6:t8} |

As illustrated in Table 2, each waveform sequence can include one or more characteristics, such as a sequence identifier, a mode, a signal type, one or more signal parameters, a modulation or stimulation frequency, and a timing schedule. As illustrated in FIG. 24B and Table 2, the sequence identifiers are 2455, 2460, 2465, 2465, 2470, 2475, and 2460.

The stimuli orchestration component 2310 can receive the characteristics of each sequence. The stimuli orchestration component 2310 can transmit, configure, load, instruct or otherwise provide the sequence characteristics to a signaling component 2330a-n. In some embodiments, the stimuli orchestration component 2310 can provide the sequence characteristics to the visual NSS 105 or the auditory NSS 905, while in some cases the stimuli orchestration component 2310 can directly provide the sequence characteristics to the visual signaling component 150 or audio signaling component 950.

The NSOS 2305 can determine, from the Table 1 data structure, that the mode of stimulation for sequences 2455, 2460 and 2465 is visual by parsing the table and identifying the mode. The NSOS 2305, responsive to determine the mode is visual, can provide the information or characteristics associated with sequences 2455, 2460 and 2465 to the visual NSS 105. The NSS 105 (e.g., via the light generation module 110) can parse the sequence characteristics and then instruct the visual signaling component 150 to generate and transmit the corresponding visual signals. In some embodiments, the NSOS 2305 can directly instruct the visual signaling component 150 to generate and transmit visual signals corresponding to sequences 2455, 2460 and 2465.

The NSOS 2305 can determine, from the Table 1 data structure, that the mode of stimulation for sequences 2470, 2475 and 2480 is audio by parsing the table and identifying the mode. The NSOS 2305, responsive to determine the mode is audio, can provide the information or characteristics associated with sequences 2470, 2475 and 2480 to the auditory NSS 905. The NSS 905 (e.g., via the light generation module 110) can parse the sequence characteristics and then instruct the audio signaling component 950 to generate and transmit the corresponding audio signals. In some embodiments, the NSOS 2305 can directly instruct the visual signaling component 150 to generate and transmit visual signals corresponding to sequences 2470, 2475 and 2480.

For example, the first sequence 2455 can include a visual signal. The signal type can include light pulses 235 generated by a light source 305 that includes a laser. The light pulses can include light waves having a wavelength corresponding to the color red in the visible spectrum. The intensity of the light can be set to low. An intensity level of low can correspond to a low contrast ratio (e.g., relative to the level of ambient light) or a low absolute intensity. The pulse width for the light burst can correspond to pulsewidth 230a depicted in FIG. 2C. The stimulation frequency can be 40 Hz, or correspond to a pulse rate interval ("PRI") of 0.025 seconds. The first sequence 2355 can run from $t_0$ to $t_8$. The first sequence 2355 can run for the duration of the session or treatment. The first sequence 2355 can run while one or more other sequences are other running. The time intervals can refer to absolute times, time periods, number of cycles, or other event. The time interval from $t_0$ to $t_8$ can be, for example, 1 minute, 2 minutes, 3 minutes, 4 minutes, 5 minutes, 7 minutes, 10 minutes, 12 minutes, 15 minutes, 20 minutes or more or less. The time interval can be cut short or terminated by the subject or responsive to feedback information. The time intervals can be adjusted based on profile information or by the subject via an input device.

The second sequence 2460 can be another visual signal that begins at $t_1$ and ends at $t_4$. The second sequence 2460 can include a signal type of a checkerboard image pattern that is provided by a display screen of a tablet. The signal parameters can include the colors black and white such that the checkerboard alternates black and white squares. The intensity can be high, which can correspond to a high contrast ratio relative to ambient light; or there can be a high contrast between the objects in the checkerboard pattern. The pulse width for the checkerboard pattern can be the same as the pulse width 230a as in sequence 2455. Sequence 2460 can begin and end at a different time than sequence 2455. For example, sequence 2460 can begin at $t_1$, which can be offset from to by 5 seconds, 10 seconds, 15 seconds, 20 seconds, 20 seconds, 30 seconds, 1 minute, 2 minutes, 3 minutes, or more or less. The visual signaling component 150 can initiate the second sequence 2460 at $t_1$, and terminate the second sequence at $t_4$. Thus, the second sequence 2460 can overlap with the first sequence 2455.

While pulse trains or sequences 2455 and 2460 can overlap with one another, the pulses 235 of the second sequence 2460 may not overlap with the pulses 235 of the first sequence 2455. For example, the pulses 235 of the second sequence 2460 can be offset from the pulses 235 of the first sequence 2455 such that they are non-overlapping.

The third sequence 2465 can include a visual signal. The signal type can include ambient light that is modulated by actuated shutters configured on frames (e.g., frames 400 depicted in FIG. 4B). The pulse width can vary from 230c to 230a in the third sequence 2465. The stimulation frequency can still be 40 Hz, such that the PRI is the same as the PRI in sequence 2460 and 2455. The pulses 235 of the third sequence 2465 can at least partially overlap with the pulses 235 of sequence 2455, but may not overlap with the pulses 235 of the sequence 2460. Further, the pulse 235 can refer to block ambient light or allowing ambient light to be perceived by the eyes. In some embodiments, pulse 235 can correspond to blocking ambient light, in which case the laser light pulses 2455 may appear to have a higher contrast ratio. In some cases, the pulses 235 of sequence 2465 can correspond to allowing ambient light to enter the eyes, in which case the contrast ratio for pulses 235 of sequence 2455 may be lower, which may mitigate adverse side effects.

The fourth sequence 2470 can include an auditory stimulation mode. The fourth sequence 2470 can include upchirp pulses 1035. The audio pulses can be provided via headphones or speakers 1205 of FIG. 12B. For example, the pulses 1035 can correspond to modulating music played by an audio player 1220 as depicted in FIG. 12B. The modulation can range from $M_a$ to $M_c$. The modulation can refer to modulating the amplitude of the music. The amplitude can refer to the volume. Thus, the NSOS 2305 can instruct the audio signaling component 950 to increase the volume from a volume level $M_a$ to a volume level $M_c$ during a duration PW 1030a, and then return the volume to a baseline level or muted level in between pulses 1035. The PRI 240 can be 0.025, or correspond to a 40 Hz stimulation frequency. The NSOS 2305 can instruct the fourth sequence 2470 to begin at $t_3$, which overlaps with visual stimulation sequences 2455, 2460 and 2465.

The fifth sequence 2475 can include another audio stimulation mode. The fifth sequence 2475 can include acoustic bursts. The acoustic bursts can be provided by the headphones or speakers 1205 of FIG. 12B. The sequence 2475 can include pulses 1035. The pulses 1035 can vary from one pulse to another pulse in the sequence. The fifth waveform 2475 can be configured to re-focus the subject to increase the subject's attention level to the neural stimulation. The fifth sequence 2475 can increase the subject's attention level by varying parameters of the signal from one pulse to the other pulse. The fifth sequence 2475 can vary the frequency from one pulse to the other pulse. For example, the first pulse 1035 in sequence 2475 can have a higher frequency than the previous sequences. The second pulse can be an upchirp pulse having a frequency that increases from a low frequency to a high frequency. The third pulse can be a sharper upchirp pulse that has frequency that increases from an even lower frequency to the same high frequency. The fifth pulse can have a low stable frequency. The sixth pulse can be a downchirp pulse going from a high frequency to the lowest frequency. The seventh pulse can be a high frequency pulse with a small pulsewidth. The fifth sequence 2475 can being at $t_4$ and end at $t_7$. The fifth sequence can overlap with sequence 2455; and partially overlap with sequence 2465 and 2470. The fifth sequence may not overlap with sequence 2460. The stimulation frequency can be 39.8 Hz.

The sixth sequence 2480 can include an audio stimulation mode. The signal type can include pressure or air provided by an air jet. The sixth sequence can begin at $t_6$ and end at $t_8$. The sixth sequence 2480 can overlap with sequence 2455, and partially overlap with sequences 2465 and 2475. The sixth sequence 2480 can end the neural stimulation session along with the first sequence 2455. The air jet can provide pulses 1035 with pressure ranging from a high pressure $M_c$ to a low pressure $M_a$. The pulse width can be 1030a, and the stimulation frequency can be 40 Hz.

The NSOS 2305 can adjust, change, or otherwise modify sequences or pulses based on feedback. In some embodiments, the NSOS 2305 can determine, based on the profile information, policy, and available components, to provide neural stimulation using both visual signals and auditory signals. The NSOS 2305 can determine to synchronize the transmit time of the first visual pulse train and the first audio pulse train. The NSOS 2305 can transmit the first visual pulse train and the first audio pulse train for a first duration (e.g., 1 minute, 2 minutes, or 3 minutes). At the end of the first duration, the NSOS 2305 can ping an EEG probe to determine a frequency of neural oscillation in a region of the brain. If the frequency of oscillation is not at the desired frequency of oscillation, the NSOS 2305 can select a sequence out of order or change the timing schedule of a sequence.

For example, the NSOS 2305 can ping a feedback sensor at $t_1$. The NSOS 2305 can determine, at $t_1$, that neurons of the primary visual cortex are oscillating at the desired frequency. Thus, the NSOS 2305 can determine to forego transmitting sequences 2460 and 2465 because neurons of the primary visual cortex are already oscillating at the desired frequency. The NSOS 2305 can determine to disable sequences 2460 and 2465. The NSOS 2305, responsive to the feedback information, can disable the sequences 2460 and 2465. The NSOS 2305, responsive to the feedback information, can modify a flag in the data structure corresponding to Table 1 to indicate that the sequences 2460 and 2465 are disabled.

The NSOS 2305 can receive feedback information at $t_2$. At $t_2$, the NSOS 2305 can determine that the frequency of neural oscillation in the primary visual cortex is different from the desired frequency. Responsive to determining the difference, the NSOS 2305 can enable or re-enable sequence 2465 in order to stimulate the neurons in the primary visual cortex such that the neurons may oscillate at the desired frequency.

Similarly, the NSOS 2305 can enable or disable audio stimulation sequences 2470, 2475 and 2480 based on feedback related to the auditory cortex. In some cases, the NSOS 2305 can determine to disable all audio stimulation sequences if the visual sequence 2455 is successfully affecting the frequency of neural oscillations in the brain at each time period $t_1$, $t_2$, $t_3$, $t_4$, $t_5$, $t_6$, $t_7$, and $t_8$. In some cases, the NSOS 2305 can determine that the subject is not paying attention at $t_4$, and go from only enabling visual sequence 2455 directly to enabling audio sequence 2455 to re-focus the user using a different stimulation mode.

Figure 25:
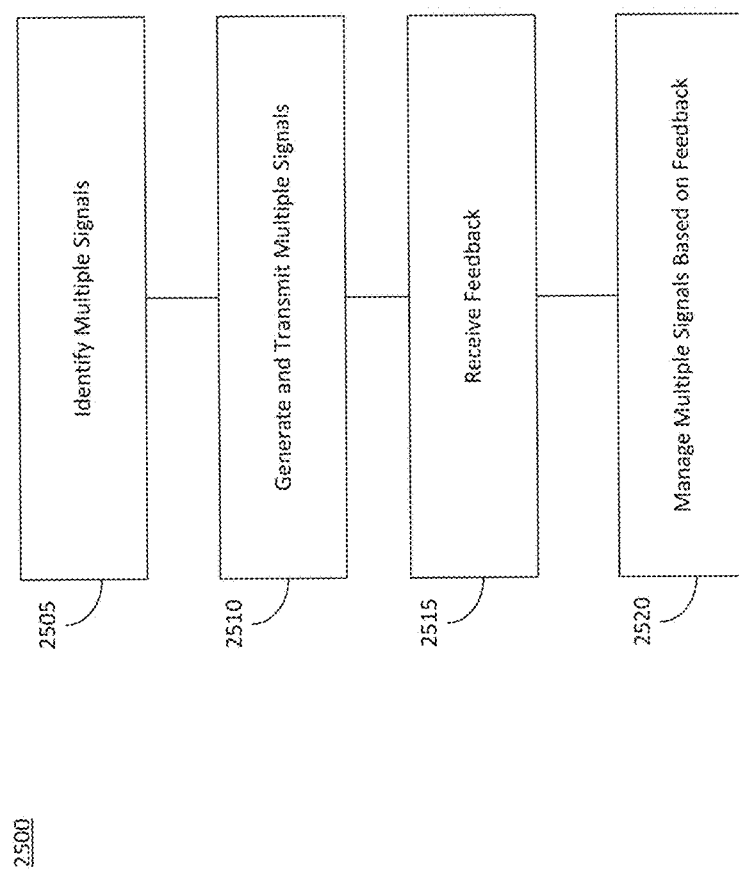
FIG. 25 is a flow diagram of a method for neural stimulation via visual stimulation and auditory stimulation in accordance with an embodiment.

Q. Method for Neural Stimulation Via Visual Stimulation and Auditory Stimulation FIG. 25 is a flow diagram of a method for neural stimulation via visual stimulation and auditory stimulation in accordance with an embodiment. The method 2500 can be performed by one or more system, component, module or element depicted in FIGS. 1-24B, including, for example, a neural stimulation orchestration component or neural stimulations system. In brief overview, the NSOS can identify an multiple modes of signals to provide at block 2505. At block 2510, the NSOS can generate and transmit the identified signals corresponding to the multiple modes. At block 2515 the NSOS can receive or determine feedback associated with neural activity, physiological activity, environmental parameters, or device parameters. At 2520 the NSOS can manage, control, or adjust the one or more signals based on the feedback.

R. Selecting Dosing Parameters of Stimulation Signals to Induce Synchronized Neural Oscillations in the Brain of a Subject Systems and methods of the present disclosure are directed to selecting dosing parameters of stimulation signals to induce synchronized neural oscillations in the brain of a subject. Multi-modal stimuli (e.g., visual, auditory, etc.) can elicit brainwave effects or stimulation. The multi-modal stimuli can adjust, control or otherwise manage the frequency of the neural oscillations to provide beneficial effects to one or more cognitive states or cognitive functions of the brain or the immune system, while mitigating or preventing adverse consequences on a cognitive state or cognitive function.

The frequency of neural oscillations, as well as other factors that may be relevant to the efficacy of treatment, also can be affected by various factors that may be specific to the subject. Subjects having certain physical characteristics (e.g., age, gender, dominant hand, cognitive function, mental illness, etc.) may respond differently to stimulation signals based on these characteristics or their combinations. In addition, other non-inherent factors, such as the stimulus method, the subject's attention level, the time of day at which the therapy is administered, and various factors related to the subject's diet (e.g., blood sugar, caffeine intake, nicotine intake, etc.) also may impact the efficacy of treatment. These and other factors also may impact the quality of therapy indirectly by affecting the subject's adherence to a therapy regimen and by increasing or decreasing unpleasant side effects or otherwise rendering the therapy intolerable for the subject.

In addition to the subject-specific factors described above, other factors also may impact the efficacy of treatment for certain subjects. Parameters related to stimulus signals may increase or decrease the efficacy of therapy for certain subjects. Such parameters may generally be referred to as dosing parameters. For example, subjects may respond to therapies differently based on dosing parameters such as the modality (or the ordered combination of modalities) of deliverance for the stimulation signal, the duration of a stimulus signal, the intensity of the stimulus signal, and the brain region targeted by the stimulus signal. Monitoring conditions associated with the subject in real time, as well as over a longer period of time (e.g., days, weeks, months, or years) can provide information that may be used to adjust a therapy regimen to make the therapy more effective and/or more tolerable for an individual subject. In some instances, the therapy also may be adjusted based in part of the subject-specific factors described above. Described further below are systems and methods for selecting dosing parameters of stimulation signals to induce synchronized neural oscillations in the brain of the subject.

Figure 26:
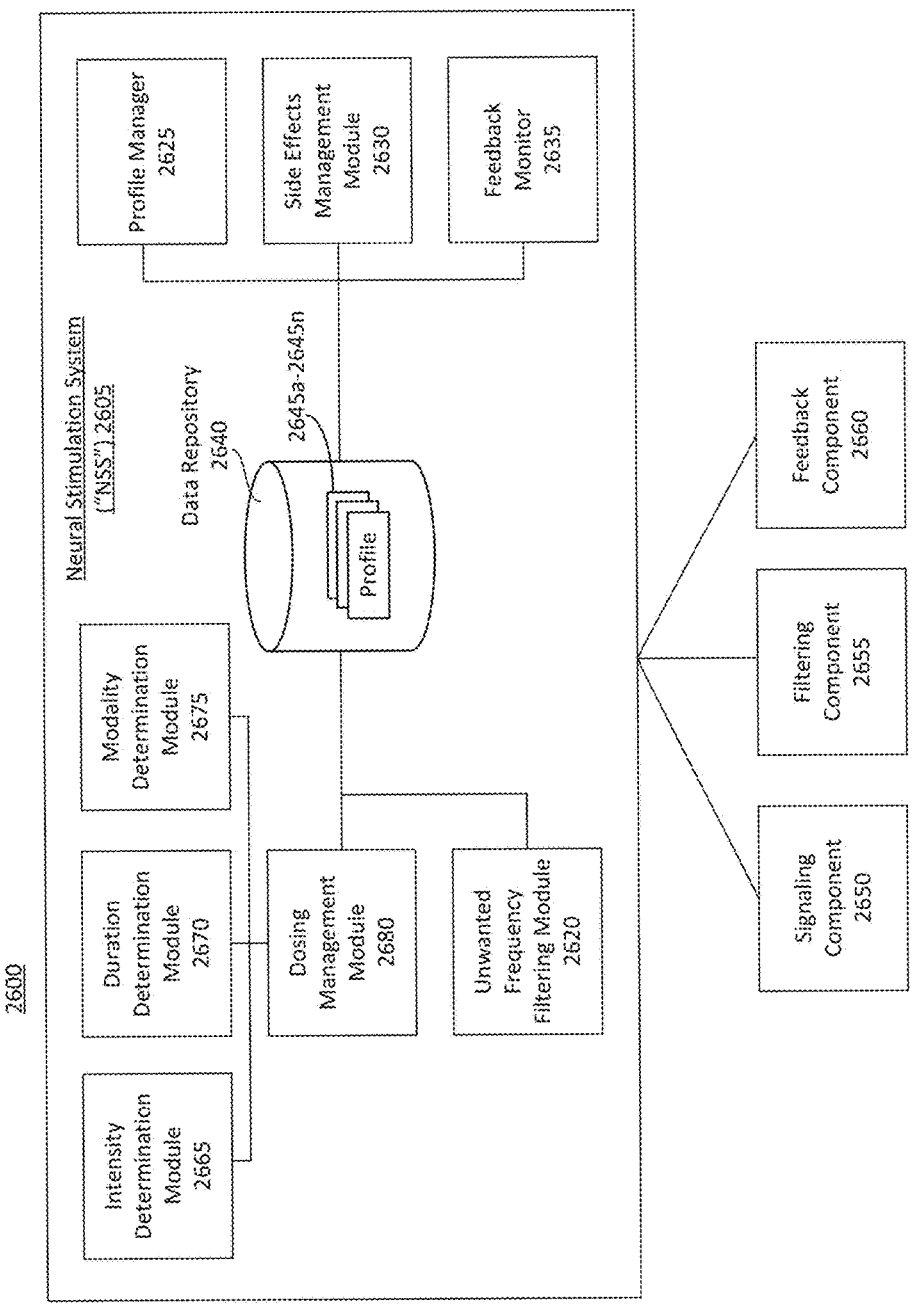
FIG. 26 is a block diagram depicting a system for selecting dosing parameters of stimulation signals to induce synchronized neural oscillations in the brain of a subject in accordance with an embodiment.

S. System for Selecting Dosing Parameters of Stimulation Signals to Induce Synchronized Neural Oscillations in the Brain of the Subject FIG. 26 is a block diagram depicting a system 2600 for selecting dosing parameters of stimulation signals to induce synchronized neural oscillations in the brain of a subject in accordance with an embodiment. The system 2600 includes components that are similar to the components of the system 100 shown in FIG. 1 and the system 900 shown in FIG. 9, and components having like reference numerals in these figures can perform similar functions. For example, the system 2600 includes a neural stimulation system (NSS) 2605 having a profile manager 2625, a side effects management module 2630, a feedback monitor 2635, a data repository 2640 storing subject profiles 2645a-2645n (generally referred to as profiles 2645), and an unwanted frequency filtering module 2620, each of which can be configured to perform functions similar to those performed by the corresponding components having similar names and identified with similar reference numerals in the systems 100 and 900 shown in FIGS. 1 and 9, respectively.

The system 2600 differs from each of the systems 100 and 900 in that the system 2600 can be used to select dosing parameters and to provide neural stimulation signals using a variety of modalities. For example, while the system 100 is intended primarily for delivering visual signals and the system 900 is intended primarily for delivering auditory signals, the system 2600 can be configured to deliver neural stimulation signals that may include any type and form of signal delivered via various mechanisms, such as visual signals and auditory signals. Thus, the system 2600 includes a signaling component 2650, which may be configured to deliver both audio and visual signals for neural stimulation signal, rather than merely a visual signaling component such as the visual signaling component 150 shown in FIG. 1 or merely an audio signaling component such as the audio signaling component 950 shown in FIG. 9. It should be understood that in some implementations, the signaling component 2650 can be implemented using a variety of hardware devices, such as devices capable of outputting light signals and auditory signals. In addition, the system 2600 also includes a filtering component 2655 and a feedback component 2660, which may be similar to the filtering components 155 and 955 and the feedback components 160 and 960 shown in FIGS. 1 and 9, respectively.

The system 2600 also includes an intensity determination module 2665, a duration determination module 2670, a modality determination module 2675, and a dosing management module 2680. Together, these components may perform functionality similar to the functionality of the light generation module 110 and the light adjustment module 115 shown in FIG. 1, as well as the audio generation module 910 and the audio generation module 915 shown in FIG. 9. In addition, the intensity determination module 2665, the duration determination module 2670, the modality determination module 2675, and the dosing management module 2680 also may be configured to select appropriate dosing parameters for a therapy regimen based on a variety of factors. The intensity determination module 2665, the duration determination module 2670, the modality determination module 2675, and the dosing management module 2680 can each include at least one processing unit or other logic device such as programmable logic array engine, or module configured to communicate with the data repository 2640. The intensity determination module 2665, the duration determination module 2670, the modality determination module 2675, and the dosing management module 2680 can be separate components, a single component, or part of the NSS 2605. The system 2600 and its components, such as the NSS 2605, may include hardware elements, such as one or more processors, logic devices, or circuits. The system 2600 and its components, such as the NSS 2605, can include one or more hardware or interface components depicted in system 700 in FIGS. 7A and 7B. For example, a component of system 2600 can include or execute on one or more processors 721, access storage 728 or memory 722, and communicate via network interface 718.

T. Subject Profile for Storing Subject-Specific Data

Figure 27:
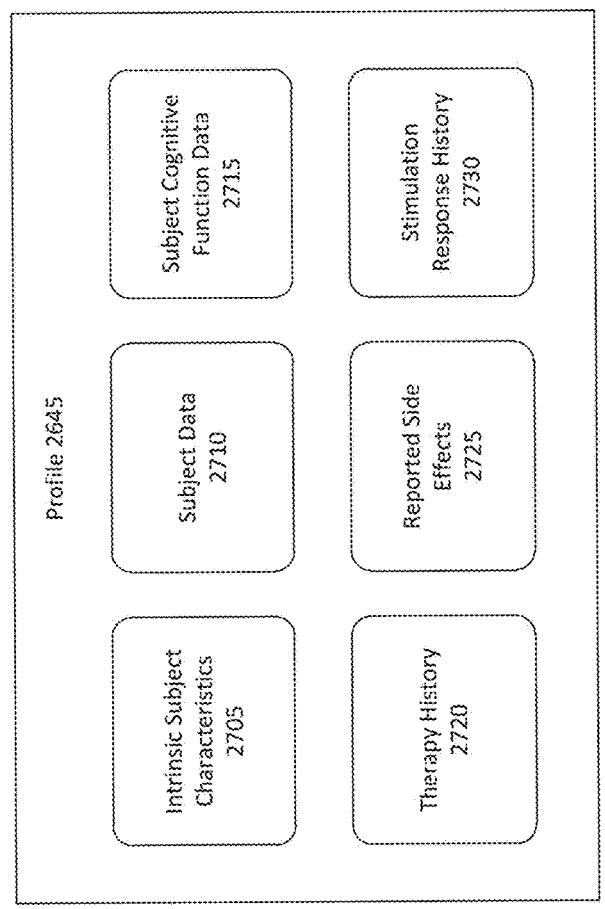
FIG. 27 is a block diagram of a subject profile that can be included in the system shown in FIG. 26 in accordance with an embodiment.

FIG. 27 is a block diagram of a subject profile 2645 that can be included in the system 2600 shown in FIG. 26 in accordance with an embodiment. It should be understood that the data repository 2640 shown in FIG. 26 can be configured to store one or more profiles 2645, and that each profile may store information related to a respective subject. Referring now to FIGS. 26 and 27, each profile 2645 stored in the data repository 2640 can include information relating to intrinsic subject characteristics 2705, subject data 2710, subject cognitive function data 2715, therapy history 2720, reported side effects 2725, and subject response history 2730. Storing such subject-specific data in respective profiles 2645 can allow each subject to receive therapy that makes use of dosing parameters that are personalized and tailored to the subject, based on the content of the subject's profile 2645. In some implementations, such personalization can be beneficial because response to a certain therapy regimen can vary widely from subject to subject. In addition, the same subject may respond differently to a given therapy regimen at different times depending on a variety of factors that may be related to the information stored in the profile 2645. Thus, personalization can result in more effective treatment for each individual subject.

Each of the components of the subject profile 2645 can be stored, for example, in a memory element of a computing system, such as a database that may be used to implement the data repository 2640. The components of the profile 2645 may be stored in any suitable format, including text-based and numerical data, and may be maintained in a variety of data structures, including character strings, arrays, linked-lists, vectors, and the like. In some implementations, the information stored in each profile 2645 may be accessible by the intensity determination module 2665, the duration determination module 2670, the modality determination module 2675, and the dosing management module 2680. For example, any one of the intensity determination module 2665, the duration determination module 2670, the modality determination module 2675, and the dosing management module 2680 may retrieve information corresponding to the intrinsic subject characteristics 2705. Intrinsic subject characteristics 2705 may include any characteristics that are inherent to the subject. Such information can include identification information used to distinguish the subject from other subjects for whom profiles 2645 exist.

The intrinsic subject characteristics 2705 may also include other subject specific information such as the subject's age, gender, ethnicity, dominant hand, documented illnesses (including mental illnesses), access to a caregiver, an assessment of the subject's senses, such as eyesight and hearing, information about the subject's mobility, information about the subject's cognitive state and functions, interests, daily routine, habits, traits, visual and auditory content preferences, among others.

The profile 2645 also can store subject data 2710. Such information may include any information relating to non-inherent characteristics of the subject. In some implementations, the subject data can include information that pertains to the subject's current physical state or condition or mental state or condition. In some implementations, the subject data can include information that pertains to one more physiological states of the subject. For instance, the subject data 2710 may include blood sugar level, caffeine level, or nicotine level, as these factors may impact the efficacy of a treatment session. Although there may be a desire to measure actual levels of physiological markers, the levels may be presumed based on information received from the subject, for instance, time since last meal or beverage, time since last caffeine intake, time since last nicotine intake, among others.

In one example, the dosing management module 2680 may determine that the subject has a low caffeine level, for example based on information reported by the subject, such as the last time the subject consumed coffee. The dosing management module 2680 may therefore further determine that therapy should be delayed until after the subject has consumed additional caffeine, and thus may select a dosing parameter corresponding to the time at which therapy should be administered to be at a future time after the subject has had an opportunity to consume additional caffeine. For some subjects, caffeine may help to increase the subject's attention level during a therapy session, which can improve efficacy of the treatment session when the subject's attention is required for effective treatment (e.g., when the subject must focus his or her eyes on a visual stimulation signal as part of the treatment session). Similarly, the subject's blood sugar and nicotine conditions may impact attentiveness, and the dosing management module 2680 may determine that a therapy session should be delayed based on such information.

In some implementations, the dosing management module 2680 can be configured to use subject cognitive function data to select dosing parameters. The profile 2645 can store this information as subject cognitive function data 2715. Such data may be collected periodically over a long period of time (e.g., once every week or once every month). A cognitive function test may be administered to the subject, and the subject's test results can be stored as the subject cognitive function data 2715. This information may be relevant to a determination of appropriate dosing parameters for the subject, particularly if the subject suffers from a disease that may impair his or her cognitive function over time, such as Alzheimer's disease.

In one example, the intensity determination module 2665 may retrieve the cognitive function data 2715 from the profile 2645, and may determine that the subject's cognitive function has been trending downwards over time. As a result, the intensity determination module 2665 may determine that the intensity of stimulation signals delivered to the subject during therapy sessions should be increased, in order to combat the subject's decreasing cognitive function. Similarly, the duration determination module 2670 may retrieve the cognitive function data 2715 from the profile 2645, and may determine that the duration of stimulation signals delivered to the subject during therapy sessions should be increased, in order to combat the subject's decreasing cognitive function.

In some implementations, the dosing management module 2680 can be configured to use subject therapy history data to select dosing parameters. The profile 2645 can store such information in the subject therapy history 2720. Such data may include any information relating to previous therapy sessions that have been administered to the subject. Therapy history 2720 may include an identification of the time at which previous therapy sessions took place, a location at which the therapy took place, the modalities used during those sessions, and the intensity, duration, frequency, and other characteristics of stimulation signals that were delivered to the subject during those sessions. In addition, the subject therapy history can include information indicating whether the therapy was completed, whether the subject was attentive during the therapy as well as indications of times during which the subject may not have been attentive. Moreover, the subject therapy history can include other subjective information pertaining to the therapy, for instance, the subject can indicate that the therapy was easy or hard, engaging or boring, enjoyable or unpleasant. Moreover, the subject can quantify how the subject performed during the therapy, especially in therapies where the subject's undivided attention is preferred.

The dosing management module 2680 may use such historical data to adjust the dosing parameters of future therapy sessions, for example based on a determination that the dosing parameters for previous sessions appear to be ineffective for the subject. Thus, in some implementations, information from multiple components of the profile 2645 may be combined by the dosing management module 2680 to select dosing parameters. For example, if the subject cognitive function data 2715 indicates that the subject's cognitive function is deteriorating over time, the dosing management module 2680 may then examine the therapy history 2720 and may select dosing parameters for future therapy sessions that differ from those represented in the therapy history 2720, based on a determination that the previous therapies do not appear to be helping to improve the subject's cognitive function.

In some implementations, the dosing management module 2680 can be configured to use side effects reported by the subject or otherwise known to select dosing parameters. The profile 2645 also stores reported side effects 2725. In some implementations, side effects may be self-reported by the subject after one or more therapy sessions have been administered. Side effects can vary from subject to subject, and may be based at least in part on the dosing parameters used in previous therapy sessions. For example, some subjects may be sensitive to certain intensities, which may trigger unpleasant side effects such as migraines. Thus, in an example, the intensity determination module 2665 may determine that the subject should be subjected to visual signals having a relatively low intensity, based on a determination that the subject has suffered from migraines after previous therapy sessions. The modality for treatment also may impact subject side effects. Some subjects may experience headaches as a result of being exposed to auditory signals. Thus, the modality determination module 2675 may determine that the subject should be treated with a different stimulus modality (e.g., visual signals), based on a determination that the reported side effects 2725 indicate the subject has suffered from headaches or nausea after previous therapy sessions involving auditory signals.

The profile 2645 also stores stimulation response history 2730. Stimulation response history 2730 may indicate how well a subject responded to previous therapy sessions (e.g., how well a desired pattern of neural oscillation was induced in the subject as a result of the previous therapy sessions). As described above, this information can be combined with other information included in the profile 2645 in order to select dosing parameters for future therapy sessions. For example, in some implementations the dosing management module 2680 can retrieve both therapy history 2720 and stimulation response history 2730 from the profile 2645. The dosing management module 2680 can then determine a correlation between the information included in the therapy history 2720 and the information included in the stimulation response history 2730. In one example, the dosing management module 2680 can determine that certain previous therapy sessions appear to result in better entrainment, and can therefore determine that future therapy sessions should make use of dosing parameters similar to those that were effective in the past. In contrast, if the dosing management module 2680 instead determines that certain previous therapy sessions do not appear to be effective based on the subject's stimulation response history 2730, the dosing management module 2680 can determine that future therapy sessions should make use of dosing parameters that differ from those that were effective in the past, such as by using different modalities than were used during the previous ineffective therapy sessions.

The dosing management module 2680 can determine such information, for example, by retrieving it from the stimulation response history 2730 of the subject profile 2645. In some implementations, the stimulation response history 2730 can be stored as entries in a database having one or more associated data fields. For example, each individual therapy session may be recorded as one entry in the database, and may include an entrainment data field indicating how well the subject responded to the therapy. In some implementations, such a data field may be formatted as an integer score (e.g., an integer between one and ten), with a higher value indicating better entrainment. Thus, in this example, the dosing management module 2680 can determine whether a particular therapy session resulted in good entrainment by comparing the value stored in the entrainment data field to a minimum threshold value (e.g., a five on a scale of one to ten). The dosing management module 2680 can determine that therapy sessions having an associated entrainment data field with a value of five or greater were effective, and can therefore select dosing parameters for future therapy sessions to be similar to those of the effective therapy sessions having entrainment data field values that meet or exceed the threshold value.

In some implementations, the dosing management module 2680 can use additional information included in the stimulation response history 2730 to select dosing parameters for a future therapy session. For example, after a therapy session has been completed, the subject may be asked to answer questions about the therapy session, and the subject's responses to the questions can be recorded as entries in the stimulation response history 2730. In some implementations, the subject may be asked whether he or she experienced any discomfort during the therapy session and, if so, what level of discomfort was experienced. Similarly, the subject may be asked whether he or she suffered from any side effects as a result of the therapy session, and also may be asked to rank the severity of the side effects.

In some implementations, such information may be recorded in the simulation response history 2730 using data fields formatted in a manner similar to that described above in connection with the entrainment data field. For example, a side effects data field may have an integer value between one and ten, with a higher value indicating more severe side effects suffered after the therapy session. A comfort level data field may have an integer value between one and ten, with a higher value indicating more a greater comfort level for the subject during the therapy session. In some implementations the dosing management module 2680 can be configured to retrieve such entries from the simulation response history 2730 and to compare the values of the entries to threshold values. If the value of the side effects data field exceeds the threshold value, the dosing management module can be configured to select different dosing parameters for future therapy sessions, in an attempt to avoid recreating the therapy that led to side effects for the subject. Similarly, if the value of the comfort level data field exceeds the threshold value, the dosing management module can be configured to select similar dosing parameters for future therapy sessions, as such parameters appear to be tolerable the subject.

U. Generation of a Personalized Therapy Regimen for a Subject

As described above, dosing parameters may include the modality (or the ordered combination of modalities) of deliverance for a stimulation signal, a duration of the stimulation signal, an intensity of the stimulation signal, or a brain region targeted by the stimulation signal, as well as other factors. Generally, selecting appropriate dosing parameters can have a number of therapeutic benefits for a subject. For example, carefully selecting dosing parameters can reduce the likelihood of complications, unwanted side effects, or other discomfort to the subject that may be caused by neural stimulation therapy. Dosing parameters also may be selected in order to increase the efficacy of a therapy regimen.

In some implementations, dosing parameters may be selected in a subject-specific fashion based on information that is unique to the subject. For example, dosing parameters for a subject having a first set of characteristics may be selected to be different from the dosing parameters for a subject having a second set of characteristics, based on the differences between the first and second sets of characteristics. In some implementations, the dosing parameters for a therapy regimen can be selected in a subject-specific fashion by using information included in the profile 2645 as shown in FIG. 27.

A therapy regimen may include multiple individual therapy sessions, each of which can be administered to the subject over a long period of time (e.g., days, weeks, months, or years). In some implementations, the frequency of individual therapy sessions for a subject may be selected based on part on the disease stage or cognitive function level of the subject. For example, a subject having a relatively advanced stage of a disease that impairs cognitive function may have more frequent therapy sessions included in the regimen (e.g., three sessions per week, five sessions per week, or seven sessions per week), while a subject whose cognitive function is stronger may require less frequent sessions (e.g., one session per week or two sessions per week). In some implementations, the dosing parameters may differ across individual sessions over the course of a regimen as well. For example, a first therapy session may include primarily visual stimulation signals, while a subsequent therapy session may include primarily auditory stimulation signals.

The dosing parameters for each therapy session can be selected based on the information included in the subject profile 2645. In some implementations, the dosing parameters may be selected based in part on the results of previous therapy sessions. For example, in some implementations, the subject may be monitored during a therapy session using a variety of sensors, such as ECG sensors, heart rate sensors, or galvanic skin response sensors, and the dosing parameters for the session may be updated in real time based on the outputs of the sensors. Such a therapy session can be referred to as a closed loop therapy session. In some other implementations, the results of a therapy session can be used to update the dosing parameters of a subsequent therapy session. For example, the subject may provide feedback on a therapy session (e.g., feedback related to the subject's comfort level during the therapy session or side effects suffered as a result of the therapy session), and this feedback can be used to adjust the dosing parameters of a future therapy session. This may be referred to as open loop therapy. These concepts are described more fully below.

i. Dosage Parameter Selection

To select dosing parameters for a given subject, the system 2600 can make use of information relating to a variety of factors. For example, personalization factors (e.g., characteristics, habits, traits, and other subject-specific information) may be accounted for in selecting dosing parameters. In some implementations, information regarding the conditions that exist during the therapy session also may impact the dosing parameters selected for the therapy session. For example, if the environment in which the therapy session is to be conducted is relatively loud, auditory signals for the therapy session may be selected to have higher amplitudes, in order to overcome the ambient noise in the environment. In some implementations, other conditions, such as the weather outdoors and the habits or interests of the subject may be used to select dosage parameters. For example, if the weather is pleasant and the subject has indicated that he or she enjoys being outdoors, the therapy session may be administered in an outdoor setting, such as through the use of headphones that deliver auditory stimulation signals to the subject while the subject takes a walk outdoors.

The use of real-time feedback also may inform decisions related to dosing parameters. For example, in an open loop therapy regimen, dosing parameters may be selected prior to a treatment session and may not be adjusted, if at all, until after the session is complete and a subsequent session is desired. In contrast, in a closed loop treatment regimen, subject conditions may be monitored during the course of a treatment session, and the dosing parameters may be adjusted in real time during the session based on the monitored conditions. Selection of dosing parameters based on these and other factors is described more fully below.

These factors may be relevant to the selection of dosing parameters for the subject both individually and in combination.

ii. Selecting Dosage Parameters Based on Eyesight of Subject

For example, in some implementations the modules of the system 2600 can be configured to determine whether a subject has poor eyesight. Such information may be stored, for example, in the intrinsic subject characteristics 2705 of the profile 2645. The modules of the system 2600 can be configured to determine that that a subject having poor eyesight should be treated with a therapy regimen that relies on modalities other than visual stimulation, because the subject may be less likely to respond well to visual stimulation as a result of poor eyesight. Thus, in this example, the modality determination module 2675 can be configured to select an alternative modality (e.g., auditory stimulation) for such a subject. However, it should be recognized that in some cases, it may be desirable to provide visual stimulation to a subject having poor eyesight as the subject may not observe or recognize the visual stimulation but may still reap from the effects of the neural stimulation caused by the visual stimulation.

In another example, the modules of the system 2600 can be configured to determine that the subject is particularly sensitive to light, such as by retrieving such information from the intrinsic subject characteristics 2705 or the stimulation response history 2730 of the subject profile 2645. Based on such a determination, the dosing management module 2680 can select an alternative modality other than visual stimulation for the subject. Such a selection may help to avoid discomfort for the subject.

In a third example, the modules of the system 2600 may retrieve intrinsic subject characteristics 2705 from the profile 2645, and may determine that the subject has difficulty seeing blue light (e.g., light having a wavelength of about 450-495 nm), but does not have trouble seeing yellow light (e.g., light having a wavelength of about 570-590 nm). As a result, the dosing management module 2680 may determine that any visual stimulation signals delivered to the subject should have a frequency in the yellow light range, rather than in the blue light range. In some implementations, the dosing management module 2680 may determine that any visual stimulation signals delivered to the subject should have a frequency in the blue light range as it may not be perceptible to the subject but may still elicit a desired neural response.

iii. Selecting Dosage Parameters Based on Hearing Ability of Subject

In some implementations, the intensity determination module 2665 may be configured to determine that the intensity of an auditory-based therapy (e.g., the amplitude of an audio stimulation signal delivered to the subject) should be increased, based on a determination that the subject has relatively poor hearing. Poor hearing may prevent the subject from responding well to audio stimulation signals that are of low intensity, and therefore the intensity determination module 2665 can determine that a higher intensity auditory signal would be more beneficial for the subject. It should be recognized that in some cases, it may be desirable to provide auditory signals at lower intensities (below what the subject can recognize) to a subject having poor hearing, as the subject may not perceive or recognize the auditory signals but may still reap from the effects of the neural stimulation caused by the auditory stimulation.

In another example, the duration determination module 2670 may determine that the duration of an auditory stimulation signal should be increased to account for the subject's poor hearing. The intensity determination module 2665, the duration determination module 2670, and the modality determination module 2675 can each report information to the dosing management module 2680. The dosing management module 2680 can then determine dosing parameters for the subject based in part on the information received from the intensity determination module 2665, the duration determination module 2670, and the modality determination module 2675.

iv. Selecting Dosing Parameters Based on Combinations of Factors

In some implementations, the dosing management module 2680 can be configured to select dosing parameters based on a combination of the information received from the intensity determination module 2665, the duration determination module 2670, and the modality determination module 2675. For example, the modality determination module 2675 may determine that the subject should be subjected to a therapy that includes visual stimulation, based on a determination that the subject has impaired hearing and therefore would not respond well to auditory signals. For the same subject, the intensity determination module 2665 may determine that the subject also has relatively poor eyesight, and that visual stimulation signals delivered to the subject should have a relatively high intensity. The dosing management module 2680 can then determine that the selected modality should be visual stimulation for this subject, and that the visual stimulation signal should have a high intensity. As discussed in this example and other examples provided herein, there may be instances where the stimulation is selected to take advantage of the subject's compromised sense to effectuate treatment without inconveniencing the subject.

V. Techniques for Generating and Utilizing a Predictive Model to Generate a Therapy Regimen In some implementations, the dosing management module 2680 also may develop a predictive model that can be used to treat subjects in the future, based on information included in the subject profiles 2645. For example, as described above, the dosing management module may determine correlations between certain forms of information included within a profile 2645, such as a correlation between subject cognitive function data 2715 or stimulation response history 2730, and information included in the intrinsic subject characteristics 2705, subject data 2710, therapy history 2720, or reported side effects 2725. In some implementations, the dosing management module 2680 may aggregate such information across multiple profiles 2645 to determine larger correlations and patterns. In one example, the dosing management module 2680 may determine that subjects in a certain age range tend to respond well to particular stimulation modalities. As a result, the dosing management module 2680 may select a similar modality for a new subject who also is in that age range, even if there is limited or no therapy history 2720, subject cognitive function data 2715, or stimulation response history 2730 for the new subject. Similarly, the dosing management module 2680 may determine that subjects who share similar intrinsic characteristics 2705 tend to report similar side effects for a particular stimulation modality, based on the information included in the reported side effects 2725 and the therapy history 2720 across a given set of profiles 2645. As a result, when selecting dosing parameters for a new subject having intrinsic subject characteristics 2705 similar to those in the set of profiles 2645, the dosing management module 2680 may select a modality different from the modality that appears to be causing unpleasant side effects for the group of subjects who share those intrinsic characteristics 2705.

W. Techniques for Promoting Subject Adherence to a Therapy Regimen

In some implementations, the dosing management module 2680 can select dosing parameters in a manner that increases subject adherence to a therapy regimen for a subject. For example, the dosing management module may retrieve therapy history 2720 for the subject. In order to increase the likelihood that the subject will adhere to a therapy regimen in the future, the dosing management module 2680 may select dosing parameters for future therapy sessions that differ from those used in previous sessions, because repeated therapy sessions may become boring or annoying for the subject if the same dosing parameters are used for every session, thereby making the subject less likely to participate in future therapy sessions. This can be particularly useful in implementations in which a therapy session may be self-administered by the subject, for example in the subject's home without the supervision of a caregiver or other medical professional.

In one example, the dosing management module 2680 may determine that visual stimulation is to be provided to the subject. In addition, the dosing management module 2680 may further determine that the visual stimulation is to be delivered to the subject while the subject views images on a video display screen. To increase subject adherence, the dosing management module 2680 can be configured to select images that are likely to keep the subject's interest. For example, in some implementations, the subject may be asked to provide photographs of loved ones, which may be stored in the subject profile 2645. The dosing management module may retrieve such images from the profile 2645 and display them to the subject during the therapy session, in order to help the subject focus on the video screen. Similarly, the subject may be asked to provide a number of topics that the subject finds interesting, and these topics may be stored in the subject profile 2645. The dosing management module may be configured to select images related to the topics provided by the subject in order to hold the subject's interest during the therapy session.

In another example, the dosing management module 2680 may determine that auditory stimulation is to be provided to the subject. To increase subject adherence, the dosing management module 2680 can be configured to select an audio file that is likely to keep the subject's interest, and such audio may be played during the therapy session (e.g., auditory stimulation pulses may be provided over the selected audio file, so that the subject can listen to the selected audio file while receiving treatment). In some implementations, the subject may be asked to provide audio files that interest the subject, which may be stored in the subject profile 2645. The dosing management module may retrieve such audio files from the profile 2645, and the selected audio files may be played (e.g., via a loudspeaker) during the therapy session, in increase the subject's enjoyment of the therapy session.

In some implementations, the modules of the system 2600 can be configured to incorporate elements of game playing in order to increase subject engagement. Such a technique can be referred to as "gamification." The dosing management module 2680 can be configured to select dosing parameters that reward the subject for adhering to a therapy regimen. For example, the dosing management module 2680 can display a message to a subject indicating that if the subject continues to focus on a display screen that is being used to administer a therapy session, then the subject can expect to see a series of images of the subject's friends or family members. The attention level of the subject can be monitored and, if the subject is attentive, the dosing management module 2680 can select a sequence of images showing friends and family members that are to be shown to the subject and updated at regular intervals while the subject remains attentive.

X. Open Loop Therapy Techniques

As described above, the intensity determination module 2665, the duration determination module 2670, the modality determination module 2675, and the dosing management module 2680 may select dosing parameters in an open loop fashion based on a variety of factors. In general, dosing parameters selected in an open loop fashion are not adjusted in response to feedback received during the therapy session. For example, an open loop therapy session may include dosing parameters selected based on a modality determined by the modality determination module 2675, a signal intensity determined by the intensity duration module 2665, and a signal duration determined by the duration determination module 2670, but these parameters may follow a static therapy regimen over the course of the therapy session. The static therapy regimen may include the use of multiple stimulation modalities and may include waveforms that vary such that there is a variation in the stimulation provided to the subject during the therapy session. However, the therapy regimen remains unchanged during the entirety of the session.

In some implementations, the modules of the system 2600 can be configured to update dosing parameters for a subsequent therapy session based on the results of a previous therapy session. For example, as described above in Section U, the dosing management module 2680 can adjust the dosing parameters of subsequent therapy sessions in order to repeat dosing parameters that appear to result in a high level of entrainment for the subject, or to avoid dosing parameters that appear to cause unwanted side effects or discomfort for the subject. Such adjust of dosing parameters for subsequent therapy sessions based on the results of previous therapy sessions also may be referred to as open loop therapy.

Y. Closed Loop Therapy Techniques

In some implementations, the intensity determination module 2665, the duration determination module 2670, the modality determination module 2675, and the dosing management module 2680 may adjust or update the dosing parameters in the middle of a therapy session, based on real-time feedback received from the subject during the session. Adjustment of dosing parameters or in the therapy regimen more generally, based on such feedback can be referred to as closed loop therapy.

Figure 28:
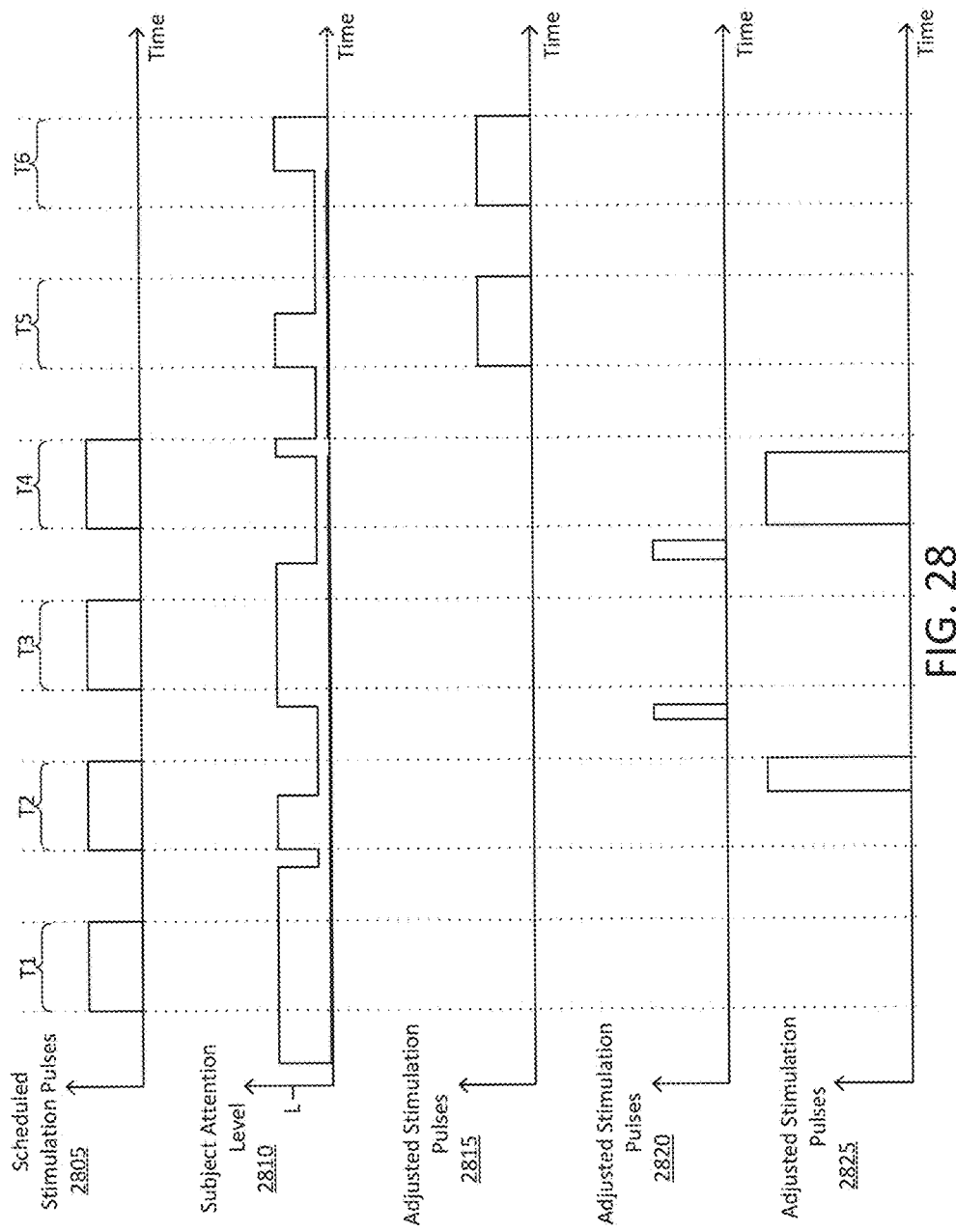
FIG. 28 is a graphical representation of adjusting a therapy session based on feedback collected during the therapy session.

FIG. 28 is a graphical representation of adjusting a therapy session based on feedback collected during the therapy session. A graph 2805 shows a series of scheduled stimulation pulses included in a single therapy session along a time axis. As shown, the pulses occur during intervals labeled as T1, T2, T3, T4, T5, and T6. In this example, the intervals T5 and T6 do not include any scheduled stimulation pulses. It should be understood that the graph 2805 may represent pulses of any modality (e.g., visual stimulation pulses or auditory stimulation pulses). It should also be understood that the amplitude of the pulses, the duration of the pulse intervals, and the frequency of the pulses is illustrative only, and that in some implementations, these factors may be varied without departing from the scope of this disclosure.

A graph 2810 shows the attention level of the subject over time. Higher values indicate that the subject is more attentive, and lower values indicate that the subject is less attentive. In some implementations, subject attention level may be correlated with quality of a therapy session, such as when the subject's attention is required for the stimulation pulses to be delivered effectively. For example, if the stimulation pulses are delivered via a video display screen, it may be necessary for the subject to focus his or her attention on the video display screen in order to receive the benefit of the stimulation pulses. Thus, the graph 2810 includes a threshold L for user attention level. In this example, it can be assumed that the user's attention level must be greater than or equal to the threshold L in order for the therapy to be effectively delivered. As shown in the graph 2810, the subject's attention level varies over time, and is sometimes below the threshold L. If the subject's attention level is below the threshold L during any of the pulse intervals, the subject may not receive the benefit of the pulses delivered during those intervals.

In some implementations, the subject's attention level can be monitored by a sensor. For example, one or more camera sensors can be configured to track the subject's eyes to determine whether they are aligned in a particular orientation that allows the subject to perceive the stimulation pulses (e.g., whether the subject's eyes are focused on a video screen that delivers the stimulation pulses). During time periods in which the subject's eyes are appropriately focused, the subject's attention level may be recorded as relatively high (e.g., above the threshold L). During time periods in which the subject's eyes are not appropriately focused, the subject's attention level may be recorded as relatively low (e.g., below the threshold L).

The graphs 2815, 2820, and 2825 show adjusted stimulation pulses that may be delivered to the subject based on the attention level of the subject over time. Referring now to the graph 2815, two additional stimulation pulses are delivered to the subject during intervals T5 and T6, which originally did not include any schedule pulses as shown in the graph 2805. In some implementations, the additional pulses delivered during the intervals T5 and T6 can be useful because the subject's attention level was below the threshold L for portions of the time periods during which the scheduled pulses were delivered (i.e., intervals T2 and T4). Because the subject may not receive the benefits of the pulses delivered during the intervals T2 and T4 as a result of the relatively low attention level during portions of these intervals, the overall effect of the therapy session may be reduced. Thus, the additional pulses delivered during the intervals T5 and T6 can be administered to compensate for the subjects low attention level during some of the scheduled pulses.

The graph 2820 shows stimulation pulses that are intended to refocus the subject's attention when it appears that the subject's attention level may be below the threshold L during certain time intervals. For example, the subject's attention level falls at the end of the interval T2. Thus, the graph 2820 includes a pulse that occurs just before the beginning of the interval T3, which is intended to recapture the subject's attention so that the subject's attention level will be above the threshold L during the interval T3. As shown in the graph 2810, the subject's attention level increases just before the beginning of the interval T3 as a result of the pulse shown on the left-hand side of the graph 2820. Before the time period T4, the subject's attention level again drops below the threshold L. As a result, the graph 2820 shows a second pulse that occurs before the interval T4 in order to refocus the subject's attention. However, the second pulse shown in the graph 2820 appears to be ineffective, as the subject's attention level does not rise above the threshold L for the beginning of the interval T4. It should be understood that the modality associated with the graph 2820 need not be the same as the modality associated with the graph 2805. For example, the scheduled pulses shown in the graph 2805 may be visual stimulation pulses, and the pulses shown in the graph 2820 may be auditory pulses that are intended to remind the subject to refocus his attention appropriately.

The graph 2825 shows adjusted stimulation pulses that are intended to combat the subject's inattention during certain time intervals. For example, the subject's attention level drops at the end of the interval T2. As a result, the graph 2825 includes a pulse that occurs simultaneous with the subject's attention dropping during the interval T2, and continues until the end of the interval T2. It should be noted that the amplitude of the adjusted pulses shown in the graph 2825 is larger than the amplitude of the scheduled pulses shown in the graph 2805. Such a larger amplitude can serve to refocus the subject's attention, or can be used to increase the effectiveness of pulses that the user is not sufficiently focused on. In some implementations, the larger amplitude of the pulses shown in the graph 2825 may correspond to a brighter visual stimulation signal or a louder auditory stimulation signal, relative to the signals used to generate the scheduled pulses shown in the graph 2805. As shown in the graph 2825, a second adjusted pulse having a high amplitude occurs during the beginning of the interval T4, when the subject's attention level is relatively low. However, when the subject's attention level changes to exceed the threshold level L towards the end of the time interval T4, the adjusted pulse is terminated, as it is no longer necessary.

In some implementations, adjusted pulses different from those shown in FIG. 28 may be used. Furthermore, adjusted pulses may be delivered to the subject in other scenarios not illustrated in FIG. 28. In some implementations, adjusted pulses may be delivered in order to increase the subject's comfort level during a therapy session. For example, if sensor data (e.g., heart rate sensor data or galvanic skin response sensor data) indicates that the subject is experiencing stress during a therapy session, and adjusted pulse having an amplitude lower than that of a scheduled pulse may be delivered to the subject, in order to reduce the discomforting effect that the scheduled pulses may have on the subject.

Figure 29A:
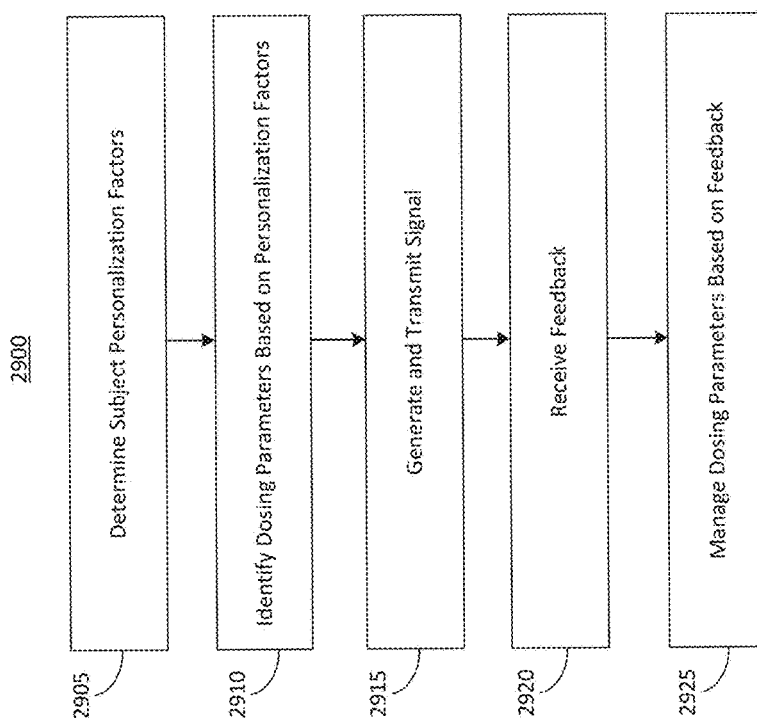
FIG. 29A is a flow diagram of a method for selecting dosing parameters of stimulation signals to induce synchronized neural oscillations in the brain of a subject in accordance with an embodiment.

Z. Method for Selecting Dosing Parameters of Stimulation Signals to Induce Synchronized Neural Oscillations in the Brain of the Subject FIG. 29A is a flow diagram of a method 2900 for selecting dosing parameters of stimulation signals to induce synchronized neural oscillations in the brain of a subject in accordance with an embodiment. In some implementations, the method 2900 can be performed by and NSS such as the NSS 2605 shown in FIG. 26. In brief overview, the NSS can determine subject personalization factors (step 2905). The NSS can identify dosing parameters for a neural stimulation signal based on the personalization factors (step 29280). The NSS can generate and transmit the signal to the subject (step 29285). The NSS can receive feedback from one or more sensors (Step 2920). The NSS can manage the dosing parameters for the neural stimulation signal, based on the feedback (step 2925).

Referring again to FIG. 29A, and in greater detail, the NSS can determine subject personalization factors (step 2905). In some implementations, subject personalization factors may include any of the information included in a subject profile, such as the profile 2645 shown in FIGS. 26 and 27. For example, the personalization factors can include intrinsic subject characteristics, subject data, subject cognitive function data, therapy history, reported side effects, and stimulation response history, as shown in FIG. 27. In some implementations, the personalization factors can be determined by one or more of an intensity determination module, a duration determination module, a modality determination module, and a dosing management module, similar to those shown in FIG. 26. In some implementations, such personalization factors can be taken into account because response to a certain therapy regimen can vary widely from subject to subject based on these factors. In addition, the same subject may respond differently to a given therapy regimen at different times depending on these factors. Thus, tailoring a therapy regimen according to these personalization factors can result in more effective treatment for each individual subject.

The NSS can identify dosing parameters for a neural stimulation signal based on the personalization factors (step 29280). As described above, personalization factors may inform the choice of dosing parameters for a neural stimulation signal. For example, the NSS can select dosing parameters that are likely to be more effective for entraining the brain of a subject, or that help to reduce the likelihood of unpleasant side effects for the subject, as described above. For example, certain subjects may respond better to visual stimulation signals than auditory stimulation signals, and the NSS can make such a choice based at least in part on the personalization factors.

The NSS can generate and transmit the signal to the subject (step 29285). In some implementations, the NSS may include hardware configured to generate a variety of neural stimulation signals, such as visual signals, auditory signals, and electrical signals. The NSS can generate the desired signal in accordance with the dosing parameters selected in step 2810. After the NSS has generated the signal, the NSS can transmit the signal to the subject. For example, a visual signal can be transmitted to a subject using a light source such as an LED, a auditory signal can be transmitted to the subject using a loudspeaker, and an electrical signal can be transmitted to the subject using an electrode.

The NSS can receive feedback from one or more sensors (Step 2920). In some implementations, a sensor can be configured to monitor conditions related to the efficacy of the therapy. For example, the sensor may be an electroencephalograph) (EEG) sensor that monitors the subject's neural oscillations. The NSS can receive the EEG sensor output, and can determine whether entrainment is occurring in the subject as a result of the neural stimulation signal transmitted to the subject in step 29285. In some other implementations, the sensors can relate to the comfort or tolerance level of the subject. For example, the sensors may be or may include any combination of electrocardiogram (ECG) sensors, heart rate variability (HRV) sensors, galvanic skin response sensors, respiratory rate sensors, or other sensors that monitor subject conditions. The NSS may be communicatively coupled to the sensors and may receive output signals from the sensors.

The NSS can manage the dosing parameters of the neural stimulation signal, based on the feedback (step 2925). Such feedback can be used to determine whether the subject is experiencing stress. For example, the NSS can determine that the subject's respiratory rate or heart rate is increasing based on feedback received from a respiratory rate sensor or an ECG sensor, respectively. This may be an indication that the subject is experiencing stress caused by the neural stimulation signal. As a result, the NSS may adjust the dosing parameters in a manner intended to reduce the stress level of the subject, such as by selecting a lower intensity for the signal, a lower duration for the signal, or a different modality for delivering the signal. The output from a galvanic skin response sensor also may indicate that the subject is under stress, and the NSS can respond by adjusting the dosing parameters for the neural stimulation signal to reduce the subject's stress level, as described above. In some implementations, the output of an EEG sensor can be used to determine whether brain entrainment is occurring in the subject, for example by determining that the brain exhibits neural oscillations at a desired frequency during the therapy session. If the NSS determines that brain entrainment is not occurring (or is not occurring at a sufficiently high level), the NSS can respond by adjusting the dosing parameters in a manner intended to increase brain entrainment for the subject. For example, the NSS can increase the signal intensity or duration, or can select a different modality for delivering the neural stimulation signal, to which the subject may be more responsive.

It should be noted that the method 2900 describes a closed loop therapy technique. In some implementations, some of the steps of the method 2900 can be used for open loop therapy. For example, steps 2905, 29280, and 29285 can be identical in an open loop therapy technique. However, open loop therapy does not make use of real-time feedback, nor does it adjust dosing parameters based on such feedback during a therapy session. Thus, steps 2920 and 2925 of the method 2900 would not be performed in an open loop therapy session.

Figure 29B:
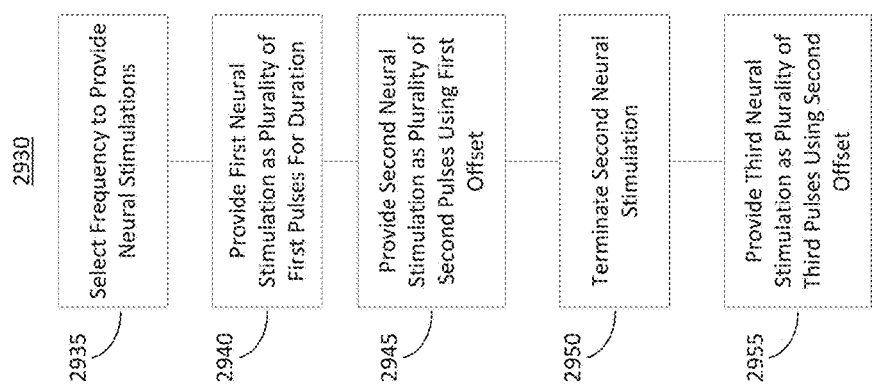
FIG. 29B is a flow diagram of a method for conducting a therapy session in accordance with an embodiment.

FIG. 29B is a flow diagram of a method 2930 for conducting therapy sessions, including therapy sessions for inducing synchronized neural oscillations in the brain of a subject, in accordance with an embodiment. In some implementations, the method 2930 can be performed by an NSS such as the NSS 2605 shown in FIG. 26. In brief overview, the NSS can select a frequency for applying neural stimulations (step 2935). The NSS can provide a first neural stimulation to the subject as a plurality of pulses for a duration (step 2940). The NSS can provide a second neural stimulation as a plurality of second pulses using a first offset (step 2945). The NSS can terminate the second stimulation (step 2950). The NSS can provide a third neural stimulation as a plurality of third pulses using a second offset (step 2955).

Referring again to FIG. 29B, and in greater detail, the NSS can select a frequency at which to provide a first neural stimulation having a first stimulation modality, a second neural stimulation having a second stimulation modality, and a third neural stimulation having the second stimulation modality. The stimulation modalities may be of an auditory stimulation modality, a visual stimulation modality, or a peripheral nerve stimulation modality. In some embodiments, the first stimulation modality is one of auditory, visual, or peripheral nerve, and the second and third stimulation modalities are an other of auditory, visual, or peripheral nerve (e.g., first stimulation modality is audio, second and third stimulation modalities are visual). As such, even where the stimulation modalities are of different types, the stimulation modalities may be provided at the same frequency.

The NSS can provide to the subject, for a duration, the first neural stimulation (step 2940). The first neural stimulation can be provided as a plurality of first pulses at the frequency, during the duration. The NSS can generate and modulate pulses (or control signals used to control a stimulation generator for delivering neural stimulation) in a manner as described with reference to FIGS. 2C-2F, 10F-10I, 17A-17D, 23B, 24B, 28, or other pulse generation methods described herein.

The NSS can provide to the subject, during a first portion of the duration, the second neural stimulation as a plurality of second pulses at the frequency (step 2945). The plurality of second pulses can be offset from the plurality of first pulses by a first offset. For example, during the first portion, each second pulse can be initiated (e.g., ramped up) at a time which is subsequent to an initiation of a corresponding first pulse by the first offset. In some embodiments, offsetting the plurality of second pulses relative to the plurality of first pulses can improve operation of the NSS by expanding or varying a duty cycle of the neural stimulation, which may help target regions of the brain of the subject which may not necessarily be responsive to a single pulse train.

The NSS can terminate the second neural stimulation (step 2950). For example, the NSS can terminate the second neural stimulation responsive to detecting an expiration of the first portion of the duration.

The NSS can provide a third neural stimulation to the subject as a plurality of third pulses using a second offset (step 2955). The third neural stimulation can be provided during a second portion of the duration, subsequent to the first portion of the duration. The second offset can be different from the first offset, which can further expand or vary the duty cycle of the neural stimulation. In some embodiments, the first offset and the second offset are selected as random values. For example, the offsets can be selected as random values which are greater than zero and less than a time constant equal to an inverse of the frequency (e.g., a random value greater than a minimum value at which the second or third pulses would coincide with an earlier pulse among a pair of the first pulses and less than a maximum value at which the second or third pulses would coincide with a later pulse among a pair of the first pulses).

Figure 29C:
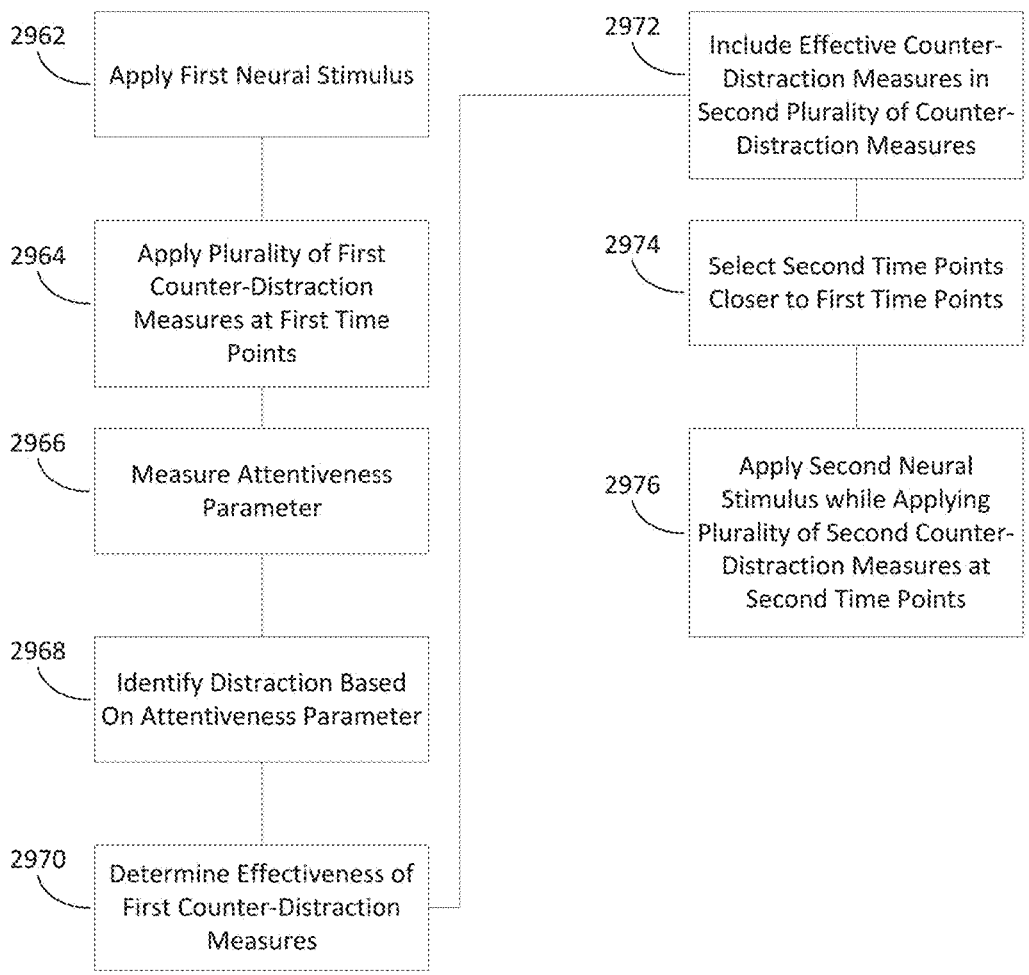
FIG. 29C is a flow diagram of a method for counteracting distractions while applying a neural stimulus in accordance with an embodiment.

FIG. 29C is a flow diagram of a method 2960 for counteracting distraction while applying a neural stimulus, in accordance with an embodiment. In some implementations, the method 2960 can be performed by an NSS such as the NSS 2605 shown in FIG. 26. In brief overview, the NSS can apply a first neural stimulus to a subject (step 2962). The NSS can apply a plurality of first counter-distraction measures at a plurality of first time points (step 2964). The NSS can measure an attentiveness parameter (step 2966). The NSS can identify a distraction of the subject based on the attentiveness parameter (step 2968). The NSS can determine an effectiveness of each of the first counter-distraction measures (step 2970). The NSS can include effectiveness counter-distraction measures in a second plurality of counter-distraction measures (step 2972). The NSS can select a plurality of second time points which are closer to times of the distractions than the first time points (step 2974). The NSS can apply a second neural stimulus while applying the plurality of second counter-distraction measures at the second time points (step 2976).

Referring again to FIG. 29C, and in greater detail, the NSS can apply a first neural stimulus to a subject (step 2962). The first neural stimulus can include at least one of an auditory stimulus, a visual stimulus, or peripheral nerve stimulus. The first neural stimulus may be characterized by a plurality of pulses at a predetermined frequency.

The NSS can apply a plurality of first counter-distraction measures at a plurality of first time points during the first neural stimulus (step 2964). The plurality of first counter-distraction measures can include at least one of an audible alert or a visible alert. The audible alert may be a tone, or a spoken message indicating instructions to return attention to the first neural stimulus. The visible alert may be an output of light at a specific intensity and/or color, or may be a specific image, such as an image of a family member.

The NSS can measure an attentiveness parameter during the first neural stimulus (step 2966). The attentiveness parameter can include at least one of an eye direction, a head position, a heart rate, or a respiration rate of the subject. For example, the attentiveness parameter can indicate whether a change in behavior of the subject may be occurring during the first neural stimulus.

The NSS can compare the attentiveness parameter to a corresponding first threshold to identify a distraction and a corresponding time of distraction (step 2968). For example, if the attentiveness parameter includes an eye direction, the NSS can compare the eye direction to a threshold indicating eyes of the subject are looking in a direction outside of an expected direction for paying attention to the first neural stimulus. In some embodiments, the threshold is adaptively updated during the first neural stimulus (e.g., the threshold may be associated with a moving average of the attentiveness parameter, such that if the attentiveness parameter differs from the moving average by the threshold amount, the distraction may be identified).

The NSS can determine an effectiveness of each of the first counter-distraction measures by comparing a change in the attentiveness parameter before and after each counter-distraction measure to a corresponding second threshold (step 2970). For example, if the difference between the attentiveness parameter before and after each counter-distraction measure indicates an increase in attentiveness (or a restoration from a distracted state to an attentive state), then the counter-distraction measure can be determined to be effective for the subject.

The NSS can include effectiveness counter-distraction measures in a second plurality of counter-distraction measures (step 2972). In some embodiments, including the effectiveness counter-distraction measures includes ranking the counter-distraction measures based on the change in the attentiveness parameter, and preferentially including counter-distraction measures which are ranked higher.

The NSS can select a plurality of second time points which are closer to the identified times of distraction than the plurality of first time points (step 2974). For example, the NSS can compare each first time point to a closest time of distraction, and decrease a difference between each first time point and the closest time of distraction to shift first time point(s). It will be appreciated that there may be fewer times of distraction than first time points, in which case the closest first time point to each time of distraction may be shifted; or there may be greater times of distraction than first time points, in which case additional second time points may be introduced in addition to the first time points. In some embodiments, first time points are only shifted to be earlier than corresponding times of distraction, which may ensure that the second time points anticipate the times of distraction.

The NSS can apply a second neural stimulus to the subject while applying the plurality of second counter-distraction measures at the second time points (step 2976). In various such embodiments, the NSS can improve operation by anticipating times of distraction and executing counter-distraction measures before distraction occurs.

In some embodiments, the NSS can increment a count of distractions in response to identifying each distraction. The NSS can reset the count of distractions subsequent to each effective first counter-distraction measure (e.g., if distractions are identified at times a, b, c, d, and e, and an effective first counter-distraction measure took place between times c and d, the NSS can count five total distractions, with a first count of distractions before the effective first counter-distraction measure being equal to three, and a second count after the effective first counter-distraction measure equal to two). The count of distractions may thus provide an additional measure of effectiveness, by indicating which counter-distraction measures were effectiveness when others were not. The NSS can rank the plurality of effective first counter-distraction measures based on magnitude of the corresponding counts of distractions.

AA. Environment for Modifying an External Stimulus Based on Feedback from a Subject Performing an Assessment Task Systems and methods of the present disclosure are directed to providing assessments for neural stimulation on subjects in response to external stimuli. The external stimuli may adjust, control, or otherwise manage the frequency of the neural oscillations of the brain. When the neural oscillations of the brain are entrained to a particular frequency, there may be beneficial effects to the cognitive states or functions of the brain, while mitigating or preventing adverse consequence to the cognitive state or functions. To determine whether the application of the external stimuli entrains the brain of a subject to the particular frequency and affects the cognitive states or functions of the brain, cognitive assessments may be performed on the subject.

To determine which type of external stimuli is to be applied to the nervous system of a subject, a cognitive and physiological assessment may be performed on the subject. Certain types of external stimuli may not be as effective in inducing neural oscillations of the brain at the particular frequency. For example, applying an auditory stimulus to a subject with severe hearing loss may not result in inducing neural oscillations of the brain at the particular frequency, as the auditory cortex and other related cortices of the brain may not pick up the external auditory stimuli due to hearing loss. Based on the results of the cognitive and physiological assessments, the type of external stimuli to apply to the nervous system of the subject may be identified.

By applying the external stimuli to the nervous system of the subject, neural oscillations may be induced in the brain of the subject. The external stimuli may be delivered to the nervous system of the subject via the visual system of the subject using visual stimuli, auditory system of the subject using auditory stimuli, or peripheral nerve stimuli. The neural oscillations of the brain of the subject may be monitored using brain wave sensors, electroencephalography (EEG) devices, electrooculography (EOG) devices, and magnetoencephalography (MEG) devices. Various other signs and indications (e.g., attentiveness, physiology, etc.) from the subject may also be monitored using accelerometers, microphones, videos, cameras, gyroscopes, motion detectors, proximity sensors, photo sensors, photo detectors, physiological sensors, ambient light sensors, ambient temperature sensors, and actimetry sensors, among others. After having applied the external stimuli to the nervous system of the subject, additional cognitive and physiological assessments may be repeatedly performed over time to determine whether the external stimuli were effective in entraining the brain of the subject to the particular frequency and in improving the cognitive states or functions of the brain.

Neural oscillation occurs in humans or animals and includes rhythmic or repetitive neural activity in the central nervous system. Neural tissue can generate oscillatory activity by mechanisms within individual neurons or by interactions between neurons. Oscillations can appear as either oscillations in membrane potential or as rhythmic patterns of action potentials, which can produce oscillatory activation of post-synaptic neurons. Synchronized activity of a group of neurons can give rise to macroscopic oscillations, which can be observed by electroencephalography ("EEG"). Neural oscillations can be characterized by their frequency, amplitude, and phase. These signal properties can be observed from neural recordings using time-frequency analysis.

For example, electrodes for an EEG device can measure voltage fluctuations (in the magnitude of microvolts) from currents within the neurons along the epidermis of the subject. The voltage fluctuations measured by the EEG device may correspond to oscillatory activity among a group of neurons, and the measured oscillatory activity can be categorized into frequency bands as follows: delta activity corresponds to a frequency band from 1-4 Hz; theta activity corresponds to a frequency band from 4-8 Hz; alpha activity corresponds to a frequency band from 8-12 Hz; beta activity corresponds to a frequency band from 13-30 Hz; and gamma activity corresponds to a frequency band from 30-60 Hz. The EEG device may then sample voltage fluctuations picked up by the electrodes (e.g., at 50 Hz-2000 Hz or randomly using compressed sensing techniques) and convert to a digital signal for further processing.

The frequency of neural oscillations can be associated with cognitive states or cognitive functions such as information transfer, perception, motor control, and memory. Based on the cognitive state or cognitive function, the frequency of neural oscillations can vary. Further, certain frequencies of neural oscillations can have beneficial effects or adverse consequences on one or more cognitive states or functions. However, it may be challenging to synchronize neural oscillations using external stimulus to provide such beneficial effects or reduce or prevent such adverse consequences.

Brainwave entrainment (e.g., neural entrainment or brain entrainment) occurs when an external stimulation of a particular frequency is perceived by the brain and triggers neural activity in the brain that results in neurons oscillating at a frequency corresponding to the particular frequency of the external stimulation. Thus, brain entrainment can refer to synchronizing neural oscillations in the brain using external stimulation such that the neural oscillations occur at frequency that corresponds to the particular frequency of the external stimulation.

Figure 30:
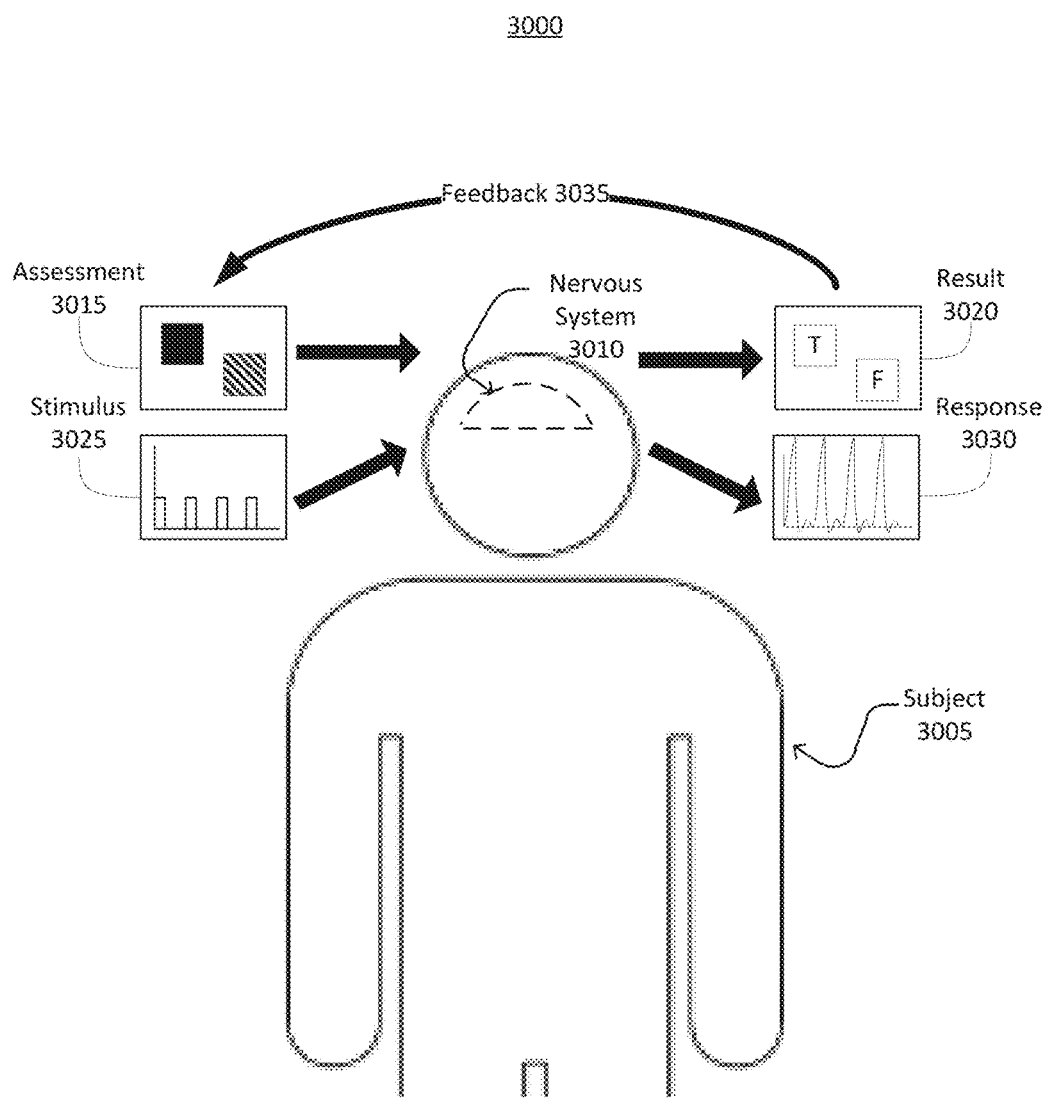
FIG. 30 is a block diagram depicting an environment for modifying an external stimulus based on a response by a subject to an assessment task, in connection with the systems and methods described herein.

FIG. 30 is a block diagram depicting an environment 3000 for modifying an external stimulus 3025 based on a response by a subject 3005 to an assessment 3015, in accordance to an embodiment. In overview, the environment 3000 can include a subject 3005, a nervous system 3010 (e.g., brain), a result 3020, and a response 3030. The assessment 3015 may be administered to the subject 3005 using an input/output interface (e.g., mouse, keyboard, or display, etc.) of a computing device (e.g., desktop, laptop, tablet, smartphone, etc.). The assessment 3015 may be designed to test at least one of a cognitive function, a reaction, or a physiological response of the subject 3005. The assessment 3015 may be delivered to the subject 3005 via the auditory system, the visual system, and/or the, or peripheral nerve stimulation system of the subject 3005. The assessment 3015 may be one of, for example, an N-back task, a serial reaction time test, a visual coordination test, a voluntary movement test, or a force production test, among others. In the example depicted in FIG. 30, the assessment 3015 may include a visual n-back test. While the assessment 3015 is performed, the result 3020 to the assessment 3015 by the subject 3005 may be recorded or logged by the computing device administering the assessment 3015. Using the result 3020, which type of assessment 3015 to administer next and which type of external stimulus 3025 may be identified.

The external stimulus 3025 may be applied to excite or stimulate the nervous system 3010 of the subject 3005. In some embodiments, the external stimulus 3025 may be applied to the subject 3005 simultaneously as the assessment 3015. The external stimulus 3025 may be delivered to the nervous system 3010 of the subject 3005 via the visual system of the subject using visual stimuli, auditory system of the subject using auditory stimuli, or peripheral nerve system of the subject using physical stimuli, among other techniques. The external stimulus 3025 may be generated by a stimulus generator and/or a stimulus output device. The modulation or a pulse scheme of the external stimulus 3025 may be set and dynamically modified, so as to entrain the neural oscillations of the nervous system 3010 of the subject 3005 to a particular or specified frequency. Upon the application of the external stimulus 3025 to the nervous system 3010 of the subject 3005, the neural response of the subject 3005 may be measured in the form of the response 3030. The response 3030 may be of the neural response (or evoked response) of the nervous system 3010 of the subject 3005, and may be measured using EEG or MEG, among other techniques.

Upon measurement, the result 3020 and/or the response 3030 of the subject 3005 may be used to generate the feedback signal 3035. The result 3020 and/or the response 3030 may indicate where cognitive functions or states of the nervous system 3010 of the subject 3005 has changed (e.g., improved, deteriorated, or unaffected) in response to the application of the external stimulus 3025. The feedback signal 3035 may indicate to the computing device administering the assessment 3015 to alter the administration of the assessment. Modifications of the assessment 3015 may include changing the stimulus used in the assessment 3015 and/or selecting a different type of assessment 3015, among others. The feedback signal 3035 may also specify the stimulus generator and/or the stimulus output device applying the stimulus 3025 to modify the external stimulus 3025. Modifications of the external stimulus 3025 may include increasing or decreasing the intensity of the stimulus 3025, increasing or decreasing the intervals of the modulation or pulse scheme of the stimulus 3025, altering the pulse shape of the stimulus 3025, changing a type of stimulus 3025 (e.g., from visual to auditory), and/or terminating the application of the stimulus 3025, among others.

Figure 31:
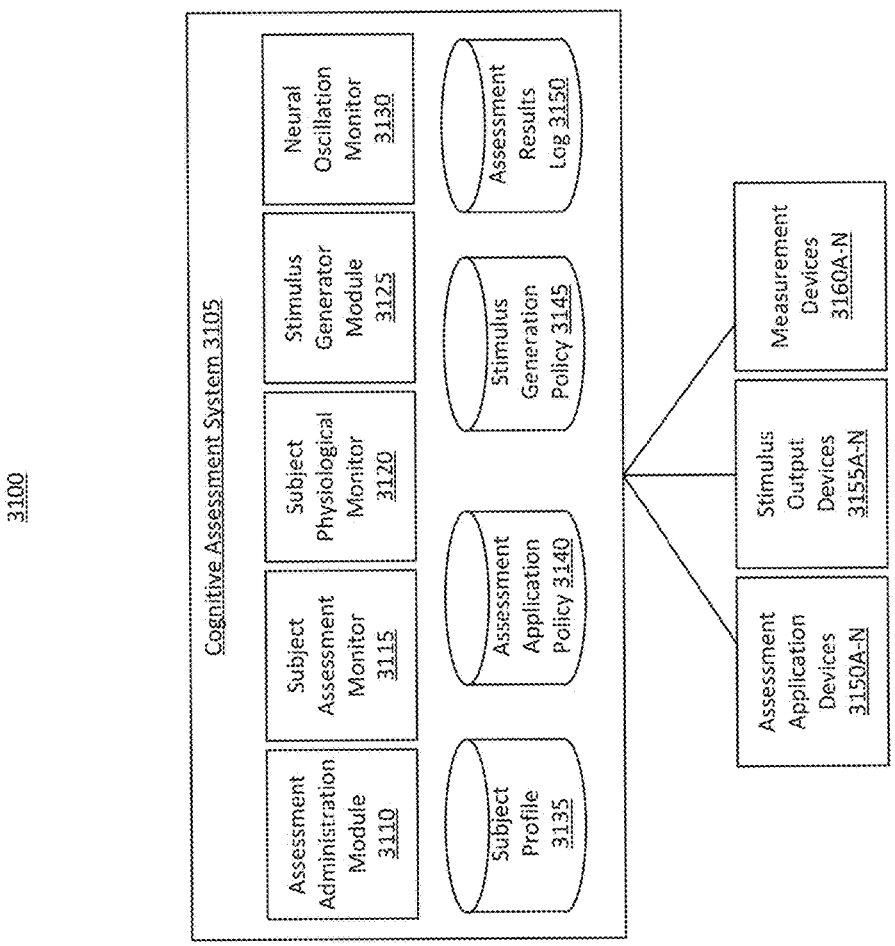
FIG. 31 is a block diagram depicting a system for providing assessments for neural stimulation, in accordance to an embodiment.

BB. Overview of Systems for Performing Assessments to Measure Effects of Neural Stimulation Referring now to FIG. 31, FIG. 31 is a block diagram depicting a system 3100 for providing assessments for neural stimulation, in accordance to an embodiment. The system 3100 can include a cognitive assessment system ("CAS") 3105. The ("CAS") can be part of or can be communicatively coupled to any of one or more of the NSS 105, 905, 1605, or the NSOS 2305 or any other system described herein. In brief overview, the cognitive assessment system 3105 can include, access, interface with, or otherwise communicate with one or more of an assessment administration module 3110, a subject assessment monitor 3115, a subject physiological monitor 3120, a stimulus generator module 3125, a neural oscillation monitor 3130, a subject profile database 3135, an assessment application policy database 3140, a stimulus generation policy database 3145, an assessment results log 3150, one or more assessment application devices 3150A-N, one or more stimulus output devices 3155A-N, and/or one or more measurement devices 3160A-N. The assessment administration module 3110, the subject assessment monitor 3115, the subject physiological monitor 3120, the stimulus generator module 3125, and the neural oscillation monitor 3130 can each include at least one processing unit or other logic device such as programmable logic array engine, or module configured to communicate with the subject profile database 3135, the assessment application policy database 3140, a stimulus generation policy database 3145, the assessment results log 3150, the one or more assessment application devices 3150A-N, the one or more stimulus output devices 3155A-N, and the one or more measurement devices 3160A-N. The assessment administration module 3110, the subject assessment monitor 3115, the subject physiological monitor 3120, the stimulus generator module 3125, and the neural oscillation monitor 3130 can each be separate components, a single component, or a part of the CAS 3105.

The system 3100 and the components therein, such as the CAS 3105, may include hardware elements, such as one or more processors, logic devices, or circuits. The system 3100 and the components therein, such as the CAS 3105, can include one or more hardware or interface component depicted in system 700 in FIGS. 7A and 7B. The system 3100 and the components therein, such as the CAS 3105, the one or more stimulus generators 3150A-N, the one or more stimulus output devices 3155A-N, and/or the one or more measurement devices 3160A-N can be communicatively coupled to one another, using one or more wireless protocols such as Bluetooth, Bluetooth Low Energy, ZigBee, Z-Wave, IEEE 802, Wi-Fi, 3G, 4G, LTE, near field communications ("NFC"), or other short, medium or long range communication protocols, etc.

In further detail, the CAS 3105 can include at least one assessment administration module 3110. The assessment administration module 3110 can be communicatively coupled to the subject profile database 3135, the assessment application policy database 3140, the one or more assessment application devices 3150A-N, and/or the assessment administration module 3110. The assessment administration module 3110 can be designed and constructed to interface with the one or more assessment application devices 3150A-N to provide a control signal, a command, instructions, or otherwise cause or facilitate the one or more assessment application devices 3150A-N to run or execute the assessment 3015. The assessment 3015 run on or be administered to the subject 3005 may be, for example, an N-back task, a serial reaction time test, a visual coordination test, a voluntary movement test, or a force production test, among others. Additional details of the functionalities of the assessment administration module 3110 in operation in conjunction with the other components of the CAS 3105 are described herein in reference to FIG. 3.

The one or more assessment application devices 3150A-N may include a visual display, such as one or more cathode ray tubes (CRT), liquid crystal displays (LCD), a plasma display panels (PDP), incandescent light bulbs, and light emitting diodes (LED), or any other device, among others, designed to generate light within the visual spectrum to administer the assessment 3015 to the visual system of the subject 3005. The one or more assessment application devices 3150A-N may include an auditory source, such as a loudspeaker, dynamic speaker, headphones, temple transducer, or any type of electroacoustic transducer, among others, designed or configured to generate soundwaves to administer the assessment 3015 to the auditory system of the subject 3005. The one or more assessment application devices 3150A-N may include a peripheral nerve stimulation source upon the subject 3005 to administer the assessment 3015 based on the inputs from the assessment administration module 3110.

The CAS 3105 can include at least one subject assessment monitor 3115. The subject assessment monitor 3115 can be communicatively coupled to the assessment results log 3150, the one or more measurement devices 3160A-N, and/or the assessment administration module 3110. Additional details of the functionalities of the subject assessment monitor 3115 in operation in conjunction with the other components of the CAS 3105 are described herein in reference to FIG. 3.

The CAS 3105 can include at least one subject physiological monitor 3120. The subject physiological monitor 3120 can be communicatively coupled to the assessment results log 3150, the one or more measurement devices 3160A-N, and/or the assessment administration module 3110. The subject physiological monitor 3120 can measure a physiological status (e.g., heartrate, blood pressure, breathing rate, perspiration, etc.) of the subject 3005 in response to the stimulus 3025. Additional details of the functionalities of the subject physiological monitor 3120 in operation in conjunction with the other components of the CAS 3105 are described herein in reference to FIG. 3.

The CAS 3105 can include at least one stimulus generator module 3125. The stimulus generator module 3125 can be communicatively coupled to the subject profile database 3135, the stimulus generation policy database 3145, the one or more stimulus output devices 3155A-N, and/or the neural oscillation monitor 3130. The stimulus generator module 3125 can be designed and constructed to interface with the one or more stimulus output devices 3155A-N to provide a control signal, a command, instructions, or otherwise cause or facilitate the one or more stimulus output devices 3155A-N to generate the stimulus 3025, such as a visual stimulus, an auditory stimulus, or peripheral nerve stimuli among others. The stimulus 3025 may be controlled or modulated as a burst, a pulse, a chirp, a sweep, or other modulated fields having one or more predetermined parameters. The one or more predetermined parameters may define the pulse schema or the modulation of the stimulus 3025. The stimulus generator module 3125 can control the stimulus 3025 outputted by the one or more stimulus output devices 3155A-N according to the one or more defined characteristics, such as magnitude, type (e.g., auditory, visual, etc.), direction, frequency (or wavelength) of the oscillations of the stimulus 3025. Additional details of the functionalities of the stimulus generator module 3125 in operation in conjunction with the other components of the CAS 3105 are described herein in reference to FIG. 3.

The one or more stimulus output devices 3155A-N may include a visual source, such as one or more cathode ray tubes (CRT), liquid crystal displays (LCD), a plasma display panels (PDP), incandescent light bulbs, and light emitting diodes (LED), or any other device, among others, designed to generate light within the visual spectrum to apply to the visual system of the subject 3005. The one or more stimulus output devices 3155A-N may include an auditory source, such as a loudspeaker, dynamic speaker, headphones, temple transducer, or any type of electroacoustic transducer, among others, designed or configured to generate soundwaves to apply to the auditory system of the subject 3005. The one or more stimulus output devices 3155A-N may include an electric current source, such as an electroconvulsive device or machine designed or configured to apply an electric current to the subject 3005.

The CAS 3105 can include at least one neural oscillation monitor 3130. The neural oscillation monitor 3130 can be communicatively coupled to the one or more measurement devices 3160A-N and/or to the stimulus generator module 3125. The neural oscillation monitor 3130 can measure a neural response of the subject 3005 to the stimulus 3025. The neural oscillation monitor 3130 can receive a measurement of the subject 3005 from the one or more measurement devices 3160A-N. The measurement of the subject 3005 may represent or may be indicative of a response (or lack of response) of the subject 3005 to the stimulus 3025 applied to the subject 3005. The one or more measurement devices 3160A-N may include EEG monitoring devices, MEG monitoring devices, EOG monitoring devices, accelerometers, microphones, videos, cameras, gyroscopes, among others, to measure the response of the subject 3005 to the stimulus 3025 and the effect of ambient noise on the stimulus 3025. Each of the one or more measurement devices 3160A-N can sample the neural response measurement of the subject 3005 at any sample rate (e.g., 310 Hz to 310,000 Hz). In some embodiments, each of the one or more measurement devices 3160A-N can sample at randomly in accordance to compressed sensing techniques. The neural oscillation monitor 3130 can send a feedback signal to the stimulus generator module 3125 to adjust the control signal, command, or instructions used by the stimulus generator module 3125 to cause or facilitate the one or more stimulus output devices 3155A-N to modify the stimulus 3025. Additional details of the functionalities of the neural oscillation monitor 3130 in operation in conjunction with the other components of the CAS 3105 are described herein in reference to FIG. 3.

Figure 32:
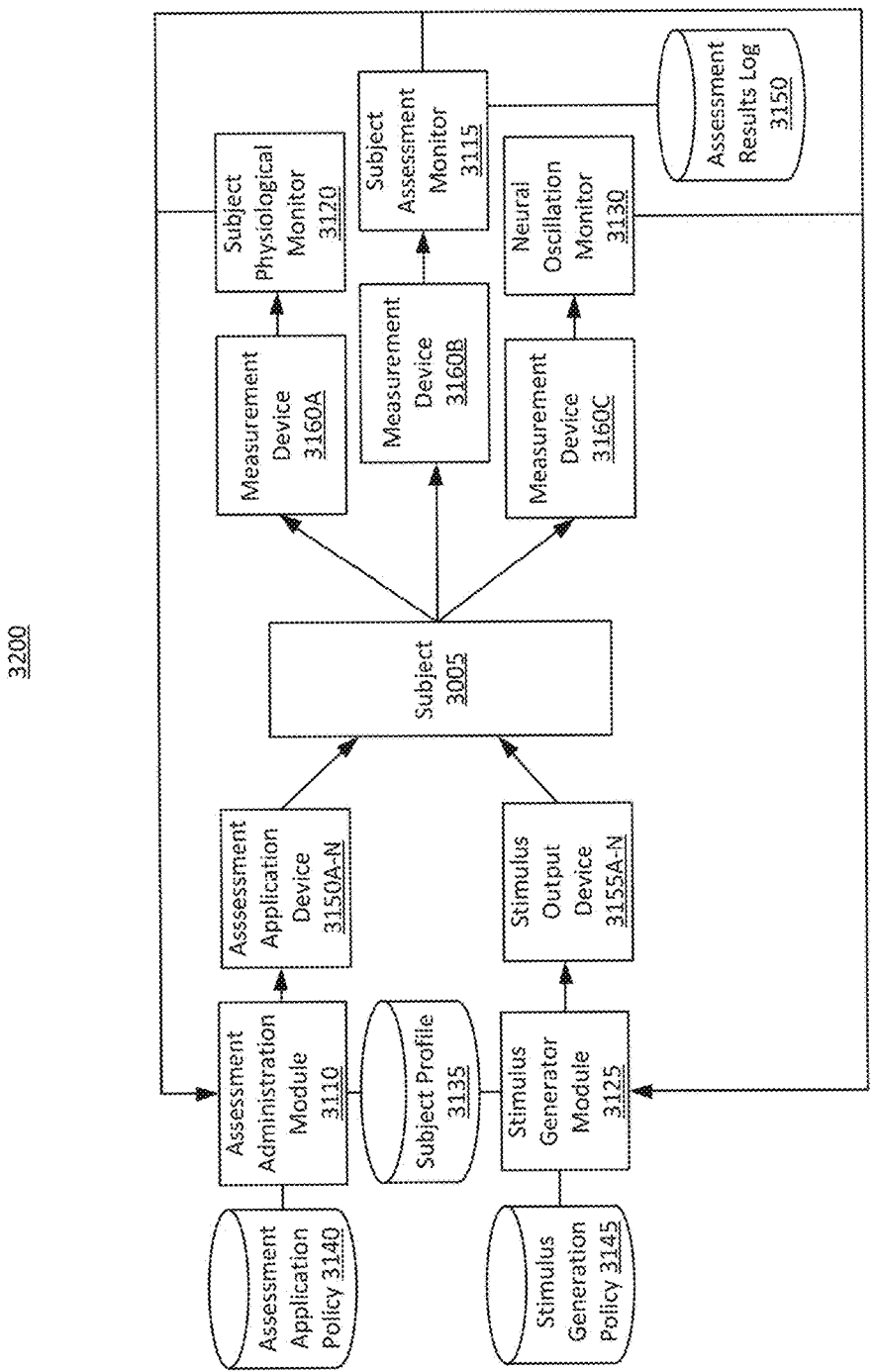
FIG. 32 is a block diagram depicting a system for providing assessments for neural stimulation on a subject in response to stimulation, in accordance to an embodiment.

Referring now to FIG. 3, FIG. 32 is block diagram a system 300 for sensing neural oscillations induced by the external stimulus 3025, in accordance to an embodiment. In brief overview, the system 300 can include the assessment administration module 3110, the subject assessment monitor 3115, the subject physiological module 3120, the stimulus generator module 3125, the neural oscillation monitor 3130, the subject profile database 3135, the assessment application policy database 3140, the stimulus generation policy database 3145, the assessment results log 3150, the one or more assessment application devices 3150A-N, the one or more stimulus output devices 3155A-N, and/or the one or more measurement devices 3160A-N. The one or more components of the system 300 may be in any environment or across multiple environments, such as in a treatment center, a clinic, a residence, an office, a pharmacy, or any other suitable location.

CC. Modules in Administering Assessments and Applying Stimulus on the Subject

In the context of FIG. 32, the assessment administration module 3110 can transmit or relay a control signal to the one or more assessment application devices 3150A-N to administer or execute an assessment 3015 on the subject 3005. The assessment administration module 3110 can identify a type of assessment for the one or more assessment application devices 3150A-N to administer on the subject 3005. The assessment administration module 3110 can access a profile of the subject 3005 from the subject profile database 3135. The profile of the subject 3005 may specify or indicate one or more physical characteristics of the subject 3005, such as height, weight, age, sensory-related disabilities (e.g., sight, hearing, etc.), blood pressure, insulin levels, and demographics, among others. The assessment administration module 3110 can access one or more assessment policies from the assessment application policy database 3140. The one or more assessment policies may specify a type of assessment (e.g., n-back testing, serial reaction time task, force production, etc.). The one or more assessment policies may specify a sensory system to be assessed (e.g., visual, auditory, or peripheral nerve). The one or more assessment policies may specify a time duration assessment (e.g., 30 seconds to 4 hours). The one or more assessment policies may specify an intensity of cue in the assessment 3015 to be administered to the subject 3005.

The assessment administration module 3110 can select or identify an assessment policy from the assessment application policy database 3140 based on the profile of the subject 3005. For example, if the profile of the subject 3005 indicates that the subject 3005 is visually impaired, the assessment administration module 3110 can select the assessment policy specifying that visual assessments are to be first administered to verify whether there is a neural response to the assessment 3015. In this scenario, the assessment policy can further specify that auditory assessments is to be administered to the subject 3005 if there is no neural response. Based on the identified assessment policy, the assessment administration module 3110 can generate the control signal corresponding to the identified assessment policy. The control signal may specify to the one or more assessment application devices 3150A-N which type of assessment, time duration assessment, and/or intensity of stimuli used in the assessment 3015 is to be executed. Once the control signal is generated, the assessment administration module 3110 can send, relay, or otherwise transmit the control signal to the one or more assessment application devices 3150A-N. Upon receiving the control signal from the assessment administration module 3110, the one or more assessment application devices 3150A-N may execute the assessment 3015 based on the specifications of the control signal. For example, the control signal may specify that the one or more assessment application devices 3150A-N is to run an n-back test. In this example, the one or more assessment application devices 3150A-N may include a computer with touch-screen display to run and present the n-back test to the subject 3005. In some embodiments, the assessment administration module 3110 can select or identify a subset of the one or more assessment application devices 3150A-N based on the one or more assessment policies. Responsive to identifying the subset, the assessment administration module 3110 can transmit or relay the control signal to the respective subset of the one or more assessment application devices 3150A-N.

The stimulus generator module 3125 can transmit or relay a control signal to the stimulus output devices 3155A-N to generate the stimulus 3025 to apply to the nervous system 3010 of the subject 3005. The stimulus generator module 3125 can access the profile of the subject 3005 from the subject profile database 3135. The stimulus generator module 3125 can access one or more stimulus generation policies from the stimulus generation database 3145. The one or more stimulus generation policies may specify a type of stimulus (e.g., visual, auditory, etc.), a magnitude of stimulus, a specified frequency or wavelength, and/or a pulse schema or the modulation, among others, for the stimulus 3025 to be applied to the nervous system 3010 of the subject 3005. Based on the one or more stimulus generation policies from the stimulus generation policy database 3145, the stimulus generator module 3125 can generate the control signal. The control signal may be a continuous-time signal or a periodic discrete signal. The control signal can specify one or more defined characteristics based on the one or more stimulus generation policies. In some embodiments, the stimulus generator module 3125 can identify a subset of the one or more stimulus output devices 3155A-N based on the one or more defined characteristics. For example, if the one or more defined characteristics specify the type of stimulus 3025 as visual, the stimulus generator module 3125 can identify the subset of the one or more stimulus output devices 3155A-N corresponding to an electronic display. Responsive to identifying the subset, the stimulus generator module 3125 can transmit or relay the control signal to the subset of the one or more stimulus output devices 3155A-N.

In response to receiving the control signal from the stimulus generator module 3125, the one or more stimulus output devices 3155A-N can generate the stimulus 3025 to apply to the subject 3005. The one or more stimulus output devices 3155A-N may include a visual source, an auditory source, among others. The stimulus 3025 applied to the subject 3005 may be at least one of a visual stimulus originating from the visual source or an auditory stimulus originating from the auditory source The one or more stimulus output devices 3155A-N each can receive the control signal from the stimulus generator module 3125. The one or more stimulus output devices 3155A-N each can identify or access the one or more defined characteristics from the received control signal. The one or more stimulus output devices 3155A-N each can determine whether the stimulus 3025 is to be outputted or applied to the subject 3005 based on the one or more defined characteristics. For example, the control signal may specify that the stimulus 3025 is to be an auditory stimulus. In such a case, a subset of the one or more stimulus output devices 3155A-N corresponding to visual sources may determine that the responsive stimulus output devices 3155A-N are not to output the stimulus 3025. Each of the one or more stimulus output devices 3155A-N can determine the stimulus 3025 to apply to the subject 3005 based on the one or more defined characteristics of the control signal. Each of the one or more stimulus output devices 3155A-N can convert the control signal to the stimulus 3025 based on the control signal. For example, the control signal may be an electrical signal and upon receipt of the control signal, each of the one or more stimulus output devices 3155A-N can convert the electrical signal corresponding to the control signal to an analog, physical signal corresponding to the stimulus 3025.

DD. Modules in Measuring Data from Subject During Assessment

While administering the assessment 3015 and/or the stimulus 3025 to the subject 3005, the subject physiological monitor 3120 can determine the physiological status (e.g., heartrate, blood pressure, breathing rate, perspiration, etc.) of the subject 3005. In response to receiving measurements from the first measurement device(s) 3160A, the subject physiological monitor 3120 can monitor the physiological status of the subject 3005 with the administering of the assessment 3015 via the one or more assessment application devices 3150A-N and/or the application of the stimulus 3025 via the one or more stimulus output devices 3155A-N. The first measurement device(s) 3160A can measure data related to a physiological status of the subject 3005. The physiological status of the subject 3005 may include vital signs of the subject 3005, such as heartrate, blood pressure, breathing rate, and perspiration, among others. The first measurement device(s) 3160A can include a heart rate monitor, a blood pressure monitor, a breathing rate monitor, a perspiration detector, a camera, and an eye tracker, or any other suitable device to monitor the physiological status of the subject 3005.

The subject physiological monitor 3120 can apply any number of signal processing techniques to the measurements from the first measurement device(s) 3160A. The subject physiological monitor 3120 can apply signal reconstruction techniques to the equally spaced sampled measurements received from the first measurement device(s) 3160A to determine the physiological status of the subject 3005. The subject physiological monitor 3120 can apply compressed sensing techniques to the randomly sampled measurements received from the first measurement device(s) 3160A to determine the physiological status of the subject 3005. The subject physiological monitor 3120 can apply pattern recognition algorithms from the measurements received from the first measurement device(s) 3160A to identify one or more cues from the subject 3005. For example, if the measurement device(s) is a heartrate monitor to measure the heartrate of the subject 3005, the subject physiological monitor 3120 can apply filtering techniques to identify an increase or decrease in the heartrate of the subject 3005. Based on the one or more cues, the subject physiological monitor 3120 can identify or determine the physiological status of the subject 3005. The subject physiological monitor 3120 can transmit or relay the identified physiological status of the subject 3005 to the assessment administration module 3110 and/or the stimulus generator module 3125 as feedback data.

While administering the assessment 3015 and/or the stimulus 3025 on the subject 3005, the subject assessment monitor 3115 can identify a task response (e.g., result 3020) to the assessment 3015 administered to the subject 3005. In response to receiving measurements from the second measurement device(s) 3160B, the subject assessment monitor 3115 can identify the task response to the assessment 3015 administered to the subject 3005 via the one or more assessment application devices 3150A-N. The second measurement device(s) 3160B can measure data related to a task response of the subject 3005 to the administered assessment 3015. The task response of the subject 3005 may include one or more parameters of user interactions with the one or more assessment application devices 3150A-N during the administration of the assessment 3015. For example, if the assessment 3015 is a serial reaction time test, the task response of the subject 3005 may include a time interval between an onset of the cue and the response by the subject 3005. The second measurement device(s) 3160B can include a mouse, a keyboard, a microphone, a touch screen, a touchpad, or any other suitable device to monitor the task response of the subject 3005, during the administration of the assessment 3015. In some embodiments, the second measurement device(s) 3160B may be the same or share the same devices or components as the one or more assessment application devices 3160A-N. The subject assessment monitor 3115 can record the measurements from the second measurement device(s) 3160B to the assessment results log database 3150. The subject assessment monitor 3115 can index each stored measurement from the second measurement device(s) 3160B by the sensory system to be assessed, time duration assessment, and/or intensity of cue in the assessment 3015. The subject assessment monitor 3115 can transmit or relay the measurements to the assessment administration module 3110 and/or the stimulus generator module 3125 as feedback data.

While administering the assessment 3015 and/or the stimulus 3025 on the subject 3005, the neural oscillation monitor 3130 can measure a neural response of the subject 3005 to the stimulus 3025 applied by the one or more stimulus devices 3155A-N. In response to receiving the measurements from the third measurement device(s) 3160C, the neural oscillation monitor 3110 can monitor neural oscillations of the nervous system 3010 of the subject 3005 in response to the stimulus 3025. The third measurement device(s) 3160C can measure the neural response of the nervous system 3010 of the subject 3005 to the stimulus 3025. The third measurement device(s) 3160C can include an EEG device or an MEG device, or any suitable device, to measure the neural response of the nervous system 3010 of the subject 3005 to the stimulus 3025. The third measurement device(s) 3160C can transmit the neural response of the nervous system 3010 of the subject 3005 to the stimulus 3025 to the neural oscillation monitor 3130. The neural oscillation monitor 3130 can also apply signal reconstruction techniques to the equally spaced sampled measurements received from the third measurement device(s) 3160C to calculate the neural response of the nervous system 3010 of the subject 3005. The neural oscillation monitor 3130 can also apply compressed sensing techniques to the randomly sampled measurements received from the third measurement device(s) 3160C to calculate the neural response of the nervous system 3010 of the subject 3005. The neural oscillation monitor 3130 can transmit or send the monitored neural oscillations of the nervous system 3010 of the subject 3005 to the stimulus generator module 3125 as feedback data.

EE. Modules in Modifying the Assessment Using Feedback Data

Using the feedback data from the subject physiological monitor 3120, the subject assessment monitor 3115, and/or the neural oscillation monitor 3130, the stimulus generator module 3125 can modify the control signal sent to the one or more stimulus output devices 3155A-N. Based on the feedback data, the stimulus generator module 3125 can modify the one or more predefined characteristics, such as the magnitude, the type (e.g., auditory, visual, etc.), the direction, the pulse modulation scheme, or the frequency (or wavelength) of the oscillations of the stimulus 3025. The stimulus generator module 3125 can identify the one or more stimulus generation policies of the stimulus generation policy database 3145 based on the feedback data. The one or more stimulus generation policies can also specify a modification to the one or more predefined characteristics for the control signal sent to the one or more stimulus output devices 3155A-N. Modifications to the stimulus 3025 may include increasing or decreasing the intensity of the stimulus 3025, increasing or decreasing the intervals of the modulation or pulse scheme of the stimulus 3025, altering the pulse shape of the stimulus 3025, changing a type of stimulus 3025 (e.g., from visual to auditory), and/or terminating the application of the stimulus 3025.

In some embodiments, based on the feedback data from the neural oscillation monitor 3130, the stimulus generator module 3125 can calculate a frequency response (e.g., power spectrum) of the neural response of the nervous system 3010 of the subject 3005 using Fourier transform techniques (e.g., Fast Fourier Transform (FFT)). Based on the calculated frequency response, the stimulus generator module 3125 can identify a global maximum frequency corresponding to a global maximum of the frequency response of the neural response of the nervous system 3010 of the subject 3005. The stimulus generator module 3125 can compare the global maximum frequency to the pre-specified frequency to determine a level of entrainment relative to the pre-specified frequency of the control signal. The level of entrainment may be a measure (e.g., percentage) at the pre-specified frequency versus other frequencies in the power spectrum the neural response of the nervous system 3010. The stimulus generator module 3125 can determine whether the nervous system 3010 of the subject 3005 is entrained to the pre-specified frequency of the control signal by comparing the level of entrainment to a threshold. Responsive to determining that the level of entrainment is less than the threshold, the stimulus generator module 3125 can modify the control signal sent to the one or more stimulus output devices 3155A-N. The stimulus generator module 3125 can also identify the one or more stimulus generation policies of the stimulus generation policy database 3145 based on the determination (e.g., a difference between the global maximum frequency and the pre-specified frequency). In addition, responsive to determining that the level of entrainment is greater than or equal to the threshold, the stimulus generator module 3125 can terminate the application of the stimulus 3025 on the subject 3005 by the one or more stimulus output devices 3155A-N. The stimulus generator module 3125 can store, write, or otherwise update the profile of the subject 3005 in the subject profile database 3135 with the one or more predefined characteristics of the control signal corresponding to the determination of the level of entrainment being greater than or equal to the threshold.

Using the feedback data, the assessment administration module 3110 can modify the control signal sent to the one or more assessment application devices 3150A-N. At this point, the feedback data may indicate that the nervous system 3010 of the subject 3005 may or may not have reached a desired level (e.g., threshold) of entrainment to the pre-specified frequency. The assessment administration module 3110 can write or store the feedback indicating that the nervous system 3010 of the subject 3005 has reached the desired level of entrainment onto the subject profile database 3135. The profile of the subject 3005 may be also updated to indicate the task response to the assessment 3015 administered to the subject.

Based on the feedback data indicating that the nervous system 3010 has reached the desired level of entrainment, the assessment administration module 3110 can select or identify the one or more assessment policies of the assessment application policy database 3140. The one or more assessment policies may specify a modification to the type of assessment, the sensory system to be assessed, time duration of assessment, and/or intensity of the cue (or stimuli) in the assessment 3015 to be administered to the subject 3005, given that the nervous system 3010 has reached the desired level of entrainment in response to the application of the stimulus 3025. For example, the assessment 3015 administered may be an n-back test. If the feedback data indicates that the nervous system 3010 of the subject 3005 has reached the desired level of entrainment, the speed at which the stimuli of the assessment 3015 in the n-back test is to be delivered to the subject 3005 may be increased. The assessment administration module 3110 can generate a new control signal based on the one or more assessment policies identified based on the feedback data. The assessment administration module 3110 can transmit the new control signal, and can continue to send or transmit the control signal to the one or more assessment application devices 3150A-N, while receiving the feedback data from the subject assessment monitor 3115.

In some embodiments, the assessment administration module 3110 can determine a termination condition for the assessment 3015 based on the feedback data from the subject assessment monitor 3115. The termination condition may correspond to a termination of the assessment 3015 administered to the subject 3005 via the one or more assessment administration devices 3150A-N. The termination condition may correspond to sending of a control signal specifying the termination of the assessment 3015 administered via the one or more assessment application devices 3150A-N. Using the feedback data from the subject assessment monitor 3115, the assessment administration module 3110 can determine whether the task response of the subject 3005 to the assessment 3015 satisfies an assessment effectiveness policy. The assessment effectiveness policy may indicate or specify a change in the task response by a predefined percentage or score in the feedback data from the subject assessment monitor 3115. The feedback data, for example, may indicate that the subject 3005 has improved in performance i (e.g., assessment score increased by 5%) than previously to the assessment 3015 administered to the subject 3005, and as a result may satisfy the assessment policy. If the assessment policy is satisfied, the assessment administration module 3110 can determine the termination condition.

In some embodiments, responsive to the termination of the stimulus 3025 on the subject 3005, the assessment administration module 3110 can determine an initiation condition for the assessment 3025. The initiation condition may correspond to an initiation or commencement of the assessment 3015 administered to the subject 3005 via the one or more assessment administration devices 3150A-N. The initiation condition may correspond to sending of a control signal specifying the initiation of the assessment 3025 administered via the one or more assessment application devices 3150A-N. In some embodiments, the assessment administration module 3110 can maintain a timer to identify a time elapsed since the termination of the stimulus 3025 applied to the subject 3005 via the one or more stimulus output devices 3155A-N. The assessment administration module 3110 can determine whether the time elapsed since the termination of the stimulus 3025 is greater than a time threshold. The time threshold may correspond to the time duration at which neural oscillations of the nervous system 3010 of the subject 3005 are restored to a non-excited state or normal state (e.g., without application of the stimulus 3025). If the time elapsed since the termination of the stimulus 3025 is greater than the time threshold, the assessment administration module 3110 can identify the initiation condition and can generate a new control signal to send to the one or more assessment administration devices 3150A-N to initiate administration of the assessment 3015.

Figure 33:
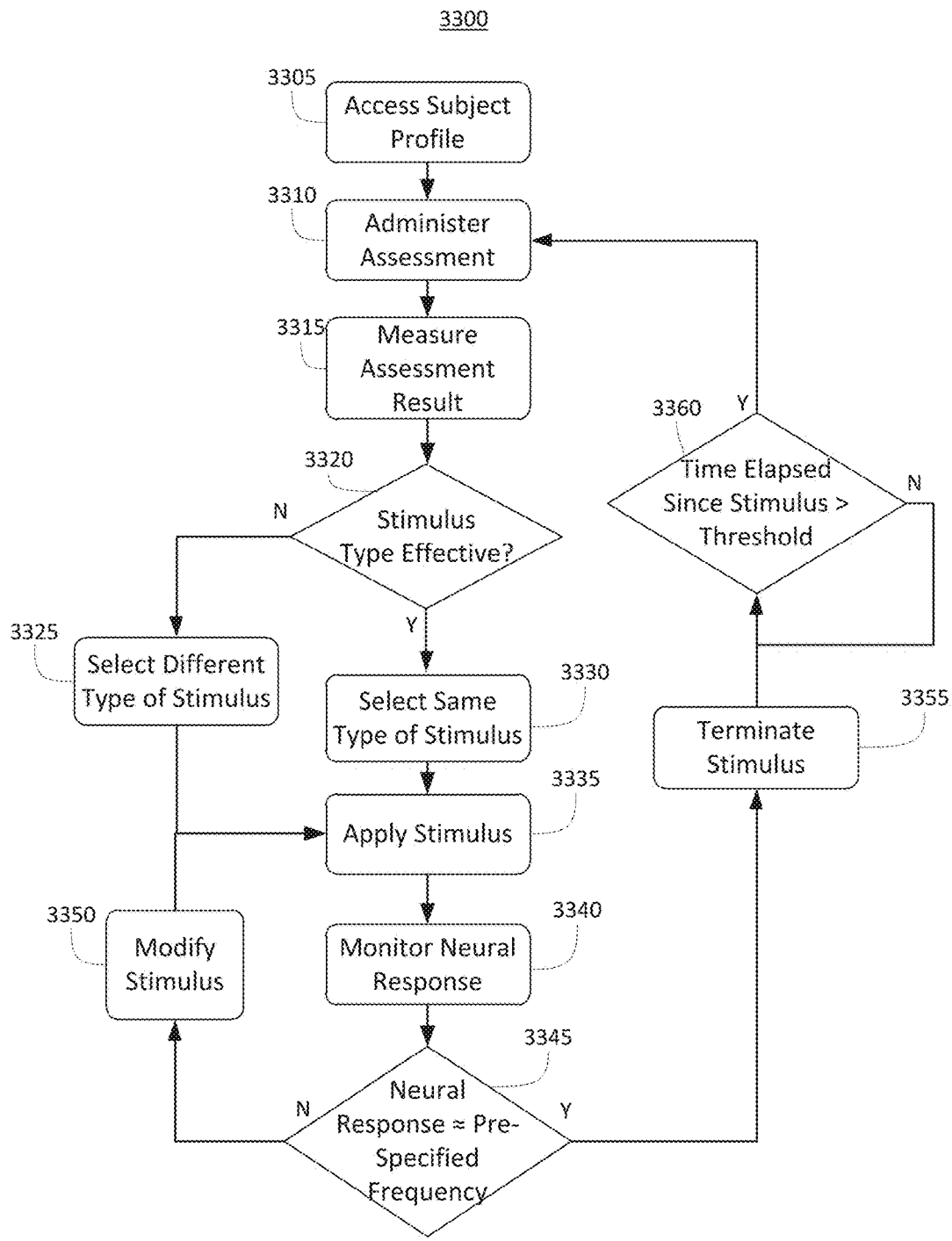
FIG. 33 is a flow diagram depicting a method of providing assessments for neural stimulation on a subject in response to stimulation.

FF. Methods of Performing Assessments on a Subject in Response to Neural Stimulation Referring now to FIG. 33, FIG. 33 is a flow diagram depicting a method 3300 of performing assessments on a subject in response to stimulation, in accordance to an embodiment. The method 3300 can be performed by one or more of the systems, components, modules, or elements depicted in FIGS. 31 and 32, including the CAS 3105. In brief overview, at block 3305, the CAS can access a subject profile for a subject. At block 3310, the CAS can administer an assessment to the subject. At block 3315, the CAS can measure an assessment result of the subject. At block 3320, the CAS can determine whether a type of stimulus applied to the subject is effective. At block 3325, if the stimulus type is determined not to be effective, the CAS can select a different type of stimulus to apply to the subject. At block 3330, if the stimulus type is determined to be effective, the CAS can select the same type of stimulus to apply to the subject. At block 3335, the CAS can apply the selected stimulus to the subject. At block 3340, the CAS can monitor a neural response of the subject. At block 3345, the CAS can determine whether a maximum frequency of the neural response is approximately equal to the specified frequency. At block 3350, if the maximum frequency of the neural response is not approximately equal to the specified frequency. CAS can modify the stimulus, and the CAS can repeat the functionalities of blocks 3335-3345. At block 3355, if the maximum frequency of the neural response is approximately equal to the specified frequency, the CAS can terminate the application of the stimulus on the subject. At block 3360, the CAS can determine whether the time elapsed since the termination of the stimulus is greater than a threshold. If the time elapsed since the termination of the stimulus is greater than the threshold, the CAS can repeat the functionalities of blocks 3305-3360. If the time elapsed since the termination of the stimulus is less than or equal to the threshold, the CAS can repeat the functionality of block 3355 until otherwise. The CAS can repeat blocks 3305-3360 any number of times and execute the functionalities of blocks 3305-3360 in any sequence.

At block 3305, the CAS can access a subject profile for a subject. To build the subject profile, the CAS may, for example, prompt the subject to complete an evaluation intake form. The form may have questionnaires concerning health, physical activities, habits, traits, allergies, and medical conditions, among others. The form may have questions about recent physiological status of the subject (e.g., body temperature, pulse rate, stress, etc.) The form may have questionnaires regarding substance intake by the subject (e.g., smoking, drinking, coffee, pharmacological agents, etc.) In some embodiments, the subject using the CAS may be using or under the effect of one or more pharmacological agents. The pharmacological agents may reduce side effects, such as migraines and pain, from the administration of the assessment to the subject or the application of the stimulus on the subject. The pharmacological agents may include topical ointments, analgesics, and other stimulants, such as caffeine. The evaluation intake form may be used to identify the state of the subject at which the stimulus is most effective in changing a cognitive function or state of the subject.

At block 3310, the CAS can administer an assessment to the subject. The CAS may determine which type of assessment to administer based on the evaluation intake form completed by the subject. In accordance with the determined type of assessment, the CAS may administer the assessment using assessment application devices, such as displays, loudspeakers, or mechanical devices. The CAS can administer various types of assessments in any sequence. For example, the CAS may administer an auditory assessment, then a visual assessment, then a peripheral nerve assessment, etc.

At block 3315, the CAS can measure an assessment result of the subject. The subject may actively respond to the administered assessment. The CAS can measure the assessment response by the subject with various measurement devices, such as EEG monitoring devices, MEG monitoring devices. EOG monitoring devices, accelerometers, microphones, videos, cameras, gyroscopes, among others. The CAS can determine an assessment score based on the measurements by the various measurement devices.

At block 3320, the CAS can determine whether a type or modality of stimulus applied to the subject is effective. In some instances, a stimulus (e.g., auditory, visual, etc.) may have been applied to the subject, prior to the assessment. Furthermore, the subject may have taken various assessments multiple times. The CAS can identify a previously applied stimulus to the subject from the subject profile database. Using the measurements, the CAS can determine whether a change in assessment score for the subject is greater than or equal to a threshold. If the change in assessment score is greater than or equal to the threshold, the CAS can determine that the type of stimulus applied to the subject is effective. If the change in the assessment score is less than the threshold, the CAS can determine that the type of stimulus applied to the subject is ineffective.

At block 3325, after determining whether or not the stimulus type administered for assessment is effective in inducing neural oscillations at the target frequency, the CAS can select a different type of stimulus to apply to the subject to determine whether or not the different type of stimulus is effective. For example, if the first stimulus applied on the subject is an auditory stimulus and was determined to be not effective, the CAS can select a visual stimulus for the next stimulus to apply. The CAS can select the different type of stimulus to apply based on a stimulus generation policy. The stimulus generation policy may specify a sequence of types of stimuli to apply. For example, the stimulus generation policy may specify that an auditory stimulus is to be applied first, then peripheral nerve stimulus, then visual stimulation At block 3330, if the stimulus type is determined to be effective, the CAS can select the same type of stimulus to apply to the subject. For example, the CAS can identify the previously applied stimulus from the subject profile database. In this manner, various types of stimuli may be applied in any sequence on the nervous system of the subject.

At block 3335, the CAS can apply the selected stimulus to the subject. For example, the CAS can apply the stimulus via a stimulus output device, such as displays, loudspeakers, or mechanical devices. The CAS can identify a particular type of stimulus output device to apply the stimulus to the subject. The stimulus may excite a part of the nervous system of the subject.

At block 3340, the CAS can monitor a neural response of the subject. The CAS can measure the neural response by the subject to the stimulus with various measurement devices, such as EEG monitoring devices, MEG monitoring devices, EOG monitoring devices, among others.

At block 3345, the CAS can determine whether a maximum frequency of the neural response is approximately equal to the specified frequency. The CAS can sample the neural response received from the measurement devices and convert the neural response from a time domain signal to a frequency domain signal.

At block 3350, if the maximum frequency of the neural response is not approximately equal to the specified frequency, the CAS can modify the stimulus, and the CAS can repeat the functionalities of blocks 3335-445. In this manner, the CAS can stimulate the nervous system of the subject at the pre-specified frequency. The CAS can also identify a time elapsed between the first stimulus and the stimulus to result in the stimulation of the nervous system at the pre-specified frequency.

At block 3355, if the maximum frequency of the neural response is approximately equal to the specified frequency, the CAS can terminate the application of the stimulus on the subject. The application of the stimulus may be terminated to measure how long and how much the cognitive functions and state of the nervous system of the subject has changed.

At block 3360, the CAS can determine whether the time elapsed since the termination of the stimulus is greater than a threshold. The threshold may correspond to pause between the application of the stimulus and the next administration of the assessment. In this manner, the CAS may verify whether the effects of the stimulus on the nervous system of the subject are long-lasting. If the time elapsed since the termination of the stimulus is less than or equal to the threshold, the CAS can repeat the functionality of block 3355 until otherwise. If the time elapsed since the termination of the stimulus is greater than the threshold, the CAS can repeat the functionalities of blocks 3305-3360. In this manner, each time the brain is stimulated, the CAS can measure and assess the effect of the stimulation on the cognitive functioning and state of the nervous system of the subject, by administering assessments. From measuring the responses to the assessments, the CAS can also determine a timespan in which the application of the stimulus is most effective. In addition, the effect of each type of stimulus on the cognitive functioning and the state of the nervous system of the subject may be assessed.

Figure 34:
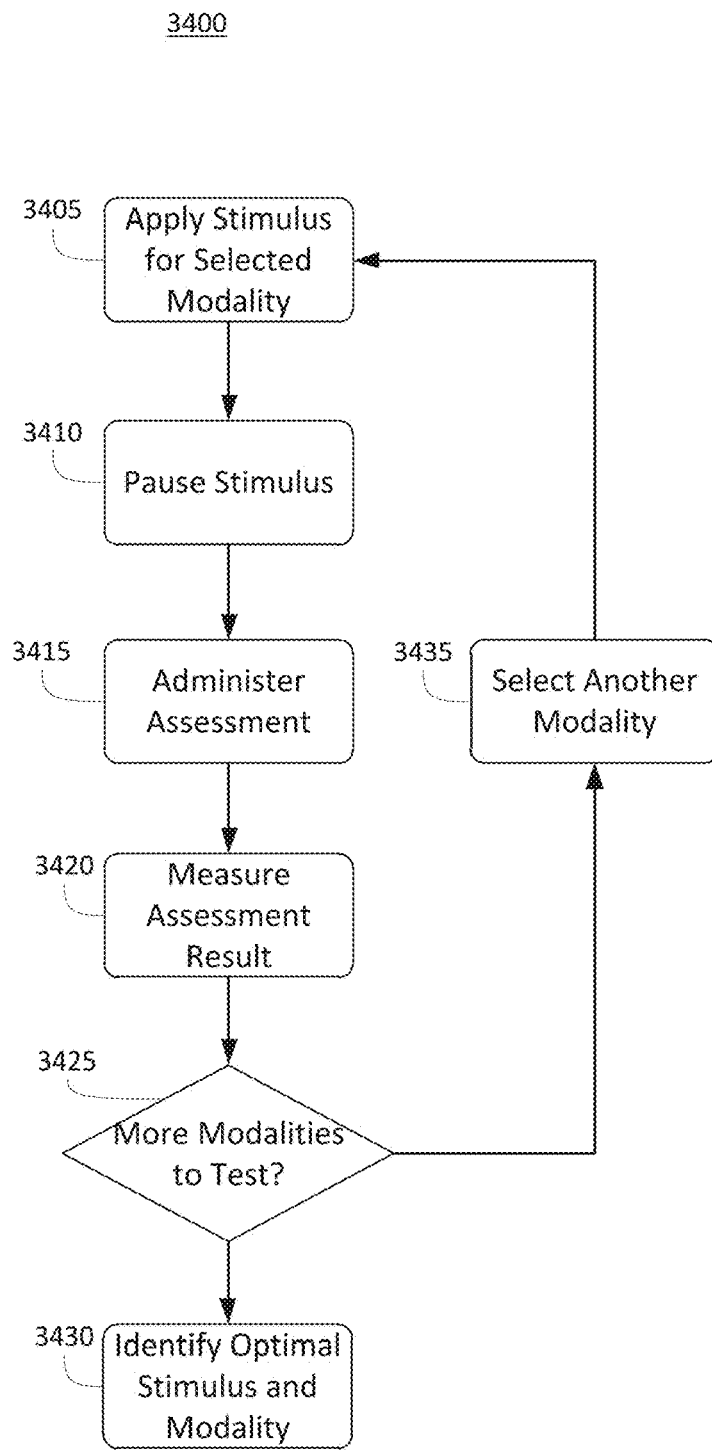
FIG. 34 is a flow diagram depicting a method of providing assessments for neural stimulation on a subject in response to stimulation.

Referring now to FIG. 34, the method 3400 can be performed by one or more of the systems, components, modules, or elements depicted in FIGS. 31 and 32, including the CAS 3105. In brief overview, at block 3405, the CAS can apply a stimulus for the selected modality. At block 3410, the CAS can pause the stimulus. At block 3415, the CAS can administer an assessment. At block 3420, the CAS can measure assessment result. At block 3425, the CAS can determine whether there are more modalities to test. At block 3430, if there are no more modalities to test, the CAS can identify an optimal stimulus and modality. At block 3435, if there are more modalities to test, the CAS can select another modality. The CAS 3105 can repeat blocks 3405-3435 any number of times and execute the functionalities of blocks 3405-3435 in any sequence.

In further detail, at block 3405, the CAS can apply a stimulus for the selected modality (e.g., visual, auditory, or peripheral nerve, etc.). The CAS can apply the stimulus based on a stimulus generation policy. The stimulus generation policy may specify a type of stimulus (e.g., visual, auditory, etc.), a magnitude of stimulus, a specified frequency or wavelength, and/or a pulse schema or the modulation, among others, for the stimulus to be applied to the nervous system of the subject. The stimulus may cause neurons from one or more portions of the nervous system of the subject to oscillate at a target frequency.

At block 3410, the CAS can pause the stimulus. The CAS can determine whether the nervous system of the subject is sufficiently entrained to a target frequency. In response to determining that the subject is sufficient entrained, the CAS can terminate the application of the stimulus for a predefined period of time. The predefined period of time may correspond to an amount of time that the nervous system takes to return to a natural state (e.g., prior to application of the stimulus). In this manner, the CAS can assess whether the effects of the stimulus on the cognitive functioning and state of the subject is long-lasting. In some implementations, the CAS can be configured to provide a stimulus that is designed to cause the nervous system to return to a natural state, for instance, by stimulating the subject with signals at various random, pseudo random or controlled different frequencies.

At block 3415, the CAS can administer an assessment. The assessment may test or evaluate a cognitive function or state of the subject. The assessment may be one of, for example, an N-back task, a serial reaction time test, a visual coordination test, a voluntary movement test, or a force production test, among others.

At block 3420, the CAS can measure the assessment result. While administering the assessment, the CAS can record the result of the assessment (e.g., task response) from the subject. The assessment result may include an assessment score. The assessment score may indicate a performance rate of the subject taking the assessment. By administering the assessment multiple times, the CAS may determine a change in the assessment score through multiple assessments.

At block 3425, the CAS can determine whether there are more modalities to test. The CAS can identify a number of modalities previously assessed. By assessing multiple modalities of the subject, the CAS can administer various assessments and can aggregate assessment results across different modalities.

At block 3430, if there are no more modalities to test, the CAS can identify an optimal stimulus and modality. Using aggregating assessment results, the CAS can identify an optimal stimulus and modality. The CAS can also identify parameters used to generate the stimulus, such as intensity, content, duration, and pulse modulation, among others. The CAS can also identify which parameters correspond to a shortest time to achieve sufficient entrainment in the nervous system of the subject. At block 3435, if there are more modalities to test, the CAS can select another modality. The CAS can repeat blocks 3405-3435 any number of times and execute the functionalities of blocks 3405-3435 in any sequence.

Figure 35A:
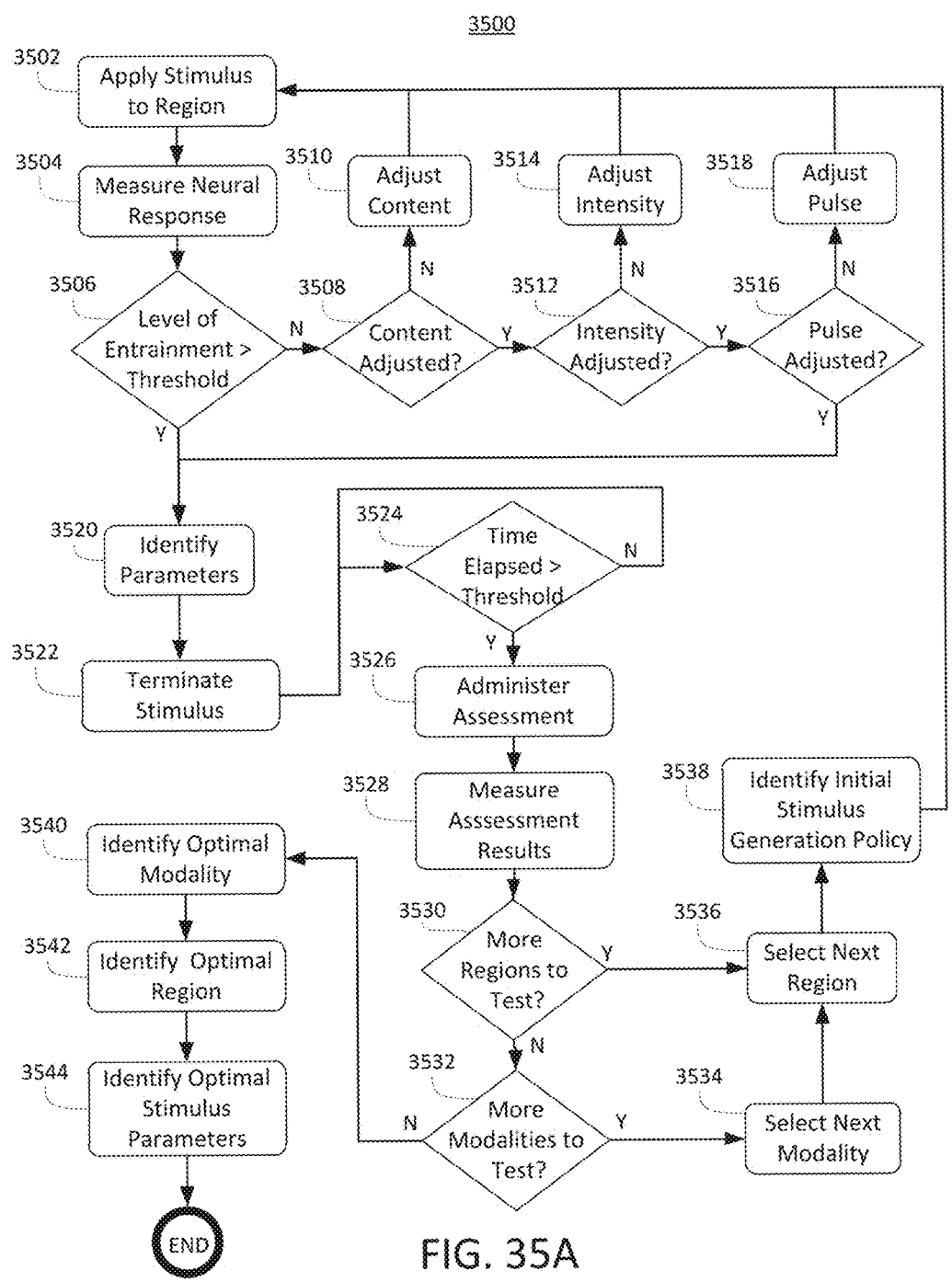
FIG. 35A is a flow diagram depicting a method of providing assessments for neural stimulation on a subject in response to iterative stimulation.

Referring now to FIG. 35A, the method 3500 can be performed by one or more of the systems, components, modules, or elements depicted in FIGS. 31 and 32, including the CAS 3105. In relation to FIG. 34, the method 3500 may be the functionalities of each block 3405-3435 of method 3400 in further detail. In brief overview, at block 3502, the CAS can apply a stimulus to a region. At block 3504, the CAS can measure a neural response. At block 3506, the CAS can determine whether a level of entrainment is greater than a threshold. At block 3508, if the level of entrainment is less than or equal to the threshold, the CAS can determine whether content of the stimulus was previously adjusted. At block 3510, if the content of the stimulus was not previously adjusted, the CAS can adjust the content of the stimulus. At block 3512, if the content of the stimulus was previously adjusted, the CAS can determine whether an intensity of the stimulus was previously adjusted. At block 3514, if the intensity of the stimulus was not previously adjusted, the CAS can determine adjust the intensity. At block 3516, if the intensity of the stimulus was previously adjusted, the CAS can adjust a pulse modulation of the stimulus. At block 3518, if the pulse modulation of the stimulus was previously adjusted, the CAS can adjust the pulse modulation of the stimulus. At block 3520, if the level of entrainment is greater than the threshold, the CAS can identify parameters of the stimulus. At block 3522, the CAS can terminate the application of the stimulus on the subject. At block 3524, the CAS can determine whether an elapsed time since termination is greater than a threshold. At block 3526, if the elapsed time since termination is greater than the threshold, the CAS can administer an assessment to the subject. At block 3528, the CAS can measure assessment results. At block 3530, the CAS can determine whether there are more regions to test. At block 3532, if there are no more regions to test, the CAS can determine whether there are more modalities to test. At block 3534, if there are more modalities to test, the CAS can select a next modality. At block 3536, the CAS can select a next region. At block 3538, the CAS can identify an initial stimulus generation policy. At block 3540, if there are no more modalities to test, the CAS can identify an optimal modality. At block 3542, the CAS can identify an optimal region. At block 3544, the CAS can identify optimal stimulus parameters.

In further detail, at block 3502, the CAS can apply a stimulus to a region of a subject. The region may correspond to any portion of the body of the subject. The stimulus may be one of a visual stimulus, an auditory stimulus, among others. For example, the CAS can apply a light of a particular color in the visible spectrum to the left eye of the subject. The stimulus may be configured to excite the nervous system of the subject at the region to a target frequency.

At block 3504, the CAS can measure a neural response of the subject at the region. The neural response may correspond neurons of the regions firing or oscillating in response to the application of the stimulus. The CAS may measure the neural response of the subject at the region, using EEG or MEG devices, among others, attached or aimed at the region of focus. For example, if a colored light was applied to the left eye of the subject, the CAS can measure the neural response from the visual cortex corresponding to the left eye of the subject.

At block 3506, the CAS can determine whether a level of entrainment is greater than a threshold. Using the measurements from the neural response of the subject at the region, the CAS can determine a power spectrum by calculating the frequency domain of the neural response over a sample window. The CAS can then identify the level of entrainment using the power spectrum of the neural response. The level of entrainment may indicate a number of samples in the frequency domain around the target frequency versus a number of samples at other frequencies. The threshold, to which the level of entrainment may be compared, may represent a threshold number of samples in the power spectrum about and including the target frequency of the stimulus.

In blocks 3508-618, if the level of entrainment is less than the threshold, the CAS can adjust various parameters to adjust or modify the stimulus. The parameters may include content (or type), an intensity, and/or a pulse modulation of the stimulus. At block 3508, the CAS can determine whether content of the stimulus was previously adjusted. For a visual stimulus, for example, the adjusting of the content can include change of color and/or change of shape of the stimulus, among others. For an auditory stimulus, for example, the adjusting of the content can include change of pitch and speech cue, among others. At block 3510, if the content of the stimulus was not previously adjusted, the CAS can adjust the content of the stimulus. At block 3512, if the content of the stimulus was previously adjusted, the CAS can determine whether an intensity of the stimulus was previously adjusted. At block 3514, if the intensity of the stimulus was not previously adjusted, the CAS can determine adjust the intensity. At block 3516, if the intensity of the stimulus was previously adjusted, the CAS can adjust a pulse modulation of the stimulus. At block 3518, if the pulse modulation of the stimulus was previously adjusted, the CAS can adjust the pulse modulation of the stimulus. By iteratively adjusting the parameters used to generate the stimulus, the CAS can later identify the set of parameters to cause the level of entrainment of the subject to increase.

At block 3520, if the level of entrainment is greater than the threshold, the CAS can identify parameters of the stimulus. The parameters may correspond to those that caused the nervous system of the subject to reach sufficient entrainment. The CAS may also identify the region of the subject to which the stimulus was applied. At block 3522, the CAS can terminate the application of the stimulus on the subject. At block 3524, the CAS can determine whether an elapsed time since termination is greater than a threshold. Once the nervous system of the subject is sufficiently entrained to the target frequency, the CAS can then commence assessing the effectives of the stimulation to the cognitive functions and state of the subject. The application of the stimulus may be terminated to measure how long and how much the cognitive functions and state of the nervous system of the subject remain changed thereafter.

At block 3526, if the elapsed time since termination is greater than the threshold, the CAS can administer an assessment to the subject. The CAS can administer any variety of tests or assessments to evaluate changes to the cognitive functioning and state of the subject. The CAS can identify the assessment to administer based on the stimulus applied previously to the subject. The assessment may be configured to particular to the region the stimulus was applied. At block 3528, the CAS can measure assessment results. While administering the assessment, the CAS can receive input from the subject via a measurement device to measure the assessment result. Using the assessment results, the CAS can calculate an assessment score for the subject. In some embodiments, the CAS can skip blocks 3526-628 and may omit the administering of the assessment. In some embodiments, the CAS can analyze the neural response of the subject after the termination of the application of the stimulus as part of the assessment.

At block 3530, the CAS can determine whether there are more regions to test. The CAS can identify which regions of the subject the stimulus has been applied. The CAS can also identify which regions of the subject the assessment has been ministered. At block 3532, if there are no more regions to test, the CAS can determine whether there are more modalities to test. The CAS can identify which modalities or sensory organs (e.g., visual, auditory, etc.) to which the stimulus has been applied. The CAS can identify which modalities or sensory organs (e.g., visual, auditory, etc.) to which the assessment has been applied. At block 3534, if there are more modalities to test, the CAS can select a next modality. At block 3536, the CAS can select a next region. At block 3538, the CAS can identify an initial stimulus generation policy. The initial stimulus generation policy can specify parameters for generating the stimulus to apply to the subject. In this manner, the CAS can apply various stimuli and administer various assessments to different regions of the subject. The CAS can also aggregate assessment measurements from the different modalities and different regions of the subject.

At block 3540, if there are no more modalities to test, the CAS can identify an optimal modality. At block 3542, the CAS can identify an optimal region. At block 3544, the CAS can identify optimal stimulus parameters (e.g., content, intensity, pulse modulation, etc.). By aggregating the assessment measurements from the different modalities and different regions of the subject, the CAS can identify the optimal modality, the optimal region, and the optimal stimulus parameters. The optimal modality, the optimal region, and the optimal stimulus parameters may correspond to those that lead to the optimal (e.g., greatest) increase in the assessment score of the score. In some embodiments, the CAS may determine an optimal sequence of the stimulus. For example, the CAS may determine the optimal sequence of the stimulus to be a visual stimulus to the right eye of the subject, followed by an auditory stimulus to the left ear of the subject, and followed by an electrical current applied to a neck of the subject. In this manner, the CAS may increase or improve the cognitive functions or state of the subject.

Figure 35B:
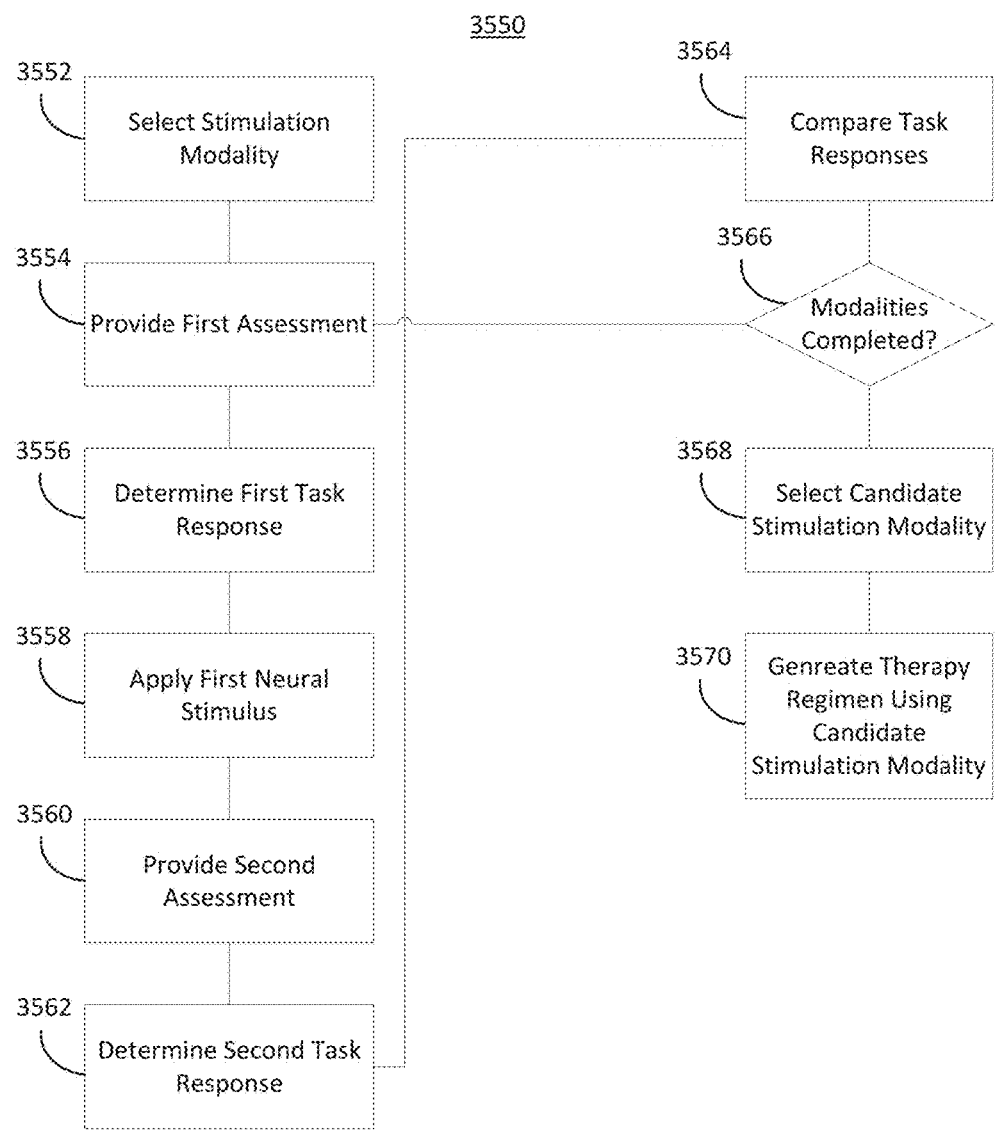
FIG. 35B is a flow diagram depicting a method for generating therapy regimens based on comparison of assessments for different stimulation modalities.

Referring now to FIG. 35B, a method 3550 for generating therapy regimens based on comparisons of assessments for different stimulation modalities is shown according to an embodiment. The method 3550 can be performed by one or more of the systems, components, modules, or elements depicted in FIGS. 31 and 32, including the CAS 3105. In brief overview, at block 3552, the CAS can select a first stimulation modality. At block 3554, the CAS can provide a first assessment to the subject. At block 3556, the CAS can determine a first task response. At block 3558, the CAS can apply a first neural stimulus. At block 3560, the CAS can provide a second assessment. At block 3562, the CAS can determine a second task response. At block 3564, the CAS can compare the first and second task responses. At block 3566, the CAS can determine if each modality has been completed, returning to block 3554 if additional modalities are to be executed. At block 3568, the CAS can select a candidate stimulation modality. At block 3570, the CAS can generate a therapy regimen using the candidate stimulation modality.

At block 3552, the CAS can select a stimulation modality. The stimulation modality can be at least one of an auditory stimulation modality, a visual stimulation modality and a peripheral nerve stimulation modality.

At block 3554, the CAS can provide a first assessment to the subject. The first assessment may include at least one of an N-back test, a serial reaction time test, a visual coordination test, a voluntary movement test, or a force production test.

At block 3556, the CAS can determine a first task response. The first task response may be determined based on the first assessment. The first task response may be a first score of the first assessment.

At block 3558, the CAS can apply a first neural stimulus. The first neural stimulus can be applied using the selected stimulation modality. The first neural stimulus may be applied at a predetermined frequency.

At block 3560, the CAS can provide a second assessment. The second assessment may be of a same type as the first assessment (e.g., a same at least one of an N-back test, a serial reaction time test, a visual coordination test, a voluntary movement test, or a force production test). The second assessment may be provided subsequent to termination of the first neural stimulus.

At block 3565, the CAS can determine a second task response. The second task response may be determined based on the second assessment. The second task response may be a second score of the first assessment. The second task response may be indicative of a change in neural activity of the subject. At 3570, the CAS can compared the first task response to the second task response, such as to determine whether the second task response indicates a particular neural activity response of the subject.

At block 3566, the CAS can determine whether each desired stimulation modality has been executed (e.g., by providing the first assessment, determining the first task response, applying the first neural stimulus, providing the second assessment, determining the second task response, and comparing the task responses for the modality). If each desired stimulation modality has not been executed, then the providing the first assessment, determining the first task response, applying the first neural stimulus, providing the second assessment, determining the second task response, and comparing the task responses can be executed for the remaining desired stimulation modalities.

If each desired stimulation modality has been executed, then at block 3568, the CAS can select a candidate stimulation modality. For example, the candidate stimulation modality can be selected from amongst the auditory stimulation modality, the visual stimulation modality, and the peripheral nerve stimulation modality, based on the comparisons of the first and second task responses. In some embodiments, the CAS selects the candidate stimulation modality by selecting the modality associated with at least one of a highest increase in score of the second assessment relative to the first assessment, or a highest score of the second assessment. In some embodiments, the CAS selects the candidate stimulation modality by selecting at least one modality associated with at least one of an increase in score of the second assessment which is greater than an increase threshold, or a score of the second assessment being greater than a score threshold; as such, multiple candidate stimulation modalities may be selected, as long as their scores satisfy the associated thresholds.

At block 3570, the CAS can generate a therapy regimen using the candidate stimulation modality. The therapy regimen may include applying one or more neural stimuli based on parameters of the candidate stimulation modality.

In some embodiments, the CAS can apply a placebo stimulation to determine whether one or more of the candidate neural stimuli should not be used to generate the therapy regimen (e.g., if the candidate neural stimuli were selected for the therapy regimen based on a false positive). The placebo stimulation can be at least one of the auditory, visual, or peripheral nerve stimulation (e.g., corresponding to the modalities of the first neural stimuli). The CAS can select a third neural stimulus including at least one of an auditory stimulation modality, a visual stimulation modality, or a peripheral stimulation modality for the third neural stimulus. The CAS can set an amplitude of the third neural stimulus to be less than a placebo threshold amplitude. The CAS can provide a third assessment to the subject, and determine a third task response based on the third assessment. The CAS can apply the third neural stimulus, and subsequent to applying the third neural stimulus, provide a fourth assessment to the subject. The CAS can determine a fourth task response based on the fourth assessment. The CAS can compare the fourth task response to the third task response to determine whether the fourth task response indicates the particular neural activity response of the subject. Responsive to the fourth task response indicating the particular neural activity response, the CAS can deselect any candidate stimulation modality being of the same modality as the third neural stimulus prior to generating the therapy regimen using the candidate stimulation modality. For example, if the third neural stimulus is an auditory stimulus, the fourth task response indicates the particular neural activity response, and one of the select candidate neural stimuli is an auditory stimulus, the CAS can deselect the auditory stimulus candidate neural stimulus prior to generating the therapy regimen.

GG. Adjusting an External Stimulus to Induce Neural Oscillations Based on Subject Monitoring and Feedback Systems and methods of the present disclosure are directed to adjusting an external stimulus to induce neural oscillations based on subject monitoring and feedback. When the neural oscillations of the brain occur at or around a particular frequency, there may be beneficial effects to one or more cognitive states or functions of the brain of the subject. To ensure that the neural oscillations of the brain occur at or around a particular frequency, the external stimuli provided to, perceived or experienced by the subject may be adjusted, modified, or changed based on measurements of the neural oscillations of the brain as well as other physiological traits of the subject.

To induce neural oscillations in the brain of a subject, external stimuli may be applied to the subject. The external stimuli may be delivered to the nervous system of the subject via the visual system of the subject using visual stimuli, auditory system of the subject using auditory stimuli, among others. The neural oscillations of the brain of the subject may be monitored using electroencephalography (EEG) and magnetoencephalography (MEG) readings. Various other signs and indications (e.g., attentiveness, physiology, etc.) from the subject may also be monitored while applying the external stimuli. These measurements may then be used to adjust, modify, or change the external stimuli to ensure that the neural oscillations are entrained to the specified frequency. The measurements may also be used to determine whether the subject is receiving the external stimuli.

Neural oscillations occur in humans or animals and includes rhythmic or repetitive neural activity in the central nervous system. Neural tissue can generate oscillatory activity by mechanisms within individual neurons or by interactions between neurons. Oscillations can appear as either oscillations in membrane potential or as rhythmic patterns of action potentials, which can produce oscillatory activation of post-synaptic neurons. Synchronized activity of a group of neurons can give rise to macroscopic oscillations, which can be observed by electroencephalography ("EEG"). Neural oscillations can be characterized by their frequency, amplitude, and phase. These signal properties can be observed from neural recordings using time-frequency analysis.

For example, electrodes for an EEG device can measure voltage fluctuations (in the magnitude of microvolts) from currents or other electrical signals within the neurons along the epidermis of the subject. The voltage fluctuations measured by the EEG device may correspond to oscillatory activity among a group of neurons, and the measured oscillatory activity can be categorized into frequency bands as follows: delta activity corresponds to a frequency band from 1-4 Hz; theta activity corresponds to a frequency band from 4-8 Hz; alpha activity corresponds to a frequency band from 8-12 Hz; beta activity corresponds to a frequency band from 13-30 Hz; and gamma activity corresponds to a frequency band from 30-60 Hz. The EEG device may then sample voltage fluctuations picked up by the electrodes (e.g., at 120 Hz-2000 Hz or randomly using compressed sensing techniques) and convert to a digital signal for further processing.

The frequency of neural oscillations can be associated with cognitive states or cognitive functions such as information transfer, perception, motor control, and memory. Based on the cognitive state or cognitive function, the frequency of neural oscillations can van. Further, certain frequencies of neural oscillations can have beneficial effects or adverse consequences on one or more cognitive states or functions. However, it may be challenging to synchronize neural oscillations at one or more desired frequencies using external stimulus to provide such beneficial effects or reduce or prevent such adverse consequences.

Brainwave stimulation (e.g., neural stimulation or neural stimulation) occurs when an external stimulus of a particular frequency is perceived by the brain and triggers neural activity in the brain that results in neurons oscillating at a frequency corresponding to the particular frequency of the external stimulation. Thus, neural stimulation can refer to synchronizing neural oscillations in the brain using external stimulation such that the neural oscillations occur at frequency that corresponds to the particular frequency of the external stimulation.

Figure 36:
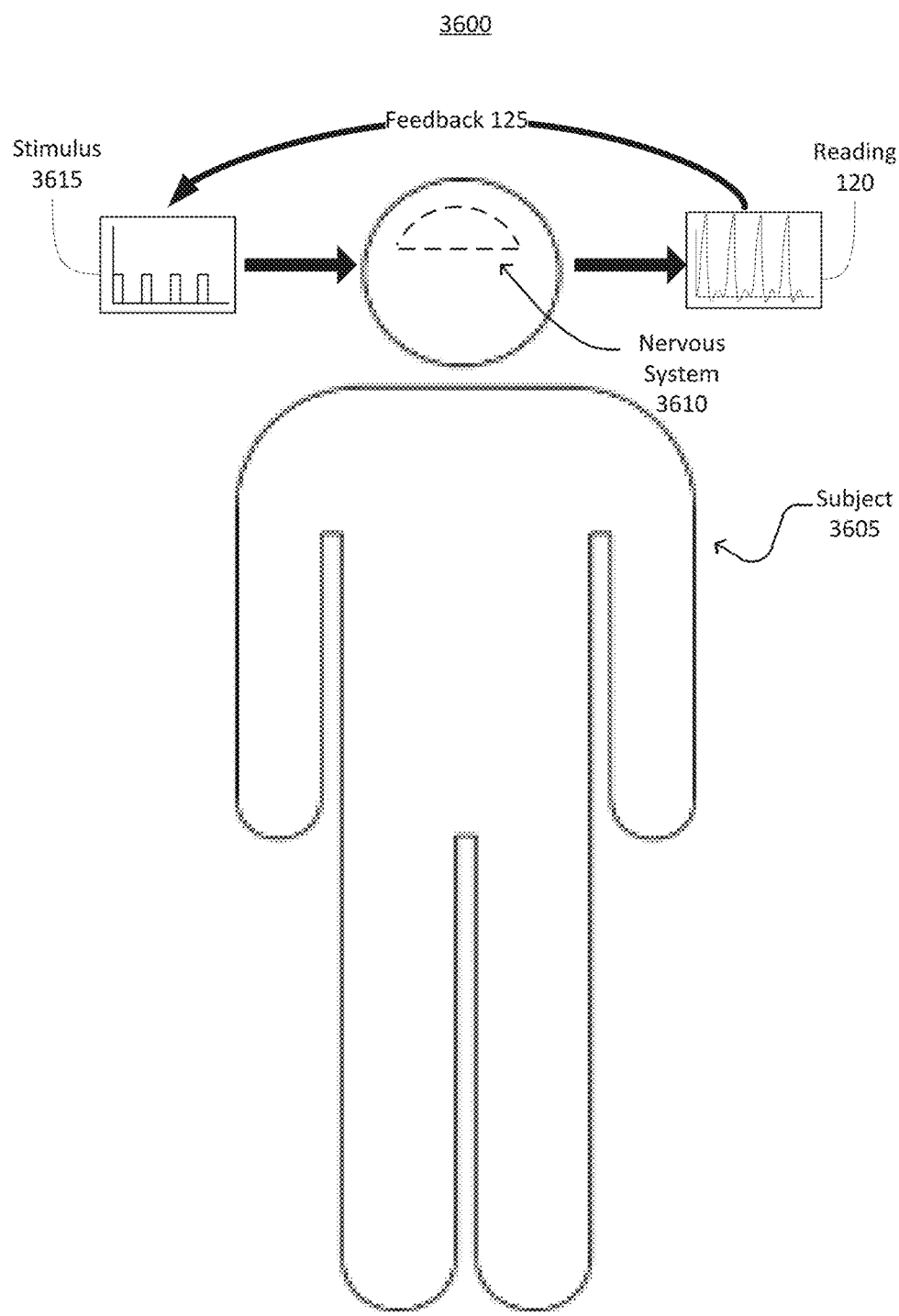
FIG. 36 is a block diagram depicting an environment for adjusting an external stimulus to induce neural oscillations based on measurements on a subject, in connection with the systems and methods described herein.

FIG. 36 is a block diagram depicting an environment 3600 for adjusting an external stimulus to induce synchronized neural oscillations based on measurements on a subject, in accordance to an embodiment. In overview, the environment 3600 can include a subject 3605, a nervous system 3610 (e.g., brain), an external stimulus 3615, a reading 3620, and a feedback 3625. The external stimulus 3615 may be applied by a system to excite or stimulate the nervous system 3610 of the subject 3605. The external stimulus 3615 may be delivered to the nervous system 3610 of the subject 3605 via the visual system of the subject using visual stimuli, auditory system of the subject using auditory stimuli to the subject 3605. The external stimulus 3615 may be generated by a stimulus generator and/or a stimulus output device of the system. The modulation or a pulse scheme of the external stimulus 3615 may be set and dynamically adjusted, so as to cause the neural oscillations of the nervous system 3610 of the subject 3605 to occur at a particular or specified frequency.

Upon applying the stimulus 3615 to induce neural activity at the central nervous system 3610 of the subject 3605, the subject response may be measured or captured in the form of the reading 3620. The reading 3620 may be of the neural response (or evoked response) of the nervous system 3610 of the subject 3605, and may be measured using EEG or MEG, among other devices. The reading 3620 may also be of the subject attentiveness or of the subject physiological status of the subject 3605, and may be detected using electrooculography (EOG), accelerometer, gyroscope, cameras, among other devices. Other responses, characteristics, and traits of the subject 3605 may be monitored in the environment 3600.

From the reading 3620, the system may determine that the nervous system 3610 of the subject 3605 is not stimulated to the specified frequency. From the reading 3620, the system may determine that the subject 3605 is not attentive or otherwise not responding to the stimulus 3615 applied to the subject 3605. In either event, the reading 3620 may then be used by the system to generate the feedback signal 3625 to adjust, change, or modify the stimulus 3615, so as to entrain the nervous system 3610 of the subject 3605 to the specified frequency. Adjustments to the stimulus 3615 may include increasing or decreasing the intensity of the stimulus 3615, increasing or decreasing the intervals of the modulation or pulse scheme of the stimulus 3615, altering the pulse shape of the stimulus 3615, changing a type of stimulus 3615 (e.g. from visual to auditory), and/or terminating the application of the stimulus 3615.

Figure 37:
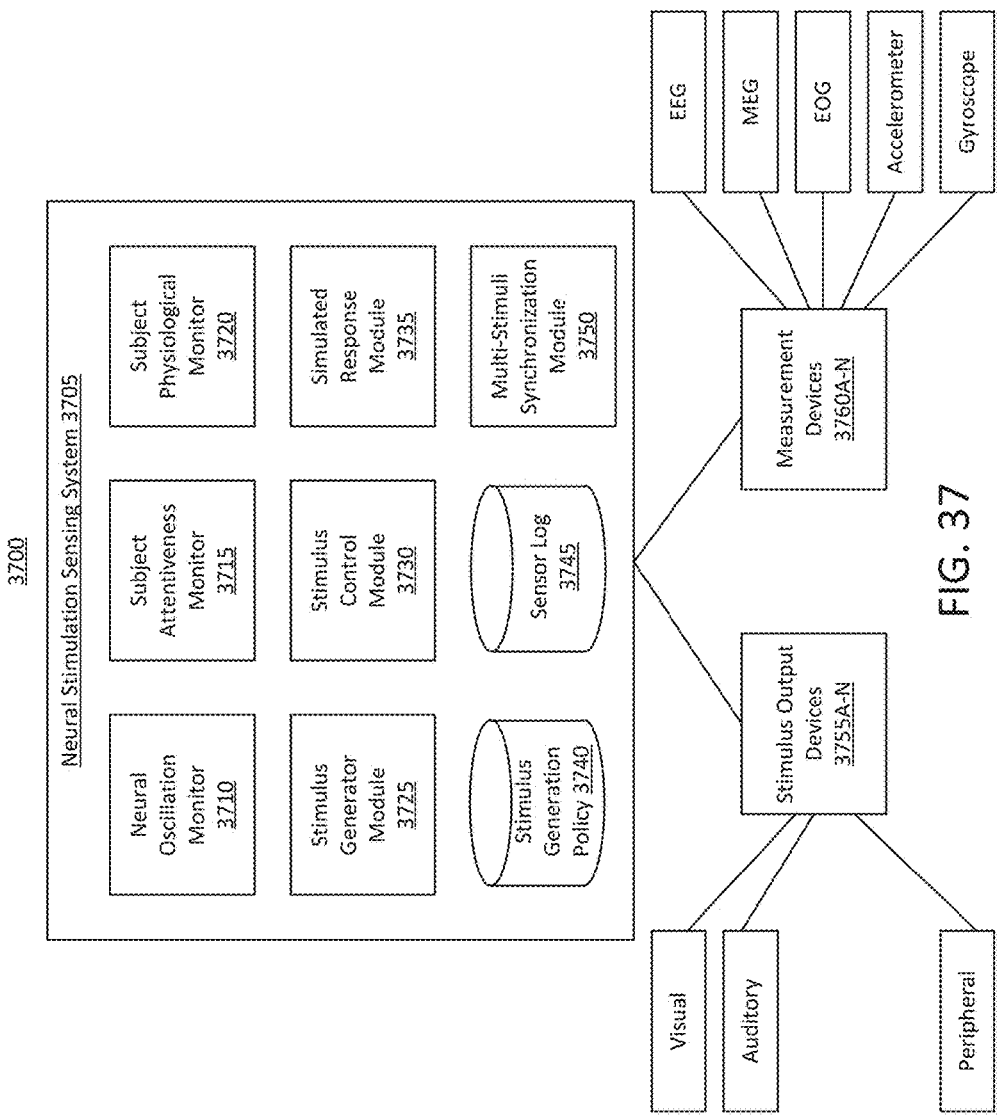
FIG. 37 is a block diagram depicting a system for neural stimulation sensing, in accordance to an embodiment.

Referring now to FIG. 37, FIG. 37 is a block diagram depicting a system 3700 for neural stimulation sensing, in accordance to an embodiment. The system 3700 can include a neural stimulation sensing system 3705. In brief overview, the neural stimulation sensing system ("NSSS") 3705 can include, access, interface with, or otherwise communicate with one or more of a neural oscillation monitor 3710, a subject attentiveness monitor 3715, a subject physiological monitor 3720, a stimulus generator module 3725, a stimulus control module 3730, a simulated response module 3735, a stimulus generation policy database 3740, a sensor log 3745, a multi-stimuli synchronization module 3750, one or more stimulus output devices 3755A-N, and one or more measurement devices 3760A-N. The neural oscillation monitor 3710, the subject attentiveness monitor 3715, the subject physiological monitor 3720, the stimulus generator module 3725, the stimulus control module 3730, the simulated response module 3735, the multi-stimuli synchronization module 3750 can each include at least one processing unit or other logic device such as programmable logic array engine, or module configured to communicate with the stimulus generation policy database 3740 and/or the sensor log 3745. The neural oscillation monitor 3710, the subject attentiveness monitor 3715, the subject physiological monitor 3720, the stimulus generator module 3725, the stimulus control module 3730, the simulated response module 3735, the multi-stimuli synchronization module 3750 can be separate components, a single component, or a part of the NSSS 3705. The system 3700 and the components therein, such as the NSSS 3705, may include hardware elements, such as one or more processors, logic devices, or circuits. The system 3700 and the components therein, such as the NSSS 3705, can include one or more hardware or interface component depicted in system 3700 in FIGS. 7A and 7B. The system 3700 and the components therein, such as the NSSS 3705, the one or more stimulus generators 3755A-N, and the one or more measurement devices 3760A-N can be communicatively coupled to one another, using one or more wireless protocols such as Bluetooth, Bluetooth Low Energy, Zig-Bee, Z-Wave, IEEE 802, Wi-Fi, 3G, 4G, LTE, near field communications ("NFC"), or other short, medium or long range communication protocols, etc.

In further detail, the NSSS 3705 can include at least one stimulus generator module 3725. The stimulus generator module 3725 can be communicatively coupled to the one or more stimulus output devices 3755A-N and to the stimulus control module 3730. The stimulus generator module 3725 can be designed and constructed to interface with the one or more stimulus output devices 3725A-N to provide a control signal, a command, instructions, or otherwise cause or facilitate the one or more stimulus output devices 3725A-N to generate the stimulus 3615, such as a visual stimulus, an auditory stimulus, among others. The stimulus 3615 may be controlled or modulated as a burst, a pulse, a chirp, a sweep, or other modulated fields having one or more predetermined parameters. The one or more predetermined parameters may define the pulse schema or the modulation of the stimulus 3615. The stimulus generator module 3725 can control the stimulus 3615 outputted by the one or more stimulus output devices 3755A-N according to the one or more defined characteristics, such as magnitude, type (e.g., auditory, visual, etc.), direction, frequency (or wavelength) of the oscillations of the stimulus 3615.

The one or more stimulus output devices 3755A-N may include a visual source, such as one or more cathode ray tubes (CRT), liquid crystal displays (LCD), a plasma display panels (PDP), incandescent light bulbs, and light emitting diodes (LED), or any other device, among others, designed to generate light within the visual spectrum to apply to the visual system of the subject 3605. The one or more stimulus output devices 3755A-N may include an auditory source, such as a loudspeaker, dynamic speaker, headphones, temple transducer, or any type of electroacoustic transducer, among others, designed or configured to generate soundwaves to apply to the auditory system of the subject 3605. The one or more stimulus output devices 3755A-N may include an electric current source, such as an electroconvulsive device or machine designed or configured to apply an electric current to the subject 3605.

The NSSS 3705 can include at least one neural oscillation monitor 3710, at least one subject attentiveness monitor 3715, and/or at least one subject physiological monitor 3720. In overview, the neural oscillation monitor 3710 can measure a neural response of the subject 3605 to the stimulus 3615. The subject attentiveness monitor 3715 can detect whether the subject 3605 is attentive while the stimulus 3615 is applied to the subject 3605. The subject physiological monitor 3720 can measure a physiological status (e.g., heartrate, blood pressure, breathing rate, perspiration, etc.) of the subject 3605 to the stimulus 3615. One or more of the neural oscillation monitor 3710, the at least one subject attentiveness monitor 3715, and/or the at least one subject physiological monitor 3720 can be communicatively coupled to the stimulus control module 3730, the simulated response module 3735, the multi-stimuli synchronization module 3750, and/or the one or more measurement devices 3760A-N. One or more of neural oscillation monitor 3710, the at least one subject attentiveness monitor 3715, and/or the at least one subject physiological monitor 3720 receive a measurement of the subject 3605 from the one or more measurement devices 3760A-N. The measurement of the subject 3605 may represent or may be indicative of a response (or lack of response) of the subject 3605 to the stimulus 3615 applied to the subject 3605. The one or more measurement devices 3760A-N may include a brain wave sensors, EEG monitoring devices, MEG monitoring devices, EOG monitoring devices, accelerometers, microphones, videos, cameras, gyroscopes, motion detectors, proximity sensors, photo detectors, temperature sensors, heart or pulse rate monitors, physiological sensors, ambient light sensors, ambient temperature sensors, actimetry sensors, among others, to measure the response of the subject 3605 to the stimulus 3725 and the effect of ambient noise on the stimulus 3725. Each of the one or more measurement devices 3760A-N can sample the measurement of the subject 3605 at any sample rate (e.g., 370 Hz to 370,000 Hz). In some embodiments, each of the one or more measurement devices 3760A-N can sample at randomly in accordance to compressed sensing techniques. One or more of neural oscillation monitor 3710, the at least one subject attentiveness monitor 3715, and/or the at least one subject physiological monitor 3720 can send or relay the measurement of the subject 3605 to the stimulus control module 3730. Additional details of the functionalities of the neural oscillation monitor 3710 in conjunction with the other modules of the NSSS 3705 are discussed herein in Sections BB-DD and GG. Additional details of the functionalities of the subject attentive monitor 3715 are discussed herein in Section EE. Additional details of the functionalities of the subject physiological monitor 3720 are discussed herein in Section FF.

The NSSS 3705 can include a simulated response module 3735. The simulated response module 3735 can receive an input from one or more measurement devices 3760A-N. The simulated response module 3735 can maintain a model to generate a simulated response of the subject 3605 to the stimulus 3615 based on the stimulus 3615 and any ambient noise measured by the one or more measurement devices 3760A-N. The stimulated response may represent or may be indicative of a predicted or simulated response of the subject 3605 to the stimulus 3615. The simulated response may be at least one of a simulated neural response, simulated attentiveness, or simulated physiological response. The simulated response module 3735 can send or relay the simulated response to at least one of the neural oscillation monitor 3710, the subject attentiveness monitor 3715, and the subject physiological monitor 3720. Additional details of the functionalities of the simulated response module 3735 in operation with the other components of NSSS 3705 are described herein in reference to FIGS. 3-11.

The NSSS 3705 can include at least one stimulus control module 3730. The stimulus control module 3730 can be communicatively coupled to the stimulus generator module 3725, to the stimulus generation policy database 3740, and to at least one of the neural oscillation monitor 3710, the subject attentiveness monitor 3715, and the subject physiological monitor 3720. The stimulus control module 3730 can receive inputs from at least one of the neural oscillation monitor 3710, the subject attentiveness monitor 3715, and the subject physiological monitor 3720. Using the received inputs, the stimulus control module 3730 can adjust the control signal, command, or instructions used by the stimulus generator module 3725 to cause or facilitate the one or more stimulus output devices 3725A-N to adjust the stimulus 3615. Additional details of the functionalities of the stimulus control module 3730 in operation in conjunction with the other components of NSSS 3705 are described herein in reference to FIGS. 3-11.

HH. Systems for Sensing Neural Oscillations Induced by External Stimuli

Figure 38:
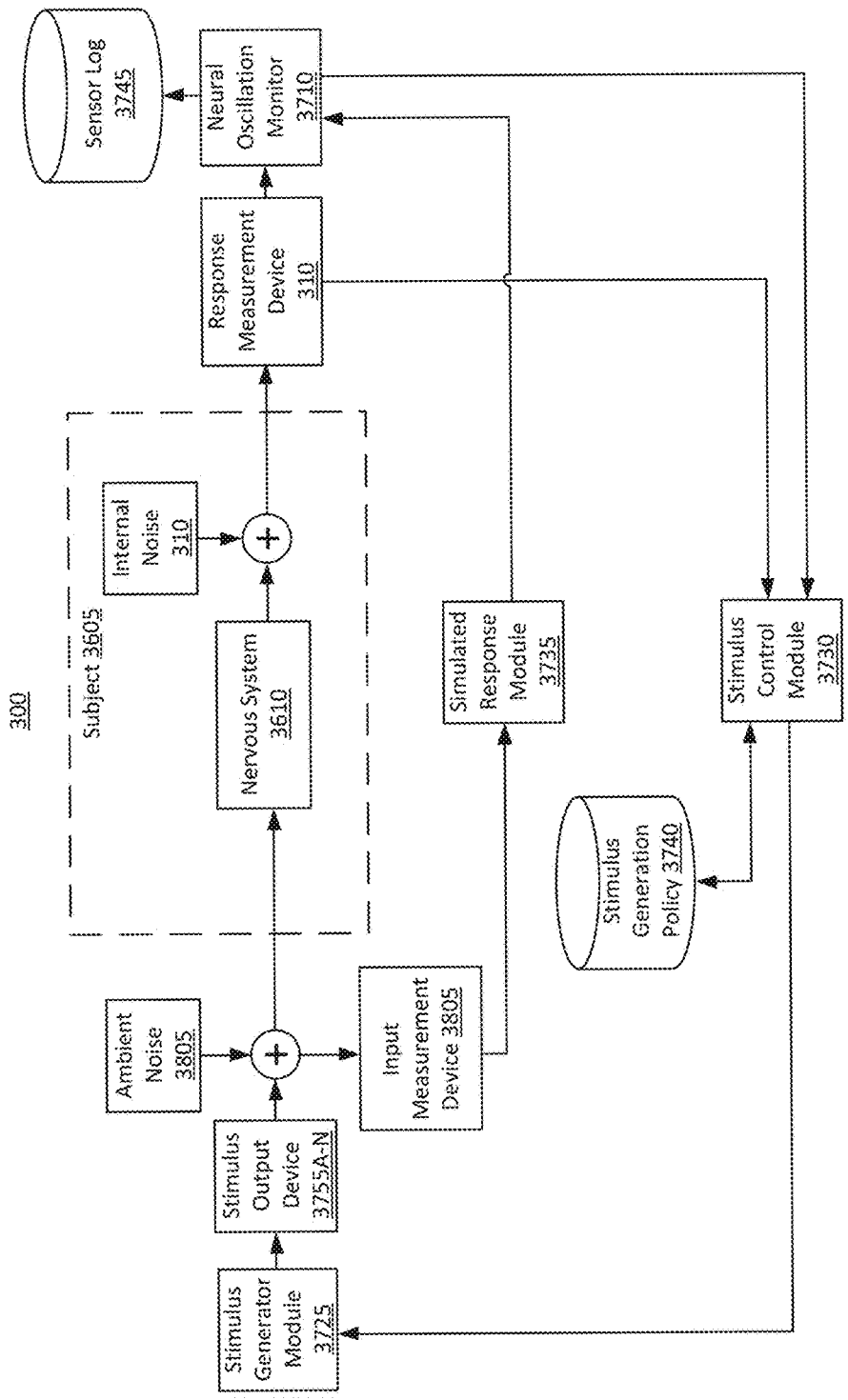
FIG. 38 is a block diagram depicting a system for sensing neural oscillations induced by an external stimulus, in accordance to an embodiment.

Referring now to FIG. 38, FIG. 38 is block diagram a system 3800 for sensing neural oscillations induced by the external stimulus 3615, in accordance to an embodiment. In brief overview, the system 3800 can include the stimulus generator module 3725, the one or more stimulus output devices 3755A-N, the input measurement device 315 (e.g., one or more measurement devices 3760A-N), the response measurement device 320 (e.g., one or more measurement devices 3760A-N), the simulated response module 3735, the neural oscillation monitor 3710, the sensor log 3745, the stimulus control module 3730, and the stimulus generation policy database 3740. The one or more components of the system 3800 may be in any environment or across multiple environments, such as in a treatment center, a clinic, a residence, an office, a pharmacy, or any other suitable location. In addition to the stimulus 3615, the subject 3605 may be exposed to or be affected by ambient noise 3805 originating outside the sensory system of the subject 3605. There may also be internal noise 310 originally within the sensory system of subject 3605 that may also affect the nervous system 3610 (e.g., any visual, auditory, or peripheral nerve stimulation originating within the subject 3605).

In context of FIG. 38, the stimulus generator module 3725 can transmit or relay a control signal to the stimulus output devices 3755A-N to generate the stimulus 3615 to apply to the nervous system 3610 of the subject 3605. The stimulus generator module 3725 can generate the control signal. The control signal may be a continuous-time signal or a periodic discrete signal. The control signal can specify one or more defined characteristics. The stimulus generator module 3725 can set or define the one or more defined characteristics for the control signal. The one or more defined characteristics may be set to excite or stimulate the nervous system 3610 (or in some implementations, the brain) of the subject 3605 to a specified frequency. The one or more defined characteristics can include a magnitude, a type (e.g., auditory, visual, etc.), a direction, a pulse modulation scheme, a frequency (or wavelength) of the oscillations of the stimulus 3615. In some embodiments, the stimulus generator module 3725 can identify a subset of the one or more stimulus output devices 3755A-N based on the one or more defined characteristics. For example, if the one or more defined characteristics specify the type of stimulus 3615 as visual, the stimulus generator module 3725 can identify the subset of the one or more stimulus output devices 3755A-N corresponding to an electronic display. Responsive to identifying the subset, the stimulus generator module 3725 can transmit or relay the control signal to the subset of the one or more stimulus output devices 3755A-N.

In response to receiving the control signal from the stimulus generator module 3725, the stimulus output devices 3755A-N can generate the stimulus 3615 to apply to the subject 3605. The stimulus output devices 3755A-N may include a visual source, an auditory source, among others. The stimulus 3615 applied to the subject 3605 may be at least one of a visual stimulus originating from the visual source or an auditory stimulus originating from the auditory source.

The stimulus output devices 3725A-N each can receive the control signal from the stimulus generator module 3725. The stimulus output devices 3725A-N each can identify or access the defined characteristics from the received control signal. The stimulus output devices 3725A-N each can determine whether the stimulus 3615 is to be outputted or applied to the subject 3605 based on the defined characteristics. For example, the control signal may specify that the stimulus 3615 is to be an auditory stimulus. In such a case, stimulus output devices 3725 corresponding to auditory stimulation will use the control signal to output the audio stimulation based on the defined characteristics included in the control signal while other stimulation output devices corresponding to other stimulation modalities (e.g., visual) may be configured to not generate an output.

The input measurement device 315 can measure the stimulus 3615 and the ambient noise 3805. The first measurement device(s) 3760 can include a camera, a microphone, a force meter, gyroscope, accelerometer, or any suitable device, to measure the effect of the ambient noise 3805 on the stimulus 3615. The input measurement device 315 can transmit the measurement of the stimulus 3615 applied to the subject 3605 and the ambient noise 3805 to the simulated response module 3735. In some embodiments, the input measurement device 315 can transmit the measurements of the stimulus 3615 and the ambient noise 3805 to the neural oscillation monitor 3710.

In some implementations, ambient noise or signals in the environment can be captured or collected via sensors positioned on or around the subject. Depending on the type and/or characteristics of stimulation being provided to the subject, different sensors may be utilized to detect ambient noise. For instance, in implementations where audio stimulation is provided to the subject, the subject may wear a device or a component that includes one or more microphones to record ambient sounds. The microphones can be mounted on a wearable device, such as ear muffs, a headset, etc. The microphones can be strategically positioned at or near a subject's ears to pick up ambient audio signals that may be perceived by the subject. In some implementations, one or more microphones can be positioned on the front, center, back or sides of the head to pick up ambient audio signals that can be used as an input in the system 3800.

In some implementations where the stimulation provided is in the form of visual stimulation, there may be a desire to determine the ambient light to which the subject is exposed. An ambient light sensor can be configured to determine the intensity, brightness or other visual characteristics of the ambient light. The sensor measurements can be provided as input into the system 3800. In some implementations, the sensor can be positioned on glasses or eyewear that the subject may wear during the visual stimulation. In some implementations, the sensor may be positioned on the device that is delivering the visual stimulation to the subject. In some implementations, the system 3800 can be configured to receive the sensor measurements of multiple sensors to determine the amount of ambient light and the impact the ambient light may have on the stimulation being provided.

As further shown in FIG. 38, the simulated response module 3735 can receive the stimulus 3615 and the ambient noise. The simulated response module 3735 can determine a predicted or simulated neural response of the subject 3605 to the stimulus 3615 with the ambient noise 3805. The simulated response module 3735 can maintain a model for the subject 3605 based on historical response data for one or more subjects, including the subject 3605. The model for the subject 3605 may be a simulated neural response to the type of stimuli (e.g., auditory, visual, etc.). For example, the model for the subject 3605 may specify the neural response of the nervous system 3610 corresponding to the visual cortex may be minimal or otherwise indicate a lack of response to an auditory stimulus. In this example, the model may also specify that the visual cortex of the nervous system 3610 may respond in one manner to one type of visual stimulus character (e.g., color and intensity, duration, etc.) and another manner to another type of visual stimulus character.

In some embodiments, the model for the subject 3605 may be based on one or more parameters of a model generated for the subject or for a group of subjects. The one or more parameters may include any physical characteristic of the subject 3605, such as age, height, weight, heart rate, etc. The one or more parameters may be received from the subject 3605 via a prompt or from the NSSS 3705. In some embodiments, the one or more parameters may be measured, determined, or updated by the one or more measurement devices 3760A-N, prior to application of the stimulus 3615 on the subject 3605. The simulated response module 3735 can continuously determine the predicted or simulated neural response of the subject 3605, as the stimulus 3615 is applied on the subject 3605. The simulated response module 3735 can feed forward or otherwise transmit the predicted or simulated neural response of the subject 3605 to the neural oscillator monitor 3710.

Referring again to FIG. 38, as simulated response module 3735 is generating the predicted or simulated response, the response measurement device 320 can measure the neural response of the nervous system 3610 of the subject 3605 to the stimulus 3615. The response measurement device 320 can also measure any internal noise 310 to the neural response of the nervous system 3610 of the subject 3605. The response measurement device 320 can include an EEG device or an MEG device, or any suitable device, to measure the neural response of the nervous system 3610 of the subject 3605 to the stimulus 3615. The second measurement device(s) 3760B can transmit the neural response of the nervous system 3610 of the subject 3605 to the stimulus 3615 to the neural oscillation monitor 3710 and/or to the stimulus control module 3730.

In response to receiving the measurements from the response measurement device 320, the neural oscillation monitor 3710 as shown in FIG. 38 can monitor neural response of the nervous system 3610 of the subject 3605 in response to the stimulus 3615. The neural oscillation monitor 3710 can apply any number of signal processing techniques to the measurements from the response measurement device 320 to isolate the neural response of the nervous system 3610 to the stimulus 3615 from neural activity corresponding to ambient signals. The neural oscillation monitor 3710 can also apply signal reconstruction techniques to the equally spaced sampled measurements received from the response measurement device 320 to measure or determine the neural response of the nervous system 3610 of the subject 3605. The neural response of the nervous system 3610 may correspond to a combination (e.g., weighted average) of responses by the individual neurons to the stimulus 3615. The neural oscillation monitor 3710 can also apply compressed sensing techniques to the randomly sampled measurements received from the response measurement device 320 to determine the neural response of the nervous system 3610 of the subject 3605.

The neural oscillation monitor 3710 can store, save, or write to the sensor log 3745, while receiving measurements from the response measurement device 320. The neural oscillation monitor 3710 can index each stored measurement response measurement device 320 by which the response measurement device 320. The neural oscillation monitor 3710 can index each stored measurement by each region measured by the response measurement device 320. For example, for each stimulation modalities, different cortices may be more active than others. As further described in FIG. 40, different electrodes may measure different regions of the brain, and the measurements may be indexed by the different regions. The neural oscillation monitor 3710 can index each stored measurement by the one or more defined characteristics used to generate the stimulus 3615 applied to the subject 3605. The storing of the neural response of the subject 3605 onto the sensor log 3745 may be to build a profile of the subject 3605. The sensor log 3745 can log measurement data from the neural oscillation monitor 3710. The sensor log 3745 can include a data structure to keep track of measurement data. For example, the data structure in the sensor log 3745 may be a table. Each entry of the table may include the stimulation modality of the stimulus 3615 (e.g., visual, auditory, etc.), a duration of the stimulus 3615, an intensity of the stimulus 3615, a region of the application of the stimulus 3615 on the body of the subject, a pulse modulation of the stimulus 3615, a neural response reading from the response measurement device 310, and a power spectrum of the neural response of the subject 3605, among others. In addition, the table can include information elicited from the subject about the stimulation, including but not limited to self-reported data. For example, the table can store data regarding subject satisfaction, subject comfort, as well as any side effects experienced, etc. The table can also store information relating to the subject's attentiveness during the stimulation, among others.

The neural oscillation monitor 3710 can determine feedback data to send to the stimulus control module 3730 to adjust the stimulus based on the measurements from the response measurement device 320 and/or the simulated neural response from the simulated response module 3735. Using the measurements from the response measurement device 320 and/or the simulated neural response from the simulated response module 3735, the neural oscillation monitor 3710 can identify one or more artefacts from the measurements of the response measurement device 320. The neural oscillation monitor 3710 can utilize any number of signal processing techniques to identify the one or more artefacts from the measurements of the response measurement device 320. In some embodiments, neural oscillation monitor 3710 can subtract the simulated neural response from the simulated response module 3735 from the measurements from the response measurement device 320. In some embodiments, the neural oscillation monitor 3710 can use blind signal separation techniques (e.g., principal component analysis, independent component analysis, singular value decomposition, etc.) to separate the ambient noise 3805 and the internal noise 310 from the response of the nervous system 3610 to identify the one or more artefacts from the measurements of the response measurement device 320. In some embodiments, the neural oscillation monitor 3710 can apply a filtering technique (e.g., low-pass, band-pass, high-pass, or adaptive filter, etc.) to suppress the effect of internal noise 310 and the ambient noise 3805 in the measurements from the response measurement device 320 to identify the one or more artefacts. The neural oscillation monitor 3710 can transmit the feedback data to the stimulus control module 3730. In some embodiments, the feedback data can include identified one or more artefacts.

Referring again to FIG. 38, responsive to feedback data received from the neural oscillation monitor 3710 and/or measurements from the response measurement device 320, the stimulus control module 3730 can determine an adjustment to the control signal to be generated by the stimulus generator module 3725. The adjustment to the control signal may be a change or a modification to the one or more predefined characteristics, such as the magnitude, the type (e.g., auditory, visual, etc.), the direction, the pulse modulation scheme, the frequency (or wavelength) of the oscillations of the stimulus 3615. The stimulus control module 3730 can determine the adjustment to the control signal based on the stimulus generation policy database 3740. The stimulus generation policy database 3740 can specify the adjustment to the control signal based on the feedback data from the neural oscillation monitor 3710. For example, if the feedback data indicates that the nervous system 3610 of the subject 3605 is firing at a frequency higher than the specific frequency, the stimulus generation policy database 3740 can specify that the stimulus control module 3730 is to set the one or more predefined characteristics such that the stimulus 3615 is at a set of different frequencies. In another example, if the feedback indicates that the neural response of the nervous system 3610 of the subject 3605 to a visual stimuli is null, the stimulus generation policy database 3740 can specify that the stimulus control module 3730 is to set the one or more predefined characteristics such that application of the visual stimuli is terminated and the peripheral nerve stimulus for the stimulus 3615 is to be applied. The stimulus control module 3730 can transmit the adjustment to the stimulus generator module 3725.

Continuing on FIG. 38, upon receipt of the adjustment to control signal from the stimulus control module 3730, the stimulus generator module 3725 can in turn apply the adjustment to the control signal sent to the one or more stimulus output devices 3755A-N. The stimulus generator module 3725 can adjust the one or more predefined characteristics specified in the control signal based on the adjustment received from the stimulus control module 3730. It should be appreciated that the functionalities of the components and modules in system 3800 may be repeated until the nervous system 3610 of the subject 3605 is entrained to the specified frequency.

Figure 39:
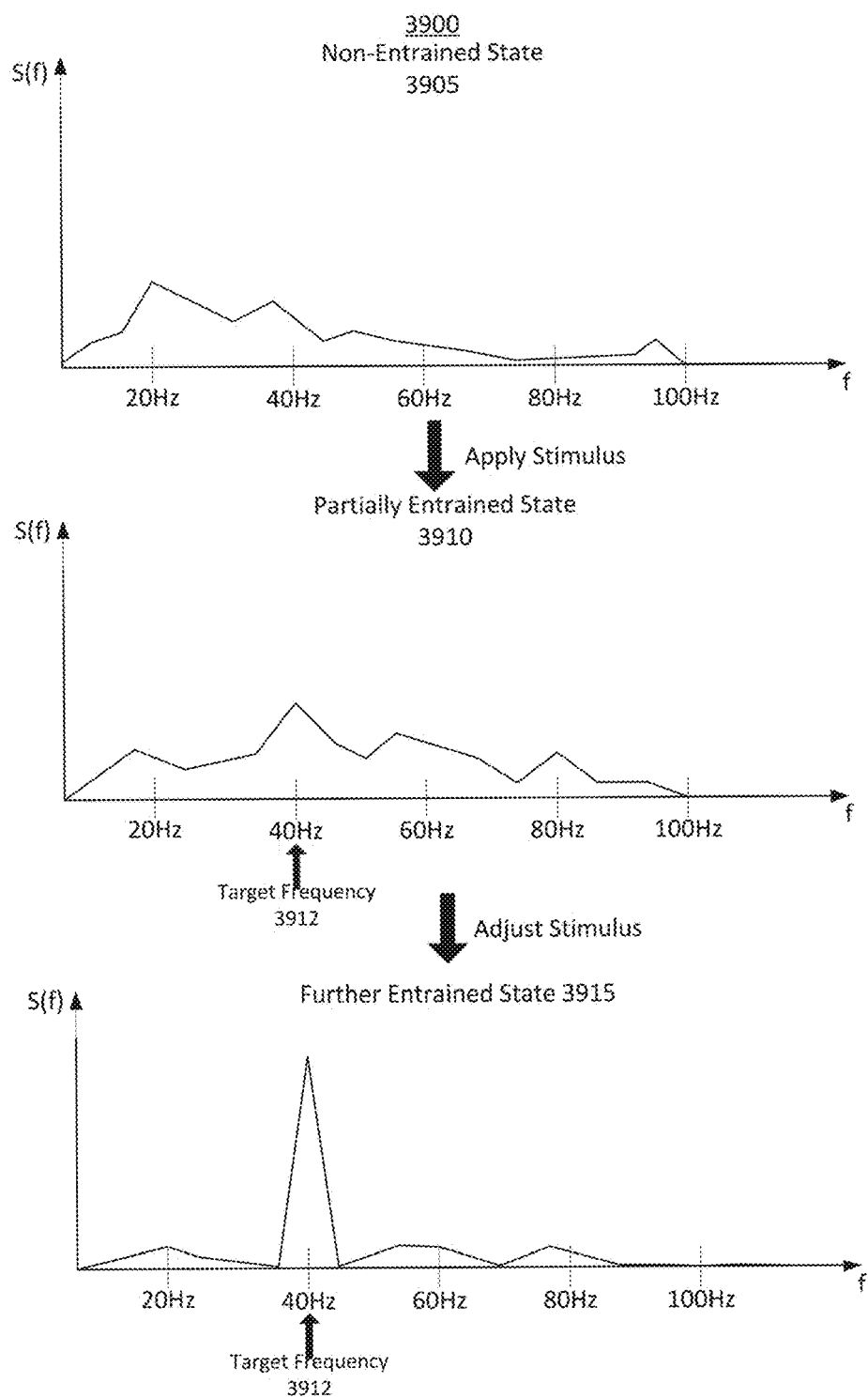
FIG. 39 illustrates graphs depicting frequency-domain measurements of various states of neural stimulation, in accordance to an embodiment.

II. Adjusting Stimulus to Further Induce Neural Oscillations to a Target Frequency Referring now to FIG. 39, FIG. 39 illustrates graphs 3900 depicting frequency-domain measurements of various states 3905-3915 of neural stimulation, in accordance to an embodiment. The graphs 3900 may be indicative of the frequencies at which the neurons of the brain of the subject 3605 are oscillating. The frequencies at which the neurons of the brain of the subject 3605 are oscillating may be measured using the response measurement device 320 and the neural oscillation monitor 3710 as detailed herein. In the non-entrained state 405, the neurons of the brain of the subject 3605 may be oscillating at a natural state (e.g., no stimulus 3615). In the example depicted in FIG. 39, some of the neurons of the brain of the subject 3605 may be oscillating at one or more rest or natural oscillation frequencies.

The stimulus 3615 may be applied by the stimulus output device 3755A-N to the subject 3605 to induce neural oscillations to oscillate at a target frequency 3912 (e.g., 40 Hz). Subsequent to the stimulus 3615 being applied to the subject 3605, some of the neurons of the brain of the subject 3605 may begin to oscillate at frequencies different from the non-entrained state 405. In the partially entrained state 3910, a plurality of neurons of the brain of the subject 3605 may be oscillating at the target frequency 3912 of 40 Hz. In this state, however, many of the neurons may still be oscillating at frequencies different from the target frequency 3912.

As shown in FIG. 39, using feedback data determined by the neural oscillation monitor 3710, the stimulus 3615 may be adjusted by the stimulus control module 3730 and the stimulus generator module 3725 over time, such that the nervous system 3610 of the subject 3605 is further entrained such that a majority of the neurons oscillate at the target frequency 3912. In the further entrained state 3915, a greater number of neurons may oscillate at the target frequency 3912 of 40 Hz, with a smaller number of neurons oscillating at frequencies different from the target frequency 3912. When the brain reaches the further entrained state such that a majority of neurons oscillate at the target frequency, there may be beneficial effects to the cognitive states or functions of the brain while mitigating or preventing adverse consequence to the cognitive state or functions. To this end, the components and modules of system 3800 may adjust the stimulations provided to the subject to cause neurons in the brain to oscillate at the target frequency.

JJ. Measurement Devices for Measuring Neural Oscillations

Figure 40:
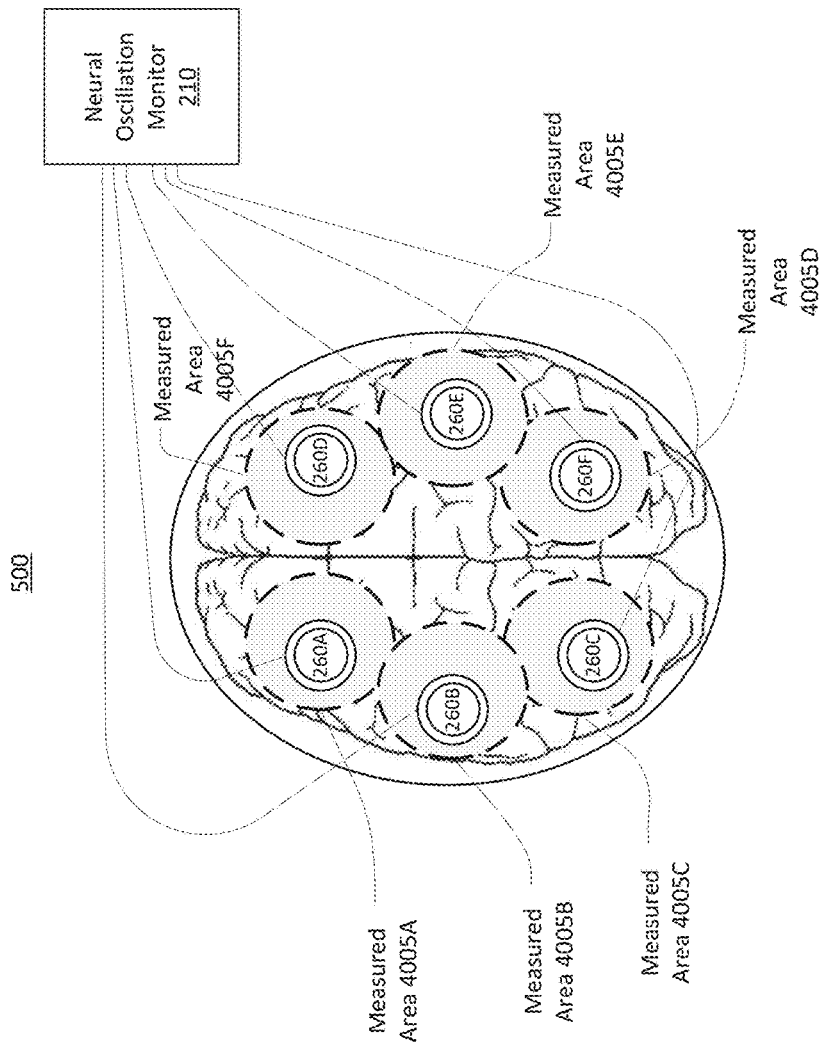
FIG. 40 illustrates an EEG device for measuring neural activity at the brain, in accordance to an illustrative embodiment.

Referring now to FIG. 40, FIG. 40 illustrates an EEG device 4000 for measuring stimulation, in accordance to an illustrative embodiment. The EEG device 4000 can include six electrode pads 3760A-F as the measurement devices. Each of the electrode pads 3760A-F may measure voltage fluctuations from current across the neurons within six different areas 4005A-F of the brain of the subject 3605. The voltage fluctuations may be indicative of the neural response to the stimulus 3615 as well as internal noise 310. At least one of the electrode pads 3760A-F can function as a ground lead. At least one other of the electrode pads 3760A-F can function as a positive reference lead. At least one of the other electrode pads 3760A-F can function as a negative reference lead. The voltage fluctuations from the brain may be measured on the epidermis of the cranium of the subject 3605 via the positive reference lead and the negative reference lead. The measurements of each of the electrode pads 3760A-F may be fed to the neural oscillation monitor 3710. The neural oscillation monitor 3710 in turn can execute additional signal processing as detailed herein.

Figure 41:
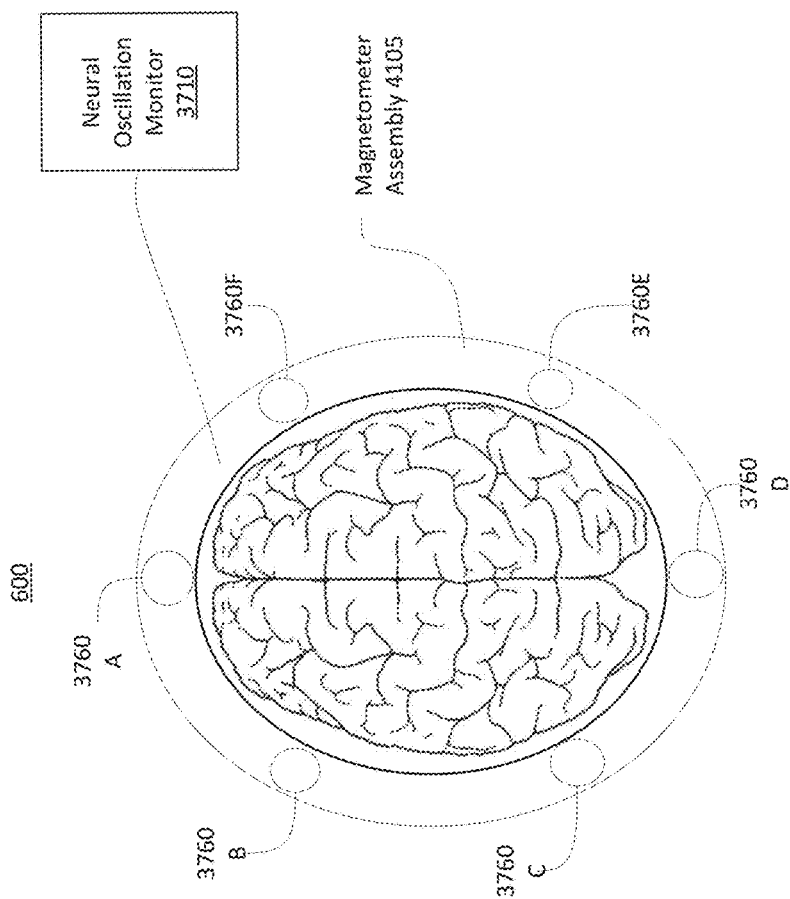
FIG. 41 illustrates an MEG device for measuring neural activity at the brain, in accordance to an illustrative embodiment.

Referring now to FIG. 41, FIG. 41 illustrates an MEG device 4100 for measuring stimulation, in accordance to an illustrative embodiment. The MEG device 4100 can include an MEG apparatus 4105 to hold six inductive coils 3760A-3760F as the measurement devices. Each of the inductive coils 3760A-3760F may measure the magnetic field of current fluctuations from the neurons within the brain of the subject 3605. The magnetic field may be indicative of the neural response to the stimulus 3615 as well as internal noise 310. Upon reacting with the magnetic field generated from the brain of the subject 3605, the inductive coils 3760A-3760F may generate a current. Relative to the EEG device 4000, the MEG device 4100 may measure the neural response of the brain of the subject 3605 to the stimulus 3615 with higher temporal and spatial resolution. The measurements of each of the inductive coils 3760A-F may be fed to the neural oscillation monitor 3710. The neural oscillation monitor 3710 can analyze the distribution of magnetic field readings from each of the inductive coils 3760A-3760F. The neural oscillation monitor 3710 in turn can execute additional signal processing as detailed herein.

In addition, there may be other types of measuring devices that may be used to measure the neural response of the subject 3605 as the stimulus 3615 is applied. For example, the one or more measurement devices 3760A-3760N may be a magnetic resonance imaging (MRI) scanning device and the neural oscillation monitor 3710 can generate a functional magnetic resonance imaging (fMRI) scan from the readings of the measurement devices 3760A-3760N. The one or more measurement devices 3760A-3760N may be any suitable device for measuring the neural response of the nervous system 3610 of the subject 3605 to the stimulus 3615.

Figure 42:
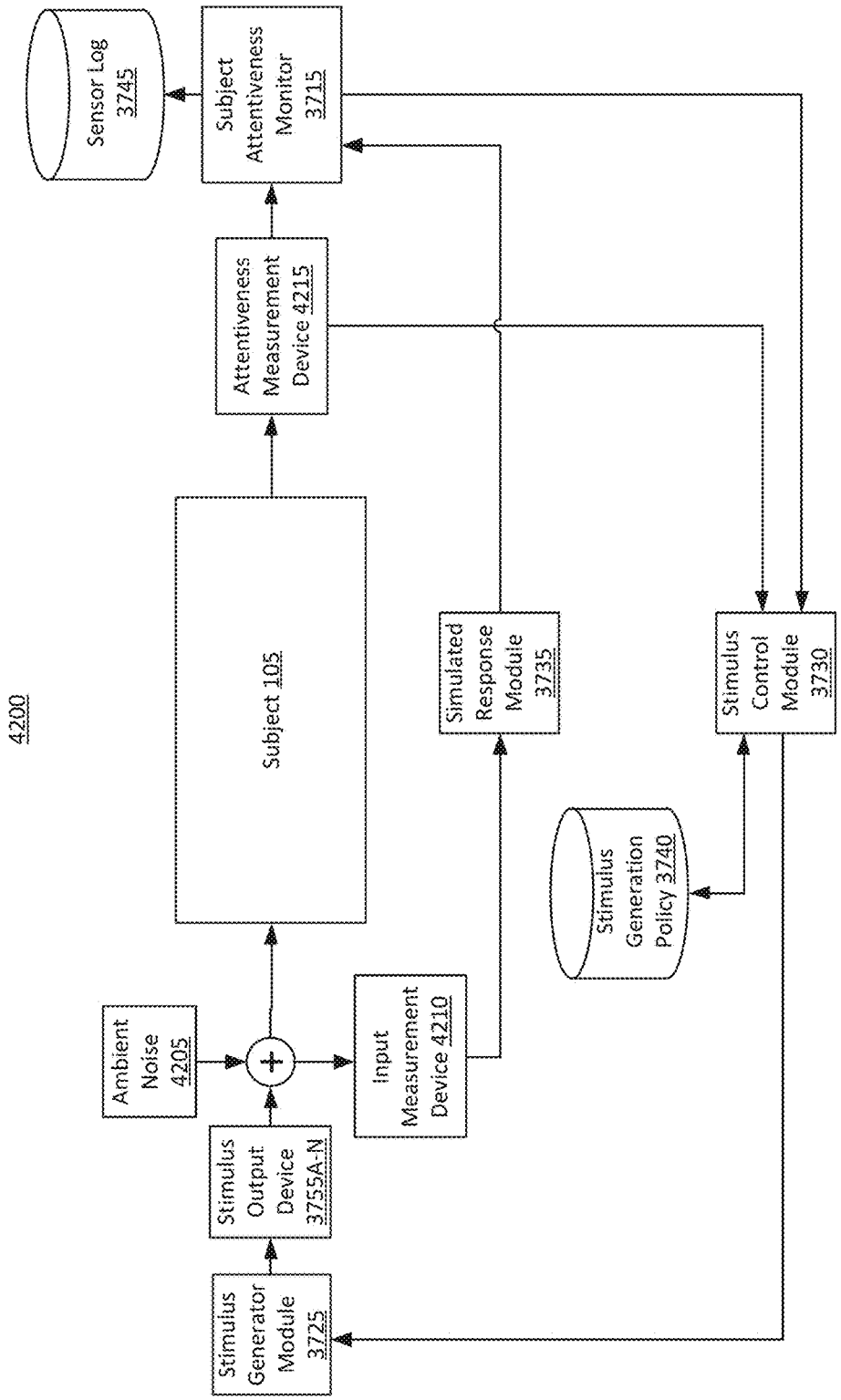
FIG. 42 is a block diagram depicting a system for monitoring subject attentiveness during application of an external stimulus to induce neural oscillations, in accordance to an illustrative embodiment.

KK. Systems for Monitoring Subject Attentiveness During Application of an External Stimulus to Induce Neural Oscillations Referring now to FIG. 42, FIG. 42 is a block diagram depicting a system 4200 for monitoring subject attentiveness during application of an external stimulus to induce neural oscillations, in accordance with an illustrative embodiment. Whether the subject 3605 is attentive may correlate to how effective the stimulus 3615 is in entraining the nervous system 3610 of the subject 3605 to the specified frequency or in inducing neural oscillations at a desired target frequency. For example, if the subject 3605 is focused on the stimulus 3615, the nervous system 3610 of the subject 3605 may be more likely to be entrained to the specified frequency resulting in more neurons oscillating at the target frequency. The system 4200 may be similar to system 3800 as detailed herein in reference to FIGS. 3-6, with the exception of the neural oscillator monitor 3710 being replaced by the subject attentiveness monitor 3715. In addition, the ambient noise 4205 may be different or the same type as the ambient noise 3805 and the input measurement device 4210 (e.g., one or more measurement devices 3760A-N) and the attentiveness measurement device 4215 (e.g., one or more measurement devices 3760A-N) used in system 4200 may be different or the same type as the input measurement device 315 and the response measurement device 320 of system 3800. By replacing the neural oscillation monitor 3710 with the subject attentiveness monitor 3715, the functionalities of the other components and modules in system 4200 may also change.

The attentiveness measurement device 4210 can measure an action response of the subject 3605 to the stimulus 3615. The action response of the subject 3605 may include, for example, involuntary, autonomic, reflex, and voluntary, responses to the stimulus, depending on whether the subject 3605 is aware or attentive of the application of the stimulus 3615. The attentiveness measurement device 4210 can include a camera, a microphone, a force meter, gyroscope, accelerometer, or any suitable device, to measure the action response of the nervous system 3610 of the subject 3605 to the stimulus 3615. In some embodiments, the attentiveness measurement device 4210 may be set on the subject 3605. The second measurement device (s) 3760B can transmit the action response of the subject 3605 to the stimulus 3615 to the subject attentiveness monitor 3715 and to the stimulus control module 3730.

Continuing in reference to FIG. 42, in response to receiving the measurements from the attentiveness measurement device 4210, the subject attentiveness monitor 3715 can monitor the action response of the subject 3605 with the application of the stimulus 3615. The subject attentiveness monitor 3715 can apply any number of signal processing techniques to the measurements from the attentiveness measurement device 4210. The subject attentiveness monitor 3715 can apply signal reconstruction techniques to the equally spaced sampled measurements received from the attentiveness measurement device 4210 to determine the action response of the subject 3605. The subject attentiveness monitor 3715 can apply compressed sensing techniques to the randomly sampled measurements received from the attentiveness measurement device 4210 to determine the action response of the subject 3605. The subject attentiveness monitor 3715 can apply pattern recognition algorithms from the measurements received from the attentiveness measurement device 4210 to identify one or more cues from the subject 3605. For example, if the measurement device(s) 3760B is a camera aimed at the full body of the subject 3605, the subject attentiveness monitor 3715 can apply object recognition techniques from the images taken by the measurement device(s) 3760B to detect the action response of the subject 3605 (e.g., posture, motion, etc.).

The subject attentiveness monitor 3715 can store, save, or write to the sensor log 3745, while receiving measurements from the attentiveness measurement device 4210. The subject attentiveness monitor 3715 can index each stored measurement by which of the attentiveness measurement device 4210. The subject attentiveness monitor 3715 can index each stored measurement by each modality of the stimulus 3615 (e.g., visual, auditory, etc.). The subject attentiveness monitor 3715 can index each stored measurement by the one or more defined characteristics used to generate the stimulus 3615 applied to the subject 3605. The storing of the action response of the subject 3605 onto the sensor log 3745 may be to build or update a profile of the subject 3605. The sensor log 3745 can log measurement data from the subject attentiveness monitor 3715. The sensor log 3745 can include a data structure to keep track of measurement data. For example, the data structure in the sensor log 3745 may be a table. Each entry of the table may include the stimulation modality of the stimulus 3615 (e.g., visual, auditory, etc.), a duration of the stimulus 3615, an intensity of the stimulus 3615, an region of the application of the stimulus 3615 on the body of the subject, a pulse modulation of the stimulus 3615, the measurements from the attentiveness measurement device 4215, among others.

The subject attentiveness monitor 3715 can determine feedback data to send to the stimulus control module 3730 to adjust the stimulus 3615 based on the measurements from the attentiveness measurement device 4210 and/or the simulated action response from the simulated response module 3735. Using the measurements from the attentiveness measurement device 4210 and/or the simulated action response from the simulated response module 3735, the subject attentiveness monitor 3715 can determine whether the subject 3605 is attentive, during the application of the stimulus 3615. In some embodiments, the subject attentiveness monitor 3715 can determine a difference between the simulated action response from the simulated response module 3735 and the measurements from the attentiveness measurement device 4210. The difference may be indicative of a disparity between the action response of the subject 3605 while the subject is attentive and the action response of the subject 3605 while the subject is not attentive to the stimulus or the application of the stimulus 3615. Using the determined difference, the subject attentiveness monitor 3715 can determine whether the subject 3605 is attentive during the application of the stimulus 3615.

In some embodiments, the subject attentiveness monitor 3715 can use the one or more cues identified using pattern recognition algorithms applied on the measurements from the attentiveness measurement device 4210 to determine whether the subject 3605 is attentive. A subset of the one or more cues may be indicative of the subject 3605 being attentive during the application of the stimulus 3615. Another subset of the one or more cues may be indicative of the subject 3605 not being attentive during the application of the stimulus 3615. The subject attentiveness monitor 3715 can send the determination of whether the subject 3605 is attentive during the application of the stimulus 3615 as the feedback data to the stimulus control module 3730.

Still referring to FIG. 42, responsive to feedback data received from the subject attentiveness monitor 3715 and/or measurements from the attentiveness measurement device 4210, the stimulus control module 3730 can determine an adjustment to the control signal to be generated by the stimulus generator module 3725. The adjustment to the control signal may be a change or a modification to the one or more predefined characteristics, such as the magnitude, the stimulation modality (e.g., auditory, visual, etc.), characteristics of the stimulation modality, the direction, the pulse modulation scheme, the frequency (or wavelength) of the oscillations of the stimulus 3615. The stimulus control module 3730 can determine the adjustment to the control signal based on the stimulus generation policy database 3740. The stimulus generation policy database 3740 can specify the adjustment to the control signal based on the feedback data from the subject attentiveness monitor 3715.

For example, if the feedback data indicates that the subject 3605 is not attentive during the application of the stimulus 3615, the stimulus generation policy database 3740 can specify that the stimulus control module 3730 is to set the one or more predefined characteristics such that the stimulus 3615 is of a different type (e.g., auditory stimulus to current stimulus). The stimulus control module 3730 can transmit the adjustment to the stimulus generator module 3725.

Upon receipt of the adjustment to control signal from the stimulus control module 3730, the stimulus generator module 3725 can in turn apply the adjustment to the control signal sent to the one or more stimulus output devices 3755A-N. The stimulus generator module 3725 can adjust the one or more predefined characteristics specified in the control signal based on the adjustment received from the stimulus control module 3730. It should be appreciated that the functionalities of the components and modules in system 3800 may be repeated until the nervous system 3610 of the subject 3605 is entrained to the specified frequency or until the subject 3605 is attentive to the application of the stimulus 3615.

Figure 43:
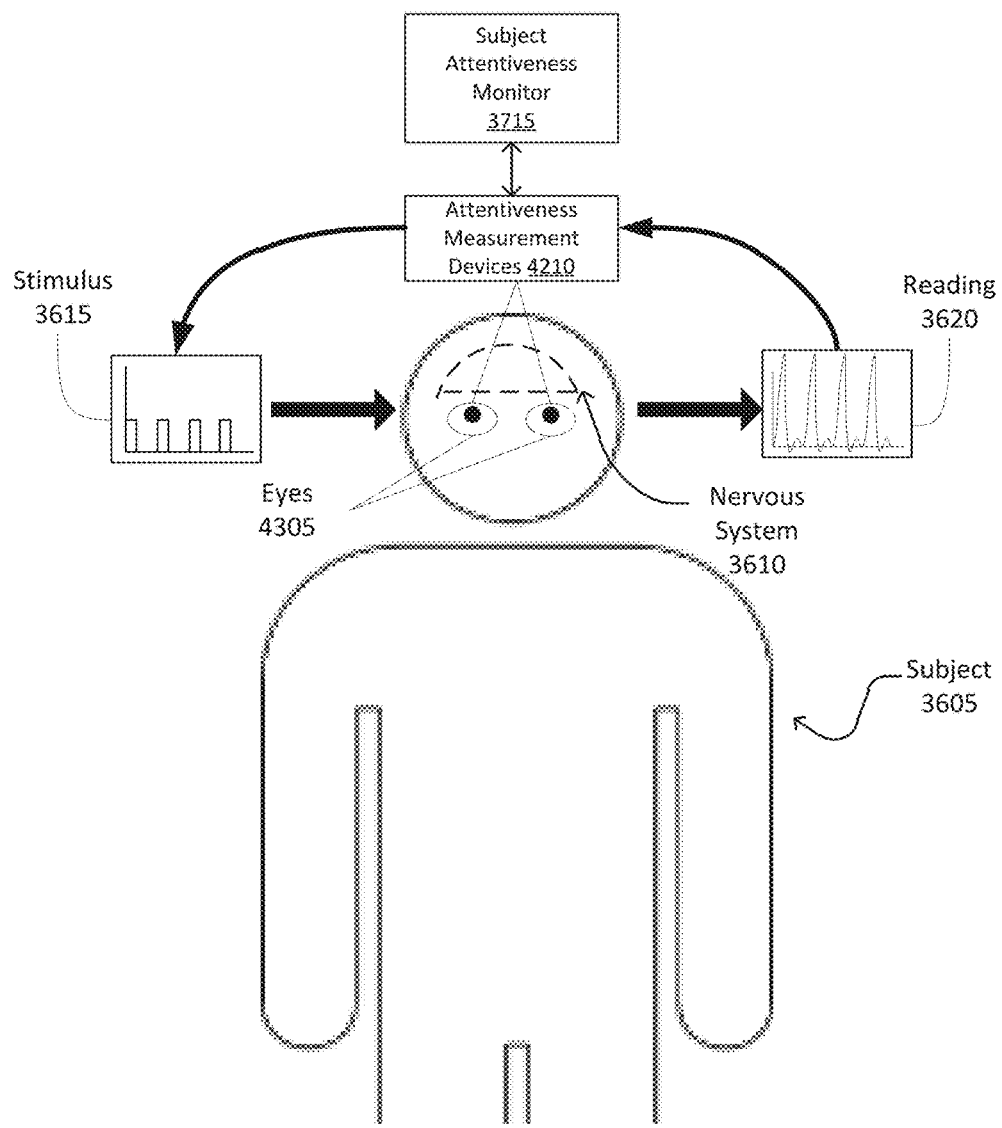
FIG. 43 is a block diagram depicting an environment for adjusting an external stimuli to induce neural oscillations based on subject attentiveness, in connection with the systems and methods described herein.

Referring now to FIG. 43, FIG. 43 is a block diagram depicting an environment 4300 for adjusting an external stimulus to induce neural oscillation based on subject attentiveness, in connection with the systems and methods described herein. The environment 4300 may be similar to or the same as environment 3600 as detailed in reference to FIG. 36. In the example depicted in FIG. 43, the stimulus 3615 applied to excite or stimulate the nervous system 3610 of the subject 3605 may be a visual stimulus. The stimulus output device 3755A-N outputting the stimulus 3615 may be directed to the eyes 4305 of the subject 3605. To measure the subject action response from the eyes 4305, the attentiveness measurement device 4210 may be an eye tracker with a camera, an accelerometer, and a gyroscope. The attentiveness measurement device 4210 may also be an EOG device to measure the differential between the front and back of the eyes 4305.

In the context of FIG. 42, while applying the stimulus 3615 to the subject 3605, the attentiveness measurement device 4210 can record the action response of the eyes 4305 of the subject 3605. In some embodiments, the attentiveness measurement device 4210 may be an eye tracking or gazing tracking device, and the subject attentiveness monitor 3715 may use the reading from the attentiveness measurement device 4210 to determine the level of attention the user is providing to the light pulses based on the gaze direction of the retina or pupil. The attentiveness measurement device 4210 can measure eye movement to determine the level of attention the user is paying to the light pulses. Responsive to determining that the subject 3605 is not paying a satisfactory amount of attention to the light pulses (e.g., a level of eye movement that is greater than a threshold or a gaze direction that is outside the direct visual field of the light source), feedback from the subject attentiveness monitor 3715 may be used to change a parameter of the light source to gain the user's attention. For example, the stimulus output devices 3755A-N can increase the intensity of the light pulse, adjust the color of the light pulse, or change the duration of the light pulse. The stimulus output devices 3755A-N can randomly vary one or more parameters of the light pulse. The stimulus output devices 3755A-N can initiate an attention seeking light sequence configured to regain the attention of the subject 3605. For example, the light sequence can include a change in color or intensity of the light pulses in a predetermined, random, or pseudo-random pattern. The attention seeking light sequence can enable or disable different light sources if the visual signaling component includes multiple light sources. Thus, the stimulus output devices 3755A-N and the attentiveness measurement device 4210 can interact with the subject attentiveness monitor 3715 to determine a level of attention the user is providing to the light pulses, and adjust the light pulses to regain the user's attention if the level of attention falls below a threshold. In some embodiments, the stimulus output devices 3755A-N can change or adjust one or more parameter of the light pulse or light wave at predetermined time intervals (e.g., every 5 minutes, 10 minutes, 15 minutes, or 370 minutes) to regain or maintain the user's attention level.

During the application of the stimulus 3615, the eyes 4305 of the subject 3605 may involuntarily respond (e.g., twitch or other movement). Some of the tracked movements by the eyes 4305 of the subject 3605 may be part of a natural or involuntary fluctuation (e.g., retinal jitters or other movement that occur with or without stimulus 3615), and may not correspond to that the subject 3605 being non-attentive. Other tracked movements by the eyes 4305 of the subject may be part of a voluntary response to the application of the stimulus 3615, and may indicate that the subject 3605 is not attentive or is in discomfort. The subject attentiveness monitor 3715 can store known movements corresponding to the natural fluctuations of the eyes 4305 (e.g., a threshold change in pupil position by few micrometers). The reading 3620 or the measurements of the eyes 4305 of the subject 3605 may be taken by the attentiveness measurement device 4210, and may be fed to the subject attentiveness monitor 3715.

Still referring to FIG. 42 in context of FIG. 43, the subject attentiveness monitor 3715 can in turn process the reading 3620 from the attentiveness measurement device 4210 to determine whether the subject 3605 is attentive during the application of the stimulus 3615. The subject attentiveness monitor 3715 can calculate a rate of change in eye pupil position from the measurements of the attentiveness measurement device 4210 from one sample time to the next sample time. The subject attentiveness monitor 3715 can also calculate a frequency of change in eye pupil position from the measurements of the attentiveness measurement device 4210 across multiple samples. The subject attentiveness monitor 3715 can also calculate a timing of change in eye pupil position from the measurements of the attentiveness measurement device 4210 relative to the initial application of the stimulus 3615. The threshold change may be pre-set as a cutoff indication to distinguish between involuntary and voluntary movement of the eye pupil. The subject attentiveness monitor 3715 can compare the calculated rate of change or the frequency of change to the threshold change to determine whether the subject 3605 is attentive during the application of the stimulus 3615. The threshold change may be indicative of whether the eye pupil movement is involuntary or voluntary.

Upon determining that the calculated rate of change is less than the threshold change, the subject attentiveness monitor 3715 can determine that the eye pupil movement was involuntary (or natural) and determine that the subject 3605 is attentive to the application of the stimulus 3615. Responsive to the determination that the calculated frequency of change is less than the threshold change, the subject attentiveness monitor 3715 can also determine that the eye pupil movement was involuntary (or natural) and determine that the subject 3605 is attentive to the application of the stimulus 3615. In response to determining that the calculated timing of change is less than the threshold change, the subject attentiveness monitor 3715 can also determine that the eye pupil movement was involuntary (or natural) and determine that the subject 3605 is attentive to the application of the stimulus 3615.

The subject attentiveness monitor 3715 can determine that the subject 3605 is attentive to the application of the stimulus 3615 based on various measurements from the attentiveness measurement device 4210. The subject attentiveness monitor 3715 may use other cues from the readings to determine whether the subject 3605 is attentive while the stimulus 3615 is being applied, such as head position, body position, body orientation, etc. The subject attentiveness monitor 3715 can then feed the determination of whether the subject 3605 is attentive during the application of the stimulus 3615 back to the stimulus control module 3730, the stimulus generator module 3725, and the stimulus output device 3755A-N. The stimulus 3615 may in turn be adjusted based on the feedback from the subject attentiveness monitor 3715.

On the other hand, upon determining that the calculated rate of change is greater than the threshold change, the subject attentiveness monitor 3715 can determine that the eye pupil movement was voluntary and determine that the subject 3605 is non-attentive to the application of the stimulus 3615. Responsive to the determination that the calculated frequency of change is less than the threshold change, the subject attentiveness monitor 3715 can also determine that the eye pupil movement was voluntary and determine that the subject 3605 is non-attentive to the application of the stimulus 3615. In response to determining that the calculated timing of change is less than the threshold change, the subject attentiveness monitor 3715 can also determine that the eye pupil movement was voluntary and determine that the subject 3605 is non-attentive to the application of the stimulus 3615. The subject attentiveness monitor 3715 can determine that the subject 3605 is non-attentive to the application of the stimulus 3615 based on various measurements from the attentiveness measurement device 4210. In continuing with FIG. 42. Responsive to determining that the subject 3615 is non-attentive to the application of the stimulus 3615, the subject attentiveness monitor 3715 can transmit feedback data to the stimulus control module 3730. The stimulus control module 3730 in turn can access the stimulus generation policy database 3740 to identify one or more stimulus generation policies to get the subject 3605 to be attentive to the stimulus 3615. Examples of the one or more stimulus generation policies may include: change in color, intensity of color, or duration of the light pulse for a visual stimulus; change in volume, change in tone, or change in duration of the sound wave for an auditory stimulus; change in intensity, duration of intensity for a peripheral nerve stimulus; change in amplitude, change in pulse modulation, among others.

Once the one or more stimulus generation policies to get the subject 3605 to be attentive to the stimulus 3615 is identified, the stimulus control module 3730 can transmit or relay the one or more stimulus generation policies to the stimulus generator module 3725. Similar techniques may be applied to determine whether the subject 3605 is attentive to the application of the stimulus 3615 for other types of stimuli (e.g., auditory, etc.) and to make the subject 3605 be attentive to the stimulus 3615 based on the feedback data.

In some embodiments, with receipt of the feedback data indicating that the subject 3605 is non-attentive, the stimulus generator module 3725 can send a control signal to the stimulus output device to prompt the subject 3605. The prompt may be displayed on an electric display of the stimulus output device 3755. The prompt may, for example, include a questionnaire asking the subject 3605 for input as to why the subject 3605 is non-attentive. The input from the subject 3605 taken by the stimulus output device 3755 may be the stimulus generator module 3725 and/or the stimulus control module 3730 to select one or more stimulus generation policies from the stimulus generation policy database 3740.

Figure 44:
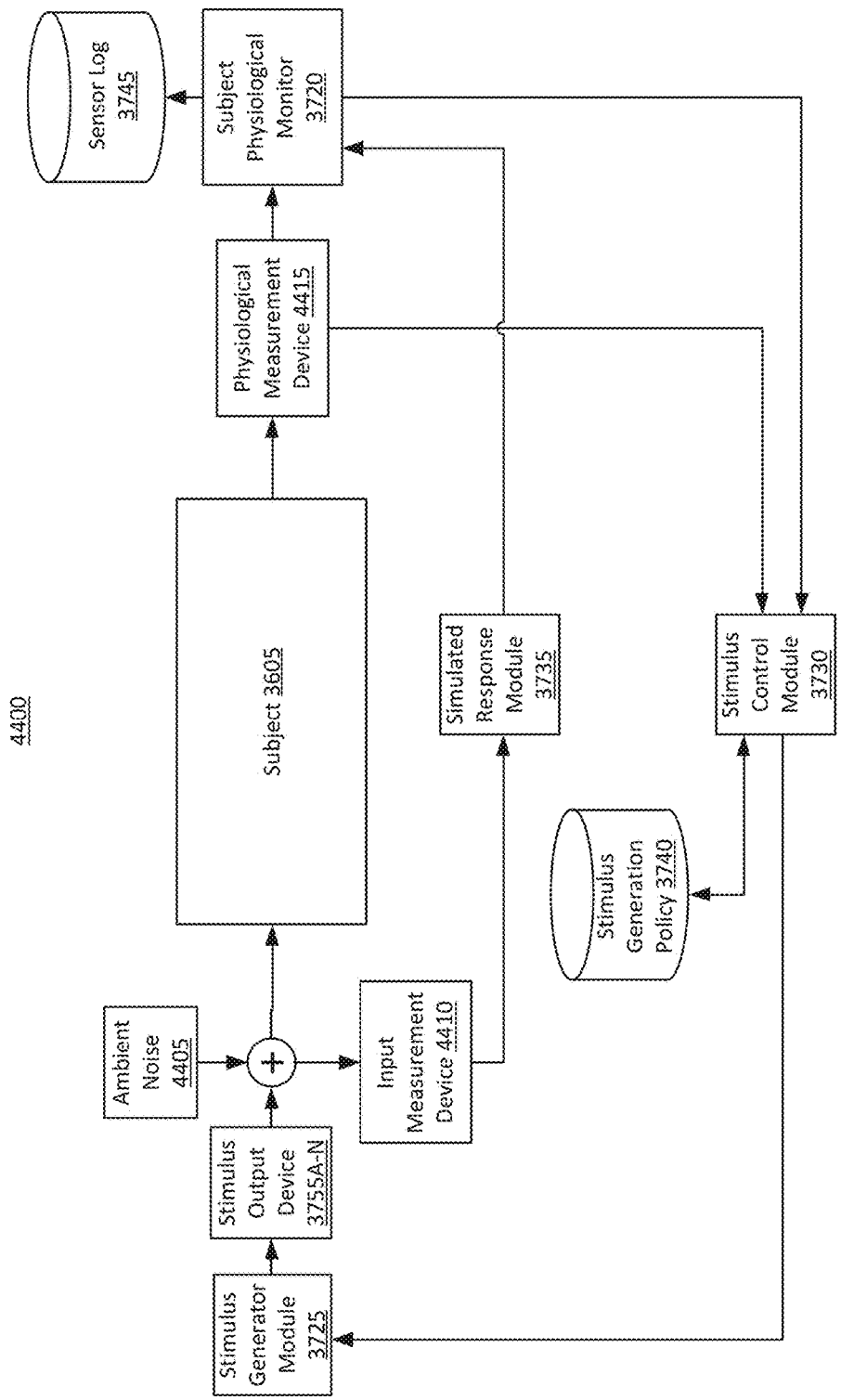
FIG. 44 is a block diagram depicting a system for monitoring subject physiology during application of an external stimulus to induce neural oscillation, in accordance to an illustrative embodiment.

LL. Systems for Monitoring Physiological Status of the Subject During Application of an External Stimulus to Induce Neural Oscillations Referring now to FIG. 44, FIG. 44 is a block diagram depicting a system 4400) for monitoring subject physiology during application of an external stimulus to induce neural oscillations, in accordance to an embodiment. Certain physiological responses may indicate that the nervous system 3610 of the subject 3605 is responsive to the stimulus 3615. How the subject 3605 reacts physiologically may correlate to how effective the stimulus 3615 is in entraining the nervous system 3610 of the subject 3605 to the specified frequency. For example, if the subject 3605 exhibits pain or another distressing feeling in response to the stimulus 3615, the stimulus 3615 may not be effective in entraining the nervous system 3610 of the subject 3605 to the specified frequency. The system 4400 may be similar to system 3800 as detailed herein in reference to FIGS. 3-6, with the exception of the neural oscillator monitor 3710 being replaced by the subject physiological monitor 3720. In addition, the ambient noise 4405 may be different or the same type as the ambient noise 3805 and input measurement device 4410 (e.g., one or more measurement devices 3760A-N) and the physiological measurement device 4415 (e.g., one or more measurement devices 3760A-N) used in system 4400 may be different or the same type as input measurement device 310 and the response measurement device 320 of system 3800. By replacing the neural oscillation monitor 3710 with the subject physiological monitor 3720, the functionalities of the other components and modules in system 4400 may also change.

In response to receiving the measurements from the physiological measurement device 4415, the subject physiological monitor 3720 can monitor the physiological response of the subject 3605 with the application of the stimulus 3615. The subject physiological monitor 3720 can apply any number of signal processing techniques to the measurements from the physiological measurement device 4415. The subject physiological monitor 3720 can apply signal reconstruction techniques to the equally spaced sampled measurements received from the physiological measurement device 4415 to determine the physiological response of the subject 3605. The subject physiological monitor 3720 can apply compressed sensing techniques to the randomly sampled measurements received from the physiological measurement device 4415 to determine the physiological response of the subject 3605.

As illustrated in FIG. 44, the subject physiological monitor 3720 can apply pattern recognition algorithms from the measurements received from the physiological measurement device 4415 to identify one or more cues from the subject 3605. In some embodiments, the physiological measurement device 4415 may be a heartrate monitor to measure the heartrate of the subject 3605. The subject physiological monitor 3720 can apply filtering techniques to identify an increase or decrease in the heartrate of the subject 3605. In some embodiments, the physiological measurement device 4415 may be a body temperature thermometer. The subject physiological monitor 3720 can apply filtering techniques to identify an increase or decrease in the body temperature of the subject 3605. In some embodiments, the physiological measurement device 4415 may be a blood pressure meter. The subject physiological monitor 3720 can apply filtering techniques to identify an increase or decrease in the blood pressure of the subject 3605. In some embodiments, the physiological measurement device 4415 may be a breathing rate meter to measure a respiration rate of the subject 3605. The subject physiological monitor 3720 can apply filtering techniques to identify an increase or decrease in the respiration rate the subject 3605. In some embodiments, the physiological measurement device 4415 may be an electrodermal measurement device, similar to EEG device 4000 but applied to other portions of the body of the subject 3605, to measure the galvanic skin response of the subject 3605. The subject physiological monitor 3720 can apply filtering techniques to identify an increase or decrease in the galvanic skin response of the subject 3605. The physiological measurement device 4415 may be any device to measure the physiological state of the subject 3605, during the application of the stimulus 3615.

The subject physiological monitor 3720 can store, save, or write to the sensor log 3745 while receiving measurements from the physiological measurement device 4415. The subject physiological monitor 3720 can index each stored measurement from the physiological measurement device 4415. The subject physiological monitor 3720 can index each stored measurement by each modality of the stimulus 3615 (e.g., visual, auditory, etc.). The subject physiological monitor 3720 can index the stored data by the physiological measurement device 4415. The subject physiological monitor 3720 can index the stored data by the one or more defined characteristics used to generate the stimulus 3615 applied to the subject 3605. The storing of the physiological state or response of the subject 3605 onto the sensor log 3745 may be to build a profile of the subject 015. The sensor log 3745 can log measurement data from the subject physiological monitor 3720. The sensor log 3745 can include a data structure to keep track of measurement data. For example, the data structure in the sensor log 3745 may be a table. Each entry of the table may include the stimulation modality of the stimulus 3615 (e.g., visual, auditory, etc.), a duration of the stimulus 3615, an intensity of the stimulus 3615, an region of the application of the stimulus 3615 on the body of the subject, a pulse modulation of the stimulus 3615, and/or a physiological reading from the subject physiological monitor 3720, among others.

The subject physiological monitor 3720 can determine feedback data to send to the stimulus control module 3730 to adjust the stimulus 3615 based on the measurements from the physiological measurement device 4415 and/or the simulated physiological response from the simulated response module 3735. Using the measurements from the physiological measurement device 4415 and/or the simulated physiological response from the simulated response module 3735, the subject physiological monitor 3720 can determine whether the subject 3605 is responsive to the application of the stimulus 3615. In some embodiments, the subject physiological monitor 3720 can determine a difference between the simulated physiological response from the simulated response module 3735 and the measurements from the physiological measurement device 4415. The difference may be indicative of disparity between the physiological responses of the subject 3605 while responsive and physiological response of the subject 3605 while not responsive to the application of the stimulus 3615. Using the determined difference, the subject physiological monitor 3720 can determine whether the subject 3605 is responsive to the application of the stimulus 3615. In some embodiments, the subject physiological monitor 3720 can use the one or more cues identified using pattern recognition algorithms applied to the measurements from the physiological measurement device 4415 to determine whether the subject 3605 is responsive. A subset of the one or more cues may be indicative of the stimulus 3615 having an effect on the subject 3605. Another subset of the one or more cues may be indicative of the stimulus 3615 not having an effect on the subject 3605. The subject physiological monitor 3720 can send the determination of whether the subject 3605 is responsive to the application of the stimulus 3615 as the feedback data to the stimulus control module 3730.

Responsive to feedback data received from the subject physiological monitor 3720, the stimulus control module 3730 can determine an adjustment to the control signal to be generated by the stimulus generator module 3725. The adjustment to the control signal may be a change or a modification to the one or more predefined characteristics, such as the magnitude, the type (e.g., auditory, visual, etc.), the direction, the pulse modulation scheme, or the frequency (or wavelength) of the oscillations of the stimulus 3615. The stimulus control module 3730 can determine the adjustment to the control signal based on the stimulus generation policy database 3740. The stimulus generation policy database 3740 can specify the adjustment to the control signal based on the feedback data from the subject physiological monitor 3720. Certain feedback data may indicate that the subject 3605 is reacting to the stimulus 3615 in an undesirable manner. For example, the feedback data may specify that the blood pressure of the subject 3605 is increasing responsive to the application of the stimulus 3615, indicating that the subject 3605 may be in pain. The stimulus generation policy database 3740 can specify that the stimulus control module 3730 is to set the one or more predefined characteristics such that the stimulus 3615 is to be of a lower intensity (e.g., decreasing the volume of an auditory stimulus or decrease amps for an electrical current stimulus) to decrease the pain or any other discomfort of the subject 3605. In another example, the feedback data may indicate that the galvanic skin response of the subject 3605 has increased, corresponding to an increasing of sweat from the sweat glands of the subject and possibly discomfort. The stimulus generation policy data 3740 can specify that the stimulus control module 3730 is to set the one or more predefined characteristics such that the stimulus 3615 is to be turned off until the galvanic skin response of the subject 3605 has decreased to normal. The stimulus control module 3730 can transmit the adjustment to the stimulus generator module 3725.

Upon receipt of the adjustment to control signal from the stimulus control module 3730, the stimulus generator module 3725 can in turn apply the adjustment to the control signal sent to the one or more stimulus output devices 3755A-N. The stimulus generator module 3725 can adjust the one or more predefined characteristics specified in the control signal based on the adjustment received from the stimulus control module 3730. It should be appreciated that the functionalities of the components and modules in system 3800 may be repeated until the nervous system 3610 of the subject 3605 is entrained to the specified frequency or until the subject 3605 is attentive to the application of the stimulus 3615.

Figure 45:
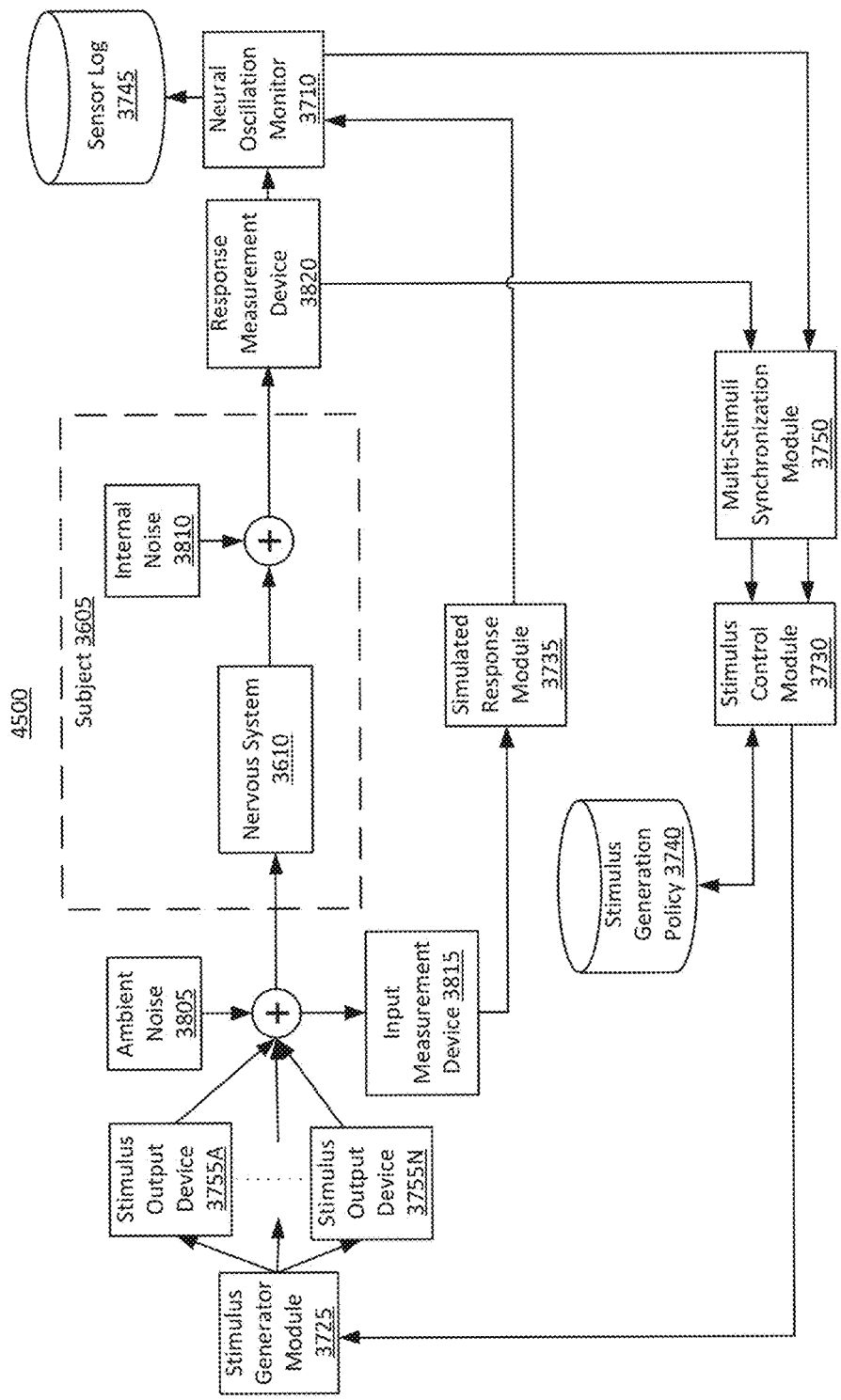
FIG. 45 is a block diagram depicting a system for synchronizing multiple stimuli to induce neural oscillation, in accordance to an illustrative embodiment.

MM. Systems for Synchronizing Multiple Stimuli During Application of an External Stimulus to Induce Neural Oscillations Referring now to FIG. 45, FIG. 45 is a block diagram depicting a system 4500 for synchronizing multiple stimuli to induce neural oscillation, in accordance to an illustrative embodiment. The system 4500 may be similar to system 3800 as detailed herein in reference to FIGS. 38-41, with the addition of a plurality of stimulus output devices 3755A-N and the multi-stimuli synchronization module 3750. The plurality of stimuli from the corresponding plurality of stimulus output devices 3755A-N may be applied to the nervous system 3610 of the subject 3605. The nervous system 3610 of the subject 3605 in turn may be partially or further entrained (e.g., partially entrained state 3910 and further entrained state 3915 in FIG. 39) to the specified frequency of the stimulus 3615, but the neural oscillations in different regions of the nervous system 3610 may not be in phase (e.g., not firing around the same time). In addition, there may be a desire to have different parts of the nervous system 3610 slightly out of phase to prolong the effect of the stimulus 3615 upon the nervous system 3610 of the subject 3605. The multi-stimuli synchronization module 3750 in conjunction with the stimulus control module 3730 may be configured to align the phases of the neural oscillations in the different regions of the nervous system 3610 of the subject 3605.

In system 4500, the response measurement device 320 can measure the neural response of the nervous system 3610 of the subject 3605 in response to the plurality of stimuli 3615 for each measured region of the nervous system 3610 of the subject 3605. The neural oscillation monitor 3710 can process the measurements from the response measurement device 320 at each of the measurement regions of the nervous system 3610 of the subject to generate feedback data. The response measurement device 320 can send the measurements to the multi-stimuli synchronization module 3750 for each of the measured regions. The neural oscillation monitor 3710 can also send the feedback data to the multi-stimuli synchronization module 3750 for each of the measurement regions.

As illustrated in FIG. 45, using the measurements from the response measurement device 320 and/or the neural oscillation monitor 3710, the multi-stimuli synchronization module 3750 can determine whether the nervous system 3610 is inducing neural oscillations at the specified frequency. If the nervous system 3610 is not sufficiently entrained to the specified frequency, the multi-stimuli synchronization module 3750 can pass the measurements from the response measurement device 320 and/or the neural oscillation monitor 3710 to the stimulus control module 3730. If the nervous system 3610 appears to be sufficiently entrained to the specified frequency based on the frequencies of the detected neural oscillations, the multi-stimuli synchronization module 3750 can determine a phase difference between the measurements of each two measured regions of the nervous system 3610, using any number of signal processing techniques. The phase difference may be indicative of a time delay between the firing of neurons in various regions of the nervous system 3610 of the subject 3605. In some embodiments, the multi-stimuli synchronization module 3750 can calculate a correlation (or cross-correlation) between the measurements between the two regions of the nervous system 3610. Based on the calculated correlation, the multi-stimuli synchronization module 3750 can determine the phase difference between the measurements of each two measured regions of the nervous system 3610. The multi-stimuli synchronization module 3750 can send or transmit the determined phase difference to the stimulus control module 3730 to entrain the neural oscillations in the nervous system 3610 to the specified frequency with minimal phase differences among the measured regions. In some implementations, there may be desire to reduce the phase offset between various stimulations to reduce any offsets in the timing of the detected neural response. In some other implementations, there may be a desire to maintain a slight phase offset in the neural response across different regions of the brain such that the duration of time over which neurons are oscillating the desired frequency is extended, which can result in an improvement in one or more cognitive functions of the brain.

Responsive to receiving the determined phase difference from the multi-stimuli synchronization module 3750, the stimulus control module 3730 can determine a phase adjustment to the control signal to be generated by the stimulus generator module 3725. The phase adjustment to the control signal may be a change or a modification to the pulse modulation scheme of the one or more predefined characteristics in the control signal. The stimulus control module 3730 can determine the phase adjustment to the control signal based on the stimulus generation policy database 3740. The stimulus generation policy database 3740 can specify the phase adjustment to the control signal based on the phase difference determined by the multi-stimuli synchronization module 3750. For example, if the neural oscillations at a first measured region of the nervous system 3600 is 15 degrees (or a corresponding amount of time) out of phase with the neural oscillations at a second measured region, the stimulus generation policy database 3740 can specify that the stimulus output device 3755A-N corresponding to the first measured region is to delay the outputting of the stimulus 3615 by a predefined time delay. The stimulus control module 3730 can transmit the phase adjustment to the stimulus generator module 3725. In some implementations, there may be desire to reduce the phase offset between various stimulations to reduce any offsets in the timing of the detected neural response. In some other implementations, there may be a desire to maintain a slight phase offset in the neural response across different regions of the brain such that the duration of time over which neurons are oscillating the desired frequency is extended, which can result in an improvement in one or more cognitive functions of the brain.

Upon receipt of the phase adjustment to control signal from the stimulus control module 3730, the stimulus generator module 3725 can in turn apply the phase adjustment to the control signal sent to the one or more stimulus output devices 3755A-N. The stimulus generator module 3725 can adjust the one or more predefined characteristics specified in the control signal based on the phase adjustment received from the stimulus control module 3730. It should be appreciated that the functionalities of the components and modules in system 4500 may be repeated until the nervous system 3610 of the subject 3605 is entrained to the specified frequency with minimal difference in phase.

Figure 46A:
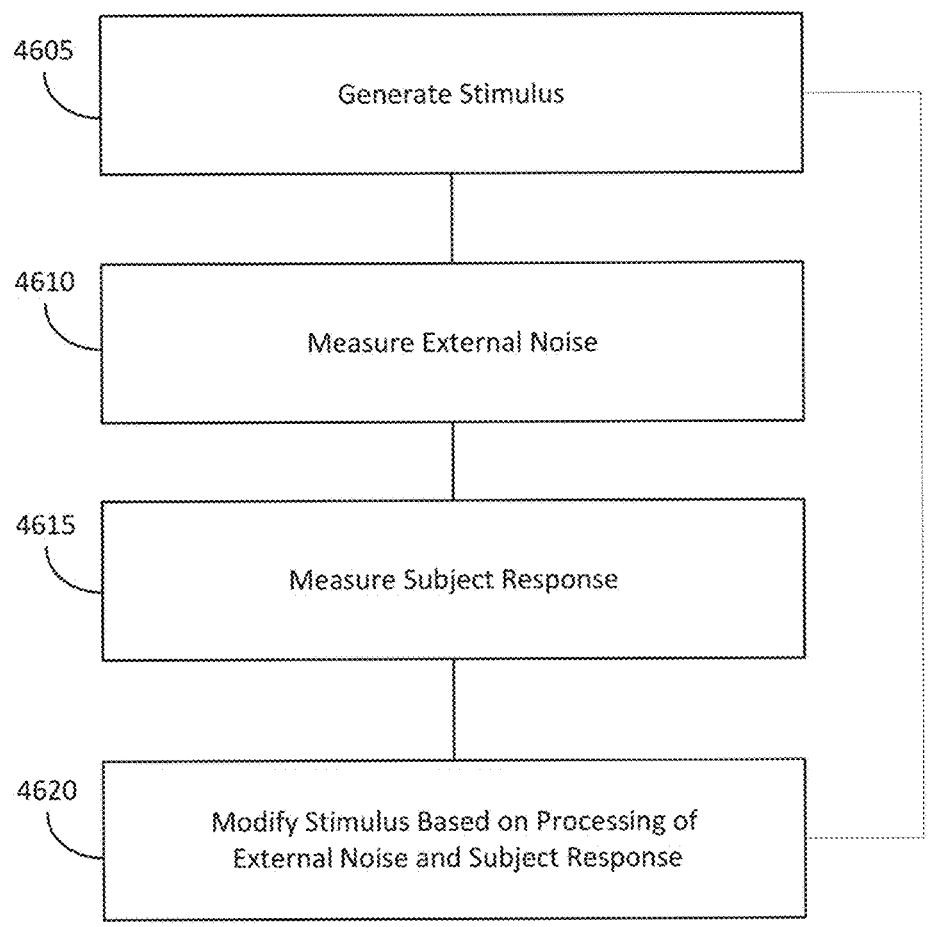
FIG. 46A is a flow diagram illustrating a method of sensing neural oscillations induced by an external stimulus and subject attentiveness during application of the external stimuli, in accordance to an embodiment.

NN. Method of Adjusting an External Stimulus to Induce Neural Oscillations Based on Measurement on a Subject Referring now to FIG. 46A, FIG. 46A is a flow diagram depicting a method 4600 of adjusting an external stimulus to induce neural oscillations based on measurement of a subject, in accordance with an embodiment. The method 4600 can be performed by one or more of the systems, components, modules, or elements depicted in FIGS. 36-45, including the neural stimulation sensing system (NSSS). In brief overview, at block 4605, the NSSS can generate a stimulus to apply to the subject. At block 4610, the NSSS can measure the external noise affecting the subject. At block 4615, the NSSS can measure subject response while applying the stimulus. At block 4620, the NSSS can modify the stimulus based on the measured external noise and the subject response. The NSSS can repeat blocks 4605-4620 any number of times and execute the functionality of blocks 4605-4620 in any sequence.

Figure 46B:
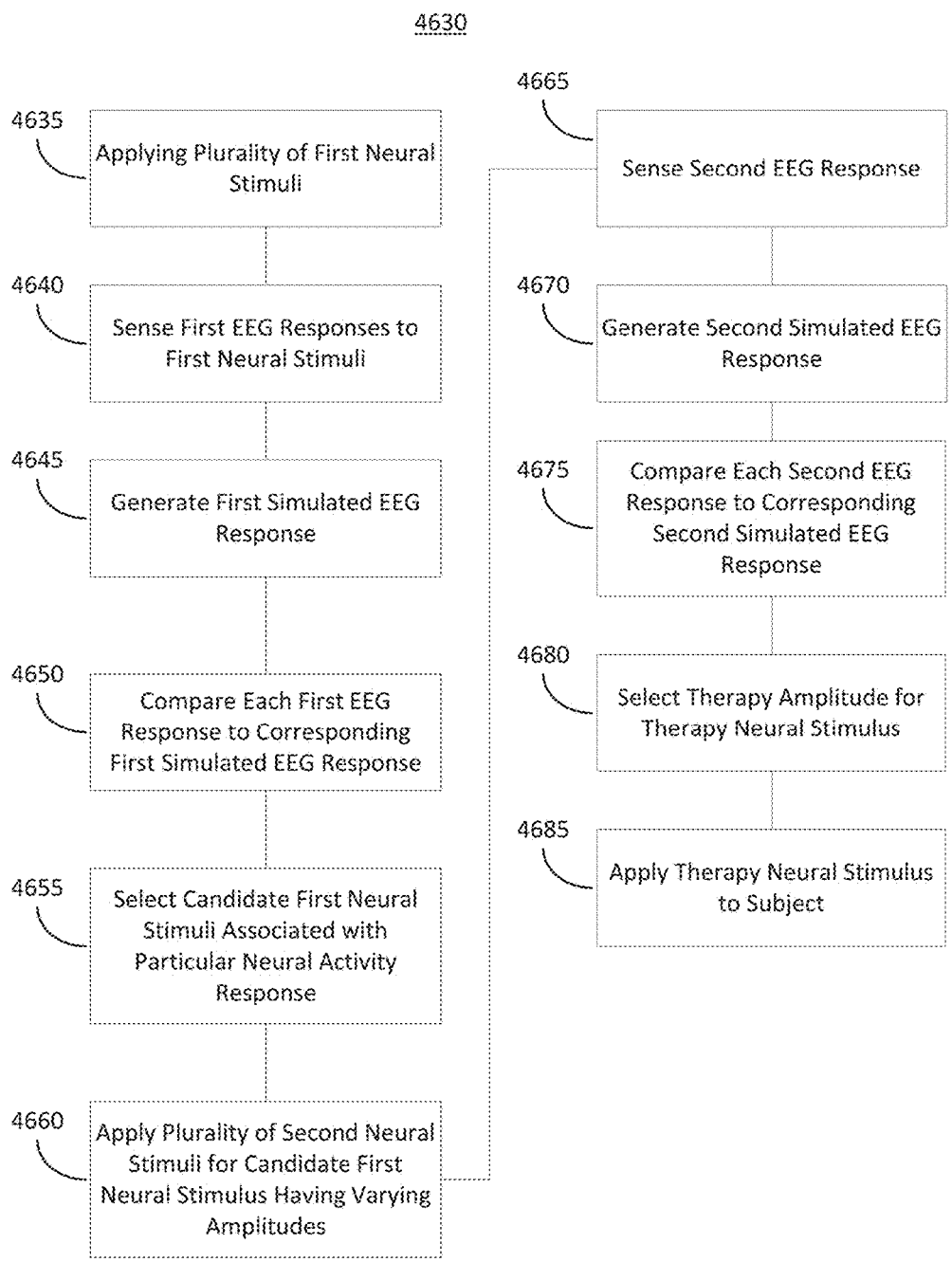
FIG. 46B is a flow diagram of a method for evaluating neural responses to different stimulation modalities for subjects, in accordance to an embodiment.

Referring now to FIG. 46B, FIG. 46B is a flow diagram depicting a method 4630 for evaluating neural responses to different stimulation modalities, in accordance with an embodiment. The method 4630 can be performed by one or more of the systems, components, modules, or elements depicted in FIGS. 36-45, including the neural stimulation sensing system (NSSS). In brief overview, the NSSS can apply a plurality of first neural stimuli (step 4635). The NSSS can sense first EEG responses to the first neural stimuli (step 4640). The NSSS can generate first simulated EEG responses (step 4645). The NSSS can compare each first EEG response to a corresponding first simulated EEG response (step 4650). The NSSS can select one or more candidate first neural stimuli associated with a particular response based on the comparisons (step 4655). The NSSS can apply a plurality of second neural stimuli for the candidate neural stimulus, the plurality of second neural stimuli having varying values of amplitude (step 4660). The NSSS can sense a second EEG response (step 4665). The NSSS can generate a second simulated EEG response (step 4670). The NSSS can compare each second EEG response to a corresponding second simulated EEG response (step 4675). The NSSS can select a therapy amplitude for a therapy neural stimulus based on the comparison (step 4680). The NSSS can apply the therapy neural stimulus to the subject (step 4685).

Referring again to FIG. 46B, and in greater detail, the NSSS can sequentially apply a plurality of first neural stimuli to the subject (step 4635). Each first neural stimulus can be defined by a predetermined amplitude. Each first neural stimulus can be associated with a different modality of neural stimulus including an auditory stimulation modality, a visual stimulation modality, and a peripheral nerve stimulation modality. In some embodiments, at least one first neural stimulus includes a plurality of stimulation modalities to be applied simultaneously (e.g., auditory stimulation simultaneous with visual stimulation).

The NSSS can sense, while applying each first neural stimulus to the subject, a first EEG response to the corresponding first neural stimulus (step 4640). The NSSS can associate the first EEG response with the first neural stimulus, including parameters of the first neural stimulus such as the predetermined amplitude.

In some embodiments, the NSSS senses the first EEG response for a predetermined period of time. The predetermined period of time may correspond to a signal to noise ratio (SNR) of the first EEG response. For example, the predetermined period of time may correspond to a minimum time required to capture sufficient EEG data so that the SNR of the first EEG response is greater than an SNR threshold. In some embodiments, the NSSS calculates the predetermined period of time based on the first neural stimulus (e.g., using a response model as described below). In some embodiments, the NSSS dynamically adjusts the predetermined period of time while applying the first neural stimulus. For example, while applying the first neural stimulus and sensing the first EEG response for a first period of time, the NSSS can calculate a first SNR of the first EEG response, and compare the first SNR to the SNR threshold. Responsive to the first SNR being less than the SNR threshold the NSSS can extend the application of the first neural stimulus and the sensing of the first EEG response, such as by applying the first neural stimulus and sensing the first EEG response for a second period of time subsequent to the first period of time. The second period of time may be calculated based on a difference between the first SNR and the SNR threshold (e.g., as the difference increases, the second period of time can be increased as well). In some embodiments, the NSSS applies the first neural response and senses the first EEG response until the first SNR of the first EEG response is greater than or equal to the SNR threshold.

The NSSS can generate a first simulated EEG response based on each first neural stimulus (step 4645). The NSSS can execute a response model mapping stimulus parameters to simulated EEG responses. In some embodiments, the response model is generated based on a historical response for the subject. The NSSS can generate each simulated response by maintaining the response model for the subject based on historical response data for one or more subjects, the historical response data associated prior physiological responses with corresponding neural stimuli, the model based on at least one of an age parameter, a height parameter, a weight parameter, or a heart rate parameter of the subject.

The NSSS can compare each first EEG response to each corresponding first simulated EEG response to determine if the first EEG response indicates a particular neural activity response of the subject (step 4650). For example, if a difference between the first EEG response and the simulated EEG response is less than a threshold difference, the first EEG response may indicate the particular neural activity response.

The NSSS can select, based on the comparison, a candidate first neural stimulus associated with an EEG response associated with the particular neural activity response of the subject (step 4655). For example, the NSSS can select one or more candidate first neural stimuli for which the difference between the first EEG response and the simulated EEG response is less than the threshold difference.

The NSSS can apply, for each candidate first neural stimulus, a plurality of second neural stimuli to the subject (step 4660). The plurality of second neural stimuli can have varying amplitudes (e.g., varying in a linear, Gaussian, or other distribution relative to the predetermined amplitude).

The NSSS can sense, while applying each second neural stimulus to the subject, a second EEG response of the subject (step 4665). The NSSS can generate, based on each second neural stimulus, a corresponding second simulated EEG response to the second neural stimulus, such as by using the response model (step 4670).

The NSSS can compare each second EEG response to the corresponding second simulated EEG response to determine if the second EEG response indicates the particular neural activity response of the subject (step 4675). As such, the NSSS can identify magnitudes of the second neural stimuli which may be associated with the particular neural activity response.

The NSSS can select, based on the comparison, a therapy amplitude for a therapy neural stimulus corresponding to the second neural stimulus associated with the particular neural activity response (step 4680). For example, the NSSS can identify the amplitude(s) from the varied amplitudes of the second neural stimuli which is associated with the particular neural activity response.

The NSSS can apply the therapy neural stimulus to the subject using the therapy amplitude (step 4685). In some embodiments, the therapy neural stimulus may be of a specific modality which resulted in the particular neural activity response (e.g., based on the application of the plurality of first neural stimuli) and having a particularized amplitude (e.g., based on the application of the plurality of second neural stimuli).

In some embodiments, the NSSS can sense an attentiveness response of the subject by executing at least one of eye tracking of eyes of the subject, monitoring heart rate of the subject, or monitoring an orientation of at least one of a head or a body of the subject. The NSSS can use the attentiveness response to determine if the particular neural activity response is indicated (e.g., if the attentiveness response indicates the subject was not paying attention to the neural stimulus, the particular neural activity response may not be indicated).

In some embodiments, the NSSS can vary a therapy parameter of each therapy neural stimulus when applying the therapy neural stimulus. For example, the NSSS can vary a duty cycle; the duty cycle may be maintained at a value less than fifty percent, in some embodiments. The NSSS can vary a pitch of the therapy neural stimulus where the therapy neural stimulus is an auditory stimulation. The NSSS can vary at least one of a color or an image selection of the therapy neural stimulus where the therapy neural stimulus is a visual stimulation. The NSSS can van, a location of the therapy neural stimulus where the therapy neural stimulus is a peripheral nerve stimulation.

While this specification contains many specific implementation details, these should not be construed as limitations on the scope of any inventions or of what can be claimed, but rather as descriptions of features specific to particular embodiments of particular aspects. Certain features described in this specification in the context of separate embodiments can also be implemented in combination in a single embodiment. Conversely, various features described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that the described program components and systems can generally be integrated in a single software product or packaged into multiple software products.

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and 'B'.

Thus, particular embodiments of the subject matter have been described. In some cases, the actions recited in the claims can be performed in a different order and still achieve desirable results. In addition, the processes depicted in the accompanying figures do not necessarily require the particular order shown, or sequential order, to achieve desirable results.

The present technology, including the systems, methods, devices, components, modules, elements or functionality described or illustrated in, or in association with, the figures can treat, prevent, protect against or otherwise affect Alzheimer's Disease. The following are examples of how the present technology can be used to affect Alzheimer's Disease.

Definitions

As used herein, the terms "treating," "treatment," or "alleviation" refer to both therapeutic treatment and prophylactic or preventative measures, wherein the object is to prevent or slow down (lessen) the targeted pathologic condition or disorder. A subject is successfully "treated" for a disease or condition if, after receiving therapeutic methods of the present technology the subject shows observable and/or measurable reduction in or absence of one or more signs and symptoms of a particular disease or condition. It is also to be appreciated that the various modes of treatment or prevention of medical conditions as described are intended to mean "substantial," which includes total but also less than total treatment or prevention, and wherein some biologically or medically relevant result is achieved.

As used herein, "prevention" or "preventing" of a disorder or condition with reference to a treatment method means that the method reduces the occurrence of the disorder or condition in treated subjects relative to an untreated control subjects.

As used herein, the words "protect" or "protecting" refer to decreasing the likelihood and/or risk that the subject treated with methods of the present technology will develop a given disease or disorder, or delaying the onset or reducing the severity of one or more symptoms of the disease, disorder or condition. Typically, the likelihood of developing the disease or disorder is considered to be reduced if the likelihood is decreased by at least about 10%, at least about 25%, at least about 50%, at least about 75%, at least about 90%, in comparison to the likelihood and/or risk that the same subject untreated with a method of the present technology will develop a relevant disorder. In some embodiments, the methods protect a subject against the development of a disorder where the methods are administered before the onset of the disorder.

Combination Therapies

In one aspect, the present disclosure provides combination therapies comprising the administration of one or more additional therapeutic regimens in conjunction with methods described herein. In some embodiments, the additional therapeutic regimens are directed to the treatment or prevention of the disease or disorder targeted by methods of the present technology.

In some embodiments, the additional therapeutic regimens comprise administration of one or more pharmacological agents known in the art to treat or prevent disorders targeted by methods of the present technology. In some embodiments, methods of the present technology facilitate the use of lower doses of pharmacological agents known in the art to treat or prevent targeted disorders. In some embodiments, the pharmacological agent is aducanumab.

In some embodiments, the additional therapeutic regimens comprise non-pharmacological therapies known in the art to treat or prevent disorders targeted by methods of the present technology such as, but not limited to, cognitive or physical therapeutic regimens.

In some embodiments, a pharmacological agent is administered in conjunction with therapeutic methods described herein. In some embodiments, the pharmacological agent is directed to inducing a relaxed state in a subject administered methods of the present technology. For example, in some embodiments, the pharmacological agent is an anesthetic or a sedative. In some embodiments, the pharmacological agent is a sedative such as, but not limited to, barbiturates and benzodiazepines. In some embodiments, the sedative is amobarbital (Amytal), aprobarbital (Alurate), butabarbital (Butisol), mephobarbital (Mebaral), methohexital (Brevital), pentobarbital (Nembutal), phenobarbitol (Luminal), primidone (Mysoline), secobarbital (Seconal), thiopental (Penothal), alcohol (ethanol), alprazolam (Xanax), chloral hydrate (Somnote), chlordiazepoxide (Librium), clorazepate (Tranxene), clonazepam (Klonopin), diazepam (Valium), estazolam (Prosom), flunitrazepam (Rohypnol), flurazepam (Dalmane), lorazepam (Ativan), midazolam (Versed), nitrazepam (Mogadon), oxazepam (Serax), temazepam (Restoril), or triazolam (Halcion). In some embodiments, the sedative is ketamine. In some embodiments, the sedative is nitrous oxide.

In some embodiments, the pharmacological agent is directed to inducing a heightened state of awareness in a subject administered methods of the present technology. For example, in some embodiments, the pharmacological agent is a stimulant. In some embodiments, the stimulant is an amphetamine or methylphenidate. In some embodiments, the stimulant is lisdexamfetamine, dextroamphetamine, or levoamphetamine. In some embodiments, the stimulant is Biphetamine, Dexedrine, Adderall, Vyvanse, Concerta, Methylin, or Ritalin. In some embodiments, the stimulant is caffeine or nicotine.

In some embodiments, the pharmacological agent is directed to modulating neuronal and/or synaptic activity. In some embodiments, the agent promotes neuronal and/or synaptic activity. In some embodiments, the agent targets a cholinergic receptor. In some embodiments, the agent is a cholinergic receptor agonist. In some embodiments, the agent is acetylcholine or an acetylcholine derivative. In some embodiments, the agent is an acetylcholinesterase inhibitor. In some embodiments, the agent is Aricept/donepezil.

In some embodiments, the agent inhibits neuronal and/or synaptic activity. In some embodiments, the agent is a cholinergic receptor antagonist. In some embodiments, the agent is an acetylcholine inhibitor or an acetylcholine derivative inhibitor. In some embodiments, the agent is acetylcholinesterase or an acetylcholinesterase derivative.

EXAMPLES

Example 1: Methods and Devices of the Present Technology for the Prevention or Treatment of Alzheimer's Disease This example demonstrates the use of methods and devices of the present technology in the prevention or treatment of Alzheimer's Disease (AD) animal in models and human subjects.

Animal Models

Murine models of AD suitable for use in this example include, but are not limited to, animals having loss- or gain-of-function mutations, and transgenic animals. For example, the 3×Tg-AD or 5×FAD transgenic mouse. Protocols for use of the 3×Tg-AD mouse are provided below as illustrative.

Animals Groups:

3×Tg-AD mice are obtained by crossing heterozygous APPswe/PS1dE9 double transgenic mice (Jackson Laboratory, Bar Harbor, Me. USA) with heterozygous P301L tau transgenic mice (Taconic Labs, Germantown, N.Y.). Male C57BL/6J mice (Shanghai SLAC Laboratory Animal CO., Ltd. Shanghai, China) and 3×Tg-AD mice are maintained in a controlled environment at 25±1° C. with a 12/12 h light-dark cycle. Experimental protocols are performed according to accepted guidelines for animal experimentation.

Fifty male 3×Tg-AD mice are randomly divided into five groups (each n ¼ 10): the 3×Tg-AD group, three groups of 3×Tg-AD mice treated with methods and devices of the present technology. Wildtype C57BL/6J mice are used for the control group.

Subjects are behaviorally tested after 2 months of treatment using methods known and accepted in the art, including, but not limited to, open field testing (OFT), elevated plus-maze (EPM), Morris water maze (MWM). The animals are sacrificed and the brains preserved for analysis. Half of the brain is used for immunofluorescence, and half for western blotting and enzyme-linked immunosorbent assay (ELISA).

Immunohistochemistry:

The 3×Tg-AD mice are anesthetized with pentobarbital, perfused with saline, and then perfused with 4% paraformaldehyde in 0.1 M phosphate-buffered saline (PBS), pH 7.4. Brains are fixed in 4% paraformaldehyde for 24 h and transferred into PBS containing 30% sucrose. Each brain is sectioned in the coronal plane at an instrument setting of 10 mm. Free floating sections are washed with PBS three times before being permeabilized with 0.3% Triton X-100 for 10 min, blocked with 3% bovine serum albumin (BSA) for 1 h, and incubated overnight at 4° C. with the following primary antibodies: rabbit anti-A$\beta$42 (1:200, Abcam, Cambridge, Cambs, UK) and mouse anti-202/205 phosphorylated tau (AT8, 1:100, Life Technologies, Carlsbad, Calif., USA). After several washes in PBS, the slides are incubated for 1 h at room temperature with the secondary antibody: DyLight 594 goat anti-rabbit IgG (1:500, Thermo Scientific, Rockford, Ill., USA). Nuclei were detected using 40, 6-diamidino-2-phenylindole (DAPI, 1:500, Thermo Scientific). After washing three times in PBS, the sections are mounted on charged slides for immunofluorescence detection using an Olympus microscope with DP-70 software. The imaging data are analyzed and quantified using Image pro-plus version 6.0.

Western Blotting Analysis:

Frozen brains are lysed with an ice-cold RIPA lysis buffer (Beyotime Institute of Biotechnology, Jiangsu. China) with complete protease inhibitor cocktail and phosphatase inhibitor cocktail (Roche, Indianapolis, Ind., USA). Lysates are centrifuged at 12,000 g for 20 min at 4° C. The supernatants are collected and total protein concentrations estimated using the Bradford method by means of the protein assay kit (Beyotime Institute of Biotechnology). Total proteins are denatured at 100° C. for 8 min and 60 mg proteins per lane are separated on 10% SDS-polyacrylamide gel and electrotransferred onto a polyvinylidene difluoride membrane (Millipore. Bedford, Mass., USA). Membranes are blocked with 5% BSA in Tris-buffered saline with 1% Tween-20 (TBST) for 2 h at room temperature and then incubated overnight at 4° C. with the following primary antibodies: rabbit anti-interleukin-1$\beta$ (IL-1$\beta$), rabbit anti-APP Thr668, rabbit anti-tumor-necrosis-factor-$\alpha$ (TNF$\alpha$), rabbit anti-bcl-2 and anti-bax (1:1000, Life Technologies); rabbit anti-PS1 (1:2000, Life Technologies); rabbit anti-interleukin-6 (IL-6) and mouse anti-caspase-3 (1:1000, Abcam), mouse anti-202/205 phosphorylated tau (AT8, 1:100)). GAPDH (1:8000, Life Technologies) is used as a loading control. Membranes are washed with TBST three times for 10 min and then incubated in the secondary antibody, anti-rabbit or anti-mouse IgG HRP-linked antibody (1:4000, Life Technologies) for 2 h. Blots are visualized by chemiluminescence (Amersham, Arlington Heights, Ill., USA). Optical densities are measured and protein levels normalized to GAPDH.

ELISA:

Brain hemispheres are homogenized in ice-cold PBS containing 5 M guanidine hydrochloric acid and 1× protease inhibitor mixture (pH 8.0). The levels of A$\beta$42 are quantified by ELISA according to manufacturer instructions (Invitrogen, Camarillo, Calif., USA) and expressed as ng/g protein. The oxidant-antioxidant status of tissues is assessed by determining the activities of superoxide dismutase (SOD), catalase (CAT), and glutathione peroxidase (GPx), and the concentration of malondialdehyde (MDA).

Statistical Analyses:

SPSS statistical software 16.0 for windows is used. All results are evaluated using one-way ANOVA and Dunnett's multiple range tests. All values are expressed as mean±standard error of the mean (S.E.M). Statistical significance is assumed if $P<0.05$.

Results:

It is predicted that methods of the present technology will induce reversal of symptoms and/or pathologies of AD in animal models. These results will show that methods of the present technology are useful and effective for the prevention or treatment of AD.

Human Clinical Trials

Human subjects diagnosed as having or suspected to have AD presently displaying one or more symptoms and/or pathologies of AD, including, but not limited to memory loss, cognitive disorder, and AD biomarkers, such as, but not limited to beta-amyloid in cerebrospinal fluid, amyloid-positive PET imaging, and genotypic markers (e.g., ApoE), are recruited using selection criteria known and accepted in the art.

In some studies, subjects are diagnosed as having or suspected to have a sporadic AD. In some studies, subjects are diagnosed as having or suspected to have a familial AD. In some studies, subjects are diagnosed as having or suspected to have early-onset AD. In some studies, subjects are diagnosed as having or suspected to have late-onset AD.

Clinical studies are conducted in accordance with accepted practices, such as, for example, the protocol of An, et al., *J. Alzheimer's Dis. Oct.* 4 (2016).

Methods of Prevention and Treatment:

Subjects are administered methods of the present technology at a dosage and frequency commensurate with the stage and severity of disease. In some embodiments the method is administered once daily, once weekly, or once monthly. In some embodiments, the method is administered multiple times daily, weekly, or monthly.

To demonstrate methods of prevention and treatment in human subjects and animal models, subjects are administered methods of the present technology prior to or subsequent to the development of symptoms and/or pathologies or AD and assessed for reversal of symptoms/pathologies or attenuation of expected symptoms/pathologies using methods known in the art.

Efficacy of prevention and treatment methods of the present technology may be assessed using methods known in the art, including, but not limited to the Alzheimer's Disease Assessment Scale Cognitive Portion (ADAS-Cog), the MMSE, and the Neuropsychological Test Battery (NTB). In addition, global assessments and assessments of activities of daily living may be obtained through the subject's caregiver, including, but not limited to the Basic Activities of Daily Living (BADL), the Clinical Dementia Rating (CDR), the Dependence Scale, the Instrumental Activities of Daily Living (IADLs), and the Neuropsychiatric Inventory (NPI).

Results:

It is predicted that methods of the present technology will induce reversal of symptoms and/or pathologies of AD in human subjects. These results will show that methods of the present technology are useful and effective for the prevention or treatment of AD.

Figure 47:
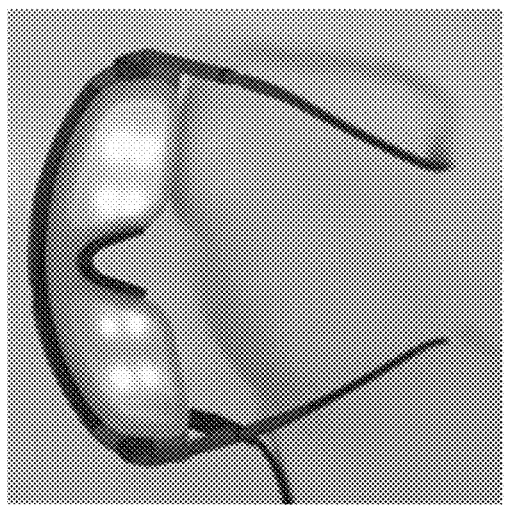
FIG. 47 shows an illustrative Combinatorial Stimulation System.

FIG. 47 shows an illustrative neural stimulation orchestration system. The device comprises a pair of opaque glasses with a LED illumination on the interior of the glasses. Headphones worn by the user during the stimulation session provide the auditory stimulation. These headphones may be in-ear or over the ear headphones. On the right, the location of the illumination for the visual stimulation is seen from a patient's perspective.

Figure 48:
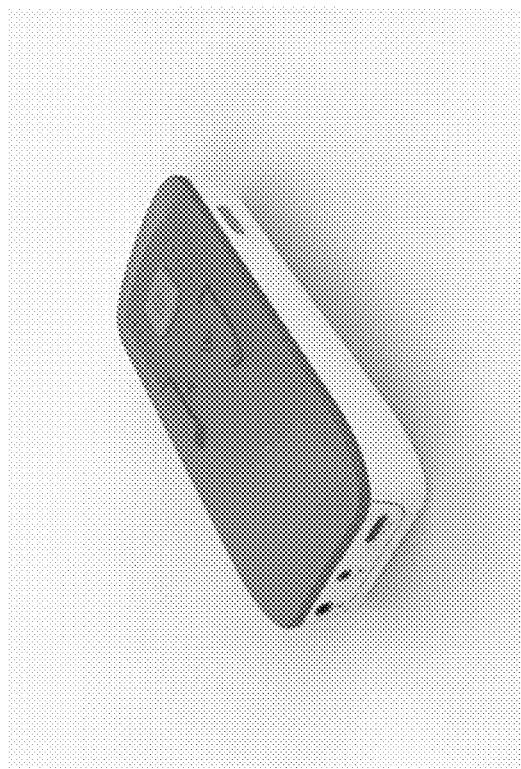
FIG. 48 is a rendering of a Combinatorial Stimulation System controller.

FIG. 48 is a rendering of a neural stimulation orchestration system controller. The controller allows the subject and/or caregiver to adjust output amplitude of audio and visual stimulation within a predefined safe operating range. The subject or caregiver can pause the stimulation session.

Figure 49:
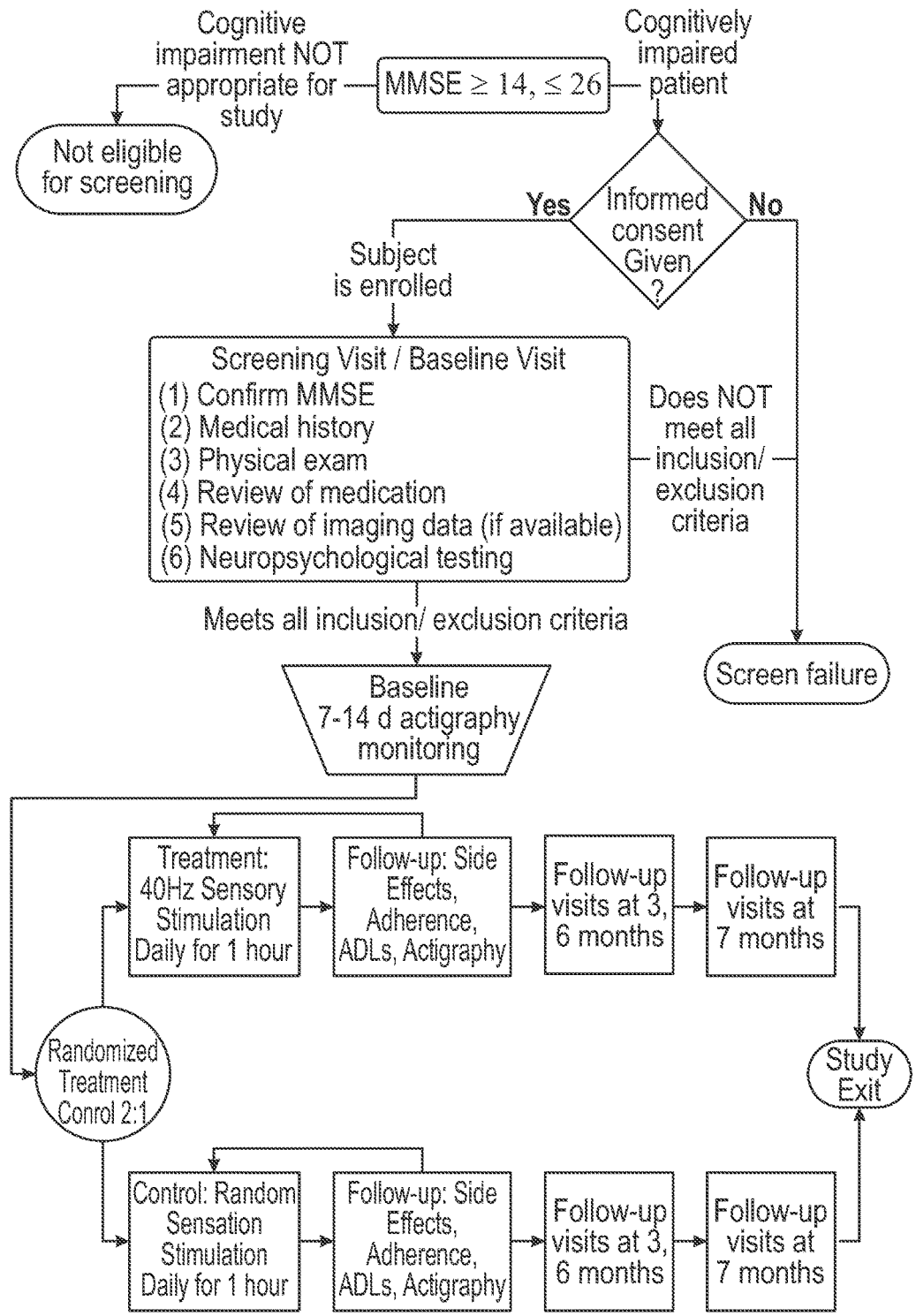
FIG. 49 is an overview of study design and of patient enrollment process.

FIG. 49 is an overview of study design and of patient enrollment process.

Neural Stimulation Orchestration System: The neural stimulation orchestration system is a non-invasive means of inducing gamma brainwave activity. The System is comprised of a reusable visual stimulator in the form of subject worn glasses and auditory stimulator in the form of subject worn headphones. The neural stimulation orchestration system generates short-duration flashes of white light by means of a solid-state LED (light emitting diode). The flashes are controlled by an embedded microcontroller and typically occur at a repetition rate of 40 Hz. The neural stimulation orchestration system also generates short-duration clicks of sound, which are 100% amplitude modulated at a repetition rate of 40 Hz.

From a subject's perspective, the flashing light and auditory click stimulation results in the desired induced gamma brainwave activity, but an individual wearing the device is readily able to converse and carry out other cognitive tasks and voluntary movements such as holding the hand of their caregiver while remaining seated. The flickering of the light is quite quick, so it is less apparent to the subject that there is an off period for the visual stimulation. For comparison, most modern flat-screen displays (computer monitors and televisions) refresh the content on the screen at 60 Hz; at this rate, the flickering is not apparent to the viewer.

In this embodiment, the neural stimulation orchestration system (FIG. 47 is worn on the head, and it is positioned in front of the eyes and over the ears by the subject or with assistance from a caregiver. The subject wearing the neural stimulation orchestration system should remain comfortably seated throughout the treatment session, as the glasses are an opaque white screen.

Instructions for Use are included with each neural stimulation orchestration system. The system is designed for ease of use for older adults, with no requirements for high dexterity manipulation of the device and is accompanied by simple visual instructions in large print.

The System includes a hand-held controller (FIG. 48) which allows the subject, with the assistance from a caregiver if needed, to turn the device on, independently adjust the output amplitude for both the auditory and visual stimulation, and to pause and resume the stimulation during a session.

Applicant has performed a comprehensive set of bench testing studies that have shown that the stimulation outputs from the neural stimulation orchestration system produces accurate and precise stimuli with controlled intensity, frequency, and duty cycle.

Usage: All relevant information about the neural stimulation orchestration system is contained in the Instructions for Use included with this submission. This includes: indications for use, contraindications, warnings, and precautions, instructions for use, recommendations for patients and caregivers during the use period, instructions for contacting the device manufacture and for return of the device.

a. Choice of Comparator: In order to provide a sham treatment arm for the study, the sham neural stimulation orchestration system will produce visual flicker auditory clicks at an average of 35 Hz frequency with random timing between pulses. The choice of this comparator comes from a combination of published and unpublished preclinical data demonstrating in the 5×FAD mouse model of Alzheimer's disease that random stimulation at 40 Hz did not demonstrate a significant difference from baseline with regards to $A\beta 1$-42 clearance as compared to normalized mice exposed to normalized dark or constant light conditions.

b. Overview: The study is a multicenter, prospective, single-blind, randomized, controlled study of the adherence rates and efficacy of non-invasive, multi-modal sensory stimulation in subjects with mild to moderate Alzheimer's disease. Daily treatment will be performed for the study duration using the neural stimulation orchestration system. This study will enroll approximately 180 subjects into the screening phase of the study, of which up to 60 subjects will be treated with sensory stimulation. The study will be conducted at up to 8 actively enrolling research sites.

c. Study Objective: To assess adherence rates and the efficacy of non-invasive sensory stimulation for patients with cognitive impairment.

d. Study Population: The primary enrollment target is 60 randomized subjects. Potentially eligible subjects will be consented and entered into a screening period to establish legally authorized representative/health care proxy and degree of cognitive impairment.

Subjects who meet all criteria after the screening period will undergo baseline assessments to evaluate cognitive performance, quality of life, general clinical impression, sleep and activity patterns via actigraphy monitoring. A subset of patients may undergo EEG monitoring for response to sensory stimulation and/or magnetic resonance (MR) imaging and/or PET imaging for collection of feasibility data for future study endpoints.

Eligible subjects will be randomized at a 2:1 ratio of treatment group to control group.

Treatment Group: Subjects are treated with the neural stimulation orchestration system daily and are maintained on baseline symptomatic medications without changes for 6 months.

Control Group: Subjects are treated with the sham neural stimulation orchestration system daily and are maintained on baseline symptomatic medications without changes for 6 months.

Subjects will be blinded to their randomized group assignment by a combination of lack of familiarity of the stimulation and inability to discern difference in the output of the system (i.e. subjects will not know the difference between the treatment device output and the sham device output).

Enrollment will continue until 60 subjects are enrolled. It is estimated that approximately 180 subjects will be screened to yield 60 subjects.

e. Selection Criteria: be selected based on the following inclusion and exclusion criteria. An answer of "NO" to any inclusion criteria or an answer of "YES" to any exclusion criterion disqualifies a participant from further screening and from participation in the study.

Inclusion Criteria
1. Individual is ≥55 years old at the time of screening.
2. Individual has a Mini-Mental State Exam (MMSE) score ranging from 14-26, inclusive.
3. Individual has a diagnosis of a clinical syndrome of cognitive impairment consistent with prodromal AD or MCI due to AD per National Institute on Aging-Alzheimer's Association (NIA-AA) diagnostic criteria.
4. Individual can identify (or have already identified) a health care proxy or legally authorized representative who can verify study inclusion/exclusion criteria.
5. Individual has a reliable caregiver or informant (defined as an individual who knows them well and has contact with them for at least 10 hours each week).

Exclusion Criteria
1. Self- or caregiver report of current profound hearing or visual impairment.
2. Self- or caregiver report of history of seizure.
3. Active treatment or current prescription with one or more anti-seizure/anti-epileptic medications including but not limited to: brivaracetam (Briviact™), carbamazepine (Carbatrol™, Tegretol™), Diazepam (Valium™), lorazepam (Activan™), clonazepam (Klonopin™), eslicarbzepine (Apitom™), ethosuximide (Zarontin™), felbamate (Felbatol™), lacosamide (VIMPAT™), lamotrigine (Lamictalm), levetiracetam (Keppra™), oxcarbazepine (Oxtellar XR™, Trileptalm), perampanel (Fycompa™), phenobarbital, phenytoin (Dilantin™), pregabalin (Lyrica™), tiagabine (Gabitril™), topiramate (Topamaxr), valproate/valproic acid (Depakene™, Depakote™), and zonisamide (Zonegran™).
4. Prior ischemic stroke, intracerebral hemorrhage, or subarachnoid bleed within the past 24 months.
5. Self- or caregiver reported usage of any new medication within the past 60 days, or current/expected titration of dosage of any medications during the study period.
6. Active treatment or current prescription with memantine (Namenda™, Namzaric™)
7. Self- or caregiver report of physician-diagnosis of Parkinson's disease.
8. Self- or caregiver report of physician-diagnosis of major depressive disorder.
9. Current prescription of any psychiatric agent, or self-report of clinically-significant psychiatric illness or behavioral problem that may interfere with study completion, as determined by study physician.
10. Self- or caregiver reported alcohol or substance abuse within the past year.
11. Self- or caregiver reported current enrollment in any anti-amyloid clinical trial within the past 5 months.
12. Subjects who, in the investigator's opinion will not comply with study procedures.
13. Subjects with active implantable neurological devices including deep brain stimulators (DBS). If patients are going to undergo MR imaging (optional assessment), then all active implantable devices including pacemakers, implantable cardioversion defibrillators (ICDs), spinal cord stimulators, and non-MR compatible surgical implants will be included as an exclusion criteria.
14. Subject is pregnant, lactating, or of childbearing potential (i.e. women must be two years post-menopausal or surgically sterile).
15. Exclusion for amyloid imaging with 18F-AV-45: Current or recent participation in any procedures involving radioactive agents such that the total radiation dose exposure to the subject in any given year would exceed the limits of annual and total dose commitment set forth in the US Code of Federal Regulations (CFR) Title 21 Section 361.1.

f. Study Endpoints

Primary

The primary efficacy endpoint is the change in ADAS-Cog14 from baseline to 6 months following daily sensory stimulation treatment sessions.

The primary safety endpoint is the incidence and nature of adverse events (AE) and serious adverse events (SAE).

Secondary

Secondary endpoints in this study include:

Changes in Alzheimer's Disease Assessment Scale-Cognitive 14 Item Subscore (ADAS-Cog14) from baseline to 3 months, 6 months, and 7 months Changes in Neuropsychiatric Inventory (NPI) from baseline to 3 months, 6 months, and 7 months Changes in Alzheimer's Disease Cooperative Study Clinical Global Impression of Change (CGIC) from baseline to 3 months, 6 months, and 7 months Changes from baseline in Alzheimer's Disease Cooperative Study Activities of Daily Living Inventory (ADCS-ADL) from baseline to 1 month, 2 months, 3 months, 4 months, 5 months, 6 months, and 7 months Changes from baseline in Quality of Life Alzheimer's Disease (QoL-AD) from baseline to 1 month, 3 months, and 6 months Caregiver burden measures from baseline to 1 month, 3 months, and 6 months Treatment adherence as measured by patient diary, via video recordings, and data reports from system.

Changes in actigraphy assessments compared from baseline at stated time points include:

1) Changes from baseline Assessment of daytime mean motor activity (dMMA) via actigraphy starting at 1-month, 3-month, and 6-month time points as assessed by 60 second epochs;
2) Assessment of nighttime mean motor activity (nMMA) via actigraphy starting at 1-month, 3-month, and 6-month time points as assessed by 60 second epochs;
3) Day time napping as defined by inactivity between final wakeup time and subsequent bedtime starting at 1-month, 3-month, and 6-month time points as assessed by 60 second epochs;
4) Assessment of sleep time duration and quality as compared to baseline period at 1-month, 3-month, and 6-month time points g. Subject Recruitment: The study enrolls individuals with mild-to-moderate cognitive impairment as determined during an in-person screening visit. Investigational Sites may utilize several methods to identify and recruit potential subjects. These methods may include evaluation of patients from their existing clinical practice, referrals from other physicians, medical record search, review of available databases, or direct subject recruitment via advertising. The initial recruitment effort should identify those subjects that Sites have reasonable knowledge of having cognitive impairment consistent with Alzheimer's disease, specifically patients:
1. Subjects with mild to moderate cognitive impairment consistent with Alzheimer's disease or a prior diagnosis of Alzheimer's disease.
2. Subjects, if receiving acetylcholinesterase inhibitors (AChEI), have been on a stable dose of for at least 60 days prior to enrollment and who are not being treated with memantine (Namenda™, Namzaric™).
3. Subjects that are able to identify (or have already identified) a health care proxy who can verify study information and consents to have the study staff interact with this individual.
4. Subjects that have a reliable caregiver to aid in the administration of the stimulation and for providing observations of changes in activities of daily living or side effects that may occur.

All interested individuals will complete an initial phone screen or in-person discussion during which they will be provided with a basic study overview and asked multiple questions related to study inclusion and exclusion criteria. At the beginning of this phone screen or in-person discussion, the participant will be asked if they would like to obtain a copy of the study's Informed Consent Form (ICF) prior to continuing. If they answer "yes", the ICF will be mailed or emailed to the participant and the phone screen will be rescheduled to a later date.

As part of the initial phone or in-person screen, the individual will be asked to identify "the family member or other individual that they trust most for help on making healthcare decisions," and to provide consent for the study team to contact this individual to gain their assent for the potential participant's involvement in this study.

The study staff will confirm that the individual identified by the subject are the health care proxy/legally authorized representative (LAR) for the subject; if they are not the health care proxy/LAR, the study staff will continue to identify that individual through the subject, caregiver, and identified contacts. Once confirmed, the health care proxy/legally authorized representative (LAR) will be strongly encouraged to attend the informed consent and the initial study visit. The health care proxy/LAR may or may not be the subject's caregiver.

The intent of the study is to maintain all enrolled subjects on their baseline medications without changes for at least 6 months; therefore Investigators (and the subjects' managing physicians) should not intend or expect to change medications for at least 6 months after enrollment. A subject may not be enrolled if the Investigator, subject, or managing physician does not agree to establish (prior to enrollment) and maintain a medication regimen without changes for at least 6 month (unless changes are medically necessary due to a clinically important event). Investigators, in collaboration with a subject's managing physicians, should thoroughly consider the subject's medication level in light of his/her cognitive impairment, to ensure that the baseline medications/doses can be maintained without changes for at least 6 months. If pre-enrollment medication changes are made, the subject must be allowed to stabilize for at least 30 days prior to the initial screening visit.

After enrollment, medication changes may be necessary due to a clinically important event that affects a subject's symptomatic medication regimen. If medications are changed after enrollment but prior to randomization and first treatment, the subject will be either excluded as a screen failure or must wait for the 30 days for "stabilization" on the new medication regimen. If medications are changed after randomization and first treatment, the subject will be withdrawn from the study.

h. Informed Consent; Once a subject with mild to moderate cognitive impairment, as described in the above Subject Recruitment section, has been identified, the study will be presented to the subject and appropriate legally authorized representative (LAR)/health care proxy for consideration. In addition to the consent process from the subject LAR/health care proxy, consent for the subject's caregiver will be sought in order to include measures of caregiver burden.

i. Determining Decision Capacity to Consent and Surrogate Consent; An evaluation by a researcher under the supervision of a clinician who is experienced in the evaluation of patients with cognitive impairment will be identified at each site. The capacity must be assessed based on a direct examination of the subject; the report of others will not suffice.

Subjects who are not capable of consent to research still must assent to research in order to take part. Assent implies willingness or, minimally, lack of objection to taking part in the study. An interpretable statement from the subject regarding assent must be taken as valid.

The decision capacity assessment should be performed by a researcher or physician and recorded on the associated CRF. If the patient has not objected to participating in the study but does not demonstrate decision making capacity to participate in the study, surrogate consent will be sought via the legally authorized representative (LAR)/health care proxy. For all subjects, a legally authorized representative (LAR)/health care proxy will be identified at the start of the study due to the progressive nature of cognitive impairment and Alzheimer's disease and in consideration of the duration of the study. The decision capacity will be re-assessed periodically throughout the study to ensure that any decisions regarding the study include the appropriate the subject and LAR/health care proxy.

The subject and legally authorized representative (LAR)/health care proxy will be given adequate time to have all of their questions answered and to carefully consider participation; this may include taking an unsigned copy home to discuss participation with family or friends before making a decision. If, after understanding the purpose, potential risks and benefits, and requirements of the study, as well as their rights as research participants, the individual and health care proxy agrees to participate, written informed consent shall be obtained. Informed consent shall be documented in the subject's medical record and, as applicable, in accordance with any other Site-specific regulatory requirements. Subjects and the legally authorized representatives (LAR)/health care proxy will be informed that they may discontinue the subject's participation at any time without penalty or loss of benefits to which the subject is otherwise entitled.

Once a participant and legally authorized representative (LAR)/health care proxy have consented to the trial and the caregiver has consented, the subject is considered enrolled and must undergo screening to ensure that they meet all of the entry criteria. Subjects who are determined to be ineligible for the study at any time during the screening process will not be treated and will be considered a screen failure.

j. Screening 1 Visit; Following the consent process, the screening will occur in 1 visit: Screening 1 Visit. The preferred screening order and timing are provided as guidance; however, it is understood that for a given subject, the order and/or timing of a test(s) may be modified, as appropriate. A flow chart depicting the study design overview and a patient's enrollment process is provided in FIG. 49.

1. Mini-Mental Status Examination (MMSE) assessment: To confirm the subject has cognitive impairment within the inclusion criteria of the study of 12-26, inclusive.
2. Medical history: To evaluate for prior or existing medical conditions and/or procedures that may exclude subjects from the study and to identify any pre-existing conditions that may be pertinent to the study's safety evaluation. The intent of the study is to maintain all subjects on their baseline medications without changes for the 6-month treatment and follow-up period.
3. Review of medications: To confirm doses and history of medications that may be pertinent to the study's efficacy evaluation.
4. Physical exam: To further evaluate for prior or existing medical conditions that may exclude subjects from the study and to establish the subject's baseline medical condition.
5. Confirm Inclusion/Exclusion Criteria k. Baseline Visit
6. Review of prior imaging (if available): To identify and assess amyloid status and other findings from available MR or PET imaging data.
7. Confirm Prior Inclusion/Exclusion Criteria: To confirm that subjects still meet eligibility criteria that were evaluated at the Screening 1 Visit.
8. Neuropsychological Testing: All cognitive testing will be performed by a trained psychometric grader. All tests and questionnaires should be administered in the same order with the ADAS-Cog given first. The same person should administer each scale at all visits and at the same time of the day. The interviewed caregiver (ADCS-ADL, NPI, and CGIC) should remain the same person the whole study.
   A. Alzheimer's Disease Assessment Scale—Cognitive (ADAS-Cog)
   B. Neuropsychiatric Inventory (NPI)
   C. Clinicians Global Impression of Change (CGIC)
   D. Alzheimer's Disease Cooperative Study—Activities of Daily Living (ADCS-ADL)
   E. Quality of Life—Alzheimer's Disease (QOL-AD)—administered to patient and caregiver
9. Baseline actigraphy: To record movement and sleep patterns for a minimum of 7 to 14 days prior to initiation of sensory stimulation.
10. MR Imaging (Optional Assessment): To record anatomy and pathophysiology or absence thereof present at baseline.
11. EEG Study (Optional Assessment): To record brainwave activity at baseline.
12. Amyloid PET Imaging (Optional Assessment): To record presence of beta amyloid at baseline.

l. Randomization: Randomization will be stratified by study center at a 2:1 ratio to:
1. Treatment Group: Subjects remain blinded and receive a neural stimulation orchestration system device which outputs sensory stimulation at a 40 Hz frequency.
2. Control Group: Subjects remain blinded and receive a neural stimulation orchestration system device which outputs sensory stimulation at a random distribution of time around a mean of 35 Hz.

All study staff and necessary personnel will be instructed that subjects and caregivers are not to be informed of their randomization assignments and appropriate measures should be taken to minimize the risk of premature unblinding. Investigators performing study follow-up visits and the subject's referring/managing physicians will not be proactively informed of a subject's treatment assignment to minimize potential bias in subject care decisions, To minimize potential bias in the measurement of the primary endpoint, ADAS-Cog testing, each investigational site will specify several designated "blinded" members of their study staff that will not be informed of the subjects' group assignments and will be responsible for performing the ADAS-Cog assessment through the 6 month follow-up visit. Prior to unblinding, the effectiveness of blinding will be assessed by asking subjects and assessors which group they believe the subject was randomized to. All subjects will be unblinded after the completion of all required 6 month follow-up testing.

m. Initial Treatment Session: After the Screening 1 Visit and completion of the baseline actigraphy recording, the subject and caregiver will be trained on the use of the neural stimulation orchestration system for use during the treatment period. The training and initial therapy session will take place under the supervision of the research staff. The default output settings for the neural stimulation orchestration system will be configured and recorded by the study staff. The subject and caregiver will be "blinded" to the output pattern of the device. The output of the treatment and sham devices will appear similar to the user.

The Instructions for Use will be provided along with contact information for the study site and customer support. The side effects questionnaire will be completed following the initial stimulation. The research staff shall confirm the current medications, assess for side effects and adverse events, and review study requirements with the subject to help ensure compliance with the follow-up schedule. Multiple telephone numbers and email addresses should be obtained from the participant and caregiver to ensure the ability to contact him/her at the required follow-up times (e.g. home, mobile).

Treatment: Subjects will then undergo daily treatment with the Visual auditory sensory stimulation device for a target treatment time of 60 minutes per day. The subject and/or caregiver will decide the time of day best suited for them to deliver the stimulation. The subject will be seated in a comfortable chair throughout the treatment session. A consistent time of day is preferred, but the treatment does not have to be at the same time each day. The subjects/caregivers will be provided with a "treatment diary" to record the time of day the stimulation is delivered and any comments that they have regarding the treatment and its effects each day. An electronic data capture system in the form of a tablet will be used to remind subjects and caregivers regarding the treatment session. The subject and caregiver will be in communication with the research staff via phone or videoconferencing to assist and monitor with the treatment session.

n. Follow-up Procedures: Table 1 lists the assessment and procedures required at each follow-up time point for both the Treatment and Control groups. Additional visits may be required. For example, if it is determined that the patient was non-compliant, has had a recent life event that may affect an accurate cognitive assessment at the follow-up visit, the follow-up visit should be rescheduled/repeated within the follow-up window.

All subjects will be followed-up with office assessments at 3, 6, and 7 months. Additional cognitive testing at dates other than that which is specified by the schedule of activities may be performed at the discretion of the investigator. Some of the follow-up visits will be conducted by study staff via phone interviews with the caregiver. The phone visits will be used to assess side effects (and if additional in-person follow-up is required), therapy adherence, and instrumental activities of daily living. The phone visits will be performed at a minimum of a monthly basis for all subjects, but they may be performed and recorded on a more frequent basis at the discretion of the site and sponsor.

EEG Assessment (Optional Assessment): For a subset of subjects at selected sites, an EEG study may be performed to record baseline activity and response to sensory stimulation. It is expected that this assessment will require an additional 45-60 minutes to complete.

MR Imaging Assessment (Optional Assessment): For a subset of subjects at selected sites, a MR imaging study may be performed to record anatomy. It is expected that this assessment will require an additional 45-60 minutes to complete.

Amyloid PET Imaging Assessment (Optional Assessment): For a subset of subjects at selected sites, an amyloid PET imaging study may be performed to record extent of beta-amyloid.

It is expected that this assessment will require an additional 120 minutes to complete.

TABLE 1

Schedule of Testing

| Required Testing | Screening V1 | Baseline V2 | Initial Tx | 1 M | 2 M | 3 M | 4 M | 5 M | 6 M | Follow Up 7 M |
|---|---|---|---|---|---|---|---|---|---|---|
| MMSE | X | | | | | | | | | |
| Medical History | X | | | | | | | | | |
| Physical Exam | X | | | | | X | | | X | X |
| Review Medications | X | | | | | X | | | X | X |
| Review of Imaging Data | | X | | | | | | | | |
| NPI1 | | X | | | | X | | | X | X |
| ADAS-Cog14 | | X | | | | X | | | X | X |
| CGIC1 | | X | | | | X | | | X | X |
| Clock Drawing Test | | X | | | | X | | | X | X |
| ADL1 | | X | | P | P | X | P | P | X | X |
| QOL-AD1 | | X | | P | P | X | P | P | X | X |
| Review of Side Effects | | | X | P | P | X | P | P | X | X |
| Actigraphy Monitoring | | A | | A | A | A | A | A | A | |
| Decision Capacity assessment | | | | | | X | | | X | |
| Blinding assessment | | | X | | | | | | X | |
| EEG assessment | | O | | | | O | | | O | O |
| MRI assessment | | O | | | | O | | | O | O |
| Amyloid PET assessment | | O | | | | O | | | O | |

X = Office assessment
P = Phone assessment
A = In-home assessment
O = Optional assessment
1 = Includes caregiver interview o. Screen Failure and Withdrawal: All reasonable measures should be taken to retain subjects enrolled in this study. However, it is acknowledged that subjects have the right to discontinue participation at any time without penalty or loss of benefits to which the subject is otherwise entitled. The Investigator may deem study withdrawal an appropriate action for a given subject due to documented medical reasons.

Screen Failure: If a subject withdraws consent or is excluded by the Investigator prior to or at the time of the Treatment Session 1, he/she is considered a screen failure. Data will be collected up to the point of exclusion.

Withdrawal: In the event that a subject is withdrawn from the study after Treatment Session 1, either by his/her choice or that of the Investigator (i.e. documented medical reason), the following procedures should be adhered to by the Site:
1. Document the reason for the withdrawal and date of the last study contact
2. Obtain the subject's written withdrawal request, whenever feasible
3. If withdrawal occurs:
   A. Between Treatment Session 1 and 3 Month Follow-up Visit
      i. Report all data that had been collected up to the time of study withdrawal (last study contact).
      ii. Request that the subject come into the office for the 3 Month evaluations to minimally assess safety, however, if the subject declines or is unable to come in, conduct an interview for side effects via phone at 1 month.
   B. After the 3 Month Follow-up Visit
      i. Report all data that had been collected up to the time of study withdrawal (last study contact).
      ii. No additional follow-up is required.

A subject that has withdrawn from the trial will not be replaced. Subjects in whom the investigational therapy was delivered for less than 1 month will not be followed for the duration of the study as part of the intention to treat (ITT) population.

Risk Analysis: The progression of mild cognitive impairment and Alzheimer's disease and associated morbidity and mortality is well known. Beyond the risk to the individual, the care for these individuals results in significant stress and economic burden for families and is a growing challenge for healthcare systems across the world.

Individuals involved in this study will complete assessments of cognitive and physical function, be subjected to relatively low levels of non-invasive visual and auditory sensory stimulation, and may undergo EEG, MR, and PET imaging using standard procedures. Caregivers will be asked to complete assessments of caregiver burden. Risks associated with each of these study activities are minimal, as list below.

p. Potential Benefits: Although no assurances or guarantees can be made, there is reasonable expectation that the sensory stimulation may be beneficial to the subject. Evidence in the literature suggests that reduction of symptoms of cognitive impairment may a) reduce negative events that trigger hospital visits (falls and other accidents) b) improve compliance with medical treatments for comorbidities c) reduce costs d) delay institutionalization of subject, and e) increase caregiver productivity.

q. Potential Risks: The sensory stimulation treatments being evaluated by this study are very similar to devices that are readily available as consumer products without prescription by physician such as an MP3 player (e.g. iPod™) and visual stimulators such as the Delight from Mind Alive. The subject can easily and safely remove the non-invasive devices at any time throughout a stimulation treatment without assistance.

The following are potential risks of the sensory stimulation treatments which are described based on common terminology criteria for adverse events (CTCAE):
1. Seizure—a disorder characterized sudden onset of uncontrolled electrical discharge in the brain causing alterations in behavior, sensation, or consciousness.
2. Headache—a disorder characterized by a sensation of marked pain or discomfort in various parts of the head, not necessarily confined to the area of distribution of any nerve.
3. Insomnia—a disorder characterized by difficulty in falling asleep and/or remaining asleep.
4. Nausea—a sensation of unease and discomfort in the upper gastrointestinal tract
5. Dizziness—a disorder characterized by a disturbing sensation of abnormal movement including but not limited to lightheadedness, unsteadiness, giddiness, spinning, or rocking.
6. Ear Pain—a disorder characterized by a sensation of marked discomfort in the ear.
7. Eye Pain—a disorder characterized by a sensation of marked discomfort in the eye.
8. Dry eye—a disorder characterized by dryness of the cornea and conjunctiva.
9. Anxiety—a disorder characterized by apprehension of danger and dread accompanied by restlessness, tension, tachycardia, and dyspnea unattached to a clearly identifiable stimulus.
10. Confusion—a disorder characterized by a lack of clear and orderly thought and behavior.
11. Restlessness—a disorder characterized by an inability to rest, relax, or be still.

There are additional risks that could possibly be associated with the tests and procedures performed for the clinical study. These potential risks are described below:

Risks associated with assessments of cognitive testing: Risks associated with cognitive assessments are minimal, but participants may experience mental fatigue and/or anxiety during this form of testing.

Risks associated with EEG: There are no known risks of EEG. It is considered safe and painless.

Risks associated with MR Imaging: The risks of MR imaging are well-established including physical risks from the strong, static magnetic field, risk to hearing, risk of heating of the body from radiofrequency energy used during the examination, and risk to electrically active implants. The rate of adverse events is extremely low; the FDA reports 300 events annually for several million MR imaging studies performed each year in the United States.

Risks associated with Amyloid PET Imaging: The primary risk related to PET is that of radiation exposure associated with the CT scan or transmission scan and the injected radiotracers. There is also minor risk associated with the venipuncture and radioisotope injection (pain and bruising or painful infiltration of a failed injection). The estimated absorbed radiation dose for [18F]-FDG (rad/mCi) for a 70 kg adult is presented in the table below. These estimates were calculated from human data (Jones et al., 1982) and used the data published by the International Commission on Radiological Protection for [18F] FDG for a 70 kg adult with assumptions on biodistribution from Jones, et al, 1982 and using MIRDDOSE 2 software ("International Commission on Radiological Protection for 18[F]

FDG," 1987). The critical organ is the urinary bladder wall, followed by heart, spleen and pancreas. This radiation dose is not expected to produce any harmful effects, although there is no known minimum level of radiation exposure considered to be totally free of the risk of causing genetic defects or cancer. The risk associated with the amount of radiation exposure participants receive in this study is considered low and comparable to every day risks. No PET studies will be performed on pregnant or potentially pregnant women, as the protocol requires female subjects to be postmenopausal as a condition of participation.

In brief, florbetapir F 18 is an imaging agent that will be used at low (tracer) doses. The most common adverse events in human clinical trials include headache, injection site reactions (injection site rash, extravasation, hemorrhage, irritation and puncture site hematoma), musculoskeletal pain, fatigue, and nausea. However, the possibility exists for a rare reaction to any of the drugs or procedures to which the participant will be exposed. The full potential for drug-drug interactions is not presently known. In the event of a study related adverse event, subjects should not be discharged from the imaging facility until the event has resolved or stabilized. As with any investigational study, there may be adverse events or side effects that are currently unknown and it is possible that certain unknown risks could be permanent, serious, or life-threatening. However, if any new risks become known in the future participants will be informed of them. Participation in this study may involve some added risks or discomforts, which are outlined below.

| Organ | FDG (rad/mCi) | 18F-AV-45 (rad/mCi) |
|---|---|---|
| Adrenals | 0.048 | 0.05 |
| Brain | 0.07 | 0.037 |
| Breasts | 0.034 | 0.023 |
| Gallbladder Wall | 0.049 | 0.529 |
| Lower Large Intestine Wall | 0.051 | 0.103 |
| Small Intestine | 0.047 | 0.242 |
| Upper Large Intestine Wall | 0.046 | 0.276 |
| Heart Wall | 0.22 | 0.048 |
| Kidneys | 0.074 | 0.048 |
| Liver | 0.058 | 0.238 |
| Lungs | 0.064 | 0.032 |
| Muscle | 0.039 | 0.032 |
| Ovaries | 0.053 | 0.065 |
| Pancreas | 0.096 | 0.053 |
| Red marrow | 0.047 | 0.053 |
| Skin | 0.03 | 0.022 |
| Spleen | 0.14 | 0.033 |
| Testes | 0.041 | 0.025 |
| Thymus | 0.044 | 0.027 |
| Thyroid | 0.039 | 0.025 |
| Urinary bladder wall | 0.32 | 0.1 |
| Uterus | 0.062 | 0.058 |
| Effective Dose | — | 0.069 |
| Total Body | 0.043 | 0.043 |

Potential psychosocial (non-medical) risks, discomforts, inconvenience of study procedures: It is reasonable to expect that a patient may experience some mild anxiety or stress from disorientation to their environment due to the opaque glasses and auditory stimulation masks normal sounds from their surroundings. It is expected that the presence of their caregiver and once the individual becomes more familiar with the treatment that this anxiety or stress will be reduced.

The study may involve unknown or unforeseen side effects or complications other than those mentioned above. If the above complications occur, they may lead to follow-up evaluation, monitoring, and care.

r. Minimization of Risk: The following measures will also be taken to minimize risk to participants as part of this investigational plan:
1. Physicians and research staff will receive appropriate training prior to using the system. Training will include instruction on setup and treatment session management.
2. Patients with history of or risk factors for seizure will be excluded from participation in the study.
3. Instructions for Use are provided with each system.
4. Patients will be closely monitored at regularly scheduled intervals for the duration of the study.

s. Summary: The detrimental effects of cognitive impairment are well established and a novel treatment approach is worthy of investigation. Non-invasive sensory stimulation may provide one such novel therapy. Although there are several theoretical risks that could be associated with the device and treatment, the likelihood and severity of those risks is believed to be low and will be carefully monitored in the study. The potential benefits could include symptomatic relief and slowed disease progression, which justify the investigation of non-invasive sensory stimulation in this study.

t. Sponsor Role and Responsibilities: The study sponsor's responsibilities include:
1. Ensuring that the study is designed and managed in compliance with all appropriate regulatory standards and is conducted according to the study protocol.
2. Selecting Investigators, qualified by training and experience, to conduct the study.
3. Providing appropriate training to Investigators, site study staff, and all sponsor representatives.
4. Providing the neural stimulation orchestration system only to participating Investigators and subjects, and tracking the shipment and disposition of all product.
5. Monitoring study data at research sites, including confirmation that participant informed consent is obtained and on-going safety levels remain acceptable for the duration of the trial.
6. Ensuring that prior to commencement of the study in each participating center, the sponsor has on file:
   A. Written IRB approval
   B. Approved study-specific participant informed consent
   C. Signed Investigator's Agreement
   D. Investigators' current curriculum vitae
   E. Identified and coordination with local representative Amendments: The CIP, Investigator Brochure, case report forms, informed consent form and other subject information, or other clinical investigation documents shall be amended as needed throughout the clinical investigation, and a justification statement shall be included with each amended section of a document. Proposed amendments to the CIP shall be agreed upon between the sponsor and principal investigator, or the coordinating investigator. The amendments to the CIP and the subject's informed consent form shall be notified to, or approved by, the IRB. The version number and date of the amendments shall be documented.

u. Statistical Analysis Plan Summary: This is a multi-center, prospective, non-randomized, controlled study designed to evaluate the safety and clinical utility of sensory stimulation in the treatment of Alzheimer's disease. The primary effectiveness endpoint of this trial is the change in ADAS-Cog from baseline to 6 months. The primary safety endpoint is the incidence and nature of Adverse Events (AE).

Repeated objective measures such as data classified from actigraphy recordings may allow for sufficient statistical power to discern effects between the treatment and control groups. The variance of the psychometric scales have been demonstrated longitudinally on health control populations, mild cognitive impairment, and more advanced Alzheimer's patients through projects such as the Alzheimer's Disease Neuroimaging Initiative. A substantial treatment effect from the sensory stimulation would be required to demonstrate a difference between the treatment and control groups in the design of this study. Therefore, descriptive statistics will be used to evaluate the primary and secondary endpoints, and ad-hoc secondary analyses will be performed to inform the subsequent design of clinical studies based on this feasibility data.

What is claimed is:

1. A system for treating cognitive dysfunction in a subject in need thereof, comprising:
    a light source;
    a speaker;
    a visual signaling component executed by a visual neural stimulation system and configured to provide, via the light source, visual stimulation having a first value of a first parameter;
    an audio signaling component executed by an auditory neural stimulation system configured to provide, via the speaker, audio stimulation having a second value of the second parameter; and
    a stimuli orchestration component executed by a neural stimulation orchestration system and configured to:
        receive an indication of an ambient condition and an indication of a physiological condition of the subject;
        select, for a first time interval, an offset between the visual stimulation and the audio stimulation to vary based on a policy and the indication of the ambient condition and the indication of the physiological condition of the subject, and
        provide instructions to at least one of the visual neural stimulation system or the auditory neural stimulation system corresponding to the selected offset between the visual stimulation and the audio stimulation to vary to cause the at least one of the visual neural stimulation system or the auditory neural stimulation system to vary the offset between the visual stimulation and the audio stimulation.

2. The system of claim 1, wherein the neural stimulation orchestration system is further configured to:
    select, for a second time interval subsequent to the first time interval, one of the visual stimulation or the audio stimulation to vary based on the policy;
    select, for the second time interval, the other of the visual stimulation or the audio stimulation to keep constant based on the policy; and
    provide instructions to the visual neural stimulation system or the auditory neural stimulation system corresponding to the selected one of the visual stimulation or the audio stimulation to vary during the second time interval to cause the one of the visual neural stimulation system or the auditory neural stimulation system to vary the one of the visual stimulation or the audio stimulation during the second time interval.

3. The system of claim 1, comprising:
    a feedback monitor configured to detect the physiological condition of the subject during the first time interval, wherein the neural stimulation orchestration system is further configured to select, using the policy and based on the detected physiological condition, one of the visual stimulation or the audio stimulation to vary during the first time interval.

4. The system of claim 1, comprising:
    a microphone configured to detect an ambient sound level; and
    a photodiode configured to detect an ambient light level, wherein the neural stimulation orchestration system is further configured to select, based on the ambient sound level and the ambient light level, one of the visual stimulation or the audio stimulation to vary during the first time interval.

5. The system of claim 1, comprising:
    an electrode to provide peripheral nerve stimulation to the subject, wherein
    wherein the neural stimulation orchestration system is further configured to select, based on the policy, one of the visual stimulation, the audio stimulation, or the peripheral nerve stimulation to vary during a second time interval.

6. The system of claim 1, wherein the visual stimulation is selected for varying during the first time interval, the system comprising:
    an electrode to provide peripheral nerve stimulation to the subject during the first time interval; and
    a feedback monitor configured to detect the physiological condition of the subject during the first time interval, wherein the neural stimulation orchestration system is further configured to:
        select, responsive to detecting the physiological condition, one of the audio stimulation or the peripheral nerve stimulation to vary during a second time interval subsequent to the first time interval;
        select, for the second time interval, the visual stimulation to keep constant;
        provide instructions to the visual neural stimulation system to keep constant during the second time interval;
        provide instructions to the auditory neural stimulation system to vary during the second time interval; and
        provide instructions to the electrode to keep constant during the second time interval.

7. The system of claim 1, wherein the cognitive dysfunction comprises Alzheimer's disease.

8. The system of claim 1, comprising:
    a feedback monitor configured to detect the physiological condition of the subject during the first time interval, wherein the neural stimulation orchestration system is further configured to:
        select, responsive to detecting the physiological condition, the of the visual stimulation or the audio stimulation to vary during a second time interval subsequent to the first time interval;
        select, for the second time interval, the other of the visual stimulation or the audio stimulation to keep constant; and
    provide instructions to the visual neural stimulation system or the auditory neural stimulation system corresponding to the selected one of the visual stimulation or the audio stimulation to vary during the second time interval to cause the one of the visual neural stimulation system or the auditory neural stimulation system to vary the one of the visual stimulation or the audio stimulation during the second time interval.

9. A system for treating cognitive dysfunction in a subject in need thereof, comprising:

a visual neural stimulation system configured to provide, via a light output source, visual stimulation having a first value of a first parameter;
an auditory neural stimulation system configured to provide, via an audio output source, audio stimulation having a second value of the second parameter; and
a neural stimulation orchestration system configured to:
receive an indication of an ambient condition and an indication of a physiological condition of the subject;
select, for a first time interval, an offset between the visual stimulation and the audio stimulation to vary based on a policy and the indication of the ambient condition and the indication of the physiological condition of the subject, and
provide instructions to at least one of the visual neural stimulation system or the auditory neural stimulation system corresponding to the selected offset between the visual stimulation and the audio stimulation to vary to cause the at least one of the visual neural stimulation system or the auditory neural stimulation system to vary the offset between the visual stimulation and the audio stimulation.

10. The system of claim 9, wherein the neural stimulation orchestration system is further configured to:
select, for a second time interval subsequent to the first time interval, one of the visual stimulation or the audio stimulation to vary based on the policy;
select, for the second time interval, the other of the visual stimulation or the audio stimulation to keep constant based on the policy; and
provide instructions to the visual neural stimulation system or the auditory neural stimulation system corresponding to the selected one of the visual stimulation or the audio stimulation to vary during the second time interval to cause the one of the visual neural stimulation system or the auditory neural stimulation system to vary the one of the visual stimulation or the audio stimulation during the second time interval.

11. The system of claim 9, comprising:
a feedback monitor configured to detect the physiological condition of the subject during the first time interval,
wherein the neural stimulation orchestration system is further configured to select, using the policy and based on the detected physiological condition, one of the visual stimulation or the audio stimulation to vary during the first time interval.

12. The system of claim 9, comprising:
a feedback monitor configured to detect the physiological condition of the subject during the first time interval,
wherein the neural stimulation orchestration system is further configured to:
select, responsive to detecting the physiological condition, one of the visual stimulation or the audio stimulation to vary during a second time interval subsequent to the first time interval;
select, for the second time interval, the other of the visual stimulation or the audio stimulation to keep constant; and
provide instructions to the visual neural stimulation system or the auditory neural stimulation system corresponding to the selected one of the visual stimulation or the audio stimulation to vary during the second time interval to cause the one of the visual neural stimulation system or the auditory neural stimulation system to vary the one of the visual stimulation or the audio stimulation during the second time interval.

13. The system of claim 9, comprising:
a microphone configured to detect an ambient sound level; and
a photodiode configured to detect an ambient light level,
wherein the neural stimulation orchestration system is further configured to select, based on the ambient sound level and the ambient light level, one of the visual stimulation or the audio stimulation to vary during the first time interval.

14. The system of claim 9, comprising:
an electrode to provide peripheral nerve stimulation to the subject,
wherein the neural stimulation orchestration system is further configured to select, based on the policy, one of the visual stimulation, the audio stimulation, or the peripheral nerve stimulation to vary during a second time interval.

15. The system of claim 9, wherein the visual stimulation is selected for varying during the first time interval, the system comprising:
an electrode to provide peripheral nerve stimulation to the subject during the first time interval; and
a feedback monitor configured to detect the physiological condition of the subject during the first time interval,
wherein the neural stimulation orchestration system is further configured to:
select, responsive to detecting the physiological condition, one of the audio stimulation or the peripheral nerve stimulation to vary during a second time interval subsequent to the first time interval;
select, for the second time interval, the visual stimulation to keep constant;
provide instructions to the visual neural stimulation system to keep constant during the second time interval;
provide instructions to the auditory neural stimulation system to vary during the second time interval; and
provide instructions to the electrode to keep constant during the second time interval.

16. The system of claim 9, wherein the cognitive dysfunction comprises Alzheimer's disease.

17. A system for treating cognitive dysfunction in a subject in need thereof, comprising:
a visual neural stimulation system;
an auditory neural stimulation system;
a neural stimulation orchestration system;
a light output source;
an audio output source; and
one or more processors configured to execute one or more programs to treat a subject in need of a treatment of a brain disease, the one or more programs including instructions for conducting a therapy session, the therapy session comprising:
providing, via the light output source, visual stimulation having a first value of a first parameter;
providing, via the audio output source, audio stimulation having a second value of the second parameter;
receiving an indication of an ambient condition and an indication of a physiological condition of the subject;
selecting, for a first time interval, an offset between the visual stimulation and the audio stimulation to vary based on a policy and the indication of the ambient condition and the indication of the physiological condition of the subject, and providing instructions to at least one of the visual neural stimulation system or the auditory neural stimulation system corresponding to the selected offset between the visual stimulation and the audio stimulation to vary to cause the at least one of the visual neural stimulation system or the auditory neural stimulation system to vary the offset between the visual stimulation and the audio stimulation.

18. The system of claim 17, wherein the therapy session comprises:
   selecting, for a second time interval subsequent to the first time interval, the other of the visual stimulation or the audio stimulation to vary based on the policy;
   selecting, for the second time interval, the other of the visual stimulation or the audio stimulation to keep constant based on the policy; and
   providing instructions to the visual neural stimulation system or the auditory neural stimulation system corresponding to the selected one of the visual stimulation or the audio stimulation to vary during the second time interval to cause the one of the visual neural stimulation system or the auditory neural stimulation system to vary the one of the visual stimulation or the audio stimulation during the second time interval.

19. The system of claim 17, wherein the therapy session comprises:
   detecting the physiological condition of the subject during the first time interval,
   selecting, using the policy and based on the detected physiological condition, one of the visual stimulation or the audio stimulation to vary during the first time interval.

20. The system of claim 17, wherein the therapy session comprises:
   detecting the physiological condition of the subject during the first time interval;
   selecting, responsive to detecting the physiological condition, the other of the visual stimulation or the audio stimulation to vary during a second time interval subsequent to the first time interval;
   selecting, for the second time interval, the other of the visual stimulation or the audio stimulation to keep constant; and
   providing instructions to the visual neural stimulation system or the auditory neural stimulation system corresponding to the selected one of the visual stimulation or the audio stimulation to vary during the second time interval to cause the one of the visual neural stimulation system or the auditory neural stimulation system to vary the one of the visual stimulation or the audio stimulation during the second time interval.

21. The system of claim 17, wherein the therapy session comprises:
   detecting an ambient sound level;
   detecting an ambient light level; and
   selecting, based on the ambient sound level and the ambient light level, one of the visual stimulation or the audio stimulation to vary during the first time interval.

22. The system of claim 17, wherein the therapy session comprises:
   providing, via an electrode, peripheral nerve stimulation to the subject; and
   selecting, based on the policy, one of the visual stimulation, the audio stimulation, or the peripheral nerve stimulation to vary during a second time interval.

23. The system of claim 17, wherein the visual stimulation is selected for varying during the first time interval, the therapy session further comprising:
   providing, via an electrode, peripheral nerve stimulation to the subject during the first time interval;
   detecting the physiological condition of the subject during the first time interval;
   selecting, responsive to detecting the physiological condition, one of the audio stimulation or the peripheral nerve stimulation to vary during a second time interval subsequent to the first time interval;
   selecting, for the second time interval, the visual stimulation to keep constant;
   providing instructions to the visual neural stimulation system to keep constant during the second time interval;
   providing instructions to the auditory neural stimulation system to vary during the second time interval; and
   providing instructions to the electrode to keep constant during the second time interval.

24. The system of claim 17, wherein the cognitive dysfunction comprises Alzheimer's disease.

25. A method for treating cognitive dysfunction in a subject in need thereof, comprising administering a stimulus to the subject using a system comprising:
   a light source;
   a speaker;
   a visual signaling component executed by a visual neural stimulation system and configured to provide, via the light source, visual stimulation having a first value of a first parameter;
   an audio signaling component executed by an auditory neural stimulation system configured to provide, via the speaker, audio stimulation having a second value of the second parameter; and
   a stimuli orchestration component executed by a neural stimulation orchestration system and configured to:
      receive an indication of an ambient condition and an indication a physiological condition of the subject;
      select, for a first time interval, an offset between the visual stimulation and the audio stimulation to vary based on a policy and the indication of the ambient condition and the indication of the physiological condition of the subject, and
      provide instructions to at least one of the visual neural stimulation system or the auditory neural stimulation system corresponding to the selected offset between the visual stimulation and the audio stimulation to vary to cause the at least one of the visual neural stimulation system or the auditory neural stimulation system to vary the offset between the visual stimulation and the audio stimulation.

26. The method of claim 25, wherein the cognitive dysfunction comprises Alzheimer's disease.

* * * * *